US011851655B2

(12) United States Patent
Prakash et al.

(10) Patent No.: US 11,851,655 B2
(45) Date of Patent: *Dec. 26, 2023

(54) COMPOSITIONS AND METHODS FOR MODULATING APOLIPOPROTEIN (A) EXPRESSION

(71) Applicant: Ionis Pharmaceuticals, Inc., Carlsbad, CA (US)

(72) Inventors: Thazha P. Prakash, Carlsbad, CA (US); Punit P. Seth, Carlsbad, CA (US); Eric E. Swayze, Encinitas, CA (US); Mark J. Graham, San Clemente, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 17/060,440

(22) Filed: Oct. 1, 2020

(65) Prior Publication Data

US 2021/0087566 A1 Mar. 25, 2021

Related U.S. Application Data

(63) Continuation of application No. 15/891,156, filed on Feb. 7, 2018, now Pat. No. 10,883,104, which is a continuation of application No. 14/839,580, filed on Aug. 28, 2015, now Pat. No. 9,957,504, which is a continuation of application No. 14/588,061, filed on Dec. 31, 2014, now Pat. No. 9,181,550, which is a continuation of application No. PCT/US2014/036460, filed on May 1, 2014.

(60) Provisional application No. 61/986,867, filed on Apr. 30, 2014, provisional application No. 61/976,991, filed on Apr. 8, 2014, provisional application No. 61/880,790, filed on Sep. 20, 2013, provisional application No. 61/871,673, filed on Aug. 29, 2013, provisional application No. 61/843,887, filed on Jul. 8, 2013, provisional application No. 61/823,826, filed on May 15, 2013, provisional application No. 61/818,442, filed on May 1, 2013.

(51) Int. Cl.

| | |
|---|---|
| ***C07H 21/02*** | (2006.01) |
| ***C07H 21/04*** | (2006.01) |
| ***C12N 15/113*** | (2010.01) |
| ***A61K 47/54*** | (2017.01) |
| ***C12N 15/11*** | (2006.01) |
| ***A61K 31/7088*** | (2006.01) |
| ***A61K 31/713*** | (2006.01) |

(52) U.S. Cl.

CPC ........ *C12N 15/113* (2013.01); *A61K 31/7088* (2013.01); *A61K 31/713* (2013.01); *A61K 47/549* (2017.08); *C07H 21/04* (2013.01); *C12N 15/111* (2013.01); *C12N 2310/11* (2013.01); *C12N 2310/113* (2013.01); *C12N 2310/17* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2310/353* (2013.01); *C12N 2310/3511* (2013.01); *C12N 2310/3513* (2013.01); *C12N 2310/3515* (2013.01); *C12N 2310/3525* (2013.01); *C12N 2320/32* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,751,219 | A | 6/1988 | Kempen et al. |
| 4,845,205 | A | 7/1989 | Huynh Dinh et al. |
| 4,981,957 | A | 1/1991 | Lableu et al. |
| 5,023,243 | A | 6/1991 | Tullis |

(Continued)

FOREIGN PATENT DOCUMENTS

| | | |
|---|---|---|
| CA | 2450022 | 12/2002 |
| CN | 102753186 | 10/2012 |

(Continued)

OTHER PUBLICATIONS

Maher et al., "Comparitive bybrid arrest by tandem antisense oligodeoxyribonucleotides or oligodeoxyribonucleoside methylphosphonates in a cell-free system", Nucl. Acid. Res. (1988) 16(8):3341-3358.

(Continued)

*Primary Examiner* — Traviss C McIntosh, III

(74) *Attorney, Agent, or Firm* — Timothy P. O'Dea

(57) ABSTRACT

Provided herein are oligomeric compounds with conjugate groups targeting apoplipoprotein (a) [apo(a)]. In certain embodiments, the apo(a) targeting oligomeric compounds are conjugated to N-Acetylgalactosamine. Also disclosed herein are conjugated oligomeric compounds targeting apo (a) for use in decreasing apo(a) to treat, prevent, or ameliorate diseases, disorders or conditions related to apo(a) and/or Lp(a). Certain diseases, disorders or conditions related to apo(a) and/or Lp(a) include inflammatory, cardiovascular and/or metabolic diseases, disorders or conditions. The conjugated oligomeric compounds disclosed herein can be used to treat such diseases, disorders or conditions in an individual in need thereof.

33 Claims, No Drawings

Specification includes a Sequence Listing.

(56) References Cited

U.S. PATENT DOCUMENTS

| | | | |
|---|---|---|---|
| 5,034,506 | A | 7/1991 | Summerton et al. |
| 5,118,800 | A | 6/1992 | Smith et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,177,198 | A | 1/1993 | Spielvogel et al. |
| 5,223,618 | A | 6/1993 | Cook et al. |
| 5,185,444 | A | 8/1993 | Summerton et al. |
| 5,256,775 | A | 10/1993 | Froehler |
| 5,264,562 | A | 11/1993 | Matteucci |
| 5,264,564 | A | 11/1993 | Matteucci |
| 5,319,080 | A | 6/1994 | Eumann |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,432,272 | A | 7/1995 | Benner |
| 5,434,257 | A | 7/1995 | Matteucci et al. |
| 5,446,137 | A | 8/1995 | Maag et al. |
| 5,457,187 | A | 10/1995 | Gmelner et al. |
| 5,459,255 | A | 10/1995 | Cook et al. |
| 5,466,786 | A | 11/1995 | Buhr et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,134 | A | 5/1996 | Acevedo et al. |
| 5,525,711 | A | 6/1996 | Hawkins et al. |
| 5,552,540 | A | 9/1996 | Haralambidis |
| 5,567,811 | A | 10/1996 | Mistura et al. |
| 5,576,427 | A | 11/1996 | Cook et al. |
| 5,587,469 | A | 12/1996 | Cook et al. |
| 5,591,722 | A | 1/1997 | Montgomery et al. |
| 5,594,121 | A | 1/1997 | Froehler et al. |
| 5,596,091 | A | 1/1997 | Switzer |
| 5,597,909 | A | 1/1997 | Urdea et al. |
| 5,602,240 | A | 2/1997 | DeMesmaeker et al. |
| 5,610,289 | A | 3/1997 | Cook et al. |
| 5,610,300 | A | 3/1997 | Altmann et al. |
| 5,614,617 | A | 3/1997 | Cook et al. |
| 5,625,050 | A | 4/1997 | Beaton et al. |
| 5,627,053 | A | 5/1997 | Usman et al. |
| 5,639,873 | A | 6/1997 | Barascut et al. |
| 5,645,985 | A | 7/1997 | Froehler et al. |
| 5,646,265 | A | 7/1997 | McGee |
| 5,670,633 | A | 9/1997 | Cook et al. |
| 5,681,941 | A | 10/1997 | Cook et al. |
| 5,698,685 | A | 12/1997 | Summerton et al. |
| 5,700,920 | A | 12/1997 | Altmann et al. |
| 5,750,692 | A | 5/1998 | Cook et al. |
| 5,763,588 | A | 6/1998 | Matteucci et al. |
| 5,792,847 | A | 8/1998 | Buhr et al. |
| 5,801,154 | A | 9/1998 | Baracchini et al. |
| 5,830,653 | A | 11/1998 | Froehler et al. |
| 5,994,517 | A | 11/1999 | Ts'o et al. |
| 5,998,203 | A | 12/1999 | Matulic-Adamic |
| 6,005,096 | A | 12/1999 | Matteucci et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,525,031 | B2 | 2/2003 | Manoharan |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,620,916 | B1 | 9/2003 | Takahara et al. |
| 6,660,720 | B2 | 12/2003 | Manoharan et al. |
| 6,670,461 | B1 | 12/2003 | Wengel et al. |
| 6,727,064 | B2 | 4/2004 | Karras |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 6,908,903 | B1 | 6/2005 | Theodore et al. |
| 7,034,133 | B2 | 4/2006 | Wengel et al. |
| 7,053,207 | B2 | 5/2006 | Wengel |
| 7,259,150 | B2 | 8/2007 | Crooke et al. |
| 7,262,177 | B2 | 8/2007 | Ts'o et al. |
| 7,267,819 | B2 | 9/2007 | Ferrara et al. |
| 7,399,845 | B2 | 7/2008 | Seth et al. |
| 7,399,853 | B2 | 7/2008 | Freier et al. |
| 7,425,544 | B2 | 9/2008 | Dobie et al. |
| 7,427,672 | B2 | 9/2008 | Imanishi et al. |
| 7,439,043 | B2 | 10/2008 | DeFrees et al. |
| 7,482,117 | B2 | 1/2009 | Cargill et al. |
| 7,491,805 | B2 | 2/2009 | Vargeese et al. |
| 7,563,884 | B2 | 7/2009 | Cowsert et al. |
| 7,569,686 | B1 | 8/2009 | Bhat et al. |
| 7,582,744 | B2 | 9/2009 | Manoharan et al. |
| 7,598,227 | B2 | 10/2009 | Crooke et al. |
| 7,696,344 | B2 | 4/2010 | Khvorova et al. |
| 7,723,509 | B2 | 5/2010 | Manoharan et al. |
| 7,741,457 | B2 | 6/2010 | Swayze et al. |
| 7,750,141 | B2 | 7/2010 | Crooke et al. |
| 7,750,142 | B2 | 7/2010 | Freier et al. |
| 7,851,615 | B2 | 12/2010 | Manoharan et al. |
| 7,935,796 | B2 | 5/2011 | Lee et al. |
| 7,989,612 | B2 | 8/2011 | Mcswiggen et al. |
| 8,084,437 | B2 | 12/2011 | Freier et al. |
| 8,093,222 | B2 | 1/2012 | Freier et al. |
| 8,101,743 | B2 | 1/2012 | Brown-Driver et al. |
| 8,106,022 | B2 | 1/2012 | Manoharan et al. |
| 8,137,695 | B2 | 3/2012 | Rozema et al. |
| 8,143,230 | B2 | 3/2012 | Bhanot et al. |
| 8,158,601 | B2 | 4/2012 | Chen et al. |
| 8,216,786 | B2 | 7/2012 | Shiffman et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |
| 8,530,640 | B2 | 9/2013 | Seth et al. |
| 8,541,376 | B2 | 9/2013 | Ferrara et al. |
| 8,541,548 | B2 | 9/2013 | Rozema |
| 8,546,556 | B2 | 10/2013 | Seth et al. |
| 8,552,163 | B2 | 10/2013 | Lee et al. |
| 8,642,752 | B2 | 2/2014 | Swayze et al. |
| 8,653,047 | B2 | 2/2014 | Crooke et al. |
| 8,664,190 | B2 | 3/2014 | Freier et al. |
| 8,673,632 | B2 | 3/2014 | Crooke et al. |
| 8,697,860 | B1 | 4/2014 | Monia et al. |
| 8,742,075 | B2 | 6/2014 | Lee et al. |
| 9,127,276 | B2 | 9/2015 | Prakash et al. |
| 9,133,461 | B2 | 9/2015 | Betancourt et al. |
| 9,145,558 | B2 | 9/2015 | Prakash et al. |
| 9,163,239 | B2 | 10/2015 | Prakash et al. |
| 9,181,549 | B2 | 11/2015 | Prakash et al. |
| 9,181,550 | B2 | 11/2015 | Prakash et al. |
| 9,322,018 | B2 | 4/2016 | Bettencourt et al. |
| 9,550,988 | B2 | 1/2017 | Swayze et al. |
| 9,884,045 | B2 | 2/2018 | Takahashi |
| 9,957,292 | B2 | 5/2018 | Prakash et al. |
| 9,957,505 | B2 | 5/2018 | Hauser |
| 9,994,855 | B2 | 6/2018 | Prakash et al. |
| 10,023,861 | B2 | 7/2018 | Prakash et al. |
| 10,280,423 | B2 | 5/2019 | Prakash et al. |
| 10,294,477 | B2 | 5/2019 | Swayze |
| 10,883,104 | B2 * | 1/2021 | Prakash ................ C12N 15/111 |
| 2001/0053519 | A1 | 12/2001 | Fodor et al. |
| 2002/0082227 | A1 | 6/2002 | Henry |
| 2003/0017488 | A1 | 1/2003 | Koishi et al. |
| 2003/0077829 | A1 | 4/2003 | MacLachlan |
| 2003/0119724 | A1 | 6/2003 | Ts'o et al. |
| 2003/0170249 | A1 | 9/2003 | Hakomori et al. |
| 2003/0228597 | A1 | 12/2003 | Cowsert et al. |
| 2004/0038274 | A1 | 2/2004 | Cook et al. |
| 2004/0171564 | A1 | 9/2004 | Honkanen et al. |
| 2004/0171570 | A1 | 9/2004 | Allerson et al. |

(56) References Cited

U.S. PATENT DOCUMENTS

| | | | |
|---|---|---|---|
| 2004/0203145 | A1 | 10/2004 | Zamore et al. |
| 2004/0208856 | A1 | 10/2004 | Crooke et al. |
| 2004/0242516 | A1 | 12/2004 | Crooke et al. |
| 2004/0259086 | A1 | 12/2004 | Schlegel et al. |
| 2005/0009088 | A1 | 1/2005 | Crooke et al. |
| 2005/0112118 | A1 | 5/2005 | Cimbora et al. |
| 2005/0130923 | A1 | 6/2005 | Bhat et al. |
| 2005/0153337 | A1 | 7/2005 | Manoharan |
| 2005/0164235 | A1 | 7/2005 | Manoharan et al. |
| 2005/0244869 | A1 | 11/2005 | Brown-Driver et al. |
| 2005/0255487 | A1 | 11/2005 | Khvorova et al. |
| 2006/0148740 | A1 | 7/2006 | Platenburg |
| 2006/0183886 | A1 | 8/2006 | Tso et al. |
| 2007/0031844 | A1 | 2/2007 | Khorova et al. |
| 2007/0054856 | A1 | 3/2007 | Gerber et al. |
| 2007/0088154 | A1 | 4/2007 | Khvorova et al. |
| 2007/0287831 | A1 | 12/2007 | Seth et al. |
| 2008/0039618 | A1 | 2/2008 | Allerson et al. |
| 2008/0108801 | A1 | 5/2008 | Manoharan et al. |
| 2008/0113351 | A1 | 5/2008 | Nalto et al. |
| 2008/0177045 | A1 | 7/2008 | Lee et al. |
| 2008/0206869 | A1 | 8/2008 | Smith et al. |
| 2008/0255030 | A1 | 10/2008 | Yu et al. |
| 2008/0281041 | A1 | 11/2008 | Rozema et al. |
| 2008/0281044 | A1 | 11/2008 | Manoharan et al. |
| 2009/0012281 | A1 | 1/2009 | Swayze et al. |
| 2009/0203132 | A1 | 8/2009 | Swayze et al. |
| 2009/0203135 | A1 | 8/2009 | Forst et al. |
| 2009/0239814 | A1 | 9/2009 | Manoharan et al. |
| 2009/0286973 | A1 | 11/2009 | Manoharan et al. |
| 2009/0306180 | A1 | 12/2009 | Bhanot et al. |
| 2009/0318536 | A1 | 12/2009 | Freier et al. |
| 2009/0326040 | A1 | 12/2009 | Geary et al. |
| 2010/0093085 | A1 | 4/2010 | Yamada et al. |
| 2010/0240730 | A1 | 9/2010 | Beigelman et al. |
| 2010/0331390 | A1 | 12/2010 | Crooke et al. |
| 2011/0039910 | A1 | 2/2011 | Crooke et al. |
| 2011/0077386 | A1 | 3/2011 | Lee et al. |
| 2011/0097264 | A1 | 4/2011 | Wang et al. |
| 2011/0097265 | A1 | 4/2011 | Wang et al. |
| 2011/0123520 | A1 | 5/2011 | Manoharan et al. |
| 2011/0124853 | A1 | 5/2011 | Chen et al. |
| 2011/0201798 | A1 | 8/2011 | Manoharan et al. |
| 2011/0207799 | A1 | 8/2011 | Rozema et al. |
| 2011/0243948 | A1 | 10/2011 | Lee et al. |
| 2011/0269814 | A1 | 11/2011 | Manoharan et al. |
| 2011/0294868 | A1 | 12/2011 | Monia et al. |
| 2012/0035115 | A1 | 2/2012 | Manoharan et al. |
| 2012/0071641 | A1 | 3/2012 | Manoharan et al. |
| 2012/0095075 | A1 | 4/2012 | Manoharan et al. |
| 2012/0101148 | A1 | 4/2012 | Aking et al. |
| 2012/0122958 | A1 | 5/2012 | Dawson et al. |
| 2012/0128760 | A1 | 5/2012 | Manoharan et al. |
| 2012/0136042 | A1 | 5/2012 | Manoharan et al. |
| 2012/0157509 | A1 | 6/2012 | Hadwiger et al. |
| 2012/0165393 | A1 | 6/2012 | Rozema et al. |
| 2012/0183602 | A1 | 7/2012 | Chen et al. |
| 2012/0225927 | A1 | 9/2012 | Sah et al. |
| 2012/0230938 | A1 | 9/2012 | Rozema et al. |
| 2013/0004427 | A1 | 1/2013 | El-Sayed et al. |
| 2013/0017250 | A1 | 1/2013 | Ginsberg et al. |
| 2013/0023579 | A1 | 1/2013 | Crooke et al. |
| 2013/0035366 | A1 | 2/2013 | Swayze et al. |
| 2013/0053431 | A1 | 2/2013 | Tachas et al. |
| 2013/0109817 | A1 | 5/2013 | Yurkovetskiy et al. |
| 2013/0121954 | A1 | 5/2013 | Wakefield et al. |
| 2013/0178512 | A1 | 7/2013 | Manoharan et al. |
| 2013/0236968 | A1 | 9/2013 | Manoharan et al. |
| 2013/0317085 | A1 | 11/2013 | Crooke et al. |
| 2014/0107184 | A1 | 4/2014 | Swayze et al. |
| 2014/0256797 | A1 | 9/2014 | Monia et al. |
| 2014/0343123 | A1 | 11/2014 | Prakash et al. |
| 2014/0357701 | A1 | 12/2014 | Swayze et al. |
| 2015/0057329 | A1 | 2/2015 | Bhanot et al. |
| 2015/0126720 | A1 | 5/2015 | Prakash et al. |
| 2016/0046939 | A1 | 2/2016 | Prakash et al. |
| 2016/0222389 | A1 | 8/2016 | Grossman et al. |
| 2018/0256629 | A1 | 9/2018 | Crooke et al. |

FOREIGN PATENT DOCUMENTS

| | | | |
|---|---|---|---|
| JP | 2005-520489 | | 7/2005 |
| JP | 2009-524431 | | 7/2009 |
| RU | 2145964 | | 5/1999 |
| RU | 2249463 | | 3/2000 |
| RU | 2249458 | | 11/2003 |
| RU | 2392966 | | 8/2008 |
| SU | 1834904 | A3 | 8/1993 |
| WO | 1994002499 | | 2/1994 |
| WO | 1994017093 | | 8/1994 |
| WO | 1995019433 | A2 | 7/1995 |
| WO | 9614329 | A1 | 5/1996 |
| WO | 1997020563 | | 6/1997 |
| WO | 1997046098 | | 12/1997 |
| WO | 1998013381 | | 4/1998 |
| WO | 1998039352 | | 9/1998 |
| WO | 1999014226 | | 3/1999 |
| WO | 0010599 | A | 3/2000 |
| WO | 2000014048 | | 3/2000 |
| WO | 2000063364 | | 10/2000 |
| WO | 2000076554 | A1 | 12/2000 |
| WO | 2001005825 | | 1/2001 |
| WO | 0107602 | A2 | 2/2001 |
| WO | 2001049687 | | 7/2001 |
| WO | 2001053528 | A1 | 7/2001 |
| WO | 2002043771 | | 6/2002 |
| WO | 2002092772 | A2 | 11/2002 |
| WO | 2003004602 | | 1/2003 |
| WO | 2003010284 | A2 | 2/2003 |
| WO | 2003014307 | A2 | 2/2003 |
| WO | 2003044172 | | 5/2003 |
| WO | 2004035765 | | 10/2003 |
| WO | 2004024757 | | 3/2004 |
| WO | 2004044181 | | 5/2004 |
| WO | 2004045543 | A2 | 6/2004 |
| WO | 2004063208 | | 7/2004 |
| WO | 2004071407 | A2 | 8/2004 |
| WO | 2004072046 | A2 | 8/2004 |
| WO | 2004078922 | A2 | 9/2004 |
| WO | 2004093783 | | 11/2004 |
| WO | 2004096016 | A2 | 11/2004 |
| WO | 2004096996 | A2 | 11/2004 |
| WO | 2004101619 | | 11/2004 |
| WO | 2004106356 | | 12/2004 |
| WO | 2005000201 | | 1/2005 |
| WO | 2005005599 | A2 | 1/2005 |
| WO | 2005021570 | | 3/2005 |
| WO | 2005028628 | A2 | 3/2005 |
| WO | 2005071080 | A2 | 8/2005 |
| WO | 2005083124 | A1 | 9/2005 |
| WO | 2005097155 | | 10/2005 |
| WO | 2005121371 | | 12/2005 |
| WO | 2006014729 | | 2/2006 |
| WO | 2006014729 | A2 | 2/2006 |
| WO | 2006031461 | | 3/2006 |
| WO | 2006044531 | A2 | 4/2006 |
| WO | 2006047842 | | 5/2006 |
| WO | 2007035759 | | 3/2007 |
| WO | 2007035771 | A2 | 3/2007 |
| WO | 2007089584 | A2 | 8/2007 |
| WO | 2007090071 | | 8/2007 |
| WO | 2007131237 | A2 | 11/2007 |
| WO | 2007134014 | A2 | 11/2007 |
| WO | 2007134181 | | 11/2007 |
| WO | 2007136988 | A2 | 11/2007 |
| WO | 2007143317 | A2 | 12/2007 |
| WO | 2007146511 | A2 | 12/2007 |
| WO | 2008036825 | A2 | 3/2008 |
| WO | 2008066776 | A2 | 6/2008 |
| WO | 2008073300 | | 6/2008 |
| WO | 2008098788 | | 8/2008 |
| WO | 2008101157 | | 8/2008 |
| WO | 2008150729 | | 12/2008 |
| WO | 2008154401 | | 12/2008 |

(56) References Cited

FOREIGN PATENT DOCUMENTS

| | | |
|---|---|---|
| WO | 2009003009 | 12/2008 |
| WO | 2009006478 | 1/2009 |
| WO | 2009029293 A2 | 3/2009 |
| WO | 2009046141 A2 | 4/2009 |
| WO | 2009061851 A2 | 5/2009 |
| WO | 2009073809 | 6/2009 |
| WO | 2009082607 | 7/2009 |
| WO | 2009126933 | 10/2009 |
| WO | 2009134487 | 11/2009 |
| WO | 2009143369 | 11/2009 |
| WO | 2009148605 A2 | 12/2009 |
| WO | 2010017509 A1 | 2/2010 |
| WO | 2010036696 | 4/2010 |
| WO | 2010036698 | 4/2010 |
| WO | 2010045509 A2 | 4/2010 |
| WO | 2010048228 A2 | 4/2010 |
| WO | 2010048549 | 4/2010 |
| WO | 2010048585 | 4/2010 |
| WO | 2010054406 | 5/2010 |
| WO | 2010077578 | 7/2010 |
| WO | 2010083615 | 7/2010 |
| WO | 2010088537 | 8/2010 |
| WO | 2010101951 | 9/2010 |
| WO | 2010103204 | 9/2010 |
| WO | 2010121074 A1 | 10/2010 |
| WO | 2010129709 | 11/2010 |
| WO | 2010144740 | 12/2010 |
| WO | 2010148013 | 12/2010 |
| WO | 2011005786 A2 | 1/2011 |
| WO | 2011005860 | 1/2011 |
| WO | 2011005861 | 1/2011 |
| WO | 2011038356 | 3/2011 |
| WO | 2011047312 A1 | 4/2011 |
| WO | 2011085271 | 7/2011 |
| WO | 2011100131 | 8/2011 |
| WO | 2011115818 | 9/2011 |
| WO | 2011120053 | 9/2011 |
| WO | 2011133871 | 10/2011 |
| WO | 2011139702 | 10/2011 |
| WO | 2011139702 | 11/2011 |
| WO | 2011139917 A1 | 11/2011 |
| WO | 2011163121 | 12/2011 |
| WO | 2012037254 | 3/2012 |
| WO | 2012068187 | 5/2012 |
| WO | 2012083046 | 6/2012 |
| WO | 2012083185 | 6/2012 |
| WO | 2012089352 | 7/2012 |
| WO | 2012089602 | 7/2012 |
| WO | 2012135736 | 10/2012 |
| WO | 2012142458 A1 | 10/2012 |
| WO | 2012145674 | 10/2012 |
| WO | 2012145697 | 10/2012 |
| WO | 2012149495 | 11/2012 |
| WO | 2012174154 A1 | 12/2012 |
| WO | 2012177639 A2 | 12/2012 |
| WO | 2012177784 | 12/2012 |
| WO | 2012177947 | 12/2012 |
| WO | 2013033230 | 3/2013 |
| WO | 2013043817 A1 | 3/2013 |
| WO | 2013075035 | 5/2013 |
| WO | 2013119979 | 8/2013 |
| WO | 2013142514 A1 | 9/2013 |
| WO | 2013142571 | 9/2013 |
| WO | 2013155204 A2 | 10/2013 |
| WO | 2013165816 | 11/2013 |
| WO | 2013166121 | 11/2013 |
| WO | 2013173789 | 11/2013 |
| WO | 2013177468 | 11/2013 |
| WO | 2013192233 A1 | 12/2013 |
| WO | 2014025805 A1 | 2/2014 |
| WO | 2014076195 | 5/2014 |
| WO | 2014076196 | 5/2014 |
| WO | 2014118267 | 8/2014 |
| WO | 2014118272 | 8/2014 |
| WO | 2014179620 | 11/2014 |
| WO | 2014179625 | 11/2014 |
| WO | 2014179626 | 11/2014 |
| WO | 2014179627 | 11/2014 |
| WO | 2014179629 | 11/2014 |
| WO | 2014207232 | 12/2014 |
| WO | 2014207232 A1 | 12/2014 |
| WO | 2015002971 A2 | 1/2015 |
| WO | 2015006740 A2 | 1/2015 |
| WO | 2015179693 | 11/2015 |
| WO | 2015188194 | 12/2015 |
| WO | 2017079739 A1 | 5/2017 |
| WO | 2017079745 A1 | 5/2017 |

OTHER PUBLICATIONS

Makino et al., "Intravenous Injection with Antisense Oligodeoxyribonucleotides Against Angiotensinogen Decreases Blood Pressure in Spontaneously Hypertensive RatS", Hypertension (1998) 31:1166-1170.

Martin, "New access to 2'-O-alkylated ribonucleosides and properties of 2'-O-alkylated oligoribonucleotides", Hely. Chim. Acta. (1995) 78:486-504.

Martin-Campos et al., "Identification of a novel mutation in the ANGPTL3 gene in two families diagnosed of familial hypobetalipoproteinemia without APOB mutation", Clin. Chim. Acta. (2012) 413(5-6):552-555.

Minicocci et al., "Clinical Characteristics and plasma lipids in subjects with familial combined hypolipidemia: a pooled analysis", J. Lipid. Res. (2013) 54(12):3481-3490.

Minicocci et al., "Mutations in the ANGPTL3 gene and familial combined hypolipidemia: a clinical and biochemical characterization", J. Clin. Endocrinol. Metab. (2012) 97(7):E1266-E1275.

Musunuru et al., "Exome sequencing, ANGPTL3 mutations, and familial combined hypolipidemia", N. Eng. J. Med. (2010) 363(23):2220-2227.

Naoumova et al., "A new drug target for treatment of dyslipidaemia associated with type 2 diabetes and the metabolic syndrome?" Lancet (2002) 359(9325):2215-2216.

Nauwelaerts et al., "Cyclohexenyl nucleic acids: conformationally flexible oligonucleotides", Nucl. Acids Res. (2005) 33(8):2452-2463.

Nauwelaerts et al., "Structural characterization and biological evaluation of small interfering RNAs containing cyclohexenyl nucleosides", J. Am. Chem. Soc. (2007) 129(30):9340-9348.

New England Biolabs 1998/99 Catalog (cover page and pp. 121 and 284).

Noto et al., "Prevalence of ANGPTL3 and APOB gene mutations in subjects with combined hypolipidemia", Arterioscler. Thromb. Vasc. Biol. (2012) 32(3):805-809.

Pal-bhadra et al., "Heterochromatic silencing and HP1 localization in *Drosophila* are dependent on the RNAi machinery", Science (2004) 303(5658):669-672.

Pisciotta et al., "Characterization of three kindreds with familial combined hypolipidemia caused by loss-of-function mutations of ANGPTL3", Circ. Cardiovasc. Genet. (2012) 5(1):42-50.

Reynolds et al., "Rational siRNA design for RNA interference", Nature Biotechnology (2004) 22(3):326-330.

Robeyns et al., "Oligonucleotides with cyclohexene-nucleoside building blocks: crystallization and preliminary X-ray studies of a left-handed sequence GTGTACAC", Acta. Crystallogr. Sect. F. Struct. Biol. Cryst. Commun. (2005) 61 (Pt 6):585-586.

Robeyns et al., "Structure of the fully modified left-handed cyclohexene nucleic acid sequence GTGTACAC", J. Am. Chem. Soc. (2008) 130(6):1979-1984.

Romeo et al., "Rare loss of-function mutations in ANGPTL family members contribute to plasma triglyceride levels in humans", J. Clin. Invest. (2009) 119(1):70-79.

Sanan et al., "Low density lipoprotein receptor-negative mice expressing human apolipoprotein B-100 develop complex atherosclerotic lesions on a chow diet: No accentuation by apolipoprotein(a)", PNAS (1998) 95:4544-4549.

(56) References Cited

OTHER PUBLICATIONS

Sanghvi et al., "Heterocyclic Base Modifications in Nucleic Acids and Their Applications in Antisense Oligonucleotides", Antisense Research and Applications (1993) pp. 273-288.
Shimamura et al., Biochem. Biophys. Res. Commun. (2003) 301:604-609.
Shimamura et al., "Angiopoietin-like protein3 regulates plasma HDL cholesterol through suppression of endothelial lipase", Arterioscler. Thromb. Vasc. Biol. (2007) 27(2):366-372.
Shimamura et al., "Leptin and insulin down-regulate angiopoietin-like protein 3, a plasma triglyceride-increasing factor", Biochem. Biophys. Res. Commun. (2004) 322(3):1080-1085.
Shimizugawa et al., "ANGPTL3 decreases very low density lipoprotein triglyceride clearance by inhibition of lipoprotein lipase", J. Biol. Chem. (2002) 277:33742-33748.
Sindelka et al., "Association of obesity, diabetes, serum lipids and blood pressure regulates insulin action", Physiol. Res. (2002) 5(1):85-91.
Smith et al., "Comparison of biosequences", Adv. Appl. Math. (1981) 2(4):482-489.
Sonnenburg et al., "GPIHP1 stabilizes lipoprotein lipase and prevents its inhibition by angiopoietin-like 3 and angiopoietin-like 4", The Journal of Lipid Research (2009) 50(12):2421-2429.
Valdivielso et al., "Association of moderate and severe hypertriglyceridemia with obesity, diabetes mellitus and vascular disease in the Spanish working population: results of the ICARIA study", Atherosclerosis (2009) 207(2):573-578.
Verbeure et al., "RNase H mediated cleavage of RNA by cyclohexene nucleic acid (CeNA)" Nucleic Acids Res. (2001) 29(24):4941-4947.
Verdel et al., "RNAi-mediated targeting of heterochromatin by the RITS complex", Science (2004) 303(5668):672-676.
Volpe et al., "regulation of heterochromatic silencing and histone H3 lysine-9 methylation by RNAi", Science (2002) 297(5588):1833:1837.
Wang et al., "A straightforward stereoselective synthesis of D- and L-5-hydroxy-4-hydroxymethyl-2-cyclohexenylguanine", J. Org. Chem. (2001) 66(25):8478-8482.
Wang et al., "Cyclohexene nucleic acids (CeNA) form stable duplexes with RNA and induce RNase H activity", Nucleosides Nucleotides Nucleic Acids (2001) 20(4-7):785-788.
Wang et al., "Cyclohexene Nucleic Acids (CeNA): Serum Stable Oligonucleotides that Activate RNase H and Increase Duplex Stability with Complementary RNA", J. Am. Chem. Soc. (2000) 122(36):8595-8602.
Wang et al., "Stereocontrolled synthesis of ara-type cyclohexenyl nucleosides", J. Org. Chem. (2003) 68(11):4499-4505.
Willer et al., "Newly identified loci that influence lipid concentrations and risk of coronary artery disease", Nat. Genet. (2008) 40(2):161-169.
Woolf et al., "Specificity of antisense oligonucleotides in vivo", PNAS (1992) 89:7305-7309.
Yu et al., "Effects of ANGPTL3 antisense oligodeoxynucleotides transfection on the cell growths and invasion of human hepatocellular carcinoma cells", Hepatogastroenterology (2011) 58(110-111):1742-1746.
Zhang et al., "PowerBLAST: A New Network BLAST Application for Interactive or Automated Sequence Analysis and Annotation", Genome Res. (1997) 7:649-656.
Zhang et al., "Spontaneous atherosclerosis in aged lipoprotein lipase-deficient mice with severe hypertriglyceridemia on a normal chow diet", Circ. Res. (2008) 102(2):250-256.
Zhao et al., "Synthesis and preliminary biochemical studies with 5'-deoxy-5'methylidyne phosphonate linked thymidine bligonucleotides", Tet. Lett. (1996) 37(35):6239-6242.
Akinc et al., "Targeted Delivery of RNAi Therapeutics with Endogenous and Exogenous Ligand-Based Mechanisms", Molecular Therapy (2010) 18(7):1357-1364.
Albaek et al., "Analogues of a Locked Nucleic Acid with Three-Carbon 2',4'-Linkages: Synthesis by Ring-Closing Metathesis and Influence of Nucleic Acid Duplex Stability", J. Org. Chem. (2006) 71:7731-7740.
Andre et al., "Determination of modulation of ligand properties of synthetic complex-type biantennary N-glycans by introduction of bisecting GlcNAc in silico, in vitro and in vivo", Eur. J. Biochem. (2004) 271:118-134.
Atsma et al., "Partial characeterization of low density lipoprotein preparations isolated from fresh and frozen plasma after radiolabeling by seven different methods", J. Lipid Res (1991) 32(1):173-181.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14:1784-1792.
Biessen et al., "Synthesis of Cluster Galactosides with High Affinity for the Hepatic Asialoglycoprotein Receptor", J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent", J. Med. Chem. (1995) 38:1846-1852.
Braasch et al., "Locked nucleic acid (LNA): fine-tuning the recognition of DNA and RNA", Chem. Biol. (2001) 8:1-7.
Braasch et al., "Novel Antisense and Peptide Nucleic Acid Strategies for Controlling Gene Expresssion", Biochemsitry (2002) 41(14):4503-4510.
Trappeniers et al., "6'-derivatised alpha-GalCer analogues capable of inducing strong CD1d-mediated Th1-biased NKT cell responses in mice", J. Am. Chem. Soc. (2008) 130(49):16468-9.
Abifadel et al., "Mutations in PCSK9 cause autosomal dominant hypercholesterolemia", Nat. Genet. (2003) 34(2):154-156.
Sousa et al., "Neurodegeneration in familial amyloid polyneuropathy: from pathology to molecular signaling", Prog. Neurobiol. (2003) 71:385-400.
Yadav et al., "Carbohydrate functionalized iron (III) complexes as biomimetic siderophores", Chem. Comm. (2012) 48(11):1704-1706.
Brubaker et al., "Structure-Function of the Glucagon Receptor Family of G Protein-Coupled Receptors: The Glucagon, GIP, GLP-1, and GLP-2 Receptors", Receptors and Channels (2002) 8:179-188.
Chen et al., "Strand-specific 5'-O-methylation of siRNA duplexes controls guide strand selection and targeting specificity", RNA (2008) 14:263-74.
Chiang et al., Antisense Oligonucleotides Inhibit Intercellular Adhesion Molecule 1 Expression by Two Distinct Mechanisms, J. Biol. Chem. (1991) 266:18162-18171.
Costa et al., "Amyloid fibril protein related to prealbumin in familial amyloidotic polyneuropathy", PNAS (1978) 75(9):4499-4503.
Crew et al., "Eukaryotic initiation factor-4E in superficial and muscle invasive blader cancer and its correlation with vascular endothelial growth factor expression and tumour preogression", Br. J. Cancer (2000) 82(1):161-166.
Debenedetti et al., "Overexpression of eukaryotic protein synthesis initiation factor 4E in Hela cells results in aberrant growth and morphology", PNAS (1990) 87:8212-8216.
Dickson et al., "Rat Choroid Plexus Specializes in the Synthesis and the Secretion of Transthyretin", J. Biol. Chem. (1986) 261(8):3475-3478.
Dubuc et al., "Statins upregulate PCSK9, the gene encoding the proprotein convertase neural apoptosis-regulated convertase-1 iumplicated in familial hypercholesterolemia", Arterioscler. Thromb. Vasc. Biol. (2004) 24(8):1454-1459.
Elchebly et al., "Increased Insulin Sensitivity and Obesity Resistance in Mice Lacking the Protein Tyrosine Phosphatase-1B Gene", Science (1999) 283:1544-1548.
Yang et al., "STAT3 complements defects in an interferon-resistant cell line: Evidence for an essential role for STAT3 in interferon signaling and biological activities", PNAS (1998) 95:5568-5572.
Fried et al., "HBeAg and hepatitis B virus DNA as outcome predictors during therapy with peginterferon alfa-2a for HBeAg-positive chronic hepatitis B", Hepatology (2008) 47(2):428-434.

(56) References Cited

OTHER PUBLICATIONS

Fukada et al., "Two Signals are necessary for cell proliferation induced by a cytokine receptor gp130: involvement of STAT3 in anti-apoptosis", Immunity (1996) 5(5):449-460.
Ganem et al., "Hepatitis B Virus Infection—Natural History and Clinical Consequences", N. Engl. J. Med. (2004) 350:1118-1129.
Geary et al., "Effect of Dose and Plasma Concentration on Liver Uptake and Pharmacologic Activity of a 2'- Methoxyethyl Modified Chimeric Antisense Oligonucleotide Targeting PTEN", Biochem. Pharmacol. (2009) 78(3):284-91.
Gehring et al., "Assignment of the human gene for the glucocorticoid receptor to chromosome 5", PNAS (1985) 82:3751-3755.
Wang et al., "Expression of the Eukaryotic Translation Initiation Factors 4E and 2alpha in Non-Hodgkins Lymphomas", Am. J. Pathol. (1999) 155(1): 247-255.
Seeger et al., "Hepatitis B virus biology", Microbiol. Mol. Biol. Rev. (2000) 64(1): 51-68.
Gough et al., "Mitochondrial STAT3 supports Ras-dependent oncogenic transformation", Science (2009) 324 (5935):1713-1716.
Graff et al., "Translational control and metastatic progression: Enhanced activity of the mRNA cap-binding protein elF-4E selectively enhances translation of metastasis-related mRNAs", Clin. Exp. Mestastasis (2003) 20:265-273.
Graham et al., "Cardiovascular and Metabolic Effects of ANGPTL3 Antisense Oligonucleotides", New England Journal of Medicine (2017) 377:3, 222-232.
Saraiva et al., "Amyloid Fibril Protein in Familial Amyloidotic Polyneuropathy, Portuguese Type. Definition of molecular abnormality in transthyretin (prealbumin).", J. Clin. Invest. (1984) 74:104-119.
Haydon et al., "Progression of elF4E Gene Amplification and Overexpression in Benign and Malignant Tumors of the Head and Neck", Cancer (2000) 88(12):2803-2810.
Hollenberg et al., "Primary structure and expression of a functional human glucocorticoid receptor cDNA" Nature (1985) 318:635-641.
Horton et al., "Combined analysis of oligonucleotide microarray data from transgenic and knockout mice identifies direct SREBP target genes", PNAS (2003) 100(21):12027-12032.
Jain et al., "Repression of Stat3 activity by activation of mitogen-activated protein kinase (MAPK)", Oncogene (1998) 17(24):3157-3167.
Jervis et al., "New CD1d agonists: synthesis and biological activity of 6'-triazole-substituted alpha-galactosyl ceramides", Bioorg Med Chem Lett (2012) 22(13):4348-52.
Jiang et al., "Glucagon and regulation of glucose metabolism", Am J Physiol Endocrinol Metab (2003) 284:E671-E678.
Weinberger et al., "Identification of Human Glucocorticoid Receptor Complementary DNA Clones by Epitope Selection", Science (1985) 228:740-742.
Zhong et al., "Stat3 and Stat4: Members of the family of signal transducers and activators of transcription", PNAS (1994) 91:4806-4810.
Klaman et al., "Increased Energy Expenditure, Decreased Adiposity, and Tissue-Specific Insulin Sensitivity in Protein—Tyrosine Phosphate 1B-Deficient Mice", Mol. Cell. Biol. (2000) 20(15):5479-5489.
Kurosawa et al., "Selective silencing of a mutant transthyretin allele by small interfering RNAs", Biochemical and Biophysical Research Communications (2005) 337(3):1012-1018.
Nishimura et al., "Synthetic Glycoconjugates. 4. Use of omega-(Acrylamido)alkyl Glycosides for the Preparation of Cluster Glycopolymers", Macromolecules (1994) 27(18):4876-4880.
Liang et al., "Hepatitis B e Antigen—The Dangerous Endgame of Hepatitis B", N. Engl. J. Med. (2002) 347:208-210.
Lima et al., "Single-stranded siRNAs activate RNAi in animals", Cell (2012) 150: 883-94.
Bhattacharjee et al., "Inhibition of Vascular Permeability by Antisense-Mediated Inhibition of Plasma Kallikrein and Coagulation Factor 12", Nucleic Acid Therapeutics (2013) 23(3):175-187.
Maxwell et al., "Novel putative SREBP and LXR target genes identified by microarray analysis in liver of cholesterol—fed mice", J. Lipid. Res. (2003) 44(11):2109-2119.
Moucari et al., "Early serum HBsAg drop: a strong predictor of sustained virological response to pegylated interferon alfa-2a in HBeAg-negative patients", Hepatology (2009) 49(4):1151-1157.
Taylor et al., "Curbing activation: proprotein convertases in homeostasis and pathology", FASEB J. (2003) 17:1215-1227.
Norata et al., "Gene silencing approaches for the management of dyslipidaemia", Trends in Pharmacological Sciences (2013) 34(4):198-205.
Palha, "Transthyretin as a Thyroid Hormone Carrier: Function Revisited", Clin. Chem. Lab. Med. (2002) 40(12):1292-1300.
Tanskanen et al., "Senile systemic amyloidosis affects 25% of the very aged and associated with genetic variation in alpha2-macroglobulin and tau: A population-based autopsy study", Ann. Med. (2008) 40(3):232-239.
Quesada et al., "Physiology of the pancreatic alpha-cell and glucagon secretion: role in glucose homeostasis and diabetes", J Endocrinol. (2008) 199:5-19.
Sehgal et al., "Liver as a target for oligonucleotide therapeutics", Journal of Hepatology (2013) 59(6):1354-1359.
Saison-Behmoaras et al., "Short modified antisense oligonucleotides directed against Ha-ras point mutation induce selective cleavage of the mRNA and inhibit T24 cells proliferation", EMBO J. (1991) 10(5):1111-1118.
International Search Report for Application PCT/US14/56630 dated Dec. 24, 2014.
International Search Report for Application PCT/US14/43731 dated Dec. 10, 2014.
Allshire, "Molecular biology, RNAi and heterochromatin—a hushed-up affair", Science (2002) 297(5588):1818-1819.
Altmann et al., "Second Generation Antisense Oligonucleotudes-Inhibition of PKC-alpha and c-raf Kinase Expression by Chimeric Oligonucleotides Incorporating 6"-Substituted Carbocyclis Nucleosides and 2"-O-Ethylene Glycol Substitutes Ribonucleosides" Nuclewsodies Nucleotides, (1997) 16:917-926.
Altmann et al., "Second Generation of Antisense Oligonucleotides: From Nuclease Resistance to Biological Efficacy in Animals", Chimia (1996) 50(4):168-176.
Altmann et al., "Second-generation antisense oligonucleotides: structure-activity relationships and the design of improved signal-transduction inhibitors", Biochem. Soc. Trans. (1996) 24:630-637.
Ando et al., "A decreased expression of angiopoetin-like 3 is protective against atherosclerosis in apoE-deficient mice", J. Lipid Res. (2003) 44(6):1216-23.
Angelakopoulou et al., "Comparative analysis of genome-wide association studies signal for lipids diabetes, and coronary heart disease: Cardiovascular Biomarker genetics Collaboration", Eur. Heart J. (2012) 33(3):393-407.
Asseline et al., "Modification of the 5' Terminus of Oligodeoxyribonucleotides for Conjugation with Ligands", Current Protocols in Nucleic Acid Chemistry, 2001, Supplement 5, Chapter 4: Unit 4.9 (4.9.1-4.9.28); John Wiley & Sons.
Baker et al., "2'-O-(2-Methoxy)ethyl-modified Anti-intercellular Adhesion molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Beaucage et al., "The functionalization of oligonucleotides via phosphoramidate derivatives" Tetrahedron (1993) 49(10):1925-1963.
Bligh et al., "A rapid method of total lipid extraction and purification" Can j. Biochem. Physiol. (1959) 37(8):911-917.
Branch et al., "A good antisense molecule is hard to find", TIBS (1998) 23:45-50.
Browning et al., "Molecular mediators of hepatic steatosis and liver injury", J. Clin. Invest. (2004) 114(2):147-152.
Camenisch et al., "ANGPTL3 stimulates endothelial cell adhesion and migration via integrin alpha vbeta 3 and induces blood vessel formation in vivo", J. Biol. Chem. (2002) 277(919):17281-17290.
Chin, "on the Preparation and Utilization of Isolated and Purified Oligonucleotides" Document purportedly located on a CD-ROM

(56) References Cited

OTHER PUBLICATIONS and contributed to the public collection of the Katherine R. Everett law Library of the University of North Carolina on Mar. 14, 2002.
Conklin et al., "Identification of a mammalian angiopoietin-related protein expressed specifically in liver", Genomics (1999) 62(3):477-482.
Crooke et al., "Basic principles of Antisense Therapeutics" Antisense Research and Application (1998) Chapter 1:1-50.
EMBL Accession No. BG400407, *Homo sapiens* cDNA clone, Mar. 17, 2001, retrieved from the internet Apr. 3, 2013 <http://www.ebi.ac.uk/Tools/dbfetch/emblfetch?id=BG400407&Submit=Go>.
European Search Report for application EP 11732249.5 dated Aug. 7, 2014.
EXpert Panel on Detection, Evaluation, and Treatment of High Blood Cholesterol in Adults., "Executive Summary of The Third Report of The National Cholesterol Education Program (NCEP) Expert Panel on Detection, Evaluation, And Treatment of High Blood Cholesterol In Adults (Adult Treatment Panel III)" JAMA. (2001) 285(18):2486-2497.
Fujimoto et al., "Angptl3-null mice show low plasma lipid concentrations by enhanced lipoprotein lipase activity" Exp. Anim. (2006) 55(1):27-34.
Gao et al., "Angiopoietin-like protein 3 regulates the motility and permeability of podocytes by altering nephrin expression in vitro" Biochem. Biophy. Res. Comm. (2010) 399:31-36.
Gautschi et al., "Activity of a Novel bcl-2/bcl-XL-Bispecific Antisense Oligonucleotide Against Tumors of Diverse Histologic Origins", J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue" Anal. Biochem. (1999) 274(2):241-248.
GenBank Accession No. NM_014495.1. *Homo sapiens* angiopoietin-like 3 (ANGPTL3) mRNA, retrieved from the Internet on Apr. 18, 2013, downloaded from http://www.ncbi.nlm.nih.gov/nuccore/NM_014495.1.
Graham et al., "Antisense oligonucleotide inhibition of apolipoprotein C-III reduces plasma triglycerides in rodents, honhuman primates, and humans", Circ. Res. (2103) 112(11):1479-1490.
Gu et al., "Base pairing properties of D-and L-cyclohexene nucleic acids (CeNA)", Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis", Tetrahedron (2004) 60(9):2111-2123.
Guzaev et al., "A conformationally preorganized universal solid support for efficient oligonucleotide synthesis", J. Am. Chem. Soc. (2003) 125(9):2380-2381.
Hall et al., "Establishment and maintenance of a heterochomatin domain", Science (2002) 297(5590):2232-2237.
Hanessian et al., "Synthesis of chemically and functionally diverse scaffolds from pentaerythritol", Canadian Journal of Chemistry (1996) 74(9):1731-1737.
Hatsuda et al., "Association between Plasma Angiopoietin-Like Protein 3 and Arterial Wall Thickness in Healthy Subjects", J. Vas. Res. (2007) 44:61-66.
Hooper et al., "Recent developments in the genetics of LDL deficiency" Curr. Opin. Lipidol. (2013) 24(2):111-115.
Horvath et al., "Stereoselective synthesis of (−)-ara-cyclohexenyl-adenine", Tet. Lett. (2007) 48:3621-3623.
Ichimura et al., "Serum Angiopoietin-like Protein 3 Levels: Possible Correlation with Progressive Skin Sclerosis, Digital Ulcers and Pulmonary Vascular Involvement in Patients with Systemic Sclerosis" Acta Derma. Venereol. (2013) 1-6.
Inaba et al., "Angiopoietin-like protein 3 mediates hypertriglyceridemia induced by the liver X receptor", J. Biol. Chem. (2003) 278(24):21344-21351.
International Search Report for application PCT/US11/20606 dated Jun. 27, 2011.
Inukai et al., "ANGPTL3 is increased in both insulin-deficient and -resistant diabetic states", Biochem. Biophys. Res. Commun. (2004) 317(4):1075-1079.
Ishibashi et al., "Hypercholesterolemia in low density lipoprotein receptor knockout mice and its reversal by adenovirus-mediated gene delivery", J. Clin. Invest. (1993) 92(2):883-893.
Jenuwein, "Molecular biology, An RNA-guided pathway for the epigenome", Science (2002) 297(5590):2215-2218.
Jones et al., "RNA quantitation by fluorescence-based solution assay: RiboGreen reagent characterization", Anal. Biohem. (1998) 265(2):368-374.
Kaplan et al., "Regulation of the angiopoietin-like protein 3 gene by LXR" J. Lipid. Res. (2003) 44(1):136-143.
Koishi et al., "Angptl3 regulates lipid metabolism in mice" Nat. Genet. (2002) 30(2):151-157.
Korstanje et al., "Locating Ath8, a locus for murine atherosclerosis susceptibility and testing several of its candidate genes in mice and humans" Atherosclerosis (2004) 177:443-450.
Koster et al., "Transgenic angiopoietin-like (angptl)4 overexpression and targeted disruption of angptl4 and angptl3: regulation of triglyceride metabolism" Endocrinology (2005) 146(11):4943-50.
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)" J. Biol. Chem. (2009) 284(20):13735-13745.
Leeds et al., "Quantitation of phosphorothioate oligonucleotides in human plasma" Anal. Biochem. (196) 235(1):36-43.
Lichtenstein et al., "Modulation of plasma TG lipolysis by Angiopoietin-like proteins and GPIHBP1" Biochimica and Biophysica Acta (2010) 1801(4):415-420.
Linton et al., "Transgeneic mice expressing high plasma concentrations of human apolipoprotein B100 and lipoprotein (a)" J. Clin. invest. (1993) 92:3029-3037.
Machida et al. "Bivalent inhibitors for disrupting protein surface-substrate interactions and for dual inhibition of protein prenyltransferases" J. Am. Chem. Soc. (2011) 133(4):958-963.
Branda et al., "Amplifications of antibody production by phosphorothioate oligodeoxynucleotides", J. Lab. Clin. Med. (1996) 128(3):329-338.
Coltart et al., "Principles of Mucin Architecture: Structural Studies on Synthetic Glycopeptides Bearing Clustered Mono-, Di-, Tri-, and Hexasaccharide Glycodomains", J. Am. Chem. Soc. (2002), 124:9833-9844.
Connolly et al., "Binding and Endocytosis of Cluster Glycosides by Rabbit Hepatocytes", J. Biol. Chem. (1982) 257:939-945.
Crooke et al., "Pharmacokinetic Properties of Several Novel Oligonucleotide Analogs in mice", J. Pharmacol. Exp. Ther. (1996) 277(2):923-937.
Crooke et al., "Pharmacological Properties of 2'-O-Methoxyethyl Modified Oligonucleotides" in Antisense a Drug Technology, Chapter 10, pp. 273-303, Crooke, S.T., ed., 2008.
Crooke et al. "Toxicologic Properties of 2-O-Methoxyethyl Chimeric Antisense Inhibitors in Animals and man", in Antisense a Drug Technology, Chapter 12, pp. 342-351, Crooke, S.T., ed., 2008.
Czech et al., "RNAi-based therapeutic strategies for metabolic disease", Nature Rev. Endocrin. (2011) 7:473-484.
Davidson et al., "Apolipoprotein B: mRNA Editing, Lipoprotein Assembly, and Presecretory Degradation", Annu. Rev. Nutr. (2000) 20:169-193.
Dellinger et al., "Solid-Phase Chemical Synthesis of Phosphonoacetate and Thiophosphonoacetate Oligodeoxynucleotides", J. Am. Chem. Soc. (2003) 125:940-950.
Duff et al., Intrabody Tissue-Specific Delivery of Antisense Conjugates in Animals: Ligand-Linker-Antisense Oligomer Conjugates:, Methods in Enzymology (1999) 313:297-321.
Dupouy et al., "Watson-Crick Base-Pairing Properties of Nucleic Acid Analogues with Stereocontrolled a and b Torsion Angles (a,b-D-CNAs)", Angew. Chem. Int. Ed. (2006) 45:3623-3627.
Elayadi et al., "Application of PNA and LNA oligomers to chemotherapy", Curr. Opin. Invens. Drugs (2001) 2:558-561.

(56) References Cited

OTHER PUBLICATIONS

Englisch et al., "Chemically Modified Oligonucleotides as Probes and Inhibitors", Agnew Chem. Int. Ed. Engl. (1991) 30:613-629.
Freier et al., "The ups and downs of nucleic acid duplex stability: structure-stability studies on chemically-modified DNA:RNA duplexes", Nucleic Acids Research (1997) 25(22):4429-4443.
Frieden et al., "Expanding the design horizon of antisense oligonucleotides with alph-L-LNA", Nucl. Acids Res. (2003) 31(21):6365-6372.
Geary et al., "Pharmacokinetic Properties of 2'-O-(2-Methoxyethyl)-Modified Oligonucleotide Analogs in Rats", J. Pharm. Exp. Ther. (2001) 296:890-897.
Toffman et al., "Brain-type' N-glycosylation of asialo-transferrin from human cerebrospinal fluid", FEBS Letters (1995) 359:164-168.
Horn et al., "Chemical synthesis and characterization of branched oligodeoxyribonucleotides (bDNA) for use as signal amplifiers in nucleic acid quantification assays", Nucl. Acids Res. (1997) 25:4842-4849.
Jayaprakash et al., "Non-Nucleoside Building Blocks for Copper-Assisted and Copper-Free Click Chemistry for the Efficient Synthesis of RNA Conjugates", Org. Lett. (2010) 12(23):5410-5413.
Jiang et al. "The Design and Synthesis of Highly Branched and Spherically Symmetric Fluorinated Oils and Amphiles", Tetrahedron (2007) 63(19):3982-3988.
Jin et al., "Use of alpha-N,N-bis[Carboxymethyl]lysine-Modified Peroxidase in Immunoassays", Anal. Biochem. (1995) 229:54-60.
Kanasty et al., "Delivery Materials for siRNA Therapeutics", Nature Materials (2013) 12:967-977.
Kassim et al., "Gene therapy for dyslipidemia: a review of gene replacement and gene inhibition strategies", Clinical Lipidology (2010) 5(6):793-809.
Kato et al., "N-acetylgalactosamine incorporation into a peptide containing consecutive threonine residues by UDP-N-acetyl-D-galactosaminide:polypeptide N-acetylgalactosaminyltransferases", Glyobiology (2001) 11:821-829.
Khorev et al., "Trivalent, Gal/GalNAc-containing ligands designed for the asialoglycoprotein receptor", Bioorg. Med. Chem. (2008) 16:5216-5231.
Kim et al., "Oligomeric Glycopeptidomimetics Bearing the Cancer Related TN-Antigen", Tet. Lett. (1997) 38(20):3487-3490.
Kim et al., "Synthesis of Novel Phosphoramidite Building Blocks from Pentaerythritol", Synlett (2003) 12:1838-1840.
Koller et al., "Mechanisms of single-stranded phosphorothioate modified antisense oligonucleotide accumulation in hepatocytes", Nucl. Acids Res. (2011) 39(11):4795-4807.
Kornilova et al., "Development of a fluorescence polarization binding assay for asialoglycoprotein receptor", Analytical Biochemistry (2012) 425:43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition", Tetrahedron (1998) 54:3607-3630.
Kroschwitz, "Polynucleotides", Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA", Bioorg. Med. Chem. Lett. (1998) 8:2219-2222.
Lazaris-Karatzas et al., "Malignant transformation by a eukaryotic initiation factor subunit that binds to mRNA 5' cap", Nature (1990) 345:544-547.
Lee et al., "Synthesis of some cluster glycosides suitable for attachment to proteins or solid matrices", Carbohydrate Res. (1978) 67:509-514.
Lee et al., "Facile Synthesis of a High-Affinity Ligand for Mammalian Hepatic Lectin Containing Three Terminal N-Acetylgalactosamine Residues", Bioconj. Chem. (1997) 8:762-765.
Lee et al., "New and more efficient multivalent glyco-ligands for asialoglycoprotein receptor of mammalian hepatocytes", Bioorg. Med. Chem. (2011) 19:2494-2500.
Lee et al., "Preparation of Cluster Glycosides of Nacetylgalactosamine That Have Subnanomolar Binding Constants Towards the Mammalian Hepatic Gal/GalNAc-specific Receptor", Glycoconjugate J. (1987) 4:317-328.
Lee et al., "Synthesis of Peptide-Based Trivalent Scaffold for Preparation of Cluster Glycosides", Methods in Enzymology (2003) 362:38-43.
Lee et al., "New synthetic cluster ligands for galactose/N-acetylgalactosamine-specific lectin of mammalian liver", Biochem. (1984) 23:4255-4261.
Lee et al., "Protein microarrays to study carbohydrate-recognition events", Bioorg. Med. Chem. Lett. (2006) 16(19):5132-5135.
Lee et al., "Synthesis of multivalent neoglyconjugates of MUC1 by the conjugation of carbohydrate-centered, triazole-linked glycoclusters to MUC1 peptides using click chemistry", J. Org. Chem. (2012) 77:7561-7571.
Lee et al., "Antisense Technology: An Emerging Platform for Cardiovascular Disease Therapeutics", J. Cardiovasc. Trans. Res. (2013) 6:969-980.
Letsinger et al., "Cholesterol-conjugated oligonucleotides: Synthesis, properties, and activity as inhibitors of replication of human immunodeficiency virus in cell culture", PNAS (1989) 86:6553-6556.
Leumann et al., "DNA Analogues: From Supramolecular Principles to Biological Properties", Bioorg. Med. Chem. (2002) 10:841-854.
Link, "Pharmacological regulation of hepatic glucose production", Curr. Opin. Investig. Drugs (2003) 4:421-429.
Maier et al., "Synthesis of Antisense Oligonucleotides Conjugates to a Multivalent Carbohydrate Cluster for Cellular Targeting", Bioconj. Chem. (2003) 14:18-29.
Maierhofer et al., "Probing multivalent carbohydrate-lectin interactions by an enzyme—linked lectic assay employing covalently immobilized carbohydrates", Bioorg. Med. Chem. (2007) 15:7661-7676.
Manoharan et al., "Chemical Modifications to Improve Uptake and Bioavailability of Antisense Oligonucleotides", Ann. N.Y. Acad. Sci. (1992) 660:306-309.
Manoharan et al., "Cholic Acid-Oligonucleotide Conjugates for Antisense Applications", Bioorg. Med. Chem. Lett. (1994) 4:1053-1060.
Manoharan et al., "Introduction of a Lipophilic Thioether Tether in the Minor Groove of Nucleic Acids for Antisense Applications", Bioorg. Med. Chem. Lett. (1993) 3(12):2765-2770.
Rajeev, "Conjugation Strategies for In Vitro siRNA Delivery", 8th Annual Meeting of the Oligonucleotide Therapeutics Society (2012) presentation.
Bock et al., "Glycosylation Reactions with Di-O-Acetyl-2, 6-Dibromo-2,6-Dideoxy-Alpha-D-Mannopyranosyl Bromide: A Simple Synthesis of Methyl 2,6-Dideoxy-Barabino-Hexopyranoside", Acta Chemica Scandinavica (1988) B42: 640-645.
Encio et al., "The Genomic Structure of the Human Glucocorticoid Receptor", J. Biol Chem (1991) 266(11):7182-7188.
Kerekatte et al., "The proto-oncogene/translation factor elF4E: a survey of its expression in breast carcinomas", Int J. Cancer (1995) 64:27-31.
Sakaki et al., "Human Transthyretin (Prealbumin) Gene and molecular Genetics of Familial Amyloidotic Polyneuropathy", Mol Biol Med. (1989) 6:161-168.
Zimmerman et al., "Carbohydrate conjugation to siRNA for liver-specific delivery", Hepatology (2010) 52(1): pp. 587A, Abstract 547, Retrieved from STN, Accession No. 0050381852 EMBASE [retrieved on Jun. 25, 2018].
Henry et al., "Drug Properties of second-generation antisense oligonucleotides: how do they measure up to their predecessors", Curr Opin Investig Drugs (2001) 2:1444-1449.
Swayze et al., "The Medicinal Chemistry of Oligonucleotides", Antisense Drug Technology: Principles, Strategies, and Applications, Chap. 6, 2nd Ed (2007) 143-182.

(56) References Cited

OTHER PUBLICATIONS

Bergeron et al., "Subtilase-like pro-protein convertases: from molecular specificity to therapeutic applications." J Mol Endocrinol. (2000) 24(1): 1-22.
Gensberg et al., "Subtilisin-related serine proteases in the mammalian constitutive secretory pathway." Semin Cell Dev Biol. (1998) 9(1): 11-17.
Giguere et al., "Functional Domains of the Human Glucocorticoid Receptor" Cell (1986) 46: 645-652.
Hansen et al., "Glucagon Receptor mRNA Distribution in Rat Tissues" Peptides (1995) 16(6): 1163-1166.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:2, 327-330.
Leren, "Mutations in the PCSK9 gene in Norwegian subjects with autosomal dominant hypercholesterolemia." Clin. Genet. (2004) 65(5): 419-422.
Neel et al., "Protein tyrosine phosphatases in signal transduction." Curr Opin Cell Biol. (1997) 9(2): 193-204.
Prakash et al., "Identification of metabolically stable 5'-phosphate analogs that support single-stranded siRNA activity" Nucleic Acids Res. (2015) 43:6, 2993-3011.
Rosenwald et al., "Upregulation of protein synthesis initiation factor elF-4E is an early event during colon carcinogenesis" Oncogene (1999) 18: 2507-2517.
Rosenwald et al., "Growth factor-independent expression of the gene encoding eukaryotic translation initiation factor 4E in transformed cell lines" Cancer Lett. (1995) 98: 77-82.
Shioji et al., "Genetic variants in PCSK9 affect the cholesterol level in Japanese." J. Hum. Genet. (2004) 49: 109-114.
Tachas et al., "A GH receptor antisense oligonmucleotide inhibits hepatic GH receptor expression, IGF-I production and body weight gain in normal mice," Journal of Endocrinology (2006) 189: 147-154.
Timms et al., "A mutation in PCSK9 causing autosomal-dominant hypercholesterolemia in a Utah pedigree." Hum. Genet. (2004) 114(4): 349-353.
Winkler et al., "Oligonucleotide conjugates for therapeutic applications" Ther Deliv. (2013) 4(7):791-809.
Machida et al., "Postmortem findings in a patient with cerebral amyloid angiopathy actively treated with corticosteroid" Amyloid (2012) 19:1, 47-49.
Tsimikas, S, et al., "Antisense therapy targeting apolipoprotein(a): a randomised, double-blind, placebo-controlled phase 1 study", Lancet, (2015) 388(10057):2239-2253.
International Search Report for Application PCT/US14/36463 dated Dec. 30, 2014.
Sehgal et al., "RNAi-Mediated Inhibition of Natural Anticoagulants for Treatment of Hemophilia" Alnylam (2012) 1 pg.
Manoharan et al., "Lipidic Nucleic Acids", Tet. Lett. (1995) 36(12):3651-3654.
Manoharan et al., "N-(2-Cyanoethoxycarbonyloxy)succinimide: A New Reagent for Protection of Amino Groups in Oligonucleotides", J. Org. Chem (1999) 64:6468-6472.
Manoharan et al., "Oligonucleotide Conjugates: Alteration of the Pharmacokinetic Properties of Antisense Agents", Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action", Antisense & Nucleic Acid Drug Development (2002) 12:103-128.
Marcaurelle et al., "Synthesis of Oxime-Linked Mucin Mimics Containing the Tumor-Related TN and Sialyl TN Antigens", Org. Lett. (2001) 3(23):3691-3694.
Merwin et al., "Targeted delivery of DNA using YEE(GalNAcAH)3, a synthetic glycopeptide ligand for the asialoglycoprotein receptor", Bioconjug. Chem. (1994) 5(6):612-620.
Mishra et al., "Improved leishmanicidal effect of phosphorotioate antisense oligonucleotides by LDL-mediated delivery", Biochim. Biophys. Acta. (1995) 1264:229-237.
Miura et al., "Fluorometric determination of total mRNA with oligo(dT) immobilized on microtiter plates", Clin. Chem. (1996) 42:1758-1764.
Oberhauser et al., "Effective incorporation of 2'-O-methyl-oligoribonucleotides into liposomes and enhanced cell association through modifications with thiocholesterol", Nucl. Acids. Res. (1992) 20(3):533-538.
Orum et al., "Locked nucleic acids: A promising molecular family for gene-function analysis and antisense drug development", Curr. Opinion Mol. Ther. (2001) 3:239-243.
Park et al., "The asialoglycoprotein receptor clears glycoconjugates terminating with sialic acid a2,6GalNAc", PNAS (2005) 102(47):17125-17129.
Pavia et al., "Synthetic TN glycopeptide related to human glycophorin AM. High-field proton and carbon-13 nuclear magnetic resonance study", Int. J. Pep. Protein Res (1982) 22:539-548.
Petrova et al., "Carrier-free cellular uptake and the gene-silencing actiity of the lipophilic siRNAs is strongly affected by the length of the linker between siRNA and lipophilic group", Nucl. Acids Res. (2012) 40(5):2330-2344.
Pujol et al., "A Sulfur Tripod Glycoconjugates that Releases a High-Affinity Copper Chelator in Hepatocytes", Angew. Chem. Int. Ed. (2012) 51:7445-7448.
Rajur et al., "Covalent Protein-Oligonucleotide Conjugates for Efficient Delivery of Antisense Molecules", Bioconj. Chem. (1997) 8:935-940.
Raouane et al., "Synthesis, Characterization, and in Vivo Delivery of siRNA-Squalene Nanoparticles Targeting Fusion Oncogene in Papillary Thyroid Carcinoma", J. Med. Chem. (2011) 54:4067-4076.
Rensen et al., "Design and Synthesis of Novel N-Acetylgalactosamine-Terminated Glycolipids for Targeting of Lipoproteins to the Hepatic Asialoglycoprotein Receptor", J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo", J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor", Arterioscler. Thromb. Vasc. Biol. (2006) 26:169-175.
Rossenberg et al., "Stable polyplexes based on arginine-containing oligopeptides for in vivo gene delivery", Gene Therapy (2004) 11:457-464.
Rouchaud et al., "A New and Efficient Synthesis of Derivatives of Octahydro-4H-pyrrolo[1,2-c]pyrido[1',2'-a]jimidazole", Eur. J. Org. Chem. (2011) 12:2346-2353.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering-Activity", J. Am. Chem. Soc. (2004) 126:14013-14022.
Seth et al., "Synthesis and biophysical characterization of R-6'-Me-alpha-L-LNA modified oligonucleotides", Bioorg. Med. Chem. (2011) 21(4):1122-1125.
Seth et al., "Synthesis and Biophysical Evaluation of 2',4'-Constrained 2'O-Methoxylethyl and 2',4'- Constrained 2'O-Ethyl Nucleic Acid Analogues", J. Org. Chem (2010) 75(5):1569-1581.
Seth et al., "Design, Synthesis and Evaluation of Constrained Methoxyethyl (cMOE) and Constrained Ehtyl (cEt) Nucleoside Analogs", Nucleic Acids Symposium Series (2008) 52(1):553-554.
Shchepinov et al., "Oligonucleotide dendrimers: synthesis and use as polylabelled DNA probes", Nucl. Acids Res. (1997) 25(22):4447-4454.
Shchepinov et al., "Oligonucleotide dendrimers: stable nano-structures" Nucl. Acids Res. (1999) 27(15):3035-3041.
Shea et al., "Synthesis, hybridization properties and antiviral activity of lipid-oligodeoxynucleotide conjugates", Nucl. Acids Res (1990) 18(13):3777-3783.

(56) References Cited

OTHER PUBLICATIONS

Singh et al., "LNA (locked nucleic acids): synthesis and high-affinity nucleic acid recognition", Chem. Commun. (1998) 455-456.
Singh et al., "Synthesis of 2'-amino-LNA: A novel conformationally restricted high-affinity oligonucleotide analogue with a handle", J. Org. Chem. (1998) 63:10035-10039.
Sliedregt et al., "Design and Synthesis of Novel Amphiphilic Dendritic Galactosides for Selective Targeting of Liposomes to the Hepatic Asialoglycoprotein Receptor", J. Med. Chem. (1999) 42:609-618.
Sofia et al., "Discovery of a beta-d-2'-deoxy-2'-alpha-fluoro-2'-beta-c-methyluridine Nucleotide Prodrug (PSA-7977) For the Treatment of Hepatitis C virus", J. Med. Chem. (2010) 53(19):7202-7218.
Srivastava et al., "Five- and Six-Membered Conformationally Locked 2',4'-Carbocyclic ribo-Thymidines: Synthesis, Structure, and Biochemical Studies", J. Am. Chem. Soc. (2007) 129(26):8362-8379.
Svinarchuk et al., "Inhibition of HIV proliferation in MT-4 cells by antisense oligonucleotide conjugated to lipophilic groups", Biochimie (1993) 75:49-54.
Tober et al., "Self-Metathesis of Polyol Allyl Ethers towards Carbohydrate-Based Oligohydroxy Derivatives", Eur. J. Org. Chem. (2013) 3:566-577.
Tomiya et al., "Liver-targeting of primaquine-(poly-c-glutamic acid) and its degradation in rat hepatocytes", Bioorg. Med. Chem. (2013) 21:5275-5281.
Toyokuni et al., "Synthetic vaccines: I. Synthesis of multivalent Tn antigen cluster-lysyllysine conjugates", Tet. Lett (1990) 31(19):2673-2676.
Valentijn et al., "Solid-phase Synthesis of Lysine-based Cluster Galactosides with High Affinity for the Asialoglycoprotein Receptor", Tetrahedron (1997) 53(2):759-770.
Van Rossenberg et al., "Stable polyplexes based on arginine-containing oligopeptides for in vivo gene delivery", Gene Ther. (2004) 11:457-464.
Wahlestedt et al., "Potent and nontoxic antisense oligonucleotide containing locked nucleic acids", Proc. Natl. Acad. Sci. USA (2000) 97:5633-5638.
Weber et al., "Design and synthesis of P2-P1'-linked macrocyclic human renin inhibitors", J. Med. Chem. (1991) 34(9):2692-2701.
Westerlind et al., "Ligands of the asialoglycoprotein receptor for targeted gene delivery, part 1: Synthesis of and binding studies with biotinylated cluster glycosides containing N-acetylgalactosamine", Glycoconjugate Journal (2004) 21:227-241.
Wu et al., "A New N-Acetylgalactosamine Containing Peptide as a Targeting Vehicle for Mammalian Hepatocytes Via Asialoglycoprotein Receptor Endocytosis", Curr. Drug Deliv. (2004) 1:119-127.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties", J. Org. Chem. (2009) 74:118-134.
Zhou et al., "Proteolytic processing in the secretory pathway", J. Biol. Chem. (1999) 274(30):20745-20748.
International Search Report for Application PCT/US12/52884 dated Nov. 20, 2012.
International Search Report for Application PCT/US14/36460 dated Oct. 10, 2014.
International Search Report for Application PCT/US14/36466 dated Dec. 1, 2014.
International Search Report for Application PCT/US14/36462 dated Dec. 23, 2014.
Graham, et al., Antisense inhibition of apolipoprotein(a) in cynomolgus monkeys significantly reduces plasma apolipoprotein(a) levels without affecting plasminogen or other major lipid classes, Circulation, 2012, Abstract A11050, 126(21).
Mney, et al., Antisense oligonucleotides targeting apolipoprotein(a) in people with raised lipoprotein(a): two randomised, double-blind, placebo-controlled, dose-ranging trials, Lancet, Nov. 5, 2016, 388(10057), 2239-2253.
Tsimikas, et al., Antisense therapy targeting apolipoprotein(a): a randomised, double-blind, placebo-controlled phase 1 study, Lancet, 2015, 2239-2253, 388(10057).

* cited by examiner

SEQUENCE LISTING

```
<160> NUMBER OF SEQ ID NOS: 167

<210> SEQ ID NO 1
<211> LENGTH: 6489
<212> TYPE: DNA
<213> ORGANISM: Homo sapiens

<400> SEQUENCE: 1

aggtaccttt ggggctggct ttctcaagga agcccagctc cctgtgattg agaatgaagt     60

gtgcaatcgc tatgactggg attgggacac actttctggg cactgctggc cagtcccaaa    120

atggaacata aggaagtggt tcttctactt cttttatttc tgaaatcagc agcacctgag    180

caaagccatg tggtccagga ttgctaccat ggtgatggac agagttatcg aggcacgtac    240

tccaccactg tcacaggaag gacctgccaa gcttggtcat ctatgacacc acatcaacat    300

aataggacca cagaaaacta cccaaatgct ggcttgatca tgaactactg caggaatcca    360
```

gatgctgtgg cagctcctta ttgttatacg agggatcccg gtgtcaggtg ggagtactgc 420
aacctgacgc aatgctcaga cgcagaaggg actgccgtcg cgcctccgac tgttaccccg 480
gttccaagcc tagaggctcc ttccgaacaa gcaccgactg agcaaaggcc tggggtgcag 540
gagtgctacc atggtaatgg acagagttat cgaggcacat actccaccac tgtcacagga 600
agaacctgcc aagcttggtc atctatgaca ccacactcgc atagtcggac cccagaatac 660
tacccaaatg ctggcttgat catgaactac tgcaggaatc cagatgctgt ggcagctcct 720
tattgttata cgagggatcc cggtgtcagg tgggagtact gcaacctgac gcaatgctca 780
gacgcagaag ggactgccgt cgcgcctccg actgttaccc cggttccaag cctagaggct 840
ccttccgaac aagcaccgac tgagcaaagg cctggggtgc aggagtgcta ccatggtaat 900
ggacagagtt atcgaggcac atactccacc actgtcacag gaagaacctg ccaagcttgg 960
tcatctatga caccacactc gcatagtcgg accccagaat actacccaaa tgctggcttg 1020
atcatgaact actgcaggaa tccagatgct gtggcagctc cttattgtta tacgagggat 1080
cccggtgtca ggtgggagta ctgcaacctg acgcaatgct cagacgcaga agggactgcc 1140
gtcgcgcctc cgactgttac cccggttcca agcctagagg ctccttccga acaagcaccg 1200
actgagcaga ggcctggggt gcaggagtgc taccacggta atggacagag ttatcgaggc 1260
acatactcca ccactgtcac tggaagaacc tgccaagctt ggtcatctat gacaccacac 1320
tcgcatagtc ggaccccaga atactaccca aatgctggct tgatcatgaa ctactgcagg 1380
aatccagatg ctgtggcagc tccttattgt tatacgaggg atcccggtgt caggtgggag 1440
tactgcaacc tgacgcaatg ctcagacgca gaagggactg ccgtcgcgcc tccgactgtt 1500
accccggttc caagcctaga ggctccttcc gaacaagcac cgactgagca aaggcctggg 1560
gtgcaggagt gctaccatgg taatggacag agttatcgag gcacatactc caccactgtc 1620
acaggaagaa cctgccaagc ttggtcatct atgacaccac actcgcatag tcggacccca 1680
gaatactacc caaatgctgg cttgatcatg aactactgca ggaatccaga tgctgtggca 1740
gctccttatt gttatacgag ggatcccggt gtcaggtggg agtactgcaa cctgacgcaa 1800
tgctcagacg cagaagggac tgccgtcgcg cctccgactg ttaccccggt tccaagccta 1860
gaggctcctt ccgaacaagc accgactgag caaaggcctg gggtgcagga gtgctaccat 1920
ggtaatggac agagttatcg aggcacatac tccaccactg tcacaggaag aacctgccaa 1980
gcttggtcat ctatgacacc acactcgcat agtcggaccc cagaatacta cccaaatgct 2040
ggcttgatca tgaactactg caggaatcca gatgctgtgg cagctcctta ttgttatacg 2100
agggatcccg gtgtcaggtg ggagtactgc aacctgacgc aatgctcaga cgcagaaggg 2160
actgccgtcg cgcctccgac tgttaccccg gttccaagcc tagaggctcc ttccgaacaa 2220
gcaccgactg agcaaaggcc tggggtgcag gagtgctacc atggtaatgg acagagttat 2280
cgaggcacat actccaccac tgtcacagga agaacctgcc aagcttggtc atctatgaca 2340
ccacactcgc atagtcggac cccagaatac tacccaaatg ctggcttgat catgaactac 2400
tgcaggaatc cagatgctgt ggcagctcct tattgttata cgagggatcc cggtgtcagg 2460
tgggagtact gcaacctgac gcaatgctca gacgcagaag ggactgccgt cgcgcctccg 2520
actgttaccc cggttccaag cctagaggct ccttccgaac aagcaccgac tgagcagagg 2580
cctggggtgc aggagtgcta ccacggtaat ggacagagtt atcgaggcac atactccacc 2640
actgtcactg gaagaacctg ccaagcttgg tcatctatga caccacactc gcatagtcgg 2700
accccagaat actacccaaa tgctggcttg atcatgaact actgcaggaa tccagatcct 2760
gtggcagccc cttattgtta tacgagggat cccagtgtca ggtgggagta ctgcaacctg 2820
acacaatgct cagacgcaga agggactgcc gtcgcgcctc caactattac cccgattcca 2880
agcctagagg ctccttctga acaagcacca actgagcaaa ggcctggggt gcaggagtgc 2940
taccacggaa atggacagag ttatcaaggc acatacttca ttactgtcac aggaagaacc 3000
tgccaagctt ggtcatctat gacaccacac tcgcatagtc ggaccccagc atactaccca 3060
aatgctggct tgatcaagaa ctactgccga aatccagatc ctgtggcagc cccttggtgt 3120
tatacaacag atcccagtgt caggtgggag tactgcaacc tgacacgatg ctcagatgca 3180
gaatggactg ccttcgtccc tccgaatgtt attctggctc caagcctaga ggcttttttt 3240
gaacaagcac tgactgagga aacccccggg gtacaggact gctactacca ttatggacag 3300
agttaccgag gcacatactc caccactgtc acaggaagaa cttgccaagc ttggtcatct 3360
atgacaccac accagcatag tcggacccca gaaaactacc caaatgctgg cctgaccagg 3420
aactactgca ggaatccaga tgctgagatt cgcccttggt gttacaccat ggatcccagt 3480
gtcaggtggg agtactgcaa cctgacacaa tgcctggtga cagaatcaag tgtccttgca 3540
actctcacgg tggtcccaga tccaagcaca gaggcttctt ctgaagaagc accaacggag 3600
caaagccccg gggtccagga ttgctaccat ggtgatggac agagttatcg aggctcattc 3660
tctaccactg tcacaggaag gacatgtcag tcttggtcct ctatgacacc acactggcat 3720
cagaggacaa cagaatatta tccaaatggt ggcctgacca ggaactactg caggaatcca 3780
gatgctgaga ttagtccttg gtgttatacc atggatccca atgtcagatg ggagtactgc 3840
aacctgacac aatgtccagt gacagaatca agtgtccttg cgacgtccac ggctgtttct 3900
gaacaagcac caacggagca aagccccaca gtccaggact gctaccatgg tgatggacag 3960
agttatcgag gctcattctc caccactgtt acaggaagga catgtcagtc ttggtcctct 4020
atgacaccac actggcatca gagaaccaca gaatactacc caaatggtgg cctgaccagg 4080
aactactgca ggaatccaga tgctgagatt cgcccttggt gttataccat ggatcccagt 4140
gtcagatggg agtactgcaa cctgacgcaa tgtccagtga tggaatcaac tctcctcaca 4200
actcccacgg tggtcccagt tccaagcaca gagcttcctt ctgaagaagc accaactgaa 4260
aacagcactg gggtccagga ctgctaccga ggtgatggac agagttatcg aggcacactc 4320
tccaccacta tcacaggaag aacatgtcag tcttggtcgt ctatgacacc acattggcat 4380
cggaggatcc cattatacta tccaaatgct ggcctgacca ggaactactg caggaatcca 4440
gatgctgaga ttcgcccttg gtgttacacc atggatccca gtgtcaggtg ggagtactgc 4500
aacctgacac gatgtccagt gacagaatcg agtgtcctca caactcccac agtggccccg 4560
gttccaagca cagaggctcc ttctgaacaa gcaccacctg agaaaagccc tgtggtccag 4620
gattgctacc atggtgatgg acggagttat cgaggcatat cctccaccac tgtcacagga 4680
aggacctgtc aatcttggtc atctatgata ccacactggc atcagaggac cccagaaaac 4740
tacccaaatg ctggcctgac cgagaactac tgcaggaatc cagattctgg gaaacaaccc 4800
tggtgttaca caaccgatcc gtgtgtgagg tgggagtact gcaatctgac acaatgctca 4860
gaaacagaat caggtgtcct agagactccc actgttgttc cagttccaag catggaggct 4920
cattctgaag cagcaccaac tgagcaaacc cctgtggtcc ggcagtgcta ccatggtaat 4980
ggccagagtt atcgaggcac attctccacc actgtcacag gaaggacatg tcaatcttgg 5040
tcatccatga caccacaccg gcatcagagg accccagaaa actacccaaa tgatggcctg 5100

-continued acaatgaact actgcaggaa tccagatgcc gatacaggcc cttggtgttt taccatggac 5160
cccagcatca ggtgggagta ctgcaacctg acgcgatgct cagacacaga agggactgtg 5220
gtcgctcctc cgactgtcat ccaggttcca agcctagggc ctccttctga acaagactgt 5280
atgtttggga atgggaaagg ataccggggc aagaaggcaa ccactgttac tgggacgcca 5340
tgccaggaat gggctgccca ggagccccat agacacagca cgttcattcc agggacaaat 5400
aaatgggcag gtctggaaaa aaattactgc cgtaaccctg atggtgacat caatggtccc 5460
tggtgctaca caatgaatcc aagaaaactt tttgactact gtgatatccc tctctgtgca 5520
tcctcttcat ttgattgtgg gaagcctcaa gtggagccga agaaatgtcc tggaagcatt 5580
gtaggggggt gtgtggccca cccacattcc tggccctggc aagtcagtct cagaacaagg 5640
tttggaaagc acttctgtgg aggcacctta atatccccag agtgggtgct gactgctgct 5700
cactgcttga agaagtcctc aaggccttca tcctacaagg tcatcctggg tgcacaccaa 5760
gaagtgaacc tcgaatctca tgttcaggaa atagaagtgt ctaggctgtt cttggagccc 5820
acacaagcag atattgcctt gctaaagcta agcaggcctg ccgtcatcac tgacaaagta 5880
atgccagctt gtctgccatc cccagactac atggtcaccg ccaggactga atgttacatc 5940
actggctggg gagaaaccca aggtaccttt gggactggcc ttctcaagga agcccagctc 6000
cttgttattg agaatgaagt gtgcaatcac tataagtata tttgtgctga gcatttggcc 6060
agaggcactg acagttgcca gggtgacagt ggagggcctc tggtttgctt cgagaaggac 6120
aaatacattt tacaaggagt cacttcttgg ggtcttggct gtgcacgccc caataagcct 6180
ggtgtctatg ctcgtgtttc aaggtttgtt acttggattg agggaatgat gagaaataat 6240
taattggacg ggagacagag tgaagcatca acctacttag aagctgaaac gtgggtaagg 6300
atttagcatg ctggaaataa tagacagcaa tcaaacgaag acactgttcc cagctaccag 6360
ctatgccaaa ccttggcatt tttggtattt ttgtgtataa gcttttaagg tctgactgac 6420
aaattctgta ttaaggtgtc atagctatga catttgttaa aaataaactc tgcacttatt 6480
ttgatttga 6489

<210> SEQ ID NO 2
<211> LENGTH: 150001
<212> TYPE: DNA
<213> ORGANISM: Homo sapiens

<400> SEQUENCE: 2
atctttcagc ctctatatta ttttattgtg atttttaatt tccttgaatt ggattttgcc 60
attgtgctaa atcttgatga tcttcatttg tatccgtagt ctgaattata tttctgtcat 120
ttgagttagc tcagtcttgt taagaaccct tgttggaaaa ctggtgcagt tgtttggagg 180
acatatgacc ttctggccat ttgatttatt ggagttctta cgttggttct ttctcatgtc 240
tctgtgtggg tgtttcttta actgcagtgt agattgagta cagccaatag acttcttctt 300
tggaggtttt cacagggcca aggccttgta cagggtcttt atttgtagct gacttcttgt 360
ctttggtttc atagtggggc atgttagcaa aatagttttg ctgttgaagt tttggggtgt 420
gatccatttt ttattttaat gattgtgtat ttcctttata cctaaaacaa gcagaaaacc 480
agtaaaggtc tttgagtctc tgaattcata actccagcat tcatattgct tcctcaggta 540
agtggggttt tcacccagcc cttaagggtg ttagattatt ttttatgtga aattagccag 600
attgtatttc taaacatgat gtaaaacaat aatgacaaaa gttataataa actagccttc 660
ttaccaaatc cacatgtcta atgtgtgtgg gagggtgtta ggcaggggac ctgcagctaa 720

```
gggagaggca gacaggcccc atggccccaa atctaggata gtatttggta ttggttgatg    780
ggtgagagaa agagagggaa catctgtgca ggatgtggta tcagcacctg gactacatct    840
tagggattcc ttcttcattt ttcagtatgc cctgacaata attatatcta tcagacttac    900
ccccttgacc actggaacac taagactgtt ttgggatctc tgcctgactt tctcagaggt    960
gctggtgagg acattatgag tctggaacct agaaaagcgt tctgactctg ctgactttct   1020
cagaggtgct ggtgaggaca ttatgagtct ggagccctag aaaagcgttc tgactctgcc   1080
actagccaga cagacctgga ctaggcacgt taactctttg tatgacttga ctccaacccc   1140
tcatttgtaa aaccagcatt ttcaagtggt gttttccaca tcagcctttt gcataagctg   1200
tcatttgaag aaaggttttt gtttgtttgt tttttgttta acaaaaaggt taaaaaccac   1260
tggtctagat aattgcaaag tttgctttcc tttttctgtg ctttttctac tatttttaaa   1320
atgtcatcct ccttggtttc ttgatccccc tttctgcact cctgagtctg ggaacactga   1380
ggccaactaa aaggaaactt ggcaaaagag gaacaccttt gggtgtgcca ggctgctccc   1440
agtgttttgc acttataaaa atttaaatgc tgcaaacctc taagacttag atattattgt   1500
tcctatttta caagtgagga acctgaggct cagagaaggt gcaggatggc acagggagac   1560
ctgaattgga accctggttc ccacttactg gctgtcggga cttagaaaag tcatgaactc   1620
tcattgattg ttttcttata tgaaatgggg gctgcagggt tgtcggggga gaaacaataa   1680
gaatgtgcat caagtgtcga gcacgtgcta cgcactccat catggcagct cctactaata   1740
tacagaatag agttgtatct aacatgactc tttcttgcaa gtgacagaaa atccaactta   1800
agatggatta agcaaaaaag gggaattctt gttgagctga aaagtcttta ggctcacatg   1860
atggccccag ggcccaggcc ctgtccagcc atgcagtagg catcatcctt gggcacaaag   1920
gtgagattct tgtggtggca gatgctgtgg cagctcttgc tttgccagga aagactgagg   1980
aaggccactg tccccattaa gtgaacaata gttggccagg tctgagaggt tgaacttggg   2040
tcacaggcct gtccctgaac ccatcactga ttggctccaa cctgcatcag ctattacatg   2100
ctagaggtgg aggcaggacc ccactcatac ccagaagggc aaagggtgga tccctcaaca   2160
ggattatggg atgtagggtg atagactgct gggcagccag aaagcaaaca gatcctctcc   2220
aatacctcaa ctgatgaaag caccaagcta aaatcataag gatctgggtg tgaattctgg   2280
ctctaccatc ttccatgtga cattgggcag ttatttaatc tcttttagcc ttggctttct   2340
tacctgtact aacatataag gtgattgtga tgagcatcat catcgtcaac atcatcatca   2400
ccatccacat tgccaccacc actcccatta tcatcttcat caacatcatc accaccgcca   2460
ccatcaccat tatcattacc accaccgcta tcactattat catcaccctc aacatcatca   2520
ccatcatcac tatcatcacc accaccatca tcgttactac cactaccacc accatcatca   2580
ccacagccac caccaccatc accatcatta ctactcagca ccaccatcat cattccacca   2640
ccatcaccat cattccacca tcaccattat cattaccacc accactgtca ctattatcat   2700
caccctcaac atcatcacca ccaccatcat cattactacc accaccacca ccatcaccat   2760
catcatcatt ctaccaccat caccattatc atcaccatca ccatcaccac cgctatcatc   2820
atgataatca ttatcattac caccaccatt agcattatca ttaccaccac catcactatc   2880
actatcacca tcaccacgac cactaccacc atcaccaaca ccatcattac tacccaccac   2940
caccatcatc atcattccac caccatcaca attattacca ccaccaccat caccaccacc   3000
accaccatca ctatcatcat cagtagacat catataacca gtttgtagct ggcccagagc   3060
```

-continued

```
ctacttgctg tttcttctgc cccacaacca tccacacatt tctaaccacc atcccccact   3120
aggcttctgc ctcgcctggt ctcacctgca ggtccactga gaaaatgatt ctcagaacac   3180
taactagacc atgaggtgcc acaaaacata actcaggcct gttcatcaat tttctacatg   3240
tcaataatga catcaggtca attggcgttc tcagcctctg agagggaggt caaagttttc   3300
ctgctctccc cttcatgttt ccaggtgttc cctgacttgg atcaaatgca gagtttggag   3360
gtgttgaggc caaggggatt ttccaggtca gtcgtcatcc acaatcaatg gactgatcct   3420
gccgctggac ttaccctgct gccctctccc caaggcccca tcagggaggg cttcaatcct   3480
cttgtcacct gtggcctacc tgccctcaga gatgacatct ctatgtcggc cactggatgg   3540
cagcacctac tcgcagacca catcaacttt cctggcaact tgcggtaggt tttcaccatt   3600
atcaggatgt ttgccttgct caaatagcag attctagaga acggtgctcc ctcacacaac   3660
tatgtagtcc aggtgatgca ccctctgccc gatgcttggt agtcagaaac ttccatcatg   3720
cagctctgcc cagattgagc tgagctggcc tctggagtga ggtgctggga caaacatctt   3780
ccatgctgct catgtcaact ccagatgcag tcaggtttct gaaccaaagt caatgatcta   3840
agtgcagtca aaggctctgg gggaagaaag agagagtgcc tcatctcttg cctgtgccat   3900
gctcgcaaag caaggatttt tgcaaaattc taatgaaagc tgggcttgca aaattagaaa   3960
actggattat ttgtgagaac actgaaacat ccctgggtgt gtccatctgg aaaaacagca   4020
tttcctctgg caattttgca accgttctat ttgaatttgg caaagaaaat aaagcagttt   4080
ttcacaaaag aataaacaca accaggagaa tcttcactct cccaaattgt caaagaagta   4140
taaattagaa aatgaatcag gacaatttca acctgttaga ttagctaata tttaaaaatt   4200
gaacactcat acaagtgtgg tgaagtgatt gttttctagt gacattttac actgtcataa   4260
ccttctagaa aataaattgg cagtgttatt gggagacaga aatatgtcta tataatttat   4320
gggaacttag gctcagaaaa tattaaggaa taagaatgaa ctttatgaac aaagatgtgg   4380
agggttggaa gcaagagggg ggccaacgcg cacggggagg aagcatttgg gcagtgactc   4440
cgcagaccca ggctcaggtt gaactagaca acctccttac acctcagttt ccttaactgt   4500
agagcaggag tgatggaact gcctgtttca taggactgtt gtgaggatga agtgagatac   4560
accacattat aagcttgtgc ctggaaagga taatgcttag taaatgatga ctattctttt   4620
ttattgcaat aaaatgtaca cagcgtaaga gttactattt taaccatttt tgcagggtac   4680
caccaagtgg catttagtac attcacagtg gtgtgcaacc atcatcatat ttccagaata   4740
ttttcctcat ccccaaagga aacctcatgc tcattaatca gtagctctcc tttaaaatat   4800
tagttatgaa gatcatagca ctatacaaaa ctcattatgt aatgttgagt gaaaaaatca   4860
gggtgtgaaa ttttgtgata tgatgtaatt agtgaaagaa gcatacaaaa agtctgaaaa   4920
tataaaaaca atagcaattg catttctcag actctacatt taaacattat tctttatggt   4980
tttaaaagca aagaaaaagg taaagaaaca acaaccaacc gcaaagcacc atgacaaagc   5040
tcagattgtt aaatccaggt ttttggaaca tagactctta tatgacgttt acactctcca   5100
gggttcagag agtctggcag cattgggagc tgccttgtgt tctacagcct cacggacaga   5160
caggaggtcc atcaccactg ctctgttctt ctggagtttc cttgtgaaca tgttgtggac   5220
gtagttacca tttctttcat ctttttaaac acaggtacct ttggggctgg ctttctcaag   5280
gaagcccagc tccctgtgat tgagaatgaa gtgtgcaatc gctatgagtt tctgaatgga   5340
agagtcaaat ccactgagct ctgtgctggg catttggctg gaggcattga cagttgcaag   5400
gtaagaaaag atcaagagac caaagttagt cttgtgctct cctgtctcag tctcagtccc   5460
```

```
ttagacttga gtcccaaagt agcgaattca agtaggattt aatcaatgga agaccccagt   5520
ctaagtgttg ctcagaaact ccctagatct gtcccaaatg tatattcaga tcatccaagg   5580
ggacttcttg ggcttgagt tccagatcag cagcaaggga gccataagtg ccataactac   5640
ctcagaccac tcaccctcct ggggtgtccc ggtggccagg gactaaagtg gtgatttttc   5700
tggtagggaa ggaggtagag ggtacaggac agagactaac tgcacacaat atctgagact   5760
ggagctcaga tattgctgat gatcagagtt ggcgtgtctc cccaattgat ttacaactgg   5820
ggcttggata ctgttttaaa cgggaggagc ctcctaacca tcttgacaca accactgacg   5880
tgactacact agagatagac tctttccact taattctacc actcttgctt tacttcatga   5940
gaacgaaaat gtaagattgc accatgaatt catttgcgga aagattgata ctatgctttt   6000
attttatttt attttatttt attttatttt attttatttt attgagactc tcaccccggt   6060
tgaagtgcac tgacgtgatt ttggctcact gcaacttcca cctcctgggt tcaagtgaat   6120
actccagcct ccctagtagc tgggattaca ggtgcccacc accacgcctg gctaattttt   6180
gtatttttag tagagatggg gtttcaccac attggcctgg ctggtctcaa actcctgacc   6240
ttgtgatcca cctgtcttgg cctcccaaag tgctgggatt acagagttga gccaccgcac   6300
tcgaccctat gttttatttt taaaaatatt tatttattta tttaagccac aactactaga   6360
ataggaagga ttgatatttt attaatttta tttggtattt attatttttt tttctttcct   6420
gagacattct tgctctgtca cccaggctgg agtgcagtgg cacattcttg gctcactgca   6480
acctccatct cctgtgttca agcaattcta gtgcctcagc ctacttagta gctgggatga   6540
ctggcatgtg cctccacacc cagctaattt ttgtattttt tgtagagaca gggttttggc   6600
atgttgccca ggcttgtctc aaactcctgg cctcaggtga tccatctgcc gtggcctccc   6660
aaaatgctgg gattataggc atgagccacc accccctcct ggaaggattg atatcttata   6720
acataattta taattacaga aaacatgtga gttcactagg aataaataaa ttttgaagat   6780
aataaaagat tttcacttat gttgtcattt cggcacagtt tggtatagga tgtggagatg   6840
ttaacattta tacctagctt gctcgtaaac taagacctga aagggttgtg tctatcagct   6900
gcacccctgg gtagcgacac aacctcggga aggcctcagc cccctcctcg tacagcactg   6960
cctgttggaa agcttgaggg aggctatgga tgtgcagcac ttggcagagg gtctggtcat   7020
ggaagttacc agcaaatatg agctactttt atgattttat tttatccaaa agaaagagaa   7080
tgaaagaaga ggggaggaaa caagactaat caggaaagat gaaggtctag gggtgaggga   7140
aggagtaagg agacataaag gcaatgtgga gcagctgagg ggggaaatgg ctttcaccac   7200
ttcccagcat ctattgacat tgcactctca aatattttat aagactctat attcaaggta   7260
atgtttgaac cctgctgagc cagtggcatg ggtctctgag agaatcatta acttaatttg   7320
actatctggt ttgtgggtgc gtttactctc atgtaagtca acaatgtcct gggattggga   7380
cacactttct gggcactgct ggccagtccc aaaatggaac ataaggaagt ggttcttcta   7440
cttcttttat ttctgaaatc aggtaagaca tagttttttt aaattataag aattattttt   7500
tctcccacaa tgtagtaaaa atacatatgc catggcttta tgtgcaattc atttaatttt   7560
tgattcatga aattcccagt tcaaaatctt gtatatgatt gaaaaattct taaaaaaata   7620
agtttaattt ccccgtgaag actgtcacgg tgctggaatg aatgggcaga aaaaataatg   7680
gttgattttt ctaatctaaa agagtgtgcc tacatgatgg ccagtctggc tgaaaaataa   7740
atagccattg tagctaacta tgcaaaggat ggctaagctc ttcgcttggt tctcagtttc   7800
```

-continued

```
attaatttat atcatctctg ttcaggtgcc atgctcccct cactagcaag ttgaaacaat   7860
gaaataactc tttgaatatg tttggttcct tgacctgttc atggagtggg actcagcatt   7920
tctctctttg ttatggcctg agtaaggctt tccatcggta tacatttgct tcttatccct   7980
ggagaaatta tacacatcca tttgccagat gatatacgca tataatgatt caacaaatac   8040
tcagggtatt tgttgagtgg gttaggtccc cacattttta tacatacata cacacataca   8100
caccgtgtgt gattgtgaat gtaagtgtgt gtcctttaca aatactagct tatttagctc   8160
atggtatagg tagggtagca tagtcatccc cattttataa acaaagaaat ctagacttag   8220
gaaaatcatg ttatttgtct cgtgaccaaa ttcccaaatc aaggaaataa agaaacctgg   8280
atttaagcca gatttccaag aaaaaatcta gggctcttct cactttttca tctttgttcc   8340
aacatttgaa aaaataaatc taaacacatt ccaatgtaac tgaagagcag gttaattgtt   8400
tgccacttgc agaatccaat taagaagaga gaagtctggt ataaagaaag tgatttgctt   8460
ccaaagctag cttaggggaa gaaatgcagc agtcctgccg tactacttca ctttaggagc   8520
agaaagtggc acttttaaaa ggcaacagag gaggcgagca aggattcagg ggtccatgct   8580
agcttgggca ccttatccac caggtagttg agcagttgcc tgctggtgcc tttgtgagca   8640
gggtgttgtc ccttgaggca aatctctgga gggtgagagt tttgtagtgg gcatgctttg   8700
gtttataaat cacctgtgaa ctcaggagtt ccatcttgaa gcacatacat agttagatga   8760
acttgccctg cagggagagt ctgatgaaag ggaggtagat gcttgcaatt taatctataa   8820
attaccagat aaaattttac aagttgactt taaagtcaaa cacatttgaa tttagtggaa   8880
gccattcaag aaaatatcaa agaaaataca gagcaggaga agattaagca aagagttttt   8940
tggggaaatt ggtgtctatg tctgtgtgtg tagggagtgc aggggatatg aatattctat   9000
ttcagcccat ggaaactagg atgtagatca ctgtgaactt attcagcagg ctacacccaa   9060
aggctagaac aaacttctct gccacaggat taacatatgt tttaatcgac ctggggggca   9120
cattctctga taagctcttt tggaaagcca ggctttctgt ggacgtgtta tctttccaat   9180
gtgtgctgga atgcccgggg agaggaaaaa gtttctttta cagccatgct cagtgagaag   9240
cggagaaaca tcttctattc acaaattgct aagtctttta cacatgcaaa tatgcataca   9300
cattcacaca ccacagtgag gaagaaattc tcacaccatt aataaaatac atttacttca   9360
gtagcaatat acatctacat tttgcctata atataaaagt atttttccta ttaaaagatt   9420
tgtttaatgt ttcttcacca acaaataaac cctattaaat ccccattgcc atatgagccc   9480
tggaggtgaa tcagagaaac aaaaggattg tggaaaaatc atcaggttaa aaaaagaaaa   9540
attgattctg ttttgggata tttcctagca acatgagctg gggaggggat ctcagcagtg   9600
atgctctatg aagcataata aaatgacaca gttacaggta acttagttaa agggggaaat   9660
aaatggaagt ttcctctttt tgaatatcaa ttgtagcctg ctctgctaca tttcaaaaac   9720
actcttcaaa atgtttaact gaactcactg taggaagcac cttattaatt tattgtgtgt   9780
tttgaagtca cactgtgagc tatagaattt acccaagcac aactcttcct ggaaaagaga   9840
gttcaaatga gaaacagtgc ggggtgaaga catggatatg ggcctaaaat atctatttct   9900
caatgatatt ttgatatatc tatcaagtgc tttttagtgg attaggttca gaatgcatca   9960
gccaatgcct gttcaataat ccagttttcc agcatagagc atattaaatt gaggaaggac  10020
aaagtcacag aggtggggag caggtggact gtggccaagg actttgcatg aaacagtgag  10080
cgtgcatcct cctccttgcc ctgccctcat ggtctgtgta ctctcaggag gtcaggacag  10140
gcctttctga gaatgagaat ctgttcatct gcctttctac tggatacttg tcatcggcat  10200
```

acaaacacat gttctctgca gtgtgtcatc tttcagaacc tcccctgacc ctgtattccc 10260
tagaagtctc gctgctttca gagccaggct tctctcctgc tgccaccccc actgctcttc 10320
tagtcactct ttaacccact ccatctgcat gtggccccca ccacacccct caaagtggtc 10380
aaggttgtcc tgttgcttaa ttccatggaa gcttggctat cttcatttta ttagcctctt 10440
ttggcctctc accctgtgaa aatcactaca ttttgtgcca gagatggagc tggcatctcc 10500
aggcttggaa gagggctgct gaagctcagc caggtgtcct aaggagcctc aggacagggg 10560
atgctcagta gccttgcaat gggaacacag ctgagcccca cttggccacc ctttgccaca 10620
accaggcaga aagcagcttt tgaacagatt tgttgcctca gatttgatct caaagaaaaa 10680
tcgtgggcag tattggtccc aggttctgct tttttacaat ttcctctgaa atctggatgc 10740
ctatcaacac cttggaaaaa ctgaattctc cccaactaat agtggtgtgt cactgtagta 10800
agcctagtac aaaaatggcc ttctttgtgg aggagcttca tatcctccat tttttttttg 10860
cttaattttt gcccaagatg agaacataat ttagttcact ttttatttat tcccaacatc 10920
atccatgcac caacattttt gtaactaaag gagggaccat tcagaagatg cttatcaact 10980
gtcaaagtga cagtgttaca accaatgcac atattgtaag aaatcaaaca atggcctcca 11040
aggttcattt ctacacaggg attagcagat caacatcaat cttggcaaca cagttgccac 11100
tgatggtgtc ttattttttt tatcatgaca tggcaatcaa gagcaaacat gatttattct 11160
tatttaagat tttatggtta gactaggcag atagctagat atgagcagga ggtggaagcc 11220
cctgagagaa tggaggtctg gagaatctga aaccccagag attacccaag tcctgcatgc 11280
tagacatgag tggaggaggg ggaataccta ggtagaaaag aatgcccctt aagatgccca 11340
gcagtcgctc actgtgcagt taacttttca gaatgctgct agatacatgc tgatagggag 11400
ggaagagggc aaaggagaaa ttcctaagag atacacggtt gcagttagta tacatctgag 11460
tgctatacaa ccttctttgg gtggtggcaa gaagcaatgc agccattacg tagaattcat 11520
atcaaacacc tgtatcacag gtgttaaaga aacaagaaac attgtacttc ttgtattctt 11580
aataatgatt tgcaatattg tctttagtat cactgcaaac ctctataaat atgattttta 11640
aaaagtattt ctttaggttg gaattacttc tacgcattga cttatcttcc tgggtttcat 11700
tagccgtacc cgttgtactt tcttccttac cactgtttat ctcaaactct tgagattaaa 11760
gtatgggctc aggagggagc gaggagcttc aggactctca cggacctcca gcacagtgta 11820
gctgccttat ggaaaagtgg ccacactgtt ttctgcactg gtccctgccc ctactattcc 11880
tcactgggca gagcacagcc accctggccc tgcctgaaca ttttagtcag tgttggctct 11940
gtgcttctct ggggaggaaa tccaagagac aacccacagc ccctctgcca tttcagctgc 12000
agcagtacca ccgttaatgc ccttgggctt gagaaagaag ggacctggcc acttccctga 12060
cacctccagc acacagcagg gaaagaattc cagtttctct ttcttgtgag ctttcacctg 12120
ctactcttca ccaggcaagg ctcctggctt gggcccacag tgcaggcacc tcgaactcag 12180
ttgaacattt ccactggctg cactctgtgt ttttgtgggg tgaagctccc agaggtgact 12240
gaaagtcctt ctgccactaa cactgcagtc atactgccct tgctgtactt ggactaggga 12300
aggaaaaaag atcctgagtg ctttactcac accccagtgt gccccagcca ccctatggaa 12360
aagaggccag tgtgtcatcc ctgcaagcac cctgaggccc ctgcccctgc tgcccccaag 12420
ctgtagagcc agaatataaa gctggcagaa aaatgtaaaa aggctagact ggcttagcct 12480
cccagcctac atctttctcc tgtgctggat ccttcctgct cttgaacatc ggactccaag 12540

-continued

```
ttcttcagct gtgggacttg gactgtcttc cttgctcctc agattgcagg tggcctatta  12600
tgggaccttg taatcttgtg agttaatacc acttaataag ctcccctttg tgtgagtata  12660
tctatatcta tagatagata taggtatact cactatatat acacatatat acatatactc  12720
tctctctctc tctctcatat atatatatat ataatctcct attagttctg tccctctaga  12780
gaaccccgac taatacagat tttcatacca gaagtggttc ttgaggaaca gaatattaag  12840
gatggaattc tttcattggt tttgggactt ctggtgttgg ctgattaata tgattagacc  12900
aaaaaatgct aaggactcta cttctaatag tatggagaac actgatagta cttggcctga  12960
attgtttaga gagttatgca aaataaatgc atttgacact actgattcat cacttatgag  13020
aggcaaggag tttagtgact ctatacataa tacctttgac tatatgtgga gaaccaagga  13080
acataatgaa gttggttgat tgctcctaag ttctctggag aaagagatga aagaaaatga  13140
tgatctcagg ggatctgtct cccaccttca gaagcagata ctgagccaca aatctgctaa  13200
gattgccctg aatgagagtt ttaactcctg tagagaaaga gttgaaattg tgaaaaaaca  13260
gagacaagct gttatcatgc gagtagctga tctgcaacaa gaggtgcatg cacagccttg  13320
ccaggtgttt actgttaaag tgagggcatt gactggaaaa aaatgggacc ctggaacttg  13380
gagtggggat gtgtgggaga accctgatga agctgaggac actgagtttg tgaactctga  13440
tgaaactttt ttgccagaag aaacagtttc cccatcccca gtagtggtaa catcccctcc  13500
ctgacccgtg ctgccattag cctttccacc tttgtctgag gatgtaaacc ctgcactgct  13560
tgaggcaaca gtgatggcct tccctgaggc agctgccagg caagataatg ttgattctcc  13620
tcaagaggca cccctaatgc ccctgaatgc ttctagacct ataactaggc taaattcctt  13680
gcgggcccca gaggtgaggt tcagagtgtg acccatgagg aggtgcatta tactctaaaa  13740
gaactgctta agctttctaa tttatattgg cagaaatctg gagaacaggc atgggaatgg  13800
atattaaggg taagggataa tggtggaagg gacatagagt tggatcaagc tgaatttatt  13860
ggtttggccc tactaagtag ggattctgca tttaatgttg cagctcgggg acttagaaaa  13920
ggttctgata gggccgggag cagtggctca cgcctgtaat cccagcacct tgggaggcgg  13980
gggcgggcag atcacgagat caggagattg agacaattct ggctaaaatg gtgaaacccc  14040
atctctgcta aaaatacaaa aattagctgg gcatggtgat gcgtaactgt aatctcatct  14100
acttgggagg ctgaggcaag agaactgctt gaacctgtga ggcagagatt gcagtgagcc  14160
aagatcgccc cactgcattc cagcctggta acagagcaag actccatttc caaaaaaaaa  14220
aaaaaaaaag ttataatagt ttatttgctt ggttagctga aatatggatt aaaagatggt  14280
ccaatgttag tgagctggaa atgccttggt ttaatgtaga ggaagtgatc caaaggctta  14340
gggagattag gatggtggag tggattagtc actttagacc tactcatccc agctgggagg  14400
gtccagaaga tacacccttg gccgaagctt tgtgaaatag atttgtgaga gcagcacctg  14460
tatttttgaa gagcccgtaa ttgctcttct ctgtatgtca gatctaacag taggaaccac  14520
agtcactcaa ctacaaaatt taaatacaat gggaataatt ggatcctgag gtggcagggg  14580
ccaagtgttg gcactgaacc atcaaaggca aggtgggcat aactaccata atagacagca  14640
gaggcaaagc agccatcaga atagtctgac tcatgtagag ctctggcatt ggctaattaa  14700
tcatggtgtt cctagaagtg aaattgatgg gaaacctact gtattcctac ttgatttata  14760
taaacaaaaa actgccaggt agaatggact aaagactaat ctgaattata aaaacagaga  14820
atcatgggcc ctcaatcaat ttccagactc gaacctgtta cagttccaga acccactgaa  14880
tgaaggggag gctggatccc cttgaggaag gacaccacta ggctactgac aacttatgct  14940
```

```
gttactcttt ctcccatcct tccctaagga gacctctggc cttttaccag ggtaactgtg  15000
tgtactggag aaagggaagt aatgagacat ttcagaaagt actggacact ggctctgagc  15060
tgacgttgat tccagggtac ccaaaacgtt attgtggttc cccagttaaa gtaggggctt  15120
atggaggtta ggtaattaat ggagttttag ctcatttctg acttacagtg gttccagtgg  15180
gtccctggac ttatcctctg gtcattttcc cagtgccaaa atgcataatt tgtatagaca  15240
tacttattag ctggcagaaa tgccacattg gctccctgac tggtaggatg agggctatta  15300
tggtgggaaa ggccaaacag aagccattag agctgtctct acctagaaaa ataaaaaaat  15360
caaaaacaat atcccatccc tggagggact gaagtgatta gtgtcaccat caaggacttg  15420
aaagacgcag ggtggtgat tcccaccaca tccctgttca actctcccat ttgacctgtg  15480
cagaggacag atggatcttg gaaaatgatg gtggattatt ttaagcttaa ccaagtggtg  15540
actccaattg cagctgctct accagttgtg gttttgttgc ttgagcaaat taacacatct  15600
cctggtgcct ggtatgcagc cattggcttg gcaagtggct ttttctccat tcctgtccat  15660
aagacccacc agaagcaatt tgccttcagc tgacaaggcc agcattatac ctttaccacc  15720
ctacctcagg ggtgtatcaa ctctccagct ttgtgtcata atcttatttg gagagacctt  15780
gctcgctttt cacttccacg agatataaca ctggtccatt acattcatga cattatgatg  15840
attggataca gtgagcaaga agtagcaaac acactgaact tattggtgag acatttgtat  15900
gccagaggat gggaaataaa tccagctaaa atttagggac tttctacctc ggtaaaattt  15960
ctagggttcc agtggcatga gacctatgga gatattcctt ctaaggtgaa gcataacttg  16020
ctgcgtttgg cccctcttac aaccaagaaa gaggcacaat gcctggtggg cctatttgga  16080
ttttggaggc aacacattcc tcgtttgggt gtgttactct ggcccattta tcgagtgacc  16140
tgaaaggctg ccagatttaa gtgcagtcta gaacaaaaga aggctctgaa acaggtccag  16200
gctgctgtga aagctgctct gccatttggg ccacatgacc ccgcagatcc aatggtgctt  16260
gaggtgtcag tggcagatag ggatgctgtt tggagccttt ggcaggcccc cataggtgaa  16320
tcacagtgga gacctctagg attttggagc aaggccctgc cacttctgca gataactact  16380
ctccttttga gagacagcta ttggtctgtt attgggcttt ggtggtaact gaacgtttga  16440
ctgtgggtca taaagtcacc atgctacctg aacctgccta tcatgaactg gttgctttct  16500
gacccatcta gccatgaagt gggtcagcac agcggcattt catcatcaaa ttgaagtggt  16560
gtgtatgtga tcgggcttga gcaggtcctg aaggcacaag taagttacat aaggaagtgg  16620
ctcaaatgcc catgttctcc actcatgcca ccctgccttc cctcccccag cctgcaccaa  16680
tggcctcatg gggagttccc tatgatcagt tgacagagga agggaagact aaggactggt  16740
tcatagatgg ttctgcacga tatgcaggca ccacccgaaa gtggacagct gcagcactat  16800
atccactttc taaatgcatg tgtacacttg tgctaagaaa atatctttat tttatttcct  16860
ttatttttcc tttatcatgt gaccttagat ttatggactt cacatcagca tttaagcatt  16920
taagtgttgt tcatatcagc atttaaatat tgttaacctt atgtaataac ttttggtttg  16980
gggattggtg cgtttctggt tgtatgagga tagttgtatt atattaggca taattatgac  17040
cttattattg tctttatttg aagattatgt atgatttcag gatgtgtgta tgggttcaag  17100
ttgacaagga gttggacttg tgatggttaa tactgtcaac ttgattggat tgaaagatgc  17160
aaagtattaa tctcggttat gtctgtgagg gtgtggcaaa aggagattaa catttgagtc  17220
agtgggctgg gaaggcagac ccacccttaa tctgggtaca caccatctaa tcaagttcca  17280
```

```
gtgtggccag attgtaaagc agggagaaaa atgtgaaaag actagactga attagcttcc  17340
cagcctacat ctttctcctg tgccaaatgc ttcctgctct tgaacatcgg actccaagtt  17400
cttcagcgtt gggagttgga ctggctttct tgctcctcag cttgcagagg gcctgttgtg  17460
gaaccttgtg atccgctgag ttaatactac ttaataagat cccctttata tacatataat  17520
atattatatt atatataata tatataatat atattatata taatatatat aatatattat  17580
atattatata taatatatat tatatattat atataatata tattatatat aatatatatt  17640
atatattata tattatatat aatatatatt atatataata tatataaaat atatatatat  17700
cctattagtt ctgtccctct agagaaccct gactaataca atttatgtca ttaatctcat  17760
ttattgattt gtatacattg aaccaacctt atatcccagg aataaaacct acttgattgt  17820
ggtggattag ctttttgatg tactcttgga ttcaattgct ggtattttat tgagaatttt  17880
tgcatctgtg ttcatcaagg atattggctt gaagttttct ttttttgttg ttccatatca  17940
gaatgatgac gacctcatag aatgagttag tctgtcctct tttatctttt ggaattgttt  18000
caggaggctt gatatcagct cttctttata tgactggtat actttggcta ggaatctctc  18060
tggtccaggg gtttttctgg tgtaggtttt taattactga ttcaacttca gaactcatta  18120
ctcattattg agttctaaaa ctcactttca tgtactcttc aaaagactgt cttcttctgt  18180
tgttgagcgg ggtgttctct caaggtcgtt taggtgaagg tggttgctgg tgttcttctg  18240
tatccttact gcttgtcttt ctcttttttt attgactact gaggattaat ggtgatgtgt  18300
ccaactttaa ctctagatta gtctatttct cttttagatt gtaactctgt tttatatatt  18360
ttgaagctct gttgttaggc atgtgtattt ggattgttag gtcttcttga tgatgacctt  18420
tatcattatg taatgtttct tcttatctct ggaagtattc gttgttctga agtctatttg  18480
tgctgatatg aatacagcct tcacagctct attttcacta gtatttgtat atctttttct  18540
cagcttttaa attgagatgt tcagaccatt tgcattaaag tagttgttaa taggattaaa  18600
tttaaatcta ccattaagtt ggttatttct ctttgtccca tttaaacttt gttccttttt  18660
tcatattttt ctgccttcat ttatattgag tttatctcca cgacttactt attaaattaa  18720
tttttaatgg ttttagtatt ttccacaatg tttataatat atactttgat tttttcacat  18780
tccaccttca aatgacagaa ttatactgga tatatagaaa tcttacatca ttgcacttct  18840
ccttcctccc tctcaaaatg ttgtgctatt gctctttgta atagaggctt acttctatta  18900
tgttatagct ctcataatac attgacacta tttttaccct gaataatcag ttgtttttta  18960
aagtgattat gactacaaat attttgaata atttctttat tttaccattt ctggtgctcc  19020
ttatctttta cagtagatcc caatttccat ctggagtcac attctttctg tgaaaaacaa  19080
cctttagcat ttcttatagc acgggactgc tgttgctgtt gtctttcagc ttttctttgt  19140
ctgaagaagt ctttattttg ccttcagttt ttaaaagtga ttttgctgag tatagatact  19200
gggttgagag tttcattcct tgtatcattt taacaatgat gttccattat attccgtttt  19260
gaatagtttc tgactagaaa tctgatcttt gtttctttgt attcaatagt tccttttcct  19320
ctgactgcct ttaagatatt ctcatctttg tttttcaaca gtttgactat aatttgttta  19380
ttattaactt tttgtattta ttctgcttga ggtttcctga gctccttgga tttgcagatt  19440
gttgattttt attgttttg taaaattcat agccattatc tattctactg ttttgttttt  19500
tttttcactt ctctctctct gtattcttct ttttggactg taagtattca aatgttagat  19560
cattcatatt gcttcataaa ccttatatgc ttcttctgct tttttttttt tgtcaggaac  19620
tctttttttg tatctgtgtt ggtttggata agttctagta gactatgttc aagtttatgg  19680
```

attattttgt tagttgtgtc taattgactc ctcagtgcat tcagagaatt cttcatctct 19740
gatattataa atctcttcct agcattttca tgttactctt ttctatagtt tccatctctt 19800
tgctgaaatt ctccccctat ccatggatat tgtccacctt taccacaaga ttctttaaca 19860
tattaacata ggtatcatac aaacccaaac tgatagtttc cagatggtgt cttttctgag 19920
tctgtctgtc ttgattgctt tattatttaa cagtgactta tcttccctct tcagcttttg 19980
gtgtgtcttg taattgttta atcaaacact gggtatcata aatggaggaa cagtagagat 20040
tgcagtaaat attatttatg ctttgaaatg ggcacccatc ttctgttgaa aatatgtttt 20100
gtggtcaatt gagtcaacct agtaactggt tgaactgaat ttggcatttg tgcttgttgc 20160
ttttatctta aatgcaccac aggtttaaat tcctccagtg atgggttgct gctatctttt 20220
gcttagagtg gggcctgggg tgtggaagaa ttttctcagt gttcctatct attattagat 20280
tttagcagtc actgcatgcc tgcactacag aggggatatc ttcatacaca taatctaacc 20340
ccattgaaac tgctgtttct tcttaatgaa tgctcaatct ttggtggaaa taaacaaatg 20400
ctgtatctcc tggagccact tcagtcttag tcaggttctg cagggctttg aagggaatgc 20460
attctcagta ttcttgtgcc ttatttggat ggaacttgaa cctgtggtgg gtttggagag 20520
aaagagtagc agacgtctgc tatgttgcaa tgcaggatgc tgggcacaag aaaatttcca 20580
gtctctcctc caaggaaata agatttgatc atctacctat ccctgagaag tgaagggctt 20640
tgcctgcggt gctagatgca aaaccatttt tctcccccca ttgcccagaa acttaaggct 20700
ttggcttttc tgagcagtgg tctagggaat tgtgcaaggt tttcatattt gaccctgaca 20760
gcccatcacc acctacagct tgcagtgcca aatgtatctc cctctgatct ctcctgtcct 20820
gtggtcctca tgaacattaa gaagagattt ctaaaaaaga gcttgcacat gagcatagtt 20880
tctggtgaga agaattctga tatgttaact tcctctaaac ttttaaataa aatatttcta 20940
agaattaaat aaagttctag aatgatatga atctattcct ttggtttttt gcacgtctgt 21000
ctgcctgcta atcaagagaa gagaatggtc gtaattctca gagacttttt cctgtttgtg 21060
tcataaatga cttcacattt ttttctgttc taagaactat tcagcttgat ttcttctgtt 21120
ttaattttag cagcacctga gcaaagccat gtggtccagg attgctacca tggtgatgga 21180
cagagttatc gaggcacgta ctccaccact gtcacaggaa ggacctgcca agcttggtca 21240
tctatgacac cacatcaaca taataggacc acagaaaact acccaaatgc gtatgtcatt 21300
aatcttacag taagcaaaac aaggtccaag taaaatttgt cttagaaaag gtgtgcgtca 21360
agctaacttc ttatgattaa atttttctca cacatagaat gcatggcaaa atgtctgaga 21420
aacattactt tgagcaaaga gtatgataga agagaaatgt taagctggct ctctttcctg 21480
agagtttgat aaaatcagga gaatatctgg cggtggtgag gccacaataa tggaaaatca 21540
gaatgtttag acagagtcag cttcaacaac actcactaaa ggtcaatgtg atctttaccc 21600
cttgaaattc tataattcta atctccaatt cctgaagtga aggttgtgtt ggccttttct 21660
gtcttggctc acaagtaaat gatatgtgca tatctatgga aaggcgaatc tatctttttc 21720
tatatctatg tctattccaa cgggtagaaa caccctgggt cctgagcacc agtggtctga 21780
aggaatacgg gttgccagga agagagaagc aaaggcagga aggcagatga aagtaagaaa 21840
tgagacagat gctaaacaat aaaaagtgcg ggaagataga cagaagctgg ggtctgacca 21900
caccatggcc agtctttcac acataagtga ctaccaaaga caagaaaaaa tgatttccgc 21960
ttgttggaca atagatggta gaggaccaag ggaattgcga gagagagaac aatgagatca 22020

-continued

```
actcaacaga tgcactggtt ttcttcctgg agacccttcc tgcactgaag ggcaggagat  22080
ggagcccaaa aaaaactgta gccatcttgc tgaacagagg agggacattg gagtttggga  22140
ttattcaggt ggctaggatt ttctaggcct gctaacaatg agaacagatt tgtggaggaa  22200
aggagttcta gaaatatgca tagaaatctc ctcgagtcat tggctaaaca tgaagctgca  22260
tgtacacaga aaatagatcc acaagaaagt agggcaaaga acatctacgg aagagcagca  22320
actacaatgg aacagtgagc tcaataaaca tgacagagct caaatagcac taagggatat  22380
tggagtttgg accacacaga ggagagagac ttcactgaac atcttgggca ttcagtagag  22440
acccaggaaa agccatactt taggagtaga attagtatat tcttagaata aaggcagctc  22500
cacacaaaca atagcaaaac tgaaaaggaa gtctccaagc atcagaatga tgtccaagtc  22560
aatgaactgc ctctgagagg aaaactcaac catctttaga ggtaaacatc aaagtcaagt  22620
ggctcagcta tgcagtatcc acagtgtgag gcctaaatat aaaacttgac tacacataga  22680
aacctttag tgtgacccac aagcaggagg aaaatcagcc aatacaaaca gacccagaag  22740
agacagaaat gattagaatg gcataaaaat ttgacatatc actatataat aattgagttc  22800
taggatttaa gaaaacatga atatagaatg caacagacac cttatccaga gacagtaaga  22860
gtataaagag ccaaatcgaa gaactactaa gagatatgtc ttaaatgaaa aaattactag  22920
atggcctccc catctagtta gacatttcag aagaaaatac caaatgaaaa ataattgcat  22980
agaacctaca gaaccagata cacacataca aaacacacgc atgcatacac acacactcaa  23040
acatgtataa gcttacaaac acacacacac atccacaaat gctgaaaaat gaaatcaacc  23100
gagccacaca gacataaagg aaaacataaa aagatttcct acatgtggga agcaagtcac  23160
agaaaggggg aaggagattg gaacagaaat atatactgaa agcaaggatg gctgaaaatt  23220
ttccaaatat aaagaagatt aaaaaatcac ggactcaaga agctcaatgg atcagaaaaa  23280
taatttctaa aatgacaatt ataggatgcc actgggtaca tagcagttca actgtcagag  23340
ggcaaagaca taatacacag aaaaatctcg taaggaacgg gaaaaacaaa aagctgtgtc  23400
ttgctagagg aacagtgata caagtgacta atgtgttccc atcagaaaca ctgcaacctg  23460
gacacaaaag aataacatta aagtaataaa cgtaagaaag aagagctcaa ctgagaaggc  23520
tacatccagc aataaaatgc cttgaagttc atccatgttg gaggaatgca cattgtgcac  23580
tcccctaaac aaagaaaccg gaaactgtaa gactttggaa tcagcaggct tatgtaacaa  23640
aagaggtgac cctaaggaat taaggagaag aagaatagaa caagaaggga actttctgca  23700
gcctatataa tgaagaacct agcaattggc aaatgtagat gaaaatgcta catgttttct  23760
tgatcaaacg tttatatctt tttaaatgag agttgacgag ttgaagcaaa atgataccaa  23820
tatatttaac tttaccatat gtagaagtaa aaatttgaac atgtagcata aatcatgtag  23880
ggattaattg gaagtgtacc actgtaagtt tcttacctca tgcacgatag tatgtaatac  23940
taataaaagg ttaatgtgtg ggttcaaagg gatattgcaa atcctagagc aatcacaaag  24000
tttttaactc tgaggtttgt tgtataataa caatatttta tgtattcaaa agagggaagc  24060
caaggaagaa aaaaaagtct ttaaagagct ctggctctta gtacatccag ttgctcattg  24120
aatgagcttc ctggaatgga gggtctggga ctgagactag gccacatgtg tagagccact  24180
agagacacaa tgttggatcc ccatggccca taatacattt cccattttct caggcagcca  24240
caggtcatga atgtgaggat actgagaggt tggagcaacg ttcttgggag gcataaggaa  24300
gagcgaatgc ttcaagatcc ccgcagccca aactcctcag ctgctttgcc tcctaattca  24360
ttgtttttg ctcctccata gctgtccgac ctcttcagat ctcttagtct tcctgccatc  24420
```

ttcctttatg ccatgggacc cactgttctt tcaactcatc ccccagttct ggagtggctg 24480
tggacagcag aggatagact gagagcagga gagaaggtcc tgcccaggaa cccattctag 24540
agatactgca ttctgcctgg gagcaagttt tccagggcag ctttgagaag tcttgcagaa 24600
acaaacctac ttgaccgaca tgatatggga atgacagaca gtaatactat ttgcacaatg 24660
cttttccatg ggaaaggtag agccttttca ctaggttttg agtacatgga gtgtgagagt 24720
tgacctggaa aggttatcct ccttgatgcc atgttttctc tgaagaacta catgttcgtt 24780
gcaactccca cattagaata tgaagtccta ccgagagaga tacggagact agacagatac 24840
agatgcattt gcatgtgaat acacaatccc acaatacaga cgtcaaaacc cataccagtt 24900
attccagaga gatggattgg gcagaaggca gaaggagaat actctgatcg tttttcggcc 24960
acgtgtgtgt gttatctcag tgtttctaag aagcgtttgc tactttagat tttttattta 25020
aaaaaaatag taataatcta ttaagtatga gagatgtgca gagaggatta gtgatcgaga 25080
gccatttttg ctggtggcaa tcatatggta cttttaatgg gaatattaga aaggcaccgg 25140
taatgacctt gttgcagcac aaaggagaga gtgtggggtg cccctgcatg ttgtcccacc 25200
tcttgtgacg tgtatcgttt tggaatttcc agtggcttga tcatgaacta ctgcaggaat 25260
ccagatgctg tggcagctcc ttattgttat acgagggatc ccggtgtcag gtgggagtac 25320
tgcaacctga cgcaatgctc agacgcagaa gggactgccg tcgcgcctcc gactgttacc 25380
ccggttccaa gcctagaggc tccttccgaa caaggtaagg agtctgtggc cagacatcta 25440
cacgcttcga tgctgggatg aaaagccatg gaaattccca ctgatgcagc cgccttcaat 25500
ggtaaacgga tgctcgagtg ttgcctgagt tctaccatgt aggaggaagc ctccgtgcac 25560
tctctggggg agccagcgga gtgatttctg gtgcaacgtg gttgggcttt gtctttagga 25620
tgggcacaaa ccctccaggg ggatcgactt caaaattcac cttgttgtaa aacgggctac 25680
ctcagtgtcc cagccaaaat ttttattgta acatgctgtc aggtgtgtca ctctttccaa 25740
gccagtaagc ttttccgggg atttcttcaa gtagccagca ttcagagcaa tcttcagcat 25800
tgcagattct gagaaatgtg gctctggagc ctgtcaccct cgagaaacct aagagggctg 25860
cattgattcc atgtggccct gggtctatgg agcagtacat gagctcccag tgctctaagg 25920
ctcttcagcc ctaggctttg aagggagtga tttctcagta ttcttaaacc tctttctgat 25980
gacacttgta cctgtgaggg gtctagagag aaagagtagt agactcctac tttactacaa 26040
ttcaggatgc agggcatgag aggattccct ctctcctcca agggaagaag cttttggcgt 26100
gcacacatcc ctgagaagca aagtgtcttt gtcttcagtc agatacatag gaccgttttc 26160
tgccccatgg cccggaagcc aaaggccttg gctttcatga tcaacggtct agggaaacat 26220
gcaaaatttc catgtctgtc ccaaactctg cccccgacag ccaattacca cctgcagccc 26280
gcattgccaa atgcggtgcc gtttgcatga agattcagta gagtttccta gaaaggtgct 26340
acctcgtgag ctcactttcc aatgaggaat ctgatctgtt gtgtttctct aaggtgtcag 26400
gtgaaatatt tccaagaact tactacagtt ctagaatggg aggaatctgt tgctttggtg 26460
tttgtttgtt ggtcggtttt ctcacatcca tctgcctatg gataaggaaa agagaacggt 26520
cgtaattctc atagactcct ttctggttgt gtcacaaatg gcttcacatg tttctctatg 26580
ctcagagata ctcagcttga tttcccgtgt tttcatttca gcaccgactg agcaaaggcc 26640
tggggtgcag gagtgctacc atggtaatgg acagagttat cgaggcacat actccaccac 26700
tgtcacagga agaacctgcc aagcttggtc atctatgaca ccacactcgc atagtcggac 26760
cccagaatac tacccaaatg cgtatgtctt tgttctttac cataagagaa gaaagggcca 26820
agtgaagttt ctgttacaag agatgtgtct caagctgagt tctccgaact caacttgtga 26880
cagatgcaga tggcgtagca aaatgtctca ggatgattgc cttggagcta agggtctgag 26940
agaagggaaa tgttaagctc cctctccttc ctcctagttc tattgagcag aagggaaatc 27000
tggaggtgag gagatcacat tatgaagaaa gtcagaatga caaaggacca gacacttaga 27060
ttacccttcc acaacaccaa ctaaacgtca atggagactt tccagttgga attccgttat 27120
tctggcttcc acttcctgaa gggaaggttg cgtttgcctt ttctctctgg gttcaagagg 27180
aaagaatagg tgcttattta tggacaggtg aattgatctg tttctatatc tacgtatatt 27240
ccgattgtca gaaaaacact cgttcctaag taccagtggc ctgaagggat acaggttccc 27300
agcaagagaa gatccaagga aggaaggcag atgagagtca gcacagagag ggatgctgaa 27360
aagtaaaagg gatgggtgga tggagagaag cccgggtctg accacccaat ggccaatatt 27420
ttggccacaa gcgactacca gagacatgga aaaatggttt ctacatgtgg gacaacagat 27480
ggtagaggac ctagagaatt gagagagggg caatgatggg ctccactccg cagatgcctt 27540
ggctttcttc ctggataccc ttcctgcact gaatagcaag gagatggagc ccaagcagac 27600
tgtagccatc ttgctgaatg gaggagaggg attggagttt gggatgactg tggtagctga 27660
aatttttcta ggtctgctag aaataagaac tggtttgtgt ggaggaaaag agctctacaa 27720
atacgcatag aagtctcctc cagtcgttgg cctgacatga cgctgcctgt gcacaggaaa 27780
tggttccacg agaaagtgtg gcaaagaaca tttactgaga aacagcaagt acaagagcac 27840
aggaagctca ataaagaaga gagagatcac atagcactct gggatactgg agttcttccc 27900
agctagacca gagagtcctc acggagcaca ttgccaattc agtggagacc ccagaacagc 27960
cgtaatttaa aggtacactt agtatattac tagaataaag tcagctgcag acaacccctt 28020
gcacagctgg aaagcaagtg tccaagcatc aaatcggttt ccaatcaatg aagtgcctgt 28080
gagaggaaat ctcaactctc tttagaagta aacaacaaag tcgattgcct cagctatgcg 28140
gtatccgcag agtgagtcct aaatttaaaa tctgactaca tgtagaaaag cgtttcgtgt 28200
gacccatgac caggaaataa atcgggtaat acaaacaggc tcaggaatga gagaaatgat 28260
tagaattgcg tgaaaatttg acatatcagt atgataactg atttcaaata tttaaaaaaa 28320
caacatgcaa gaaagcagat atcatatcaa gagaaattaa cagtacagaa tagccaaatt 28380
aaattaaaga ggtagtataa aaaaagtatg tcttaattga aaaaaattac tgtatggccg 28440
gctgatcaat ttagacgttt cagaggaaaa cattacccaa cacacaattc tagagaacct 28500
acagaatgag ctacacacac acacacacac acacacacac acactgaaaa cacacccata 28560
ctcacacaca cgcagaaact cacaagttct aacacacaca gacacgcgca cccctgaaga 28620
aacagtgaaa tataaaatta agcgagcctc acagacatgt aggaaaatat gaaaagattt 28680
cctgcatgtg ggaagcaagt cacagtaaag agcaagggag tttataatag aaacaaatac 28740
cagaatcaag gatggctgat aacttttcaa ttacgaagaa cattaaaaaa aatcacagaa 28800
tcgtgaaact caagggatca tatagggaat ttcggaaaaa aaacccaacc tgtatgatgt 28860
acttttgtac atcacagttc gaaggtaaca aggcaaagat gtaataagaa gaaacctgtc 28920
acgagaaact ggaggaaaaa gagctgtgtc ttcctacaag tacactgata caaattgcca 28980
atgtgttcac ctcagaaaca ctggaagcca gataccaggg aatattgtta aaatgataat 29040
caggaacaaa aagagatcaa ccgggaatgc tgaatccagc aataaaatgc cttgaaggtc 29100
atccatgtcg gataaatgca tattgtgcac tgccccaaag aaagaaaccg gaaactgtaa 29160

-continued

```
gaattggaaa tcagcaggct tatgtaacaa gagaggtgac ccgaaggaat taggtagaag  29220
aagaattgaa caagaaagga actttctgca gcccacgtaa tgaagaatcc agcaattggc  29280
aaatgtagat agatgtaaat gcaaaatatt ttcttgatca aatttctata tctttgtaaa  29340
tgagagttga ctacttgaaa caaaatgata gcaagatatt taacttcagc atatgtagag  29400
gtaagaattt gaaatggtag cataaatcac gaagggatta attcgaagtg taccgttgta  29460
agtttcttta cctcatgcac gatggtgtgt catattaata aaagggtact gtgcgggttc  29520
gaagggatat tgcaaatcct agagcaatca caaaggtttg aactctgagg tttttggtat  29580
aataagaata gtccatgcat tcaaaagagg gaagccaagg aagaactaga agtctttcaa  29640
gagctcaggc tcttatacat ccagttgctc attgaaccag cttcctggaa tggagggtct  29700
ggggttgaga ctaggccaca agtctagagt ctctagagag acagtgttgg aaccccatgg  29760
cccataatac atttcccatt ttctcaggca gccagaggtc atgaatgtga ggatactggg  29820
aggttggagc aacgttcttg ggaggcataa ggaagagcga atgcttcaag atccccgcag  29880
cccaaactac tcgcctgctt tgccccctaa tgcatttttc tctgctgctc cgtagctgtc  29940
cgacctcttc agatctctta gtccaccctg ccgtcttcct ttatgccatg ggtcccactg  30000
ttctttcaac tcatccccct ttccctcagt cccggagtag ctgcggccag cagagggtag  30060
actgagagca ggagagaagg acctgcctag gaaccccttc tagagatact gcatcctgcc  30120
tgggagcaag ttttccaggg cagctttgag aagtcttgga gaaacaaacc tactaaacct  30180
gacagacagt aatactattt gcacaatgct tttctgtggg aaaggtagag ccttttcact  30240
acgtattgag tacatagagt gtgagggttg acctggaacg gctatcctcc tggatgacgt  30300
gtgttttctg aagaactaca tgttcgttgc aactcccaca ttagaatatg aagtcctacc  30360
gagagagata cggagactag acagatacag atgcatttgc atgtgaatac acaatcccac  30420
aatacagacg tcaaaaccca taccagttat tccagagaga tggattgggc agaaggcaga  30480
aggagaatac tctgatcgtt tttcggccac gtgtgtgtgt tatctcagtg tttctaagaa  30540
gcgtttgcta ctttagattt tttatttaaa aaaatagtaa taatctatta agtatgagag  30600
atgtgcagag aggattagtg atcgagagcc atttttgctg gtggcaatca tatggtactt  30660
ttaatgggaa tattagaaag gcaccggtaa tgaccttgtt gcagcacaaa ggagagagtg  30720
tggggtgccc ctgcatgttg tcccacctct tgtgacgtgt atcgttttgg aatttccagt  30780
ggcttgatca tgaactactg caggaatcca gatgctgtgg cagctcctta ttgttatacg  30840
agggatcccg gtgtcaggtg ggagtactgc aacctgacgc aatgctcaga cgcagaaggg  30900
actgccgtcg cgcctccgac tgttaccccg gttccaagcc tagaggctcc ttccgaacaa  30960
ggtaaggagt ctgtggccag acatctacac gcttcgatgc tgggatgaaa agccatggaa  31020
attcccactg atgcagccgc cttcaatggt aaacggatgc tcgagtgttg cctgagttct  31080
accatgtagg aggaagcctc cgtgcactct ctgggggagc cagcggagtg atttctggtg  31140
caacgtggtt gggctttgtc tttaggatgg gcacaaaccc tccaggggga tcgacttcaa  31200
aattcacctt gttgtaaaac gggctacctc agtgtcccag ccaaaatttt tattgtaaca  31260
tgctgtcagg tgtgtcactc tttccaagcc agtaagcttt tccggggatt tcttcaagta  31320
gccagcattc agagcaatct tcagcattgc agattctgag aaatgtggct ctggagcctg  31380
tcaccctcga gaaacctaag agggctgcat tgattccatg tggccctggg tctatggagc  31440
agtacatgag ctcccagtgc tctaaggctc ttcagcccta ggctttgaag ggagtgattt  31500
```

ctcagtattc ttaaacctct ttctgatgac acttgtacct gtgaggggtc tagagagaaa 31560
gagtagtaga ctcctacttt actacaattc aggatgcagg gcatgagagg attccctctc 31620
tcctccaagg gaagaagctt ttggcgtgca cacatccctg agaagcaaag tgtctttgtc 31680
ttcagtcaga tacataggac cgttttctgc cccatggccc ggaagccaaa ggccttggct 31740
ttcatgatca acggtctagg gaaacatgca aaatttccat gtctgtccca aactctgccc 31800
ccgacagcca attaccacct gcagcccgca ttgccaaatg cggtgccgtt tgcatgaaga 31860
ttcagtagag tttcctagaa aggtgctacc tcgtgagctc actttccaat gaggaatctg 31920
atctgttgtg tttctctaag gtgtcaggtg aaatatttcc aagaacttac tacagttcta 31980
gaatgggagg aatctgttgc tttggtgttt gtttgttggt cggttttctc acatccatct 32040
gcctatggat aaggaaaaga gaacggtcgt aattctcata gactcctttc tggttgtgtc 32100
acaaatggct tcacatgttt ctctatgctc agagatactc agcttgattt cccgtgtttt 32160
catttcagca ccgactgagc aaaggcctgg ggtgcaggag tgctaccatg gtaatggaca 32220
gagttatcga ggcacatact ccaccactgt cacaggaaga acctgccaag cttggtcatc 32280
tatgacacca cactcgcata gtcggacccc agaatactac ccaaatgcgt atgtctttgt 32340
tctttaccat aagagaagaa agggccaagt gaagtttctg ttacaagaga tgtgtctcaa 32400
gctgagttct ccgaactcaa cttgtgacag atgcagatgg cgtagcaaaa tgtctcagga 32460
tgattgcctt ggagctaagg gtctgagaga agggaaatgt taagctccct ctccttcctc 32520
ctagttctat tgagcagaag ggaaatctgg aggtgaggag atcacattat gaagaaagtc 32580
agaatgacaa aggaccagac acttagatta cccttccaca acaccaacta aacgtcaatg 32640
gagactttcc agttggaatt ccgttattct ggcttccact tcctgaaggg aaggttgcgt 32700
ttgccttttc tctctgggtt caagaggaaa gaataggtgc ttatttatgg acaggtgaat 32760
tgatctgttt ctatatctac gtatattccg attgtcagaa aaacactcgt tcctaagtac 32820
cagtggcctg aagggataca ggttcccagc aagagaagat ccaaggaagg aaggcagatg 32880
agagtcagca cagagaggga tgctgaaaag taaaagggat gggtggatgg agagaagccc 32940
gggtctgacc acccaatggc caatattttg gccacaagcg actaccagag acatggaaaa 33000
atggtttcta catgtgggac aacagatggt agaggaccta gagaattgag agaggggcaa 33060
tgatgggctc cactccgcag atgccttggc tttcttcctg gatacccttc ctgcactgaa 33120
tagcaaggag atggagccca agcagactgt agccatcttg ctgaatggag gagagggatt 33180
ggagtttggg atgactgtgg tagctgaaat ttttctaggt ctgctagaaa taagaactgg 33240
tttgtggagg aaaagagctc tacaaatacg catagaagtc tcctccagtc gttggcctga 33300
catgacgctg cctgtgcaca ggaaatggtt ccacgagaaa gtgtggcaaa gaacatttac 33360
tgagaaacag caagtacaag agcacaggaa gctcaataaa gaagagagag atcacatagc 33420
actctgggat actggagttc ttcccagcta gaccagagag tcctcacgga gcacattgcc 33480
aattcagtgg agaccccaga acagccgtaa tttaaaggta cacttagtat attactagaa 33540
taaagtcagc tgcagacaac cccttgcaca gctggaaagc aagtgtccaa gcatcaaatc 33600
ggtttccaat caatgaagtg cctgtgagag gaaatctcaa ctctctttag aagtaaacaa 33660
caaagtcgat tgcctcagct atgcggtatc cgcagagtga gtcctaaatt taaaatctga 33720
ctacatgtag aaaagcgttt cgtgtgaccc atgaccagga aataaatcgg gtaatacaaa 33780
caggctcagg aatgagagaa atgattagaa ttgcgtgaaa atttgacata tcagtatgat 33840
aactgatttc aaatatttaa aaaaacaaca tgcaagaaag cagatatcat atcaagagaa 33900
attaacagta cagaatagcc aaattaaatt aaagagctag tataaaaaaa gtatgtctta 33960
attgaaaaaa attactgtat ggccggctga tcaatttaga cgtttcagag gaaaacatta 34020
cccaacacac aattctagag aacctacaga atgagctaca cacacacaca cacacacaca 34080
cacaaactga aaacacaccc atactcacac acacgcagaa actcacaagt tctaacacac 34140
acagacacgc gcacccctga agaaacagtg aaatataaaa ttaagcgagc ctcacagaca 34200
tgtaggaaaa tatgaaaaga tttcctgcat gtgggaagca agtcacagta aagagcaagg 34260
gagtttggaa tagaaacaaa taccggaatc aaggatggct gataactttt caattacgaa 34320
gaacattaaa aaaaatcaca gaatcgtgaa actcaaggga tcacataggg aatttcggaa 34380
aaaaaaccca acctgtatga tgtacttttg tacatcacag ttcgaaggta acaaggcaaa 34440
gatataataa gaagaaacct gtcacgagaa actggaggaa aaagagctgt gtcttcctac 34500
aagtacactg atacaaattg ccaatgtgtt cacctcagaa acactggaag ccagatacca 34560
gggaatattg ttaaaatgat aatcaggaac aaaaagagat caaccgggaa tgctgaatcc 34620
agcaataaaa tgccttgaag atcatccatg tcggataaat gcatattgtg cactgcccca 34680
aagaaagaaa ccggaaactg taagaattgg aaatcagcag gcttatgtaa caagagaggt 34740
gacccgaagg aattaggtag aagaagaatt gaacaagaaa ggaactttct gcagcccacg 34800
taatgaagaa tccagcaatt ggcaaatgta gatagatgta aatgcaaaat attttcttga 34860
tcaaatttct atatctttgt aaatgagagt tgactacttg aaacaaaatg atagcaagat 34920
atttaacttc agcatatgta gaggtaagaa tttgaaatgg tagcataaat cacgaaggga 34980
ttaattcgaa gtgtaccgtt gtaagtttct ttacctcatg cacgatggtg tgtcatatta 35040
ataaaagggt actgtgcggg ttcgaaggga tattgcaaat cctagagcaa tcacaaaggt 35100
ttgaactctg aggtttttgg tataataaga atagtccatg cattcaaaag agggaagcca 35160
aggaagaact agaagtcttt caagagctca ggctcttata catccagttg ctcattgaac 35220
cagcttcctg gaatggaggg tctggggttg agactaggcc acaagtctag agtctctaga 35280
gagacagtgt tggaacccca tggcccataa tacatttccc attttctcag gcagccagag 35340
gtcatgaatg tgaggatact gggaggttgg agcaacgttc ttgggaggca taaggaagag 35400
cgaatgcttc aagatccccg cagcccaaac tactcgcctg ctttgccccc taatgcattt 35460
ttctctgctg ctccgtagct gtccgacctc ttcagatctc ttagtccacc ctgccgtctt 35520
cctttatgcc atgggtccca ctgttctttc aactcatccc cctttccctc agtcccggag 35580
tagctgcggc cagcagaggg tagactgaga gcaggagaga aggacctgcc taggaacccc 35640
ttctagagat actgcatcct gcctgggagc aagttttcca gggcagcttt gagaagtctt 35700
ggagaaacaa acctactaaa cctgacagac agtaatacta tttgcacaat gcttttctgt 35760
gggaaaggta gagccttttc actacgtatt gagtacatag agtgtgaggg ttgacctgga 35820
acggctatcc tcctggatga cgtgtgtttt ctgaagaact acatgttcgt tgcaactccc 35880
acattagaat atgaagtcct accgagagag atacggagac tagacagata cagatgcatt 35940
tgcatgtgaa tacacaatcc cacaatacag acgtcaaaac ccataccagt tattccagag 36000
agatggattg ggtaggaggc agaaggagaa tactctgatc gtttttcggc cacgtgtgtg 36060
tgttatctca gtgtttctaa gaagcgtttg ctactttaga ttttttattt aaaaaaaaata 36120
gtaataatct attaagtatg agagatgtgc agagaggatt agtgatcgag agccattttt 36180
gctggtggca atcatatggt acttttaatg ggaatattag aaaggcaccg gtaatgacct 36240
tgttgcagca caaaggagag agtgtggggt gcccctgcat gttgtcccac ctcttgtgac 36300
gtgtatcgtt ttggaatttc cagtggcttg atcatgaact actgcaggaa tccagatgct 36360
gtggcagctc cttattgtta tacgagggat cccggtgtca ggtgggagta ctgcaacctg 36420
acgcaatgct cagacgcaga agggactgcc gtcgcgcctc cgactgttac cccggttcca 36480
agcctagagg ctccttccga acaaggtaag gagtctgtgg ccagacatct acacgcttcg 36540
atgctgggat gaaaagccat ggaaattccc actgatgcag ccgccttcaa tggtaaacgg 36600
atgctcgagt gttgccggag ttctgccatg ttgggggaag cctccgtgta ctctctgggg 36660
gagccagcgg agtgatttct ggtgcaactt gggtgggctt tgtctttaga atgggcacaa 36720
accttccagg gtgatgggct tcacaactca cctccttcta aaatgggcta tctcagtgtc 36780
ttagccaaaa tttttattgt aacgtgctgt caggtgtgtg attctttctg tcgcagtaag 36840
cttttctggg gatttcttca agtagccagc agtcagtgca atcttcagca ttgcagattt 36900
caaaaaatgt ggctctggag cctgtcatcc tcgagaaacc taacagggct gcattaattc 36960
catatggtcc tgggtctatg gagcagtata tgagctccca atgctctaag gctcttcagt 37020
cctaggcttt gaagggagtg atttctcagt gttcttaaac ctctttctga tggcacttgt 37080
acctgtgagg ggtctagaga gaaaggttag tagacttctc ctttactgca attcaggatg 37140
cagggcatga gaagattccc tccctcctcc aagggaagaa ggttttggcg tgcacacatc 37200
cttgagaagc aaagtgtctt tgccttcagt cagatatata ggatcgtttt ctgccccatg 37260
gcctggaagc cagaggcctt ggctttcatg atcaacgatc tagggaaaca tgcaaaattt 37320
ccatgtcttt cccctcctct gccctcgaca gccaattacc acctgcatcc tgcattgcca 37380
aatgcagtgc cctttgtatg aacattcagt agagtttcat agaaaggtgc tacttcgtga 37440
gcgcactttg cagtgagaag gagtctgttc tgttctgttt ttctaaggat ttcaggtgaa 37500
atatttccta gaacttacta cagttctaga ttggtaggaa tctgtaggtt tgctgtatgt 37560
tttttggttg gttttctccc atccatctgc ctacaggtaa gggaaagata acgttcgtaa 37620
ttctcataga ctcctttctg gttgtgtcat aaatggcttc acatatttcg ttattctcag 37680
agatactcag tttatttctt gtgttttcat ttcagcaccg actgagcaga ggcctggggt 37740
gcaggagtgc taccacggta atggacagag ttatcgaggc acatactcca ccactgtcac 37800
tggaagaacc tgccaagctt ggtcatctat gacaccacac tcgcatagtc ggaccccaga 37860
atactaccca aatgcgtatg tctttgttct ttaccataag agaagaaagg gccaagtgaa 37920
gtttctgtta caagagatgt gtctcaagct gagttctccg aactcaactt gtgacagatg 37980
cagatggcgt agcaaaatgt ctcaggatga ttgccttgga gctaagggtc tgagagaagg 38040
gaaatgttaa gctccctctc cttcctccta gttctattga gcagaaggga aatctggagg 38100
tgaggagatc acattatgaa gaaagtcaga atgacaaagg accagacact tagattaccc 38160
ttccacaaca ccaactaaac gtcaatggag actttccagt tggaattccg ttattctggc 38220
ttccacttcc tgaagggaag gttgcgtttg ccttttctct ctgggttcaa gaggaaagaa 38280
taggtgctta tttatggaca ggtgaattga tctgtttcta tatctacgta tattccgatt 38340
gtcagaaaaa cactcgttcc taagtaccag tggcctgaag ggatacaggt tcccagcaag 38400
agaagatcca aggaaggaag gcagatgaga gccagcacag agagggatgc tgaaaagtaa 38460
aagggatggg tggatggaga gaagcccggg tctgaccacc caatggccaa tattttggcc 38520
acaagcgact accagagaca tggaaaaatg gtttctacat gtgggacaac agatggtaga 38580
ggacctagag aattgagaga ggggcaatga tgggctccac tccgcagatg ccttggcttt 38640
cttcctggat acccttcctg cactgaatag caaggagatg gagcccaagc agactgtagc 38700
catcttgctg aatggaggag agggattgga gtttgggatg actgtggtag ctgaaatttt 38760
tctaggtctg ctagaaataa gaactggttt gtggaggaaa agagctctac aaatacgcat 38820
agaagtctcc tccagtcgtt ggcctgacat gacgctgcct gtgcacagga aatggttcca 38880
cgagaaagtg tggcaaagaa catttactga gaaacagcaa gtacaagagc acaggaagct 38940
caataaagaa gagagagatc acatagcact ctgggatact ggagttcttc ccagctagac 39000
cagagagtcc tcacggagca cattgccaat tcagtggaga ccccagaaca gccgtaattt 39060
aaaggtacac ttagtatatt actagaataa agtcagctgc agacaacccc ttgcacagct 39120
ggaaagcaag tgtccaagca tcaaatcggt ttccaatcaa tgaagtgcct gtgggaggaa 39180
atctcaactc tctttagaag taaacaacaa agtcgattgc ctcagctatg cggtatccgc 39240
agagtgagtc ctaaatttaa aatctgacta catgtagaaa agcgtttcgt gtgacccatg 39300
accaggaaat aaatcgggta atacaaacag gctcaggaat gagagaaatg attagaattg 39360
cgtgaaaatt tgacatatca gtatgataac tgatttcaaa tatttaaaaa aacaacatgc 39420
aagaaagcag atatcatatc aagagaaatt aacagtacag aatagccaaa ttaaattaaa 39480
gagctagtat aaaaaaagta tgtcttaatt gaaaaaaatt actgtatggc cggctgatca 39540
aattagacgt ttcagaggaa aacattaccc aacacacaat tctagagaac ctacagaatg 39600
agctacacac acacacacac acacacacac acacactgaa aacacaccca tactcacaca 39660
cacgcagaaa ctcacaagtt ctaacacaca cagacacgcg cacccctgaa gaaacagtga 39720
aatataaaat taagcgagcc tcacagacat gtaggaaaat atgaaaagat ttcctgcatg 39780
tgggaagcaa gtcacagtaa agagcaaggg agtttggaat agaaacaaat accggaatca 39840
aggatggctg ataacttttc aattacgaag aacattaaaa aaaatcacag aatcgtgaaa 39900
ctcaagggat catataggga atttcggaaa aaaaacccaa cctgtatgat gtacttttgt 39960
acatcacagt tcgaaggtaa caaggcaaag atataataag aagaaacctg tcacgagaaa 40020
ctggaggaaa aagagctgtg tcttcctaca agtacactga tacaaattgc caatgtgttc 40080
acctcagaaa cactggaagc cagataccag ggaatattgt taaaatgata atcaggaaca 40140
aaaagagatc aaccgggaat gctgaatcca gcaataaaat gccttgaaga tcatccatgt 40200
cggataaatg catattgtgc actgccccaa agaaagaaac cggaaactgt cagaattgga 40260
aatcagcagg cttatgtaac aagagaggtg acccgaagga attaggtaga agaagaattg 40320
aacaagaaag gaactttctg cagcccacgt aatgaagaat ccagcaattg gcaaatgtag 40380
atagatgtaa atgcaaaata ttttcttgat caaatttcta tatctttgta aatgagagtt 40440
gactacttga aacaaaatga tagcaagata tttaacttca gcatatgtag aggtaagaat 40500
ttgaaatggt agcataaatc acgaagggat taattcgaag tgtaccgttg taagtttctt 40560
tacctcatgc acgatggtgt gtcatattaa taaaagggta ctgtgcgggt tcgaagggat 40620
attgcaaatc ctagagcaat cacaaaggtt tgaactctga ggtttttggt ataataagaa 40680
tagtccatgc attcaaaaga gggaagccaa ggaagaacta gaagtctttc aagagctcag 40740
gctcttatac atccagttgc tcattgaacc agcttcctgg aatggagggt ctggggttga 40800
gactaggcca caagtctaga gtctctagag agacagtgtt ggaaccccat ggcccataat 40860
acatttccca ttttctcagg cagccagagg tcatgaatgt gaggatactg ggaggttgga 40920
gcaacgttct tgggaggcat aaggaagagc gaatgcttca agatccccgc agcccaaact 40980
actcgcctgc tttgcccccct aatgcatttt tctctgctgc tccgtagctg tccgacctct 41040
tcagatctct tagtccaccc tgccgtcttc ctttatgcca tgggtcccat tgttctttca 41100
actcatcccc ctttccctca gtcccggagt agctgcggcc agcagagggt agactgagag 41160
caggagagaa ggacctgcct aggaacccct tctagagata ctgcatcctg cctgggagca 41220
agttttccag ggcagctttg agaagtcttg gagaaacaaa cctactaaac ctgacagaca 41280
gtaatactat ttgcacaatg cttttctgtg ggaaaggtag agccttttca ctacgtattg 41340
agtacataga gtgtgagggt tgacctggaa cggctatcct cctggatgac gtgcgttttc 41400
tgaagaacta catgttcgtt gcaactccca cattagaata tgaagtccta ccgagagaga 41460
tacggagact agacagatac agatgcattt gcatgtgaat acacaatccc acaatacaga 41520
cgtcaaaacc cataccagtt attccagaga gatggattgg gcagaaggca gaaggagaat 41580
actctgatcg tttttcggcc acgtgtgtgt gttatctcag tgtttctaag aagcgtttgc 41640
tactttagat tttttattta aaaaaaatag taataatcta ttaagtatga gagatgtgca 41700
gagaggatta gtgatcgaga gccatttttg ctggtggcaa tcatatggta cttttaatgg 41760
gaatattaga aaggcaccgg taatgacctt gttgcagcac aaaggagaga gtgtggggtg 41820
cccctgcatg ttgtcccacc tcttgtgacg tgtatcgttt tggaatttcc agtggcttga 41880
tcatgaacta ctgcaggaat ccagatgctg tggcagctcc ttattgttat acgagggatc 41940
ccggtgtcag gtgggagtac tgcaacctga cgcaatgctc agacgcagaa gggactgccg 42000
tcgcgcctcc gactgttacc ccggttccaa gcctagaggc tccttccgaa caaggtaagg 42060
agtctgtggc cagacatcta cacgcttcga tgctgggatg aaaagccatg gaaattccca 42120
ctgatgcagc cgccttcaat ggtaaacgga tgctcgagtg ttgcctgagt tctaccatgt 42180
aggaggaagc ctccgtgcac tctctggggg agccagcgga gtgatttctg gtgcaacgtg 42240
gttgggcttt gtctttagga tgggcacaaa ccctccaggg ggatcgactt caaaattcac 42300
cttgttgtaa aacgggctac ctcagtgtcc cagccaaaat ttttattgta acatgctgtc 42360
aggtgtgtca ctctttccaa gccagtaagc ttttccgggg atttcttcaa gtagccagca 42420
ttcagagcaa tcttcagcat tgcagattct gagaaatgtg gctctggagc ctgtcaccct 42480
cgagaaacct aagagggctg cattgattcc atgtggccct gggtctatgg agcagtacat 42540
gagctcccag tgctctaagg ctcttcagcc ctaggctttg aagggagtga tttctcagta 42600
ttcttaaacc tctttctgat gacacttgta cctgtgaggg gtctagagag aaagagtagt 42660
agactcctac tttactacaa ttcaggatgc agggcatgag aggattccct ctctcctcca 42720
agggaagaag cttttggcgt gcacacatcc ctgagaagca aagtgtcttt gtcttcagtc 42780
agatacatag gaccgttttc tgccccatgg cccggaagcc aaaggccttg gctttcatga 42840
tcaacggtct agggaaacat gcaaaatttc catgtctgtc ccaaactctg cccccgacag 42900
ccaattacca cctgcagccc gcattgccaa atgcggtgcc gtttgcatga agattcagta 42960
gagtttccta gaaaggtgct acctcgtgag ctcactttcc aatgaggaat ctgatctgtt 43020
gtgtttctct aaggtgtcag gtgaaatatt tccaagaact tactacagtt ctagaatggg 43080
aggaatctgt tgctttggtg tttgtttgtt ggtcggtttt ctcacatcca tctgcctatg 43140
gataaggaaa agagaacggt cgtaattctc atagactcct ttctggttgt gtcacaaatg 43200
gcttcacatg tttctctatg ctcagagata ctcagcttga tttcccgtgt tttcatttca 43260
gcaccgactg agcaaaggcc tggggtgcag gagtgctacc atggtaatgg acagagttat 43320
cgaggcacat actccaccac tgtcacagga agaacctgcc aagcttggtc atctatgaca 43380

-continued

```
ccacactcgc atagtcggac cccagaatac tacccaaatg cgtatgtctt tgttctttac  43440
cataagagaa gaaagggcca agtgaagttt ctgttacaag agatgtgtct caagctgagt  43500
tctccgaact caacttgtga cagatgcaga tggcgtagca aaatgtctca ggatgattgc  43560
cttggagcta agggtctgag agaagggaaa tgttaagctc cctctccttc ctcctagttc  43620
tattgagcag aagggaaatc tggaggtgag gagatcacat tatgaagaaa gtcagaatga  43680
caaaggacca gacacttaga ttacccttcc acaacaccaa ctaaacgtca atggagactt  43740
tccagttgga attccgttat tctggcttcc acttcctgaa gggaaggttg cgtttgcctt  43800
ttctctctgg gttcaagagg aaagaatagg tgcttattta tggacaggtg aattgatctg  43860
tttctatatc tacgtatatt ccgattgtca gaaaaacact cgttcctaag taccagtggc  43920
ctgaagggat acaggttccc agcaagagaa gatccaagga aggaaggcag atgagagtca  43980
gcacagagag ggatgctgaa aagtaaaagg gatgggtgga tggagagaag cccgggtctg  44040
accacccaat ggccaatatt ttggccacaa gcgactacca gagacatgga aaaatggttt  44100
ctacatgtgg gacaacagat ggtagaggac ctagagaatt gagagagggg caatgatggg  44160
ctccactccg cagatgcctt ggctttcttc ctggataccc ttcctgcact gaatagcaag  44220
gagatggagc ccaagcagac tgtagccatc ttgctgaatg gaggagaggg attggagttt  44280
gggatgactg tggtagctga aatttttcta ggtctgctag aaataagaac tggtttgtgg  44340
aggaaaagag ctctacaaat acgcatagaa gtctcctcca gtcgttggcc tgacatgacg  44400
ctgcctgtgc acaggaaatg gttccacgag aaagtgtggc aaagaacatt tactgagaaa  44460
cagcaagtac aagagcacag gaagctcaat aaagaagaga gagatcacat agcactctgg  44520
gatactggag ttcttcccag ctagaccaga gagtcctcac ggagcacatt gccaattcag  44580
tggagacccc agaacagccg taatttaaag gtacacttag tatattacta gaataaagtc  44640
agctgcagac aaccccttgc acagctggaa agcaagtgtc caagcatcaa atcggtttcc  44700
aatcaatgaa gtgcctgtga gaggaaatct caactctctt tagaagtaaa caacaaagtc  44760
gattgcctca gctatgcggt atccgcagag tgagtcctaa atttaaaatc tgactacatg  44820
tagaaaagcg tttcgtgtga cccatgacca ggaaataaat cgggtaatac aaacaggctc  44880
aggaatgaga gaaatgatta gaattgcgtg aaaatttgaa atatcagtat gataactgat  44940
ttcaaatatt taaaaaaaca acatgcaaga aagcagatat catatcaaga gaaattaaca  45000
gtacagaata gccaaattaa attaaagagc tagtataaaa aaagtatgtc ttaattgaaa  45060
aaaattactg tatggccggc tgatcaattt agacgtttca gaggaaaaca ttacccaaca  45120
cacaattcta gagaacctac agaatgagct acacacacac acacacacac acacacaaac  45180
tgaaaacaca cccatactca cacacacgca gaaactcaca agttctaaca cacacagaca  45240
cgcgcacccc tgaagaaaca gtgaaatata aaattaagcg agcctcacag acatgtagga  45300
aaatatgaaa agatttcctg catgtgggaa gcaagtcaca gtaaagagca agggagtttg  45360
gaatagaaac aaataccaga atcaaggatg gctgataact tttcaattac gaagaacatt  45420
aaaaaaaatc acagaatcgt gaaactcaag ggatcacata gggaatttcg gaaaaaaaac  45480
ccaacctgta tgatgtactt ttgtacatca cagttcgaag gtaacaaggc aaagatataa  45540
taagaagaaa cctgtcacga gaaactggag gaaaaagagc tgtgtcttcc tacaagtaca  45600
ctgatacaaa ttgccaatgt gttcacctca gaaacactgg aagccagata ccagggaata  45660
ttgttaaaat gataatcagg aacaaaaaga gatcaaccgg gaatgctgaa tccagcaata  45720
```

```
aaatgccttg aagatcatcc atgtcggata aatgcatatt gtgcactgcc ccaaagaaag  45780
aaaccggaaa ctgtaagaat tggaaatcag caggcttatg taacaagaga ggtgacccga  45840
aggaattagg tagaagaaga attgaacaag aaaggaactt tctgcagccc acgtaatgaa  45900
gaatccagca attggcaaat gtagatagat gtaaatgcaa aatattttct tgatcaaatt  45960
tctatatctt tgtaaatgag agttgactac ttgaaacaaa atgatagcaa gatatttaac  46020
ttcagcatat gtagaggtaa gaatttgaaa tggtagcata aatcacgaag ggattaattc  46080
gaagtgtacc gttgtaagtt tctttacctc atgcacgatg gtgtgtcata ttaataaaag  46140
ggtactgtgc gggttcgaag ggatattgca aatcctagag caatcacaaa ggtttgaact  46200
ctgaggtttt tggtataata agaatagtcc atgcattcaa aagagggaag ccaaggaaga  46260
actagaagtc tttcaagagc tcaggctctt atacatccag ttgctcattg aaccagcttc  46320
ctggaatgga gggtctgggg ttgagactag gccacaagtc tagagtctct agagagacag  46380
tgttggaacc ccatggccca taatacattt cccattttct caggcagcca gaggtcatga  46440
atgtgaggat actgggaggt tggagcaacg ttcttgggag gcataaggaa gagcgaatgc  46500
ttcaagatcc ccgcagccca aactactcgc ctgctttgcc ccctaatgca tttttctctg  46560
ctgctccgta gctgtccgac ctcttcagat ctcttagtcc accctgccgt cttcctttat  46620
gccatgggtc ccactgttct ttcaactcat ccccctttcc ctcagtcccg gagtagctgc  46680
ggccagcaga gggtagactg agagcaggag agaaggacct gcctaggaac cccttctaga  46740
gatactgcat cctgcctggg agcaagtttt ccagggcagc tttgagaagt cttggagaaa  46800
caaacctact aaacctgaca gacagtaata ctatttgcac aatgcttttc tgtgggaaag  46860
gtagagcctt ttcactacgt attgagtaca tagagtgtga gggttgacct ggaacggcta  46920
tcctcctgga tgacgtgtgt tttctgaaga actacatgtt cgttgcaact cccacattag  46980
aatatgaagt cctaccgaga gagatacgga gactagacag atacagatgc atttgcatgt  47040
gaatacacaa tcccacaata cagacgtcaa aacccatacc agttattcca gagagatgga  47100
ttgggcagaa ggcagaagga gaatactctg atcgtttttc ggccacgtgt gtgtgttatc  47160
tcagtgtttc taagaagcgt ttgctacttt agattttta tttaaaaaaa atagtaataa  47220
tctattaagt atgagagatg tgcagagagg attagtgatc gagagccatt tttgctggtg  47280
gcaatcatat ggtactttta atgggaatat tagaaaggca ccggtaatga ccttgttgca  47340
gcacaaagga gagagtgtgg ggtgcccctg catgttgtcc cacctcttgt gacgtgtatc  47400
gttttggaat ttccagtggc ttgatcatga actactgcag gaatccagat gctgtggcag  47460
ctccttattg ttatacgagg gatcccggtg tcaggtggga gtactgcaac ctgacgcaat  47520
gctcagacgc agaagggact gccgtcgcgc ctccgactgt taccccggtt ccaagcctag  47580
aggctccttc cgaacaaggt aaggagtctg tggccagaca tctacacgct tcgatgctgg  47640
gatgaaaagc catggaaatt cccactgatg cagccgcctt caatggtaaa cggatgctcg  47700
agtgttgcct gagttctacc atgtaggagg aagcctccgt gcactctctg gggagccag  47760
cggagtgatt tctggtgcaa cgtggttggg ctttgtcttt aggatgggca caaaccctcc  47820
agggggatcg acttcaaaat tcaccttgtt gtaaaacggg ctacctcagt gtcccagcca  47880
aaatttttat tgtaacatgc tgtcaggtgt gtcactcttt ccaagccagt aagcttttcc  47940
ggggatttct tcaagtagcc agcattcaga gcaatcttca gcattgcaga ttctgagaaa  48000
tgtggctctg gagcctgtca ccctcgagaa acctaagagg gctgcattga ttccatgtgg  48060
ccctgggtct atggagcagt acatgagctc ccagtgctct aaggctcttc agccctaggc  48120
```

tttgaaggga gtgatttctc agtattctta aacctctttc tgatgacact tgtacctgtg 48180
aggggtctag agagaaagag tagtagactc ctactttact acaattcagg atgcagggca 48240
tgagaggatt ccctctctcc tccaagggaa gaagcttttg gcgtgcacac atccctgaga 48300
agcaaagtgt ctttgtcttc agtcagatac ataggaccgt tttctgcccc atggcccgga 48360
agccaaaggc cttggctttc atgatcaacg gtctagggaa acatgcaaaa tttccatgtc 48420
tgtcccaaac tcttccccccg acagccaatt accacctgca gcccgcattg ccaaatgcgg 48480
tgccgtttgc atgaagattc agtagagttt cctagaaagg tgctacctcg tgagctcact 48540
ttccaatgag gaatctgatc tgttgtgttt ctctaaggtg tcaggtgaaa tatttccaag 48600
aacttactac agttctagaa tgggaggaat ctgttgcttt ggtgtttgtt tgttggtcgg 48660
ttttctcaca tccatctgcc tatggataag gaaaagagaa cggtcgtaat tctcatagac 48720
tcctttctgg ttgtgtcaca aatggcttca catgtttctc tatgctcaga gatactcagc 48780
ttgatttccc gtgttttcat ttcagcaccg actgagcaaa ggcctggggt gcaggagtgc 48840
taccatggta atggacagag ttatcgaggc acatactcca ccactgtcac aggaagaacc 48900
tgccaagctt ggtcatctat gacaccacac tcgcatagtc ggaccccaga atactaccca 48960
aatgcgtatg tctttgttct ttaccataag agaagaaagg gccaagtgaa gtttctgtta 49020
caagagatgt gtctcaagct gagttctccg aactcaactt gtgacagatg cagatggcgt 49080
agcaaaatgt ctcaggatga ttgccttgga gctaagggtc tgagagaagg gaaatgttaa 49140
gctccctctc cttcctccta gttctattga gcagaaggga aatctggagg tgagaagatc 49200
acattatgaa gaaagtcaga atgacaaagg accagacact tagattaccc ttccacaaca 49260
ccaactaaac gtcaatggag actttccagt tggaattccg ttattctggc ttccacttcc 49320
tgaagggaag gttgcgtttg ccttttctct ctgggttcaa gaggaaagaa taggtgctta 49380
tttatggaca ggtgaattga tctgtttcta tatctacgta tattccgatt gtcagaaaaa 49440
cactcgttcc taagtaccag tggcctgaag ggatacaggt tcccagcaag agaagatcca 49500
aggaaggaag gcagatgaga gtcagcacag agagggatgc tgaaaagtaa aagggatggg 49560
tggatggaga gaagcccggg tctgaccacc caatggccaa tattttggcc acaagcgact 49620
accagagaca tggaaaaatg gtttctacat gtgggacaac agatggtaga ggacctagag 49680
aattgagaga ggggcaatga tgggctccac tccgcagatg ccttggcttt cttcctggat 49740
acccttcctg cactgaatag caaggagatg gagcccaagc agactgtagc catcttgctg 49800
aatggaggag agggattgga gtttgggatg actgtggtag ctgaaatttt tctaggtctg 49860
ctagaaataa gaactggttt gtgtggagga aaagagctct acaaatacgc atagaagtct 49920
cctccagtcg ttggcctgac atgacgctgc ctgtgcacag gaaatggttc cacgagaaag 49980
tgtggcaaag aacatttact gagaaacagc aagtacaaga gcacaggaag ctcaataaag 50040
aagagagaga tcacatagca ctctgggata ctggagttct tcccagctag accagagagt 50100
cctcacggag cacattgcca attcagtgga gaccccagaa cagccgtaat ttaaaggtac 50160
acttagtata ttactagaat aaagtcagct gcagacaacc ccttgcacag ctggaaagca 50220
agtgtccaag catcaaatcg gtttccaatc aatgaagtgc ctgtgagagg aaatctcaac 50280
tctctttaga agtaaacaac aaagtcgatt gcctcagcta tgcggtatcc gcagagtgag 50340
tcctaaattt aaaatctgac tacatgtaga aaagcgtttc gtgtgaccca tgaccaggaa 50400
ataaatcggg taatacaaac aggctcagga atgagagaaa tgattagaat tgcgtgaaaa 50460

-continued tttgacatat cagtatgata actgatttca aatatttaaa aaaacaacat gcaagaaagc 50520
agatatcata tcaagagaaa ttaacagtac agaatagcca aattaaatta aagaggtagt 50580
ataaaaaaag tatgtcttaa ttgaaaaaaa ttactgtatg gccggctgat caatttagac 50640
gtttcagagg aaaacattac ccaacacaca attctagaga acctacagaa tgagctacac 50700
acacacacac acacacacac acaaactgaa aacacaccca tactcacaca cacgcagaaa 50760
ctcacaagtt ctaacacaca cagacacgcg cacccctgaa gaaacagtga aatataaaat 50820
taagcgagcc tcacagacat gtaggaaaat atgaaaagat ttcctgcatg tgggaagcaa 50880
gtcacagtaa agagcaaggg agtttggaat agaaacaaat accggaatca aggatggctg 50940
ataacttttc aattacgaag aacattaaaa aaaatcacag aatcgtgaaa ctcaagggat 51000
cacataggga atttcggaaa aaaaacccaa cctgtatgat gtacttttgt acatcacagt 51060
tcgaaggtaa caaggcaaag atataataag aagaaacctg tcacgagaaa ctggaggaaa 51120
aagagctgtg tcttcctaca agtacactga tacaaattgc caatgtgttc acctcagaaa 51180
cactggaagc cagataccag ggaatattgt taaaatgata atcaggaaca aaaagagatc 51240
aaccgggaat gctgaatcca gcaataaaat gccttgaagg tcatccatgt cggataaatg 51300
catattgtgc actgccccaa agaaagaaac cggaaactgt aagaattgga aatcagcagg 51360
cttatgtaac aagagaggtg acccgaagga attaggtaga agaagaattg aacaagaaag 51420
gaactttctg cagcccacgt aatgaagaat ccagcaattg gcaaatgtag atagatgtaa 51480
atgcaaaata ttttcttgat caaatttcta tatctttgta aatgagagtt gactacttga 51540
aacaaaatga tagcaagata tttaacttca gcatatgtag aggtaagaat ttgaaatggt 51600
agcataaatc acgaagggat taattcgaag tgtaccgttg taagtttctt tacctcatgc 51660
acgatggtgt gtcatattaa taaaagggta ctgtgcgggt tcgaagggat attgcaaatc 51720
ctagagcaat cacaaaggtt tgaactctga ggtttttggt ataataagaa tagtccatgc 51780
attcaaaaga gggaagccaa ggaagaacta gaagtctttc aagagctcag gctcttatac 51840
atccagttgc tcattgaacc agcttcctgg aatggagggt ctggggttga gactaggcca 51900
caagtctaga gtctctagag agacagtgtt ggaaccccat ggcccataat acatttccca 51960
ttttctcagg cagccagagg tcatgaatgt gaggatactg ggaggttgga gcaacgttct 52020
tgggaggcat aaggaagagc gaatgcttca agatccccgc agcccaaact actcgcctgc 52080
tttgccccct aatgcatttt tctctgctgc tccgtagctg tccgacctct tcagatctct 52140
tagtccaccc tgccgtcttc ctttatgcca tgggtcccac tgttctttca actcatcccc 52200
ctttccctca gtcccggagt agctgcggcc agcagagggt agactgagag caggagagaa 52260
ggacctgcct aggaacccct tctagagata ctgcatcctg cctgggagca agttttccag 52320
ggcagctttg agaagtcttg gagaaacaaa cctactaaac ctgacagaca gtaatactat 52380
ttgcacaatg cttttctgtg ggaaaggtag agccttttca ctacgtattg agtacataga 52440
gtgtgagggt tgacctggaa cggctatcct cctggatgac gtgcgttttc tgaagaacta 52500
catgttcgtt gcaactccca cattagaata tgaagtccta ccgagagaga tacggagact 52560
agacagatac agatgcattt gcatgtgaat acacaatccc acaatacaga cgtcaaaacc 52620
cataccagtt attccagaga gatggattgg gcagaaggca gaaggagaat actctgatcg 52680
tttttcggcc acgtgtgtgt gttatctcag tgtttctaag aagcgtttgc tactttagat 52740
tttttattta aaaaaaatag taataatcta ttaagtatga gagatgtgca gagaggatta 52800
gtgatcgaga gccatttttg ctggtggcaa tcatatggta cttttaatgg gaatattaga 52860
aaggcaccgg taatgacctt gttgcagcac aaaggagaga gtgtggggtg cccctgcatg 52920
ttgtcccacc tcttgtgacg tgtatcgttt tggaatttcc agtggcttga tcatgaacta 52980
ctgcaggaat ccagatgctg tggcagctcc ttattgttat acgagggatc ccggtgtcag 53040
gtgggagtac tgcaacctga cgcaatgctc agacgcagaa gggactgccg tcgcgcctcc 53100
gactgttacc ccggttccaa gcctagaggc tccttccgaa caaggtaagg agtctgtggc 53160
cagacatcta cacgcttcga tgctgggatg aaaagccatg gaaattccca ctgatgcagc 53220
cgccttcaat ggtaaacgga tgctcgagtg ttgcctgagt tctaccatgt aggaggaagc 53280
ctccgtgcac tctctggggg agccagcgga gtgatttctg gtgcaacgtg gttgggcttt 53340
gtctttagga tgggcacaaa ccctccaggg ggatcgactt caaaattcac cttgttgtaa 53400
aacgggctac ctcagtgtcc cagccaaaat ttttattgta acatgctgtc aggtgtgtca 53460
ctctttccaa gccagtaagc ttttccgggg atttcttcaa gtagccagca ttcagagcaa 53520
tcttcagcat tgcagattct gagaaatgtg gctctggagc ctgtcaccct cgagaaacct 53580
aagagggctg cattgattcc atgtggccct gggtctatgg agcagtacat gagctcccag 53640
tgctctaagg ctcttcagcc ctaggctttg aagggagtga tttctcagta ttcttaaacc 53700
tctttctgat gacacttgta cctgtgaggg gtctagagag aaagagtagt agactcctac 53760
tttactacaa ttcaggatgc agggcatgag aggattccct ctctcctcca agggaagaag 53820
cttttggcgt gcacacatcc ctgagaagca aagtgtcttt gtcttcagtc agatacatag 53880
gaccgttttc tgccccatgg cccggaagcc aaaggccttg gctttcatga tcaacggtct 53940
agggaaacat gcaaaatttc catgtctgtc ccaaactctg cccccgacag ccaattacca 54000
cctgcagccc gcattgccaa atgcggtgcc gtttgcatga agattcagta gagtttccta 54060
gaaaggtgct acctcgtgag ctcactttcc aatgaggaat ctgatctgtt gtgtttctct 54120
aaggtgtcag gtgaaatatt tccaagaact tactacagtt ctagaatggg aggaatctgt 54180
tgctttggtg tttgtttgtt ggtcggtttt ctcacatcca tctgcctatg gataaggaaa 54240
agagaacggt cgtaattctc atagactcct ttctggttgt gtcacaaatg gcttcacatg 54300
tttctctatg ctcagagata ctcagcttga tttcccgtgt tttcatttca gcaccgactg 54360
agcaaaggcc tggggtgcag gagtgctacc atggtaatgg acagagttat cgaggcacat 54420
actccaccac tgtcacagga agaacctgcc aagcttggtc atctatgaca ccacactcgc 54480
atagtcggac cccagaatac tacccaaatg cgtatgtctt tgttctttac cataagagaa 54540
gaaagggcca agtgaagttt ctgttacaag agatgtgtct caagctgagt tctccgaact 54600
caacttgtga cagatgcaga tggcgtagca aaatgtctca ggatgattgc cttggagcta 54660
agggtctgag agaagggaaa tgttaagctc cctctccttc ctcctagttc tattgagcag 54720
aagggaaatc tggaggtgag gagatcacat tatgaagaaa gtcagaatga caaaggacca 54780
gacacttaga ttacccttcc acaacaccaa ctaaacgtca atggagactt tccagttgga 54840
attccgttat tctggcttcc acttcctgaa gggaaggttg cgtttgcctt ttctctctgg 54900
gttcaagagg aaagaatagg tgcttattta tggacaggtg aattgatctg tttctatatc 54960
tacgtatatt ccgattgtca gaaaaacact cgttcctaag taccagtggc ctgaagggat 55020
acaggttccc agcaagagaa gatccaagga aggaaggcag atgagagtca gcacagagag 55080
ggatgctgaa aagtaaaagg gatgggtgga tggagagaag cccgggtctg accacccaat 55140
ggccaatatt ttggccacaa gcgactacca gagacatgga aaaatggttt ctacatgtgg 55200

```
gacaacagat ggtagaggac ctagagaatt gagagagggg caatgatggg ctccactccg  55260
cagatgcctt ggctttcttc ctggataccc ttcctgcact gaatagcaag gagatggagc  55320
ccaagcagac tgtagccatc ttgctgaatg gaggagaggg attggagttt gggatgactg  55380
tggtagctga aatttttcta ggtctgctag aaataagaac tggtttgtgt ggaggaaaag  55440
agctctacaa atacgcatag aagtctcctc cagtcgttgg cctgacatga cgctgcctgt  55500
gcacaggaaa tggttccacg agaaagtgtg gcaaagaaca tttactgaga aacagcaagt  55560
acaagagcac aggaagctca ataaagaaga gagagatcac atagcactct gggatactgg  55620
agttcttccc agctagacca gagagtcctc acggagcaca ttgccaattc agtggagacc  55680
ccagaacagc cgtaatttaa aggtacactt agaatattac tagaataaag tcagctgcag  55740
acaacccctt gcacagctgg aaagcaagtg tccaagcatc aaatcggttt ccaatcaatg  55800
aagtgcctgt gagaggaaat ctcaactctc tttagaagta aacaacaaag tcgattgcct  55860
cagctatgcg gtatccgcag agtgagtcct aaatttaaaa tctgactaca tgtagaaaag  55920
cgtttcgtgt gacccatgac caggaaataa atcgggtaat acaaacaggc tcaggaatga  55980
gagaaatgat tagaattgcg tgaaaatttg acatatcagt atgataactg atttcaaata  56040
tttaaaaaaa caacatgcaa gaaagcagat atcatatcaa gagaaattaa cagtacagaa  56100
tagccaaatt aaattaaaga gctagtataa aaaaagtatg tcttaattga aaaaaattac  56160
tgtatggccg gctgatcaaa ttagacgttt cagaggaaaa cattacccaa cacacaattt  56220
tagagaacct acagaatgag ctacacacac acacacacac acacacacac acacaaactg  56280
aaaacacacc catactcaca cacacgcaga aactcacaag ttctaacaca cacagacacg  56340
cgcacccctg aagaaacagt gaaatataaa attaagcgag cctcacagac atgtaggaaa  56400
atatgaaaag atttcctgca tgtgggaagc aagtcacagt aaagagcaag ggagtttata  56460
atagaaacaa ataccagaat caaggatggc tgataacttt tcaattacga agaacattaa  56520
aaaaaatcac agaatcgtga aactcaaggg atcatatagg gaatttcgga aaaaaaaccc  56580
aacctgtatg atgtactttt gtacatcaca gttcgaaggt aacaaggcaa agatgtaata  56640
agaagaaacc tgtcacgaga aactggagga aaaagagctg tgtcttccta caagtacact  56700
gatacaaatt gccaatgtgt tcacctcaga aacactggaa gccagatacc agggaatatt  56760
gttaaaatga taatcaggaa caaaaagaga tcaaccggga atgctgaatc cagcaataaa  56820
atgccttgaa ggtcatccat gtcggataaa tgcatattgt gcactgcccc aaagaaagaa  56880
accggaaact gtaagaattg gaaatcagca ggcttatgta acaagagagg tgacccgaag  56940
gaattaggta gaagaagaat tgaacaagaa aggaactttc tgcagcccac gtaatgaaga  57000
atccagcaat tggcaaatgt agatagatgt aaatgcaaaa tattttcttg atcaaatttc  57060
tatatctttg taaatgagag ttgactactt gaaacaaaat gatagcaaga tatttaactt  57120
cagcatatgt agaggtaaga atttgaaatg gtagcataaa tcacgaaggg attaattcga  57180
agtgtaccgt tgtaagtttc tttacctcat gcacgatggt gtgtcatatt aataaaaggg  57240
tactgtgcgg gttcgaaggg atattgcaaa tcctagagca atcacaaagg tttgaactct  57300
gaggtttttg gtataataag aatagtccat gcattcaaaa gagggaagcc aaggaagaac  57360
tagaagtctt tcaagagctc aggctcttat acatccagtt gctcattgaa ccagcttcct  57420
ggaatggagg gtctggggtt gagactaggc cacaagtcta gagtctctag agagacagtg  57480
ttggaacccc atggcccata atacatttcc cattttctca ggcagccaga ggtcatgaat  57540
gtgaggatac tgggaggttg gagcaacgtt cttgggaggc ataaggaaga gcgaatgctt  57600
```

caagatcccc gcagcccaaa ctactcgcct gctttgcccc ctaatgcatt tttctctgct 57660
gctccgtagc tgtccgacct cttcagatct cttagtccac cctgccgtct tcctttatgc 57720
catgggtccc actgttcttt caactcatcc ccctttccct cagtcccgga gtagctgcgg 57780
ccagcagagg gtagactgag agcaggagag aaggacctgc ctaggaaccc cttctagaga 57840
tactgcatcc tgcctgggag caagttttcc agggcagctt tgagaagtct tggagaaaca 57900
aacctactaa acctgacaga cagtaatact atttgcacaa tgcttttctg tgggaaaggt 57960
agagcctttt cactacgtat tgagtacata gagtgtgagg gttgacctgg aacggctatc 58020
ctcctggatg acgtgcgttt tctgaagaac tacatgttcg ttgcaactcc cacattagaa 58080
tatgaagtcc taccgagaga gatacggaga ctagacagat acagatgcat ttgcatgtga 58140
atacacaatc ccacaataca gacgtcaaaa cccataccag ttattccaga gagatggatt 58200
gggcagaagg cagaaggaga atactctgat cgtttttcgg ccacgtgtgt gtgttatctc 58260
agtgtttcta agaagcgttt gctactttag attttttatt taaaaaaaat agtaataatc 58320
tattaagtat gagagatgtg cagagacgat tagtgatcga gagccatttt tgctggtggc 58380
aatcatatgg tacttttaat gggaatatta gaaaggcacc ggtaatgacc ttgttgcagc 58440
acaaaggaga gagtgtgggg tgcccctgca tgttgtccca cctcttgtga cgtgtatcgt 58500
tttggaattt ccagtggctt gatcatgaac tactgcagga atccagatgc tgtggcagct 58560
ccttattgtt atacgaggga tcccggtgtc aggtgggagt actgcaacct gacgcaatgc 58620
tcagacgcag aagggactgc cgtcgcgcct ccgactgtta ccccggttcc aagcctagag 58680
gctccttccg aacaaggtaa ggagtctgtg gccagacatc tacacgcttc gatgctggga 58740
tgaaaagcca tggaaattcc cactgatgca gccgccttca atggtaaacg gatgctcgag 58800
tgttgcctga gttctaccat gtaggaggaa gcctccgtgc actctctggg ggagccagcg 58860
gagtgatttc tggtgcaacg tggttgggct ttgtctttag gatgggcaca aaccctccag 58920
ggggatcgac ttcaaaattc accttgttgt aaaacgggct acctcagtgt cccagccaaa 58980
atttttattg taacatgctg tcaggtgtgt cactctttcc aagccagtaa gcttttccgg 59040
ggatttcttc aagtagccag cattcagagc aatcttcagc attgcagatt ctgagaaatg 59100
tggctctgga gcctgtcatc ctcgagaaac ctaacagggc tgcattaatt ccatatggtc 59160
ctgggtctat ggagcagtat atgagctccc aatgctctaa ggctcttcag tcctaggctt 59220
tgaagggagt gatttctcag tgttcttaaa cctctttctg atggcacttg tacctgtgag 59280
gggtctagag agaaaggtta gtagacttct cctttactgc aattcaggat gcagggcatg 59340
agaagattcc ctccctcctc caagggaaga aggttttggc gtgcacacat ccttgagaag 59400
caaagtgtct ttgccttcag tcagatatat aggatcgttt tctgccccat ggcctggaag 59460
ccagaggcct tggctttcat gatcaacgat ctagggaaac atgcaaaatt tccatgtctt 59520
tcccctcctc tgccctcgac agccaattac cacctgcatc ctgcattgcc aaatgcagtg 59580
ccctttgtat gaacattcag tagagtttca tagaaaggtg ctacttcgtg agcgcacttt 59640
gcagtgagaa ggagtctgtt ctgttctgtt tttctaagga tttcaggtga aatatttcct 59700
agaacttact acagttctag attggtagga atctgtaggt ttgctgtatg ttttttggtt 59760
ggttttctcc catccatctg cctacaggta agggaaagat aacgttcata attctcatag 59820
actcctttct ggttgtgtca taaatggctt cacatatttc gttattctca gagatactca 59880
gtttatttct tgtgttttca tttcagcacc gactgagcag aggcctgggg tgcaggagtg 59940

```
ctaccacggt aatggacaga gttatcgagg cacatactcc accactgtca ctggaagaac    60000
ctgccaagct tggtcatcta tgacaccaca ctcgcatagt cggaccccag aatactaccc    60060
aaatgcgtat gtctttgttc tttaccataa gagaataaag ggccaactga agtttctgtg    60120
acaagagaca tgcttcaagc tgagttctcc gaactcaact tgtgtcagat tcagatggtg    60180
tagcaaaatg tctcaggatg atttccttgg agctaagggt ctgagagaag agaaatgtta    60240
agctgcctca ccttcctcct agttttgtgg agcagaaggg aaatgaggag gcgaggagat    60300
caccttatga agaaagtcag aatgacgaac caccaaacac ttagattacc cttgcccaac    60360
acccactaag cgtcaatgaa gactttccag ttggaattcc gttattctga cttccaattc    60420
ctgaagggaa gattgtgttt gccttttctg tctgggctca tgaggaaagt ttatgtgctt    60480
acttatggac aggtgaattg atctgtttct atttctacct gtattccaat agggagaaaa    60540
tctcttggtc ctaagtacca gtggcctgaa aggatagagg ttcccagcaa gagaagatcc    60600
aaggaaggaa ggcagatgag agtcagcaca gagagggatg ctgaaaagta aaagggatgg    60660
gtagatggat agaagccctg gtctgaccac cccatggcca atcatttggc cataatcaac    60720
aaccaaagac atggaaaaat ggtttctaca tgtgggacaa cagatggtag aggacctaga    60780
gaattgagag agggccaatg atgagctcaa ctccatagat gccttggctt tcttcctgga    60840
tacccttcct gcactgaata gcaaggagat ggagctcaag cagcctgtag ccatctagct    60900
gagcagagga gagggattgg agtttgggat gactctggta ttttctaggt ccgctacaaa    60960
taagaactgg tttgtggagg aaaggagctc tacaaatacg catagaagtc tcctccagta    61020
gttggcctca catgacactg catgtgcaca gaaaatggtt ctacagaaag tgtggcaaag    61080
aacatttact gagaaacagc aactacaaga gaacagcaag ctcaattaag aagatagaga    61140
tcacatagca ctctgtgtta ttggagttct taccagctag atgagagagt gctcacggaa    61200
cacattgcca attcagtgga gaccccagaa cagccataat ttcaaagtac aattagtata    61260
ttactagaat aaaggcagct gcagacaacc ccttgcacag ctgaaaagca agtgtccaag    61320
catcaaatgg gtttccaatc aatgaagtgc ctgtgagagg aaatctcaac tctcttcaga    61380
agtaaacaac aaagtcaatt gcctcagcta tgcggtatcc ccagagtgag tcctaaatta    61440
aaaatttgac tacgtgtaga aaagaatttc gtgtgatcca tgaccagaaa ataaatcagg    61500
caatacaaac aggctcagaa atgacatcga taattagaat tgcatgaaaa tttgacatat    61560
cagtatgata actgatttca gatatttaaa aaaagtgcaa caaagcaggt atcatatcaa    61620
gacaaattaa tagtatagaa tagccaaatc aaattaaaga actattatac aaaaagtatg    61680
tcttaaatga agaaattact gtatgtccgc ctgaaaaatt tagatgtttc agaagaaaaa    61740
attaaccaaa aacaattctg cagaacctac agaatgagcc acacacacac acattcaaaa    61800
cacacccata cacacacaca tgcaaaaact cacaagttct aacacacaca caaacacaca    61860
cacacatgca catccctaaa gaaataggga aatataaaat taaccgaccc tcagagacat    61920
gcaggaaaat ataagaagat ttcctgcatg tgggaagcaa gtcacagtaa agagcaaggg    61980
agtttggagt agatacaaat accggaatca cggatggctg ataacttttc aattatgaag    62040
aacgttagaa aaatcacaga ttcatgaaac taaagggatc aaataggaaa tttcgagaaa    62100
aaaaactaca tgatgcactt ctctacatca cagttcaaag gtaacaaggc aaggatataa    62160
gaagaagaaa catctcacga gaaactggag aaaaaagagc tgtgtcttcc tagagtacag    62220
tgatacaaat tgctaatgcg ttcacctcag aaacactgga agccagatac cagggaatat    62280
tattaaaatg ataatgagga acaagaagag atcaaccgag aatgctgaat ccagcaataa    62340
```

aatgccttga agatcatcca tgttggataa atgcatattg tgcactgccc aaaacaaaga 62400
aactggaaag tgtaagactt tggaatcagc aggcttatgt agcaacagag gtgacccgaa 62460
agaattaggt ataagaagaa tagaagaatt gcatgaaaat ttgacatatg actaagataa 62520
ctatttcaaa tatttaaaaa aagatgaata tgtaataaaa cagataaaat atcaaaagaa 62580
agtaacagta ttgactagcc aaatcaaatt aaagacttag tgtaaaaagc tatgtcttaa 62640
aagaaaaaat tactggatgg ctgcctgatc aatttagaca tttctgaata ggaaactaac 62700
caaaaatcaa ttctacagaa ccaactacac acatatatac acatacaaca cacccataca 62760
cacccacgca aaaactcaca agttcacaca cacacacaca cacacacaac cctcaagaaa 62820
tagtgaaata gaaaaccaac cgaacctcac agacatgttg caaaatagga aaagatttcc 62880
tgcatatggg aagcaagtca cagaaaagag aacgggagat tggaaacaga aacaaatacc 62940
ggaatcaagg atggccgaaa acttttcatt gatcaagaat attaacaaaa tcgcaaaaac 63000
acgaaattca atgcatcaaa taggcgtttc gaaaaaaaga aaaaatctgg tatgatgcac 63060
ttttgtactt cacattttca cggtaagaag acaaagatat aataacaaga aacttcttat 63120
gagaaactgg ggaaaaacaa gctgtttctt gctagaagaa cagtgataca aattgctaat 63180
gcattctcgt caaaaacact ggaagccaga taccgggaat gttattaatg tggtaaacag 63240
gaacaagaag agatcaacca agaatgctaa atccagcaat aaaatgcctt gaagatcatc 63300
catgctgcat aaatgtatgt tgtgcactgc cccaaacaaa gaaaccggaa actgtaagaa 63360
tttggaatca gcaggctgat gtaacaagag aggtgaccca aaggaattag gtagaagaag 63420
aatagtacaa gaagggaact ttctgcagcc catgtaatga agaacccagc aattggcaaa 63480
tgtagatgta aatgcaaaat attttcttga ccaaatttct atatattttt aaatgagcgt 63540
tgactactgg aaacaaaatg atagcaatat atttaatttt agcatatgta gaggtaagaa 63600
tttgaacaag tagcgtaaat catgtaggga ataattagaa gtgtaccatt gtaagtttct 63660
tacctcatgc acaatggtat gtaatattaa taaaatgtta ctgtgtgggt tcaaggagat 63720
attgcaaatc ctagagcaat cacaaagttt tgaactctga ggtatattgt ataataagaa 63780
tattccatgt attcaaaaga gagaagccaa ggaagaaaga aatttgtcac gagtttgggc 63840
tcttagtaca tcctgtagct cattgaacca gcttcctgga atggagggtc tgggattgac 63900
actaggccac atgtatagag tctctagaga gacagtgttt catccccatg gcccgtaata 63960
catttcccat tttctcaggc agccacaggt catgaatgtg aggatagaga gaggttggag 64020
caacgttctt gggaggcata aggaagagca aatgcttcaa gatccccgca gcccaaactc 64080
ctacctgctt tgccccctaa tgcagtgttc ctccgtagct gtccgacctc ttcagatctc 64140
ttagtctacc ctgccatctt cctttatgcc atgggtccca ctgttctttc aactcatccc 64200
cctttccctc agtgcagagt agctgcggcc agcagagggt agactgagag caggagagaa 64260
ggtcctgccc aggaacccat tctagagatg ctgcattctg cctgggagca agttttccag 64320
ggcagctttg agaagtcttg cagaaacaaa cctatttgac ccacatgata tgggaatgac 64380
agaaagtaat acaatttgca cagtgctttt ccatgggaaa agtagagcct tttcgcgagg 64440
ttttgagtac atagagagtg aaggttgacc tggaaaggtt atcctcctgg atcccatgtt 64500
ttttctgaag aactacctgt tagttgcaac ttgcacatta gaatatgaag tcctaccgag 64560
agagatacgg agaactagat aaatacagat acttttgtat gtgaataaac gattccacaa 64620
tacacacatc aaaatccata ccagttattc cagagagatg gattgggcag aaggcagaag 64680
gagaatactc tgatcgtttt ttgcccacgt gtatgtatta tctcagtgtt tctaagaagc 64740
gtttgctact ttagattttt ttttataata ataatctttt aagtatgaga aatgtgcaga 64800
caggattagt gattgagagc catttgtgct tgtggcaatc atatggtact tttatgggaa 64860
tattagaaag gcactggtaa tgaccttgtt gcagcacaaa ggagagggtg tggggtgccc 64920
ctgcatattg tcccacctct tgtgacgtgt atcgttttgg aatttccagt ggcttgatca 64980
tgaactactg caggaatcca gatcctgtgg cagcccctta ttgttatacg agggatccca 65040
gtgtcaggtg ggagtactgc aacctgacac aatgctcaga cgcagaaggg actgccgtcg 65100
cgcctccaac tattaccccg attccaagcc tagaggctcc ttctgaacaa ggtaaggagc 65160
ctgtggccag aaacctacac gtttcgatgc tgggatgaaa agccatggaa attcccactg 65220
atgcagcagc ctccaatggt aaacggatgc tcgagtgttg actgagttct gtcatgtagg 65280
aggaagcctc cgtgcactct ctgggggagc cagcggattg atttctggta caacgttggg 65340
tgggctgtgt ctttagaatt ggcacaaacc ctccagggtg atcgacttca caactcacct 65400
cgttgaaaaa tgggctatct cagtgtctta gccaaaattt ttattgtaac atgctgtcag 65460
atgtgtgact ctttccaagc cagtaagctt ttcctgggac ttcttcaatt agccagcatt 65520
cagtgcaatc ttcagcattg cagattcaga gaaatgtggc tctggagcct gtcacccttg 65580
agaaacaggg ctaacagggt tgcattaatt ccaaatcacc ctggttctat ggagcagtac 65640
atgaactccc aatgatctat gtttcaggac ttcctcagtc ataggtgggc tctgcagccc 65700
taggttttta agtgagtgac tgccccgtgt tctggtggca gttgtacctg tgagcggtct 65760
ggatagaaag agtcggagac ttctgtatta ttgcaactca ggatgtgggt catgagagga 65820
tttcatctct cctgcagggg agtaagctgt tcgcctccac ccatccctga taactgaagt 65880
gtctttgtct gcagtcctag acgaaggact gttgtctctc ccatggccca gaagctgaag 65940
accttgcctt ttgttatgaa acgttcattg ttttcatgtc tgtccgtttc tctgccccta 66000
acacccaatc accatgtatg gcctgtaccc ccaaatgcat cgtgctttgc tgtttgctgc 66060
cccatagtcc tcatgaacat tcagtagaaa ttcccataaa tgtgcttgca cgtgagcaca 66120
gtttccattg agaagccctc tcatttgtcc tttttttcta agcttttatg tgaaatattt 66180
ctaagaactt actacagttc taaagtgtta ggaatttgtt tctttggtgt ttttgtttgt 66240
tggttggttg ttgcttttct caagtccatc tgcctacaaa taaagaaaca agaatgttac 66300
ttgtcatatt ctcctgaggt cataattctc agagactttt ttctggtttg tgccataagt 66360
ggcttcacat gtttgtctct tcttggaaac actcagtttg atttcttttc ttttcatttc 66420
agcaccaact gagcaaaggc ctggggtgca ggagtgctac cacggaaatg gacagagtta 66480
tcaaggcaca tacttcatta ctgtcacagg aagaacctgc caagcttggt catctatgac 66540
accacactcg catagtcgga ccccagcata ctacccaaat gcgtatgtct attttcttta 66600
ccataagtga aggaagggtc agtggaaatt tctgttagta gagtcatgct tcaagctgag 66660
tgttcaggac tcaagttgtc tcagatgaac agtgcatagc aaaatgtctc aggaacattg 66720
tctttgagca aagagtctaa gagaagacaa atgttaatct ggctctcctt cctcctagtt 66780
taatggagca gaaaggtatc tggaggcaag gatatcacat taagaaacaa gtcaagatga 66840
caaatgatga aactcttaga gtacccttcc acaacaccca ctaaggttca atgcagcctt 66900
ttctccttgg aattctatta aactaaactc caattcctga agtgaaggtt ctgttggggt 66960
tttctgtttt ggcttacaag gaaagtatat atgtatatct atggagaggc aaatctatct 67020
ctttctatat ctacgtctat tccaatatgt agaaacacag tcggttctga ccaccagtgg 67080
tctgaaggga tactggttgt tagagaataa aaatggcagg aaggcagatg agagtcagca 67140
aagagagaga tcctgtaaag taaaagggtg gatagatgga cagaagccca ggtctgacca 67200
gcccatggcc aggctttagg ccataagtga caccaaagac atggaaaaat ggtttctaca 67260
tgttggacaa cagacagtag tggaccaaaa gaatagtgac agggggaaca atgagatcaa 67320
ctccatagat accttggctt tcttcctgga ggcccttctt gcactgaaga gcaaggtgat 67380
ggagcccaga tggactgtag ccatcttcct gaatgcagga gagagattgg aatttgggac 67440
tactgtggta gctaggattt tataggcctg ctgagaatga gaatggattt gtggatgaaa 67500
ggagctccag gggcacgcat agtagtctcc tcgaatcttt ggctaaacat gacgttgcat 67560
gtgcccagaa aaaggttcca caagaaagta gagaaaagaa tatatcctga ggaatagcaa 67620
ctgcgattga acagtgagct caataaagag gacagagccc tcatagcatt ctgggatact 67680
ggagttctga ccagctggag gagagacctc actgaacctc ttgggaatac agtagagact 67740
ccagaaaagt catactttag gagtagaatt agtaaatttc tagaaaaaaa ggcagctcta 67800
gacaaaccct ggcaaaactg aaaagcaagt ctccaagcat taaaatcatt tccaagtcaa 67860
ttaactgcct gggagaggaa aaccctcttt agaggtaaac aacaaagtca agtggctcag 67920
ctatgtggtg ttcacagtgt gagttctaaa tttaaaactt gactacacat agagaagctt 67980
ttagtatgaa ccatgaccag gtgaaaaatc agtcaataca aatagaccta gaaatgacag 68040
aaatgattag aatggcaaaa aatttgacat atcaatatgt caactgagtt ttaggtttta 68100
agaaaacatg aatacggaat gaagcagata ccatatcaag agacagtaac agtatagaag 68160
agccaaatta aattaaagaa ctagtataag aaggtatgtc ttaaatgaaa aaattactgg 68220
atgtattccc aatggagtga gatgtttcag aagtaaaaac taactgaaaa acaattttat 68280
accacctaca gaaccagcta cacatacaca aatgacacac acatatacac acatactcac 68340
acatgcacag gcttagaaac atgcacgcac acacacacac acacacacac acacctccac 68400
aaatactaaa aaatgaaatc cactgatcct cacagacagg cgggaaaata taaaaagatt 68460
tcctgcatgt gggtaggaag tcacagaagg agaggaagga gagattgcta caggaacaaa 68520
tactggaagc aaggatagct aaaaactttt caaataagaa gaatattaaa aaccacagat 68580
tcaagaagct gaatgaatca gacagggaat ttccaaaaaa aaaaaaaaaa aaactgtatg 68640
attcactttt gtacatcacc gttcaacagt cagaaggcaa agatataata acaagaaaca 68700
tctcatgaga aactggagga aaaagagctg tgtcttgcta gaagaacagt gatacaaatt 68760
gctaatgcat tctcatcaga aacactggaa cccagttaac aggggatatc attaaaatga 68820
taaactagaa aaaaaagaga tcaaatgaga atgctacatc cagcaataaa atgccttgaa 68880
gatcatccat gttggataaa tgcatattgt gcactgcccc aaataaataa accaaaaact 68940
aataatttgg aatcagcagg cttgtgtaac aagagatgtt gcccaaagaa aattagctag 69000
aagaagaata gttcaagagg agaactttct gcagcccacg taatgaagaa cccagcaaat 69060
ggcaaatgta gatgtaaatg caaaatattt tcttgatcaa atttctatat ctttttaaat 69120
gagagttgac tacttgaagc aaaatgatag caatatattt aactttagca tatgtagagg 69180
taaaaatttg aacatataga ctaaatcatg tggggaataa ttggaagtgt accattgtaa 69240
gtttcttacc ttatccacga tggtatgtaa tattaatgaa aggttgaatt tgtgggtcca 69300
aagggatatt gtaaatccta aagcaatcat aaaattttga attctgaggg atattatata 69360
ataagaattt tccatgtatc caaaagaggg aagccaagga agaaaaagaa gtctttcaag 69420
tactcaagct ctgagcacat ccagttgctc attgaaccag cttcctggaa tggagggtct 69480
gggcttgaga ctaggtcaca tgtgtagagt ctctagagag acagtgttgg atccccatgg 69540
cccataatac atttcccgtt ttcccaggca gccacaggtc acgaatggga ggattctgag 69600
aggttggagc aatgttctta ggaggcataa ggaggagtga atgctctgag atttccccag 69660
cctgaggtcc tccatagctg cccgacctct tcagacctca tagtctgccc agctgtctcc 69720
ctttatgcca tgagtgccac tgttctttca actcatcccc cattccctca gtcccggaat 69780
tgctgtggcc agcagaggat ggactgagag caggagagga agtcctgacc aggaacccat 69840
cctagagata ctgcatcctg cctgaaagct aggtttccag ggcagctttg agaagtcttg 69900
cagaaagaaa cccacttgac ccacctgata cggtatcgac agacaggaat actttttgtg 69960
caatggtttt acatgctgaa catagagcct tttggctaca ttttgagtac attgaatgag 70020
actgctggcc tgggaaggat atcatgctgg atgccatttt tttctctgga gaactatgtg 70080
ttagttccaa ctcgcacatt actatatgaa gtcctacaca gagagatacg gagagctaga 70140
cagatagaga tacttttgta tgtgcataac caattccaca atacacacgt caaaatccat 70200
accagttatt ccagagagat ggattgggca gaaggcagaa ggaggatatt ctgatccctt 70260
tttggccaca tgtatgtata atctcagtgt ttctaggaag tgtgtgctgc attagatttt 70320
ttttctttaa aaaaagtgat aatatattaa gtatgagaaa tgtgcagaga ggattagaga 70380
ttgagagcca tttgtcattg tggcaattgt atggtatctc ttttgggaat atttcaaagg 70440
caccagtaat gaccttgttg tagcaaaata tacagtgttc ctgcatatgt acccattttt 70500
tgtgatgtgt attcttttgg aatttccagt ggcttgatca agaactactg ccgaaatcca 70560
gatcctgtgg cagccccttg gtgttataca acagatccca gtgtcaggtg ggagtactgc 70620
aacctgacac gatgctcaga tgcagaatgg actgccttcg tccctccgaa tgttattctg 70680
gctccaagcc tagaggcttt ttttgaacaa ggtaagaagt tgtgccagac atttacctgc 70740
ttggatgctg ggatgaaaag ccatggatac cccccactgac gcacaaccct tcagtgctac 70800
actggttctc gtgtgttggt tctgggtctg ccatgtggga ggaagcctta gcgcactctc 70860
tgggggagcc agaggtgtga tttttggtgc aacctgtgcg agctgtgtct ttaggatggg 70920
cggaaaccat tctgggtgct cgacttcacc actcccctca ttgtaaaagg ggctatctca 70980
ttgtcctaga caaaattctt attgtaatat gctgtcagat gtgtgtgtct ttccaagcca 71040
gtaaactttt ccagggattt cttcaagtag acagcattca gtgcaatctt cagcattgca 71100
gattccgaga aatgtggctc tagatcctgt tatccttgag aaacctaact gggttgcatt 71160
aattccatat ctccctgggt ctgtggagta gtacatgagc tcccgaagct ctatctctca 71220
ggtctttttc agtccgaggc aggttgtgca gttcttagct ttgaagggag tgattttttc 71280
gtgtgctttt gcctctttct gatggaactt gtacctgcgg ggggtctgga gaaaaagagt 71340
agtagacttt tgctttattg caatgcatta tgctgggcac gagaggattc cctatcttat 71400
tgtaggtgat aagcttttgg cctccactca tccctgagaa gtgaagtgtt gttgcctaca 71460
gttttagctg caggactgtt gtctgcccca tcaccaggag tttaatgctt tctttttga 71520
gcaatcatct agggacacat gcaaggtttt tatatgtcct tgcctcctcc ccaaaaaaacc 71580
attttaatgc ttggagactt gcttttcagc tttgccaaat gcatcaccct ttcttctatg 71640
ctgttccatg tcgtcatgaa cactctgtag agattcctag aaatgagctt ccatgttagt 71700
ggagtttccg atgagaagca atctgatatt tcttttccac taagttttac atgaaatatt 71760
tctaagaact tactacagtt ctagaatggt aggcatctct tactttcgtg tttgtttgtg 71820

-continued

```
tgttttctca tgtccatttg cctattaata aagaatagag aatggttgta aatctcagtg  71880
actctttttt ggtttatgtc ataaatggct tcctgtattt ttctgttcta ggaaataata  71940
agcttgatgt cttctgtttt aatttcagca ctgactgagg aaaccccccgg ggtacaggac  72000
tgctactacc attatggaca gagttaccga ggcacatact ccaccactgt cacaggaaga  72060
acttgccaag cttggtcatc tatgacacca caccagcata gtcggacccc agaaaactac  72120
ccaaatgcgt acgtctttgt tctttaccat aagcgaagga agggccaatg gaagtttctg  72180
ttagaagagt catgcttcaa ggtgactgct caggactcaa cttggctcag atgcagagga  72240
acatttcctg tgagcaaaag ttcttagaga agactttgtt tttttgagac agagtcttgc  72300
tttgttgccc aggctggagt gcagtggcat gatctcggct cactgcaagc tccgcctccc  72360
gggttcacac cattctcctg cttcagcctc tctagcagct gggactacag gcacccacca  72420
ccacacccgg ctaatttttt gtatttttag tagagacagg gtttcactgt tctagccagg  72480
atggtcttgg tctcctgacc tcgtgatccg cctgcctcag cctcccaaag tgctgggatt  72540
acaggcgtga gccaccgtgc ctggctgaga agacattttt taagctggct ctccttcctc  72600
ctagttttat ggaagcagaa ggatatatgg agttgagaag atcttattaa taaaacagcc  72660
gggatgacaa atgaccaaag agttagagta tccttctaca acatcggctg agggttaata  72720
caacctttc accttggaat tctatcattc taagctctag tccctgaagt gaatgttgtg  72780
ttggcctttt gcatcttggg tcacagggaa ttgatacttg cacatctatg gagaggcaaa  72840
tctttttcta tctacttctt tttcaatggg tacaaacaca cttggtcctg agcaccagtg  72900
gtctgaagag atacggtctg cccagaggag aagaacaaag gcaggaaagc agatgagagt  72960
cagcaaaggg gcgatgctga aaagtaaaag gggcgggtag atggacagaa gccatgatct  73020
ggccattcta tggccagtct ttcggccata agtgactacc aaagacacgg caaaacggtt  73080
tccacatgtt gaacaacaga tgctagagga ccaagagtat tgcaagaggg agaaaatgag  73140
atcaacccat caatgccttg gctttcttca aggagaccct tcctgcactg aagagcaagg  73200
agatggagcc caagctgact gtagccatgt tgctgaacag aggagagtga ttggactttg  73260
ggattactca ggtagttagg attttctagc catgctaaga gtaagaatgg acttgtggag  73320
gataggagct ccaggcatag aagtctcctc aagtgttagt ctaaacataa agcagcactt  73380
gcatagaaga ttttccacaa gaaaatatgg caaaaaaaca ccatatattg aggaacaaca  73440
actacaaggg aacagtgagc ttaataaagg tgacagagct cacatagtgc tctggaatat  73500
tggagttttg accagctaga gagaagagac ctcattgaaa atcttgggca ttcagtagag  73560
acctcagaaa agtcagactt tatgagtaga ctttgtatat tcctagaata aaggcagctc  73620
cagaaaaaac ctagcaaagc tgaaaagcaa atctccaagc attaaaatgg tgtcctagtc  73680
aattaactgc cttctagaag aaaactcaac actctttaca ggtgaacaac aaagttaagt  73740
tgctgagcta tgcaatatcc acagtgtgag tcctaaattt ataactttac tacacataaa  73800
aaagcattta gtgtgaacca taaccaggaa aataatcagt caataaaaat agaaccagga  73860
atgatagaaa tgatttaaat ggcatgagaa tttgacatat tagtatcata actgcattgc  73920
tggatttaag aaaacataaa catggaacgt aacagatatc atatcaaggg aaagtaaaag  73980
gataaaagag tcaaatcaaa ttaaaggact attaaaaggt atatcttaaa tgaaaaattc  74040
actggatggt ctcccaatca ggttagttgt ttccagggaa aaaattaact gaaaaataat  74100
tcaatagaat ctacagaaat agctgcacat atatacacac aatggcacac gtgcacacac  74160
```

-continued

```
ccacacccac acaggtgtga atcctagagc cacacgagca ttgaaacata gagaagtaaa  74220
aattgttcat tgaggaatat gtagcaatgc tcaatgtgtt ttaccctaat aagagctttt  74280
gtgatgtatg attgaaaaac tgacacaact gaagagagaa atagataagc ccacactctg  74340
agttagagat ttccttgatt ctctcactat ggttataaat ctttcccaaa cacaacaggc  74400
tagaacaaat atgcagaaaa ttagacatag tatctttgtt ctcaataaaa acgtcgacct  74460
atttaacatt ataccgaact accgagtaca cattaaagtg tgcatggagc attcactgag  74520
gtgtactcta cacatgacct tccagcaagt ctccatagat ttaaaagaat taaagtcata  74580
cagagtgtgt cactttattc tcccagaata aagtgagata tgaataatga gaagtttgcc  74640
agcttctcaa atatttggga gtcatacggt gcatttcaaa atactctttg ggacaaagaa  74700
aacatcacta aggaatttag aaaagttttg aactgagtaa gaatataaca caatttatcc  74760
aaacttagga gatgcagtga atgtctttag gcttttacat aattttagat gctcttaggg  74820
aaaaacagaa gcatgtaata atcaagattt caaactgcaa ttctcaaagt gtagtctaga  74880
gaaacctgag gacctttgag taccttcaga gacagtccat gaggttaaag gactttgcta  74940
cgtgaaaagt aagatgctat tggccctttt tactttcatt ttccaacaag agaagagggg  75000
agttttccag cagttacata atatgtaatg gcatcatgtc tctgatggct aagaaaatgg  75060
gcaattgttg actttgtgtg ttaaaaaaat tctcagtgtt ggtttcttat actataaata  75120
ttcatcttgt gttttgaaaa agaaaagctc tttggaatcc cctatgaaca aagactttga  75180
cagttgttga tctaagacca cagcttaaat atctacacaa gaaaaaaaaa aaaagcaaat  75240
aagagccaag gaaagcagat ggaaggaagt agtccaaacc agtgacattc agtgaacaag  75300
aaaagagacc aacaagggag taaactcttg aaacagaaag ttgattcttt gaaaagatcc  75360
atatgattga acacagtctg gctaaacaaa tgacagacca atgagggtgc acaaccatca  75420
ccatctggag taacagagga gaggtgccat tactatagca tcttccagtt ctgaaagctg  75480
aaaagaagat tttgagaaca attgtatgtg aataaattca ggaatgttaa tcatgtgggc  75540
caattcctga ggaagacaac aaatcagcaa accagatgct gaatagttag tgtagtcctg  75600
tagagagaca tacagagagg ctgacagaga aatatttgta tgtgcataaa acaatctaca  75660
agacacactt caaaatcaat ctcagttaat ctggaggaac atatttcaca gaaggtggaa  75720
ggagggtatt ctgatcctct tgtacattgt acaacattgt acaatgtaca gagtataatt  75780
gtacaagtac aattgaagtt gtacaagtac aagtgcaact tgcacaatgt acagagtaaa  75840
cattgatgtt tactctcaat tttcttatgg agcacagatg actttggatg tgttacaata  75900
tgaatgataa tttgtctttg agatgttcgc agttgtttag aagttgagga ccatttgtgc  75960
atattatggg acctttagtg aaaatatttc aaagtctctt tttacacttt gttacagcaa  76020
aatgtagagg gcgctaagtg cccttgaatc ttctcccatc tctggtgacc tgtgttgttt  76080
tgaaatttgc agtggcctga ccaggaacta ctgcaggaat ccagatgctg agattcgccc  76140
ttggtgttac accatggatc ccagtgtcag gtgggagtac tgcaacctga cacaatgcct  76200
ggtgacagaa tcaagtgtcc ttgcaactct cacggtggtc ccagatccaa gcacagaggc  76260
ttcttctgaa gaaggtagga agtctatggc cagacaacca caccctagga cgttgggatg  76320
aaaagagttg caaaatctta gtgatataga agccttccat gctcacacaa ttccaagtag  76380
aatgtggact cagggtcagc cactgggaag gaacactcag cgccttctct gggagaacca  76440
gagctgtgat gtttggtacc ctgtgaaagg gtggtatcta taggaagggt gcagaccctc  76500
tagggcactg gacttaccac tcccctggtt attcaaagga tcattttagt gtcttagcca  76560
```

-continued

```
gaagaatatt ctaacatttt gccaaatttg tgaagattta ccaagctcat gataagcctt  76620
tcatggtatt tcttcaagta gtcagtgttc attgcatctt tggctttgcg gtttcggagg  76680
aatgcggttt ttgagtctgt catccttgag aaacctaata tgacttttct tagttccata  76740
tacttctggg tccaggtagc agtacatagc caacaaatgc tccatcgttc tggcctatct  76800
ccatcttaag ccagtcctgc acaactaggc tttgatggga gggatctctc agtgttcttg  76860
cccctccttc tcatggaaca tatatctgtg ttggtctctg agaagaagag tagtggatat  76920
ctactttgtt gcaatgcaga atcctgggcc aaagatacca gccatccctc caagggaata  76980
aaattttggc cagtagccct ctctgagaga caatttgtct ttgcctacga gtcctagatg  77040
caggaccgct tcctgcccca tcttcaagaa gctgaaggct ttggctttgg aggatcagca  77100
gtctagggaa atgtgtgacg gtttcatgtc tgtccccact gacagtcaat caccacctac  77160
aacctgcaca gcctgatgca tagcagtcta gtttcctgcc ttattctcag gaacacccag  77220
aagatgtcta tattaaagag catgcacatg agtgcaattt tgactgatag gcactctgat  77280
ctttcctttg gtgcctgtgt tttaaaggaa atctttctaa gaactcgtta aagttctaga  77340
atgctatgaa tctttgggtt ttattattgg tatgtccatc tgcctgctag tacagaacag  77400
agcatggtag tctttctcag agacaatgat cctgtttcag tcacagattt cttctgatgc  77460
ttctgtgttc tagaaattac tcagcttgat ttctcctctt tgaatttcag caccaacgga  77520
gcaaagcccc ggggtccagg attgctacca tggtgatgga cagagttatc gaggctcatt  77580
ctctaccact gtcacaggaa ggacatgtca gtcttggtcc tctatgacac cacactggca  77640
tcagaggaca acagaatatt atccaaatgg gtacaacctt gagttttctt caaagacaga  77700
cagcagcccc cttacatttc tcttggaagg gccatgcttc caactaactt cttatgacaa  77760
atttatctca gatctggaat gttgggtaga atgtctcagg cttctttctt caggcacagt  77820
gtctgaaagg agagaaatgt caggccagct ctcttttctc atagttgaca gaagcaggag  77880
gatatttgaa ggtggtgagt tctcatgaat agaaagctca ggacacatgg ccacgtgctt  77940
agaaatagca ccattccaca atgcccacta aagaccaatg caatagttca accagggatt  78000
tctgtcattc taatctccaa gtcctgaagt gaaggttgta ttagccatgt tcatcttggg  78060
caacaaataa aggatatcta tgttgacatc cagatcttcc aatcactttc tcctctaacc  78120
tgtacctggg ttctgagaac aaggtatctg aagagctatg tgttgccagc acatgagggg  78180
caaaagtagg aaggcagctg agagtcagga agtataaaga ttctgaagag ttacacatgc  78240
aggaagatgg acagaaaccc agttcagacc acgtcagcgt ttctgccatg aaggactatc  78300
aaatacatag gaaaagtgtt ttcataggtt ggacaacaga catgacaggc ctgagaaaat  78360
tcagaaaggg aatcaaagga gatcaacctt atcatgtccc tggcatcctt ccttgagacc  78420
cttgaagggc aagcagatgg agcccagctg accacagcag tcttgcttaa ctgaggagag  78480
agactggagt ttgtgatgcc tcaggcatct gacgtattct aggctggcta agaatgagag  78540
gggatttgtg gaggaaagga gctccaagaa tacacaccga agtcttctca aggctttggc  78600
taaatacaaa gctgcgtatg cacaaggaga gttttcacaa agaaagaaca ataaagaaaa  78660
gctactgggg aaagaacaac tgcaagggaa cagtgagctc aatggagatg ctagagctca  78720
catagcactg gggatattt gagttctgac cactcagagg agagacacct cactgaacat  78780
cttgggcatt cagtagaggt caaagaaagc cataatttgg gagtaggatc ttcggattcc  78840
tagaaataag gtgactccag aaacactcca gcaacccttc ttccaagcca gtctaaaagg  78900
```

atccaaatga tttccaagta aattaactgc cttccagaaa aaagtaaact caaccctcct 78960
tagaggtaag gaacgaatac aagtttctca gttatatgac atccccagag tgcaacttgc 79020
atttaaaaat ttactagaca caaaagaagt tttcactgtg atccataact gggagaaaaa 79080
tcactcaaca caaataggcc cagaaataat agaaattatg gcattggcaa gaacatttaa 79140
aatgcacctc tgagaactgt gtttcaggaa aatgtcagca aaagctgacc atgagagaaa 79200
tgaatgcata atatcagaaa agaaaagaat tgaagagcca aatggaaatt taaaaactga 79260
gaaaagttat atctgtaatg aggaattcac tggatggcct tataaccagt ttagatatta 79320
tggtaggaaa aggtgaacga gaaaatgatt caattaaagc tagacaaacc acaagacaga 79380
cagacagaca caaatacaca tacacacaat gactgaacca attaatcaac agagcctcaa 79440
ggacatctag gaaaacatcc acacatttaa tatatgtgtt aggcaagtca cagaaagaga 79500
ggaaaaagat aatgtgacag aagttatact tgaagccatg acggctgaca aatttccaaa 79560
catacagaaa atgagaaatt catagtcatg aagctcaatg actcaggtat agatttttaa 79620
agagcaaaac tctgatttac tggggtacat catagttaaa ttgtctgatt tcaaagctaa 79680
gaagaaaaaa agggggttcc tatgaacaaa cattttgaca gttgatctaa gaccacagct 79740
taaatatcta ggcaaggaaa agcaaataag acacaaggaa aggggatgga tggaaatagt 79800
ccaaaccaat gacattcagt gaacaagaaa atagaccaac aaaggagtaa atccatgaaa 79860
cagaaagttg gttctttgaa aagattcatg tgattgacca cagtctggct gaacagatga 79920
cagaccaagg agggagtaca accatcacca tttgaagtaa caggggagag gagccattgc 79980
tataccatac tccaggtctg aaagctgaca agaagatatc aagaaaaact gtatgtgaat 80040
aaattcatga atgtagatca tgtggatcaa ttccttaggt aaacaacaaa tcagcaaacc 80100
agatactgaa tagattgggt actcctatag aaagacatac agatagccag acagagaaac 80160
atttgtacgt gcataaaaca atctacaaga ctcacttcaa aatctctcag ttaatccaaa 80220
gtaacatatt tggcagaagg tggaaggagg gtattctgat cctttcttgt acacattgat 80280
gttttctctc ggttttctta tggagtatag acgagtttgg atgtgttaca ataagaatga 80340
taatctgtct ttgaaatgtt cacagttgtt tagaagttga ggacgatttg tgattgttac 80400
aggaccttta gtgagaatat ttcaaagtca ctttttacca ctttgttaca acaaaatgta 80460
gaggatgtct ggtgcccttg tatcttctcc catctctggt gaactgtatt gttttgtaat 80520
ttgcagtggc ctgaccagga actactgcag gaatccagat gctgagatta gtccttggtg 80580
ttataccatg gatcccaatg tcagatggga gtactgcaac ctgacacaat gtccagtgac 80640
agaatcaagt gtccttgcga cgtccacggc tgtttctgaa caaggtaaga agtctctggc 80700
cagacaacca cacccttgga cgttgggata aaaagagttg caaaatctta gtgatacaga 80760
agccttccat gctgcacggg aatctgaatg tggactcagg gtcagccaat gggaaggaag 80820
cctcagcgcc ttctctgggg gaaccagggc tgagattttt ggcaccccgt gacagggtgg 80880
tgtctttagg aagcgtgcag accttctagg gcactggatt taccactccc ctggttattc 80940
aatagattat ttcagtgtcc tagtgaaaat ggatattcta acatcctgcc aaatttgtga 81000
tgatttacca agctcatcat gagcctttcc tggtatttct tcaagtagac agtactcatt 81060
gcaaacttca gctttacagt ttcagaggaa tgtggttttt gagtctgtca tccttgagaa 81120
acctgatatg actttactta gttccatatc ctcctgggtc taggtaacag tacatagcca 81180
gcaaatgctc tatctccctg tctaccttaa tcttaggcag gtgctgcaca cctaggcttt 81240
gatggaaggg atttcttagt gttcttgccc ctccttctca tggaacacgt atctgtgttg 81300
ctgtttgtga agaagagtag tggatgtcta ctttgttgca atgcaggatc ctgggcccaa 81360
gatttcccgc cgtccctcca agggaataaa attttggcca gtacccctct ctgagagaca 81420
atgtgtcttt gcctggaagt cctagatgga ggaccacttc ctgccccatc ttccagaaac 81480
ttaaggcttt ggctttggag gatcagtgct ctggagaaat gtgtgacggt ttcatgtctg 81540
cccccactga caaccaccac ctacagcctg caccgcctga tgcatggcac tctggtctcc 81600
tgccttgttc tcaggaacac ccaaaagaga tctttgccaa agaacaggca catgagtgca 81660
attttgactg ataggcactc tgatctgtcc tttggtgccc aggttttaaa gaaaatcttt 81720
ctaaaaactc attgaagttc cagaatgcta tgaatctttg agctttgtta ttggcatgtc 81780
catctgccta ctaatgtaga acagagcatg gtcgtcattt tcagagatga tgtcctgttt 81840
ctatcatgga tttttttct catgcttctg tgttctggaa attactcagt ttgttttctc 81900
ctctttgaat ttcagcacca acggagcaaa gccccacagt ccaggactgc taccatggtg 81960
atggacagag ttatcgaggc tcattctcca ccactgttac aggaaggaca tgtcagtctt 82020
ggtcctctat gacaccacac tggcatcaga gaaccacaga atactaccca aatgggtatg 82080
tctttgagtt ttctcccaag agaaacagcc acccacttaa atttctcctg gaagagccat 82140
gcttccagct aacttcttat gacccaattt ctctcagacc cagaatgttg gacagaatgt 82200
ctcaggcttc ttgctttggg cacagggtct gagaggagag aaatgtcagg ccagctctct 82260
tttctcatag ttgatagaag taggaggata cttggaggtg gtgaggtctc atgaatagaa 82320
agctcagaag aacatatgac catgtgctta gaaatagcac cattccacaa tgcccactaa 82380
agaccagtga aatagttcaa ccagggaatt ctgtcattct aatctccaag ccctggagtg 82440
aaggttgtgt ttgccatgtt tgtcttgggt aacaagtgaa ggatatctat attgacttcg 82500
agatcttccg atcactttct cctctaacct gtataaacac attgggttct gagaacaagg 82560
tgtctgaaaa gctatgtgtt gccagcccat gaggggcaaa aggaggaagg cagctgagag 82620
tcaggaagta tagagatgct gaagagttac acattcagga agatggacag aaacccatgt 82680
ctggctatgc cagcctttct gccatgaagg actatcaaat acatgagaaa acagttttca 82740
caggttggac aacagatatg gtaggcttga gagaactgag aaagggaatc aaaggagatc 82800
aacttcatca ttaacctgtc ttccttcctg gacacagtgt tggattgaag gacaagcaga 82860
tggagcccag ctgaccacag cagtcttgct taactgagga gagagactgg agtctgcgat 82920
gcctcaggca gctgatgtgt tctaggctgg ctaagaatga gaagggattt gtggaagaaa 82980
ggagctccag gaatacacac agaagtctcc tcaaggcttt ggctaaatac aaagctgcgt 83040
atgcacaggg agagttttca taaagaaaga acaacaaaga aaagctactt gggaaagaac 83100
aactgcaggg gaacagtaag ctcaatggag atgccagagc tcacatagca ctgggggata 83160
tttgaattct gaccactcag aggagaaaca cctcactaca ttttgggcat tcagtagaga 83220
ccaaagaaag ctgtattttg ggattgggat catcttattc ctagaatcaa ggtgactcca 83280
gaaaaactcc aacaaccctt cttccaagcc agtctaaaag gatccaaatg atctccaagt 83340
aaattaactg cattccacaa gaaaaaaaaa actcaacccc ccttagaggc aagggacaaa 83400
tacaagttgc tcagttatat ggcattccta ttgcgttact tctatttaaa aatttaatag 83460
agacacaaga agctttcact gtgatacata actgggagaa aaaatcactc aacacaaaca 83520
ggcccagaaa ttatagaatt gatgacattg gtgagaacat ttaaaatgca cctctgagaa 83580
ctgtgtttca ggaaaatgtc agcaaaagct gaccatgaga gaaacaaaag cagaatagca 83640

-continued agagaaaaga aaagaaccgg agagccaaat gaaaattaaa gaactgagaa aaggtacatc 83700
tctaatgaag aactcactgg atggccttat catcacttta gacattacgg taggaaaggt 83760
gacctagaaa ataattcaat aggagctaca caaatcacag gacagacaga cagaccaaca 83820
gacagaaaca cacacacaca cacacacaca cacacacaca cacacacaca cacacaaaga 83880
ctgaacctat taatcaacag agcctcaagg gcatctagga aaaatccaca catttaatat 83940
atgtgttagg caagtcacag aaggagaaga aaaagatatc atgacagaca ttatacttga 84000
agcgatgatg gctcgcaaca cgccaaatat acagaaaaca agaaactcat agtcaagaag 84060
ctaaatgact caggtataga attttaaaga gcaaaactct atgatttact gggatatatc 84120
atagttaagt tgcctcaatt caaagctaaa aagaaaaaaa gggggttcct atgaacaaca 84180
gctttgacag ctgttgatct aagaccacag cttaaatatc taggcaagga aaagcaaata 84240
aggcacaagg aaagaggatg gaaggaaata gtccaaacca atgacattca gtggaaaaga 84300
aaatagacca acaaaggagt aaatccatga aacagaaagt taggttcttt gaaaagtcta 84360
tatgattggc caaagtctgg ctaaacagat gacagaccaa ggagggagca tatccatcac 84420
catcatgagt aacaggagag agatgccatt gctatagcat cctccaggtg tgaaagctga 84480
gaagtagata ttgagatcaa ctgtatgtaa ataaattcat gaatgtagat catgtggatg 84540
gattgcttag gtaaataaca aatcagcaaa tcaaacactg aatagatcat gcagttttat 84600
agagacttac agacagcctg acagataaac atttgtatgt acgtgaaaca atctccaaga 84660
cacacttcaa aatccctctc ggttaatcca aaggaatgta tttggcagaa ggtagaagga 84720
gggtattctg atcctttctg gtacacattg atgttttctc tcagttttct tataaagcat 84780
agattacttt gaatgtgtta caataagaat cataagctgt ctttgaaatg ttgacagttg 84840
tttagaagtt gaggaccatt tgtgagtgtt atgggacttt agtgagaata tttcaaattt 84900
gcttgtttac actttgttac aagaaaacat agagggtgcc aggtggtgct gtatcttctc 84960
caatctctgg tgacctgtat tgttttggaa tttgcagtgg cctgaccagg aactactgca 85020
ggaatccaga tgctgagatt cgcccttggt gttataccat ggatcccagt gtcagatggg 85080
agtactgcaa cctgacgcaa tgtccagtga tggaatcaac tctcctcaca actcccacgg 85140
tggtcccagt tccaagcaca gagcttcctt ctgaagaagg taagaagcct gcagtcagac 85200
aaccataccc tcggacattg ggataaaaag atttgcaaaa tctttgtgat gcagaaaact 85260
tccatgctgc acaggaagtc gaaggtgaag tcatggacag ccaatgggaa ggaagcttca 85320
gtgccttctc tggggggacc agagctggga tgttgagtgc cttgtgaggg atggtgtctt 85380
taaaaggggc acagaccctc taggacactg gatttatcac ttccctgtta tcaaacgaat 85440
catattagtg tcctagccaa gatggatatt ctaacatcct gccaaacttg tgaagatata 85500
ccaagctcct aagcctgtcc agccctttct tcaagtaggc agtgtttatt gcagtcttca 85560
gctttaccat tttgaaggaa tgccattttt gaggctgttg ttcttgagaa acctaacatg 85620
tcttcattag atccgtattg tcctgagact ttgaagcagt acatagccac caaattgttt 85680
atctccccag cctaccttca tcttgggcat gccttccaca cctaggattt gagggaaggg 85740
atttctcagt gttctcatcc ctgcttctca tggaacattt atctccgttg ttttttgaga 85800
agaagagtag tggatgtcag ctttcttgta atgagggatc ctgggcccaa gattccctgt 85860
ctcccctcct aggctataaa attttggcct gtactccttc tccctgagag gcaatgtgtc 85920
tttacctaca agtcctagat gcaagatcct tttctgcccc acaccccaga atctgaaggc 85980
ttttgctttg gaggagcagt ggtctagtgt gcaagggttt catgtatacc ccccactaac 86040
agccaatcac cacctatagc ctgaacagct tgatgcatgg caccctggtc tcctgccttg 86100
ttctcatgaa cacccagaag aggtgtaagc aaaagaccat tcacatgagt gtaattttga 86160
agtataggca ctctgatctg ttttttgttt gtttctttgt ttgtttgttt tccagggttg 86220
aattaaaata tttatgacta cttattaaat ttctagaatc ctataagtct atttgtattt 86280
ttattctaca tttcaatttg catgctaata tagaagagtg taaattgtta atcctcagat 86340
tattccactt tgtgtgtcat aattttttttc acatttccct tttctaggca atactgagct 86400
tgattttctc ttttaatttc agcaccaact gaaaacagca ctggggtcca ggactgctac 86460
cgaggtgatg gacagagtta tcgaggcaca ctctccacca ctatcacagg aagaacatgt 86520
cagtcttggt cgtctatgac accacattgg catcggagga tcccattata ctatccaaat 86580
gcgtatgtct atcatgttag ccataaaagg aacaatagtc aactaaaatt tctcttagct 86640
ggcccatgct acaagctcac ttcctaggtc caaatttctc atagactcag agtttgtagc 86700
aaaatgtctc aggaaactta cttttgagca aaaggtctga atgaagagaa gttttaggat 86760
tgctatcttt cataacaatt tgatggaagc agcaggatat atggaggtgg tgaagtctca 86820
ttaatgtaaa gctaaggaga tcaaatgacc aaatgctgag acaaagtatc attccacaat 86880
gcccactaaa ggtccatgca gtctttcaac catgcaattc tatcattcta tcctccattc 86940
cctgaagtga aatttgtgtt tgccattttt gacacgaatc agaagtaaca aattcaggct 87000
gggtgcagtg gctcaggcct gtgatcccaa cactttggga ggacaagacg ggcagatcac 87060
cagaggtcag gagttcaaga ccagcctggc taacatggca aaaccccatc tctacgaaaa 87120
attaaaaaat tagccggtca tggtggtggg tacctgtaat tccaactact tgggaggctg 87180
aggcaggaga aacacttgag cctgggattc agagtttgct gtgagccgag aacatgccac 87240
tgcactccag cctgggtgac agagcaagac tcaatctcaa aaaaaaaaaa aaagaagaag 87300
aagaagaaaa gaagaagagg aagaagaaga agaggaagaa gaagaagaag aagaagagga 87360
agaggaagag gaggaggagg aggaggagga agaagaagaa gaagaagaag aagaagaaga 87420
agaagaagaa gaagaagaag aagaagaaga agaagaaaat agaaatgagt gcatatattt 87480
atatatgagt actagcctgt atgaacacac tgggttctaa gcaccagttt tctgaaggga 87540
tatgggttgt caggcagagt aaaagcagga atgcagatga gagtcaggaa gtaaacagat 87600
gtggtgatta aaatgggcag gtacatggac aaaaaaatgc atgtctgaca aaaactggcc 87660
tcttgccata agtgagtatg aataatatgg aaaaactgtt tgcacatgtt gaacagcaga 87720
cagtacaacc tgagatagtt tagaaaggga aacaaataag atcaacccca taattaccct 87780
tcctagactt aagggcaaag agttttaacc aaagcattcc acagcagtct tgctaaactg 87840
gggagagaga ctggagtttt gtttactaat aaaaccgaga ttttctaggt taggtaataa 87900
tgagaaagta tttgtggaga aaaggagctc caggaataca cacagaagtc tcttcaagtc 87960
tctggctgaa cagaaagctg tgtatgcaca gaaagagttt ccagagagaa aggagaacaa 88020
agaacagcta ctggggaaag aacaactgct ggggaacagt gagctcaatg aagatgccag 88080
agctcacata gcactgggag gtatttgagc tctgaccagc ctgaggagag acacttcatt 88140
gaacatcttg ggcattcagc aaagacccca aaaaaccata cttcaggagt agaattaatg 88200
cattcctaga ataaagtcta ctccagaaac accctagaaa agcttagaaa ccaagtctaa 88260
aaagatccaa atgatctcca agtaaattaa ttgcctgtca gaagaaaaca acctcttcag 88320
aggtaaacaa caaaattaaa ttgctcaatt atatagtatg cacaatgtgt ggcatacatt 88380

-continued

```
taaaaatttg ctaaacatac aaaaagcatt tagtgtgacc cataaccagg agaaaaatca  88440
gtcaatacaa atagacccaa aaatgataaa aataacagaa ttggcaagga gatttaaaat  88500
gtatgtatca taattgtgtt caaggattta aagaaagcgt ggacaagaaa taaataaatg  88560
gataatatca acagaaagaa aaattgtaaa aggaccaaat ggagagtcaa gaactgaaaa  88620
aaaagacatc tctttaatga gaaaatcact acatggcctt ataatcatat tagatagtac  88680
agatgataaa gctaactaga aaatattagg gtggtgcaaa ccatagcacg cttatacaaa  88740
gcctgagaag ataaacagag cctcaaggac atctatgaaa atatcaaaat atttaatatt  88800
tgtttaaagc aagtcacaga ggaagggaaa gagatattgg aacagaaaaa atacttgaag  88860
cagtgatggc tgatgacttt ctaaatatgg aaaaaatgat aaactcacat agtcaagaag  88920
ctcaatggat cagatatagg attttaaaaa gtaaagctgt atgatttatt tggacacatc  88980
ataattaaat tgtccataat caaagataga aagtaaaatc ttatttgaag cccaagggaa  89040
aaaacatacc tttacataga gtaacagtga cacaaatgac tgatgccttc tcatcagaaa  89100
caacacaaat cagaaacaat agaataacac ctttagagtg gtaagaagaa aaaaagatca  89160
aatcagaaac aacaaaataa cacgtttaga gtggtaagga ggaaaacaag atcaaatcag  89220
aaacaatgga ataacacctt tagagtgtaa gaaagaaaaa aagatcaaat caggaacaac  89280
agaataacgc cttcagagtg gtaagaagga aaacaagata aaatcagaaa caatgaaata  89340
acacctttag agtagtaaga agaagaaaag atcaggtcag aaaaaatgga ataatatgct  89400
aagaagaaaa aaaaagatca agtcagaaac aatggaataa cacctttaga gtgaaaagaa  89460
ggaaaaaaac ccagcaagct taaacgctat gcacagcaaa caattccact gaaaatgaat  89520
gttacgtaag tacatattct gtcctcctaa aaacaaagaa caaataaaag aatgtttcat  89580
cagcaggatt atgtaataaa agatgtgaaa gaatgctatg taagtagaag aaaaataata  89640
ccatatggga attggcatca aaaccacaaa atactatcaa aacaaaaaaa ctttattgat  89700
aaatttaaca caatatgcaa aagaactata ccatgtatac tacataacat tggtgagaag  89760
aaaattagaa gatctaaata aagacacatc atgcttatag attaaaaaat ccaatgtcac  89820
ttttcacaaa actgatcttt agtttcaacc cacacccaag cagaattcct gcagtctttt  89880
cttgaaaacc taacagaatg tatatgctag aatcaccaag acaatcttta aaaagaataa  89940
aaaacttgga ataaaatcac aagtttgtgg gatagatgca tatggtaata tggaaattct  90000
cataaagaca cagtaatcaa gacatgtggt attggctggg acgcttggct gtaatcctaa  90060
cactttggga ggccaagatg agaggattgc ctgagatgag gagttgcaga caagcctggg  90120
caacatagca agaccctcat ctctacaaat atttaaaaaa attagccagg tttggtgcca  90180
tgtgcctgta gtcccagcta ttcaggaagc tgaggtggga ggatcactgg agcccatgag  90240
gtggaggctg aaatgagcca tgattgtgct actgaacttt agcctgggag acagattaaa  90300
accttccctc tctctctcaa acaaacaaac aaaaaataca tagtattggg caaaacatat  90360
gcaaacaaaa acagaaaagg gtcagcataa atttacatat atggtcaatt tattttcaat  90420
acaggtagca aagcaattta atgaggaaat ttttttccaa aattggtctg aaacaactgg  90480
atagccatag aaaaaaacta taacaaatgt gacgcttgaa tcctactgta tgactcaaat  90540
taaattaatt tgagatagct cttagacctc aatgtaacag ctaattctga ggctgaaata  90600
taagactgct atgaaaaagt atagtatctt ataaccttgg agaaggaaaa attttttgag  90660
ggaagaacca gaaaacacta actgtaaaag aaaacaaatg ataatgtgga cattcattga  90720
ataaaaactt atgctcacca aatatgactg ttaagaaaat aaataagtaa gtaacacact  90780
```

-continued ggaagaaaaa cactctcatc catatatctg acaaatggcc tgtatccaga gtatagaaac 90840
atttctccca ctcactaatc agaggacaaa caacctaatc aaaatgggca acaggcttga 90900
atagtcattt cttaggagaa gatgcacaca gagccaacaa tcacctgaaa aagtgcacaa 90960
catcttagcc atcaaaaatc aagagttata accctcataa gatgacactg aacatccagt 91020
gtacatggat atcattaaga agacacaata ataagtggtg tcaccgattt ggagctagaa 91080
tgtgccactc tctcatatgc tggtggaagt tcaaaatcat acaacaaatt aaaaaatcag 91140
tctgatgctt tcttataaag ttcgataaat atgcatctat cctacaaacc tgtaattcta 91200
ttcttgaata tttacccccc aaaatgaaaa cataagtcca caaaaatcta tataaatatt 91260
catagcagct ttatgtttta taaactcaaa ataaaaacta tttcaatgtt ttcatcaaaa 91320
gaaaatgaaa actatttaaa tggtttcatc aaaagaaaat gaaaaaagaa tttccagtat 91380
atttatacaa aggaatacta ttcatcaaca aggaacaagt tactgatagt ctcagaagca 91440
tgaacaaacc tcaaaaatat attaaggaaa gaagccagac gtcaaagtgt atagtctgta 91500
tgagtccatt catgtgagtt tatagaaaac acaatttatg gtgaaagaaa ccaatagcat 91560
ttgacactgg ccgtgggaag agggtagcag agattgattg agcagccaca caagggagtt 91620
tctggggtgg tgaaaatgtt ctgcattgtg agggcagtgt gggctacaca agtatatgta 91680
tttatcaaat ctcatccagc tacatttaag atctgtgcat ctcactctat gtgaaaatat 91740
actcaactga aaaacagagc aggtatctgt ttcaggtgct acatcacttg atacgtccag 91800
ttgtgttaaa aaccactgcc taacatcctc aaatgggga tctgggcttg agactaggtc 91860
acatgtgtag agtctctaca gagaccgtgt tggattccca tgctccataa tacgttccaa 91920
gttttctcag acagccacag gtcatgaatg tgaggattct gagaggttgg agcaacgttc 91980
ttgggaggca taatggggaa ggcattctcc aagattcctc cagcctgggg tcttcacctg 92040
ctgtgcctct tactgcattg ttttctgact catccatagc cacttgaccc cttcagatcc 92100
catagtctac ctagccgtct ccctttatgc cttgggtccc gctgttcttt caactcatca 92160
cccattcctt cagtcccaga gtggctgcag ccagcagagg atggactgag agcaggagag 92220
gaggtcgtgc ccatgaaccc atcctagaga agcagcatcc tgcctgggag ctagttttcc 92280
agggaagctt ttataagtcc tgtagaccca aacccacttg ctctaccaga tacagtattt 92340
atagtaatac tattttcatg attattttat attgcaaatg tagagcattt atgctacact 92400
atgagtaaat agagtaaggg ggctggcatg ggaattatat aatcttggat gccacttctt 92460
ccttggggaa atgtatttga gttccaactt acatattact atatagtctt atagagagag 92520
agacaaagag ctagacagac agagatatct ttgtatgtgc attaaaaaat ctaagataca 92580
tatttcaaaa tctgtgtcat ttattctgga ggaaagtatt tggcagaagg tgaaaggaag 92640
atattctgat cctttcttgt acagacatgt attatctcag ttttcataga gagcatatac 92700
tacttttgat gttttaaaac aaaaattata atctgtgatg tgtccacagt tgtttaaaag 92760
ttgaagctga agaccatttg tgcttgtggc aatattattg tggtataatg ggaatatttc 92820
aaaggcactt gttaacactt tgttacagca aaatgtagag ggcgctaagt gcccttgaat 92880
attctcccat ctctggtgac ctgtgttgtt ttgaaatttg cagtggcctg accaggaact 92940
actgcaggaa tccagatgct gagattcgcc cttggtgtta caccatggat cccagtgtca 93000
ggtgggagta ctgcaacctg acacgatgtc cagtgacaga atcgagtgtc ctcacaactc 93060
ccacagtggc cccggttcca agcacagagg ctccttctga acaaggtaag aaatttgtgg 93120

-continued ttagacatct atatactggg atgaaaaacc atggaaaatc ttactgatgc agaagccttc 93180
agtggtacac tggagggttg gttgagggtc tgcaatgtgg aggaaagcct cagcgccctc 93240
tctgggggat ccagaactgt gatttttggc acgctgtgag gaggcagtgt ctttaggaag 93300
ggcacggtgt ctttaggaag ggcacagacc cgccagggca ctggacttac cactcccctg 93360
gttattaaat gggtcatttc agtgtcctag ccaaaatgga tattctaaca gcctgccaaa 93420
tatgtgaaga tttccaagcc aataagcctt tccagtgatt taaagtagac ttttttcatt 93480
gcaatctaca gtttgcagtt tcttaagaac atggcctttg agtatgatat cctagagaaa 93540
cctaaggaga ctgcattatt tttctattgt cctggggctg catagcagga ggtaaccaac 93600
gaatgctgtc tctccctggc ctatctcagt ctttcacagg ctctgttcac ctcagctttg 93660
aagttagaaa tttctaggtg ttcttgcctc ttcttctcat gaaacctgca ttggcagtga 93720
gtctacagaa gaagaggaag agaattctgc tttgttacaa ttcaggactc tgggcactag 93780
aagattccct atctctcctc caagggaata agttgtttgt ctctaaccct ccttgagaaa 93840
caatgagtct ttgcctgcac tcctaaatgt aggatgattt cctgcccaaa ttttcaaaag 93900
attaagcctt ttgccttggt atgagcaatg gtctagggaa atgcgcaagg gtcttgtgtc 93960
ggcccctgac tgaccaccag tcacctccta cagcctgcac caaggaatgc attgcattct 94020
ggtcttctgc cctgtggttc tcatgaaaac cagcagagat tcatatgatg gagctgcaca 94080
tgaatgtaat ttccaatgtc cagcattctc ctctgttctt tatctttaga tttaaaaata 94140
atgtttctat gaacttatta aaattctaga atactatgaa tctactgggt cttttcacat 94200
ccttttgcta ctagtagaaa aaagaatagt aataattttc agaggctact gtccagtatg 94260
tgacataaat tgtctcccat gtttctctgc tcatgcaatt actgagtatg atttatttta 94320
ttttaatttc agcaccacct gagaaaagcc ctgtggtcca ggattgctac catggtgatg 94380
gacggagtta tcgaggcata tcctccacca ctgtcacagg aaggacctgt caatcttggt 94440
catctatgat accacactgg catcagagga ccccagaaaa ctacccaaat gcgtatgtat 94500
ttgattaaaa ccataagagg agcaacagcc aactcaaata ttggttagaa gacccatgct 94560
ttaagctcac ttcctaggga caaatttctc ttagactcac attttggcaa aatgtctcag 94620
gacctttgct tttgagcaaa gagtctaaga gaagagaaat tttaggcctg ctatttttcc 94680
taatagtttt atggaaggag tagaatatac ggaagtggcg aagtcatatt aatgtaaagc 94740
tcagaagata aatgaccaaa gcttaaacac agcaccattc cacaatgccc actaaaaatc 94800
aatgtcatct ttcactcgtg caattctgtc attctaaatt tcaattcccg aaggtttgtt 94860
tgccattttt gtcatgggta ataagtaaaa aaaaaaaaat taagatgtgt atatatatat 94920
atatatatat atatatacac acacacacac acacacaaac atctgaatat ttatatatat 94980
gtctgaatat ttatatactt gtgtataaaa cttatattta aatttttgca taaatttata 95040
tatttttaat atttcattaa aaattatatt gtttcactat gtatgtctga gtatttttat 95100
atattttaat ataacatttt aaatatttat atataaatat tcaggtatgt aactgaatat 95160
tcatttacac acacaaatat atgtgtgcat gtgtgtatat atatatatac ccatatatat 95220
atatatatat atatatacat atatatatat atatatatat gtatatatat atatatatat 95280
atatatacac acacacacac acacacatac atacaggtat aaacacactg ggcctgaagc 95340
accagtggtc tgaaaggaca tgtgttgcca ggacttgaag agcaaaagca ggaaggcgga 95400
tgagagtcag gaggtacaca aacgctgaaa agtaaaatgg acaagtacat ggacaaaaag 95460
caggtataag cataacagcc ttttggaagt aaatgactat aaaatatatg aaaatactgt 95520

```
tttcacaagt tgcacaacag atagtagtgt attgagataa tttagaacag aaaacaaatg  95580
tgatcaaccc cataagtgtg ctgtatttca tcatggattg aaggaaaaag agatggagcc  95640
caagaagacc acagcagtct tgatgaactg agagacacca gagtttggga ttacaaaggc  95700
agctgggatt ttctacactt ggtaataatg agaaagaatt tgtggagata aagagctaca  95760
gtcatgtacc tagaagtcac ctcagtgtaa tataaatctg catatgcaca gggagtgatt  95820
ccacaatgaa agtaggacaa agaacagcta ctggggaaag aataactaca agggaacaat  95880
gagttcaatg gagatggcag agctcacaaa gcactggggg atatttgagt tcttaccagc  95940
tagaaaagag acctcattgc aaatcttggg cattcagtag agaccccaga aaagccactc  96000
tttggaaaca gagttgatgt attttaagag caaaatctac tccacaaaaa tcctagcaaa  96060
attgaaaagc aagtcagaaa gaccaaaatc ctctcaacat aaattagttg cccatcagaa  96120
gaaagcttaa cctcttcata ggtaaacaat aaaatcaaat tgctcagtta tctggcatcc  96180
acaatatgtg acataaattt aaaaatttac tagacataca agaagcattt agtgtgatcc  96240
ataaccagga gaaaaatcat tcaatacaaa tagacccaga aatgacagaa atgatagaat  96300
tagcaaaaac atttaaaata tacatatgat catttgatct tgtgatcaga tatcacaaga  96360
gaagaaagag atacttgaac agaaaaaatg cctgaagcaa tgatggctga aaactttcca  96420
aatatgaaga aaaaaaagct cacagattca agaaaactaa tcaatcagaa atatgatttt  96480
gaaaagtaaa aatgtatgat ttactttggc aaatcttctt ggttaaattg tctaaaatca  96540
aagaaagcta ggaaaatttt ataagccaga ggaaaaaaga ttgtttatat aaaggaacag  96600
ttacacaaat gactgatgcc ttctcatcag aaacaatgaa agtcagaaac aataaagtaa  96660
catctttaaa gtaatagaag aaaaacccaa gaggtgaggg atcgtggcag acaggaggca  96720
ggactagatt gcagctctgg acagagcagc atgcagaggc tcatattgtg aattttagcc  96780
ccatattgac tgcaagaaca gaccagcaat cctgagagga cccacagacc gtgtgaagga  96840
agcagactgc tcctgcagga taagggagac accccaaata ctgtgagttc cccaactgca  96900
gaagtggaaa agggaggcct tactccctca aacacacccc acaactggag aagctgaaag  96960
tctgtttgca ggagaagttc ccaactttac ctgggcctca gtaaatttag agagctgagc  97020
caagcaaaat ataggggtag aggaagcagc agagaagacc tcagagcttg ctggatcccc  97080
aagcagctca ttcctgcctg gcaccacaga gatccatcag aagtgtggcc aaaggaacag  97140
agggtaaaac tccacatgga ggactgctct acctgaactt tctaacaatt tgaacagggg  97200
gagaagcctc ctggccagaa cttgggggag ggcatgaatc tggtttgcag acttcacagg  97260
tgggggaagg actaaagccc ttttctttca cagctgggag gtggaaagcc tcaggcaagt  97320
tttcaagcct gactttcccc ccacctggaa acagacttgg agctgttgcg gggttggggg  97380
catggtggga gtaagaccag cccttcagtt tgcatgggtg ctgggtgagg cctgtgactg  97440
acagcttccc tccacttccc cgacaactca gatgactcag cagaggcagc cataatcctc  97500
ctaggtacac aactccagtg acctgggaac ttcaccccca caccatacag aagcttcagt  97560
aagacgtgcc caaggaaagt ctgagctcag acacgcctag tcccaccccc aactgatggt  97620
ccttccctac ccaccctggt agcagaagac aaagagcata taatctttgg agttctaggg  97680
cccacccacc tctagtccct ctccacacta gtatagctga tgcaggaggc caaccagcac  97740
aaaaatagag cattaaacca ccaaagctag gaacccctat ggagtccatt gcaccctcct  97800
ccacctccac cagaacaggc actggtatcc acagctgaga gacccataga tggttcacat  97860
```

```
cacaggactc tgtacagaca gtccccagta ccagcccaga gctgggtaga cttgctaggt  97920
ggcaagaccc agaagacagg caataatcac tgcagttcag ctcacaggaa gccacatcca  97980
taggaaaaga gggagagtac tacatcaagg gaacacccca tgggataaaa acatctgaac  98040
aacagccttc agccctacct tccctctgac acagtctacc caaatgagaa ggaaccagaa  98100
aaccaaccct ggtaatatga caaaacaagg ctcatcacac tcccagttca ccagcaatgg  98160
atccaaacca agaagaaatc cctgatttac ctgaaagaga attcaggagg ttagttatta  98220
agctaatcag ggagggacca gagaaaggca aagcccaatg caaggaaatc caaaaaaaaa  98280
aaggtataag aagtaaaagg tgaaatattc aacaaaatag atagcttaat aaaaaaacaa  98340
taaaaaattc agtagacttt ggacacacct ttggaaatgt gacatgctct ggaaagtctc  98400
agcaatagaa ctgaacaagt agaaaaaata aattcagagc tcaaagacaa ggacttcaaa  98460
ttaacccaat ccaacaaaga caaagaataa aggataagaa aatatgaaca aagccttcaa  98520
gatgtctggg attatgttaa atgaccaaat ataagaataa tcgtggctcc tgaggaaaaa  98580
gacaatacta aaagcttgga aaacatattt gggggaataa ctggggaaaa cttacctggc  98640
cttgctggac acctagacat gcaaatacaa gaaacacaaa gaacatgtaa atacaagcag  98700
cacaaagaac acctgggaaa ttcatcacaa aaagatctta gcctaggcac attctcatca  98760
ggttatgcaa agttaagacg aaggcaagaa tcttaagagc tgtgagacag aagcaccagg  98820
taatgtataa aggaaaccct atcagattaa cagccagttt ttcagcagga actgtacaag  98880
ctataaagga ttggagccct atcatagcct cctcaaacaa aacaattatc agtcaagaat  98940
tttgtatcca gcgaaagtaa gcatcatata tgaaggaaag atacagtcgt ttttggacaa  99000
acaaatgcta agagaattca ccattaccaa gtcaccacta gaagaactgc taaaaggagc  99060
tctaaatctt gaaacaaatc ctagaaacac atgaaaacag aatctcttta aagcataaat  99120
cacacaggac ctataaaaca aaagtacaag ttaaaaaaca aaaacaaaaa acaaaaccaa  99180
agtacggagg caataaagaa tatgatgaat gcagtggcac ctcacatttc aatgctaaaa  99240
ttgaatctaa atggcctaaa tgctccactt aaaggataca aaaagagttg gtggctggca  99300
agatggctga ataggaacag ctccagtctg ccgctccccg tgagatcaac acatagggtg  99360
ggtcatttct gcatttccaa ccaaggtacc cggctcatct cattgggact ggttagacag  99420
tgggtgcagc ccacagaggg tgacctgaag cagggtgggg tgtcacctca cctgggaagt  99480
ggaaggggtc agggaactcc ctcccctagc caaaggaagc cgtgagggac tgtgccgtga  99540
agaccagtgc attctggcac aaatactatg cttttcccac ggtctttgca acctgaagac  99600
caggagattc ccttgggtgc ctacaccacc agggccctgg atttcaagcc caaaactggg  99660
ctggcatttg ggcagacact aagctagctg caggagtttt ttttcatacc ccagtggtcc  99720
ctggaatgcc agcaagacag aaccattcac ccccgtgaag aaagggctga agccagggag  99780
ctaagtggtc tttctcagtg gatcccaccc ccatggagcc cagcaagcta agctccactg  99840
gcttgaaatt cttgctgcca gcacagcagt ctgaagttga cctgggacgc tcaagcttgg  99900
tgggaggagg ggtatccaca aatactgggg cttgagtagg aggttttccc ctcacagtgt  99960
aagcaaaacc gctaggaagt ttgaactggg cagggtgcac tgcagcttgg caaagccatt 100020
gtagcaagag tgcctctcta gattcctcct ctctgggcag ggcatctctg aaagaaaggc 100080
agcagcccca gtcagaagct tatagataaa actcccatct ccctgggaca gagcaactgg 100140
aggaaggggt ggctgtgagt gcagctccag cagacttagt ttcctgcctg ccagctctga 100200
aaagagcacc agatccccca acacagcact agagctctga taagggacag actgcctcct 100260
```

-continued caagtgggtc ctggtttcag aagataataa gaaactcctc tgagctaaag gagcatgttc 100320
taacacaatg caaggaagct aagaaccttg aaaaaggtca gaggaattgc taactacagt 100380
aagcagttta gagaagaaca taaatgacct tagggagctg aaaaacacag cacgagaact 100440
tcatgacaca tacacaagta tcaatagcaa aatcgatcaa gtggaagaaa ggatatcaga 100500
gattgaaaat caacttaatg aagtaaagcg tgaaaacaag attaaggaat aaagaatgaa 100560
aaggaatgaa caaatcctcc aagtatggga ctatgtgaaa agattgaacc tacgtttgat 100620
tggtgtacct gaaagtgatg ggagaatgga accaagttgg aaaacactct tcaggatatt 100680
atccaggaga acttccccaa cctagcaaga caggccaaca ttcaaattaa ggaaatacag 100740
agaataccac attcaaattc aggaaataca gagaacacca caaagatact cctcaagaag 100800
agcaacctga agacacataa tcgtcagatt caccaaggtt gaaatgaagg aaaaaaatgt 100860
tgagggcagc cagagagaaa gtttgggtta cccacaaagg gaaccccatc agactaacag 100920
tggatcttcc tgcagaaact ctacaagcca gaagagagtg ggaggccaat attcaacatt 100980
ctttttact attattatac tttaagttct agggtacatg tgcacaaggt gcaggtttgt 101040
tacatatgta tacatgtgcc atgttggtgt gctgcaccca ttaactcttc atttacatta 101100
ggtatatctc ctaatactat ccctccccac tccccccatc ccatgacagg ccccggtgtg 101160
tgatgttccc cactctgtgt ccatgtactc tcattgttca attcccacct atgagtgaga 101220
acattcggtg tttggatttc tgtccttgtg atagtttgct gagaatgatg gtttccagct 101280
tcatccacat ccctacaaag gacatgaagt catccttctt tatggctgca tagtattcca 101340
tggtgtatat gtgccacatt ttcttaatcc agtctaccat tgatggacgt ttgtgttggt 101400
tccaagtctt tgctattgtg aatagtgccg caataaacat atgtgtgcat gtgtctttat 101460
agcagcatga tttataatcc tttagatata tatccagtaa ttgtatggct gtgtcaaatg 101520
gtatttctag ttctaaatcc ttgaggaatc accgcactgt cttccacaat ggttgaacta 101580
gtttacagtc ccaccaccag tgtaaaaatg ttcctatttc tccacatcct ctctagcatc 101640
tgttgtttcc tgacttttta atgatcacca ttctaactgg tatgagatgg tatctcattg 101700
tggttttgat ttgcatttct ctgatggcca gtgatggtga gcactttttc atgtgtctct 101760
tgactgcata aaagttttct tttgagaatt gtctgttaat atcctttgcc aactttttga 101820
tggggttgtt tgattttttt tcttgtaaat ttgtttatgt tctttgtaga ttctggatat 101880
tagccctttg tcagatgggt agattgtaaa aattttctcc cattctgtag cttgcctgtt 101940
cattctgagg gtagtttctt ttgctgtgca gaagctcttt agtttaatta gatcccattg 102000
gtcaattttg gcttttgttg ctattgcttt tggtgattta gtcatgaagt ccttgcccat 102060
gcctatgtcc tgaatggtat tgcttaggtt ttcttctagg gtttatatgg ttttaggtct 102120
aacatttaag tctttaatcc atcttgaatt aatttttata taaggtgtaa ggaagggatc 102180
cagtttcagc tttctacata tggctaggca gttttcccag caccatgtat taaataggga 102240
aacctttccc tatttcttgt ttttgtcagg tttgtcatag atcagatggt tgtagatgtg 102300
tggtattatt tctgagggct ctgttctgtt ccattggtct atatctctgt tttggtacca 102360
gtaccatgct gttttggtta ctgtagcctt gtaatgtagt ttgaagtcag gcagagtgat 102420
gcctccagct ttgctttttt ggcttaggat tgtcttggca atgcatgctc ttttttgttc 102480
catatgaact ttaaagtagt tttttccaat tctgtgaaga aagtcattgg tagcttgatg 102540
gggatggcat tgaatctata aattacctta ggcagtatgg ccattttcac aatattgatt 102600

-continued cttcctatcc atgagcatgg aatgttcttc catttgtttg tgtcctcttt tatttcatta 102660
agcagtggtt tgtagttctc cttgaagagg tccttcccat cccttgtaag ttggattcct 102720
aggtatttta ttctctttga agcaattgtg aatgggagtt catccatgtc cctacaaagg 102780
acatgaagtc atgtatggga atgcttgtga tttttgcaca ttgattttgt atcttgagac 102840
tttgctgaag ttgcttatca gcttaaggag attttggtct gagaagatgg ggttttctaa 102900
atatacaatc atgtcatctg caaacaggga caatttaact tcctcttttc ctaactgaat 102960
accctttatt tccttctcct gcctaattgc cctggccaga acttccaaca ctatgttgaa 103020
taggagtggt gagagagggc atccctgtct tgtgccagtt ttcaaaggga atgcttccag 103080
tttttgccca ttcagtatga tattggctat gggtttgtca taaatagctc ttattatttt 103140
gagatatgtc ccatcaatac atagtttatt gagagttcag catggagagc tgttgaattt 103200
tgtcaaaggc cttttctgca tctattgaga taatcatgtg gtttttgtct ttggttctgt 103260
ttatatgatg gattacattt attgatttgc atatgttgaa ccagccttgc atcccaggga 103320
taaagccaac ttgatcatgg tggataagct tttgatgtg ctgctggatt cggtttgcca 103380
gtattttatt gaggattttt gcatcaatgt tcatcatgga tgttggtcta aaattctcat 103440
ttttgttgtg tctctgccag gatttggtat caggatgatg ctggcctcat aaaatgagtt 103500
agggaggatt ccctcttttt ctatgattgg aatagtttca gaagaattgg taccagctcc 103560
tctttgtatc tgtggtagaa ttcggctatg aatctctcct ggactttttt tggttggtag 103620
gctcttaatt attgcctcaa tttcagagcc tgttattggt ctattcaagg attcaatttc 103680
tttctggttt agtcttggta gggtgtatgt gtccaggaat ttttccattt cttctagatt 103740
ttctagttta tttgcacaga ggtgtttata atattctctg atggtagttt gtatttctgt 103800
gggattggta gtgatatccc ctttatcatt ttttattgca tctatttgat tcttctctct 103860
tttcttcttt attagtcttg ctagtggtct atcaattttg ttgatctttt caaaaaacca 103920
gctcctggat tcattgatgt tttgaaggtt tttttgtgtc tctatctcct tcagttctgc 103980
tctggtctta gttatttctt gccttctgct agctttttaa tgtgtttgct cttgcttctc 104040
tagttctttt aatggtgatg ttagggtgtc aattttagat ctttcctgct ttctcttgtg 104100
ggcatttagt gctgtaaatc tcccccctaca cactgcttta aatgtgtccc agagattctg 104160
gtatgttgtg tctttgttgt cattggtttc aaagaatatc tttatttctg ccttcatttc 104220
gttacatacc cagtagtcac tcaggtgcag gttgttcagt ttccatatag ttgagcagtt 104280
tttaatgagt ttcttaatcc tgagtcctag tttgattgca ctgtggtctg agagacagtt 104340
tgttataatt tctgttcttt tacatttgct gaggaatgcc tcacttccaa ctatctggtc 104400
aatttcagaa taagtgcgat gtggtgctga gaagaatgta tattctgttg atttggggtg 104460
gagagttctg tagatgtcta ttaggtctgc ttggtgcaga gctgagttca attcctggat 104520
atccatgtta actttctgtc tcattgatct gtctaatgtt gacagtgggg tgttaaagtc 104580
tcccattatt attgtgtggg agtctaagtc tctttgtagg tctctaagga cttgctttat 104640
gaatctaggt gctcctgtat tgggtgcata tatatttagg atagttagct cttcttgtta 104700
aattggtccc tttaccatta tgtaatggcc ttctttgtct cttttgatct ttgttagttt 104760
aaagtctgtt ttatcagaga ctaggattgc aacccctgct ttttttgttg ttttccattt 104820
gcttggtaga tcttcctcca tccctttatt ttgagcctat gtgtgtctct gcacgtgaga 104880
tgtgtcttca gaatacagca cactgatgga tcttgactct ttatccaatt ttccagtctg 104940
tgtcttttaa ttggagcatt tagcccattt acatttaagg ttaatatttt tatgtgtgaa 105000
tttgatcctg tcatcatgat gttcgctggt tattttgctc attagttgat gcagtttctt 105060
cctagcatcg atggttttta caatttggca tgtttgtgca gtggctgata ccgattgttt 105120
ctttccatgt ttagtgcttc cttcaggagc tcttgtaagg caggcctggt ggtgacaaaa 105180
tctctcagca tttgcttgtc tgtaaaggat tttatttctc cttcacttat gaagcttagt 105240
ttggctggat atgatattct cagttgaaaa ttcttttctt taagaatgtt gaatattggc 105300
tgccactctc ttctggcttg tagagtttct gctgagagat ctgctgttag tctgatgggc 105360
ttccctttgt gggtaacccg acctttctgg tgaatctgac aattatgtgt cttggagtta 105420
ctcttctcga ggagtatttt tgtggcattc tctgtatttc ctgaatttga atgttggcct 105480
gcctttgtag gttggggaag ttctcctgga taatatcctg aagagtgttt tccaacttgg 105540
ttccattctc ctcgtcactt tcaggtacac caagcagatg tagatttggt cttttcacat 105600
agtcccatat ttattggagg ctttgttcat ttctttttac tcctttttt ctctaaactt 105660 ctcttctcgc ttcatttcat tcatttgatc tttaatcact gataccttt cttccacttg 105720 attgaatcaa ctactgaaac ttgttcatgt gtcacgtagt tctcgtgcca tggttttcag 105780
ctccattaga tcatttaagg tcttctctat gctgtttatt ttagtctgcc attcatctaa 105840
actttttcaa ggtttttagc ttctttgcaa tgggttcgaa catccttctt tagctcggag 105900
aaatttgtta ttacagatcg tctgaagcct tcttctctca actcatcaaa gtcattctct 105960
gtccagcttt gttctgttgc tcgtgaggag ctgcgttcct tcggaggaga agaggcaccc 106020
tgatttttag aattttcagc tgttctgctc tggtttctcc ccatctttgt ggtttatcta 106080
cctttggttc ttgatgatgg tgatgtacag atggggtttt ggtgtggatg tcttttctgt 106140
ttgttagttt tccttctaac agtcaggacc ctcagctgca ggtctgttgg agtttgctgg 106200
aggtccactc cagtccctgt ttgcctgggt attaccagtg gaggctgcag aacagcaaat 106260
attacagaac agcaaatgtt gctgcctgat tcttcctctg gaagcttcat ctcagagggg 106320
cacccagctg tatgaggtgt cagttggccc ctactgggag gtgtccccca gttaggctac 106380
tcgggggtca cggacccact tgaggaggca gtctgtccat tctcagatct caaactctct 106440
gctgggagaa ccactactct cttcaaagct gtcagacagg gatgtttaag tctgcagaag 106500
tttctgctgc cttttgttca gctatgccct gcccccagag gtggagtcta cagaggcagg 106560
caggtctcct tgagctgtgg tgggctccac ccagtttgag cttcctggtc gctttgttta 106620
cctactcaag tctcagcaat ggcagacgcc cctcccccag ctttgctgcc gccttgcagt 106680
tcggtctcag actactgtgc tagcagttca atctcagact gctgtactag cagtgagcaa 106740
ggctctgtgg gcatgggacc ctctgagcca tgtgcaggat ataatctcct ggtgtgccgt 106800
ttgctaagac cattggaaaa gtgcaatatt agggtgggag tgtcccgatt ttccgggtac 106860
atctgtcatg gcttcccttg gctaggaaag ggaattccct gaccccttac acttcccggg 106920
tgaggcaata tcccgccttg cttcggctca ctctccgtgg gctgcaccca ctgtctgaca 106980
agccccggtg agatgaaccc agtacctcag ctggaaatgc agaaaccacc catcttctgc 107040
tttgctcatg ctgggaactg tggactggag ctgttcctat tcggccatct tgaaacctcc 107100
cctctctcac gatcacaagg tcccacaata ggccgtctgc aggctgagga gcaagaaaag 107160
ccagtctgaa ttccaaaact gaagaaattg gagtctgatg ttcaagggca ggaaacatcc 107220
agtgccaaag aaagatgtag aatattcaac attcttaaag aaaataattt tcaacctaga 107280
atttcatatc cagccaaact aagctttata acaaaggaga agtaaaatcc tttacaaaca 107340
agcaaatgct gaggaatttt gtcaacacca ggcctgcctt acaagaggtc ctgaagaaaa 107400
cactaaatat ggaaaggaaa aaccagtaac agctactgca aaaacatacc aaattgtaaa 107460
caccatcaac actataaaga aactgcatca actaatgggc aaaatagcca gctagcatca 107520
taatgacagg atcaaattca cacataacaa tattaacctt aaatgtaaat gggctaaatg 107580
ccccaattaa aagacacaga ctgggaaatt gaataaagag tcaagaccca ttggtttgct 107640
gtgttcagaa gacccatctc agggtgaaaa gacatacatg ggctcaaaat aaagaaatga 107700
aggaatattt accaagcaaa tggaaagaaa aaaaaagcag cggttgcaat cttagtcttt 107760
gatgaaacag actttaaacc atcaaagatc aaaagagaca aaggagggca ttacctaatg 107820
gtaaaagtat caatgcaaca agaagatctg actgtcctac ttatatatgc acccaataca 107880
ggagcaccca gattaataaa gcaagttctt agagacctac aaagagactt agacttccac 107940
acaaaaatag tgggagactt taacacccca cagccaatat tagatcgacg tgacagaaaa 108000
ttaacaagga tattcaggac gtgaattcag ctctggacca agctgaccta atagacatct 108060
acagaactcg acaccacaaa tcaacagaat atacattctt ctcagcacca cattgcactt 108120
attctaaaat tgaccacata attggaagta aaacacttct cagcaaatgc cgtagaatgg 108180
aaatcataac aaacagtctc tcagaccaaa gtgcaatcaa actagaactc aggattaata 108240
aactcactca aaaccacaca actatatgga aactgaacaa cctgctcctg aattactact 108300
gggtaaataa caaaattaag gcagaagtag ataagttctt agaaaccaaa gagaacaaag 108360
acacaatgtg ccagaatctc tggtacacag ctaaagccat gtttagaggg aaatttatag 108420
cactaaatgc ccacaggaga aagcgggaaa gatctaaaat caacacccta acatcacaat 108480
tcaaagaacc agagaagcaa gagcaaacaa atacaaaagc tagcagaaga caagaaataa 108540
ctaagatcag agcagaactg aaggggataa agacacgaaa accctttaaa aaattaataa 108600
atccaagagc tggttttttg aaaagattaa caaaatacat agaagcctag ccagactaat 108660
aaagaagaaa atagagaaga atcaaataga cacaataaag aataataaag gggatatcac 108720
caatgatgcc acagaaatac aaactaccat cagagaatac tttaaacacc tctatgcaaa 108780
taaaatagaa aatctaaaag aaatggataa attcctggac acatacaccc tcccaagact 108840
aaaccaggaa gaagtcaaat ccctgaatag accaataaca agttctgaaa tcgaggcagt 108900
aattaatagc ttaccaacca aaaaaagccc agaccagagg gattaacagt caaatcctaa 108960
cagaggtaca aagaagagct agtactattc cttctgaaac tattccacac aatagaaaaa 109020
gagggactcc tgcctaactc attttatgag gccagcatca ttctgatacc aaaacctggc 109080
agagacacaa caagaaaaga aaatttcagg ccaacatccc tgatgaacat caatgtgaaa 109140
atcctcaata aaatactggc aaactgaatc cagcagcaca tcaaaaagct tatccaccat 109200
gatcaagttg gcttcatccc tgggatgcaa ggctggttca acatattcaa atcaataaac 109260
ataatccatc acataaacag aaccaatgac aaaaaccgta tgattatcgc aatagacgca 109320
gaaaaggcct ttgataaaat tcaataccca atcatgctaa aaactcttaa taaactaggt 109380
attgatggag catgtctcaa aataataaga gctacttatg acaaatgcat agccaatatc 109440
atactgaatg agcagaagct ggaagcattc cctttgaaaa ccagcacaag acaaggatgc 109500
cctctctcac cactcctatt caacatagta ttggaaattc tgtccagggc aatcaggcaa 109560
gagaaagaaa taaaggtatt caagtgggaa gagagggagt caaattattt ctctttgcag 109620
atgacatgat tgtatattta gaaaactcta tcatctcagc ccaaaatctc cttaagctga 109680
taagcaactt cagcaaagtc tcaggataca aaatcaatgt gcaaaaatca caagcattcc 109740
tatacaccaa taagagacac agagccaaat cctgagtgaa ttcccattca caattgctac 109800
aaagagaata aaatatacct aggaatccaa cttacaaggg atgtgaagga cctcttcaag 109860
gagaactaca aaccactgct caaggaaata agataggaca caaacaaatg gaaaaacatt 109920
ccatgctaat ggattggaag aatcaatatt gtgaaaattg ccatactgcc caaagtgatt 109980
tatagattca atgttatccc catcaagcta ccattgattt cttcacataa ttagaaaaaa 110040
ctactttcaa tttcatatgg aatagaaaaa gggcctgtat atccaagaca acctaagcaa 110100
aaagaacaaa gctggaggca tcatgctatc tgacttcaaa atatactaca aggctacagt 110160
aacaaaaaca gcatggtatg gtactggtac caaaacagat atatagacca atagaacaga 110220
acagaggcct cagaaataac accacacatc tacaactatt ggatctttga caaactggac 110280
aaaaataagc aatggggaaa ggattcccta tttaataaat ggtgttggga aaactggcta 110340
gccatatgca gaaaactgaa actggatccc ttccttacac cttatacaca aattaactca 110400
agatagatta aagaattaaa tgtaagacct aaaaccataa aaaccctaga agacactttg 110460
ggaggccgag gtggatggat cacgaggtca ggagatcgag accatcttgg ctaacacagt 110520
gaaagcccat ctctactaaa aatacaaaaa attagctggg tgtggtcgtg ggcacctgta 110580
gtcccagcta cttgggaggc tgaggcagga gaatggcatg agctgaggag gttgagcttg 110640
cagcaagcca agattgtgcc actgcactcc agcctgggca acagagtgag actccatcaa 110700
aaaaacaaaa acaaaaacaa aaaatcaaac cctagaagaa aacataggca ataccattca 110760
ggacataggc atgggagaag acttcatgac taaaacagca aaaccaatgg caacaaaagc 110820
caaaatttac aaatcagatc taattaaaat aaagagcttc tgcacagcaa aaaactctca 110880
tcagagtgaa aaagcaacct atggagaaaa attctgtggt ctagccatct gacaaagggc 110940
taatgtttag aatgtacaag caacttaaac aaatgtacaa gaaaaaaaaa acaaccccat 111000
caaaaagtgg gcaaaggata tgaacagaca cttctgacag gaagaccttt atgtggctga 111060
caaacatgaa aaaagctcat catcactgtt aattagagaa atgcaaatcg aaaccacaat 111120
gagataccat ctcatgcccg ttagaatggc gatcattaaa aagtcaggaa acaacagatg 111180
ctgaagagga tgtgtggaga aagaggaaca catttacact gttggtggga gtgtaaatta 111240
gttcaaccat tgtggaagac agtgcggtga ttcctcaagg atctagaacc agaagtacca 111300
tttgacccag caatcccatt actgggtata tacccaaagg attataaatc attctacaat 111360
aaagacacat gcacacgtat gtttattgta gcactattca caatagcaaa gacttggaac 111420
caactgaaat gcccatcaat gatagactgg ataaagaaaa tgtggcacat atacactgtg 111480
gaatactatg cagccataaa acaggatgag ttcatgtctt ttgcagggac atggatgaag 111540
ctggaaacca tcattctcag caaactaaca caagaacaga aaaccaaaca ccatatgttc 111600
tcactcataa gtgtgagttg aacaatgaga acacatggac acaggaaggg gaacatcaca 111660
cacaggggcc tgttggggag ttgaggctag gggagggatt ggattaggag aaatacctaa 111720
tgtagatgat gggttgctgg gtgcagcaaa ccaccatgac acgtgtatac ctatgtaaca 111780
aacccacaca ttctacacat gtatctcaga acttaaagta taataataat aagatacaga 111840
actgcagaat gaataagaac tcaccaacca tctgctgcct tcaggagact catttaagac 111900
ataaggactc acataaactt aaagtaaatg ggtggaaata ataataagtg gtgtcactga 111960
tgtggaggta gattataaaa ctcttatcat atgctggtgg aagatcaaaa tgataaaacg 112020
aattaaaaaa tcagtcagat ggtttcttaa aaagttccat caatatgcct ctatcttaca 112080
aacctgcaat tctattcctg aatctttatc ccaaggaaat gaaaaagtaa gtccacaaag 112140
agttctatat gaatatttat aggagcttta tttattataa ttcaaactgt aaaaataatt 112200
tcaatgttca tcaataacaa aatgaaaaaa taatttgcaa cctactggta cacttgaata 112260
ctattcagca ctgagtatct taaatagcat ggatggagct caaaaatata ctcaggaaag 112320
aagccatgta tattctgtat gagttcattt acatgagatc atttacattt cctccaaaag 112380
aggaaaaact aatttctgtt gaaagaaacc aatgtatttg cctctggcag tggtaagggg 112440
gtagcacaga ttaattgggt agggactcaa gagagtttct ggggtcacag aaatgttccg 112500
tgtggtgatg ggagtttggg ctccacaggt ataggtgttg atccaaaatc atcaaaaaaa 112560
caacattgca gatctgtgca tctcactctg tgggaaagta tatctcaact gtaaaaaggg 112620
cagaaattgc ttttaaacgc tcagcctttt agcacatcca gttgcttgga gaaccagctt 112680
actcaaatgg gggtctaggc tggagactag gtcacaggca tagagtctct aaactttccc 112740
atggcacata atacgtttca ggttttctca gagagctgca ggttagtaat ctgaggattc 112800
tgacaagttg ggtcaacgtt cctaggaggc atgaatggga gtgcattctc taagatccct 112860
ccaccccagg gtccttgctt tctgtgcctc ttactccatt gttttctgac tcctctgtag 112920
ccactcgacc tcttcagatc ccattgtcta cccagccatc gccctttatg acttgggtcc 112980
cactgttctt tcatctcatc ctccattccc tcagtttcgg agtggctgcc gctagcagag 113040
gatggactga gagcaggaga ggtggtcctg cccaggaacc catcctagag aaatggcatc 113100
ctgtctggga gctagttttt tagggcaggt tttataagtc ttgtaaagcc agacacactt 113160
gatctacctg gtatgttatt tacagtaata ctattttcat aattgctttt cactctaaaa 113220
gtagagcctt ttagctacac tgtgagtaaa taaaggggct ggcctgggaa tggtatcatg 113280
ttggatgttg tttcttccct gaagtaatat atatcagtta caatttacat gttactgcag 113340
agtcctagag agagacacag agaatgagac agataccaat acatttttat gtgcattaaa 113400
aaaatctaag gccaggcgca gtggctcaca cctgtaatcc cagcactttg ggaggccgag 113460
gtgggtggat cacgaggtca ggagattgag accatcctgg ctaacacggt gaaaccctgt 113520
ctctactaaa aatacaaaaa attagccagg cgtggtggcg ggcgcctgta gtcccagcta 113580
ctcaggagac tgaggcagga gaatggcttg aacccaggag gcagaccttg cagtgagccg 113640
agattgcgcc actgcactcc agtctgggcg acagagcgag actccgtcac aaaaaaaaaa 113700
aaaaatctaa aatgcactct tcaaaatcta tgtcatttat tctggaggaa tgcagttggc 113760
agaaggagga agatattccg aatttttctt gtatacattt atgtatgatc tcagtttttt 113820
tatggatcat agaccaattt tgatatttta aaataaaaat tataatctat cttggaaatt 113880
tacatggttc tttagaactt gaggaccgtt tttgcttttc ggaatattat tgtacctaaa 113940
atgggaatat tacaacgtca ctttttaaca ctttgttata acaaagttta gacagcgctg 114000
ggtgcccctg aattttttcc cgcctcttgt gacctgtgtt gttttggaat ttgcagtggc 114060
ctgaccgaga actactgcag gaatccagat tctgggaaac aaccctggtg ttacacaacc 114120
gatccgtgtg tgaggtggga gtactgcaat ctgacacaat gctcagaaac agaatcaggt 114180
gtcctagaga ctcccactgt tgttccagtt ccaagcatgg aggctcattc tgaagcaggt 114240
aagaagtctg tggccagata tctacacatt tgaacattgg gatgaaaaga gatggaaaat 114300
ctgactgatg cagaagcctt ccatgctaca cagaaacttg agggtatggc aggtggaaag 114360
aagcctcagc actctctctg gtggagcaat ttttggcgca acgtgcgtgg gcggtgactt 114420
caggaatggt gcaaacccac ctgggcactt gacttaccac tcactttgtt atgaaagggg 114480
ttatctcggt gttccagaca aaattccaat tctaacatca ggccaaattt gtgccaaatt 114540
tcacactagt gagtgtttcc aggcatttat taaaatggac agtgttcatt gcaatcttca 114600
gcattgcagt tgctgaggta tgtggccgct gagtttgtca tcctggggaa acctaatatg 114660
atgatattta ttccatctaa tcctggggct atttggcagt aaataccaca gaatacacta 114720
tttctctggc ttatttcagt cttaggtagg ctctgcacac ctatgcttgg aaggcaggaa 114780
tttcttggtg ttcttgtgcc ttcttctcat ggaacgtgca tctttggtgt gtgttgagag 114840
gaagggtagt agacttctgc tttgttgcaa tgcaggatgc tggaacaaga ggattccctg 114900
tctctactgt aagggaataa gattttagcc tccatccttc tctaagaagc aatgtgtctt 114960
tgcctccaag tactagatgc aggaccatga actgccccgt ccaccagaag cttaaggctt 115020
tggcttttca ggagcaatca tctagggaac tgtgcagggt tttcatgtct gtcccctact 115080
gacagccaat caccatacag cctgcataac ctaatccatc atcgtctggt ttcctgcctc 115140
attgttttca tgaacaacca gtagagagcc atacgaaaga gcttgcacat gagtctttgt 115200
tccaattgta agagcactga taggtccttt tcccaccagg ttttgaatat aaaatttcta 115260
agaacttatt aaaatattag aatgttatta atctattgtt tttgcttcag catgtccttc 115320
tgcttgtgag tatactaaag agaacagtca taattctgaa actactgtcc tgtttgtgtc 115380
ataaattgct tcacatgttt ctgcatacta gtagttactc agcttgattt tgtctatttt 115440
cagcaccaac tgagcaaacc cctgtggtcc ggcagtgcta ccatggtaat ggccagagtt 115500
atcgaggcac attctccacc actgtcacag gaaggacatg tcaatcttgg tcatccatga 115560
caccacaccg gcatcagagg accccagaaa actacccaaa tgagtatgtc tttgatgtta 115620
cttgtaagag gagcaacagc caacttaagt tcctcctaga agagccttgc ttcaagctaa 115680
cttgttagga caaatttccc ttagacccag aaggtgtgtc aaaatgtcca gacaactttg 115740
cttttgatca aagagtctga gagaataggt attttaggct tgctatcttt tctaatagtc 115800
tgatggaagc agaaggctac atggagctga tgaggtcttt ttaatataaa gctcaagaga 115860
tcaaatgatc aaatacttag agtgccattc tacaaggctc ataaaagatc aatgcactct 115920
ttcacccatg caattctatc attctaacct cccttctctg aaatgaaggc tttttgccat 115980
ttttgtcatg ggtcacaagt aaataattca catgtatatg agtatatata taaccaggtg 116040
tgtttattca gactagtatg tatatatata catatatatg ttcatataag ttagtattca 116100
tatatatgtt catatatata tgttcataca gactagtatt catatatata tacatatata 116160
tatacacaca catatatata tatatatata tgttctaggg aaacatgcaa ggtttttatg 116220
tctgtccctg actgatgacc aaatacccta tagcctgcac agctgcaagc tgtatagcca 116280
tacaatttgc aggacacaca cacatacaca cacacacaca cacacacaca cactaacata 116340
taatataata taatataata taatataata taatataata taatataatt aatatatata 116400
aacctgtgtg aacacactgg gttctaagct ccagttttct gaagggatat gggttgccag 116460
gagaggaaga gcaaaagcaa gaatgtagat gagaattagg aagtaaacag atatggagat 116520
taaaatgggc aggtacatgg acaaaaaacc aggtctgaca aaaactggct ttctgccata 116580
aatgactata aaagatatta aaaaacactt tccacatgtt ggacaagaga cagtacagga 116640
ctgagataat ttagaaaagg aaatgaatga gcgcaactcc gtaactatta tgactttctt 116700
cctggagaac cttcctggac tgaagggcaa ggaattggag ccaaagccaa ccacagcagt 116760
cttgctgaac tgaggaaaga gactggagtt tgggatagct aagaaaatgt gtattttcta 116820
tgctaggtaa taatgagaaa gaatttgtgg tgaaaaggag ctgaaggaat atgcatggaa 116880
gtctaatata aactgcatat gcacagggag aaattctaca aagtgggaca gagaaccact 116940
actggggaaa ggacaaattc agggaaacag tgagctcaat ggtgacgcca gagctcacgt 117000
agcactgggg gataccgggg ttctgatcag cccgaggaga gacacctcat tgaacatctc 117060
gggcattcag tagagacccc agaaaagtca tactttagga gtaggattta tgccttctta 117120
gaataaagac taccccagaa acaccctagt aaagcttaaa aaccaagtct aaaaggaccc 117180
aaatgatctc caagtaaatt aactgcctga cagaagaaaa ctcaaccatc actggaggta 117240
aataacatga ttacagtgct ctgtaatgtt gcattcacaa ggagtgacat catttaaaaa 117300
tttatgaggc aggaaaaagc aattagtgtg atccataact aggagaaaaa ccagtcaata 117360
caaatagacc aagaaatagt agaaacgatg gaattgacaa agaaattaaa actgtatata 117420
tgataattgt gttcaaagat ttaaagaaaa catgaacatg agggaaacaa atgcagaata 117480
taaaaaaaag caaatgcgta aaacaaccaa atggaaatta aagaactaca aaaaagtata 117540
accttaataa aatactcact ggatggcctt aatattagtt tatacattac agaagaaaaa 117600
gtgaaccaga agataactca atgaaagcca tacaatctgt aagacacaca cacacgcaca 117660
cgcgcgcgcg cgcacacaca cacacacaca gagagagaga gagagagaaa gagagagaga 117720
gaaaggctga aaaaaataaa tagaacctta aggatatcag tgaaaatagc aaaagattta 117780
atatatgggt aaagcaagtc acagaaggac gggaaggaga tattgggaca gaaaaaaata 117840
ctcaaagcaa tgatggctga agactttaca cgtatgaaga aaatgataaa ctcacagtca 117900
agaagctcaa tgaatcagaa atagtatttt taaaagcaaa actctatgat ttacttgggt 117960
acattataga taaatcgtcc aacatcaaag ataacaagga taatcttata agccagagga 118020
aaacaatatc atttacatag agggacagta atgaaagtga ccgatgcctt ctccttggaa 118080
acaatggcat aacatcttta aagtgataaa gagaaataaa aacagatcaa cctaggacga 118140
catgtccagc caaaacaaac aaataaacaa aaaaaccctt taaaataaac gtgatgtaaa 118200
tacgtattct gccacctcca gaggaaacaa gcaaaaaaac aaaagaatgt ttccaaggca 118260
ggcttctgta ttaaaagatt ttaaggaaag ttattcaggt agaagaaaaa taataccaga 118320
tgggaacttt aatccatact aagtaatgaa gagccctgga aatggcaaat ggcaatgtca 118380
atataaaata ctcttattta tctaattttt aaatgtattt aaaggacaat ttgtgatatt 118440
aattaaaata ataggaatat attgttgttt caacgtatgt agtagtaaaa ttcataaaaa 118500
cagtagcaca aataatgcag atgataactg gaagtatact gttaatgagt tttttgcatt 118560
atccatgaag ttatataata ttaatagatg gttgaatgtg atagtttaag gtgggatatt 118620
ataaatccta ggacaaccaa aaaaatttaa actgagagga atggatagta agaggaatag 118680
tccttttatg caaaagaagg aagaaaaaga ggaataaaga atataaaaga tatggtgtaa 118740
acagaaaata catagcatta ttgtagacac aaactgaact accttatgag tatattaaat 118800
ataaaaggat taagcattac aaataaaagg cagagattgt aaattgaata aaaaccacag 118860
ctaagtgtgt tctttttaga ataaatactc tttaagtgta aagatctact ttaaacacca 118920
aaatatgaaa aaggatatat accatgaaaa cctgaatcat aaataagctg gagtggtgat 118980
taatggatgc aggcactcct aaagactaat aagtgaatgt ggtcaaattg aagaaacaaa 119040
agtatatacg tgctcaatgt gcaaaaactt tttctgtata catgctatga tcctttggaa 119100
aattaaagtt ttaaagcaat atcactgaca atagtatcaa aaccaaaaaa tatttagtga 119160
taaatttcac acactatgct caaggactat acaccttgca ctagaaaaca atgttgagga 119220
aagaattaaa agatctaaat atacaccatg cttatagatt aaaagactcc atatcagttc 119280
tcgtgaaatt gatctttgga tgaaacccac acccaagcac tattgcaaca gtcctttttt 119340
ggaaaaaaaa attggaggac ttatatacct taatataaag acttataaaa gtacaggaat 119400
caagacatgt ggtattggcc tggccccttg gctcatgcct gttaccccaa cattttggga 119460
ggctgagtct ggaggatggc ttgagcccag atgttcaaga ccagccttag caacagagtg 119520
agaccctctc tctacaaaaa ataaacaatt agatcgatgt gatgacttgc acatgtagtt 119580
tcagctactc ggaatgctga ggtgagagga ttgcttgact caggaggtct agccatgagt 119640
gagcattgat catgcctctg cattccagcc tggatgatgg aatgagacac tgtctcaaaa 119700
aaaaaaaaaa aaaaggatat gtgttattgg ccaaaaaagt atgcaaacct aaaaagggat 119760
ggcccaccac cagacccaca tacatatatg gtaaatggat tttccgtata gatggcaaag 119820
caattcaatg gagacaaaaa tgttttacaa aatcattctg aaccatttgg atatccatga 119880
tacaaaacaa aagcagaact tgacttttgc ttttcatctc aaattatttt gatatctctt 119940
ccacctaagt gtcagagcta aaactgaacc tgaaatatga aagttccatg aaaaaatata 120000
aaatcttcac aaccttggag aaggcaaact tttttgaggc aggagtctgt aaacactcac 120060
tataaaataa aacaaattat aatgtgggct ttcatgaaaa ctcatgctta ccaaaagtca 120120
ttgttaagaa aataaatagg caagtaacac atgagaagaa aaatgctctc tgtccatata 120180
tctgacaaat ggcttgtgtc cagaatatag gaacatttct cccactcact aaacagagga 120240
caaacaacta atgggcaaca gattgaatag gcatttcttg gggatagata gatgtacaca 120300
tagccaataa gcacctgaaa aaatgtccag tatctcagcc atgaaaaata aagagttata 120360
atcatcatga gatgtcacca aacacccaat ggacatggat attattaaga agacaccaca 120420
gtaactgatg tcactgatgt agagcaagga tgtgaaactc tctcatatgc tggtgaaagt 120480
gcaaaatgat acaaccactt ttgaaatcag tctgatagtt tctccaaaag ttcaataaat 120540
gcacttttac cctacaaacc tgcaatcctg tttgtgaata tttaccccac agaaatggaa 120600
acataagtcc acgaagacat ctccaagaat attcatagca gctttatttt ttataacccc 120660
aaactgtaga caatttcaat gtcaatcaat aagaaaatga ataaataatt tgtgaactag 120720
tcatacaatg gcatactgtt cagcaataaa agggagcatg tttttgatac tctcaaatag 120780
tatggaagat gctcaaaaat attacattaa agaaagatgc cagataacaa aaatgaacat 120840
tatgtatgag tctattgatg taaggttcca gaaaggtaaa actaatttct ggtgaaagaa 120900
accaatatca tttgcctctg gccatgggaa gagagtagca gagattgatt gagcagtaaa 120960
acgaagtttt tttctggggt gatgtaaatg tcctgtattg tgattgaagt gtgagttaca 121020
caagtgtaca tgttcatcag aagtcatcaa actacatcta agatctgtgc atttgactat 121080
acatgaaaat atacctcagt tgaaaataga tcaataacct ccctcatata ctatacttgc 121140
taacacagcc agctgcttgg agaaccagct tgctggaatg gagaatctgg gcttgagact 121200
gggtcacatg tatagagtct ctacagagac aatgttgcat tcccacggta cataatacat 121260
ttcaaggttt ctcagacagc cacatgtcat gaatgtgagg attctgagag gttggagcaa 121320
cattcctggg aggaacgaag gggagcacat tctccaagat cccccaccac cggggtcctc 121380
accggctgtg cttttttttt tttttttctt gacagagtct cgctctgtcg ccaggcagga 121440
gtgtaatggc ccaatctcgg ctgattgcag cctccaactc cagggttcaa gagattctcc 121500
tgcctcagct tcatgagtag ctgggactac agatgtgcgc cactgcgccc agctaatttt 121560
tgtattttta gtagagacgg ggttttgcca tgttggccaa gatggtctcg ctctgttgac 121620
ctcgtgatcc acccgccttg gcttcccaaa gtgctgggat tacaggcgtg agccaaagca 121680
cccagcctgt gcctctcact tactcaattg tttttctgaa ccctccatag ctggtggacc 121740
ttttcagatc ccatagtcta gccagccctc tcactttatg ccttgggtcc cactgttcct 121800
tcatctcatc ccccttctgt cagtcccgca gtggctgtgg ccagtagagg atggactgag 121860
agtaggagag gaggttctgc ccaggaaccc atcctagaga aacagcatcc tgcctgggac 121920
ctagtcttcc aggtcagctt ttataagtct tttagactca aactcacttg acccacctga 121980
agtggtattg acaataatgc tattttcatg gttgtttttc actgtaaatg cagagccttt 122040
tagctacacg actagtacag agagtaaggg aggctggcct gggaatgata tcatcttgga 122100
tggcatttcc tccttggaga aatatatgtt agttccaact cacatgttac tatacagtcc 122160
tgtagaaaga gatacagaga gttagacagg tatagacgca tttgtatatg cataacaatc 122220
tataagacac acatcaaaat ccgtataccg gttcctctag ggtatgtgc ttggcagaag 122280
gtagaaggag ggtattctgg ttcctttctt ttgcacattt atgtatgatc tcagttttta 122340
tatggagcat tgatagggtt tggctatgtc cccacccaaa atctcatctt gacttgtaat 122400
ctctataatc ctgataatcc ccatgtgtca agggcaggac caggtggagg taactggatc 122460
atgggggcag tttctcccag gctgttctca tgacagtgag agagtctcct gagatctgat 122520
ggttttgtaa gtgtctggca tttcccctac ttgcacttac tctgtcctgc cgcctgtgaa 122580
gaaggtgcct gtttctccct tgccttctgc catgactgta aatttccaga ggcctcccca 122640
gcaatgtgga actgtgagtc aattaaaact cttttctttg taacttaccc agtctgtctc 122700
gggtatttcc tcatagcaat gtgagaacgg gctaatacaa gcatatacta cttttgatat 122760
tttaaaataa aaattatcat ctatctttga aaggcatgca caaatgggaa gttgaggaac 122820
atttgtgttg tggcaattgt atgatacctt taatgggaat atttcaaaga cacttgttaa 122880
gactttgtta gaacaaaatg tagagggtgc tggatgtccc tgaatattct tccgcctcct 122940
gtaacttgta ttgctttgga atttccagtg gcctgacaat gaactactgc aggaatccag 123000
atgccgatac aggcccttgg tgttttacca tggaccccag catcaggtgg gagtactgca 123060
acctgacgcg atgctcagac acagaaggga ctgtggtcgc tcctccgact gtcatccagg 123120
ttccaagcct agggcctcct tctgaacaag gtaagaagtc tgtgtcttac cttgtctagc 123180
acatacctct ctatgtgctt ggacaacggg atgaaaagac atgaaaaacc acactgatgc 123240
agaagccttt agtgctacac gggagctcga gtgttggttg aggttctgcc atgaccaagg 123300
aagtctcagt gccgtccctg ggaaagccag agctgtgatt tttggcacaa cttgtgggag 123360
tagtgacttt aggactggcg caaaacctcc agggtgctca acttaaccac tcaccttatt 123420
ctaaaatggg ttatttcagt gtcccagtca aattcctatt ctaacatgct gtcaactgtg 123480
tgattatttc caagccaata agcatttcca gtaatttctt aaaatagtgt tcattgcagt 123540
cttcagcgtt gtggctcctg agggatgtgg cccctgattc tgtcgtccta gagaagcctg 123600
acatgactgc attgattctg tatcgtcctg ggtctatgtg gctgcctggc tgtctgtaat 123660
catctgtttt atttttattt ttttctacag actgtatgtt tgggaatggg aaaggatacc 123720
ggggcaagaa ggcaaccact gttactggga cgccatgcca ggaatgggct gcccaggagc 123780
cccatagaca cagcacgttc attccaggga caaataaatg ggcaggtctg gaaaaaaatg 123840
taagccactt tgatttggac tctttttccc tttgctgaca aatcttttca aacagaagag 123900
gggcagagga aaatactgga aagacttcag gaggctaagc gtaattagcc ttagcatgga 123960
aagtgcaagc agcacaggcc agcaaagccc cacgcgtgtg ggggttctca ggcctcttct 124020
cttttgacat ttctttactg tttccattgt tgggtgctgt ttctcgtttc tagtgcttgt 124080
cctctaagcc aggggtcccc actccagtac tggtactggt actggtactg gaactggtaa 124140
ttatctgtgg cctgttagga actgggctgc acagcaggag gtgagcttcg ggggagcaaa 124200
caaagcttca tctgtatttt ctgctgcttc ccatcactct catagctgcc tgagctctgc 124260
cagctgtcag atcagaggca gcattagatt atcatagcac aaaccctatt gtgaactgca 124320
catgtgagga atctagattg catgctcctt atgagaatct aatgcctgat gatctgtcat 124380
gcttccatca cccccagatg ggaccaccta cttgcaggaa aattagctca gggctcccac 124440
tgattttacc ttatggtgag atgcacattt atttcattat atattacaat gtaataataa 124500
ttgaaataaa gtgcacgata aatggaaggt acttgagtca tcctttaacc atcgccccct 124560
caccccaggt gcacagaaaa attgcctttt atgaaactgg tctctggtgc caaaaaagtt 124620
ggggaaccac actgctctgg gttctagtag tcagagatgc cctctatgag gcttaagtca 124680
gatttttcta gaaaagattt ggatgggcca tcaggtcacc atgagacttc ccttagcctc 124740
atgcattctc tgtgatggtt tactttgggg cctatgaata gggaagactg agatatagga 124800
aaaaccaaag tgtctgtgtt cccccactct cacacccatg taacataaca cttctcacac 124860
cagatatggg gggatttctc ctcacacccc aagcgagtct ccagcagata ccagctgggt 124920
gtcctacaat gtaactcggt cctgacactc tatctggaga cagtgtcaga tcccacaagt 124980
taaggctcag tcctacaaga ctgccccact gcagatgcca atcccaagtt gcaggctgtg 125040
acctgtactt ctgcccagct ggataaagat ctgtttttct atatgaccct ccatgggttt 125100
gattactttg ctagagtggc tcacagaact cagggaaaca cgttactttt atttacccat 125160
ttattataaa agatattaaa aaggatcctg gtgaacagcc aggtggaaga gatgcacagg 125220
gcaaggcacg tgggaagggg ctcagagcct ctatgccctc tccagtgcac cagtccccag 125280
taccctaagt gttcagcaac ccagaagctc tccaagtgca gtcttgttgg gtttttatgg 125340
aggcttcatt acagaggcac agttgattac atcattggcc atcggtgatc ggctcacctt 125400
cggcccctct tccctccctg gaggttggag ggtggggctg aacagttcca accctcaagt 125460
cacatggttg gttcccttgg caaccagccc ctggggctat ccaggaaccc accaagagtt 125520
gcttcattgc agctcccttc acccaggaaa ctccaaggga tttaggagct ctgtgttaag 125580
aactgggggg cagagaccca atatacattt cttattctat cacaatatca caggaagcta 125640
aggatgatac tgcctttgtg tgtcttggct gtggatggtg cataatgcat ggaagtaagc 125700
atttctgaat caacagcaaa caggctttat caggtagaag acccctcagc gccccaggga 125760
caaagctcat caatgatgtc ccactgtcct ctgaggctct agctctaaga cctccagtgg 125820
gtcaagctcc tggagaagtg gcacattctc caaagaccct tcagggtcac cacaccctgg 125880
ttaagggtgt ggcctcataa ctccttttga ctatgactga tggcttacag catagaaaga 125940
aataactttg tcaaaaaata taataatgat agaaaggaag aaggaacgct ccccttttgtc 126000
ttctaagaat agatgtgaaa tgtgtgtgcc ttagaatatc ttctccctct cctgctccac 126060
gtgagctgga gcttacatgc ctgcttgttt tcagtactgc cgtaaccctg atggtgacat 126120
caatggtccc tggtgctaca caatgaatcc aagaaaactt tttgactact gtgatatccc 126180
tctctgtggt aagttgcctt ctgttttggt aaggaaactg cttccttaat atggatttgg 126240
aaaaaaaaaa gcaaaaaaaa cagaaaatgg cttttgagct gagtgcttct ggggaggaga 126300
tggctgccct ctccaccaga gcctgctttt catcatggcc accttgaacc tgccctacta 126360
ttggccccat ttgttaggaa aacacccgcc cctcccacca cacacacata aataaaataa 126420
atgtcaaatt cccaaagggc aaacttagag gtgatctaat cagcccggga tagtcccacc 126480
gaacccttct ttgtctagcg tgggatgcat gaaaaacaaa tttagagtca ttatgatgaa 126540
aaactgtcct cttctgcagc tgagaagaaa aaaaaaatac gagcagcagg aaacagctaa 126600
gcatgtaatg cacattgtaa acctcagatg gccatcctag gaaatcaatg aagggtagtg 126660
cagctcttta gccccagatg gcctttctcg taagattact actcatgagt cccattagcg 126720
acattgctta gagactgctt gttaggttcc ttcctcattg ctctgagact cttattggga 126780
gtatgaggct tggatcaggg gaaggggaat tgacattaga tcttaaatga ttggggtaac 126840
aaatccatgg gggaaaaaaa gccacttgta cttgttccct attttcttcc tgctgaccaa 126900
tcaacttgtc tgtccgagtt acagaacacc accctggact tttcttttgt gtaatttggt 126960
tgcttgtggt tgggtctgcc atgtgaaggg accttgagct gggggaagaa ggttggcctc 127020
caagtccact gaagaccagc atcctgagat tgcctgggga ggtggtacag ggcagtgatg 127080
aagatcatgg gagccacact gcccatcgtc acatttgggc cactcctggg gagagcaaga 127140
gggaagaagg agaggttagg gtgataggaa agattctact tggccaatat tattataatg 127200
tggcattgtg gtctctggat ttagtgtgag ttgatagctg actttttct cgagtgggtg 127260 cttttgttct attttgtcgg tgctattgca gaagcatctt ggtggttcct ctacctcaaa 127320
gtctcttgat ggggtcagtt ccagttctcc gcttctggcc ccatctagta cacgccactg 127380
cctctcactg cctgggctct ctatccttga caggctgcct tgaatttaag cccagtctga 127440
cttacctgcc tcaaacaccc acagtagtgc ctgggactca tgcacctttg actcccatgg 127500
aagggaagtg cagtagcttc ccaggtgcaa ttctgctgtc ctcacccaca ttgaggatgt 127560
atgagaatca ggttcttaga gattggagaa agaaggaaga atgggaacaa gatttcttcc 127620
aatggactgt gaggttcccc accttacttt gatgtaagac aagtgaggtt aaccccaagc 127680
ctggtgagga gggttcccat cagacacttg gaaatcctga ggactgtttc ctgcagaagg 127740
atgtggttgg tgggatattc aggtttgact catgattgag aaagttagag cctctggttg 127800
gagaaagagt ttaataacta tttcatttcc accaacacat tcagtacgaa taataaataa 127860
gtaaaaataa atagaaacat tcagttttat tttgaatagt aggagtaggg tataatttct 127920
gtagttactc ttttagtaca atgatgcatg tttactgtat gtaaggcata ctagcagaaa 127980
ttgagctcag cactagaaaa gatgattgca ttccatgcca tgcttctttt ttacaaaaga 128040
cttctataga tagattctca aaacaaccca cagcaaatga aaagttattt ggaaaactca 128100
ggttccagat tcactggagt gtagaatctc tggttggttg gggaggaatt tcctcttgca 128160
gttgttatta ataattatat gaataattat taactatatt aatatttata gttttgaaga 128220
ccttgaaggg ctggagacaa cagagaagca tttttgaaca ccctctgtag cccctgcact 128280
gttgtaggca ttgatgggtg gtaccaaaga tgggacactt tccctacctc cagagacctt 128340
gtgggcttgc tgcagagaga aggcagggag gaggaaaaga agaatagagg cacatgtgtg 128400
taaattaccc ccacagcagt cagttagtca tgggaggctc cccagaagaa ctgtcctgaa 128460
gctggctgag agaaggcaac atttcaacat aggacagtta tccttgctac ataaaatcac 128520
atacacacat gcacatatgt ccacacacag agactcacat gcaaaagaat cctttgtgcc 128580
tttcagtaaa ctttacatgg tttagaaaga acttatattt ccttgaaagg agagtgtcct 128640
ttgttgttta ctaccacttt ttaaacttag aaagaaaaat ctaaagagtg tttatgattt 128700
taccatttaa tttcaccttt gagatgtgaa aaactagtgc ttggaattcg tcctgaatta 128760
aacgacacaa ttgctaactt ggactcaaat gcgacttctt ttcccacctt gtgccacagc 128820
atcctcttca tttgattgtg ggaagcctca agtggagccg aagaaatgtc ctggaagcat 128880
tgtagggggg tgtgtggccc acccacattc ctggccctgg caagtcagtc tcagaacaag 128940
gtaagaacag gcccagaaac catctatact gtccttccat gtaagcccca caaaaccctt 129000
ctacatttac acagaaccca cacagctgat gcatcaatac ctgcctctct gttttctgaa 129060
ggaggaaaaa atatagaaaa attaaaaaaa gttatattat tataggttct ctacttggaa 129120
aatagccaaa atacaaatct ttttcttgat ctgggcagtt ccatcaaaat ctgtaggcac 129180
agtgatttgc accaagttcc aatacttttg gaaaatattg aagatgctct gagggtttct 129240
atggatatcc attgtctcac tgtcagatga aaagaaaggg aagtttttag aaatgtgaca 129300
ctttgcagtg agggaggaca agagcaaact tacctacagt ctatcacagg cacagatttt 129360
tttttacact tttgtgaatc attgaattca atgccgaggc tattcatcta ttcacaaaca 129420
catgaacaaa ttatgggttg tgatccccat aaatgaagag taatcagtcc gaacccacag 129480
aacctggaca ttttgggtat cgtttcagtg gaacatgcaa ttcgtaagtt cagtttgctt 129540
gggtgtctct taggaagaac acataggaca cagacccatc tgcctgcatg ttttgcttcc 129600
tcatctcctt tctacaccag ggcacctgtg ctcaattgct gttctcctct aaagagactt 129660
ccttctgtaa gtttgtgaaa tgccatcgac aaacctgatc gcatcgcatt tcactctgct 129720
gttgagttga tttttcttta ctttatcgtt tgtaacttct tgctctacag agctttcacc 129780
ttccacatat ttcagattca ttctttccta aactgtgtgg tggtctatgt cctcactgac 129840
tatcaacata ctgccatcat gcacttccta tctctattcc tcttcgttgc aatctggctc 129900
caagtggctc acaccattat tctgatctat caactgccta cacagtccta gaaagtaagt 129960
gagtcaagaa acatccccca aaagtaaact tttcaggtaa gatcagaaga ccctcatgag 130020
tcactgctgc tcaggatcgt atctggctcc ttgaagagtg accttgcata gatcttgtca 130080
taaaaaatga aagagacctt gggaaggtct tgggctggtc acttttgtca gagtccaggg 130140
ctgtggggtg aaagccacag ctatagagct tcattctgga gtcacttagc tttgctctcc 130200
tggggacagg ctgtgcctat tcttgcctca ggcatcaaaa aaagtggcac agatgggccc 130260
ttctgaaaaa tctcactact ggagcacagc tcgaagtttc tactatcctg acgttgggcg 130320
gtagtccttt gctttgggaa tatgaacatg atcaaaactg agtgaacttg tcttcctggc 130380
tttctgtaca atgaagtaga acaaaccatc caatttgacc aaagccttgg catgttttct 130440
ttctaggttt ggaaagcact tctgtggagg caccttaata tccccagagt gggtgctgac 130500
tgctgctcac tgcttgaaga agtacgttta agggaaaact gacatggggt cttatcttca 130560
agactttttt cctccctctc ttcctccatc ccttctttct tcccaccctc cccttccttc 130620
ctccccacct ctcttccttt tctggaagga acactaggaa ccagggaatg catgcagaat 130680
cctgaggcag aatttccagg gcaattggat gagagaggag ggaagtgttt ctagagggaa 130740
tctgcagagg gaagacccag tgcaagtgat tttttggacc tgtataaacc gcaggacaga 130800
gctgttcact accagaggca tcaatctgta ttgcattgct ctagagcaat atctgaggct 130860
gaataattta taaagaaaag agtttaattg gcacatgttt ctgcaggctt tacaggaagc 130920
aggatgctgt catctcctct gcttctgtgt gggcctaagg aagattacaa tcatggtgga 130980
gggcaaagtg ggagcaggca tgtcacatgg ccagagcagg agcaagagac agagagagat 131040

-continued

```
ggggtggggg tgctgcacaa taccaaatga ccagactttg caagaactaa gagtgagagc 131100
tcactgatca ccatgaagat gtggcccaag ccattcaaga gggatgcacc tctatgatcc 131160
aaaccccttt cacaggccat agctccatca ctggggacta cagttgaaca cgagatttag 131220
gtggggacaa atatacaaac tatatcacag tctctgatga aacagattga gaacagacct 131280
taactgtcag tttccagcaa attgtgaatt ttgtttcttg ccactcataa gtcactgatt 131340
ctgggtggcc gagggtgtca gagggacagc gccaagttca tggcacagag gatacctgaa 131400
ggggctggac catatttttc tcttgacatc ctcatctttt ctaggtcctc aaggccttca 131460
tcctacaagg tcatcctggg tgcacaccaa gaagtgaacc tcgaatctca tgttcaggaa 131520
atagaagtgt ctaggctgtt cttggagccc acacaagcag atattgcctt gctaaagcta 131580
agcaggtact cgctcacctg tggtcttcac cccacgctgg tgaagatatt tgctttatgt 131640
ctgggtttta tgggccatgg ccactgcatg gcagtgggga ggaactgtct atcacatgaa 131700
aggctcaagg gctttgggga cagcatcaat cttcaacccc agccctgcca catgttagtt 131760
gtgctcttta aaaaggcaga aggattcgtt tcctcacgtg gaaaaagaga taccctgtta 131820
cccgtaaaac ttacttaatg ttcaccagtt catccacatt catgatcagg gaaaggttgt 131880
tattccaggc taactattct cctttcataa taatatgctg gagagaatca aatgagattg 131940
catttcaaag cgcttgaaaa accaccatat cgagccatgc ttagtgtggg cgcctctaat 132000
cactgctatt caggaggctg acgaggaaga attgcttgag cccaggactt caaggctgta 132060
ggcagctatg attgtgccac tgcactccag gctgggtgac agatcaagac cctgtctcaa 132120
caaaagaaaa gaaaacaaaa caaatgaaca gaaatattcc acaatgtcaa aaaaaaaaaa 132180
aacccacaca acatacaatt tacaaatgca aataataata ttattgttgt cttctttgat 132240
tttctctttc ctggtgaaat tttgttttat taagcctgac aaagtgatac ctttgcttac 132300
atcacttaaa gttagtctat ttggacctag gtgacagtac aatcagctaa gaaacagtat 132360
ttgtaggaga ggcaggtttg ggacaggtga caaggcatgt ggggtgctcg ctgtgctggt 132420
ggctctggaa ggcagggtgt caatgcagac agggatgagc atggcctggt tgggaaggca 132480
tggggcaggc aggagcctga gctgctctcc tgggcctggt cacaagccca tggcagcttc 132540
tctgggtctg tgaactgagg ggtgatgtcc tggaatcctc tgacactcta ggaaggagag 132600
aagggccttt ctggctcagc ctttataaac agtagctgat ctccctcttg ctccccaggg 132660
tcctccccac catcccagca aatgtgcaaa tacaagatct ctgctcctca tggtcctcag 132720
agagctgggg tgttctgatg gcttgaacaa gtcacttagg aaatgtgggg ttttggaggc 132780
attctctgat aggctgatac gttttgagtt tagagttccc accgcacatc cccacacccc 132840
tagagtctag ggcatttagt gctccatgag ggaacctgta gagtgaggac atctgcatca 132900
caggctgggc cttctagtgt ccagaagcag aaagtgtgtc tgcttcaaag ttggtgctaa 132960
tgatgatttt tggtcagaat acggcatttc tcatttccat tcctttatcc ccttgaactt 133020
actaaagtag aatcaggtct aaaaaccaga gttctaatct ttaagagtcc ctgggattct 133080
aaggtatatg aatgtccttg gaaaacaata ccatttagtt catgcaaggt gcttatttcc 133140
catcctcttt catttgatgt ctagcatttt actgcattct taccaccacg gtttagtaac 133200
attcacgagg aggaagtgga ggatccagat ggagcaactt gctctgggca cacaaggcat 133260
ttgcaatttt ataccctctt gatgatgtct cagccagaca ttctgcccag tcatcaatgc 133320
cctcttcaat taatatgaaa ggacacactt ggcatgagat tccaatcgtg cacagaatat 133380
acatgagaag tgtgcctttg tcatccctac tttcaaaggc taaggccacc ctcagtttct 133440
```

-continued tgcatgcaac tgatgccttt caaatgaaac cttacatctg tgtagtccat aggcaaccac 133500
aggcaaatgt gagggtgaaa cgctgtgttc tacattgttc tgtgtcagtg aagcaaggca 133560
gtgccagctc agagggctct ggggcttcaa ggcagggatg cctggttgta ggtactgcca 133620
cttccagctg ggcagtgaaa cataactgct aatactttcc ttacaggcct gccgtcatca 133680
ctgacaaagt aatgccagct tgtctgccat ccccagacta catggtcacc gccaggactg 133740
aatgttacat cactggctgg ggagaaaccc aaggtgagat caattccatt gcccacgtaa 133800
caaattgttt ttgaccttca gtgcatgtta caaaatgagc attttggaga tagttgtaca 133860
aattcctacc catgaatgtg gtctacccac tcctgacttt gcctggacac ctgtctatgt 133920
ctccataatc agtcttcaag ggacttgggc aaggggagcg gtgccatttc cttgagtctc 133980
tctctttttt gttttcagaa tcttttaatt ttttttgtaa tgattgtatg tttcccttac 134040
aacaaaaaca aacaccagta gaggtctttg agtctcttaa tcataatttc agcattcata 134100
ttgcttcccc aggtaagtgg ggttttgacc cagccctcaa gttaagggtg ttagattatt 134160
tttcatgtga aattagacag actgcgtttc taaacatggt gcaaaacagt aacgacaaaa 134220
gttgtaatta aactattctt cttcccaaat acccacatgt ctaatgtgtg tgtgagggtg 134280
ttaggcaggg gacctgaagc tgggggagag gcagacagtt cccatggccc caagtctagg 134340
atggcatttg gtattggttg atgggtgaga gcaagagagg gaatattttt gtgcatgatg 134400
tggtatcagc acctgtacta cattttatgg attccttctt ctctttgcgg tatgccctga 134460
caataattat atccgtcagc cttacccccct tggcagtagg aaaactgaaa ctgtcttaaa 134520
gtctcagctc tactttctca gaggtgcagg caagggcact gggagtctgg ggccctggaa 134580
aactgttctg actctgccac ttgccagata gacctgaact agacacgtta cctctttgta 134640
ccacttggct ctaatccctt atctgtaaaa ccagcatttt caaatggtgc tttgcacatc 134700
agccttttgc ataagctttg atttgataaa atgtttttttg tgtttttaaa aagattaaaa 134760
accacaggtt tagataattt caaagtaggc ttccctttttt ctgtcatttt cctattattt 134820
ttaaaacctc acctccttga ctccttgttc cctttttctg cactgctgag tctgggagca 134880
ctgaggccag gtaaaaggaa acttggcaaa tgaggggcac ctatgggtgt gggaggctgc 134940
tcctggtgtt tgcatatttt aaaatttaaa tgctacaaac cactgtgagt taggtattat 135000
tgttcctatt ttaccattga ggaagctggg gctcagagaa ggtggagggt ggtacagaca 135060
aacctgaatt ggaaccctgg ctcctgccta tgggctgtca ggacttagaa aagtcgtgag 135120
ctctcgctga ttgtttcctc agctgatgtg ggctgcaggg ctgttatggg ggaaataata 135180
agaaagtgca tcaagtgctg agcacatcct aagcactcca tcatggcagc tcctactact 135240
aataaagaat agaattatat ctaacatgat tctttcttgc aagtgacaga aaatccaact 135300
caaattggat taagcaaaac aagggaaatt cttagtgagc tgcaaagttt tcaggctcac 135360
atgatggccc caaatcccag gtcctcccaa tcatggagta ggcactattt gggggcacaa 135420
aggtgacatt cccatggctg cagatgctgt ggtgctgtgg ctgtaccggg aaagaataag 135480
aaaggccact ctcccaatta tgtgaacaat agtctgccca ctctgagaag tcaaacttgg 135540
gtcacagtcc tgcccctgaa cccatcactg actggctctg acctgcacca attgttccat 135600
gttggaggtg aaggcaagac cccactaata cccataaggg gcaaaagtta gatagatcct 135660
tcaagaggat tatgggaggt agggcaaaaa gctgctgggc agccagaaag caaacagagc 135720
ctctatgata cctcaactga tgaaagcatg aagctaaaat cataaggatc tgggtgtgag 135780
ttctggctct cccatcttcc atgtgacatt gggcagttat ttaatctctt ttagcctccg 135840
ctttctcatc ttacatatga gataattgtg aggattaaga ttacacataa tcatcatcat 135900
caccgtccac cactaccacc atcatcccca tcaacatcat cgccaccact atcatcattc 135960
ttactggcac taccatcacc atcaccacca ttccaccacc atcaccaata tcatcactgt 136020
caacatcatt accaccatca ccatcaccac caccatcatc attactacca ctaccactac 136080
taccaccatc accatcacca ccattccacc accatcacca atatcatcac tctcaacatc 136140
atcaccatca ccatcaccac caccatcatc atcattacta ccactaccac tactaccacc 136200
atcaccatca ccactgtccc actactatca gcatgacatc accatcacca ccaccatcat 136260
cattaccacc gctactacca acatcaccat caccacaatt ctactgccat caccattaac 136320
attaccacca ccatcatcac tatcaccatc accaccatca tcaccactgc cattatcact 136380
gccaccatca tcactatcct ctatatttcc tcatctgtat tatcattact accaccatca 136440
ctatcaccac catcgtcacc atcataatca ccatcaacac catctccaat accaccatca 136500
ctgtaaccat catcaccacc accatgatca ctatcaccat catcacaatg atcactgtaa 136560
ccatcattac tacccaccac catcaccact actccaccac catcaccatt atcattacca 136620
tcaccattat caccaccatc atcatcacca gcaccaccat catcaccagc accaccatca 136680
ccatcaccat cattaacacc atcactatca ccattggttt aatcatcacc accatcatca 136740
taaataaaca tcacataacc agggtgtagc tgggtgttga ccccagagcc cactcactgt 136800
ttcctctctc ccaccccat ccacacattt ctaaccacca tcctgcactg ggctcccagt 136860
ctcctctggt ctcacccaca tgtccactga gaaaaggatt ttcagaacac caactagacc 136920
aggaggagcc acatacataa ctcaggcctg cttatcaact ttctacatgt taataatgac 136980
atcagatcaa tgggtgttct cagcttctca gaaggaggtc aaaattctcc ccctctcccc 137040
ttcatgtgtc cagaccttcc cggatttgga tgtaccaagt gcagagtggt gttgaggcca 137100
aggggctcat ccatgtaagt ctcatctgca atcactgggc tgatcccgtg gccctgtctc 137160
cagggcgcca tcagagaggg cttcaatcct caggttacct gtggcccacc ctgccctcag 137220
aggtgccatc tctacattgg ccacgagatg gcagcacata ctcatagact gcattaattt 137280
cccagcaact cctggtgggt tttccctctt atcaggatgt ttgccttgct cagagagcaa 137340
atctgagagc agtgacacct aacttaactt tcagcaaaat attttgagaa gggtgcccct 137400
ttacacatct gtgcagtcca ggtgatgcat cccatgccca atgctcggta gtcaggagga 137460
gcttcctcca tgcagctctg cggaagagac tcttccacgc tgctcatgta aactccagat 137520
tcggtgtcag ttttctgaca ccgaagacaa tgatctaagt gcagtcaagg gctttgggga 137580
aagcaggaga gagtgcctca gttctagcct gtgccatgct tgcaaagttt tgcaaaattc 137640
taatgagagc tgggcttgca acattggaaa cttggattat ttgtgagagc actgagaaat 137700
ccctgggcat gtccatctgg aaaaacagca tttcctctgg cactttagca gaggttctgt 137760
ttcaatttgg cgaaggaaat taagcagttt ttcacaaaag aagaactaca acgaggagaa 137820
ttgtccctag tatttcttct ccctaattgt caaggaagtg taaattagaa aatgaatcag 137880
gacaatttcc acctactatg ttagctaata ttttaaaaat tgaatatcac aagggtgagg 137940
caaagtaatt gttttccagt gacattttcc actgtcacac ccttttagag aataatttgg 138000
caatgttact gtgagataga aatatgtcta tataattatg ggaactgaga cttcagaaag 138060
taataaggaa taagaatgaa atttatgaac aaacatgtgg aaggttggaa gcaagagtgg 138120
ggccaacacg catggggagg aagcatttgg gcagcgactc cgcagaccca gactcaagct 138180
gagctataca acctccttac gcctcagttt cctcaactga agaacaggaa tgacaagtgc 138240
ctgtttcata ggaccgttgt gaggattaag tgagatatac cacattatga gcttgtgcct 138300
ggaaaggttg attcttagta aatgatgact attcttttt attgcaataa aatttataca 138360
acatagagtt actattttaa ccatttttgc aggtaccact gagtggcatt cagtacattc 138420
acaatggtgt gcaaccgtca ccatatttcc aggacatttt tctcatcccc aaaggaaacc 138480
tcatgcccat taagcagtca ctcctcatta aaatattagt tatgaagact gtagcatttt 138540
tttaaaaact catgatataa cattgattga aaaaatcagt ataggaaatt gtgcattatg 138600
atgtaatagt aaaagaagca tataaaaatc tgaaaaaagt atataaaaag aatagcaatt 138660
gtatttctca gactctcttt acattgtaaa aatcattttg atagcttcaa aagaaaagca 138720
aaaagtacac aaacaacaac caaccccaaa gcagcatgac aaagcccaga ttgttgaatc 138780
caggtcttgg gaacataaaa tcttatatga catttgcact ttaatgggtc agagagtcca 138840
gtggcattgg gagctgcctt gtgttctgca gcctcacgga cagacaggag gtccagctcc 138900
actgctctgt tcttctggaa tttcctcgtg aacaagcttt ggcctcagta accatttctt 138960
tcatcttttt aaacacaggt acctttggga ctggccttct caaggaagcc cagctccttg 139020
ttattgagaa tgaagtgtgc aatcactata agtatatttg tgctgagcat ttggccagag 139080
gcactgacag ttgccaggta agaaaagatc aatagatcaa agtcttgtgc tctcccgtct 139140
cagtctcagt cccttagacg tcagtcccaa agtggcaaat tcaggaaggt tttgtcagtg 139200
gaagacccca gtctaagtgt tgctcagaaa ctccccagat ctgtccctga atgcatattc 139260
agatcatcta aggagacgtc ttggggcttg agttccagat ccatagcaag ggagccgtaa 139320
gtgccataac tacctcaggc cactcacctt cctggtgtgt gctggtcacc agtgactgaa 139380
gtggtggctt ttccagtaga gaggaaggta gagggtacag gaccgagaca aattacacac 139440
acttaacaat gatgtccagg ctagcccagt ctaaaggaaa caccaagtta ggaagcaatg 139500
catgcaggat tcacaaggga ttattttttt tcccaggaaa aaactaagtg atgtggtttt 139560
gttgaataga ctttgctaag tacttaagca ctgcagatgc ttgagtaata tgctcataag 139620
ttcctttctg atttgaatta ctgggaaaat gtacatatgg ataagagaag gatggcatcc 139680
catattaaaa ggttggcagc ttaaagctca catgaatttt cccctacctc tgtttagggt 139740
gacagtggag ggcctctggt ttgcttcgag aaggacaaat acattttaca aggagtcact 139800
tcttggggtc ttggctgtgc acgccccaat aagcctggtg tctatgctcg tgtttcaagg 139860
tttgttactt ggattgaggg aatgatgaga aataattaat tggacgggag acagagtgaa 139920
gcatcaacct acttagaagc tgaaacgtgg gtaaggattt agcatgctgg aaataataga 139980
cagcaatcaa acgaagacac tgttcccagc taccagctat gccaaacctt ggcatttttg 140040
gtatttttgt gtataagctt ttaaggtctg actgacaaat tctgtattaa ggtgtcatag 140100
ctatgacatt tgttaaaaat aaactctgca cttattttga tttgaattaa ttttggtttt 140160
ggtcttcaaa attttcatgc tcttttcatc ccatctattt ttatttttat tttttagact 140220
ttacgtcctg ggtacatgt gcagaatgtg caggtttgtt acatagatgt acacgtgcca 140280
tggtagtttg ctgcacccat caacctgtca tctaattcgg tatttctttt agttctatcc 140340
ctcccctagc cctccacccc ttgacaggcc caggtgtgtg atgttgccct ccctgtgtcc 140400
atgtgttctc attgttcaac tcacacttat gagtgagaac atgccgtgtt tgtttttctg 140460
ttcttgtgtt agtttgctga gaatgatagt ttccagcttc atccatgtcc ctgcaaagga 140520

```
catgaactca tcctttttta tggctgcata gaattccatg gtgtatatgt gccacatttt 140580
atccaatcta acattgatgg gcaattgggt tggttccaac tctttgctat tgtgaatagt 140640
gccacaataa acatacgtgt gcatgtgttt tcatagcaga atgatttata atcctctggg 140700
tatataccca gtaatgggat tgcagggtca aatggtgttt ctggtgctag atctttgagg 140760
aatcaccaca ctgtcttcca caatggttga actaatttat gctcccacca acaatatcaa 140820
ggcattccta tttctccaca tcctctccag catctgttgt ttcctgactt tttaatgatc 140880
gccattctaa ctggcatgag atggtatctc attgtggttt tgatttgcat ttctctaatg 140940
atcagtgatg atgagctttt ctcatatgtt tgttggctgc ataaatgcct tttttggaga 141000
agcatctgtt catatccttt gcccactttt tgatggtgtt gtttttttct ggtaaatttg 141060
tttaagttct ttgtagattc tggatattag ccttttgtca gatggataga tggcaaaaat 141120
tttatcctat tatgtaggtt gcctgttcac tccgatgata gtttcttttg ctgtgcagaa 141180
gctctttggt ttaattagat ctcatttgtc tattttggct tttgttacca ttgcttttag 141240
tgttttagtc atgaagtctt ctcccatgct atgtcctgaa tggtattgcc taagttttct 141300
tccagggttt ttatggtttt aggttttgca tttaagtctt taatccatct tgagttaatt 141360
tttgtataag taatgccctt ctttgtctct tttgatcttt gttggcttaa agtatatttt 141420
atcagagact agaattgcaa tccctgcttt tttttttctt tttgctttcc ttttgcttgg 141480
taaatattct tccatccctt tattttgagc ctatgtatgt ctgcacatga gataggtttc 141540
ctgaatacag cacaccaatg ggtcttgact ctttattcaa tttgccagtc tgtgtctttt 141600
aattgggggc atttagtcca tttacattta aggttaatat tgttatgtgt gaatttgatc 141660
ctgtcattat gatgctagcg ggttattttg cccattagtt gatgcagttt cttcatagtg 141720
tggatggcct ttacaatttg gtagtttttg cagtggctgg taccaattgt tcctttccat 141780
gtttagtgct tcgttcagga gctcttgtga ggcaggcctt gtggtgacaa aatctttcag 141840
catttgcttg tctgtaaagg attttatttc tcctttgctt atgaagctta gtttcgctgg 141900
gtatgaaatt ctgggttgaa aattattttc ttttagaatg ttgaatattg gcccccactc 141960
tcttcgggct tgttgggttt ctgcagagag atccactgtt agtctgattg gcttcccttt 142020
ccgggtaacc caacctttct ctctggctgc ccttagaaat tttccttca tttcaacctt 142080
ggtgaatctg acgattatgt cttgaggtgg ctcttctcga ggagtatctt tgtggtgttc 142140
tctgtatttc ctgaatttga atgttggtct gtcttgctag gttggggaag ctctccttga 142200
taatatcctg aagagtgttt tccaacttgg ttctattctc cccatcactt tcaggtacat 142260
caatcaaatg tagatttggt cttttcacat agtcccatat ttcttggagc ctttgtttat 142320
tccttttcat tctttatcct ctattcttgt cttcttgctt tatttcatta agttgatctt 142380
caatctctga tatcctttct tttgcttgat cgatttggct attgatactt gtatatgctt 142440
cacaaagttc ttatgctgtg tttttcagtc agatcaggtc atttatgttc ttctctaaac 142500
tggttattct acttagcaat tcatgtaacc ttttttcaag gttcttagct tctttgcatt 142560
gggttagaac atgctgcttt agctcggagg attttgttat tatacacctt atataatagc 142620
ctgatataac tataagattt ttttgtaagc accatcgtaa ccacaaagca aaaacctaaa 142680
gtagatatac aaaagataaa aaggaatcaa agcataccac tagagaaaat cacttaatca 142740
caaataaaga tacgaagagt ggaataaagg aacgaagggt ctacaaaaca accagaaagc 142800
aattaacaaa atggtgatag cagatcttac ctataaataa ttatcttgaa tggaaatgga 142860
ttaaattttc caataaaaag acatacagtg gccaaataga ttaaaaaata agatccaact 142920
```

atatgatgcc tataacacac tcacttcacc tgtaaggact caaacagact gaaagtaaag 142980
ggatggaaaa aatattctat gcaaatggaa acaagaagat agaggggtag ttatacagat 143040
tgagtatcac taatccaaac atctgaaatc tgaaatactc caaaattaaa aatgtttaag 143100
tgccaacatg atgttcaaag gaaatgttct tcggagcatt ttggattttt gtgtttaggg 143160
atgcaaaaac agtaaatata taatttgtat tagtccattc tcacactgct ataaagaata 143220
ctacaaagag actgagtaat tataaaggaa agatgtttaa ttaactcaga gttccacagg 143280
cttaacagga agcatggcta aggaggccac aggaaactta taatcatggc ggaagatgaa 143340
ggagaagcag gcaccttctt cacaaggtgg caggacggag tgtgagtgtg tgaaggagga 143400
actgtcaaac acttataaaa ccatcagatc ttgtgggaac tcactcactc tcacaagaac 143460
agcataggga aaaccgcccc catgatccaa tcccctccca ctgggctcct cccttgacac 143520
atggggatca tgagggttac aattcacgat gagatttggg tgggacacag ccaaaccata 143580
tcataatgca aacattgcaa aaacaattca aaattcaaaa catttctggt ttcaggcatt 143640
ttggataagg gaaactcaac tcaacatgag gtaaagcaga ctttaagtca aaaactgtaa 143700
aaagagacga agaagaatgt aataataagg agatcagttc attacaaata tatagcaatt 143760
ataaatatat attaatatat atacccaaaa ttgtagtacc tacatatagt aactaaaaca 143820
aacattaata gatctcacag gagagctaca ctgtaatata atcatagtag cacacttgaa 143880
tagctccact ttcactaatg gacagatcat ccagacagag aatcaatatg gaaacacgag 143940
acttaaacta cactttagcc aagtagacct aacagaaata tatagaacat tccatccaac 144000
agcagtagaa tacacattat tctcaagtgc acagggaata ttctccagaa tagatcatat 144060
gttaggtcac aaaactagtc aaaaaatgta agaagattga aatcatatca ggtttttttt 144120
ttagatcata atcgtatgaa actagaaatc aataatgggg gaatattgga aaatccacaa 144180
atagatagaa attaatcaat atgctcctga acaatcaatg agtcgaagaa gatattaaaa 144240
gaggaaattt taaaaaatca agacatgagt tcatgtcctt tgcagggaca tgaatgaagc 144300
tggaaaccat cattctcagc aaactatcat aaggacagaa atccaaacac cgcatgttct 144360
cactcatagg taggaattga acaatgagaa cacttggcca cagggcgggg aacatcacac 144420
accagggctt gtcagggggt gggaagctgg tgaagggata gcattaggag aaatatctaa 144480
tgtaaatgac gagttgatgg gtgcagcaaa ccaacacggc acatgtatac ctatgtaaca 144540
aacctgcacg ttgtgcacat gtaccccaga acttaaagta taataataaa aaaagaaata 144600
tttgtttttg atttatatgc caatcagaca aaatgtgaaa agccctactg aaattaagta 144660
tcaccatgaa agataaattc tggataattt tttcaagttt taacaatgta gctttaattg 144720
gagaaagcta tcatttggaa tgagttaatc tatcctatac taaaataagt cacttgcttt 144780
aaaacataat aaatatgatt ttgaattgaa aacaaaaaca actcaagaca aaggaaaatg 144840
gacacactaa cataccaata atttatagta tgcagcaaaa gtggttttaa gagggaagct 144900
tttaccaata aacacttcca ttaaaaaaga agatctcaaa taagcaacct aagattacac 144960
ctcaacaaac tagacaaaga actaactaac ccaaaagtta gtagaaggaa agaaataata 145020
aagatcacat cagaaatagt aaagactaaa aaactgatac caaaaagaaa taaaactact 145080
agttggtttt caataaaata acaaaattga ccaactttta gctagattaa gaaaaacaga 145140
gaatactcaa ataaaaccag aaagaggaga cattacaata gatactacag aagtacaaac 145200
gatcataaga gactactatg aataattaca tgccaacaaa ttggataact tagaagaaat 145260
ggatgaattc ctagagcaaa aaacctacaa agactgactc agaaagaaat agaaaatctg 145320
aacagaccaa taatgtgtac atgattgtat cagtaataac aagtctccca tcaatgaaaa 145380
ggccaggacc taatggcttc actgctgaag cataccaaac attacaaaga ctaatatcaa 145440
ccctcctcaa actcttctta aaaactaaaa agaaggaatg ctttcacatt cattttatga 145500
ggatagcatt acactgatac taaacacaga aaaataatac gctaataaaa gaacattaca 145560
ggcaatatcc ctgataaaca tatgtgcaaa aatccgcaac aaaatactag aaaactgaat 145620
ccagtagcac tttaaaaaga tcattcacca tgatcaagtg cgatttgttt cacgaatgca 145680
agaatagttc aacttacaca aataaataaa tgaaaggatg gatgataaaa atgtgtatct 145740
atatatatat gttttataca cacacacaca cacacacaca cacacacaca cagaggaata 145800
ttattcagcc ttaatgaaga agaaaatcct gcctttgcat caacctggag gacattataa 145860
taagtgaaat aagccagaca cagaaaggca aatactgtgt gatctcgctt acatatggaa 145920
tctaagaaag tcaaattcct agaaatagag agtagcttag tgattgccag agccgtggaa 145980
gggggaaatg gagagatgtt gatcaaagga tacaactgta tagctttgca agataaatag 146040
gttctggaga tctaatgtgc agaatggtga ctagagttaa taatactgta ttgcatactt 146100
gaaatttgct aaaagagttg atcttaagtg tcctcaccat atacacaaaa gtattatgtg 146160
aggtggtgaa tattttaatt agcttatgat aataatttca cagtgtacat ctatattaag 146220
gcattacatt gtacatctta aatatatata atttttattt gtgaagtgta cctcaataaa 146280
actggaaaaa ataattgaaa agtaatgaaa aaaattaaaa gctattatgt gtcaaatgac 146340
attatcaaga aagtgaaaag caacctactg atgaagcaaa cctattgaca aaggcctggt 146400
gtccagaata tattaagatc tctaggctgg gagcagtggc tcacacctgt aatcccagca 146460
cttggggagg ccaaggtggg aggatcactt gagcctggga gttcgacact gcagtgagct 146520
atgattgggc cactgccctc caggctgcgt gacagagtga gactgccatc tcttaaccca 146580
cttcttattt agaaaaagaa aatatgtagc ttgctgcctg catagtattc ttggggcaaa 146640
tgggaaatga gttaaaaaaa aaaaaaagaa ctcttacaac tcaacaataa aaagaaaaac 146700
aagaacgtga atagacattt tttccaaaaa agatatacaa ataggcaata agtacatgaa 146760
atgatggtca acatcattag tcattaagaa aatgccaata aaatcacaat gaaataagac 146820
ttcatatcca ttaaaatgtc tataatttaa aaaatggaaa ataacaagca tttgtgagga 146880
tgtggagaaa ttagaatcct gtatattgct ggtgggaatg tacagggaaa atggtttggc 146940
cactgtggaa aacaatttga cagttcctta aaatgctaaa catagaatta ccatgtgatc 147000
taacaatttt actcttaggt gtatatatac aagaattgaa aacaagtgcc caaacagata 147060
ccttgcatga gaatgttcat agcagcactg ttacaacagc cacacccaaa tgtcaatcaa 147120
tagatgaggg gataaacaaa ttgtggttta tacagctaca aaaaggaatg aagtactggt 147180
atccgctaca tggctgaaac ttgaaagcaa gggctgggat ggggtcatgg aaagtaccag 147240
cttattgggt actgcattgt gctttggggt catgaaaatg ttttggaact ggatggaggt 147300
ggtggttgcc aatgtgaaca tactaaatac aacgcattgt tcactataag actgctactt 147360
ttcttatgag aatttcactt caattaaaaa ataccttcca tgtatccttt ctaaggatga 147420
tactagaata tttgctttgg caaaatgagg aagtaacttt ttttaaaaag gaagatgtgg 147480
gatccatgaa acgggatcaa atatcagaga ggaaaggggg tcttctggat gacagtccat 147540
ggagatccca caactgcaca gcaggccggc tgtgcaccca ggccacacca gagcagagcc 147600
ggtggttccc gaggagctct ctggaagaaa aacgctagat ggcctgattg gtttgggggc 147660
atattgaaaa ggtatataac tgagaatttg gagtggaatt aggaaacaga cataaaagct 147720
tacagaaaag aaaataatga attctaggga gaaatataaa aggatactac aggcctcagt 147780
tacataaaca ctgaatattt acttaaccaa aattacaata taattacata attattttag 147840
gtacatatgg caaaaggatg tgtgggtgta tgtagtatgt acggtgtgtg aagtgtatgt 147900
gtgtggtatg tggacggtat gtgtatgctg tgtatgccaa taaaatcaca atgaaataag 147960
acttcatatc cattaaaatg tctataattt aaatgtctat aattttaaaa atggaaaaca 148020
cttctcatat ggcaggagca ggagcaaggg tgggggaggt accacacaca cttaaacaac 148080
cagatctcct gagaactcac tatcaggaga acagcacctg gagaaggtgc taaaccattc 148140
atgagttact gccctatgag ccaatcacct cccatcagac cccgcctcca cactaaggat 148200
tacaatttga cttgaaattt gggcatgaac acagatcgaa accatatcaa taggtaatga 148260
ctaaaactga aaaaagaagt accacagtca gaaagttatt tagagagctg aaggtaaatg 148320
ccaataggat cagttgaaag aattggaggt ggccgggtgc ggtggctcag gcctgtaatc 148380
ccagcacttt gggaggcgga ggtgggtgga tcgccctgag gtcaggagtt tgagaccagc 148440
ctggccaaca tggtgaaacc cagtctctac taaaaataca aaaattagcc aggcctggtg 148500
gtggacgccg tagtcccagc tactcaagag gctgaggcag gagaatcgct tgaaccaggg 148560
aggtgaaggt tgcagtgaac cgagatcgtg ccactgcact ccagcctggg tgacagagca 148620
aaactccatc tcaaaaataa atgaaataaa gaattggaag tgtttgcctc tggagagaag 148680
gaaacgcagt aattctgtaa aaacagaact ttttactttt tttcttttttt tttttttttt 148740
tgagacagag tctccttctg tcacccaggc tggagtgcag tggtgcagtc ttggctcacc 148800
gcaacctctg cctcttgggt tcaagcaatt cccgtgcctc agcctcccaa gtagctagga 148860
ttacagatat gggctgctat atccagctaa ttttttttta tttttattag agatgaagtt 148920
tcaccatgtt ggccaatctg gtctcaagct cctggactca tgatcctcct gcctcggcct 148980
tccaaattgc tatgattaca ggtgtgagcc accatgcctg gacagaactt tttgactctt 149040
taaactatgt gcatatataa agctgattta aaaaaaacca agtaaaataa ttttaaaatg 149100
ttccaaaaca gattggatgg gtacacactt catcatgagt ggttgaggga gactgggtta 149160
gagatgagga aattccaggg actggggaaa agttaaaatg acaaactgtt cacaattgtt 149220
aactgcaggt tgtgggaaag ttggtaagtt gctacagtgt ttgttccctc tgtaggtttg 149280
catatattta acatttctta aattagcata ataatgaact gtgtaatcag ctgtagagtt 149340
gagggtgtgg agctggcaca ggacagctga gctactggtt taaaataaat gacatttaaa 149400
aaaatggcta tttgtagaat taacagatat aagacaccct gatcaaggga tgataagaaa 149460
ggactccagg gctctgtctc agctgtcttg gcaacacctg gaagacatgg gcctctgcaa 149520
ggtctcatac tttcaggagg tgttgatgaa ggatatggac agatctgaag ctctgggcac 149580
tgcatggtct gagaagagaa gctccggaaa cgcgggagct gagtgcagat gcagaagggc 149640
tgtcatccag cagaggggta ggtgacaact ggcctagcga gtgaccctta tcatggctac 149700
atttgttgat cactttcttt gtatgaggca ctgctgtgat tgcattaaat ttccacttac 149760
ctaaatccaa cgttgtgcac ttgtgaattt ctactcttac aaaaaacaca acggcaacaa 149820
cctcaaacca gtaatctagt caaaaaagca attcccaagg catgacattc agattcatca 149880
gcactcacag agactacagt gattgctgat aacgccaact taatacctgg ccaacagcat 149940
ggatcctgac ctccactttt cttgtgtgtt tacagaacca caaaaaggtg cagtgttttc 150000
a 150001

<210> SEQ ID NO 3
<211> LENGTH: 138001
<212> TYPE: DNA
<213> ORGANISM: Homo sapiens

<400> SEQUENCE: 3
ctctcccaaa ttgtcaaaga agtataaatt agaaaatgaa tcaggacaat ttcaacctgt 60
tagattagct aatatttaaa aattgaacac tcatacaagt gtggtgaagt gattgttttc 120
tagtgacatt ttacactgtc ataaccttct agaaaataaa ttggcagtgt tattgggaga 180
cagaaatatg tctatataat ttatgggaac ttaggctcag aaaatattaa ggaataagaa 240
tgaactttat gaacaaagat gtggagggtt ggaagcaaga ggggggccaa cgcgcacggg 300
gaggaagcat ttgggcagtg actccgcaga cccaggctca ggttgaacta gacaacctcc 360
ttacacctca gtttccttaa ctgtagagca ggagtgatgg aactgcctgt ttcataggac 420
tgttgtgagg atgaagtgag atacaccaca ttataagctt gtgcctggaa aggataatgc 480
ttagtaaatg atgactattc ttttttattg caataaaatg tacacagcgt aagagttact 540
attttaacca tttttgcagg gtaccaccaa gtggcattta gtacattcac agtggtgtgc 600
aaccatcatc atatttccag aatattttcc tcatccccaa aggaaacctc atgctcatta 660
atcagtagct ctcctttaaa atattagtta tgaagatcat agcactatac aaaactcatt 720
atgtaatgtt gagtgaaaaa atcagggtgt gaaattttgt gatatgatgt aattagtgaa 780
agaagcatac aaaaagtctg aaaatataaa aacaatagca attgcatttc tcagactcta 840
catttaaaca ttattcttta tggttttaaa agcaaagaaa aaggtaaaga aacaacaacc 900
aaccgcaaag caccatgaca aagctcagat tgttaaatcc aggtttttgg aacatagact 960
cttatatgac gtttacactc tccagggttc agagagtctg gcagcattgg gagctgcctt 1020
gtgttctaca gcctcacgga cagacaggag gtccatcacc actgctctgt tcttctggag 1080
tttccttgtg aacatgttgt ggacgtagtt accatttctt tcatcttttt aaacacaggt 1140
acctttgggg ctggctttct caaggaagcc cagctccctg tgattgagaa tgaagtgtgc 1200
aatcgctatg agtttctgaa tggaagagtc aaatccactg agctctgtgc tgggcatttg 1260
gctggaggca ttgacagttg caaggtaaga aaagatcaag agaccaaagt tagtcttgtg 1320
ctctcctgtc tcagtctcag tcccttagac ttgagtccca aagtagcgaa ttcaagtagg 1380
atttaatcaa tggaagaccc cagtctaagt gttgctcaga aactccctag atctgtccca 1440
aatgtatatt cagatcatcc aaggggactt cttggggctt gagttccaga tcagcagcaa 1500
gggagccata agtgccataa ctacctcaga ccactcaccc tcctggggtg tcccggtggc 1560
cagggactaa agtggtgatt tttctggtag ggaaggaggt agagggtaca ggacagagac 1620
taactgcaca caatatctga gactggagct cagatattgc tgatgatcag agttggcgtg 1680
tctccccaat tgatttacaa ctggggcttg gatactgttt taaacgggag gagcctccta 1740
accatcttga cacaaccact gacgtgacta cactagagat agactctttc cacttaattc 1800
taccactctt gctttacttc atgagaacga aaatgtaaga ttgcaccatg aattcatttg 1860
cggaaagatt gatactatgc ttttatttta ttttatttta ttttatttta ttttatttta 1920
ttttattgag actctcaccc cggttgaagt gcactgacgt gattttggct cactgcaact 1980
tccacctcct gggttcaagt gaatactcca gcctccctag tagctgggat tacaggtgcc 2040
caccaccacg cctggctaat ttttgtattt ttagtagaga tggggtttca ccacattggc 2100

```
ctggctggtc tcaaactcct gaccttgtga tccacctgtc ttggcctccc aaagtgctgg   2160
gattacagag ttgagccacc gcactcgacc ctatgtttta tttttaaaaa tatttattta   2220
tttatttaag ccacaactac tagaatagga aggattgata ttttattaat tttatttggt   2280
atttattatt tttttttctt tcctgagaca ttcttgctct gtcacccagg ctggagtgca   2340
gtggcacatt cttggctcac tgcaacctcc atctcctgtg ttcaagcaat tctagtgcct   2400
cagcctactt agtagctggg atgactggca tgtgcctcca cacccagcta atttttgtat   2460
tttttgtaga gacagggttt tggcatgttg cccaggcttg tctcaaactc ctggcctcag   2520
gtgatccatc tgccgtggcc tcccaaaatg ctgggattat aggcatgagc caccaccccc   2580
tcctggaagg attgatatct tataacataa tttataatta cagaaaacat gtgagttcac   2640
taggaataaa taaattttga agataataaa agattttcac ttatgttgtc atttcggcac   2700
agtttggtat aggatgtgga gatgttaaca tttataccta gcttgctcgt aaactaagac   2760
ctgaaagggt tgtgtctatc agctgcaccc ctgggtagcg acacaacctc gggaaggcct   2820
cagccccctc ctcgtacagc actgcctgtt ggaaagcttg agggaggcta tggatgtgca   2880
gcacttggca gagggtctgg tcatggaagt taccagcaaa tatgagctac ttttatgatt   2940
ttattttatc caaaagaaag agaatgaaag aagaggggag gaaacaagac taatcaggaa   3000
agatgaaggt ctaggggtga gggaaggagt aaggagacat aaaggcaatg tggagcagct   3060
gaggggggaa atggctttca ccacttccca gcatctattg acattgcact ctcaaatatt   3120
ttataagact ctatattcaa ggtaatgttt gaaccctgct gagccagtgg catgggtctc   3180
tgagagaatc attaacttaa tttgactatc tggtttgtgg gtgcgtttac tctcatgtaa   3240
gtcaacaatg tcctgggatt gggacacact ttctgggcac tgctggccag tcccaaaatg   3300
gaacataagg aagtggttct tctacttctt ttatttctga aatcaggtaa gacatagttt   3360
ttttaaatta taagaattat tttttctccc acaatgtagt aaaaatacat atgccatggc   3420
tttatgtgca attcatttaa tttttgattc atgaaattcc cagttcaaaa tcttgtatat   3480
gattgaaaaa ttcttaaaaa aataagttta atttccccgt gaagactgtc acggtgctgg   3540
aatgaatggg cagaaaaaat aatggttgat ttttctaatc taaaagagtg tgcctacatg   3600
atggccagtc tggctgaaaa ataaatagcc attgtagcta actatgcaaa ggatggctaa   3660
gctcttcgct tggttctcag tttcattaat ttatatcatc tctgttcagg tgccatgctc   3720
ccctcactag caagttgaaa caatgaaata actctttgaa tatgtttggt tccttgacct   3780
gttcatggag tgggactcag catttctctc tttgttatgg cctgagtaag gctttccatc   3840
ggtatacatt tgcttcttat ccctggagaa attatacaca tccatttgcc agatgatata   3900
cgcatataat gattcaacaa atactcaggg tatttgttga gtgggttagg tccccacatt   3960
tttatacata catacacaca tacacaccgt gtgtgattgt gaatgtaagt gtgtgtcctt   4020
tacaaatact agcttattta gctcatggta taggtagggt agcatagtca tccccatttt   4080
ataaacaaag aaatctagac ttaggaaaat catgttattt gtctcgtgac caaattccca   4140
aatcaaggaa ataaagaaac ctggatttaa gccagatttc caagaaaaaa tctagggctc   4200
ttctcacttt ttcatctttg ttccaacatt tgaaaaaata aatctaaaca cattccaatg   4260
taactgaaga gcaggttaat tgtttgccac ttgcagaatc caattaagaa gagagaagtc   4320
tggtataaag aaagtgattt gcttccaaag ctagcttagg ggaagaaatg cagcagtcct   4380
gccgtactac ttcactttag gagcagaaag tggcactttt aaaaggcaac agaggaggcg   4440
```

```
agcaaggatt caggggtcca tgctagcttg ggcaccttat ccaccaggta gttgagcagt   4500
tgcctgctgg tgcctttgtg agcagggtgt tgtcccttga ggcaaatctc tggagggtga   4560
gagttttgta gtgggcatgc tttggtttat aaatcacctg tgaactcagg agttccatct   4620
tgaagcacat acatagttag atgaacttgc cctgcaggga gagtctgatg aaagggaggt   4680
agatgcttgc aatttaatct ataaattacc agataaaatt ttacaagttg actttaaagt   4740
caaacacatt tgaatttagt ggaagccatt caagaaaata tcaaagaaaa tacagagcag   4800
gagaagatta agcaaagagt tttttgggga aattggtgtc tatgtctgtg tgtgtaggga   4860
gtgcagggga tatgaatatt ctatttcagc ccatggaaac taggatgtag atcactgtga   4920
acttattcag caggctacac ccaaaggcta gaacaaactt ctctgccaca ggattaacat   4980
atgttttaat cgacctgggg ggcacattct ctgataagct cttttggaaa gccaggcttt   5040
ctgtggacgt gttatctttc caatgtgtgc tggaatgccc ggggagagga aaaagtttct   5100
tttacagcca tgctcagtga gaagcggaga aacatcttct attcacaaat tgctaagtct   5160
tttacacatg caaatatgca tacacattca cacaccacag tgaggaagaa attctcacac   5220
cattaataaa atacatttac ttcagtagca atatacatct acattttgcc tataatataa   5280
aagtattttt cctattaaaa gatttgttta atgtttcttc accaacaaat aaaccctatt   5340
aaatccccat tgccatatga gccctggagg tgaatcagag aaacaaaagg attgtggaaa   5400
aatcatcagg ttaaaaaaag aaaaattgat tctgttttgg gatatttcct agcaacatga   5460
gctggggagg ggatctcagc agtgatgctc tatgaagcat aataaaatga cacagttaca   5520
ggtaacttag ttaaaggggg aaataaatgg aagtttcctc tttttgaata tcaattgtag   5580
cctgctctgc tacatttcaa aaacactctt caaaatgttt aactgaactc actgtaggaa   5640
gcaccttatt aatttattgt gtgttttgaa gtcacactgt gagctataga atttacccaa   5700
gcacaactct tcctggaaaa gagagttcaa atgagaaaca gtgcggggtg aagacatgga   5760
tatgggccta aaatatctat ttctcaatga tattttgata tatctatcaa gtgcttttta   5820
gtggattagg ttcagaatgc atcagccaat gcctgttcaa taatccagtt ttccagcata   5880
gagcatatta aattgaggaa ggacaaagtc acagaggtgg ggagcaggtg gactgtggcc   5940
aaggactttg catgaaacag tgagcgtgca tcctcctcct tgccctgccc tcatggtctg   6000
tgtactctca ggaggtcagg acaggccttt ctgagaatga gaatctgttc atctgccttt   6060
ctactggata cttgtcatcg gcatacaaac acatgttctc tgcagtgtgt catctttcag   6120
aacctcccct gaccctgtat tccctagaag tctcgctgct ttcagagcca ggcttctctc   6180
ctgctgccac ccccactgct cttctagtca ctctttaacc cactccatct gcatgtggcc   6240
cccaccacac ccctcaaagt ggtcaaggtt gtcctgttgc ttaattccat ggaagcttgg   6300
ctatcttcat tttattagcc tcttttggcc tctcaccctg tgaaaatcac tacattttgt   6360
gccagagatg gagctggcat ctccaggctt ggaagagggc tgctgaagct cagccaggtg   6420
tcctaaggag cctcaggaca ggggatgctc agtagccttg caatgggaac acagctgagc   6480
cccacttggc cacccctttgc cacaaccagg cagaaagcag cttttgaaca gatttgttgc   6540
ctcagatttg atctcaaaga aaaatcgtgg gcagtattgg tcccaggttc tgcttttttta   6600
caatttcctc tgaaatctgg atgcctatca acaccttgga aaaactgaat tctccccaac   6660
taatagtggt gtgtcactgt agtaagccta gtacaaaaat ggccttcttt gtggaggagc   6720
ttcatatcct ccattttttt tttgcttaat ttttgcccaa gatgagaaca taatttagtt   6780
cactttttat ttattcccaa catcatccat gcaccaacat ttttgtaact aaaggaggga   6840
```

-continued

```
ccattcagaa gatgcttatc aactgtcaaa gtgacagtgt tacaaccaat gcacatattg   6900
taagaaatca aacaatggcc tccaaggttc atttctacac agggattagc agatcaacat   6960
caatcttggc aacacagttg ccactgatgg tgtcttattt tttttatcat gacatggcaa   7020
tcaagagcaa acatgattta ttcttattta agattttatg gttagactag gcagatagct   7080
agatatgagc aggaggtgga agcccctgag agaatggagg tctggagaat ctgaaacccc   7140
agagattacc caagtcctgc atgctagaca tgagtggagg agggggaata cctaggtaga   7200
aaagaatgcc ccttaagatg cccagcagtc gctcactgtg cagttaactt ttcagaatgc   7260
tgctagatac atgctgatag ggagggaaga gggcaaagga gaaattccta agagatacac   7320
ggttgcagtt agtatacatc tgagtgctat acaaccttct ttgggtggtg gcaagaagca   7380
atgcagccat tacgtagaat tcatatcaaa cacctgtatc acaggtgtta aagaaacaag   7440
aaacattgta cttcttgtat tcttaataat gatttgcaat attgtcttta gtatcactgc   7500
aaacctctat aaatatgatt tttaaaaagt atttctttag gttggaatta cttctacgca   7560
ttgacttatc ttcctgggtt tcattagccg tacccgttgt actttcttcc ttaccactgt   7620
ttatctcaaa ctcttgagat taaagtatgg gctcaggagg gagcgaggag cttcaggact   7680
ctcacggacc tccagcacag tgtagctgcc ttatggaaaa gtggccacac tgttttctgc   7740
actggtccct gcccctacta ttcctcactg ggcagagcac agccaccctg gccctgcctg   7800
aacattttag tcagtgttgg ctctgtgctt ctctggggag gaaatccaag agacaaccca   7860
cagcccctct gccatttcag ctgcagcagt accaccgtta atgcccttgg gcttgagaaa   7920
gaagggacct ggccacttcc ctgacacctc cagcacacag cagggaaaga attccagttt   7980
ctctttcttg tgagctttca cctgctactc ttcaccaggc aaggctcctg gcttgggccc   8040
acagtgcagg cacctcgaac tcagttgaac atttccactg gctgcactct gtgtttttgt   8100
ggggtgaagc tcccagaggt gactgaaagt ccttctgcca ctaacactgc agtcatactg   8160
cccttgctgt acttggacta gggaaggaaa aaagatcctg agtgctttac tcacacccca   8220
gtgtgcccca gccaccctat ggaaaagagg ccagtgtgtc atccctgcaa gcaccctgag   8280
gcccctgccc ctgctgcccc caagctgtag agccagaata taaagctggc agaaaaatgt   8340
aaaaaggcta gactggctta gcctcccagc ctacatcttt ctcctgtgct ggatccttcc   8400
tgctcttgaa catcggactc caagttcttc agctgtggga cttggactgt cttccttgct   8460
cctcagattg caggtggcct attatgggac cttgtaatct tgtgagttaa taccacttaa   8520
taagctcccc tttgtgtgag tatatctata tctatagata gatataggta tactcactat   8580
atatacacat atatacatat actctctctc tctctctctc atatatatat atatataatc   8640
tcctattagt tctgtccctc tagagaaccc cgactaatac agattttcat accagaagtg   8700
gttcttgagg aacagaatat taaggatgga attctttcat tggttttggg acttctggtg   8760
ttggctgatt aatatgatta gaccaaaaaa tgctaaggac tctacttcta atagtatgga   8820
gaacactgat agtacttggc ctgaattgtt tagagagtta tgcaaaataa atgcatttga   8880
cactactgat tcatcactta tgagaggcaa ggagtttagt gactctatac ataatacctt   8940
tgactatatg tggagaacca aggaacataa tgaagttggt tgattgctcc taagttctct   9000
ggagaaagag atgaaagaaa atgatgatct caggggatct gtctcccacc ttcagaagca   9060
gatactgagc cacaaatctg ctaagattgc cctgaatgag agttttaact cctgtagaga   9120
aagagttgaa attgtgaaaa aacagagaca agctgttatc atgcgagtag ctgatctgca   9180
```

```
acaagaggtg catgcacagc cttgccaggt gtttactgtt aaagtgaggg cattgactgg   9240
aaaaaaatgg gaccctggaa cttggagtgg ggatgtgtgg gagaaccctg atgaagctga   9300
ggacactgag tttgtgaact ctgatgaaac ttttttgcca gaagaaacag tttccccatc   9360
cccagtagtg gtaacatccc ctccctgacc cgtgctgcca ttagcctttc cacctttgtc   9420
tgaggatgta aaccctgcac tgcttgaggc aacagtgatg gccttccctg aggcagctgc   9480
caggcaagat aatgttgatt ctcctcaaga ggcacccccta atgcccctga atgcttctag   9540
acctataact aggctaaatt ccttgcgggc cccagaggtg aggttcagag tgtgacccat   9600
gaggaggtgc attatactct aaaagaactg cttaagcttt ctaatttata ttggcagaaa   9660
tctggagaac aggcatggga atggatatta agggtaaggg ataatggtgg aagggacata   9720
gagttggatc aagctgaatt tattggtttg gccctactaa gtagggattc tgcatttaat   9780
gttgcagctc ggggacttag aaaaggttct gatagggccg ggagcagtgg ctcacgcctg   9840
taatcccagc accttgggag gcgggggcgg gcagatcacg agatcaggag attgagacaa   9900
ttctggctaa aatggtgaaa ccccatctct gctaaaaata caaaaattag ctgggcatgg   9960
tgatgcgtaa ctgtaatctc atctacttgg gaggctgagg caagagaact gcttgaacct  10020
gtgaggcaga gattgcagtg agccaagatc gccccactgc attccagcct ggtaacagag  10080
caagactcca tttccaaaaa aaaaaaaaaa aaagttataa tagtttattt gcttggttag  10140
ctgaaatatg gattaaaaga tggtccaatg ttagtgagct ggaaatgcct tggtttaatg  10200
tagaggaagt gatccaaagg cttagggaga ttaggatggt ggagtggatt agtcacttta  10260
gacctactca tcccagctgg gagggtccag aagatacacc cttggccgaa gctttgtgaa  10320
atagatttgt gagagcagca cctgtatttt tgaagagccc gtaattgctc ttctctgtat  10380
gtcagatcta acagtaggaa ccacagtcac tcaactacaa aatttaaata caatgggaat  10440
aattggatcc tgaggtggca ggggccaagt gttggcactg aaccatcaaa ggcaaggtgg  10500
gcataactac cataatagac agcagaggca aagcagccat cagaatagtc tgactcatgt  10560
agagctctgg cattggctaa ttaatcatgg tgttcctaga agtgaaattg atgggaaacc  10620
tactgtattc ctacttgatt tatataaaca aaaaactgcc aggtagaatg gactaaagac  10680
taatctgaat tataaaaaca gagaatcatg ggccctcaat caatttccag actcgaacct  10740
gttacagttc cagaacccac tgaatgaagg ggaggctgga tcccccttgag gaaggacacc  10800
actaggctac tgacaactta tgctgttact ctttctccca tccttcccta aggagacctc  10860
tggcctttta ccagggtaac tgtgtgtact ggagaaaggg aagtaatgag acatttcaga  10920
aagtactgga cactggctct gagctgacgt tgattccagg gtacccaaaa cgttattgtg  10980
gttccccagt taaagtaggg gcttatggag gttaggtaat taatggagtt ttagctcatt  11040
tctgacttac agtggttcca gtgggtccct ggacttatcc tctggtcatt ttcccagtgc  11100
caaaatgcat aatttgtata gacatactta ttagctggca gaaatgccac attggctccc  11160
tgactggtag gatgagggct attatggtgg gaaaggccaa acagaagcca ttagagctgt  11220
ctctacctag aaaaataaaa aaatcaaaaa caatatccca tccctggagg gactgaagtg  11280
attagtgtca ccatcaagga cttgaaagac gcaggggtgg tgattcccac cacatccctg  11340
ttcaactctc ccatttgacc tgtgcagagg acagatggat cttggaaaat gatggtggat  11400
tattttaagc ttaaccaagt ggtgactcca attgcagctg ctctaccagt tgtggttttg  11460
ttgcttgagc aaattaacac atctcctggt gcctggtatg cagccattgg cttggcaagt  11520
ggctttttct ccattcctgt ccataagacc caccagaagc aatttgcctt cagctgacaa  11580
```

```
ggccagcatt atacctttac caccctacct caggggtgta tcaactctcc agctttgtgt  11640
cataatctta tttggagaga ccttgctcgc ttttcacttc cacgagatat aacactggtc  11700
cattacattc atgacattat gatgattgga tacagtgagc aagaagtagc aaacacactg  11760
aacttattgg tgagacattt gtatgccaga ggatgggaaa taaatccagc taaaatttag  11820
ggactttcta cctcggtaaa atttctaggg ttccagtggc atgagaccta tggagatatt  11880
ccttctaagg tgaagcataa cttgctgcgt ttggcccctc ttacaaccaa gaaagaggca  11940
caatgcctgg tgggcctatt tggattttgg aggcaacaca ttcctcgttt gggtgtgtta  12000
ctctggccca tttatcgagt gacctgaaag gctgccagat ttaagtgcag tctagaacaa  12060
aagaaggctc tgaaacaggt ccaggctgct gtgaaagctg ctctgccatt tgggccacat  12120
gaccccgcag atccaatggt gcttgaggtg tcagtggcag atagggatgc tgtttggagc  12180
ctttggcagg cccccatagg tgaatcacag tggagacctc taggattttg gagcaaggcc  12240
ctgccacttc tgcagataac tactctcctt ttgagagaca gctattggtc tgttattggg  12300
ctttggtggt aactgaacgt ttgactgtgg gtcataaagt caccatgcta cctgaacctg  12360
cctatcatga actggttgct ttctgaccca tctagccatg aagtgggtca gcacagcggc  12420
atttcatcat caaattgaag tggtgtgtat gtgatcgggc ttgagcaggt cctgaaggca  12480
caagtaagtt acataaggaa gtggctcaaa tgcccatgtt ctccactcat gccaccctgc  12540
cttccctccc ccagcctgca ccaatggcct catggggagt tccctatgat cagttgacag  12600
aggaagggaa gactaaggac tggttcatag atggttctgc acgatatgca ggcaccaccc  12660
gaaagtggac agctgcagca ctatatccac tttctaaatg catgtgtaca cttgtgctaa  12720
gaaaatatct ttattttatt tcctttattt ttcctttatc atgtgacctt agatttatgg  12780
acttcacatc agcatttaag catttaagtg ttgttcatat cagcatttaa atattgttaa  12840
ccttatgtaa taacttttgg tttggggatt ggtgcgtttc tggttgtatg aggatagttg  12900
tattatatta ggcataatta tgaccttatt attgtcttta tttgaagatt atgtatgatt  12960
tcaggatgtg tgtatgggtt caagttgaca aggagttgga cttgtgatgg ttaatactgt  13020
caacttgatt ggattgaaag atgcaaagta ttaatctcgg ttatgtctgt gagggtgtgg  13080
caaaaggaga ttaacatttg agtcagtggg ctgggaaggc agacccaccc ttaatctggg  13140
tacacaccat ctaatcaagt tccagtgtgg ccagattgta aagcagggag aaaaatgtga  13200
aaagactaga ctgaattagc ttcccagcct acatctttct cctgtgccaa atgcttcctg  13260
ctcttgaaca tcggactcca agttcttcag cgttgggagt tggactggct ttcttgctcc  13320
tcagcttgca gagggcctgt tgtggaacct tgtgatccgc tgagttaata ctacttaata  13380
agatcccctt tatatacata taatatatta tattatatat aatatatata atatatatta  13440
tatataatat atataatata ttatatatta tatataatat atattatata ttatatataa  13500
tatatattat atataatata tattatatat tatatattat atataatata tattatatat  13560
aatatatata aaatatatat atatcctatt agttctgtcc ctctagagaa ccctgactaa  13620
tacaatttat gtcattaatc tcatttattg atttgtatac attgaaccaa ccttatatcc  13680
caggaataaa acctacttga ttgtggtgga ttagcttttt gatgtactct tggattcaat  13740
tgctggtatt ttattgagaa tttttgcatc tgtgttcatc aaggatattg gcttgaagtt  13800
ttcttttttt gttgttccat atcagaatga tgacgacctc atagaatgag ttagtctgtc  13860
ctcttttatc ttttggaatt gtttcaggag gcttgatatc agctcttctt tatatgactg  13920
```

gtatactttg gctaggaatc tctctggtcc aggggttttt ctggtgtagg tttttaatta 13980
ctgattcaac ttcagaactc attactcatt attgagttct aaaactcact ttcatgtact 14040
cttcaaaaga ctgtcttctt ctgttgttga gcggggtgtt ctctcaaggt cgtttaggtg 14100
aaggtggttg ctggtgttct tctgtatcct tactgcttgt ctttctcttt ttttattgac 14160
tactgaggat taatggtgat gtgtccaact ttaactctag attagtctat ttctctttta 14220
gattgtaact ctgttttata tattttgaag ctctgttgtt aggcatgtgt atttggattg 14280
ttaggtcttc ttgatgatga cctttatcat tatgtaatgt ttcttcttat ctctggaagt 14340
attcgttgtt ctgaagtcta tttgtgctga tatgaataca gccttcacag ctctattttc 14400
actagtattt gtatatcttt ttctcagctt ttaaattgag atgttcagac catttgcatt 14460
aaagtagttg ttaataggat taaatttaaa tctaccatta agttggttat ttctctttgt 14520
cccatttaaa ctttgttcct tttttcatat ttttctgcct tcatttatat tgagtttatc 14580
tccacgactt acttattaaa ttaattttta atggttttag tattttccac aatgtttata 14640
atatatactt tgatttttttc acattccacc ttcaaatgac agaattatac tggatatata 14700
gaaatcttac atcattgcac ttctccttcc tccctctcaa aatgttgtgc tattgctctt 14760
tgtaatagag gcttacttct attatgttat agctctcata atacattgac actattttta 14820
ccctgaataa tcagttgttt tttaaagtga ttatgactac aaatattttg aataatttct 14880
ttattttacc atttctggtg ctccttatct tttacagtag atcccaattt ccatctggag 14940
tcacattctt tctgtgaaaa acaaccttta gcatttctta tagcacggga ctgctgttgc 15000
tgttgtcttt cagcttttct ttgtctgaag aagtctttat tttgccttca gtttttaaaa 15060
gtgattttgc tgagtataga tactgggttg agagtttcat tccttgtatc attttaacaa 15120
tgatgttcca ttatattccg ttttgaatag tttctgacta gaaatctgat ctttgtttct 15180
ttgtattcaa tagttccttt ttctctgact gcctttaaga tattctcatc tttgtttttc 15240
aacagtttga ctataatttg tttattatta actttttgta tttattctgc ttgaggtttc 15300
ctgagctcct tggatttgca gattgttgat ttttattgtt tttgtaaaat tcatagccat 15360
tatctattct actgttttgt tttttttttc acttctctct ctctgtattc ttctttttgg 15420
actgtaagta ttcaaatgtt agatcattca tattgcttca taaaccttat atgcttcttc 15480
tgcttttttt tttttgtcag gaactctttt tttgtatctg tgttggtttg gataagttct 15540
agtagactat gttcaagttt atggattatt ttgttagttg tgtctaattg actcctcagt 15600
gcattcagag aattcttcat ctctgatatt ataaatctct tcctagcatt ttcatgttac 15660
tcttttctat agtttccatc tctttgctga aattctcccc ctatccatgg atattgtcca 15720
cctttaccac aagattcttt aacatattaa cataggtatc atacaaaccc aaactgatag 15780
tttccagatg gtgtcttttc tgagtctgtc tgtcttgatt gctttattat ttaacagtga 15840
cttatcttcc ctcttcagct tttggtgtgt cttgtaattg tttaatcaaa cactgggtat 15900
cataaatgga ggaacagtag agattgcagt aaatattatt tatgctttga aatgggcacc 15960
catcttctgt tgaaaatatg ttttgtggtc aattgagtca acctagtaac tggttgaact 16020
gaatttggca tttgtgcttg ttgcttttat cttaaatgca ccacaggttt aaattcctcc 16080
agtgatgggt tgctgctatc ttttgcttag agtggggcct ggggtgtgga agaattttct 16140
cagtgttcct atctattatt agattttagc agtcactgca tgcctgcact acagagggga 16200
tatcttcata cacataatct aaccccattg aaactgctgt ttcttcttaa tgaatgctca 16260
atctttggtg gaaataaaca aatgctgtat ctcctggagc cacttcagtc ttagtcaggt 16320

-continued

```
tctgcagggc tttgaaggga atgcattctc agtattcttg tgccttattt ggatggaact  16380
tgaacctgtg gtgggtttgg agagaaagag tagcagacgt ctgctatgtt gcaatgcagg  16440
atgctgggca caagaaaatt tccagtctct cctccaagga aataagattt gatcatctac  16500
ctatccctga gaagtgaagg gctttgcctg cggtgctaga tgcaaaacca tttttctccc  16560
cccattgccc agaaacttaa ggctttggct tttctgagca gtggtctagg gaattgtgca  16620
aggttttcat atttgaccct gacagcccat caccacctac agcttgcagt gccaaatgta  16680
tctccctctg atctctcctg tcctgtggtc ctcatgaaca ttaagaagag atttctaaaa  16740
aagagcttgc acatgagcat agtttctggt gagaagaatt ctgatatgtt aacttcctct  16800
aaacttttaa ataaaatatt tctaagaatt aaataaagtt ctagaatgat atgaatctat  16860
tcctttggtt ttttgcacgt ctgtctgcct gctaatcaag agaagagaat ggtcgtaatt  16920
ctcagagact ttttcctgtt tgtgtcataa atgacttcac atttttttct gttctaagaa  16980
ctattcagct tgatttcttc tgttttaatt ttagcagcac ctgagcaaag ccatgtggtc  17040
caggattgct accatggtga tggacagagt tatcgaggca cgtactccac cactgtcaca  17100
ggaaggacct gccaagcttg gtcatctatg acaccacatc aacataatag gaccacagaa  17160
aactacccaa atgcgtatgt cattaatctt acagtaagca aaacaaggtc caagtaaaat  17220
ttgtcttaga aaaggtgtgc gtcaagctaa cttcttatga ttaaattttt ctcacacata  17280
gaatgcatgg caaaatgtct gagaaacatt actttgagca aagagtatga tagaagagaa  17340
atgttaagct ggctctcttt cctgagagtt tgataaaatc aggagaatat ctggcggtgg  17400
tgaggccaca ataatggaaa atcagaatgt ttagacagag tcagcttcaa caacactcac  17460
taaaggtcaa tgtgatcttt acccccttgaa attctataat tctaatctcc aattcctgaa  17520
gtgaaggttg tgttggcctt ttctgtcttg gctcacaagt aaatgatatg tgcatatcta  17580
tggaaaggcg aatctatctt tttctatatc tatgtctatt ccaacgggta gaaacaccct  17640
gggtcctgag caccagtggt ctgaaggaat acgggttgcc aggaagagag aagcaaaggc  17700
aggaaggcag atgaaagtaa gaaatgagac agatgctaaa caataaaaag tgcgggaaga  17760
tagacagaag ctggggtctg accacaccat ggccagtctt tcacacataa gtgactacca  17820
aagacaagaa aaaatgattt ccgcttgttg gacaatagat ggtagaggac caagggaatt  17880
gcgagagaga gaacaatgag atcaactcaa cagatgcact ggttttcttc ctggagaccc  17940
ttcctgcact gaagggcagg agatggagcc caaaaaaaac tgtagccatc ttgctgaaca  18000
gaggagggac attggagttt gggattattc aggtggctag gattttctag gcctgctaac  18060
aatgagaaca gatttgtgga ggaaaggagt tctagaaata tgcatagaaa tctcctcgag  18120
tcattggcta aacatgaagc tgcatgtaca cagaaaatag atccacaaga aagtagggca  18180
aagaacatct acggaagagc agcaactaca atggaacagt gagctcaata aacatgacag  18240
agctcaaata gcactaaggg atattggagt ttggaccaca cagaggagag agacttcact  18300
gaacatcttg ggcattcagt agagacccag gaaaagccat actttaggag tagaattagt  18360
atattcttag aataaaggca gctccacaca aacaatagca aaactgaaaa ggaagtctcc  18420
aagcatcaga atgatgtcca agtcaatgaa ctgcctctga gaggaaaact caaccatctt  18480
tagaggtaaa catcaaagtc aagtggctca gctatgcagt atccacagtg tgaggcctaa  18540
atataaaact tgactacaca tagaaacctt ttagtgtgac ccacaagcag gaggaaaatc  18600
agccaataca aacagaccca gaagagacag aaatgattag aatggcataa aaatttgaca  18660
```

-continued

```
tatcactata taataattga gttctaggat ttaagaaaac atgaatatag aatgcaacag  18720
acaccttatc cagagacagt aagagtataa agagccaaat cgaagaacta ctaagagata  18780
tgtcttaaat gaaaaaatta ctagatggcc tccccatcta gttagacatt tcagaagaaa  18840
ataccaaatg aaaaataatt gcatagaacc tacagaacca gatacacaca tacaaaacac  18900
acgcatgcat acacacacac tcaaacatgt ataagcttac aaacacacac acacatccac  18960
aaatgctgaa aaatgaaatc aaccgagcca cacagacata aaggaaaaca taaaaagatt  19020
tcctacatgt gggaagcaag tcacagaaag ggggaaggag attggaacag aaatatatac  19080
tgaaagcaag gatggctgaa aattttccaa atataaagaa gattaaaaaa tcacggactc  19140
aagaagctca atggatcaga aaaataattt ctaaaatgac aattatagga tgccactggg  19200
tacatagcag ttcaactgtc agagggcaaa gacataatac acagaaaaat ctcgtaagga  19260
acgggaaaaa caaaaagctg tgtcttgcta gaggaacagt gatacaagtg actaatgtgt  19320
tcccatcaga aacactgcaa cctggacaca aaagaataac attaaagtaa taaacgtaag  19380
aaagaagagc tcaactgaga aggctacatc cagcaataaa atgccttgaa gttcatccat  19440
gttggaggaa tgcacattgt gcactcccct aaacaaagaa accggaaact gtaagacttt  19500
ggaatcagca ggcttatgta acaaaagagg tgaccctaag gaattaagga gaagaagaat  19560
agaacaagaa gggaactttc tgcagcctat ataatgaaga acctagcaat tggcaaatgt  19620
agatgaaaat gctacatgtt ttcttgatca aacgtttata tctttttaaa tgagagttga  19680
cgagttgaag caaaatgata ccaatatatt taactttacc atatgtagaa gtaaaaattt  19740
gaacatgtag cataaatcat gtagggatta attggaagtg taccactgta agtttcttac  19800
ctcatgcacg atagtatgta atactaataa aaggttaatg tgtgggttca aagggatatt  19860
gcaaatccta gagcaatcac aaagttttta actctgaggt ttgttgtata ataacaatat  19920
tttatgtatt caaaagaggg aagccaagga agaaaaaaaa gtctttaaag agctctggct  19980
cttagtacat ccagttgctc attgaatgag cttcctggaa tggagggtct gggactgaga  20040
ctaggccaca tgtgtagagc cactagagac acaatgttgg atccccatgg cccataatac  20100
atttcccatt ttctcaggca gccacaggtc atgaatgtga ggatactgag aggttggagc  20160
aacgttcttg ggaggcataa ggaagagcga atgcttcaag atccccgcag cccaaactcc  20220
tcagctgctt tgcctcctaa ttcattgttt tttgctcctc catagctgtc cgacctcttc  20280
agatctctta gtcttcctgc catcttcctt tatgccatgg gacccactgt tctttcaact  20340
catcccccag ttctggagtg gctgtggaca gcagaggata gactgagagc aggagagaag  20400
gtcctgccca ggaacccatt ctagagatac tgcattctgc ctgggagcaa gttttccagg  20460
gcagctttga gaagtcttgc agaaacaaac ctacttgacc gacatgatat gggaatgaca  20520
gacagtaata ctatttgcac aatgcttttc catgggaaag gtagagcctt ttcactaggt  20580
tttgagtaca tggagtgtga gagttgacct ggaaaggtta tcctccttga tgccatgttt  20640
tctctgaaga actacatgtt cgttgcaact cccacattag aatatgaagt cctaccgaga  20700
gagatacgga gactagacag atacagatgc atttgcatgt gaatacacaa tcccacaata  20760
cagacgtcaa aacccatacc agttattcca gagagatgga ttgggcagaa ggcagaagga  20820
gaatactctg atcgtttttc ggccacgtgt gtgtgttatc tcagtgtttc taagaagcgt  20880
ttgctacttt agatttttta tttaaaaaaa atagtaataa tctattaagt atgagagatg  20940
tgcagagagg attagtgatc gagagccatt tttgctggtg gcaatcatat ggtactttta  21000
atgggaatat tagaaaggca ccggtaatga ccttgttgca gcacaaagga gagagtgtgg  21060
```

```
ggtgcccctg catgttgtcc cacctcttgt gacgtgtatc gttttggaat ttccagtggc  21120
ttgatcatga actactgcag gaatccagat gctgtggcag ctccttattg ttatacgagg  21180
gatcccggtg tcaggtggga gtactgcaac ctgacgcaat gctcagacgc agaagggact  21240
gccgtcgcgc ctccgactgt taccccggtt ccaagcctag aggctccttc cgaacaaggt  21300
aaggagtctg tggccagaca tctacacgct tcgatgctgg gatgaaaagc catggaaatt  21360
cccactgatg cagccgcctt caatggtaaa cggatgctcg agtgttgcct gagttctacc  21420
atgtaggagg aagcctccgt gcactctctg ggggagccag cggagtgatt tctggtgcaa  21480
cgtggttggg ctttgtcttt aggatgggca caaaccctcc agggggatcg acttcaaaat  21540
tcaccttgtt gtaaaacggg ctacctcagt gtcccagcca aaatttttat tgtaacatgc  21600
tgtcaggtgt gtcactcttt ccaagccagt aagcttttcc ggggatttct tcaagtagcc  21660
agcattcaga gcaatcttca gcattgcaga ttctgagaaa tgtggctctg gagcctgtca  21720
ccctcgagaa acctaagagg gctgcattga ttccatgtgg ccctgggtct atggagcagt  21780
acatgagctc ccagtgctct aaggctcttc agccctaggc tttgaaggga gtgatttctc  21840
agtattctta aacctctttc tgatgacact tgtacctgtg aggggtctag agagaaagag  21900
tagtagactc ctactttact acaattcagg atgcagggca tgagaggatt ccctctctcc  21960
tccaagggaa gaagcttttg gcgtgcacac atccctgaga agcaaagtgt ctttgtcttc  22020
agtcagatac ataggaccgt tttctgcccc atggcccgga agccaaaggc cttggctttc  22080
atgatcaacg gtctagggaa acatgcaaaa tttccatgtc tgtcccaaac tctgcccccg  22140
acagccaatt accacctgca gcccgcattg ccaaatgcgg tgccgtttgc atgaagattc  22200
agtagagttt cctagaaagg tgctacctcg tgagctcact ttccaatgag gaatctgatc  22260
tgttgtgttt ctctaaggtg tcaggtgaaa tatttccaag aacttactac agttctagaa  22320
tgggaggaat ctgttgcttt ggtgtttgtt tgttggtcgg ttttctcaca tccatctgcc  22380
tatggataag gaaaagagaa cggtcgtaat tctcatagac tcctttctgg ttgtgtcaca  22440
aatggcttca catgtttctc tatgctcaga gatactcagc ttgatttccc gtgttttcat  22500
ttcagcaccg actgagcaaa ggcctggggt gcaggagtgc taccatggta atggacagag  22560
ttatcgaggc acatactcca ccactgtcac aggaagaacc tgccaagctt ggtcatctat  22620
gacaccacac tcgcatagtc ggaccccaga atactaccca aatgcgtatg tctttgttct  22680
ttaccataag agaagaaagg gccaagtgaa gtttctgtta caagagatgt gtctcaagct  22740
gagttctccg aactcaactt gtgacagatg cagatggcgt agcaaaatgt ctcaggatga  22800
ttgccttgga gctaagggtc tgagagaagg gaaatgttaa gctccctctc cttcctccta  22860
gttctattga gcagaaggga aatctggagg tgaggagatc acattatgaa gaaagtcaga  22920
atgacaaagg accagacact tagattaccc ttccacaaca ccaactaaac gtcaatggag  22980
actttccagt tggaattccg ttattctggc ttccacttcc tgaagggaag gttgcgtttg  23040
ccttttctct ctgggttcaa gaggaaagaa taggtgctta tttatggaca ggtgaattga  23100
tctgtttcta tatctacgta tattccgatt gtcagaaaaa cactcgttcc taagtaccag  23160
tggcctgaag ggatacaggt tcccagcaag agaagatcca aggaaggaag gcagatgaga  23220
gtcagcacag agagggatgc tgaaaagtaa aagggatggg tggatggaga gaagcccggg  23280
tctgaccacc caatggccaa tattttggcc acaagcgact accagagaca tggaaaaatg  23340
gtttctacat gtgggacaac agatggtaga ggacctagag aattgagaga ggggcaatga  23400
```

```
tgggctccac tccgcagatg ccttggcttt cttcctggat acccttcctg cactgaatag  23460
caaggagatg gagcccaagc agactgtagc catcttgctg aatggaggag agggattgga  23520
gtttgggatg actgtggtag ctgaaatttt tctaggtctg ctagaaataa gaactggttt  23580
gtgtggagga aaagagctct acaaatacgc atagaagtct cctccagtcg ttggcctgac  23640
atgacgctgc ctgtgcacag gaaatggttc cacgagaaag tgtggcaaag aacatttact  23700
gagaaacagc aagtacaaga gcacaggaag ctcaataaag aagagagaga tcacatagca  23760
ctctgggata ctggagttct tcccagctag accagagagt cctcacggag cacattgcca  23820
attcagtgga gaccccagaa cagccgtaat ttaaaggtac acttagtata ttactagaat  23880
aaagtcagct gcagacaacc ccttgcacag ctggaaagca agtgtccaag catcaaatcg  23940
gtttccaatc aatgaagtgc ctgtgagagg aaatctcaac tctctttaga agtaaacaac  24000
aaagtcgatt gcctcagcta tgcggtatcc gcagagtgag tcctaaattt aaaatctgac  24060
tacatgtaga aaagcgtttc gtgtgaccca tgaccaggaa ataaatcggg taatacaaac  24120
aggctcagga atgagagaaa tgattagaat tgcgtgaaaa tttgacatat cagtatgata  24180
actgatttca aatatttaaa aaaacaacat gcaagaaagc agatatcata tcaagagaaa  24240
ttaacagtac agaatagcca aattaaatta aagaggtagt ataaaaaaag tatgtcttaa  24300
ttgaaaaaaa ttactgtatg gccggctgat caatttagac gtttcagagg aaaacattac  24360
ccaacacaca attctagaga acctacagaa tgagctacac acacacacac acacacacac  24420
acacacactg aaaacacacc catactcaca cacacgcaga aactcacaag ttctaacaca  24480
cacagacacg cgcacccctg aagaaacagt gaaatataaa attaagcgag cctcacagac  24540
atgtaggaaa atatgaaaag atttcctgca tgtgggaagc aagtcacagt aaagagcaag  24600
ggagtttata atagaaacaa ataccagaat caaggatggc tgataacttt tcaattacga  24660
agaacattaa aaaaaatcac agaatcgtga aactcaaggg atcatatagg gaatttcgga  24720
aaaaaaaccc aacctgtatg atgtactttt gtacatcaca gttcgaaggt aacaaggcaa  24780
agatgtaata agaagaaacc tgtcacgaga aactggagga aaaagagctg tgtcttccta  24840
caagtacact gatacaaatt gccaatgtgt tcacctcaga aacactggaa gccagatacc  24900
agggaatatt gttaaaatga taatcaggaa caaaaagaga tcaaccggga atgctgaatc  24960
cagcaataaa atgccttgaa ggtcatccat gtcggataaa tgcatattgt gcactgcccc  25020
aaagaaagaa accggaaact gtaagaattg gaaatcagca ggcttatgta acaagagagg  25080
tgacccgaag gaattaggta gaagaagaat tgaacaagaa aggaactttc tgcagcccac  25140
gtaatgaaga atccagcaat tggcaaatgt agatagatgt aaatgcaaaa tattttcttg  25200
atcaaatttc tatatctttg taaatgagag ttgactactt gaaacaaaat gatagcaaga  25260
tatttaactt cagcatatgt agaggtaaga atttgaaatg gtagcataaa tcacgaaggg  25320
attaattcga agtgtaccgt tgtaagtttc tttacctcat gcacgatggt gtgtcatatt  25380
aataaaaggg tactgtgcgg gttcgaaggg atattgcaaa tcctagagca atcacaaagg  25440
tttgaactct gaggtttttg gtataataag aatagtccat gcattcaaaa gagggaagcc  25500
aaggaagaac tagaagtctt tcaagagctc aggctcttat acatccagtt gctcattgaa  25560
ccagcttcct ggaatggagg gtctggggtt gagactaggc cacaagtcta gagtctctag  25620
agagacagtg ttggaacccc atggcccata atacatttcc cattttctca ggcagccaga  25680
ggtcatgaat gtgaggatac tgggaggttg gagcaacgtt cttgggaggc ataaggaaga  25740
gcgaatgctt caagatcccc gcagcccaaa ctactcgcct gctttgcccc ctaatgcatt  25800
```

```
tttctctgct gctccgtagc tgtccgacct cttcagatct cttagtccac cctgccgtct  25860
tcctttatgc catgggtccc actgttcttt caactcatcc ccctttccct cagtcccgga  25920
gtagctgcgg ccagcagagg gtagactgag agcaggagag aaggacctgc ctaggaaccc  25980
cttctagaga tactgcatcc tgcctgggag caagttttcc agggcagctt tgagaagtct  26040
tggagaaaca aacctactaa acctgacaga cagtaatact atttgcacaa tgcttttctg  26100
tgggaaaggt agagcctttt cactacgtat tgagtacata gagtgtgagg gttgacctgg  26160
aacggctatc ctcctggatg acgtgtgttt tctgaagaac tacatgttcg ttgcaactcc  26220
cacattagaa tatgaagtcc taccgagaga gatacggaga ctagacagat acagatgcat  26280
ttgcatgtga atacacaatc ccacaataca gacgtcaaaa cccataccag ttattccaga  26340
gagatggatt gggcagaagg cagaaggaga atactctgat cgtttttcgg ccacgtgtgt  26400
gtgttatctc agtgtttcta agaagcgttt gctactttag atttttatt taaaaaaata  26460
gtaataatct attaagtatg agagatgtgc agagaggatt agtgatcgag agccattttt  26520
gctggtggca atcatatggt acttttaatg ggaatattag aaaggcaccg gtaatgacct  26580
tgttgcagca caaaggagag agtgtggggt gcccctgcat gttgtcccac ctcttgtgac  26640
gtgtatcgtt ttggaatttc cagtggcttg atcatgaact actgcaggaa tccagatgct  26700
gtggcagctc cttattgtta tacgagggat cccggtgtca ggtgggagta ctgcaacctg  26760
acgcaatgct cagacgcaga agggactgcc gtcgcgcctc cgactgttac cccggttcca  26820
agcctagagg ctccttccga acaaggtaag gagtctgtgg ccagacatct acacgcttcg  26880
atgctgggat gaaaagccat ggaaattccc actgatgcag ccgccttcaa tggtaaacgg  26940
atgctcgagt gttgcctgag ttctaccatg taggaggaag cctccgtgca ctctctgggg  27000
gagccagcgg agtgatttct ggtgcaacgt ggttgggctt tgtctttagg atgggcacaa  27060
accctccagg gggatcgact tcaaaattca ccttgttgta aaacgggcta cctcagtgtc  27120
ccagccaaaa tttttattgt aacatgctgt caggtgtgtc actctttcca agccagtaag  27180
cttttccggg gatttcttca agtagccagc attcagagca atcttcagca ttgcagattc  27240
tgagaaatgt ggctctggag cctgtcaccc tcgagaaacc taagagggct gcattgattc  27300
catgtggccc tgggtctatg gagcagtaca tgagctccca gtgctctaag gctcttcagc  27360
cctaggcttt gaagggagtg atttctcagt attcttaaac ctctttctga tgacacttgt  27420
acctgtgagg ggtctagaga gaaagagtag tagactccta ctttactaca attcaggatg  27480
cagggcatga gaggattccc tctctcctcc aagggaagaa gcttttggcg tgcacacatc  27540
cctgagaagc aaagtgtctt tgtcttcagt cagatacata ggaccgtttt ctgccccatg  27600
gcccggaagc caaaggcctt ggctttcatg atcaacggtc tagggaaaca tgcaaaattt  27660
ccatgtctgt cccaaactct gcccccgaca gccaattacc acctgcagcc cgcattgcca  27720
aatgcggtgc cgtttgcatg aagattcagt agagtttcct agaaaggtgc tacctcgtga  27780
gctcactttc caatgaggaa tctgatctgt tgtgtttctc taaggtgtca ggtgaaatat  27840
ttccaagaac ttactacagt tctagaatgg gaggaatctg ttgctttggt gtttgtttgt  27900
tggtcggttt tctcacatcc atctgcctat ggataaggaa aagagaacgg tcgtaattct  27960
catagactcc tttctggttg tgtcacaaat ggcttcacat gtttctctat gctcagagat  28020
actcagcttg atttcccgtg ttttcatttc agcaccgact gagcaaaggc ctggggtgca  28080
ggagtgctac catggtaatg gacagagtta tcgaggcaca tactccacca ctgtcacagg  28140
```

```
aagaacctgc caagcttggt catctatgac accacactcg catagtcgga ccccagaata  28200
ctacccaaat gcgtatgtct ttgttcttta ccataagaga agaaagggcc aagtgaagtt  28260
tctgttacaa gagatgtgtc tcaagctgag ttctccgaac tcaacttgtg acagatgcag  28320
atggcgtagc aaaatgtctc aggatgattg ccttggagct aagggtctga gagaagggaa  28380
atgttaagct ccctctcctt cctcctagtt ctattgagca gaagggaaat ctggaggtga  28440
ggagatcaca ttatgaagaa agtcagaatg acaaaggacc agacacttag attacccttc  28500
cacaacacca actaaacgtc aatggagact ttccagttgg aattccgtta ttctggcttc  28560
cacttcctga agggaaggtt gcgtttgcct tttctctctg ggttcaagag gaaagaatag  28620
gtgcttattt atggacaggt gaattgatct gtttctatat ctacgtatat tccgattgtc  28680
agaaaaacac tcgttcctaa gtaccagtgg cctgaaggga tacaggttcc cagcaagaga  28740
agatccaagg aaggaaggca gatgagagtc agcacagaga gggatgctga aaagtaaaag  28800
ggatgggtgg atggagagaa gcccgggtct gaccacccaa tggccaatat tttggccaca  28860
agcgactacc agagacatgg aaaaatggtt tctacatgtg ggacaacaga tggtagagga  28920
cctagagaat tgagagaggg gcaatgatgg gctccactcc gcagatgcct tggctttctt  28980
cctggatacc cttcctgcac tgaatagcaa ggagatggag cccaagcaga ctgtagccat  29040
cttgctgaat ggaggagagg gattggagtt tgggatgact gtggtagctg aaatttttct  29100
aggtctgcta gaaataagaa ctggtttgtg gaggaaaaga gctctacaaa tacgcataga  29160
agtctcctcc agtcgttggc ctgacatgac gctgcctgtg cacaggaaat ggttccacga  29220
gaaagtgtgg caaagaacat ttactgagaa acagcaagta caagagcaca ggaagctcaa  29280
taaagaagag agagatcaca tagcactctg ggatactgga gttcttccca gctagaccag  29340
agagtcctca cggagcacat tgccaattca gtggagaccc cagaacagcc gtaatttaaa  29400
ggtacactta gtatattact agaataaagt cagctgcaga caaccccttg cacagctgga  29460
aagcaagtgt ccaagcatca aatcggtttc caatcaatga agtgcctgtg agaggaaatc  29520
tcaactctct ttagaagtaa acaacaaagt cgattgcctc agctatgcgg tatccgcaga  29580
gtgagtccta aatttaaaat ctgactacat gtagaaaagc gtttcgtgtg acccatgacc  29640
aggaaataaa tcgggtaata caaacaggct caggaatgag agaaatgatt agaattgcgt  29700
gaaaatttga catatcagta tgataactga tttcaaatat ttaaaaaaac aacatgcaag  29760
aaagcagata tcatatcaag agaaattaac agtacagaat agccaaatta aattaaagag  29820
ctagtataaa aaaagtatgt cttaattgaa aaaaattact gtatggccgg ctgatcaatt  29880
tagacgtttc agaggaaaac attacccaac acacaattct agagaaccta cagaatgagc  29940
tacacacaca cacacacaca cacacacaaa ctgaaaacac acccatactc acacacacgc  30000
agaaactcac aagttctaac acacacagac acgcgcaccc ctgaagaaac agtgaaatat  30060
aaaattaagc gagcctcaca gacatgtagg aaaatatgaa aagatttcct gcatgtggga  30120
agcaagtcac agtaaagagc aagggagttt ggaatagaaa caaataccgg aatcaaggat  30180
ggctgataac ttttcaatta cgaagaacat taaaaaaaat cacagaatcg tgaaactcaa  30240
gggatcacat agggaatttc ggaaaaaaaa cccaacctgt atgatgtact tttgtacatc  30300
acagttcgaa ggtaacaagg caaagatata ataagaagaa acctgtcacg agaaactgga  30360
ggaaaaagag ctgtgtcttc ctacaagtac actgatacaa attgccaatg tgttcacctc  30420
agaaacactg gaagccagat accagggaat attgttaaaa tgataatcag gaacaaaaag  30480
agatcaaccg ggaatgctga atccagcaat aaaatgcctt gaagatcatc catgtcggat  30540
```

```
aaatgcatat tgtgcactgc cccaaagaaa gaaaccggaa actgtaagaa ttggaaatca  30600
gcaggcttat gtaacaagag aggtgacccg aaggaattag gtagaagaag aattgaacaa  30660
gaaaggaact ttctgcagcc cacgtaatga agaatccagc aattggcaaa tgtagataga  30720
tgtaaatgca aaatatttc ttgatcaaat ttctatatct ttgtaaatga gagttgacta  30780
cttgaaacaa aatgatagca agatatttaa cttcagcata tgtagaggta agaatttgaa  30840
atggtagcat aaatcacgaa gggattaatt cgaagtgtac cgttgtaagt ttctttacct  30900
catgcacgat ggtgtgtcat attaataaaa gggtactgtg cgggttcgaa gggatattgc  30960
aaatcctaga gcaatcacaa aggtttgaac tctgaggttt ttggtataat aagaatagtc  31020
catgcattca aaagagggaa gccaaggaag aactagaagt ctttcaagag ctcaggctct  31080
tatacatcca gttgctcatt gaaccagctt cctggaatgg agggtctggg gttgagacta  31140
ggccacaagt ctagagtctc tagagagaca gtgttggaac cccatggccc ataatacatt  31200
tcccatttc tcaggcagcc agaggtcatg aatgtgagga tactgggagg ttggagcaac  31260
gttcttggga ggcataagga agagcgaatg cttcaagatc cccgcagccc aaactactcg  31320
cctgctttgc cccctaatgc atttttctct gctgctccgt agctgtccga cctcttcaga  31380
tctcttagtc caccctgccg tcttccttta tgccatgggt cccactgttc tttcaactca  31440
tccccctttc cctcagtccc ggagtagctg cggccagcag agggtagact gagagcagga  31500
gagaaggacc tgcctaggaa ccccttctag agatactgca tcctgcctgg gagcaagttt  31560
tccagggcag ctttgagaag tcttggagaa acaaacctac taaacctgac agacagtaat  31620
actatttgca caatgctttt ctgtgggaaa ggtagagcct tttcactacg tattgagtac  31680
atagagtgtg agggttgacc tggaacggct atcctcctgg atgacgtgtg ttttctgaag  31740
aactacatgt tcgttgcaac tcccacatta gaatatgaag tcctaccgag agagatacgg  31800
agactagaca gatacagatg catttgcatg tgaatacaca atcccacaat acagacgtca  31860
aaacccatac cagttattcc agagagatgg attgggtagg aggcagaagg agaatactct  31920
gatcgttttt cggccacgtg tgtgtgttat ctcagtgttt ctaagaagcg tttgctactt  31980
tagatttttt atttaaaaaa aatagtaata atctattaag tatgagagat gtgcagagag  32040
gattagtgat cgagagccat ttttgctggt ggcaatcata tggtactttt aatgggaata  32100
ttagaaaggc accggtaatg accttgttgc agcacaaagg agagagtgtg gggtgcccct  32160
gcatgttgtc ccacctcttg tgacgtgtat cgttttggaa tttccagtgg cttgatcatg  32220
aactactgca ggaatccaga tgctgtggca gctccttatt gttatacgag ggatcccggt  32280
gtcaggtggg agtactgcaa cctgacgcaa tgctcagacg cagaagggac tgccgtcgcg  32340
cctccgactg ttaccccggt tccaagccta gaggctcctt ccgaacaagg taaggagtct  32400
gtggccagac atctacacgc ttcgatgctg ggatgaaaag ccatggaaat tcccactgat  32460
gcagccgcct tcaatggtaa acggatgctc gagtgttgcc ggagttctgc catgttgggg  32520
gaagcctccg tgtactctct gggggagcca gcggagtgat ttctggtgca acttgggtgg  32580
gctttgtctt tagaatgggc acaaaccttc cagggtgatg ggcttcacaa ctcacctcct  32640
tctaaaatgg gctatctcag tgtcttagcc aaaattttta ttgtaacgtg ctgtcaggtg  32700
tgtgattctt tctgtcgcag taagcttttc tggggatttc ttcaagtagc cagcagtcag  32760
tgcaatcttc agcattgcag atttcaaaaa atgtggctct ggagcctgtc atcctcgaga  32820
aacctaacag ggctgcatta attccatatg gtcctgggtc tatggagcag tatatgagct  32880
```

cccaatgctc taaggctctt cagtcctagg ctttgaaggg agtgatttct cagtgttctt 32940
aaacctcttt ctgatggcac ttgtacctgt gaggggtcta gagagaaagg ttagtagact 33000
tctcctttac tgcaattcag gatgcagggc atgagaagat tccctccctc ctccaaggga 33060
agaaggtttt ggcgtgcaca catccttgag aagcaaagtg tctttgcctt cagtcagata 33120
tataggatcg ttttctgccc catggcctgg aagccagagg ccttggcttt catgatcaac 33180
gatctaggga aacatgcaaa atttccatgt ctttcccctc ctctgccctc gacagccaat 33240
taccacctgc atcctgcatt gccaaatgca gtgccctttg tatgaacatt cagtagagtt 33300
tcatagaaag gtgctacttc gtgagcgcac tttgcagtga gaaggagtct gttctgttct 33360
gtttttctaa ggatttcagg tgaaatattt cctagaactt actacagttc tagattggta 33420
ggaatctgta ggtttgctgt atgtttttttg gttggttttc tcccatccat ctgcctacag 33480
gtaagggaaa gataacgttc gtaattctca tagactcctt tctggttgtg tcataaatgg 33540
cttcacatat ttcgttattc tcagagatac tcagtttatt tcttgtgttt tcatttcagc 33600
accgactgag cagaggcctg gggtgcagga gtgctaccac ggtaatggac agagttatcg 33660
aggcacatac tccaccactg tcactggaag aacctgccaa gcttggtcat ctatgacacc 33720
acactcgcat agtcggaccc cagaatacta cccaaatgcg tatgtctttg ttctttacca 33780
taagagaaga aagggccaag tgaagtttct gttacaagag atgtgtctca agctgagttc 33840
tccgaactca acttgtgaca gatgcagatg gcgtagcaaa atgtctcagg atgattgcct 33900
tggagctaag ggtctgagag aagggaaatg ttaagctccc tctccttcct cctagttcta 33960
ttgagcagaa gggaaatctg gaggtgagga gatcacatta tgaagaaagt cagaatgaca 34020
aaggaccaga cacttagatt acccttccac aacaccaact aaacgtcaat ggagactttc 34080
cagttggaat tccgttattc tggcttccac ttcctgaagg gaaggttgcg tttgcctttt 34140
ctctctgggt tcaagaggaa agaataggtg cttatttatg gacaggtgaa ttgatctgtt 34200
tctatatcta cgtatattcc gattgtcaga aaaacactcg ttcctaagta ccagtggcct 34260
gaagggatac aggttcccag caagagaaga tccaaggaag gaaggcagat gagagccagc 34320
acagagaggg atgctgaaaa gtaaaaggga tgggtggatg gagagaagcc cgggtctgac 34380
cacccaatgg ccaatatttt ggccacaagc gactaccaga gacatggaaa aatggtttct 34440
acatgtggga caacagatgg tagaggacct agagaattga gagaggggca atgatgggct 34500
ccactccgca gatgccttgg ctttcttcct ggataccctt cctgcactga atagcaagga 34560
gatggagccc aagcagactg tagccatctt gctgaatgga ggagagggat tggagtttgg 34620
gatgactgtg gtagctgaaa tttttctagg tctgctagaa ataagaactg gtttgtggag 34680
gaaaagagct ctacaaatac gcatagaagt ctcctccagt cgttggcctg acatgacgct 34740
gcctgtgcac aggaaatggt tccacgagaa agtgtggcaa agaacattta ctgagaaaca 34800
gcaagtacaa gagcacagga agctcaataa agaagagaga gatcacatag cactctggga 34860
tactggagtt cttcccagct agaccagaga gtcctcacgg agcacattgc caattcagtg 34920
gagaccccag aacagccgta atttaaaggt acacttagta tattactaga ataaagtcag 34980
ctgcagacaa ccccttgcac agctggaaag caagtgtcca agcatcaaat cggtttccaa 35040
tcaatgaagt gcctgtggga ggaaatctca actctcttta gaagtaaaca acaaagtcga 35100
ttgcctcagc tatgcggtat ccgcagagtg agtcctaaat ttaaaatctg actacatgta 35160
gaaaagcgtt tcgtgtgacc catgaccagg aaataaatcg ggtaatacaa acaggctcag 35220
gaatgagaga aatgattaga attgcgtgaa aatttgacat atcagtatga taactgattt 35280
caaatattta aaaaaacaac atgcaagaaa gcagatatca tatcaagaga aattaacagt 35340
acagaatagc caaattaaat taaagagcta gtataaaaaa agtatgtctt aattgaaaaa 35400
aattactgta tggccggctg atcaaattag acgtttcaga ggaaaacatt acccaacaca 35460
caattctaga gaacctacag aatgagctac acacacacac acacacacac acacacacac 35520
tgaaaacaca cccatactca cacacacgca gaaactcaca agttctaaca cacacagaca 35580
cgcgcacccc tgaagaaaca gtgaaatata aaattaagcg agcctcacag acatgtagga 35640
aaatatgaaa agatttcctg catgtgggaa gcaagtcaca gtaaagagca agggagtttg 35700
gaatagaaac aaataccgga atcaaggatg gctgataact tttcaattac gaagaacatt 35760
aaaaaaaatc acagaatcgt gaaactcaag ggatcatata gggaatttcg gaaaaaaaac 35820
ccaacctgta tgatgtactt ttgtacatca cagttcgaag gtaacaaggc aaagatataa 35880
taagaagaaa cctgtcacga gaaactggag gaaaaagagc tgtgtcttcc tacaagtaca 35940
ctgatacaaa ttgccaatgt gttcacctca gaaacactgg aagccagata ccagggaata 36000
ttgttaaaat gataatcagg aacaaaaaga gatcaaccgg gaatgctgaa tccagcaata 36060
aaatgccttg aagatcatcc atgtcggata aatgcatatt gtgcactgcc ccaaagaaag 36120
aaaccggaaa ctgtcagaat tggaaatcag caggcttatg taacaagaga ggtgacccga 36180
aggaattagg tagaagaaga attgaacaag aaaggaactt tctgcagccc acgtaatgaa 36240
gaatccagca attggcaaat gtagatagat gtaaatgcaa aatattttct tgatcaaatt 36300
tctatatctt tgtaaatgag agttgactac ttgaaacaaa atgatagcaa gatatttaac 36360
ttcagcatat gtagaggtaa gaatttgaaa tggtagcata aatcacgaag ggattaattc 36420
gaagtgtacc gttgtaagtt tctttacctc atgcacgatg gtgtgtcata ttaataaaag 36480
ggtactgtgc gggttcgaag ggatattgca aatcctagag caatcacaaa ggtttgaact 36540
ctgaggtttt tggtataata agaatagtcc atgcattcaa aagagggaag ccaaggaaga 36600
actagaagtc tttcaagagc tcaggctctt atacatccag ttgctcattg aaccagcttc 36660
ctggaatgga gggtctgggg ttgagactag gccacaagtc tagagtctct agagagacag 36720
tgttggaacc ccatggccca taatacattt cccattttct caggcagcca gaggtcatga 36780
atgtgaggat actgggaggt tggagcaacg ttcttgggag gcataaggaa gagcgaatgc 36840
ttcaagatcc ccgcagccca aactactcgc ctgctttgcc ccctaatgca tttttctctg 36900
ctgctccgta gctgtccgac ctcttcagat ctcttagtcc accctgccgt cttcctttat 36960
gccatgggtc ccattgttct ttcaactcat ccccctttcc ctcagtcccg gagtagctgc 37020
ggccagcaga gggtagactg agagcaggag agaaggacct gcctaggaac cccttctaga 37080
gatactgcat cctgcctggg agcaagtttt ccagggcagc tttgagaagt cttggagaaa 37140
caaacctact aaacctgaca gacagtaata ctatttgcac aatgcttttc tgtgggaaag 37200
gtagagcctt ttcactacgt attgagtaca tagagtgtga gggttgacct ggaacggcta 37260
tcctcctgga tgacgtgcgt tttctgaaga actacatgtt cgttgcaact cccacattag 37320
aatatgaagt cctaccgaga gagatacgga gactagacag atacagatgc atttgcatgt 37380
gaatacacaa tcccacaata cagacgtcaa aacccatacc agttattcca gagagatgga 37440
ttgggcagaa ggcagaagga gaatactctg atcgtttttc ggccacgtgt gtgtgttatc 37500
tcagtgtttc taagaagcgt ttgctacttt agattttta tttaaaaaaa atagtaataa 37560
tctattaagt atgagagatg tgcagagagg attagtgatc gagagccatt tttgctggtg 37620
gcaatcatat ggtactttta atgggaatat tagaaaggca ccggtaatga ccttgttgca 37680
gcacaaagga gagagtgtgg ggtgcccctg catgttgtcc cacctcttgt gacgtgtatc 37740
gttttggaat ttccagtggc ttgatcatga actactgcag gaatccagat gctgtggcag 37800
ctccttattg ttatacgagg gatcccggtg tcaggtggga gtactgcaac ctgacgcaat 37860
gctcagacgc agaagggact gccgtcgcgc ctccgactgt taccccggtt ccaagcctag 37920
aggctccttc cgaacaaggt aaggagtctg tggccagaca tctacacgct tcgatgctgg 37980
gatgaaaagc catggaaatt cccactgatg cagccgcctt caatggtaaa cggatgctcg 38040
agtgttgcct gagttctacc atgtaggagg aagcctccgt gcactctctg gggagccag 38100
cggagtgatt tctggtgcaa cgtggttggg ctttgtcttt aggatgggca caaaccctcc 38160
agggggatcg acttcaaaat tcaccttgtt gtaaaacggg ctacctcagt gtcccagcca 38220
aaatttttat tgtaacatgc tgtcaggtgt gtcactcttt ccaagccagt aagcttttcc 38280
ggggatttct tcaagtagcc agcattcaga gcaatcttca gcattgcaga ttctgagaaa 38340
tgtggctctg gagcctgtca ccctcgagaa acctaagagg gctgcattga ttccatgtgg 38400
ccctgggtct atggagcagt acatgagctc ccagtgctct aaggctcttc agccctaggc 38460
tttgaaggga gtgatttctc agtattctta aacctctttc tgatgacact tgtacctgtg 38520
aggggtctag agagaaagag tagtagactc ctactttact acaattcagg atgcagggca 38580
tgagaggatt ccctctctcc tccaagggaa gaagcttttg gcgtgcacac atccctgaga 38640
agcaaagtgt ctttgtcttc agtcagatac ataggaccgt tttctgcccc atggcccgga 38700
agccaaaggc cttggctttc atgatcaacg gtctagggaa acatgcaaaa tttccatgtc 38760
tgtcccaaac tctgcccccg acagccaatt accacctgca gcccgcattg ccaaatgcgg 38820
tgccgtttgc atgaagattc agtagagttt cctagaaagg tgctacctcg tgagctcact 38880
ttccaatgag gaatctgatc tgttgtgttt ctctaaggtg tcaggtgaaa tatttccaag 38940
aacttactac agttctagaa tgggaggaat ctgttgcttt ggtgtttgtt tgttggtcgg 39000
ttttctcaca tccatctgcc tatggataag gaaaagagaa cggtcgtaat tctcatagac 39060
tcctttctgg ttgtgtcaca aatggcttca catgtttctc tatgctcaga gatactcagc 39120
ttgatttccc gtgttttcat ttcagcaccg actgagcaaa ggcctggggt gcaggagtgc 39180
taccatggta atggacagag ttatcgaggc acatactcca ccactgtcac aggaagaacc 39240
tgccaagctt ggtcatctat gacaccacac tcgcatagtc ggaccccaga atactaccca 39300
aatgcgtatg tctttgttct ttaccataag agaagaaagg gccaagtgaa gtttctgtta 39360
caagagatgt gtctcaagct gagttctccg aactcaactt gtgacagatg cagatggcgt 39420
agcaaaatgt ctcaggatga ttgccttgga gctaagggtc tgagagaagg gaaatgttaa 39480
gctccctctc cttcctccta gttctattga gcagaaggga aatctggagg tgaggagatc 39540
acattatgaa gaaagtcaga atgacaaagg accagacact tagattaccc ttccacaaca 39600
ccaactaaac gtcaatggag actttccagt tggaattccg ttattctggc ttccacttcc 39660
tgaagggaag gttgcgtttg ccttttctct ctgggttcaa gaggaaagaa taggtgctta 39720
tttatggaca ggtgaattga tctgtttcta tatctacgta tattccgatt gtcagaaaaa 39780
cactcgttcc taagtaccag tggcctgaag ggatacaggt tcccagcaag agaagatcca 39840
aggaaggaag gcagatgaga gtcagcacag agagggatgc tgaaaagtaa aagggatggg 39900
tggatggaga gaagcccggg tctgaccacc caatggccaa tattttggcc acaagcgact 39960
accagagaca tggaaaaatg gtttctacat gtgggacaac agatggtaga ggacctagag 40020

-continued aattgagaga ggggcaatga tgggctccac tccgcagatg ccttggcttt cttcctggat 40080
acccttcctg cactgaatag caaggagatg gagcccaagc agactgtagc catcttgctg 40140
aatggaggag agggattgga gtttgggatg actgtggtag ctgaaatttt tctaggtctg 40200
ctagaaataa gaactggttt gtggaggaaa agagctctac aaatacgcat agaagtctcc 40260
tccagtcgtt ggcctgacat gacgctgcct gtgcacagga aatggttcca cgagaaagtg 40320
tggcaaagaa catttactga gaaacagcaa gtacaagagc acaggaagct caataaagaa 40380
gagagagatc acatagcact ctgggatact ggagttcttc ccagctagac cagagagtcc 40440
tcacggagca cattgccaat tcagtggaga ccccagaaca gccgtaattt aaaggtacac 40500
ttagtatatt actagaataa agtcagctgc agacaacccc ttgcacagct ggaaagcaag 40560
tgtccaagca tcaaatcggt ttccaatcaa tgaagtgcct gtgagaggaa atctcaactc 40620
tctttagaag taaacaacaa agtcgattgc ctcagctatg cggtatccgc agagtgagtc 40680
ctaaatttaa aatctgacta catgtagaaa agcgtttcgt gtgacccatg accaggaaat 40740
aaatcgggta atacaaacag gctcaggaat gagagaaatg attagaattg cgtgaaaatt 40800
tgaaatatca gtatgataac tgatttcaaa tatttaaaaa aacaacatgc aagaaagcag 40860
atatcatatc aagagaaatt aacagtacag aatagccaaa ttaaattaaa gagctagtat 40920
aaaaaaagta tgtcttaatt gaaaaaaatt actgtatggc cggctgatca atttagacgt 40980
ttcagaggaa aacattaccc aacacacaat tctagagaac ctacagaatg agctacacac 41040
acacacacac acacacacac aaactgaaaa cacacccata ctcacacaca cgcagaaact 41100
cacaagttct aacacacaca gacacgcgca cccctgaaga aacagtgaaa tataaaatta 41160
agcgagcctc acagacatgt aggaaaatat gaaaagattt cctgcatgtg ggaagcaagt 41220
cacagtaaag agcaagggag tttggaatag aaacaaatac cagaatcaag gatggctgat 41280
aacttttcaa ttacgaagaa cattaaaaaa aatcacagaa tcgtgaaact caagggatca 41340
catagggaat ttcggaaaaa aaacccaacc tgtatgatgt acttttgtac atcacagttc 41400
gaaggtaaca aggcaaagat ataataagaa gaaacctgtc acgagaaact ggaggaaaaa 41460
gagctgtgtc ttcctacaag tacactgata caaattgcca atgtgttcac ctcagaaaca 41520
ctggaagcca gataccaggg aatattgtta aaatgataat caggaacaaa aagagatcaa 41580
ccgggaatgc tgaatccagc aataaaatgc cttgaagatc atccatgtcg gataaatgca 41640
tattgtgcac tgccccaaag aaagaaaccg gaaactgtaa gaattggaaa tcagcaggct 41700
tatgtaacaa gagaggtgac ccgaaggaat taggtagaag aagaattgaa caagaaagga 41760
actttctgca gcccacgtaa tgaagaatcc agcaattggc aaatgtagat agatgtaaat 41820
gcaaaatatt ttcttgatca aatttctata tctttgtaaa tgagagttga ctacttgaaa 41880
caaaatgata gcaagatatt taacttcagc atatgtagag gtaagaattt gaaatggtag 41940
cataaatcac gaagggatta attcgaagtg taccgttgta agtttcttta cctcatgcac 42000
gatggtgtgt catattaata aaagggtact gtgcgggttc gaagggatat tgcaaatcct 42060
agagcaatca caaaggtttg aactctgagg tttttggtat aataagaata gtccatgcat 42120
tcaaaagagg gaagccaagg aagaactaga agtctttcaa gagctcaggc tcttatacat 42180
ccagttgctc attgaaccag cttcctggaa tggagggtct ggggttgaga ctaggccaca 42240
agtctagagt ctctagagag acagtgttgg aaccccatgg cccataatac atttcccatt 42300
ttctcaggca gccagaggtc atgaatgtga ggatactggg aggttggagc aacgttcttg 42360

```
ggaggcataa ggaagagcga atgcttcaag atccccgcag cccaaactac tcgcctgctt  42420
tgccccctaa tgcatttttc tctgctgctc cgtagctgtc cgacctcttc agatctctta  42480
gtccaccctg ccgtcttcct ttatgccatg ggtcccactg ttctttcaac tcatccccct  42540
ttccctcagt cccggagtag ctgcggccag cagagggtag actgagagca ggagagaagg  42600
acctgcctag gaaccccttc tagagatact gcatcctgcc tgggagcaag ttttccaggg  42660
cagctttgag aagtcttgga gaaacaaacc tactaaacct gacagacagt aatactattt  42720
gcacaatgct tttctgtggg aaaggtagag ccttttcact acgtattgag tacatagagt  42780
gtgagggttg acctggaacg gctatcctcc tggatgacgt gtgtttctg aagaactaca  42840
tgttcgttgc aactcccaca ttagaatatg aagtcctacc gagagagata cggagactag  42900
acagatacag atgcatttgc atgtgaatac acaatcccac aatacagacg tcaaaaccca  42960
taccagttat tccagagaga tggattgggc agaaggcaga aggagaatac tctgatcgtt  43020
tttcggccac gtgtgtgtgt tatctcagtg tttctaagaa gcgtttgcta ctttagattt  43080
tttatttaaa aaaaatagta ataatctatt aagtatgaga gatgtgcaga gaggattagt  43140
gatcgagagc catttttgct ggtggcaatc atatggtact tttaatggga atattagaaa  43200
ggcaccggta atgaccttgt tgcagcacaa aggagagagt gtggggtgcc cctgcatgtt  43260
gtcccacctc ttgtgacgtg tatcgttttg gaatttccag tggcttgatc atgaactact  43320
gcaggaatcc agatgctgtg gcagctcctt attgttatac gagggatccc ggtgtcaggt  43380
gggagtactg caacctgacg caatgctcag acgcagaagg gactgccgtc gcgcctccga  43440
ctgttacccc ggttccaagc ctagaggctc cttccgaaca aggtaaggag tctgtggcca  43500
gacatctaca cgcttcgatg ctgggatgaa aagccatgga aattccccact gatgcagccg  43560
ccttcaatgg taaacggatg ctcgagtgtt gcctgagttc taccatgtag gaggaagcct  43620
ccgtgcactc tctgggggag ccagcggagt gatttctggt gcaacgtggt tgggctttgt  43680
ctttaggatg ggcacaaacc ctccaggggg atcgacttca aaattcacct tgttgtaaaa  43740
cgggctacct cagtgtccca gccaaaattt ttattgtaac atgctgtcag gtgtgtcact  43800
ctttccaagc cagtaagctt ttccggggat ttcttcaagt agccagcatt cagagcaatc  43860
ttcagcattg cagattctga gaaatgtggc tctggagcct gtcaccctcg agaaacctaa  43920
gagggctgca ttgattccat gtggccctgg gtctatggag cagtacatga gctcccagtg  43980
ctctaaggct cttcagccct aggctttgaa gggagtgatt tctcagtatt cttaaacctc  44040
tttctgatga cacttgtacc tgtgaggggt ctagagagaa agagtagtag actcctactt  44100
tactacaatt caggatgcag ggcatgagag gattccctct ctcctccaag ggaagaagct  44160
tttggcgtgc acacatccct gagaagcaaa gtgtctttgt cttcagtcag atacatagga  44220
ccgttttctg ccccatggcc cggaagccaa aggccttggc tttcatgatc aacggtctag  44280
ggaaacatgc aaaatttcca tgtctgtccc aaactcttcc cccgacagcc aattaccacc  44340
tgcagcccgc attgccaaat gcggtgccgt ttgcatgaag attcagtaga gtttcctaga  44400
aaggtgctac ctcgtgagct cactttccaa tgaggaatct gatctgttgt gtttctctaa  44460
ggtgtcaggt gaaatatttc caagaactta ctacagttct agaatgggag gaatctgttg  44520
ctttggtgtt tgtttgttgg tcggttttct cacatccatc tgcctatgga taaggaaaag  44580
agaacggtcg taattctcat agactccttt ctggttgtgt cacaaatggc ttcacatgtt  44640
tctctatgct cagagatact cagcttgatt tcccgtgttt tcatttcagc accgactgag  44700
caaaggcctg gggtgcagga gtgctaccat ggtaatggac agagttatcg aggcacatac  44760
```

tccaccactg tcacaggaag aacctgccaa gcttggtcat ctatgacacc acactcgcat 44820
agtcggaccc cagaatacta cccaaatgcg tatgtctttg ttctttacca taagagaaga 44880
aagggccaag tgaagtttct gttacaagag atgtgtctca agctgagttc tccgaactca 44940
acttgtgaca gatgcagatg gcgtagcaaa atgtctcagg atgattgcct tggagctaag 45000
ggtctgagag aagggaaatg ttaagctccc tctccttcct cctagttcta ttgagcagaa 45060
gggaaatctg gaggtgagaa gatcacatta tgaagaaagt cagaatgaca aaggaccaga 45120
cacttagatt acccttccac aacaccaact aaacgtcaat ggagactttc cagttggaat 45180
tccgttattc tggcttccac ttcctgaagg gaaggttgcg tttgcctttt ctctctgggt 45240
tcaagaggaa agaataggtg cttatttatg gacaggtgaa ttgatctgtt tctatatcta 45300
cgtatattcc gattgtcaga aaaacactcg ttcctaagta ccagtggcct gaagggatac 45360
aggttcccag caagagaaga tccaaggaag gaaggcagat gagagtcagc acagagaggg 45420
atgctgaaaa gtaaaaggga tgggtggatg gagagaagcc cgggtctgac cacccaatgg 45480
ccaatatttt ggccacaagc gactaccaga gacatggaaa aatggtttct acatgtggga 45540
caacagatgg tagaggacct agagaattga gagaggggca atgatgggct ccactccgca 45600
gatgccttgg ctttcttcct ggataccctt cctgcactga atagcaagga gatggagccc 45660
aagcagactg tagccatctt gctgaatgga ggagagggat tggagtttgg gatgactgtg 45720
gtagctgaaa tttttctagg tctgctagaa ataagaactg gtttgtgtgg aggaaaagag 45780
ctctacaaat acgcatagaa gtctcctcca gtcgttggcc tgacatgacg ctgcctgtgc 45840
acaggaaatg gttccacgag aaagtgtggc aaagaacatt tactgagaaa cagcaagtac 45900
aagagcacag gaagctcaat aaagaagaga gagatcacat agcactctgg gatactggag 45960
ttcttcccag ctagaccaga gagtcctcac ggagcacatt gccaattcag tggagacccc 46020
agaacagccg taatttaaag gtacacttag tatattacta gaataaagtc agctgcagac 46080
aaccccttgc acagctggaa agcaagtgtc caagcatcaa atcggtttcc aatcaatgaa 46140
gtgcctgtga gaggaaatct caactctctt tagaagtaaa caacaaagtc gattgcctca 46200
gctatgcggt atccgcagag tgagtcctaa atttaaaatc tgactacatg tagaaaagcg 46260
tttcgtgtga cccatgacca ggaaataaat cgggtaatac aaacaggctc aggaatgaga 46320
gaaatgatta gaattgcgtg aaaatttgac atatcagtat gataactgat ttcaaatatt 46380
taaaaaaaca acatgcaaga aagcagatat catatcaaga gaaattaaca gtacagaata 46440
gccaaattaa attaaagagg tagtataaaa aaagtatgtc ttaattgaaa aaaattactg 46500
tatggccggc tgatcaattt agacgtttca gaggaaaaca ttacccaaca cacaattcta 46560
gagaacctac agaatgagct acacacacac acacacacac acacacaaac tgaaaacaca 46620
cccatactca cacacacgca gaaactcaca agttctaaca cacacagaca cgcgcacccc 46680
tgaagaaaca gtgaaatata aaattaagcg agcctcacag acatgtagga aaatatgaaa 46740
agatttcctg catgtgggaa gcaagtcaca gtaaagagca agggagtttg gaatagaaac 46800
aaataccgga atcaaggatg gctgataact tttcaattac gaagaacatt aaaaaaaatc 46860
acagaatcgt gaaactcaag ggatcacata gggaatttcg gaaaaaaaac ccaacctgta 46920
tgatgtactt ttgtacatca cagttcgaag gtaacaaggc aaagatataa taagaagaaa 46980
cctgtcacga gaaactggag gaaaaagagc tgtgtcttcc tacaagtaca ctgatacaaa 47040
ttgccaatgt gttcacctca gaaacactgg aagccagata ccagggaata ttgttaaaat 47100
gataatcagg aacaaaaaga gatcaaccgg gaatgctgaa tccagcaata aaatgccttg 47160
aaggtcatcc atgtcggata aatgcatatt gtgcactgcc ccaaagaaag aaaccggaaa 47220
ctgtaagaat tggaaatcag caggcttatg taacaagaga ggtgacccga aggaattagg 47280
tagaagaaga attgaacaag aaaggaactt tctgcagccc acgtaatgaa gaatccagca 47340
attggcaaat gtagatagat gtaaatgcaa aatattttct tgatcaaatt tctatatctt 47400
tgtaaatgag agttgactac ttgaaacaaa atgatagcaa gatatttaac ttcagcatat 47460
gtagaggtaa gaatttgaaa tggtagcata aatcacgaag ggattaattc gaagtgtacc 47520
gttgtaagtt tctttacctc atgcacgatg gtgtgtcata ttaataaaag ggtactgtgc 47580
gggttcgaag ggatattgca aatcctagag caatcacaaa ggtttgaact ctgaggtttt 47640
tggtataata agaatagtcc atgcattcaa aagagggaag ccaaggaaga actagaagtc 47700
tttcaagagc tcaggctctt atacatccag ttgctcattg aaccagcttc ctggaatgga 47760
gggtctgggg ttgagactag gccacaagtc tagagtctct agagagacag tgttggaacc 47820
ccatggccca taatacattt cccattttct caggcagcca gaggtcatga atgtgaggat 47880
actgggaggt tggagcaacg ttcttgggag gcataaggaa gagcgaatgc ttcaagatcc 47940
ccgcagccca aactactcgc ctgctttgcc ccctaatgca tttttctctg ctgctccgta 48000
gctgtccgac ctcttcagat ctcttagtcc accctgccgt cttcctttat gccatgggtc 48060
ccactgttct ttcaactcat ccccctttcc ctcagtcccg gagtagctgc ggccagcaga 48120
gggtagactg agagcaggag agaaggacct gcctaggaac cccttctaga gatactgcat 48180
cctgcctggg agcaagtttt ccagggcagc tttgagaagt cttggagaaa caaacctact 48240
aaacctgaca gacagtaata ctatttgcac aatgcttttc tgtgggaaag gtagagcctt 48300
ttcactacgt attgagtaca tagagtgtga gggttgacct ggaacggcta tcctcctgga 48360
tgacgtgcgt tttctgaaga actacatgtt cgttgcaact cccacattag aatatgaagt 48420
cctaccgaga gagatacgga gactagacag atacagatgc atttgcatgt gaatacacaa 48480
tcccacaata cagacgtcaa aacccatacc agttattcca gagagatgga ttgggcagaa 48540
ggcagaagga gaatactctg atcgtttttc ggccacgtgt gtgtgttatc tcagtgtttc 48600
taagaagcgt ttgctacttt agattttta tttaaaaaaa atagtaataa tctattaagt 48660
atgagagatg tgcagagagg attagtgatc gagagccatt tttgctggtg gcaatcatat 48720
ggtactttta atgggaatat tagaaaggca ccggtaatga ccttgttgca gcacaaagga 48780
gagagtgtgg ggtgcccctg catgttgtcc cacctcttgt gacgtgtatc gttttggaat 48840
ttccagtggc ttgatcatga actactgcag gaatccagat gctgtggcag ctccttattg 48900
ttatacgagg gatcccggtg tcaggtggga gtactgcaac ctgacgcaat gctcagacgc 48960
agaagggact gccgtcgcgc ctccgactgt taccccggtt ccaagcctag aggctccttc 49020
cgaacaaggt aaggagtctg tggccagaca tctacacgct tcgatgctgg gatgaaaagc 49080
catggaaatt cccactgatg cagccgcctt caatggtaaa cggatgctcg agtgttgcct 49140
gagttctacc atgtaggagg aagcctccgt gcactctctg gggagccag cggagtgatt 49200
tctggtgcaa cgtggttggg ctttgtcttt aggatgggca caaaccctcc agggggatcg 49260
acttcaaaat tcaccttgtt gtaaaacggg ctacctcagt gtcccagcca aaatttttat 49320
tgtaacatgc tgtcaggtgt gtcactcttt ccaagccagt aagcttttcc ggggatttct 49380
tcaagtagcc agcattcaga gcaatcttca gcattgcaga ttctgagaaa tgtggctctg 49440
gagcctgtca ccctcgagaa acctaagagg gctgcattga ttccatgtgg ccctgggtct 49500

-continued

```
atggagcagt acatgagctc ccagtgctct aaggctcttc agccctaggc tttgaaggga  49560
gtgatttctc agtattctta aacctctttc tgatgacact tgtacctgtg aggggtctag  49620
agagaaagag tagtagactc ctactttact acaattcagg atgcagggca tgagaggatt  49680
ccctctctcc tccaagggaa gaagcttttg gcgtgcacac atccctgaga agcaaagtgt  49740
ctttgtcttc agtcagatac ataggaccgt tttctgcccc atggcccgga agccaaaggc  49800
cttggctttc atgatcaacg gtctagggaa acatgcaaaa tttccatgtc tgtcccaaac  49860
tctgcccccg acagccaatt accacctgca gcccgcattg ccaaatgcgg tgccgtttgc  49920
atgaagattc agtagagttt cctagaaagg tgctacctcg tgagctcact ttccaatgag  49980
gaatctgatc tgttgtgttt ctctaaggtg tcaggtgaaa tatttccaag aacttactac  50040
agttctagaa tgggaggaat ctgttgcttt ggtgtttgtt tgttggtcgg ttttctcaca  50100
tccatctgcc tatggataag gaaaagagaa cggtcgtaat tctcatagac tcctttctgg  50160
ttgtgtcaca aatggcttca catgtttctc tatgctcaga gatactcagc ttgatttccc  50220
gtgttttcat ttcagcaccg actgagcaaa ggcctggggt gcaggagtgc taccatggta  50280
atggacagag ttatcgaggc acatactcca ccactgtcac aggaagaacc tgccaagctt  50340
ggtcatctat gacaccacac tcgcatagtc ggaccccaga atactaccca aatgcgtatg  50400
tctttgttct ttaccataag agaagaaagg gccaagtgaa gtttctgtta caagagatgt  50460
gtctcaagct gagttctccg aactcaactt gtgacagatg cagatggcgt agcaaaatgt  50520
ctcaggatga ttgccttgga gctaagggtc tgagagaagg gaaatgttaa gctccctctc  50580
cttcctccta gttctattga gcagaaggga aatctggagg tgaggagatc acattatgaa  50640
gaaagtcaga atgacaaagg accagacact tagattaccc ttccacaaca ccaactaaac  50700
gtcaatggag actttccagt tggaattccg ttattctggc ttccacttcc tgaagggaag  50760
gttgcgtttg ccttttctct ctgggttcaa gaggaaagaa taggtgctta tttatggaca  50820
ggtgaattga tctgtttcta tatctacgta tattccgatt gtcagaaaaa cactcgttcc  50880
taagtaccag tggcctgaag ggatacaggt tcccagcaag agaagatcca aggaaggaag  50940
gcagatgaga gtcagcacag agagggatgc tgaaaagtaa aagggatggg tggatggaga  51000
gaagcccggg tctgaccacc caatggccaa tattttggcc acaagcgact accagagaca  51060
tggaaaaatg gtttctacat gtgggacaac agatggtaga ggacctagag aattgagaga  51120
ggggcaatga tgggctccac tccgcagatg ccttggcttt cttcctggat acccttcctg  51180
cactgaatag caaggagatg gagcccaagc agactgtagc catcttgctg aatggaggag  51240
agggattgga gtttgggatg actgtggtag ctgaaatttt tctaggtctg ctagaaataa  51300
gaactggttt gtgtggagga aaagagctct acaaatacgc atagaagtct cctccagtcg  51360
ttggcctgac atgacgctgc ctgtgcacag gaaatggttc cacgagaaag tgtggcaaag  51420
aacatttact gagaaacagc aagtacaaga gcacaggaag ctcaataaag aagagagaga  51480
tcacatagca ctctgggata ctggagttct tcccagctag accagagagt cctcacggag  51540
cacattgcca attcagtgga gaccccagaa cagccgtaat ttaaaggtac acttagaata  51600
ttactagaat aaagtcagct gcagacaacc ccttgcacag ctggaaagca agtgtccaag  51660
catcaaatcg gtttccaatc aatgaagtgc ctgtgagagg aaatctcaac tctctttaga  51720
agtaaacaac aaagtcgatt gcctcagcta tgcggtatcc gcagagtgag tcctaaattt  51780
aaaatctgac tacatgtaga aaagcgtttc gtgtgaccca tgaccaggaa ataaatcggg  51840
```

```
taatacaaac aggctcagga atgagagaaa tgattagaat tgcgtgaaaa tttgacatat  51900
cagtatgata actgatttca aatatttaaa aaaacaacat gcaagaaagc agatatcata  51960
tcaagagaaa ttaacagtac agaatagcca aattaaatta aagagctagt ataaaaaaag  52020
tatgtcttaa ttgaaaaaaa ttactgtatg gccggctgat caaattagac gtttcagagg  52080
aaaacattac ccaacacaca attttagaga acctacagaa tgagctacac acacacacac  52140
acacacacac acacacacaa actgaaaaca cacccatact cacacacacg cagaaactca  52200
caagttctaa cacacacaga cacgcgcacc cctgaagaaa cagtgaaata taaaattaag  52260
cgagcctcac agacatgtag gaaaatatga aaagatttcc tgcatgtggg aagcaagtca  52320
cagtaaagag caagggagtt tataatagaa acaaatacca gaatcaagga tggctgataa  52380
cttttcaatt acgaagaaca ttaaaaaaaa tcacagaatc gtgaaactca agggatcata  52440
tagggaattt cggaaaaaaa acccaacctg tatgatgtac ttttgtacat cacagttcga  52500
aggtaacaag gcaaagatgt aataagaaga aacctgtcac gagaaactgg aggaaaaaga  52560
gctgtgtctt cctacaagta cactgataca aattgccaat gtgttcacct cagaaacact  52620
ggaagccaga taccagggaa tattgttaaa atgataatca ggaacaaaaa gagatcaacc  52680
gggaatgctg aatccagcaa taaaatgcct tgaaggtcat ccatgtcgga taaatgcata  52740
ttgtgcactg ccccaaagaa agaaaccgga aactgtaaga attggaaatc agcaggctta  52800
tgtaacaaga gaggtgaccc gaaggaatta ggtagaagaa gaattgaaca agaaaggaac  52860
tttctgcagc ccacgtaatg aagaatccag caattggcaa atgtagatag atgtaaatgc  52920
aaaatatttt cttgatcaaa tttctatatc tttgtaaatg agagttgact acttgaaaca  52980
aaatgatagc aagatattta acttcagcat atgtagaggt aagaatttga aatggtagca  53040
taaatcacga agggattaat tcgaagtgta ccgttgtaag tttctttacc tcatgcacga  53100
tggtgtgtca tattaataaa agggtactgt gcgggttcga agggatattg caaatcctag  53160
agcaatcaca aaggtttgaa ctctgaggtt tttggtataa taagaatagt ccatgcattc  53220
aaaagaggga agccaaggaa gaactagaag tctttcaaga gctcaggctc ttatacatcc  53280
agttgctcat tgaaccagct tcctggaatg gagggtctgg ggttgagact aggccacaag  53340
tctagagtct ctagagagac agtgttggaa ccccatggcc cataatacat ttcccatttt  53400
ctcaggcagc cagaggtcat gaatgtgagg atactgggag gttggagcaa cgttcttggg  53460
aggcataagg aagagcgaat gcttcaagat ccccgcagcc caaactactc gcctgctttg  53520
ccccctaatg catttttctc tgctgctccg tagctgtccg acctcttcag atctcttagt  53580
ccaccctgcc gtcttccttt atgccatggg tcccactgtt ctttcaactc atccccettt  53640
ccctcagtcc cggagtagct gcggccagca gagggtagac tgagagcagg agagaaggac  53700
ctgcctagga accccttcta gagatactgc atcctgcctg ggagcaagtt ttccagggca  53760
gctttgagaa gtcttggaga aacaaaccta ctaaacctga cagacagtaa tactatttgc  53820
acaatgcttt tctgtgggaa aggtagagcc ttttcactac gtattgagta catagagtgt  53880
gagggttgac ctggaacggc tatcctcctg gatgacgtgc gttttctgaa gaactacatg  53940
ttcgttgcaa ctcccacatt agaatatgaa gtcctaccga gagagatacg gagactagac  54000
agatacagat gcatttgcat gtgaatacac aatcccacaa tacagacgtc aaaacccata  54060
ccagttattc cagagagatg gattgggcag aaggcagaag gagaatactc tgatcgtttt  54120
tcggccacgt gtgtgtgtta tctcagtgtt tctaagaagc gtttgctact ttagattttt  54180
tatttaaaaa aaatagtaat aatctattaa gtatgagaga tgtgcagaga cgattagtga  54240
```

```
tcgagagcca tttttgctgg tggcaatcat atggtacttt taatgggaat attagaaagg  54300
caccggtaat gaccttgttg cagcacaaag gagagagtgt ggggtgcccc tgcatgttgt  54360
cccacctctt gtgacgtgta tcgttttgga atttccagtg gcttgatcat gaactactgc  54420
aggaatccag atgctgtggc agctccttat tgttatacga gggatcccgg tgtcaggtgg  54480
gagtactgca acctgacgca atgctcagac gcagaaggga ctgccgtcgc gcctccgact  54540
gttaccccgg ttccaagcct agaggctcct tccgaacaag gtaaggagtc tgtggccaga  54600
catctacacg cttcgatgct gggatgaaaa gccatggaaa ttcccactga tgcagccgcc  54660
ttcaatggta aacggatgct cgagtgttgc ctgagttcta ccatgtagga ggaagcctcc  54720
gtgcactctc tgggggagcc agcggagtga tttctggtgc aacgtggttg ggctttgtct  54780
ttaggatggg cacaaaccct ccaggggat cgacttcaaa attcaccttg ttgtaaaacg  54840
ggctacctca gtgtcccagc caaaattttt attgtaacat gctgtcaggt gtgtcactct  54900
ttccaagcca gtaagctttt ccggggattt cttcaagtag ccagcattca gagcaatctt  54960
cagcattgca gattctgaga aatgtggctc tggagcctgt catcctcgag aaacctaaca  55020
gggctgcatt aattccatat ggtcctgggt ctatggagca gtatatgagc tcccaatgct  55080
ctaaggctct tcagtcctag gctttgaagg gagtgatttc tcagtgttct taaacctctt  55140
tctgatggca cttgtacctg tgaggggtct agagagaaag gttagtagac ttctccttta  55200
ctgcaattca ggatgcaggg catgagaaga ttccctccct cctccaaggg aagaaggttt  55260
tggcgtgcac acatccttga gaagcaaagt gtctttgcct tcagtcagat atataggatc  55320
gttttctgcc ccatggcctg gaagccagag gccttggctt tcatgatcaa cgatctaggg  55380
aaacatgcaa aatttccatg tctttcccct cctctgccct cgacagccaa ttaccacctg  55440
catcctgcat tgccaaatgc agtgcccttt gtatgaacat tcagtagagt ttcatagaaa  55500
ggtgctactt cgtgagcgca ctttgcagtg agaaggagtc tgttctgttc tgtttttcta  55560
aggatttcag gtgaaatatt tcctagaact tactacagtt ctagattggt aggaatctgt  55620
aggtttgctg tatgtttttt ggttggtttt ctcccatcca tctgcctaca ggtaagggaa  55680
agataacgtt cataattctc atagactcct ttctggttgt gtcataaatg gcttcacata  55740
tttcgttatt ctcagagata ctcagtttat ttcttgtgtt ttcatttcag caccgactga  55800
gcagaggcct ggggtgcagg agtgctacca cggtaatgga cagagttatc gaggcacata  55860
ctccaccact gtcactggaa gaacctgcca agcttggtca tctatgacac cacactcgca  55920
tagtcggacc ccagaatact acccaaatgc gtatgtcttt gttctttacc ataagagaat  55980
aaagggccaa ctgaagtttc tgtgacaaga gacatgcttc aagctgagtt ctccgaactc  56040
aacttgtgtc agattcagat ggtgtagcaa aatgtctcag gatgatttcc ttggagctaa  56100
gggtctgaga gaagagaaat gttaagctgc ctcaccttcc tcctagtttt gtggagcaga  56160
agggaaatga ggaggcgagg agatcacctt atgaagaaag tcagaatgac gaaccaccaa  56220
acacttagat taccccttgcc caacacccac taagcgtcaa tgaagacttt ccagttggaa  56280
ttccgttatt ctgacttcca attcctgaag ggaagattgt gtttgccttt tctgtctggg  56340
ctcatgagga aagtttatgt gcttacttat ggacaggtga attgatctgt ttctatttct  56400
acctgtattc caatagggag aaaatctctt ggtcctaagt accagtggcc tgaaaggata  56460
gaggttccca gcaagagaag atccaaggaa ggaaggcaga tgagagtcag cacagagagg  56520
gatgctgaaa agtaaaaggg atgggtagat ggatagaagc cctggtctga ccaccccatg  56580
```

gccaatcatt tggccataat caacaaccaa agacatggaa aaatggtttc tacatgtggg 56640
acaacagatg gtagaggacc tagagaattg agagagggcc aatgatgagc tcaactccat 56700
agatgccttg gctttcttcc tggataccct tcctgcactg aatagcaagg agatggagct 56760
caagcagcct gtagccatct agctgagcag aggagaggga ttggagtttg ggatgactct 56820
ggtattttct aggtccgcta caaataagaa ctggtttgtg gaggaaagga gctctacaaa 56880
tacgcataga agtctcctcc agtagttggc ctcacatgac actgcatgtg cacagaaaat 56940
ggttctacag aaagtgtggc aaagaacatt tactgagaaa cagcaactac aagagaacag 57000
caagctcaat taagaagata gagatcacat agcactctgt gttattggag ttcttaccag 57060
ctagatgaga gagtgctcac ggaacacatt gccaattcag tggagacccc agaacagcca 57120
taatttcaaa gtacaattag tatattacta gaataaaggc agctgcagac aaccccttgc 57180
acagctgaaa agcaagtgtc caagcatcaa atgggtttcc aatcaatgaa gtgcctgtga 57240
gaggaaatct caactctctt cagaagtaaa caacaaagtc aattgcctca gctatgcggt 57300
atccccagag tgagtcctaa attaaaaatt tgactacgtg tagaaaagaa tttcgtgtga 57360
tccatgacca gaaaataaat caggcaatac aaacaggctc agaaatgaca tcgataatta 57420
gaattgcatg aaaatttgac atatcagtat gataactgat ttcagatatt taaaaaaagt 57480
gcaacaaagc aggtatcata tcaagacaaa ttaatagtat agaatagcca aatcaaatta 57540
aagaactatt atacaaaaag tatgtcttaa atgaagaaat tactgtatgt ccgcctgaaa 57600
aatttagatg tttcagaaga aaaaattaac caaaaacaat tctgcagaac ctacagaatg 57660
agccacacac acacacattc aaaacacacc catacacaca cacatgcaaa aactcacaag 57720
ttctaacaca cacacaaaca cacacacaca tgcacatccc taaagaaata gggaaatata 57780
aaattaaccg accctcagag acatgcagga aaatataaga agatttcctg catgtgggaa 57840
gcaagtcaca gtaaagagca agggagtttg gagtagatac aaataccgga atcacggatg 57900
gctgataact tttcaattat gaagaacgtt agaaaaatca cagattcatg aaactaaagg 57960
gatcaaatag gaaatttcga gaaaaaaaac tacatgatgc acttctctac atcacagttc 58020
aaaggtaaca aggcaaggat ataagaagaa gaaacatctc acgagaaact ggagaaaaaa 58080
gagctgtgtc ttcctagagt acagtgatac aaattgctaa tgcgttcacc tcagaaacac 58140
tggaagccag ataccaggga atattattaa aatgataatg aggaacaaga agagatcaac 58200
cgagaatgct gaatccagca ataaaatgcc ttgaagatca tccatgttgg ataaatgcat 58260
attgtgcact gcccaaaaca aagaaactgg aaagtgtaag actttggaat cagcaggctt 58320
atgtagcaac agaggtgacc cgaaagaatt aggtataaga agaatagaag aattgcatga 58380
aaatttgaca tatgactaag ataactattt caaatattta aaaaaagatg aatatgtaat 58440
aaaacagata aaatatcaaa agaaagtaac agtattgact agccaaatca aattaaagac 58500
ttagtgtaaa aagctatgtc ttaaaagaaa aaattactgg atggctgcct gatcaattta 58560
gacatttctg aataggaaac taaccaaaaa tcaattctac agaaccaact acacacatat 58620
atacacatac aacacaccca tacacaccca cgcaaaaact cacaagttca cacacacaca 58680
cacacacaca caaccctcaa gaaatagtga aatagaaaac caaccgaacc tcacagacat 58740
gttgcaaaat aggaaaagat ttcctgcata tgggaagcaa gtcacagaaa agagaacggg 58800
agattggaaa cagaaacaaa taccggaatc aaggatggcc gaaaactttt cattgatcaa 58860
gaatattaac aaaatcgcaa aaacacgaaa ttcaatgcat caaataggcg tttcgaaaaa 58920
aagaaaaaat ctggtatgat gcacttttgt acttcacatt ttcacggtaa gaagacaaag 58980

```
atataataac aagaaacttc ttatgagaaa ctggggaaaa acaagctgtt tcttgctaga  59040
agaacagtga tacaaattgc taatgcattc tcgtcaaaaa cactggaagc cagataccgg  59100
gaatgttatt aatgtggtaa acaggaacaa gaagagatca accaagaatg ctaaatccag  59160
caataaaatg ccttgaagat catccatgct gcataaatgt atgttgtgca ctgccccaaa  59220
caaagaaacc ggaaactgta agaatttgga atcagcaggc tgatgtaaca agagaggtga  59280
cccaaaggaa ttaggtagaa gaagaatagt acaagaaggg aactttctgc agcccatgta  59340
atgaagaacc cagcaattgg caaatgtaga tgtaaatgca aaatattttc ttgaccaaat  59400
ttctatatat ttttaaatga gcgttgacta ctggaaacaa aatgatagca atatatttaa  59460
ttttagcata tgtagaggta agaatttgaa caagtagcgt aaatcatgta gggaataatt  59520
agaagtgtac cattgtaagt ttcttacctc atgcacaatg gtatgtaata ttaataaaat  59580
gttactgtgt gggttcaagg agatattgca aatcctagag caatcacaaa gttttgaact  59640
ctgaggtata ttgtataata agaatattcc atgtattcaa aagagagaag ccaaggaaga  59700
aagaaatttg tcacgagttt gggctcttag tacatcctgt agctcattga accagcttcc  59760
tggaatggag ggtctgggat tgacactagg ccacatgtat agagtctcta gagagacagt  59820
gtttcatccc catggcccgt aatacatttc ccattttctc aggcagccac aggtcatgaa  59880
tgtgaggata gagagaggtt ggagcaacgt tcttgggagg cataaggaag agcaaatgct  59940
tcaagatccc cgcagcccaa actcctacct gctttgcccc ctaatgcagt gttcctccgt  60000
agctgtccga cctcttcaga tctcttagtc taccctgcca tcttccttta tgccatgggt  60060
cccactgttc tttcaactca tccccctttc cctcagtgca gagtagctgc ggccagcaga  60120
gggtagactg agagcaggag agaaggtcct gcccaggaac ccattctaga gatgctgcat  60180
tctgcctggg agcaagtttt ccagggcagc tttgagaagt cttgcagaaa caaacctatt  60240
tgacccacat gatatgggaa tgacagaaag taatacaatt tgcacagtgc ttttccatgg  60300
gaaaagtaga gccttttcgc gaggttttga gtacatagag agtgaaggtt gacctggaaa  60360
ggttatcctc ctggatccca tgttttttct gaagaactac ctgttagttg caacttgcac  60420
attagaatat gaagtcctac cgagagagat acggagaact agataaatac agatactttt  60480
gtatgtgaat aaacgattcc acaatacaca catcaaaatc cataccagtt attccagaga  60540
gatggattgg gcagaaggca gaaggagaat actctgatcg ttttttgccc acgtgtatgt  60600
attatctcag tgtttctaag aagcgtttgc tactttagat ttttttttat aataataatc  60660
ttttaagtat gagaaatgtg cagacaggat tagtgattga gagccatttg tgcttgtggc  60720
aatcatatgg tacttttatg ggaatattag aaaggcactg gtaatgacct tgttgcagca  60780
caaaggagag ggtgtggggt gcccctgcat attgtcccac ctcttgtgac gtgtatcgtt  60840
ttggaatttc cagtggcttg atcatgaact actgcaggaa tccagatcct gtggcagccc  60900
cttattgtta tacgagggat cccagtgtca ggtgggagta ctgcaacctg acacaatgct  60960
cagacgcaga agggactgcc gtcgcgcctc caactattac cccgattcca agcctagagg  61020
ctccttctga acaaggtaag gagcctgtgg ccagaaacct acacgtttcg atgctgggat  61080
gaaaagccat ggaaattccc actgatgcag cagcctccaa tggtaaacgg atgctcgagt  61140
gttgactgag ttctgtcatg taggaggaag cctccgtgca ctctctgggg gagccagcgg  61200
attgatttct ggtacaacgt tgggtgggct gtgtctttag aattggcaca aaccctccag  61260
ggtgatcgac ttcacaactc acctcgttga aaaatgggct atctcagtgt cttagccaaa  61320
```

-continued

```
atttttattg taacatgctg tcagatgtgt gactctttcc aagccagtaa gcttttcctg  61380
ggacttcttc aattagccag cattcagtgc aatcttcagc attgcagatt cagagaaatg  61440
tggctctgga gcctgtcacc cttgagaaac agggctaaca gggttgcatt aattccaaat  61500
caccctggtt ctatggagca gtacatgaac tcccaatgat ctatgtttca ggacttcctc  61560
agtcataggt gggctctgca gccctaggtt tttaagtgag tgactgcccc gtgttctggt  61620
ggcagttgta cctgtgagcg gtctggatag aaagagtcgg agacttctgt attattgcaa  61680
ctcaggatgt gggtcatgag aggatttcat ctctcctgca ggggagtaag ctgttcgcct  61740
ccacccatcc ctgataactg aagtgtcttt gtctgcagtc ctagacgaag gactgttgtc  61800
tctcccatgg cccagaagct gaagaccttg ccttttgtta tgaaacgttc attgttttca  61860
tgtctgtccg tttctctgcc cctaacaccc aatcaccatg tatggcctgt acccccaaat  61920
gcatcgtgct ttgctgtttg ctgccccata gtcctcatga acattcagta gaaattccca  61980
taaatgtgct tgcacgtgag cacagtttcc attgagaagc cctctcattt gtcctttttt  62040
tctaagcttt tatgtgaaat atttctaaga acttactaca gttctaaagt gttaggaatt  62100
tgtttctttg gtgtttttgt ttgttggttg gttgttgctt ttctcaagtc catctgccta  62160
caaataaaga aacaagaatg ttacttgtca tattctcctg aggtcataat tctcagagac  62220
tttttctgg tttgtgccat aagtggcttc acatgtttgt ctcttcttgg aaacactcag  62280
tttgatttct tttcttttca tttcagcacc aactgagcaa aggcctgggg tgcaggagtg  62340
ctaccacgga aatggacaga gttatcaagg cacatacttc attactgtca caggaagaac  62400
ctgccaagct tggtcatcta tgacaccaca ctcgcatagt cggaccccag catactaccc  62460
aaatgcgtat gtctattttc tttaccataa gtgaaggaag ggtcagtgga aatttctgtt  62520
agtagagtca tgcttcaagc tgagtgttca ggactcaagt tgtctcagat gaacagtgca  62580
tagcaaaatg tctcaggaac attgtctttg agcaaagagt ctaagagaag acaaatgtta  62640
atctggctct ccttcctcct agtttaatgg agcagaaagg tatctggagg caaggatatc  62700
acattaagaa acaagtcaag atgacaaatg atgaaactct tagagtaccc ttccacaaca  62760
cccactaagg ttcaatgcag ccttttctcc ttggaattct attaaactaa actccaattc  62820
ctgaagtgaa ggttctgttg gggttttctg ttttggctta caaggaaagt atatatgtat  62880
atctatggag aggcaaatct atctctttct atatctacgt ctattccaat atgtagaaac  62940
acagtcggtt ctgaccacca gtggtctgaa gggatactgg ttgttagaga ataaaaatgg  63000
caggaaggca gatgagagtc agcaaagaga gagatcctgt aaagtaaaag ggtggataga  63060
tggacagaag cccaggtctg accagcccat ggccaggctt taggccataa gtgacaccaa  63120
agacatggaa aaatggtttc tacatgttgg acaacagaca gtagtggacc aaaagaatag  63180
tgacaggggg aacaatgaga tcaactccat agataccttg gctttcttcc tggaggccct  63240
tcttgcactg aagagcaagg tgatggagcc cagatggact gtagccatct tcctgaatgc  63300
aggagagaga ttggaatttg ggactactgt ggtagctagg attttatagg cctgctgaga  63360
atgagaatgg atttgtggat gaaaggagct ccaggggcac gcatagtagt ctcctcgaat  63420
ctttggctaa acatgacgtt gcatgtgccc agaaaaaggt tccacaagaa agtagagaaa  63480
agaatatatc ctgaggaata gcaactgcga ttgaacagtg agctcaataa agaggacaga  63540
gccctcatag cattctggga tactggagtt ctgaccagct ggaggagaga cctcactgaa  63600
cctcttggga atacagtaga gactccagaa aagtcatact ttaggagtag aattagtaaa  63660
tttctagaaa aaaaggcagc tctagacaaa ccctggcaaa actgaaaagc aagtctccaa  63720
```

gcattaaaat catttccaag tcaattaact gcctgggaga ggaaaaccct ctttagaggt 63780
aaacaacaaa gtcaagtggc tcagctatgt ggtgttcaca gtgtgagttc taaatttaaa 63840
acttgactac acatagagaa gcttttagta tgaaccatga ccaggtgaaa aatcagtcaa 63900
tacaaataga cctagaaatg acagaaatga ttagaatggc aaaaaatttg acatatcaat 63960
atgtcaactg agttttaggt tttaagaaaa catgaatacg gaatgaagca gataccatat 64020
caagagacag taacagtata gaagagccaa attaaattaa agaactagta taagaaggta 64080
tgtcttaaat gaaaaaatta ctggatgtat tcccaatgga gtgagatgtt tcagaagtaa 64140
aaactaactg aaaaacaatt ttataccacc tacagaacca gctacacata cacaaatgac 64200
acacacatat acacacatac tcacacatgc acaggcttag aaacatgcac gcacacacac 64260
acacacacac acacacacct ccacaaatac taaaaaatga aatccactga tcctcacaga 64320
caggcgggaa aatataaaaa gatttcctgc atgtgggtag gaagtcacag aaggagagga 64380
aggagagatt gctacaggaa caaatactgg aagcaaggat agctaaaaac ttttcaaata 64440
agaagaatat taaaaaccac agattcaaga agctgaatga atcagacagg gaatttccaa 64500
aaaaaaaaaa aaaaaaactg tatgattcac ttttgtacat caccgttcaa cagtcagaag 64560
gcaaagatat aataacaaga aacatctcat gagaaactgg aggaaaaaga gctgtgtctt 64620
gctagaagaa cagtgataca aattgctaat gcattctcat cagaaacact ggaacccagt 64680
taacagggga tatcattaaa atgataaact agaaaaaaaa gagatcaaat gagaatgcta 64740
catccagcaa taaaatgcct tgaagatcat ccatgttgga taaatgcata ttgtgcactg 64800
ccccaaataa ataaaccaaa aactaataat ttggaatcag caggcttgtg taacaagaga 64860
tgttgcccaa agaaaattag ctagaagaag aatagttcaa gaggagaact ttctgcagcc 64920
cacgtaatga agaacccagc aaatggcaaa tgtagatgta aatgcaaaat attttcttga 64980
tcaaatttct atatcttttt aaatgagagt tgactacttg aagcaaaatg atagcaatat 65040
atttaacttt agcatatgta gaggtaaaaa tttgaacata tagactaaat catgtgggga 65100
ataattggaa gtgtaccatt gtaagtttct taccttatcc acgatggtat gtaatattaa 65160
tgaaaggttg aatttgtggg tccaaaggga tattgtaaat cctaaagcaa tcataaaatt 65220
ttgaattctg agggatatta tataataaga attttccatg tatccaaaag agggaagcca 65280
aggaagaaaa agaagtcttt caagtactca agctctgagc acatccagtt gctcattgaa 65340
ccagcttcct ggaatggagg gtctgggctt gagactaggt cacatgtgta gagtctctag 65400
agagacagtg ttggatcccc atggcccata atacatttcc cgttttccca ggcagccaca 65460
ggtcacgaat gggaggattc tgagaggttg gagcaatgtt cttaggaggc ataaggagga 65520
gtgaatgctc tgagatttcc ccagcctgag gtcctccata gctgcccgac ctcttcagac 65580
ctcatagtct gcccagctgt ctccctttat gccatgagtg ccactgttct ttcaactcat 65640
cccccattcc ctcagtcccg gaattgctgt ggccagcaga ggatggactg agagcaggag 65700
aggaagtcct gaccaggaac ccatcctaga gatactgcat cctgcctgaa agctaggttt 65760
ccagggcagc tttgagaagt cttgcagaaa gaaacccact tgacccacct gatacggtat 65820
cgacagacag gaatactttt tgtgcaatgg ttttacatgc tgaacataga gccttttggc 65880
tacattttga gtacattgaa tgagactgct ggcctgggaa ggatatcatg ctggatgcca 65940
tttttttctc tggagaacta tgtgttagtt ccaactcgca cattactata tgaagtccta 66000
cacagagaga tacggagagc tagacagata gagatacttt tgtatgtgca taaccaattc 66060
cacaatacac acgtcaaaat ccataccagt tattccagag agatggattg ggcagaaggc 66120
agaaggagga tattctgatc cctttttggc cacatgtatg tataatctca gtgtttctag 66180
gaagtgtgtg ctgcattaga tttttttct ttaaaaaaag tgataatata ttaagtatga 66240
gaaatgtgca gagaggatta gagattgaga gccatttgtc attgtggcaa ttgtatggta 66300
tctcttttgg gaatatttca aaggcaccag taatgacctt gttgtagcaa aatatacagt 66360
gttcctgcat atgtacccat tttttgtgat gtgtattctt ttggaatttc cagtggcttg 66420
atcaagaact actgccgaaa tccagatcct gtggcagccc cttggtgtta tacaacagat 66480
cccagtgtca ggtgggagta ctgcaacctg acacgatgct cagatgcaga atggactgcc 66540
ttcgtccctc cgaatgttat tctggctcca agcctagagg cttttttga acaaggtaag 66600
aagttgtgcc agacatttac ctgcttggat gctgggatga aaagccatgg ataccccac 66660
tgacgcacaa cccttcagtg ctacactggt tctcgtgtgt tggttctggg tctgccatgt 66720
gggaggaagc cttagcgcac tctctggggg agccagaggt gtgatttttg gtgcaacctg 66780
tgcgagctgt gtctttagga tgggcggaaa ccattctggg tgctcgactt caccactccc 66840
ctcattgtaa aaggggctat ctcattgtcc tagacaaaat tcttattgta atatgctgtc 66900
agatgtgtgt gtctttccaa gccagtaaac ttttccaggg atttcttcaa gtagacagca 66960
ttcagtgcaa tcttcagcat tgcagattcc gagaaatgtg gctctagatc ctgttatcct 67020
tgagaaacct aactgggttg cattaattcc atatctccct gggtctgtgg agtagtacat 67080
gagctcccga agctctatct ctcaggtctt tttcagtccg aggcaggttg tgcagttctt 67140
agctttgaag ggagtgattt tttcgtgtgc ttttgcctct ttctgatgga acttgtacct 67200
gcggggggtc tggagaaaaa gagtagtaga cttttgcttt attgcaatgc attatgctgg 67260
gcacgagagg attccctatc ttattgtagg tgataagctt ttggcctcca ctcatccctg 67320
agaagtgaag tgttgttgcc tacagtttta gctgcaggac tgttgtctgc cccatcacca 67380
ggagtttaat gctttctttt ttgagcaatc atctagggac acatgcaagg tttttatatg 67440
tccttgcctc ctccccaaaa aaccatttta atgcttggag acttgctttt cagctttgcc 67500
aaatgcatca ccctttcttc tatgctgttc catgtcgtca tgaacactct gtagagattc 67560
ctagaaatga gcttccatgt tagtggagtt tccgatgaga agcaatctga tatttctttt 67620
ccactaagtt ttacatgaaa tatttctaag aacttactac agttctagaa tggtaggcat 67680
ctcttacttt cgtgtttgtt tgtgtgtttt ctcatgtcca tttgcctatt aataaagaat 67740
agagaatggt tgtaaatctc agtgactctt ttttggttta tgtcataaat ggcttcctgt 67800
atttttctgt tctaggaaat aataagcttg atgtcttctg ttttaatttc agcactgact 67860
gaggaaaccc ccggggtaca ggactgctac taccattatg gacagagtta ccgaggcaca 67920
tactccacca ctgtcacagg aagaacttgc caagcttggt catctatgac accacaccag 67980
catagtcgga ccccagaaaa ctacccaaat gcgtacgtct ttgttcttta ccataagcga 68040
aggaagggcc aatggaagtt tctgttagaa gagtcatgct tcaaggtgac tgctcaggac 68100
tcaacttggc tcagatgcag aggaacattt cctgtgagca aaagttctta gagaagactt 68160
tgttttttg agacagagtc ttgctttgtt gcccaggctg gagtgcagtg gcatgatctc 68220
ggctcactgc aagctccgcc tcccgggttc acaccattct cctgcttcag cctctctagc 68280
agctgggact acaggcaccc accaccacac ccggctaatt ttttgtattt ttagtagaga 68340
cagggtttca ctgttctagc caggatggtc ttggtctcct gacctcgtga tccgcctgcc 68400
tcagcctccc aaagtgctgg gattacaggc gtgagccacc gtgcctggct gagaagacat 68460

```
tttttaagct ggctctcctt cctcctagtt ttatggaagc agaaggatat atggagttga  68520
gaagatctta ttaataaaac agccgggatg acaaatgacc aaagagttag agtatccttc  68580
tacaacatcg gctgagggtt aatacaacct tttcaccttg gaattctatc attctaagct  68640
ctagtccctg aagtgaatgt tgtgttggcc ttttgcatct tgggtcacag ggaattgata  68700
cttgcacatc tatggagagg caaatctttt tctatctact tctttttcaa tgggtacaaa  68760
cacacttggt cctgagcacc agtggtctga agagatacgg tctgcccaga ggagaagaac  68820
aaaggcagga aagcagatga gagtcagcaa aggggcgatg ctgaaaagta aaaggggcgg  68880
gtagatggac agaagccatg atctggccat tctatggcca gtctttcggc cataagtgac  68940
taccaaagac acggcaaaac ggtttccaca tgttgaacaa cagatgctag aggaccaaga  69000
gtattgcaag agggagaaaa tgagatcaac ccatcaatgc cttggctttc ttcaaggaga  69060
cccttcctgc actgaagagc aaggagatgg agcccaagct gactgtagcc atgttgctga  69120
acagaggaga gtgattggac tttgggatta ctcaggtagt taggattttc tagccatgct  69180
aagagtaaga atggacttgt ggaggatagg agctccaggc atagaagtct cctcaagtgt  69240
tagtctaaac ataaagcagc acttgcatag aagattttcc acaagaaaat atggcaaaaa  69300
aacaccatat attgaggaac aacaactaca agggaacagt gagcttaata aaggtgacag  69360
agctcacata gtgctctgga atattggagt tttgaccagc tagagagaag agacctcatt  69420
gaaaatcttg ggcattcagt agagacctca gaaaagtcag actttatgag tagactttgt  69480
atattcctag aataaaggca gctccagaaa aaacctagca aagctgaaaa gcaaatctcc  69540
aagcattaaa atggtgtcct agtcaattaa ctgccttcta gaagaaaact caacactctt  69600
tacaggtgaa caacaaagtt aagttgctga gctatgcaat atccacagtg tgagtcctaa  69660
atttataact ttactacaca taaaaaagca tttagtgtga accataacca ggaaaataat  69720
cagtcaataa aaatagaacc aggaatgata gaaatgattt aaatggcatg agaatttgac  69780
atattagtat cataactgca ttgctggatt taagaaaaca taaacatgga acgtaacaga  69840
tatcatatca agggaaagta aaaggataaa agagtcaaat caaattaaag gactattaaa  69900
aggtatatct taaatgaaaa attcactgga tggtctccca atcaggttag ttgtttccag  69960
ggaaaaaatt aactgaaaaa taattcaata gaatctacag aaatagctgc acatatatac  70020
acacaatggc acacgtgcac acacccacac ccacacaggt gtgaatccta gagccacacg  70080
agcattgaaa catagagaag taaaaattgt tcattgagga atatgtagca atgctcaatg  70140
tgttttaccc taataagagc ttttgtgatg tatgattgaa aaactgacac aactgaagag  70200
agaaatagat aagcccacac tctgagttag agatttcctt gattctctca ctatggttat  70260
aaatctttcc caaacacaac aggctagaac aaatatgcag aaaattagac atagtatctt  70320
tgttctcaat aaaaacgtcg acctatttaa cattataccg aactaccgag tacacattaa  70380
agtgtgcatg gagcattcac tgaggtgtac tctacacatg accttccagc aagtctccat  70440
agatttaaaa gaattaaagt catacagagt gtgtcacttt attctcccag aataaagtga  70500
gatatgaata atgagaagtt tgccagcttc tcaaatattt gggagtcata cggtgcattt  70560
caaaatactc tttgggacaa agaaaacatc actaaggaat ttagaaaagt tttgaactga  70620
gtaagaatat aacacaattt atccaaactt aggagatgca gtgaatgtct ttaggctttt  70680
acataatttt agatgctctt agggaaaaac agaagcatgt aataatcaag atttcaaact  70740
gcaattctca aagtgtagtc tagagaaacc tgaggacctt tgagtacctt cagagacagt  70800
```

-continued

```
ccatgaggtt aaaggacttt gctacgtgaa aagtaagatg ctattggccc tttttacttt  70860
cattttccaa caagagaaga ggggagtttt ccagcagtta cataatatgt aatggcatca  70920
tgtctctgat ggctaagaaa atgggcaatt gttgactttg tgtgttaaaa aaattctcag  70980
tgttggtttc ttatactata aatattcatc ttgtgttttg aaaaagaaaa gctctttgga  71040
atcccctatg aacaaagact ttgacagttg ttgatctaag accacagctt aaatatctac  71100
acaagaaaaa aaaaaaaagc aaataagagc caaggaaagc agatggaagg aagtagtcca  71160
aaccagtgac attcagtgaa caagaaaaga gaccaacaag ggagtaaact cttgaaacag  71220
aaagttgatt ctttgaaaag atccatatga ttgaacacag tctggctaaa caaatgacag  71280
accaatgagg gtgcacaacc atcaccatct ggagtaacag aggagaggtg ccattactat  71340
agcatcttcc agttctgaaa gctgaaaaga agattttgag aacaattgta tgtgaataaa  71400
ttcaggaatg ttaatcatgt gggccaattc ctgaggaaga caacaaatca gcaaaccaga  71460
tgctgaatag ttagtgtagt cctgtagaga gacatacaga gaggctgaca gagaaatatt  71520
tgtatgtgca taaaacaatc tacaagacac acttcaaaat caatctcagt taatctggag  71580
gaacatattt cacagaaggt ggaaggaggg tattctgatc ctcttgtaca ttgtacaaca  71640
ttgtacaatg tacagagtat aattgtacaa gtacaattga agttgtacaa gtacaagtgc  71700
aacttgcaca atgtacagag taaacattga tgtttactct caattttctt atggagcaca  71760
gatgactttg gatgtgttac aatatgaatg ataatttgtc tttgagatgt tcgcagttgt  71820
ttagaagttg aggaccattt gtgcatatta tgggaccttt agtgaaaata tttcaaagtc  71880
tctttttaca ctttgttaca gcaaaatgta gagggcgcta agtgcccttg aatcttctcc  71940
catctctggt gacctgtgtt gttttgaaat ttgcagtggc ctgaccagga actactgcag  72000
gaatccagat gctgagattc gcccttggtg ttacaccatg gatcccagtg tcaggtggga  72060
gtactgcaac ctgacacaat gcctggtgac agaatcaagt gtccttgcaa ctctcacggt  72120
ggtcccagat ccaagcacag aggcttcttc tgaagaaggt aggaagtcta tggccagaca  72180
accacaccct aggacgttgg gatgaaaaga gttgcaaaat cttagtgata tagaagcctt  72240
ccatgctcac acaattccaa gtagaatgtg gactcagggt cagccactgg gaaggaacac  72300
tcagcgcctt ctctgggaga accagagctg tgatgtttgg taccctgtga aagggtggta  72360
tctataggaa gggtgcagac cctctagggc actggactta ccactcccct ggttattcaa  72420
aggatcattt tagtgtctta gccagaagaa tattctaaca ttttgccaaa tttgtgaaga  72480
tttaccaagc tcatgataag cctttcatgg tatttcttca agtagtcagt gttcattgca  72540
tctttggctt tgcggtttcg gaggaatgcg gtttttgagt ctgtcatcct tgagaaacct  72600
aatatgactt ttcttagttc catatacttc tgggtccagg tagcagtaca tagccaacaa  72660
atgctccatc gttctggcct atctccatct taagccagtc ctgcacaact aggctttgat  72720
gggagggatc tctcagtgtt cttgcccctc cttctcatgg aacatatatc tgtgttggtc  72780
tctgagaaga agagtagtgg atatctactt tgttgcaatg cagaatcctg ggccaaagat  72840
accagccatc cctccaaggg aataaaattt tggccagtag ccctctctga gagacaattt  72900
gtctttgcct acgagtccta gatgcaggac cgcttcctgc cccatcttca agaagctgaa  72960
ggctttggct ttggaggatc agcagtctag ggaaatgtgt gacggtttca tgtctgtccc  73020
cactgacagt caatcaccac ctacaacctg cacagcctga tgcatagcag tctagtttcc  73080
tgccttattc tcaggaacac ccagaagatg tctatattaa agagcatgca catgagtgca  73140
attttgactg ataggcactc tgatctttcc tttggtgcct gtgttttaaa ggaaatcttt  73200
```

ctaagaactc gttaaagttc tagaatgcta tgaatctttg ggttttatta ttggtatgtc 73260
catctgcctg ctagtacaga acagagcatg gtagtctttc tcagagacaa tgatcctgtt 73320
tcagtcacag atttcttctg atgcttctgt gttctagaaa ttactcagct tgatttctcc 73380
tctttgaatt tcagcaccaa cggagcaaag ccccggggtc caggattgct accatggtga 73440
tggacagagt tatcgaggct cattctctac cactgtcaca ggaaggacat gtcagtcttg 73500
gtcctctatg acaccacact ggcatcagag gacaacagaa tattatccaa atgggtacaa 73560
ccttgagttt tcttcaaaga cagacagcag ccccccttaca tttctcttgg aagggccatg 73620
cttccaacta acttcttatg acaaatttat ctcagatctg gaatgttggg tagaatgtct 73680
caggcttctt tcttcaggca cagtgtctga aaggagagaa atgtcaggcc agctctcttt 73740
tctcatagtt gacagaagca ggaggatatt tgaaggtggt gagttctcat gaatagaaag 73800
ctcaggacac atggccacgt gcttagaaat agcaccattc cacaatgccc actaaagacc 73860
aatgcaatag ttcaaccagg gatttctgtc attctaatct ccaagtcctg aagtgaaggt 73920
tgtattagcc atgttcatct tgggcaacaa ataaaggata tctatgttga catccagatc 73980
ttccaatcac tttctcctct aacctgtacc tgggttctga gaacaaggta tctgaagagc 74040
tatgtgttgc cagcacatga ggggcaaaag taggaaggca gctgagagtc aggaagtata 74100
aagattctga agagttacac atgcaggaag atggacagaa acccagttca gaccacgtca 74160
gcgtttctgc catgaaggac tatcaaatac ataggaaaag tgttttcata ggttggacaa 74220
cagacatgac aggcctgaga aaattcagaa agggaatcaa aggagatcaa ccttatcatg 74280
tccctggcat ccttccttga gacccttgaa gggcaagcag atggagccca gctgaccaca 74340
gcagtcttgc ttaactgagg agagagactg gagtttgtga tgcctcaggc atctgacgta 74400
ttctaggctg gctaagaatg agaggggatt tgtggaggaa aggagctcca agaatacaca 74460
ccgaagtctt ctcaaggctt tggctaaata caaagctgcg tatgcacaag gagagttttc 74520
acaaagaaag aacaataaag aaaagctact ggggaaagaa caactgcaag ggaacagtga 74580
gctcaatgga gatgctagag ctcacatagc actgggggat atttgagttc tgaccactca 74640
gaggagagac acctcactga acatcttggg cattcagtag aggtcaaaga aagccataat 74700
ttgggagtag gatcttcgga ttcctagaaa taaggtgact ccagaaacac tccagcaacc 74760
cttcttccaa gccagtctaa aaggatccaa atgatttcca agtaaattaa ctgccttcca 74820
gaaaaaagta aactcaaccc tccttagagg taaggaacga atacaagttt ctcagttata 74880
tgacatcccc agagtgcaac ttgcatttaa aaatttacta gacacaaaag aagttttcac 74940
tgtgatccat aactgggaga aaaatcactc aacacaaata ggcccagaaa taatagaaat 75000
tatggcattg gcaagaacat ttaaaatgca cctctgagaa ctgtgtttca ggaaaatgtc 75060
agcaaaagct gaccatgaga gaaatgaatg cataatatca gaaaagaaaa gaattgaaga 75120
gccaaatgga aatttaaaaa ctgagaaaag ttatatctgt aatgaggaat tcactggatg 75180
gccttataac cagtttagat attatggtag gaaaaggtga acgagaaaat gattcaatta 75240
aagctagaca aaccacaaga cagacagaca gacacaaata cacatacaca caatgactga 75300
accaattaat caacagagcc tcaaggacat ctaggaaaac atccacacat ttaatatatg 75360
tgttaggcaa gtcacagaaa gagaggaaaa agataatgtg acagaagtta tacttgaagc 75420
catgacggct gacaaatttc caaacataca gaaaatgaga aattcatagt catgaagctc 75480
aatgactcag gtatagattt ttaaagagca aaactctgat ttactggggt acatcatagt 75540
taaattgtct gatttcaaag ctaagaagaa aaaaaggggg ttcctatgaa caaacatttt 75600
gacagttgat ctaagaccac agcttaaata tctaggcaag gaaaagcaaa taagacacaa 75660
ggaaagggga tggatggaaa tagtccaaac caatgacatt cagtgaacaa gaaaatagac 75720
caacaaagga gtaaatccat gaaacagaaa gttggttctt tgaaaagatt catgtgattg 75780
accacagtct ggctgaacag atgacagacc aaggagggag tacaaccatc accatttgaa 75840
gtaacagggg agaggagcca ttgctatacc atactccagg tctgaaagct gacaagaaga 75900
tatcaagaaa aactgtatgt gaataaattc atgaatgtag atcatgtgga tcaattcctt 75960
aggtaaacaa caaatcagca aaccagatac tgaatagatt gggtactcct atagaaagac 76020
atacagatag ccagacagag aaacatttgt acgtgcataa aacaatctac aagactcact 76080
tcaaaatctc tcagttaatc caaagtaaca tatttggcag aaggtggaag gagggtattc 76140
tgatcctttc ttgtacacat tgatgttttc tctcggtttt cttatggagt atagacgagt 76200
ttggatgtgt tacaataaga atgataatct gtctttgaaa tgttcacagt tgtttagaag 76260
ttgaggacga tttgtgattg ttacaggacc tttagtgaga atatttcaaa gtcacttttt 76320
accactttgt tacaacaaaa tgtagaggat gtctggtgcc cttgtatctt ctcccatctc 76380
tggtgaactg tattgttttg taatttgcag tggcctgacc aggaactact gcaggaatcc 76440
agatgctgag attagtcctt ggtgttatac catggatccc aatgtcagat gggagtactg 76500
caacctgaca caatgtccag tgacagaatc aagtgtcctt gcgacgtcca cggctgtttc 76560
tgaacaaggt aagaagtctc tggccagaca accacaccct tggacgttgg gataaaaaga 76620
gttgcaaaat cttagtgata cagaagcctt ccatgctgca cgggaatctg aatgtggact 76680
cagggtcagc caatgggaag gaagcctcag cgccttctct gggggaacca gggctgagat 76740
ttttggcacc ccgtgacagg gtggtgtctt taggaagcgt gcagaccttc tagggcactg 76800
gatttaccac tcccctggtt attcaataga ttatttcagt gtcctagtga aaatggatat 76860
tctaacatcc tgccaaattt gtgatgattt accaagctca tcatgagcct ttcctggtat 76920
ttcttcaagt agacagtact cattgcaaac ttcagcttta cagtttcaga ggaatgtggt 76980
ttttgagtct gtcatccttg agaaacctga tatgacttta cttagttcca tatcctcctg 77040
ggtctaggta acagtacata gccagcaaat gctctatctc cctgtctacc ttaatcttag 77100
gcaggtgctg cacacctagg ctttgatgga agggatttct tagtgttctt gcccctcctt 77160
ctcatggaac acgtatctgt gttgctgttt gtgaagaaga gtagtggatg tctactttgt 77220
tgcaatgcag gatcctgggc ccaagatttc ccgccgtccc tccaagggaa taaaattttg 77280
gccagtaccc ctctctgaga gacaatgtgt ctttgcctgg aagtcctaga tggaggacca 77340
cttcctgccc catcttccag aaacttaagg ctttggcttt ggaggatcag tgctctggag 77400
aaatgtgtga cggtttcatg tctgccccca ctgacaacca ccacctacag cctgcaccgc 77460
ctgatgcatg gcactctggt ctcctgcctt gttctcagga acacccaaaa gagatctttg 77520
ccaaagaaca ggcacatgag tgcaattttg actgataggc actctgatct gtcctttggt 77580
gcccaggttt taaagaaaat ctttctaaaa actcattgaa gttccagaat gctatgaatc 77640
tttgagcttt gttattggca tgtccatctg cctactaatg tagaacagag catggtcgtc 77700
attttcagag atgatgtcct gtttctatca tggatttttt ttctcatgct tctgtgttct 77760
ggaaattact cagtttgttt tctcctcttt gaatttcagc accaacggag caaagcccca 77820
cagtccagga ctgctaccat ggtgatggac agagttatcg aggctcattc tccaccactg 77880
ttacaggaag gacatgtcag tcttggtcct ctatgacacc acactggcat cagagaacca 77940

```
cagaatacta cccaaatggg tatgtctttg agttttctcc caagagaaac agccacccac  78000
ttaaatttct cctggaagag ccatgcttcc agctaacttc ttatgaccca atttctctca  78060
gacccagaat gttggacaga atgtctcagg cttcttgctt tgggcacagg gtctgagagg  78120
agagaaatgt caggccagct ctcttttctc atagttgata gaagtaggag gatacttgga  78180
ggtggtgagg tctcatgaat agaaagctca gaagaacata tgaccatgtg cttagaaata  78240
gcaccattcc acaatgccca ctaaagacca gtgaaatagt tcaaccaggg aattctgtca  78300
ttctaatctc caagccctgg agtgaaggtt gtgtttgcca tgtttgtctt gggtaacaag  78360
tgaaggatat ctatattgac ttcgagatct tccgatcact ttctcctcta acctgtataa  78420
acacattggg ttctgagaac aaggtgtctg aaaagctatg tgttgccagc ccatgagggg  78480
caaaaggagg aaggcagctg agagtcagga agtatagaga tgctgaagag ttacacattc  78540
aggaagatgg acagaaaccc atgtctggct atgccagcct ttctgccatg aaggactatc  78600
aaatacatga gaaaacagtt ttcacaggtt ggacaacaga tatggtaggc ttgagagaac  78660
tgagaaaggg aatcaaagga gatcaacttc atcattaacc tgtcttcctt cctggacaca  78720
gtgttggatt gaaggacaag cagatggagc ccagctgacc acagcagtct tgcttaactg  78780
aggagagaga ctggagtctg cgatgcctca ggcagctgat gtgttctagg ctggctaaga  78840
atgagaaggg atttgtggaa gaaaggagct ccaggaatac acacagaagt ctcctcaagg  78900
ctttggctaa atacaaagct gcgtatgcac agggagagtt ttcataaaga aagaacaaca  78960
aagaaaagct acttgggaaa gaacaactgc aggggaacag taagctcaat ggagatgcca  79020
gagctcacat agcactgggg gatatttgaa ttctgaccac tcagaggaga aacacctcac  79080
tacattttgg gcattcagta gagaccaaag aaagctgtat tttgggattg ggatcatctt  79140
attcctagaa tcaaggtgac tccagaaaaa ctccaacaac ccttcttcca agccagtcta  79200
aaaggatcca aatgatctcc aagtaaatta actgcattcc acaagaaaaa aaaaactcaa  79260
ccccccttag aggcaaggga caaatacaag ttgctcagtt atatggcatt cctattgcgt  79320
tacttctatt taaaaattta atagagacac aagaagcttt cactgtgata cataactggg  79380
agaaaaaatc actcaacaca aacaggccca gaaattatag aattgatgac attggtgaga  79440
acatttaaaa tgcacctctg agaactgtgt ttcaggaaaa tgtcagcaaa agctgaccat  79500
gagagaaaca aaagcagaat agcaagagaa aagaaaagaa ccggagagcc aaatgaaaat  79560
taaagaactg agaaaaggta catctctaat gaagaactca ctggatggcc ttatcatcac  79620
tttagacatt acggtaggaa aggtgaccta gaaaataatt caataggagc tacacaaatc  79680
acaggacaga cagacagacc aacagacaga aacacacaca cacacacaca cacacacaca  79740
cacacacaca cacacacaca aagactgaac ctattaatca acagagcctc aagggcatct  79800
aggaaaaatc cacacattta atatatgtgt taggcaagtc acagaaggag aagaaaaaga  79860
tatcatgaca gacattatac ttgaagcgat gatggctcgc aacacgccaa atatacagaa  79920
aacaagaaac tcatagtcaa gaagctaaat gactcaggta tagaatttta aagagcaaaa  79980
ctctatgatt tactgggata tatcatagtt aagttgcctc aattcaaagc taaaaagaaa  80040
aaaagggggt tcctatgaac aacagctttg acagctgttg atctaagacc acagcttaaa  80100
tatctaggca aggaaaagca aataaggcac aaggaaagag gatggaagga aatagtccaa  80160
accaatgaca ttcagtggaa aagaaaatag accaacaaag gagtaaatcc atgaaacaga  80220
aagttaggtt ctttgaaaag tctatatgat tggccaaagt ctggctaaac agatgacaga  80280
```

ccaaggaggg agcatatcca tcaccatcat gagtaacagg agagagatgc cattgctata 80340
gcatcctcca ggtgtgaaag ctgagaagta gatattgaga tcaactgtat gtaaataaat 80400
tcatgaatgt agatcatgtg gatggattgc ttaggtaaat aacaaatcag caaatcaaac 80460
actgaataga tcatgcagtt ttatagagac ttacagacag cctgacagat aaacatttgt 80520
atgtacgtga aacaatctcc aagacacact tcaaaatccc tctcggttaa tccaaaggaa 80580
tgtatttggc agaaggtaga aggagggtat tctgatcctt tctggtacac attgatgttt 80640
tctctcagtt ttcttataaa gcatagatta ctttgaatgt gttacaataa gaatcataag 80700
ctgtctttga aatgttgaca gttgtttaga agttgaggac catttgtgag tgttatggga 80760
ctttagtgag aatatttcaa atttgcttgt ttacactttg ttacaagaaa acatagaggg 80820
tgccaggtgg tgctgtatct tctccaatct ctggtgacct gtattgtttt ggaatttgca 80880
gtggcctgac caggaactac tgcaggaatc cagatgctga gattcgccct tggtgttata 80940
ccatggatcc cagtgtcaga tgggagtact gcaacctgac gcaatgtcca gtgatggaat 81000
caactctcct cacaactccc acggtggtcc cagttccaag cacagagctt ccttctgaag 81060
aaggtaagaa gcctgcagtc agacaaccat accctcggac attgggataa aaagatttgc 81120
aaaatctttg tgatgcagaa aacttccatg ctgcacagga agtcgaaggt gaagtcatgg 81180
acagccaatg ggaaggaagc ttcagtgcct tctctggggg gaccagagct gggatgttga 81240
gtgccttgtg agggatggtg tctttaaaag gggcacagac cctctaggac actggattta 81300
tcacttccct gttatcaaac gaatcatatt agtgtcctag ccaagatgga tattctaaca 81360
tcctgccaaa cttgtgaaga tataccaagc tcctaagcct gtccagccct ttcttcaagt 81420
aggcagtgtt tattgcagtc ttcagcttta ccattttgaa ggaatgccat ttttgaggct 81480
gttgttcttg agaaacctaa catgtcttca ttagatccgt attgtcctga gactttgaag 81540
cagtacatag ccaccaaatt gtttatctcc ccagcctacc ttcatcttgg gcatgccttc 81600
cacacctagg atttgaggga agggatttct cagtgttctc atccctgctt ctcatggaac 81660
atttatctcc gttgtttttt gagaagaaga gtagtggatg tcagctttct tgtaatgagg 81720
gatcctgggc ccaagattcc ctgtctcccc tcctaggcta taaaattttg gcctgtactc 81780
cttctccctg agaggcaatg tgtctttacc tacaagtcct agatgcaaga tccttttctg 81840
ccccacaccc cagaatctga aggcttttgc tttggaggag cagtggtcta gtgtgcaagg 81900
gtttcatgta tacccccac taacagccaa tcaccaccta tagcctgaac agcttgatgc 81960
atggcaccct ggtctcctgc cttgttctca tgaacaccca gaagaggtgt aagcaaaaga 82020
ccattcacat gagtgtaatt ttgaagtata ggcactctga tctgtttttt gtttgtttct 82080
ttgtttgttt gttttccagg gttgaattaa aatatttatg actacttatt aaatttctag 82140
aatcctataa gtctatttgt atttttattc tacatttcaa tttgcatgct aatatagaag 82200
agtgtaaatt gttaatcctc agattattcc actttgtgtg tcataatttt tttcacattt 82260
cccttttcta ggcaatactg agcttgattt tctcttttaa tttcagcacc aactgaaaac 82320
agcactgggg tccaggactg ctaccgaggt gatggacaga gttatcgagg cacactctcc 82380
accactatca caggaagaac atgtcagtct tggtcgtcta tgacaccaca ttggcatcgg 82440
aggatcccat tatactatcc aaatgcgtat gtctatcatg ttagccataa aaggaacaat 82500
agtcaactaa aatttctctt agctggccca tgctacaagc tcacttccta ggtccaaatt 82560
tctcatagac tcagagtttg tagcaaaatg tctcaggaaa cttacttttg agcaaaaggt 82620
ctgaatgaag agaagtttta ggattgctat ctttcataac aatttgatgg aagcagcagg 82680
atatatggag gtggtgaagt ctcattaatg taaagctaag gagatcaaat gaccaaatgc 82740
tgagacaaag tatcattcca caatgcccac taaaggtcca tgcagtcttt caaccatgca 82800
attctatcat tctatcctcc attccctgaa gtgaaatttg tgtttgccat ttttgacacg 82860
aatcagaagt aacaaattca ggctgggtgc agtggctcag gcctgtgatc ccaacacttt 82920
gggaggacaa gacgggcaga tcaccagagg tcaggagttc aagaccagcc tggctaacat 82980
ggcaaaaccc catctctacg aaaaattaaa aaattagccg gtcatggtgg tgggtacctg 83040
taattccaac tacttgggag gctgaggcag gagaaacact tgagcctggg attcagagtt 83100
tgctgtgagc cgagaacatg ccactgcact ccagcctggg tgacagagca agactcaatc 83160
tcaaaaaaaa aaaaaaagaa gaagaagaag aaaagaagaa gaggaagaag aagaagagga 83220
agaagaagaa gaagaagaag aggaagagga agaggaggag gaggaggagg aggaagaaga 83280
agaagaagaa gaagaagaag aagaagaaga agaagaagaa gaagaagaag aagaagaaga 83340
aaatagaaat gagtgcatat atttatatat gagtactagc ctgtatgaac acactgggtt 83400
ctaagcacca gttttctgaa gggatatggg ttgtcaggca gagtaaaagc aggaatgcag 83460
atgagagtca ggaagtaaac agatgtggtg attaaaatgg gcaggtacat ggacaaaaaa 83520
atgcatgtct gacaaaaact ggcctcttgc cataagtgag tatgaataat atggaaaaac 83580
tgtttgcaca tgttgaacag cagacagtac aacctgagat agtttagaaa gggaaacaaa 83640
taagatcaac cccataatta cccttcctag acttaagggc aaagagtttt aaccaaagca 83700
ttccacagca gtcttgctaa actggggaga gagactggag ttttgtttac taataaaacc 83760
gagattttct aggttaggta ataatgagaa agtatttgtg gagaaaagga gctccaggaa 83820
tacacacaga agtctcttca agtctctggc tgaacagaaa gctgtgtatg cacagaaaga 83880
gtttccagag agaaaggaga acaaagaaca gctactgggg aaagaacaac tgctggggaa 83940
cagtgagctc aatgaagatg ccagagctca catagcactg ggaggtattt gagctctgac 84000
cagcctgagg agagacactt cattgaacat cttgggcatt cagcaaagac cccaaaaaac 84060
catacttcag gagtagaatt aatgcattcc tagaataaag tctactccag aaacacccta 84120
gaaaagctta gaaaccaagt ctaaaaagat ccaaatgatc tccaagtaaa ttaattgcct 84180
gtcagaagaa aacaacctct tcagaggtaa acaacaaaat taaattgctc aattatatag 84240
tatgcacaat gtgtggcata catttaaaaa tttgctaaac atacaaaaag catttagtgt 84300
gacccataac caggagaaaa atcagtcaat acaaatagac ccaaaaatga taaaaataac 84360
agaattggca aggagattta aaatgtatgt atcataattg tgttcaagga tttaaagaaa 84420
gcgtggacaa gaaataaata aatggataat atcaacagaa agaaaaattg taaaaggacc 84480
aaatggagag tcaagaactg aaaaaaaaga catctcttta atgagaaaat cactacatgg 84540
ccttataatc atattagata gtacagatga taaagctaac tagaaaatat tagggtggtg 84600
caaaccatag cacgcttata caaagcctga gaagataaac agagcctcaa ggacatctat 84660
gaaaatatca aaatatttaa tatttgttta aagcaagtca cagaggaagg gaaagagata 84720
ttggaacaga aaaaatactt gaagcagtga tggctgatga ctttctaaat atggaaaaaa 84780
tgataaactc acatagtcaa gaagctcaat ggatcagata taggatttta aaaagtaaag 84840
ctgtatgatt tatttggaca catcataatt aaattgtcca taatcaaaga tagaaagtaa 84900
aatcttattt gaagcccaag ggaaaaaaca tacctttaca tagagtaaca gtgacacaaa 84960
tgactgatgc cttctcatca gaaacaacac aaatcagaaa caatagaata acacctttag 85020

-continued

```
agtggtaaga agaaaaaaag atcaaatcag aaacaacaaa ataacacgtt tagagtggta  85080
aggaggaaaa caagatcaaa tcagaaacaa tggaataaca cctttagagt gtaagaaaga  85140
aaaaaagatc aaatcaggaa caacagaata acgccttcag agtggtaaga aggaaaacaa  85200
gataaaatca gaaacaatga aataacacct ttagagtagt aagaagaaga aaagatcagg  85260
tcagaaaaaa tggaataata tgctaagaag aaaaaaaaag atcaagtcag aaacaatgga  85320
ataacacctt tagagtgaaa agaaggaaaa aaacccagca agcttaaacg ctatgcacag  85380
caaacaattc cactgaaaat gaatgttacg taagtacata ttctgtcctc ctaaaaacaa  85440
agaacaaata aaagaatgtt tcatcagcag gattatgtaa taaaagatgt gaaagaatgc  85500
tatgtaagta gaagaaaaat aataccatat gggaattggc atcaaaacca caaaatacta  85560
tcaaaacaaa aaaactttat tgataaattt aacacaatat gcaaaagaac tataccatgt  85620
atactacata acattggtga gaagaaaatt agaagatcta aataaagaca catcatgctt  85680
atagattaaa aaatccaatg tcacttttca caaaactgat ctttagtttc aacccacacc  85740
caagcagaat tcctgcagtc ttttcttgaa aacctaacag aatgtatatg ctagaatcac  85800
caagacaatc tttaaaaaga ataaaaaact tggaataaaa tcacaagttt gtgggataga  85860
tgcatatggt aatatggaaa ttctcataaa gacacagtaa tcaagacatg tggtattggc  85920
tgggacgctt ggctgtaatc ctaacacttt gggaggccaa gatgagagga ttgcctgaga  85980
tgaggagttg cagacaagcc tggcaacat agcaagaccc tcatctctac aaatatttaa  86040
aaaaattagc caggtttggt gccatgtgcc tgtagtccca gctattcagg aagctgaggt  86100
gggaggatca ctggagccca tgaggtggag gctgaaatga gccatgattg tgctactgaa  86160
ctttagcctg ggagacagat taaaaccttc cctctctctc tcaaacaaac aaacaaaaaa  86220
tacatagtat tgggcaaaac atatgcaaac aaaaacagaa aagggtcagc ataaatttac  86280
atatatggtc aatttatttt caatacaggt agcaaagcaa tttaatgagg aaatttttt  86340
ccaaaattgg tctgaaacaa ctggatagcc atagaaaaaa actataacaa atgtgacgct  86400
tgaatcctac tgtatgactc aaattaaatt aatttgagat agctcttaga cctcaatgta  86460
acagctaatt ctgaggctga aatataagac tgctatgaaa aagtatagta tcttataacc  86520
ttggagaagg aaaaattttt tgagggaaga accagaaaac actaactgta aaagaaaaca  86580
aatgataatg tggacattca ttgaataaaa acttatgctc accaaatatg actgttaaga  86640
aaataaataa gtaagtaaca cactggaaga aaaacactct catccatata tctgacaaat  86700
ggcctgtatc cagagtatag aaacatttct cccactcact aatcagagga caaacaacct  86760
aatcaaaatg ggcaacaggc ttgaatagtc atttcttagg agaagatgca cacagagcca  86820
acaatcacct gaaaaagtgc acaacatctt agccatcaaa aatcaagagt tataaccctc  86880
ataagatgac actgaacatc cagtgtacat ggatatcatt aagaagacac aataataagt  86940
ggtgtcaccg atttggagct agaatgtgcc actctctcat atgctggtgg aagttcaaaa  87000
tcatacaaca aattaaaaaa tcagtctgat gctttcttat aaagttcgat aaatatgcat  87060
ctatcctaca aacctgtaat tctattcttg aatatttacc ccccaaaatg aaaacataag  87120
tccacaaaaa tctatataaa tattcatagc agctttatgt tttataaact caaaataaaa  87180
actatttcaa tgttttcatc aaaagaaaat gaaaactatt taaatggttt catcaaaaga  87240
aaatgaaaaa agaatttcca gtatatttat acaaaggaat actattcatc aacaaggaac  87300
aagttactga tagtctcaga agcatgaaca aacctcaaaa atatattaag gaaagaagcc  87360
agacgtcaaa gtgtatagtc tgtatgagtc cattcatgtg agtttataga aaacacaatt  87420
```

tatggtgaaa gaaaccaata gcatttgaca ctggccgtgg gaagagggta gcagagattg 87480
attgagcagc cacacaaggg agtttctggg gtggtgaaaa tgttctgcat tgtgagggca 87540
gtgtgggcta cacaagtata tgtatttatc aaatctcatc cagctacatt taagatctgt 87600
gcatctcact ctatgtgaaa atatactcaa ctgaaaaaca gagcaggtat ctgtttcagg 87660
tgctacatca cttgatacgt ccagttgtgt taaaaaccac tgcctaacat cctcaaatgg 87720
gggatctggg cttgagacta ggtcacatgt gtagagtctc tacagagacc gtgttggatt 87780
cccatgctcc ataatacgtt ccaagttttc tcagacagcc acaggtcatg aatgtgagga 87840
ttctgagagg ttggagcaac gttcttggga ggcataatgg ggaaggcatt ctccaagatt 87900
cctccagcct ggggtcttca cctgctgtgc ctcttactgc attgttttct gactcatcca 87960
tagccacttg accccttcag atcccatagt ctacctagcc gtctcccttt atgccttggg 88020
tcccgctgtt ctttcaactc atcacccatt ccttcagtcc cagagtggct gcagccagca 88080
gaggatggac tgagagcagg agaggaggtc gtgcccatga acccatccta gagaagcagc 88140
atcctgcctg ggagctagtt ttccagggaa gcttttataa gtcctgtaga cccaaaccca 88200
cttgctctac cagatacagt atttatagta atactatttt catgattatt ttatattgca 88260
aatgtagagc atttatgcta cactatgagt aaatagagta agggggctgg catgggaatt 88320
atataatctt ggatgccact tcttccttgg ggaaatgtat ttgagttcca acttacatat 88380
tactatatag tcttatagag agagagacaa agagctagac agacagagat atctttgtat 88440
gtgcattaaa aaatctaaga tacatatttc aaaatctgtg tcatttattc tggaggaaag 88500
tatttggcag aaggtgaaag gaagatattc tgatcctttc ttgtacagac atgtattatc 88560
tcagttttca tagagagcat atactacttt tgatgtttta aaacaaaaat tataatctgt 88620
gatgtgtcca cagttgttta aaagttgaag ctgaagacca tttgtgcttg tggcaatatt 88680
attgtggtat aatgggaata tttcaaaggc acttgttaac actttgttac agcaaaatgt 88740
agagggcgct aagtgccctt gaatattctc ccatctctgg tgacctgtgt tgttttgaaa 88800
tttgcagtgg cctgaccagg aactactgca ggaatccaga tgctgagatt cgcccttggt 88860
gttacaccat ggatcccagt gtcaggtggg agtactgcaa cctgacacga tgtccagtga 88920
cagaatcgag tgtcctcaca actcccacag tggccccggt tccaagcaca gaggctcctt 88980
ctgaacaagg taagaaattt gtggttagac atctatatac tgggatgaaa aaccatggaa 89040
aatcttactg atgcagaagc cttcagtggt acactggagg gttggttgag ggtctgcaat 89100
gtggaggaaa gcctcagcgc cctctctggg ggatccagaa ctgtgatttt tggcacgctg 89160
tgaggaggca gtgtctttag gaagggcacg gtgtctttag gaagggcaca gacccgccag 89220
ggcactggac ttaccactcc cctggttatt aaatgggtca tttcagtgtc ctagccaaaa 89280
tggatattct aacagcctgc caaatatgtg aagatttcca agccaataag cctttccagt 89340
gatttaaagt agactttttt cattgcaatc tacagtttgc agtttcttaa gaacatggcc 89400
tttgagtatg atatcctaga gaaacctaag gagactgcat tatttttcta ttgtcctggg 89460
gctgcatagc aggaggtaac caacgaatgc tgtctctccc tggcctatct cagtctttca 89520
caggctctgt tcacctcagc tttgaagtta gaaatttcta ggtgttcttg cctcttcttc 89580
tcatgaaacc tgcattggca gtgagtctac agaagaagag gaagagaatt ctgctttgtt 89640
acaattcagg actctgggca ctagaagatt ccctatctct cctccaaggg aataagttgt 89700
ttgtctctaa ccctccttga gaaacaatga gtctttgcct gcactcctaa atgtaggatg 89760

```
atttcctgcc caaattttca aaagattaag ccttttgcct tggtatgagc aatggtctag  89820
ggaaatgcgc aagggtcttg tgtcggcccc tgactgacca ccagtcacct cctacagcct  89880
gcaccaagga atgcattgca ttctggtctt ctgccctgtg gttctcatga aaaccagcag  89940
agattcatat gatggagctg cacatgaatg taatttccaa tgtccagcat tctcctctgt  90000
tctttatctt tagatttaaa aataatgttt ctatgaactt attaaaattc tagaatacta  90060
tgaatctact gggtcttttc acatcctttt gctactagta gaaaaaagaa tagtaataat  90120
tttcagaggc tactgtccag tatgtgacat aaattgtctc ccatgtttct ctgctcatgc  90180
aattactgag tatgatttat tttattttaa tttcagcacc acctgagaaa agccctgtgg  90240
tccaggattg ctaccatggt gatggacgga gttatcgagg catatcctcc accactgtca  90300
caggaaggac ctgtcaatct tggtcatcta tgataccaca ctggcatcag aggaccccag  90360
aaaactaccc aaatgcgtat gtatttgatt aaaaccataa gaggagcaac agccaactca  90420
aatattggtt agaagaccca tgctttaagc tcacttccta gggacaaatt tctcttagac  90480
tcacattttg gcaaaatgtc tcaggacctt tgcttttgag caaagagtct aagagaagag  90540
aaattttagg cctgctattt ttcctaatag ttttatggaa ggagtagaat atacggaagt  90600
ggcgaagtca tattaatgta aagctcagaa gataaatgac caaagcttaa acacagcacc  90660
attccacaat gcccactaaa aatcaatgtc atctttcact cgtgcaattc tgtcattcta  90720
aatttcaatt cccgaaggtt tgtttgccat ttttgtcatg ggtaataagt aaaaaaaaaa  90780
aaattaagat gtgtatatat atatatatat atatatatat acacacacac acacacacac  90840
aaacatctga atatttatat atatgtctga atatttatat acttgtgtat aaaacttata  90900
tttaaatttt tgcataaatt tatatatttt taatatttca ttaaaaatta tattgtttca  90960
ctatgtatgt ctgagtattt ttatatattt taatataaca ttttaaatat ttatatataa  91020
atattcaggt atgtaactga atattcattt acacacacaa atatatgtgt gcatgtgtgt  91080
atatatatat atacccatat atatatatat atatatatat acatatatat atatatatat  91140
atatgtatat atatatatat atatatatat acacacacac acacacacac atacatacag  91200
gtataaacac actgggcctg aagcaccagt ggtctgaaag gacatgtgtt gccaggactt  91260
gaagagcaaa agcaggaagg cggatgagag tcaggaggta cacaaacgct gaaaagtaaa  91320
atggacaagt acatggacaa aaagcaggta taagcataac agccttttgg aagtaaatga  91380
ctataaaata tatgaaaata ctgttttcac aagttgcaca acagatagta gtgtattgag  91440
ataatttaga acagaaaaca aatgtgatca accccataag tgtgctgtat ttcatcatgg  91500
attgaaggaa aaagagatgg agcccaagaa gaccacagca gtcttgatga actgagagac  91560
accagagttt gggattacaa aggcagctgg gattttctac acttggtaat aatgagaaag  91620
aatttgtgga gataaagagc tacagtcatg tacctagaag tcacctcagt gtaatataaa  91680
tctgcatatg cacagggagt gattccacaa tgaaagtagg acaaagaaca gctactgggg  91740
aaagaataac tacaagggaa caatgagttc aatggagatg gcagagctca caaagcactg  91800
ggggatattt gagttcttac cagctagaaa agagacctca ttgcaaatct tgggcattca  91860
gtagagaccc cagaaaagcc actctttgga aacagagttg atgtatttta agagcaaaat  91920
ctactccaca aaaatcctag caaaattgaa aagcaagtca gaaagaccaa aatcctctca  91980
acataaatta gttgcccatc agaagaaagc ttaacctctt cataggtaaa caataaaatc  92040
aaattgctca gttatctggc atccacaata tgtgacataa atttaaaaat ttactagaca  92100
tacaagaagc atttagtgtg atccataacc aggagaaaaa tcattcaata caaatagacc  92160
```

-continued

```
cagaaatgac agaaatgata gaattagcaa aaacatttaa aatatacata tgatcatttg  92220
atcttgtgat cagatatcac aagagaagaa agagatactt gaacagaaaa aatgcctgaa  92280
gcaatgatgg ctgaaaactt tccaaatatg aagaaaaaaa agctcacaga ttcaagaaaa  92340
ctaatcaatc agaaatatga ttttgaaaag taaaaatgta tgatttactt tggcaaatct  92400
tcttggttaa attgtctaaa atcaaagaaa gctaggaaaa ttttataagc cagaggaaaa  92460
aagattgttt atataaagga acagttacac aaatgactga tgccttctca tcagaaacaa  92520
tgaaagtcag aaacaataaa gtaacatctt taaagtaata gaagaaaaac ccaagaggtg  92580
agggatcgtg gcagacagga ggcaggacta gattgcagct ctggacagag cagcatgcag  92640
aggctcatat tgtgaatttt agccccatat tgactgcaag aacagaccag caatcctgag  92700
aggacccaca gaccgtgtga aggaagcaga ctgctcctgc aggataaggg agacacccca  92760
aatactgtga gttccccaac tgcagaagtg gaaaagggag gccttactcc ctcaaacaca  92820
ccccacaact ggagaagctg aaagtctgtt tgcaggagaa gttcccaact ttacctgggc  92880
ctcagtaaat ttagagagct gagccaagca aaatataggg gtagaggaag cagcagagaa  92940
gacctcagag cttgctggat ccccaagcag ctcattcctg cctggcacca cagagatcca  93000
tcagaagtgt ggccaaagga acagagggta aaactccaca tggaggactg ctctacctga  93060
actttctaac aatttgaaca gggggagaag cctcctggcc agaacttggg ggagggcatg  93120
aatctggttt gcagacttca caggtggggg aaggactaaa gcccttttct ttcacagctg  93180
ggaggtggaa agcctcaggc aagttttcaa gcctgacttt ccccccacct ggaaacagac  93240
ttggagctgt tgcggggttg gggcatggt gggagtaaga ccagcccttc agtttgcatg  93300
ggtgctgggt gaggcctgtg actgacagct tccctccact tccccgacaa ctcagatgac  93360
tcagcagagg cagccataat cctcctaggt acacaactcc agtgacctgg gaacttcacc  93420
cccacaccat acagaagctt cagtaagacg tgcccaagga aagtctgagc tcagacacgc  93480
ctagtcccac ccccaactga tggtccttcc ctacccaccc tggtagcaga agacaaagag  93540
catataatct ttggagttct agggcccacc cacctctagt ccctctccac actagtatag  93600
ctgatgcagg aggccaacca gcacaaaaat agagcattaa accaccaaag ctaggaaccc  93660
ctatggagtc cattgcaccc tcctccacct ccaccagaac aggcactggt atccacagct  93720
gagagaccca tagatggttc acatcacagg actctgtaca gacagtcccc agtaccagcc  93780
cagagctggg tagacttgct aggtggcaag acccagaaga caggcaataa tcactgcagt  93840
tcagctcaca ggaagccaca tccataggaa aagagggaga gtactacatc aagggaacac  93900
cccatgggat aaaaacatct gaacaacagc cttcagccct accttccctc tgacacagtc  93960
tacccaaatg agaaggaacc agaaaaccaa ccctggtaat atgacaaaac aaggctcatc  94020
acactcccag ttcaccagca atggatccaa accaagaaga aatccctgat ttacctgaaa  94080
gagaattcag gaggttagtt attaagctaa tcagggaggg accagagaaa ggcaaagccc  94140
aatgcaagga aatccaaaaa aaaaaaggta taagaagtaa aaggtgaaat attcaacaaa  94200
atagatagct taataaaaaa acaataaaaa attcagtaga ctttggacac acctttggaa  94260
atgtgacatg ctctggaaag tctcagcaat agaactgaac aagtagaaaa aataaattca  94320
gagctcaaag acaaggactt caaattaacc caatccaaca aagacaaaga ataaaggata  94380
agaaaatatg aacaaagcct tcaagatgtc tgggattatg ttaaatgacc aaatataaga  94440
ataatcgtgg ctcctgagga aaaagacaat actaaaagct tggaaaacat atttggggga  94500
```

```
ataactgggg aaaacttacc tggccttgct ggacacctag acatgcaaat acaagaaaca  94560
caaagaacat gtaaatacaa gcagcacaaa gaacacctgg gaaattcatc acaaaaagat  94620
cttagcctag gcacattctc atcaggttat gcaaagttaa gacgaaggca agaatcttaa  94680
gagctgtgag acagaagcac caggtaatgt ataaaggaaa ccctatcaga ttaacagcca  94740
gtttttcagc aggaactgta caagctataa aggattggag ccctatcata gcctcctcaa  94800
acaaaacaat tatcagtcaa gaattttgta tccagcgaaa gtaagcatca tatatgaagg  94860
aaagatacag tcgtttttgg acaaacaaat gctaagagaa ttcaccatta ccaagtcacc  94920
actagaagaa ctgctaaaag gagctctaaa tcttgaaaca aatcctagaa acacatgaaa  94980
acagaatctc tttaaagcat aaatcacaca ggacctataa aacaaaagta caagttaaaa  95040
aacaaaaaca aaaaacaaaa ccaaagtacg gaggcaataa agaatatgat gaatgcagtg  95100
gcacctcaca tttcaatgct aaaattgaat ctaaatggcc taaatgctcc acttaaagga  95160
tacaaaaaga gttggtggct ggcaagatgg ctgaatagga acagctccag tctgccgctc  95220
cccgtgagat caacacatag ggtgggtcat ttctgcattt ccaaccaagg tacccggctc  95280
atctcattgg gactggttag acagtgggtg cagcccacag agggtgacct gaagcagggt  95340
ggggtgtcac ctcacctggg aagtggaagg ggtcagggaa ctccctcccc tagccaaagg  95400
aagccgtgag ggactgtgcc gtgaagacca gtgcattctg gcacaaatac tatgcttttc  95460
ccacggtctt tgcaacctga agaccaggag attcccttgg gtgcctacac caccagggcc  95520
ctggatttca agcccaaaac tgggctggca tttgggcaga cactaagcta gctgcaggag  95580
tttttttca taccccagtg gtccctggaa tgccagcaag acagaaccat tcaccccgt  95640
gaagaaaggg ctgaagccag ggagctaagt ggtctttctc agtggatccc acccccatgg  95700
agcccagcaa gctaagctcc actggcttga aattcttgct gccagcacag cagtctgaag  95760
ttgacctggg acgctcaagc ttggtgggag gaggggtatc cacaaatact ggggcttgag  95820
taggaggttt tcccctcaca gtgtaagcaa aaccgctagg aagtttgaac tgggcagggt  95880
gcactgcagc ttggcaaagc cattgtagca agagtgcctc tctagattcc tcctctctgg  95940
gcagggcatc tctgaaagaa aggcagcagc cccagtcaga agcttataga taaaactccc  96000
atctccctgg gacagagcaa ctggaggaag gggtggctgt gagtgcagct ccagcagact  96060
tagtttcctg cctgccagct ctgaaaagag caccagatcc cccaacacag cactagagct  96120
ctgataaggg acagactgcc tcctcaagtg ggtcctggtt tcagaagata ataagaaact  96180
cctctgagct aaaggagcat gttctaacac aatgcaagga agctaagaac cttgaaaaag  96240
gtcagaggaa ttgctaacta cagtaagcag tttagagaag aacataaatg accttaggga  96300
gctgaaaaac acagcacgag aacttcatga cacatacaca agtatcaata gcaaaatcga  96360
tcaagtggaa gaaaggatat cagagattga aaatcaactt aatgaagtaa agcgtgaaaa  96420
caagattaag gaataaagaa tgaaaaggaa tgaacaaatc ctccaagtat gggactatgt  96480
gaaaagattg aacctacgtt tgattggtgt acctgaaagt gatgggagaa tggaaccaag  96540
ttggaaaaca ctcttcagga tattatccag gagaacttcc ccaacctagc aagacaggcc  96600
aacattcaaa ttaaggaaat acagagaata ccacattcaa attcaggaaa tacagagaac  96660
accacaaaga tactcctcaa gaagagcaac ctgaagacac ataatcgtca gattcaccaa  96720
ggttgaaatg aaggaaaaaa atgttgaggg cagccagaga gaaagtttgg gttacccaca  96780
aagggaaccc catcagacta acagtggatc ttcctgcaga aactctacaa gccagaagag  96840
agtgggaggc caatattcaa cattcttttt tactattatt atactttaag ttctagggta  96900
```

catgtgcaca aggtgcaggt ttgttacata tgtatacatg tgccatgttg gtgtgctgca 96960
cccattaact cttcatttac attaggtata tctcctaata ctatccctcc ccactccccc 97020
catcccatga caggccccgg tgtgtgatgt tccccactct gtgtccatgt actctcattg 97080
ttcaattccc acctatgagt gagaacattc ggtgtttgga tttctgtcct tgtgatagtt 97140
tgctgagaat gatggtttcc agcttcatcc acatccctac aaaggacatg aagtcatcct 97200
tctttatggc tgcatagtat tccatggtgt atatgtgcca cattttctta atccagtcta 97260
ccattgatgg acgtttgtgt tggttccaag tctttgctat tgtgaatagt gccgcaataa 97320
acatatgtgt gcatgtgtct ttatagcagc atgatttata atcctttaga tatatatcca 97380
gtaattgtat ggctgtgtca aatggtattt ctagttctaa atccttgagg aatcaccgca 97440
ctgtcttcca caatggttga actagtttac agtcccacca ccagtgtaaa aatgttccta 97500
tttctccaca tcctctctag catctgttgt ttcctgactt tttaatgatc accattctaa 97560
ctggtatgag atggtatctc attgtggttt tgatttgcat ttctctgatg gccagtgatg 97620
gtgagcactt tttcatgtgt ctcttgactg cataaaagtt ttcttttgag aattgtctgt 97680
taatatcctt tgccaacttt ttgatggggt tgtttgattt tttttcttgt aaatttgttt 97740
atgttctttg tagattctgg atattagccc tttgtcagat gggtagattg taaaaatttt 97800
ctcccattct gtagcttgcc tgttcattct gagggtagtt tcttttgctg tgcagaagct 97860
ctttagttta attagatccc attggtcaat tttggctttt gttgctattg cttttggtga 97920
tttagtcatg aagtccttgc ccatgcctat gtcctgaatg gtattgctta ggttttcttc 97980
tagggtttat atggttttag gtctaacatt taagtcttta atccatcttg aattaatttt 98040
tatataaggt gtaaggaagg gatccagttt cagctttcta catatggcta ggcagttttc 98100
ccagcaccat gtattaaata gggaaacctt tccctatttc ttgtttttgt caggtttgtc 98160
atagatcaga tggttgtaga tgtgtggtat tatttctgag ggctctgttc tgttccattg 98220
gtctatatct ctgttttggt accagtacca tgctgttttg gttactgtag ccttgtaatg 98280
tagtttgaag tcaggcagag tgatgcctcc agctttgctt ttttggctta ggattgtctt 98340
ggcaatgcat gctctttttt gttccatatg aactttaaag tagtttttc caattctgtg 98400 aagaaagtca ttggtagctt gatggggatg gcattgaatc tataaattac cttaggcagt 98460
atggccattt tcacaatatt gattcttcct atccatgagc atggaatgtt cttccatttg 98520
tttgtgtcct cttttatttc attaagcagt ggtttgtagt tctccttgaa gaggtccttc 98580
ccatcccttg taagttggat tcctaggtat tttattctct ttgaagcaat tgtgaatggg 98640
agttcatcca tgtccctaca aaggacatga agtcatgtat gggaatgctt gtgatttttg 98700
cacattgatt ttgtatcttg agactttgct gaagttgctt atcagcttaa ggagattttg 98760
gtctgagaag atggggtttt ctaaatatac aatcatgtca tctgcaaaca gggacaattt 98820
aacttcctct tttcctaact gaataccctt tatttccttc tcctgcctaa ttgccctggc 98880
cagaacttcc aacactatgt tgaataggag tggtgagaga gggcatccct gtcttgtgcc 98940
agttttcaaa gggaatgctt ccagtttttg cccattcagt atgatattgg ctatgggttt 99000
gtcataaata gctcttatta ttttgagata tgtcccatca atacatagtt tattgagagt 99060
tcagcatgga gagctgttga attttgtcaa aggccttttc tgcatctatt gagataatca 99120
tgtggttttt gtctttggtt ctgtttatat gatggattac atttattgat ttgcatatgt 99180
tgaaccagcc ttgcatccca gggataaagc caacttgatc atggtggata agctttttga 99240
tgtgctgctg gattcggttt gccagtattt tattgaggat ttttgcatca atgttcatca 99300
tggatgttgg tctaaaattc tcatttttgt tgtgtctctg ccaggatttg gtatcaggat 99360
gatgctggcc tcataaaatg agttagggag gattccctct ttttctatga ttggaatagt 99420
ttcagaagaa ttggtaccag ctcctctttg tatctgtggt agaattcggc tatgaatctc 99480
tcctggactt tttttggttg gtaggctctt aattattgcc tcaatttcag agcctgttat 99540
tggtctattc aaggattcaa tttctttctg gtttagtctt ggtagggtgt atgtgtccag 99600
gaatttttcc atttcttcta gattttctag tttatttgca cagaggtgtt tataatattc 99660
tctgatggta gtttgtattt ctgtgggatt ggtagtgata tccccttttat catttttttat 99720
tgcatctatt tgattcttct ctcttttctt ctttattagt cttgctagtg gtctatcaat 99780
tttgttgatc ttttcaaaaa accagctcct ggattcattg atgttttgaa ggttttttttg 99840
tgtctctatc tccttcagtt ctgctctggt cttagttatt tcttgccttc tgctagcttt 99900
ttaatgtgtt tgctcttgct tctctagttc ttttaatggt gatgttaggg tgtcaatttt 99960
agatctttcc tgctttctct tgtgggcatt tagtgctgta aatctccccc tacacactgc 100020
tttaaatgtg tcccagagat tctggtatgt tgtgtctttg ttgtcattgg tttcaaagaa 100080
tatctttatt tctgccttca tttcgttaca tacccagtag tcactcaggt gcaggttgtt 100140
cagtttccat atagttgagc agtttttaat gagtttctta atcctgagtc ctagtttgat 100200
tgcactgtgg tctgagagac agtttgttat aatttctgtt cttttacatt tgctgaggaa 100260
tgcctcactt ccaactatct ggtcaatttc agaataagtg cgatgtggtg ctgagaagaa 100320
tgtatattct gttgatttgg ggtggagagt tctgtagatg tctattaggt ctgcttggtg 100380
cagagctgag ttcaattcct ggatatccat gttaactttc tgtctcattg atctgtctaa 100440
tgttgacagt ggggtgttaa agtctcccat tattattgtg tgggagtcta agtctctttg 100500
taggtctcta aggacttgct ttatgaatct aggtgctcct gtattgggtg catatatatt 100560
taggatagtt agctcttctt gttaaattgg tccctttacc attatgtaat ggccttcttt 100620
gtctcttttg atctttgtta gtttaaagtc tgttttatca gagactagga ttgcaacccc 100680
tgcttttttt gttgttttcc atttgcttgg tagatcttcc tccatccctt tattttgagc 100740
ctatgtgtgt ctctgcacgt gagatgtgtc ttcagaatac agcacactga tggatcttga 100800
ctctttatcc aatttttccag tctgtgtctt ttaattggag catttagccc atttacattt 100860
aaggttaata tttttatgtg tgaatttgat cctgtcatca tgatgttcgc tggttatttt 100920
gctcattagt tgatgcagtt tcttcctagc atcgatggtt tttacaattt ggcatgtttg 100980
tgcagtggct gataccgatt gtttctttcc atgtttagtg cttccttcag gagctcttgt 101040
aaggcaggcc tggtggtgac aaaatctctc agcatttgct tgtctgtaaa ggattttatt 101100
tctccttcac ttatgaagct tagtttggct ggatatgata ttctcagttg aaaattcttt 101160
tctttaagaa tgttgaatat tggctgccac tctcttctgg cttgtagagt ttctgctgag 101220
agatctgctg ttagtctgat gggcttccct ttgtgggtaa cccgaccttt ctggtgaatc 101280
tgacaattat gtgtcttgga gttactcttc tcgaggagta tttttgtggc attctctgta 101340
tttcctgaat ttgaatgttg gcctgccttt gtaggttggg gaagttctcc tggataatat 101400
cctgaagagt gttttccaac ttggttccat tctcctcgtc actttcaggt acaccaagca 101460
gatgtagatt tggtcttttc acatagtccc atatttattg gaggctttgt tcatttcttt 101520
ttactccttt ttttctctaa acttctcttc tcgcttcatt tcattcattt gatctttaat 101580
cactgatacc ctttcttcca cttgattgaa tcaactactg aaacttgttc atgtgtcacg 101640

```
tagttctcgt gccatggttt tcagctccat tagatcattt aaggtcttct ctatgctgtt 101700
tattttagtc tgccattcat ctaaactttt tcaaggtttt tagcttcttt gcaatgggtt 101760
cgaacatcct tctttagctc ggagaaattt gttattacag atcgtctgaa gccttcttct 101820
ctcaactcat caaagtcatt ctctgtccag ctttgttctg ttgctcgtga ggagctgcgt 101880
tccttcggag gagaagaggc accctgattt ttagaatttt cagctgttct gctctggttt 101940
ctccccatct ttgtggttta tctacctttg gttcttgatg atggtgatgt acagatgggg 102000
ttttggtgtg gatgtctttt ctgtttgtta gttttccttc taacagtcag gaccctcagc 102060
tgcaggtctg ttggagtttg ctggaggtcc actccagtcc ctgtttgcct gggtattacc 102120
agtggaggct gcagaacagc aaatattaca gaacagcaaa tgttgctgcc tgattcttcc 102180
tctggaagct tcatctcaga ggggcaccca gctgtatgag gtgtcagttg gcccctactg 102240
ggaggtgtcc cccagttagg ctactcgggg gtcacggacc cacttgagga ggcagtctgt 102300
ccattctcag atctcaaact ctctgctggg agaaccacta ctctcttcaa agctgtcaga 102360
cagggatgtt taagtctgca gaagtttctg ctgccttttg ttcagctatg ccctgccccc 102420
agaggtggag tctacagagg caggcaggtc tccttgagct gtggtgggct ccacccagtt 102480
tgagcttcct ggtcgctttg tttacctact caagtctcag caatggcaga cgcccctccc 102540
ccagctttgc tgccgccttg cagttcggtc tcagactact gtgctagcag ttcaatctca 102600
gactgctgta ctagcagtga gcaaggctct gtgggcatgg gaccctctga gccatgtgca 102660
ggatataatc tcctggtgtg ccgtttgcta agaccattgg aaaagtgcaa tattagggtg 102720
ggagtgtccc gattttccgg gtacatctgt catggcttcc cttggctagg aaagggaatt 102780
ccctgacccc ttacacttcc cgggtgaggc aatatcccgc cttgcttcgg ctcactctcc 102840
gtgggctgca cccactgtct gacaagcccc ggtgagatga acccagtacc tcagctggaa 102900
atgcagaaac cacccatctt ctgctttgct catgctggga actgtggact ggagctgttc 102960
ctattcggcc atcttgaaac ctcccctctc tcacgatcac aaggtcccac aataggccgt 103020
ctgcaggctg aggagcaaga aaagccagtc tgaattccaa aactgaagaa attggagtct 103080
gatgttcaag ggcaggaaac atccagtgcc aaagaaagat gtagaatatt caacattctt 103140
aaagaaaata attttcaacc tagaatttca tatccagcca aactaagctt tataacaaag 103200
gagaagtaaa atcctttaca aacaagcaaa tgctgaggaa ttttgtcaac accaggcctg 103260
ccttacaaga ggtcctgaag aaaacactaa atatggaaag gaaaaaccag taacagctac 103320
tgcaaaaaca taccaaattg taaacaccat caacactata aagaaactgc atcaactaat 103380
gggcaaaata gccagctagc atcataatga caggatcaaa ttcacacata acaatattaa 103440
ccttaaatgt aaatgggcta aatgccccaa ttaaaagaca cagactggga aattgaataa 103500
agagtcaaga cccattggtt tgctgtgttc agaagaccca tctcagggtg aaaagacata 103560
catgggctca aaataaagaa atgaaggaat atttaccaag caaatggaaa gaaaaaaaaa 103620
gcagcggttg caatcttagt ctttgatgaa acagacttta aaccatcaaa gatcaaaaga 103680
gacaaaggag ggcattacct aatggtaaaa gtatcaatgc aacaagaaga tctgactgtc 103740
ctacttatat atgcacccaa tacaggagca cccagattaa taaagcaagt tcttagagac 103800
ctacaaagag acttagactt ccacacaaaa atagtgggag actttaacac cccacagcca 103860
atattagatc gacgtgacag aaaattaaca aggatattca ggacgtgaat tcagctctgg 103920
accaagctga cctaatagac atctacagaa ctcgacacca caaatcaaca gaatatacat 103980
```

tcttctcagc accacattgc acttattcta aaattgacca cataattgga agtaaaacac 104040
ttctcagcaa atgccgtaga atggaaatca taacaaacag tctctcagac caaagtgcaa 104100
tcaaactaga actcaggatt aataaactca ctcaaaacca cacaactata tggaaactga 104160
acaacctgct cctgaattac tactgggtaa ataacaaaat taaggcagaa gtagataagt 104220
tcttagaaac caaagagaac aaagacacaa tgtgccagaa tctctggtac acagctaaag 104280
ccatgtttag agggaaattt atagcactaa atgcccacag gagaaagcgg gaaagatcta 104340
aaatcaacac cctaacatca caattcaaag aaccagagaa gcaagagcaa acaaatacaa 104400
aagctagcag aagacaagaa ataactaaga tcagagcaga actgaagggg ataaagacac 104460
gaaaaccctt taaaaaatta ataaatccaa gagctggttt tttgaaaaga ttaacaaaat 104520
acatagaagc ctagccagac taataaagaa gaaaatagag aagaatcaaa tagacacaat 104580
aaagaataat aaaggggata tcaccaatga tgccacagaa atacaaacta ccatcagaga 104640
atactttaaa cacctctatg caaataaaat agaaaatcta aaagaaatgg ataaattcct 104700
ggacacatac accctcccaa gactaaacca ggaagaagtc aaatccctga atagaccaat 104760
aacaagttct gaaatcgagg cagtaattaa tagcttacca accaaaaaaa gcccagacca 104820
gagggattaa cagtcaaatc ctaacagagg tacaaagaag agctagtact attccttctg 104880
aaactattcc acacaataga aaaagaggga ctcctgccta actcatttta tgaggccagc 104940
atcattctga taccaaaacc tggcagagac acaacaagaa aagaaaattt caggccaaca 105000
tccctgatga acatcaatgt gaaaatcctc aataaaatac tggcaaactg aatccagcag 105060
cacatcaaaa agcttatcca ccatgatcaa gttggcttca tccctgggat gcaaggctgg 105120
ttcaacatat tcaaatcaat aaacataatc catcacataa acagaaccaa tgacaaaaac 105180
cgtatgatta tcgcaataga cgcagaaaag gcctttgata aaattcaata cccaatcatg 105240
ctaaaaactc ttaataaact aggtattgat ggagcatgtc tcaaaataat aagagctact 105300
tatgacaaat gcatagccaa tatcatactg aatgagcaga agctggaagc attccctttg 105360
aaaaccagca caagacaagg atgccctctc tcaccactcc tattcaacat agtattggaa 105420
attctgtcca gggcaatcag gcaagagaaa gaaataaagg tattcaagtg ggaagagagg 105480
gagtcaaatt atttctcttt gcagatgaca tgattgtata tttagaaaac tctatcatct 105540
cagcccaaaa tctccttaag ctgataagca acttcagcaa agtctcagga tacaaaatca 105600
atgtgcaaaa atcacaagca ttcctataca ccaataagag acacagagcc aaatcctgag 105660
tgaattccca ttcacaattg ctacaaagag aataaaatat acctaggaat ccaacttaca 105720
agggatgtga aggacctctt caaggagaac tacaaaccac tgctcaagga aataagatag 105780
gacacaaaca aatggaaaaa cattccatgc taatggattg gaagaatcaa tattgtgaaa 105840
attgccatac tgcccaaagt gatttataga ttcaatgtta tccccatcaa gctaccattg 105900
atttcttcac ataattagaa aaaactactt tcaatttcat atggaataga aaaagggcct 105960
gtatatccaa gacaacctaa gcaaaaagaa caaagctgga ggcatcatgc tatctgactt 106020
caaaatatac tacaaggcta cagtaacaaa aacagcatgg tatggtactg gtaccaaaac 106080
agatatatag accaatagaa cagaacagag gcctcagaaa taacaccaca catctacaac 106140
tattggatct ttgacaaact ggacaaaaat aagcaatggg gaaaggattc cctatttaat 106200
aaatggtgtt gggaaaactg gctagccata tgcagaaaac tgaaactgga tcccttcctt 106260
acaccttata cacaaattaa ctcaagatag attaaagaat taaatgtaag acctaaaacc 106320
ataaaaaccc tagaagacac tttgggaggc cgaggtggat ggatcacgag gtcaggagat 106380
cgagaccatc ttggctaaca cagtgaaagc ccatctctac taaaaataca aaaaattagc 106440
tgggtgtggt cgtgggcacc tgtagtccca gctacttggg aggctgaggc aggagaatgg 106500
catgagctga ggaggttgag cttgcagcaa gccaagattg tgccactgca ctccagcctg 106560
ggcaacagag tgagactcca tcaaaaaaac aaaaacaaaa acaaaaaatc aaaccctaga 106620
agaaaacata ggcaatacca ttcaggacat aggcatggga gaagacttca tgactaaaac 106680
agcaaaacca atggcaacaa aagccaaaat ttacaaatca gatctaatta aaataaagag 106740
cttctgcaca gcaaaaaact ctcatcagag tgaaaaagca acctatggag aaaaattctg 106800
tggtctagcc atctgacaaa gggctaatgt ttagaatgta caagcaactt aaacaaatgt 106860
acaagaaaaa aaaaacaacc ccatcaaaaa gtgggcaaag gatatgaaca gacacttctg 106920
acaggaagac ctttatgtgg ctgacaaaca tgaaaaaagc tcatcatcac tgttaattag 106980
agaaatgcaa atcgaaacca caatgagata ccatctcatg cccgttagaa tggcgatcat 107040
taaaaagtca ggaaacaaca gatgctgaag aggatgtgtg gagaaagagg aacacattta 107100
cactgttggt gggagtgtaa attagttcaa ccattgtgga agacagtgcg gtgattcctc 107160
aaggatctag aaccagaagt accatttgac ccagcaatcc cattactggg tatataccca 107220
aaggattata aatcattcta caataaagac acatgcacac gtatgtttat tgtagcacta 107280
ttcacaatag caaagacttg gaaccaactg aaatgcccat caatgataga ctggataaag 107340
aaaatgtggc acatatacac tgtggaatac tatgcagcca taaaacagga tgagttcatg 107400
tcttttgcag ggacatggat gaagctggaa accatcattc tcagcaaact aacacaagaa 107460
cagaaaacca aacaccatat gttctcactc ataagtgtga gttgaacaat gagaacacat 107520
ggacacagga aggggaacat cacacacagg ggcctgttgg ggagttgagg ctaggggagg 107580
gattggatta ggagaaatac ctaatgtaga tgatgggttg ctgggtgcag caaaccacca 107640
tgacacgtgt atacctatgt aacaaaccca cacattctac acatgtatct cagaacttaa 107700
agtataataa taataagata cagaactgca gaatgaataa gaactcacca accatctgct 107760
gccttcagga gactcattta agacataagg actcacataa acttaaagta aatgggtgga 107820
aataataata agtggtgtca ctgatgtgga ggtagattat aaaactctta tcatatgctg 107880
gtggaagatc aaaatgataa aacgaattaa aaaatcagtc agatggtttc ttaaaaagtt 107940
ccatcaatat gcctctatct tacaaacctg caattctatt cctgaatctt tatcccaagg 108000
aaatgaaaaa gtaagtccac aaagagttct atatgaatat ttataggagc tttatttatt 108060
ataattcaaa ctgtaaaaat aatttcaatg ttcatcaata acaaaatgaa aaaataattt 108120
gcaacctact ggtacacttg aatactattc agcactgagt atcttaaata gcatggatgg 108180
agctcaaaaa tatactcagg aaagaagcca tgtatattct gtatgagttc atttacatga 108240
gatcatttac atttcctcca aaagaggaaa aactaatttc tgttgaaaga aaccaatgta 108300
tttgcctctg gcagtggtaa gggggtagca cagattaatt gggtagggac tcaagagagt 108360
ttctggggtc acagaaatgt tccgtgtggt gatgggagtt tgggctccac aggtataggt 108420
gttgatccaa aatcatcaaa aaaacaacat tgcagatctg tgcatctcac tctgtgggaa 108480
agtatatctc aactgtaaaa agggcagaaa ttgcttttaa acgctcagcc ttttagcaca 108540
tccagttgct tggagaacca gcttactcaa atgggggtct aggctggaga ctaggtcaca 108600
ggcatagagt ctctaaactt tcccatggca cataatacgt ttcaggtttt ctcagagagc 108660
tgcaggttag taatctgagg attctgacaa gttgggtcaa cgttcctagg aggcatgaat 108720
gggagtgcat tctctaagat ccctccaccc cagggtcctt gctttctgtg cctcttactc 108780
cattgttttc tgactcctct gtagccactc gacctcttca gatcccattg tctacccagc 108840
catcgccctt tatgacttgg gtcccactgt tctttcatct catcctccat tccctcagtt 108900
tcggagtggc tgccgctagc agaggatgga ctgagagcag gagaggtggt cctgcccagg 108960
aacccatcct agagaaatgg catcctgtct gggagctagt tttttagggc aggttttata 109020
agtcttgtaa agccagacac acttgatcta cctggtatgt tatttacagt aatactattt 109080
tcataattgc ttttcactct aaaagtagag ccttttagct acactgtgag taaataaagg 109140
ggctggcctg ggaatggtat catgttggat gttgtttctt ccctgaagta atatatatca 109200
gttacaattt acatgttact gcagagtcct agagagagac acagagaatg agacagatac 109260
caatacattt ttatgtgcat taaaaaaatc taaggccagg cgcagtggct cacacctgta 109320
atcccagcac tttgggaggc cgaggtgggt ggatcacgag gtcaggagat tgagaccatc 109380
ctggctaaca cggtgaaacc ctgtctctac taaaaataca aaaaattagc caggcgtggt 109440
ggcgggcgcc tgtagtccca gctactcagg agactgaggc aggagaatgg cttgaaccca 109500
ggaggcagac cttgcagtga gccgagattg cgccactgca ctccagtctg ggcgacagag 109560
cgagactccg tcacaaaaaa aaaaaaaaat ctaaaatgca ctcttcaaaa tctatgtcat 109620
ttattctgga ggaatgcagt tggcagaagg aggaagatat tccgaatttt tcttgtatac 109680
atttatgtat gatctcagtt tttttatgga tcatagacca attttgatat tttaaaataa 109740
aaattataat ctatcttgga aatttacatg gttctttaga acttgaggac cgtttttgct 109800
tttcggaata ttattgtacc taaaatggga atattacaac gtcacttttt aacactttgt 109860
tataacaaag tttagacagc gctgggtgcc cctgaatttt ttcccgcctc ttgtgacctg 109920
tgttgttttg gaatttgcag tggcctgacc gagaactact gcaggaatcc agattctggg 109980
aaacaaccct ggtgttacac aaccgatccg tgtgtgaggt gggagtactg caatctgaca 110040
caatgctcag aaacagaatc aggtgtccta gagactccca ctgttgttcc agttccaagc 110100
atggaggctc attctgaagc aggtaagaag tctgtggcca gatatctaca catttgaaca 110160
ttgggatgaa aagagatgga aaatctgact gatgcagaag ccttccatgc tacacagaaa 110220
cttgagggta tggcaggtgg aaagaagcct cagcactctc tctggtggag caatttttgg 110280
cgcaacgtgc gtgggcggtg acttcaggaa tggtgcaaac ccacctgggc acttgactta 110340
ccactcactt tgttatgaaa ggggttatct cggtgttcca gacaaaattc caattctaac 110400
atcaggccaa atttgtgcca aatttcacac tagtgagtgt ttccaggcat ttattaaaat 110460
ggacagtgtt cattgcaatc ttcagcattg cagttgctga ggtatgtggc cgctgagttt 110520
gtcatcctgg ggaaacctaa tatgatgata tttattccat ctaatcctgg ggctatttgg 110580
cagtaaatac cacagaatac actatttctc tggcttattt cagtcttagg taggctctgc 110640
acacctatgc ttggaaggca ggaatttctt ggtgttcttg tgccttcttc tcatggaacg 110700
tgcatctttg gtgtgtgttg agaggaaggg tagtagactt ctgctttgtt gcaatgcagg 110760
atgctggaac aagaggattc cctgtctcta ctgtaaggga ataagatttt agcctccatc 110820
cttctctaag aagcaatgtg tctttgcctc caagtactag atgcaggacc atgaactgcc 110880
ccgtccacca gaagcttaag gctttggctt ttcaggagca atcatctagg gaactgtgca 110940
gggttttcat gtctgtcccc tactgacagc caatcaccat acagcctgca taacctaatc 111000
catcatcgtc tggtttcctg cctcattgtt ttcatgaaca accagtagag agccatacga 111060
aagagcttgc acatgagtct ttgttccaat tgtaagagca ctgataggtc cttttcccac 111120
caggttttga atataaaatt tctaagaact tattaaaata ttagaatgtt attaatctat 111180
tgtttttgct tcagcatgtc cttctgcttg tgagtatact aaagagaaca gtcataattc 111240
tgaaactact gtcctgtttg tgtcataaat tgcttcacat gtttctgcat actagtagtt 111300
actcagcttg attttgtcta ttttcagcac caactgagca aacccctgtg gtccggcagt 111360
gctaccatgg taatggccag agttatcgag gcacattctc caccactgtc acaggaagga 111420
catgtcaatc ttggtcatcc atgacaccac accggcatca gaggacccca gaaaactacc 111480
caaatgagta tgtctttgat gttacttgta agaggagcaa cagccaactt aagttcctcc 111540
tagaagagcc ttgcttcaag ctaacttgtt aggacaaatt tcccttagac ccagaaggtg 111600
tgtcaaaatg tccagacaac tttgcttttg atcaaagagt ctgagagaat aggtatttta 111660
ggcttgctat cttttctaat agtctgatgg aagcagaagg ctacatggag ctgatgaggt 111720
ctttttaata taaagctcaa gagatcaaat gatcaaatac ttagagtgcc attctacaag 111780
gctcataaaa gatcaatgca ctctttcacc catgcaattc tatcattcta acctcccttc 111840
tctgaaatga aggcttttg ccatttttgt catgggtcac aagtaaataa ttcacatgta 111900
tatgagtata tatataacca ggtgtgttta ttcagactag tatgtatata tatacatata 111960
tatgttcata taagttagta ttcatatata tgttcatata tatatgttca tacagactag 112020
tattcatata tatatacata tatatataca cacacatata tatatatata tatatgttct 112080
agggaaacat gcaaggtttt tatgtctgtc cctgactgat gaccaaatac cctatagcct 112140
gcacagctgc aagctgtata gccatacaat ttgcaggaca cacacacata cacacacaca 112200
cacacacaca cacacactaa catataatat aatataatat aatataatat aatataatat 112260
aatataatat aattaatata tataaacctg tgtgaacaca ctgggttcta agctccagtt 112320
ttctgaaggg atatgggttg ccaggagagg aagagcaaaa gcaagaatgt agatgagaat 112380
taggaagtaa acagatatgg agattaaaat gggcaggtac atggacaaaa aaccaggtct 112440
gacaaaaact ggctttctgc cataaatgac tataaaagat attaaaaaac actttccaca 112500
tgttggacaa gagacagtac aggactgaga taatttagaa aaggaaatga atgagcgcaa 112560
ctccgtaact attatgactt tcttcctgga gaaccttcct ggactgaagg gcaaggaatt 112620
ggagccaaag ccaaccacag cagtcttgct gaactgagga aagagactgg agtttgggat 112680
agctaagaaa atgtgtattt tctatgctag gtaataatga gaaagaattt gtggtgaaaa 112740
ggagctgaag gaatatgcat ggaagtctaa tataaactgc atatgcacag ggagaaattc 112800
tacaaagtgg gacagagaac cactactggg gaaaggacaa attcagggaa acagtgagct 112860
caatggtgac gccagagctc acgtagcact gggggatacc ggggttctga tcagcccgag 112920
gagagacacc tcattgaaca tctcgggcat tcagtagaga ccccagaaaa gtcatacttt 112980
aggagtagga tttatgcctt cttagaataa agactacccc agaaacaccc tagtaaagct 113040
taaaaaccaa gtctaaaagg acccaaatga tctccaagta aattaactgc ctgacagaag 113100
aaaactcaac catcactgga ggtaaataac atgattacag tgctctgtaa tgttgcattc 113160
acaaggagtg acatcattta aaaatttatg aggcaggaaa aagcaattag tgtgatccat 113220
aactaggaga aaaaccagtc aatacaaata gaccaagaaa tagtagaaac gatggaattg 113280
acaaagaaat taaaactgta tatatgataa ttgtgttcaa agatttaaag aaaacatgaa 113340
catgagggaa acaaatgcag aatataaaaa aaagcaaatg cgtaaaacaa ccaaatggaa 113400
attaaagaac tacaaaaaag tataacctta ataaaatact cactggatgg ccttaatatt 113460

-continued

```
agtttataca ttacagaaga aaaagtgaac cagaagataa ctcaatgaaa gccatacaat 113520
ctgtaagaca cacacacacg cacacgcgcg cgcgcgcaca cacacacaca cacagagaga 113580
gagagagaga gaaagagaga gagagaaagg ctgaaaaaaa taaatagaac cttaaggata 113640
tcagtgaaaa tagcaaaaga tttaatatat gggtaaagca agtcacagaa ggacgggaag 113700
gagatattgg gacagaaaaa aatactcaaa gcaatgatgg ctgaagactt tacacgtatg 113760
aagaaaatga taaactcaca gtcaagaagc tcaatgaatc agaaatagta tttttaaaag 113820
caaaactcta tgatttactt gggtacatta tagataaatc gtccaacatc aaagataaca 113880
aggataatct tataagccag aggaaaacaa tatcatttac atagagggac agtaatgaaa 113940
gtgaccgatg ccttctcctt ggaaacaatg gcataacatc tttaaagtga taaagagaaa 114000
taaaaacaga tcaacctagg acgacatgtc cagccaaaac aaacaaataa acaaaaaaac 114060
cctttaaaat aaacgtgatg taaatacgta ttctgccacc tccagaggaa acaagcaaaa 114120
aaacaaaaga atgtttccaa ggcaggcttc tgtattaaaa gattttaagg aaagttattc 114180
aggtagaaga aaaataatac cagatgggaa ctttaatcca tactaagtaa tgaagagccc 114240
tggaaatggc aaatggcaat gtcaatataa aatactctta tttatctaat ttttaaatgt 114300
atttaaagga caatttgtga tattaattaa aataatagga atatattgtt gtttcaacgt 114360
atgtagtagt aaaattcata aaaacagtag cacaaataat gcagatgata actggaagta 114420
tactgttaat gagtttttttg cattatccat gaagttatat aatattaata gatggttgaa 114480
tgtgatagtt taaggtggga tattataaat cctaggacaa ccaaaaaaat ttaaactgag 114540
aggaatggat agtaagagga atagtccttt tatgcaaaag aaggaagaaa aagaggaata 114600
aagaatataa aagatatggt gtaaacagaa aatacatagc attattgtag acacaaactg 114660
aactacctta tgagtatatt aaatataaaa ggattaagca ttacaaataa aaggcagaga 114720
ttgtaaattg aataaaaacc acagctaagt gtgttctttt tagaataaat actctttaag 114780
tgtaaagatc tactttaaac accaaaatat gaaaaaggat atataccatg aaaacctgaa 114840
tcataaataa gctggagtgg tgattaatgg atgcaggcac tcctaaagac taataagtga 114900
atgtggtcaa attgaagaaa caaaagtata tacgtgctca atgtgcaaaa actttttctg 114960
tatacatgct atgatccttt ggaaaattaa agttttaaag caatatcact gacaatagta 115020
tcaaaaccaa aaaatattta gtgataaatt tcacacacta tgctcaagga ctatacacct 115080
tgcactagaa aacaatgttg aggaaagaat taaaagatct aaatatacac catgcttata 115140
gattaaaaga ctccatatca gttctcgtga aattgatctt tggatgaaac ccacacccaa 115200
gcactattgc aacagtcctt ttttggaaaa aaaaattgga ggacttatat accttaatat 115260
aaagacttat aaaagtacag gaatcaagac atgtggtatt ggcctggccc cttggctcat 115320
gcctgttacc ccaacatttt gggaggctga gtctggagga tggcttgagc ccagatgttc 115380
aagaccagcc ttagcaacag agtgagaccc tctctctaca aaaaataaac aattagatcg 115440
atgtgatgac ttgcacatgt agtttcagct actcggaatg ctgaggtgag aggattgctt 115500
gactcaggag gtctagccat gagtgagcat tgatcatgcc tctgcattcc agcctggatg 115560
atggaatgag acactgtctc aaaaaaaaaa aaaaaaaagg atatgtgtta ttggccaaaa 115620
aagtatgcaa acctaaaaag ggatggccca ccaccagacc cacatacata tatggtaaat 115680
ggattttccg tatagatggc aaagcaattc aatggagaca aaaatgtttt acaaaatcat 115740
tctgaaccat ttggatatcc atgatacaaa acaaaagcag aacttgactt ttgcttttca 115800
tctcaaatta ttttgatatc tcttccacct aagtgtcaga gctaaaactg aacctgaaat 115860
```

atgaaagttc catgaaaaaa tataaaatct tcacaacctt ggagaaggca aacttttttg 115920
aggcaggagt ctgtaaacac tcactataaa ataaaacaaa ttataatgtg ggctttcatg 115980
aaaactcatg cttaccaaaa gtcattgtta agaaaataaa taggcaagta acacatgaga 116040
agaaaaatgc tctctgtcca tatatctgac aaatggcttg tgtccagaat ataggaacat 116100
ttctcccact cactaaacag aggacaaaca actaatgggc aacagattga ataggcattt 116160
cttggggata gatagatgta cacatagcca ataagcacct gaaaaaatgt ccagtatctc 116220
agccatgaaa aataaagagt tataatcatc atgagatgtc accaaacacc caatggacat 116280
ggatattatt aagaagacac cacagtaact gatgtcactg atgtagagca aggatgtgaa 116340
actctctcat atgctggtga aagtgcaaaa tgatacaacc acttttgaaa tcagtctgat 116400
agtttctcca aaagttcaat aaatgcactt ttaccctaca aacctgcaat cctgtttgtg 116460
aatatttacc ccacagaaat ggaaacataa gtccacgaag acatctccaa gaatattcat 116520
agcagcttta ttttttataa ccccaaactg tagacaattt caatgtcaat caataagaaa 116580
atgaataaat aatttgtgaa ctagtcatac aatggcatac tgttcagcaa taaaagggag 116640
catgtttttg atactctcaa atagtatgga agatgctcaa aaatattaca ttaaagaaag 116700
atgccagata acaaaaatga acattatgta tgagtctatt gatgtaaggt tccagaaagg 116760
taaaactaat ttctggtgaa agaaaccaat atcatttgcc tctggccatg ggaagagagt 116820
agcagagatt gattgagcag taaaacgaag tttttttctg gggtgatgta aatgtcctgt 116880
attgtgattg aagtgtgagt tacacaagtg tacatgttca tcagaagtca tcaaactaca 116940
tctaagatct gtgcatttga ctatacatga aaatatacct cagttgaaaa tagatcaata 117000
acctccctca tatactatac ttgctaacac agccagctgc ttggagaacc agcttgctgg 117060
aatggagaat ctgggcttga gactgggtca catgtataga gtctctacag agacaatgtt 117120
gcattcccac ggtacataat acatttcaag gtttctcaga cagccacatg tcatgaatgt 117180
gaggattctg agaggttgga gcaacattcc tgggaggaac gaaggggagc acattctcca 117240
agatccccca ccaccggggt cctcaccggc tgtgcttttt tttttttttt tcttgacaga 117300
gtctcgctct gtcgccaggc aggagtgtaa tggcccaatc tcggctgatt gcagcctcca 117360
actccagggt tcaagagatt ctcctgcctc agcttcatga gtagctggga ctacagatgt 117420
gcgccactgc gcccagctaa tttttgtatt tttagtagag acggggtttt gccatgttgg 117480
ccaagatggt ctcgctctgt tgacctcgtg atccacccgc cttggcttcc caaagtgctg 117540
ggattacagg cgtgagccaa agcacccagc ctgtgcctct cacttactca attgtttttc 117600
tgaaccctcc atagctggtg gaccttttca gatcccatag tctagccagc cctctcactt 117660
tatgccttgg gtcccactgt tccttcatct catccccctt ctgtcagtcc cgcagtggct 117720
gtggccagta gaggatggac tgagagtagg agaggaggtt ctgcccagga acccatccta 117780
gagaaacagc atcctgcctg ggacctagtc ttccaggtca gcttttataa gtcttttaga 117840
ctcaaactca cttgacccac ctgaagtggt attgacaata atgctatttt catggttgtt 117900
tttcactgta aatgcagagc cttttagcta cacgactagt acagagagta agggaggctg 117960
gcctgggaat gatatcatct tggatggcat ttcctccttg gagaaatata tgttagttcc 118020
aactcacatg ttactataca gtcctgtaga aagagataca gagagttaga caggtataga 118080
cgcatttgta tatgcataac aatctataag acacacatca aaatccgtat accggttcct 118140
ctaggggtat gtgcttggca gaaggtagaa ggagggtatt ctggttcctt tcttttgcac 118200
atttatgtat gatctcagtt tttatatgga gcattgatag ggtttggcta tgtccccacc 118260
caaaatctca tcttgacttg taatctctat aatcctgata atccccatgt gtcaagggca 118320
ggaccaggtg gaggtaactg gatcatgggg gcagtttctc ccaggctgtt ctcatgacag 118380
tgagagagtc tcctgagatc tgatggtttt gtaagtgtct ggcatttccc ctacttgcac 118440
ttactctgtc ctgccgcctg tgaagaaggt gcctgtttct cccttgcctt ctgccatgac 118500
tgtaaatttc cagaggcctc cccagcaatg tggaactgtg agtcaattaa aactcttttc 118560
tttgtaactt acccagtctg tctcgggtat ttcctcatag caatgtgaga acgggctaat 118620
acaagcatat actacttttg atattttaaa ataaaaatta tcatctatct ttgaaaggca 118680
tgcacaaatg ggaagttgag gaacatttgt gttgtggcaa ttgtatgata cctttaatgg 118740
gaatatttca aagacacttg ttaagacttt gttagaacaa aatgtagagg gtgctggatg 118800
tccctgaata ttcttccgcc tcctgtaact tgtattgctt tggaatttcc agtggcctga 118860
caatgaacta ctgcaggaat ccagatgccg atacaggccc ttggtgtttt accatggacc 118920
ccagcatcag gtgggagtac tgcaacctga cgcgatgctc agacacagaa gggactgtgg 118980
tcgctcctcc gactgtcatc caggttccaa gcctagggcc tccttctgaa caaggtaaga 119040
agtctgtgtc ttaccttgtc tagcacatac ctctctatgt gcttggacaa cgggatgaaa 119100
agacatgaaa aaccacactg atgcagaagc ctttagtgct acacgggagc tcgagtgttg 119160
gttgaggttc tgccatgacc aaggaagtct cagtgccgtc cctgggaaag ccagagctgt 119220
gatttttggc acaacttgtg ggagtagtga ctttaggact ggcgcaaaac ctccagggtg 119280
ctcaacttaa ccactcacct tattctaaaa tgggttattt cagtgtccca gtcaaattcc 119340
tattctaaca tgctgtcaac tgtgtgatta tttccaagcc aataagcatt tccagtaatt 119400
tcttaaaata gtgttcattg cagtcttcag cgttgtggct cctgagggat gtggcccctg 119460
attctgtcgt cctagagaag cctgacatga ctgcattgat tctgtatcgt cctgggtcta 119520
tgtggctgcc tggctgtctg taatcatctg ttttattttt atttttttct acagactgta 119580
tgtttgggaa tgggaaagga taccggggca agaaggcaac cactgttact gggacgccat 119640
gccaggaatg ggctgcccag gagccccata gacacagcac gttcattcca gggacaaata 119700
aatgggcagg tctggaaaaa aatgtaagcc actttgattt ggactctttt tccctttgct 119760
gacaaatctt ttcaaacaga agaggggcag aggaaaatac tggaaagact tcaggaggct 119820
aagcgtaatt agccttagca tggaaagtgc aagcagcaca ggccagcaaa gccccacgcg 119880
tgtgggggtt ctcaggcctc ttctcttttg acatttcttt actgtttcca ttgttgggtg 119940
ctgtttctcg tttctagtgc ttgtcctcta agccaggggt ccccactcca gtactggtac 120000
tggtactggt actggaactg gtaattatct gtggcctgtt aggaactggg ctgcacagca 120060
ggaggtgagc ttcgggggag caaacaaagc ttcatctgta ttttctgctg cttcccatca 120120
ctctcatagc tgcctgagct ctgccagctg tcagatcaga ggcagcatta gattatcata 120180
gcacaaaccc tattgtgaac tgcacatgtg aggaatctag attgcatgct ccttatgaga 120240
atctaatgcc tgatgatctg tcatgcttcc atcacccccca gatgggacca cctacttgca 120300
ggaaaattag ctcagggctc ccactgattt taccttatgg tgagatgcac atttatttca 120360
ttatatatta caatgtaata ataattgaaa taaagtgcac gataaatgga aggtacttga 120420
gtcatccttt aaccatcgcc ccctcacccc aggtgcacag aaaaattgcc ttttatgaaa 120480
ctggtctctg gtgccaaaaa agttggggaa ccacactgct ctgggttcta gtagtcagag 120540
atgccctcta tgaggcttaa gtcagatttt tctagaaaag atttggatgg gccatcaggt 120600
caccatgaga cttcccttag cctcatgcat tctctgtgat ggtttacttt ggggcctatg 120660
aatagggaag actgagatat aggaaaaacc aaagtgtctg tgttccccca ctctcacacc 120720
catgtaacat aacacttctc acaccagata tggggggatt tctcctcaca ccccaagcga 120780
gtctccagca gataccagct gggtgtccta caatgtaact cggtcctgac actctatctg 120840
gagacagtgt cagatcccac aagttaaggc tcagtcctac aagactgccc cactgcagat 120900
gccaatccca agttgcaggc tgtgacctgt acttctgccc agctggataa agatctgttt 120960
ttctatatga ccctccatgg gtttgattac tttgctagag tggctcacag aactcaggga 121020
aacacgttac ttttatttac ccatttatta taaaagatat taaaaaggat cctggtgaac 121080
agccaggtgg aagagatgca cagggcaagg cacgtgggaa ggggctcaga gcctctatgc 121140
cctctccagt gcaccagtcc ccagtaccct aagtgttcag caacccagaa gctctccaag 121200
tgcagtcttg ttgggttttt atggaggctt cattacagag gcacagttga ttacatcatt 121260
ggccatcggt gatcggctca ccttcggccc ctcttccctc cctggaggtt ggagggtggg 121320
gctgaacagt tccaaccctc aagtcacatg gttggttccc ttggcaacca gcccctgggg 121380
ctatccagga acccaccaag agttgcttca ttgcagctcc cttcacccag gaaactccaa 121440
gggatttagg agctctgtgt taagaactgg ggggcagaga cccaatatac atttcttatt 121500
ctatcacaat atcacaggaa gctaaggatg atactgcctt tgtgtgtctt ggctgtggat 121560
ggtgcataat gcatggaagt aagcatttct gaatcaacag caaacaggct ttatcaggta 121620
gaagacccct cagcgcccca gggacaaagc tcatcaatga tgtcccactg tcctctgagg 121680
ctctagctct aagacctcca gtgggtcaag ctcctggaga agtggcacat tctccaaaga 121740
cccttcaggg tcaccacacc ctggttaagg gtgtggcctc ataactcctt ttgactatga 121800
ctgatggctt acagcataga aagaaataac tttgtcaaaa aatataataa tgatagaaag 121860
gaagaaggaa cgctcccttt tgtcttctaa gaatagatgt gaaatgtgtg tgccttagaa 121920
tatcttctcc ctctcctgct ccacgtgagc tggagcttac atgcctgctt gttttcagta 121980
ctgccgtaac cctgatggtg acatcaatgg tccctggtgc tacacaatga atccaagaaa 122040
actttttgac tactgtgata tccctctctg tggtaagttg ccttctgttt tggtaaggaa 122100
actgcttcct taatatggat ttggaaaaaa aaaagcaaaa aaaacagaaa atggcttttg 122160
agctgagtgc ttctggggag gagatggctg ccctctccac cagagcctgc ttttcatcat 122220
ggccaccttg aacctgccct actattggcc ccatttgtta ggaaaacacc cgcccctccc 122280
accacacaca cataaataaa ataaatgtca aattcccaaa gggcaaactt agaggtgatc 122340
taatcagccc gggatagtcc caccgaaccc ttctttgtct agcgtgggat gcatgaaaaa 122400
caaatttaga gtcattatga tgaaaaactg tcctcttctg cagctgagaa gaaaaaaaaa 122460
atacgagcag caggaaacag ctaagcatgt aatgcacatt gtaaacctca gatggccatc 122520
ctaggaaatc aatgaagggt agtgcagctc tttagcccca gatggccttt ctcgtaagat 122580
tactactcat gagtcccatt agcgacattg cttagagact gcttgttagg ttccttcctc 122640
attgctctga gactcttatt gggagtatga ggcttggatc aggggaaggg gaattgacat 122700
tagatcttaa atgattgggg taacaaatcc atgggggaaa aaaagccact tgtacttgtt 122760
ccctattttc ttcctgctga ccaatcaact tgtctgtccg agttacagaa caccaccctg 122820
gacttttctt ttgtgtaatt tggttgcttg tggttgggtc tgccatgtga agggaccttg 122880
agctggggga agaaggttgg cctccaagtc cactgaagac cagcatcctg agattgcctg 122940
gggaggtggt acagggcagt gatgaagatc atgggagcca cactgcccat cgtcacattt 123000
gggccactcc tggggagagc aagagggaag aaggagaggt tagggtgata ggaaagattc 123060
tacttggcca atattattat aatgtggcat tgtggtctct ggatttagtg tgagttgata 123120
gctgactttt ttctcgagtg ggtgcttttg ttctattttg tcggtgctat tgcagaagca 123180
tcttggtggt tcctctacct caaagtctct tgatggggtc agttccagtt ctccgcttct 123240
ggccccatct agtacacgcc actgcctctc actgcctggg ctctctatcc ttgacaggct 123300
gccttgaatt taagcccagt ctgacttacc tgcctcaaac acccacagta gtgcctggga 123360
ctcatgcacc tttgactccc atggaaggga agtgcagtag cttcccaggt gcaattctgc 123420
tgtcctcacc cacattgagg atgtatgaga atcaggttct tagagattgg agaaagaagg 123480
aagaatggga acaagatttc ttccaatgga ctgtgaggtt ccccacctta ctttgatgta 123540
agacaagtga ggttaacccc aagcctggtg aggagggttc ccatcagaca cttggaaatc 123600
ctgaggactg tttcctgcag aaggatgtgg ttggtgggat attcaggttt gactcatgat 123660
tgagaaagtt agagcctctg gttggagaaa gagtttaata actatttcat ttccaccaac 123720
acattcagta cgaataataa ataagtaaaa ataaatagaa acattcagtt ttattttgaa 123780
tagtaggagt agggtataat ttctgtagtt actcttttag tacaatgatg catgtttact 123840
gtatgtaagg catactagca gaaattgagc tcagcactag aaaagatgat tgcattccat 123900
gccatgcttc ttttttacaa aagacttcta tagatagatt ctcaaaacaa cccacagcaa 123960
atgaaaagtt atttggaaaa ctcaggttcc agattcactg gagtgtagaa tctctggttg 124020
gttggggagg aatttcctct tgcagttgtt attaataatt atatgaataa ttattaacta 124080
tattaatatt tatagttttg aagaccttga agggctggag acaacagaga agcatttttg 124140
aacaccctct gtagcccctg cactgttgta ggcattgatg ggtggtacca aagatgggac 124200
actttcccta cctccagaga ccttgtgggc ttgctgcaga gagaaggcag ggaggaggaa 124260
aagaagaata gaggcacatg tgtgtaaatt acccccacag cagtcagtta gtcatgggag 124320
gctccccaga agaactgtcc tgaagctggc tgagagaagg caacatttca acataggaca 124380
gttatccttg ctacataaaa tcacatacac acatgcacat atgtccacac acagagactc 124440
acatgcaaaa gaatcctttg tgcctttcag taaactttac atggtttaga aagaacttat 124500
atttccttga aaggagagtg tcctttgttg tttactacca ctttttaaac ttagaaagaa 124560
aaatctaaag agtgtttatg attttaccat ttaatttcac ctttgagatg tgaaaaacta 124620
gtgcttggaa ttcgtcctga attaaacgac acaattgcta acttggactc aaatgcgact 124680
tcttttccca ccttgtgcca cagcatcctc ttcatttgat tgtgggaagc ctcaagtgga 124740
gccgaagaaa tgtcctggaa gcattgtagg ggggtgtgtg gcccacccac attcctggcc 124800
ctggcaagtc agtctcagaa caaggtaaga acaggcccag aaaccatcta tactgtcctt 124860
ccatgtaagc cccacaaaac ccttctacat ttacacagaa cccacacagc tgatgcatca 124920
atacctgcct ctctgttttc tgaaggagga aaaaatatag aaaaattaaa aaaagttata 124980
ttattatagg ttctctactt ggaaaatagc caaaatacaa atctttttct tgatctgggc 125040
agttccatca aaatctgtag gcacagtgat ttgcaccaag ttccaatact tttggaaaat 125100
attgaagatg ctctgagggt ttctatggat atccattgtc tcactgtcag atgaaaagaa 125160
agggaagttt ttagaaatgt gacactttgc agtgagggag gacaagagca aacttaccta 125220
cagtctatca caggcacaga ttttttttta cacttttgtg aatcattgaa ttcaatgccg 125280
aggctattca tctattcaca aacacatgaa caaattatgg gttgtgatcc ccataaatga 125340
agagtaatca gtccgaaccc acagaacctg gacattttgg gtatcgtttc agtggaacat 125400
gcaattcgta agttcagttt gcttgggtgt ctcttaggaa gaacacatag gacacagacc 125460
catctgcctg catgttttgc ttcctcatct cctttctaca ccagggcacc tgtgctcaat 125520
tgctgttctc ctctaaagag acttccttct gtaagtttgt gaaatgccat cgacaaacct 125580
gatcgcatcg catttcactc tgctgttgag ttgatttttc tttactttat cgtttgtaac 125640
ttcttgctct acagagcttt caccttccac atatttcaga ttcattcttt cctaaactgt 125700
gtggtggtct atgtcctcac tgactatcaa catactgcca tcatgcactt cctatctcta 125760
ttcctcttcg ttgcaatctg gctccaagtg gctcacacca ttattctgat ctatcaactg 125820
cctacacagt cctagaaagt aagtgagtca agaaacatcc cccaaaagta aacttttcag 125880
gtaagatcag aagaccctca tgagtcactg ctgctcagga tcgtatctgg ctccttgaag 125940
agtgaccttg catagatctt gtcataaaaa atgaaagaga ccttgggaag gtcttgggct 126000
ggtcactttt gtcagagtcc agggctgtgg ggtgaaagcc acagctatag agcttcattc 126060
tggagtcact tagctttgct ctcctgggga caggctgtgc ctattcttgc ctcaggcatc 126120
aaaaaaagtg gcacagatgg gcccttctga aaaatctcac tactggagca cagctcgaag 126180
tttctactat cctgacgttg ggcggtagtc ctttgctttg ggaatatgaa catgatcaaa 126240
actgagtgaa cttgtcttcc tggctttctg tacaatgaag tagaacaaac catccaattt 126300
gaccaaagcc ttggcatgtt ttctttctag gtttggaaag cacttctgtg gaggcacctt 126360
aatatcccca gagtgggtgc tgactgctgc tcactgcttg aagaagtacg tttaagggaa 126420
aactgacatg gggtcttatc ttcaagactt ttttcctccc tctcttcctc catcccttct 126480
ttcttcccac cctccccttc cttcctcccc acctctcttc cttttctgga aggaacacta 126540
ggaaccaggg aatgcatgca gaatcctgag gcagaatttc cagggcaatt ggatgagaga 126600
ggagggaagt gtttctagag ggaatctgca gagggaagac ccagtgcaag tgattttttg 126660
gacctgtata aaccgcagga cagagctgtt cactaccaga ggcatcaatc tgtattgcat 126720
tgctctagag caatatctga ggctgaataa tttataaaga aaagagttta attggcacat 126780
gtttctgcag gctttacagg aagcaggatg ctgtcatctc ctctgcttct gtgtgggcct 126840
aaggaagatt acaatcatgg tggagggcaa agtgggagca ggcatgtcac atggccagag 126900
caggagcaag agacagagag agatggggtg gggtgctgc acaataccaa atgaccagac 126960
tttgcaagaa ctaagagtga gagctcactg atcaccatga agatgtggcc caagccattc 127020
aagagggatg cacctctatg atccaaaccc ctttcacagg ccatagctcc atcactgggg 127080
actacagttg aacacgagat ttaggtgggg acaaatatac aaactatatc acagtctctg 127140
atgaaacaga ttgagaacag accttaactg tcagtttcca gcaaattgtg aattttgttt 127200
cttgccactc ataagtcact gattctgggt ggccgagggt gtcagaggga cagcgccaag 127260
ttcatggcac agaggatacc tgaaggggct ggaccatatt tttctcttga catcctcatc 127320
ttttctaggt cctcaaggcc ttcatcctac aaggtcatcc tgggtgcaca ccaagaagtg 127380
aacctcgaat ctcatgttca ggaaatagaa gtgtctaggc tgttcttgga gcccacacaa 127440
gcagatattg ccttgctaaa gctaagcagg tactcgctca cctgtggtct tcaccccacg 127500
ctggtgaaga tatttgcttt atgtctgggt tttatgggcc atggccactg catggcagtg 127560
gggaggaact gtctatcaca tgaaaggctc aagggctttg gggacagcat caatcttcaa 127620
ccccagccct gccacatgtt agttgtgctc tttaaaaagg cagaaggatt cgtttcctca 127680
cgtggaaaaa gagataccct gttacccgta aaacttactt aatgttcacc agttcatcca 127740
cattcatgat cagggaaagg ttgttattcc aggctaacta ttctcctttc ataataatat 127800
gctggagaga atcaaatgag attgcatttc aaagcgcttg aaaaaccacc atatcgagcc 127860
atgcttagtg tgggcgcctc taatcactgc tattcaggag gctgacgagg aagaattgct 127920
tgagcccagg acttcaaggc tgtaggcagc tatgattgtg ccactgcact ccaggctggg 127980
tgacagatca agaccctgtc tcaacaaaag aaaagaaaac aaaacaaatg aacagaaata 128040
ttccacaatg tcaaaaaaaa aaaaaaccca cacaacatac aatttacaaa tgcaaataat 128100
aatattattg ttgtcttctt tgattttctc tttcctggtg aaattttgtt ttattaagcc 128160
tgacaaagtg atacctttgc ttacatcact taaagttagt ctatttggac ctaggtgaca 128220
gtacaatcag ctaagaaaca gtatttgtag gagaggcagg tttgggacag gtgacaaggc 128280
atgtggggtg ctcgctgtgc tggtggctct ggaaggcagg gtgtcaatgc agacagggat 128340
gagcatggcc tggttgggaa ggcatggggc aggcaggagc ctgagctgct ctcctgggcc 128400
tggtcacaag cccatggcag cttctctggg tctgtgaact gaggggtgat gtcctggaat 128460
cctctgacac tctaggaagg agagaagggc ctttctggct cagcctttat aaacagtagc 128520
tgatctccct cttgctcccc agggtcctcc ccaccatccc agcaaatgtg caaatacaag 128580
atctctgctc ctcatggtcc tcagagagct ggggtgttct gatggcttga acaagtcact 128640
taggaaatgt ggggttttgg aggcattctc tgataggctg atacgttttg agtttagagt 128700
tcccaccgca catccccaca cccctagagt ctagggcatt tagtgctcca tgagggaacc 128760
tgtagagtga ggacatctgc atcacaggct gggccttcta gtgtccagaa gcagaaagtg 128820
tgtctgcttc aaagttggtg ctaatgatga tttttggtca gaatacggca tttctcattt 128880
ccattccttt atccccttga acttactaaa gtagaatcag gtctaaaaac cagagttcta 128940
atctttaaga gtccctggga ttctaaggta tatgaatgtc cttggaaaac aataccattt 129000
agttcatgca aggtgcttat ttcccatcct ctttcatttg atgtctagca ttttactgca 129060
ttcttaccac cacggtttag taacattcac gaggaggaag tggaggatcc agatggagca 129120
acttgctctg ggcacacaag gcatttgcaa ttttataccc tcttgatgat gtctcagcca 129180
gacattctgc ccagtcatca atgccctctt caattaatat gaaaggacac acttggcatg 129240
agattccaat cgtgcacaga atatacatga gaagtgtgcc tttgtcatcc ctactttcaa 129300
aggctaaggc caccctcagt ttcttgcatg caactgatgc ctttcaaatg aaaccttaca 129360
tctgtgtagt ccataggcaa ccacaggcaa atgtgagggt gaaacgctgt gttctacatt 129420
gttctgtgtc agtgaagcaa ggcagtgcca gctcagaggg ctctggggct tcaaggcagg 129480
gatgcctggt tgtaggtact gccacttcca gctgggcagt gaaacataac tgctaatact 129540
ttccttacag gcctgccgtc atcactgaca aagtaatgcc agcttgtctg ccatccccag 129600
actacatggt caccgccagg actgaatgtt acatcactgg ctggggagaa acccaaggtg 129660
agatcaattc cattgcccac gtaacaaatt gtttttgacc ttcagtgcat gttacaaaat 129720
gagcattttg gagatagttg tacaaattcc tacccatgaa tgtggtctac ccactcctga 129780
ctttgcctgg acacctgtct atgtctccat aatcagtctt caagggactt gggcaagggg 129840
agcggtgcca tttccttgag tctctctctt ttttgttttc agaatctttt aattttttttt 129900 gtaatgattg tatgtttccc ttacaacaaa aacaaacacc agtagaggtc tttgagtctc 129960
ttaatcataa tttcagcatt catattgctt ccccaggtaa gtggggtttt gacccagccc 130020
tcaagttaag ggtgttagat tatttttcat gtgaaattag acagactgcg tttctaaaca 130080
tggtgcaaaa cagtaacgac aaaagttgta attaaactat tcttcttccc aaatacccac 130140
atgtctaatg tgtgtgtgag ggtgttaggc aggggacctg aagctggggg agaggcagac 130200
agttcccatg gccccaagtc taggatggca tttggtattg gttgatgggt gagagcaaga 130260
gagggaatat ttttgtgcat gatgtggtat cagcacctgt actacatttt atggattcct 130320
tcttctcttt gcggtatgcc ctgacaataa ttatatccgt cagccttacc cccttggcag 130380
taggaaaact gaaactgtct taaagtctca gctctacttt ctcagaggtg caggcaaggg 130440
cactgggagt ctggggccct ggaaaactgt tctgactctg ccacttgcca gatagacctg 130500
aactagacac gttacctctt tgtaccactt ggctctaatc ccttatctgt aaaaccagca 130560
ttttcaaatg gtgctttgca catcagcctt ttgcataagc tttgatttga taaaatgttt 130620
tttgtgtttt taaaaagatt aaaaaccaca ggtttagata atttcaaagt aggcttccct 130680
ttttctgtca ttttcctatt atttttaaaa cctcacctcc ttgactcctt gttccctttt 130740
tctgcactgc tgagtctggg agcactgagg ccaggtaaaa ggaaacttgg caaatgaggg 130800
gcacctatgg gtgtgggagg ctgctcctgg tgtttgcata ttttaaaatt taaatgctac 130860
aaaccactgt gagttaggta ttattgttcc tattttacca ttgaggaagc tggggctcag 130920
agaaggtgga gggtggtaca gacaaacctg aattggaacc ctggctcctg cctatgggct 130980
gtcaggactt agaaaagtcg tgagctctcg ctgattgttt cctcagctga tgtgggctgc 131040
agggctgtta tgggggaaat aataagaaag tgcatcaagt gctgagcaca tcctaagcac 131100
tccatcatgg cagctcctac tactaataaa gaatagaatt atatctaaca tgattctttc 131160
ttgcaagtga cagaaaatcc aactcaaatt ggattaagca aaacaaggga aattcttagt 131220
gagctgcaaa gttttcaggc tcacatgatg gccccaaatc ccaggtcctc ccaatcatgg 131280
agtaggcact atttgggggc acaaaggtga cattcccatg gctgcagatg ctgtggtgct 131340
gtggctgtac cgggaaagaa taagaaaggc cactctccca attatgtgaa caatagtctg 131400
cccactctga gaagtcaaac ttgggtcaca gtcctgcccc tgaacccatc actgactggc 131460
tctgacctgc accaattgtt ccatgttgga ggtgaaggca agaccccact aatacccata 131520
aggggcaaaa gttagataga tccttcaaga ggattatggg aggtagggca aaaagctgct 131580
gggcagccag aaagcaaaca gagcctctat gatacctcaa ctgatgaaag catgaagcta 131640
aaatcataag gatctgggtg tgagttctgg ctctcccatc ttccatgtga cattgggcag 131700
ttatttaatc tcttttagcc tccgctttct catcttacat atgagataat tgtgaggatt 131760
aagattacac ataatcatca tcatcaccgt ccaccactac caccatcatc cccatcaaca 131820
tcatcgccac cactatcatc attcttactg gcactaccat caccatcacc accattccac 131880
caccatcacc aatatcatca ctgtcaacat cattaccacc atcaccatca ccaccaccat 131940
catcattact accactacca ctactaccac catcaccatc accaccattc caccaccatc 132000
accaatatca tcactctcaa catcatcacc atcaccatca ccaccaccat catcatcatt 132060
actaccacta ccactactac caccatcacc atcaccactg tcccactact atcagcatga 132120
catcaccatc accaccacca tcatcattac caccgctact accaacatca ccatcaccac 132180
aattctactg ccatcaccat taacattacc accaccatca tcactatcac catcaccacc 132240
atcatcacca ctgccattat cactgccacc atcatcacta tcctctatat ttcctcatct 132300
gtattatcat tactaccacc atcactatca ccaccatcgt caccatcata atcaccatca 132360
acaccatctc caataccacc atcactgtaa ccatcatcac caccaccatg atcactatca 132420
ccatcatcac aatgatcact gtaaccatca ttactaccca ccaccatcac cactactcca 132480
ccaccatcac cattatcatt accatcacca ttatcaccac catcatcatc accagcacca 132540
ccatcatcac cagcaccacc atcaccatca ccatcattaa caccatcact atcaccattg 132600
gtttaatcat caccaccatc atcataaata aacatcacat aaccagggtg tagctgggtg 132660
ttgaccccag agcccactca ctgtttcctc tctcccaccc ccatccacac atttctaacc 132720
accatcctgc actgggctcc cagtctcctc tggtctcacc cacatgtcca ctgagaaaag 132780
gattttcaga acaccaacta gaccaggagg agccacatac ataactcagg cctgcttatc 132840
aactttctac atgttaataa tgacatcaga tcaatgggtg ttctcagctt ctcagaagga 132900
ggtcaaaatt ctccccctct ccccttcatg tgtccagacc ttcccggatt tggatgtacc 132960
aagtgcagag tggtgttgag gccaaggggc tcatccatgt aagtctcatc tgcaatcact 133020
gggctgatcc cgtggccctg tctccagggc gccatcagag agggcttcaa tcctcaggtt 133080
acctgtggcc caccctgccc tcagaggtgc catctctaca ttggccacga gatggcagca 133140
catactcata gactgcatta atttcccagc aactcctggt gggtttttccc tcttatcagg 133200 atgtttgcct tgctcagaga gcaaatctga gagcagtgac acctaactta actttcagca 133260
aaatattttg agaagggtgc ccctttacac atctgtgcag tccaggtgat gcatcccatg 133320
cccaatgctc ggtagtcagg aggagcttcc tccatgcagc tctgcggaag agactcttcc 133380
acgctgctca tgtaaactcc agattcggtg tcagttttct gacaccgaag acaatgatct 133440
aagtgcagtc aagggctttg gggaaagcag gagagagtgc ctcagttcta gcctgtgcca 133500
tgcttgcaaa gttttgcaaa attctaatga gagctgggct tgcaacattg gaaacttgga 133560
ttatttgtga gagcactgag aaatccctgg gcatgtccat ctggaaaaac agcatttcct 133620
ctggcacttt agcagaggtt ctgtttcaat ttggcgaagg aaattaagca gtttttcaca 133680
aaagaagaac tacaacgagg agaattgtcc ctagtatttc ttctccctaa ttgtcaagga 133740
agtgtaaatt agaaaatgaa tcaggacaat ttccacctac tatgttagct aatattttaa 133800
aaattgaata tcacaagggt gaggcaaagt aattgttttc cagtgacatt ttccactgtc 133860
acaccctttt agagaataat ttggcaatgt tactgtgaga tagaaatatg tctatataat 133920
tatgggaact gagacttcag aaagtaataa ggaataagaa tgaaatttat gaacaaacat 133980
gtggaaggtt ggaagcaaga gtggggccaa cacgcatggg gaggaagcat ttgggcagcg 134040
actccgcaga cccagactca agctgagcta tacaacctcc ttacgcctca gtttcctcaa 134100
ctgaagaaca ggaatgacaa gtgcctgttt cataggaccg ttgtgaggat taagtgagat 134160
ataccacatt atgagcttgt gcctggaaag gttgattctt agtaaatgat gactattctt 134220
ttttattgca ataaaattta tacaacatag agttactatt ttaaccattt ttgcaggtac 134280
cactgagtgg cattcagtac attcacaatg gtgtgcaacc gtcaccatat ttccaggaca 134340
tttttctcat ccccaaagga aacctcatgc ccattaagca gtcactcctc attaaaatat 134400
tagttatgaa gactgtagca ttttttttaaa aactcatgat ataacattga ttgaaaaaat 134460
cagtatagga aattgtgcat tatgatgtaa tagtaaaaga agcatataaa aatctgaaaa 134520
aagtatataa aaagaatagc aattgtattt ctcagactct ctttacattg taaaaatcat 134580
tttgatagct tcaaaagaaa agcaaaaagt acacaaacaa caaccaaccc caaagcagca 134640
tgacaaagcc cagattgttg aatccaggtc ttgggaacat aaaatcttat atgacatttg 134700
cactttaatg ggtcagagag tccagtggca ttgggagctg ccttgtgttc tgcagcctca 134760
cggacagaca ggaggtccag ctccactgct ctgttcttct ggaatttcct cgtgaacaag 134820
ctttggcctc agtaaccatt tctttcatct ttttaaacac aggtaccttt gggactggcc 134880
ttctcaagga agcccagctc cttgttattg agaatgaagt gtgcaatcac tataagtata 134940
tttgtgctga gcatttggcc agaggcactg acagttgcca ggtaagaaaa gatcaataga 135000
tcaaagtctt gtgctctccc gtctcagtct cagtccctta gacgtcagtc ccaaagtggc 135060
aaattcagga aggttttgtc agtggaagac cccagtctaa gtgttgctca gaaactcccc 135120
agatctgtcc ctgaatgcat attcagatca tctaaggaga cgtcttgggg cttgagttcc 135180
agatccatag caagggagcc gtaagtgcca taactacctc aggccactca ccttcctggt 135240
gtgtgctggt caccagtgac tgaagtggtg gcttttccag tagagaggaa ggtagagggt 135300
acaggaccga gacaaattac acacacttaa caatgatgtc caggctagcc cagtctaaag 135360
gaaacaccaa gttaggaagc aatgcatgca ggattcacaa gggattattt tttttcccag 135420
gaaaaaacta agtgatgtgg ttttgttgaa tagactttgc taagtactta agcactgcag 135480
atgcttgagt aatatgctca taagttcctt tctgatttga attactggga aaatgtacat 135540
atggataaga gaaggatggc atcccatatt aaaaggttgg cagcttaaag ctcacatgaa 135600
ttttccccta cctctgttta gggtgacagt ggagggcctc tggtttgctt cgagaaggac 135660
aaatacattt tacaaggagt cacttcttgg ggtcttggct gtgcacgccc caataagcct 135720
ggtgtctatg ctcgtgtttc aaggtttgtt acttggattg agggaatgat gagaaataat 135780
taattggacg ggagacagag tgaagcatca acctacttag aagctgaaac gtgggtaagg 135840
atttagcatg ctggaaataa tagacagcaa tcaaacgaag acactgttcc cagctaccag 135900
ctatgccaaa ccttggcatt tttggtattt ttgtgtataa gcttttaagg tctgactgac 135960
aaattctgta ttaaggtgtc atagctatga catttgttaa aaataaactc tgcacttatt 136020
ttgatttgaa ttaattttgg ttttggtctt caaaatttc atgctctttt catcccatct 136080
atttttattt ttattttta gactttacgt cctggggtac atgtgcagaa tgtgcaggtt 136140
tgttacatag atgtacacgt gccatggtag tttgctgcac ccatcaacct gtcatctaat 136200
tcggtatttc ttttagttct atccctcccc tagccctcca ccccttgaca ggcccaggtg 136260
tgtgatgttg ccctccctgt gtccatgtgt tctcattgtt caactcacac ttatgagtga 136320
gaacatgccg tgtttgtttt tctgttcttg tgttagtttg ctgagaatga tagtttccag 136380
cttcatccat gtccctgcaa aggacatgaa ctcatccttt tttatggctg catagaattc 136440
catggtgtat atgtgccaca ttttatccaa tctaacattg atgggcaatt gggttggttc 136500
caactctttg ctattgtgaa tagtgccaca ataaacatac gtgtgcatgt gttttcatag 136560
cagaatgatt tataatcctc tgggtatata cccagtaatg ggattgcagg gtcaaatggt 136620
gtttctggtg ctagatcttt gaggaatcac cacactgtct tccacaatgg ttgaactaat 136680
ttatgctccc accaacaata tcaaggcatt cctatttctc cacatcctct ccagcatctg 136740
ttgtttcctg actttttaat gatcgccatt ctaactggca tgagatggta tctcattgtg 136800
gttttgattt gcatttctct aatgatcagt gatgatgagc ttttctcata tgtttgttgg 136860
ctgcataaat gcctttttg gagaagcatc tgttcatatc ctttgcccac tttttgatgg 136920
tgttgttttt ttctggtaaa tttgtttaag ttctttgtag attctggata ttagcctttt 136980
gtcagatgga tagatggcaa aaattttatc ctattatgta ggttgcctgt tcactccgat 137040
gatagtttct tttgctgtgc agaagctctt tggtttaatt agatctcatt tgtctatttt 137100
ggcttttgtt accattgctt ttagtgtttt agtcatgaag tcttctccca tgctatgtcc 137160
tgaatggtat tgcctaagtt ttcttccagg gtttttatgg ttttaggttt tgcatttaag 137220
tctttaatcc atcttgagtt aatttttgta taagtaatgc ccttctttgt ctcttttgat 137280
ctttgttggc ttaaagtata ttttatcaga gactagaatt gcaatccctg cttttttttt 137340
tctttttgct ttccttttgc ttggtaaata ttcttccatc cctttatttt gagcctatgt 137400
atgtctgcac atgagatagg tttcctgaat acagcacacc aatgggtctt gactctttat 137460
tcaatttgcc agtctgtgtc ttttaattgg gggcatttag tccatttaca tttaaggtta 137520
atattgttat gtgtgaattt gatcctgtca ttatgatgct agcgggttat tttgcccatt 137580
agttgatgca gtttcttcat agtgtggatg gcctttacaa tttggtagtt tttgcagtgg 137640
ctggtaccaa ttgttccttt ccatgtttag tgcttcgttc aggagctctt gtgaggcagg 137700
ccttgtggtg acaaaatctt tcagcatttg cttgtctgta aaggatttta tttctccttt 137760
gcttatgaag cttagtttcg ctgggtatga aattctgggt tgaaaattat tttcttttag 137820
aatgttgaat attggccccc actctcttcg ggcttgttgg gtttctgcag agagatccac 137880
tgttagtctg attggcttcc ctttccgggt aacccaacct ttctctctgg ctgcccttag 137940
aaatttttcc ttcatttcaa ccttggtgaa tctgacgatt atgtcttgag gtggctcttc 138000
t 138001

<210> SEQ ID NO 4
<211> LENGTH: 13938
<212> TYPE: DNA
<213> ORGANISM: Homo sapiens

<400> SEQUENCE: 4
ctgggattgg gacacacttt ctggacactg ctggccagtc ccaaaatgga acataaggaa 60
gtggttcttc tacttctttt atttctgaaa tcagcagcac ctgagcaaag ccatgtggtc 120
caggattgct accatggtga tggacagagt tatcgaggca cgtactccac cactgtcaca 180
ggaaggacct gccaagcttg gtcatctatg acaccacatc aacataatag gaccacagaa 240
aactacccaa atgctggctt gatcatgaac tactgcagga atccagatgc tgtggcagct 300
ccttattgtt atacgaggga tcccggtgtc aggtgggagt actgcaacct gacgcaatgc 360
tcagacgcag aagggactgc cgtcgcgcct ccgactgtta ccccggttcc aagcctagag 420
gctccttccg aacaagcacc gactgagcaa aggcctgggg tgcaggagtg ctaccatggt 480
aatggacaga gttatcgagg cacatactcc accactgtca caggaagaac ctgccaagct 540
tggtcatcta tgacaccaca ctcgcatagt cggaccccag aatactaccc aaatgctggc 600
ttgatcatga actactgcag gaatccagat gctgtggcag ctccttattg ttatacgagg 660
gatcccggtg tcaggtggga gtactgcaac ctgacgcaat gctcagacgc agaagggact 720
gccgtcgcgc ctccgactgt taccccggtt ccaagcctag aggctccttc cgaacaagca 780
ccgactgagc aaaggcctgg ggtgcaggag tgctaccatg gtaatggaca gagttatcga 840
ggcacatact ccaccactgt cacaggaaga acctgccaag cttggtcatc tatgacacca 900
cactcgcata gtcggacccc agaatactac ccaaatgctg gcttgatcat gaactactgc 960
aggaatccag atgctgtggc agctccttat tgttatacga gggatcccgg tgtcaggtgg 1020
gagtactgca acctgacgca atgctcagac gcagaaggga ctgccgtcgc gcctccgact 1080
gttaccccgg ttccaagcct agaggctcct tccgaacaag caccgactga gcaaaggcct 1140
ggggtgcagg agtgctacca tggtaatgga cagagttatc gaggcacata ctccaccact 1200
gtcacaggaa gaacctgcca agcttggtca tctatgacac cacactcgca tagtcggacc 1260
ccagaatact acccaaatgc tggcttgatc atgaactact gcaggaatcc agatgctgtg 1320
gcagctcctt attgttatac gagggatccc ggtgtcaggt gggagtactg caacctgacg 1380
caatgctcag acgcagaagg gactgccgtc gcgcctccga ctgttacccc ggttccaagc 1440
ctagaggctc cttccgaaca agcaccgact gagcaaaggc ctggggtgca ggagtgctac 1500
catggtaatg gacagagtta tcgaggcaca tactccacca ctgtcacagg aagaacctgc 1560
caagcttggt catctatgac accacactcg catagtcgga ccccagaata ctacccaaat 1620
gctggcttga tcatgaacta ctgcaggaat ccagatgctg tggcagctcc ttattgttat 1680
acgagggatc ccggtgtcag gtgggagtac tgcaacctga cgcaatgctc agacgcagaa 1740
gggactgccg tcgcgcctcc gactgttacc ccggttccaa gcctagaggc tccttccgaa 1800
caagcaccga ctgagcaaag gcctggggtg caggagtgct accatggtaa tggacagagt 1860
tatcgaggca catactccac cactgtcaca ggaagaacct gccaagcttg gtcatctatg 1920
acaccacact cgcatagtcg gaccccagaa tactacccaa atgctggctt gatcatgaac 1980
tactgcagga atccagatgc tgtggcagct ccttattgtt atacgaggga tcccggtgtc 2040
aggtgggagt actgcaacct gacgcaatgc tcagacgcag aagggactgc cgtcgcgcct 2100
ccgactgtta ccccggttcc aagcctagag gctccttccg aacaagcacc gactgagcaa 2160
aggcctgggg tgcaggagtg ctaccatggt aatggacaga gttatcgagg cacatactcc 2220
accactgtca caggaagaac ctgccaagct tggtcatcta tgacaccaca ctcgcatagt 2280
cggaccccag aatactaccc aaatgctggc ttgatcatga actactgcag gaatccagat 2340
gctgtggcag ctccttattg ttatacgagg gatcccggtg tcaggtggga gtactgcaac 2400
ctgacgcaat gctcagacgc agaagggact gccgtcgcgc ctccgactgt taccccggtt 2460
ccaagcctag aggctccttc cgaacaagca ccgactgagc aaaggcctgg ggtgcaggag 2520
tgctaccatg gtaatggaca gagttatcga ggcacatact ccaccactgt cacaggaaga 2580
acctgccaag cttggtcatc tatgacacca cactcgcata gtcggacccc agaatactac 2640
ccaaatgctg gcttgatcat gaactactgc aggaatccag atgctgtggc agctccttat 2700
tgttatacga gggatcccgg tgtcaggtgg gagtactgca acctgacgca atgctcagac 2760
gcagaaggga ctgccgtcgc gcctccgact gttaccccgg ttccaagcct agaggctcct 2820
tccgaacaag caccgactga gcaaaggcct ggggtgcagg agtgctacca tggtaatgga 2880
cagagttatc gaggcacata ctccaccact gtcacaggaa gaacctgcca agcttggtca 2940
tctatgacac cacactcgca tagtcggacc ccagaatact acccaaatgc tggcttgatc 3000
atgaactact gcaggaatcc agatgctgtg gcagctcctt attgttatac gagggatccc 3060
ggtgtcaggt gggagtactg caacctgacg caatgctcag acgcagaagg gactgccgtc 3120
gcgcctccga ctgttacccc ggttccaagc ctagaggctc cttccgaaca agcaccgact 3180
gagcaaaggc ctggggtgca ggagtgctac catggtaatg gacagagtta tcgaggcaca 3240
tactccacca ctgtcacagg aagaacctgc caagcttggt catctatgac accacactcg 3300
catagtcgga ccccagaata ctacccaaat gctggcttga tcatgaacta ctgcaggaat 3360
ccagatgctg tggcagctcc ttattgttat acgagggatc ccggtgtcag gtgggagtac 3420
tgcaacctga cgcaatgctc agacgcagaa gggactgccg tcgcgcctcc gactgttacc 3480
ccggttccaa gcctagaggc tccttccgaa caagcaccga ctgagcaaag gcctggggtg 3540
caggagtgct accatggtaa tggacagagt tatcgaggca catactccac cactgtcaca 3600

-continued

```
ggaagaacct gccaagcttg gtcatctatg acaccacact cgcatagtcg gaccccagaa   3660
tactacccaa atgctggctt gatcatgaac tactgcagga atccagatgc tgtggcagct   3720
ccttattgtt atacgaggga tcccggtgtc aggtgggagt actgcaacct gacgcaatgc   3780
tcagacgcag aagggactgc cgtcgcgcct ccgactgtta ccccggttcc aagcctagag   3840
gctccttccg aacaagcacc gactgagcaa aggcctgggg tgcaggagtg ctaccatggt   3900
aatggacaga gttatcgagg cacatactcc accactgtca caggaagaac ctgccaagct   3960
tggtcatcta tgacaccaca ctcgcatagt cggaccccag aatactaccc aaatgctggc   4020
ttgatcatga actactgcag gaatccagat gctgtggcag ctccttattg ttatacgagg   4080
gatcccggtg tcaggtggga gtactgcaac ctgacgcaat gctcagacgc agaagggact   4140
gccgtcgcgc ctccgactgt taccccggtt ccaagcctag aggctccttc cgaacaagca   4200
ccgactgagc aaaggcctgg ggtgcaggag tgctaccatg gtaatggaca gagttatcga   4260
ggcacatact ccaccactgt cacaggaaga acctgccaag cttggtcatc tatgacacca   4320
cactcgcata gtcggacccc agaatactac ccaaatgctg gcttgatcat gaactactgc   4380
aggaatccag atgctgtggc agctccttat tgttatacga gggatcccgg tgtcaggtgg   4440
gagtactgca acctgacgca atgctcagac gcagaaggga ctgccgtcgc gcctccgact   4500
gttaccccgg ttccaagcct agaggctcct tccgaacaag caccgactga gcaaaggcct   4560
ggggtgcagg agtgctacca tggtaatgga cagagttatc gaggcacata ctccaccact   4620
gtcacaggaa gaacctgcca agcttggtca tctatgacac cacactcgca tagtcggacc   4680
ccagaatact acccaaatgc tggcttgatc atgaactact gcaggaatcc agatgctgtg   4740
gcagctcctt attgttatac gagggatccc ggtgtcaggt gggagtactg caacctgacg   4800
caatgctcag acgcagaagg gactgccgtc gcgcctccga ctgttacccc ggttccaagc   4860
ctagaggctc cttccgaaca agcaccgact gagcaaaggc ctggggtgca ggagtgctac   4920
catggtaatg gacagagtta tcgaggcaca tactccacca ctgtcacagg aagaacctgc   4980
caagcttggt catctatgac accacactcg catagtcgga ccccagaata ctacccaaat   5040
gctggcttga tcatgaacta ctgcaggaat ccagatgctg tggcagctcc ttattgttat   5100
acgagggatc ccggtgtcag gtgggagtac tgcaacctga cgcaatgctc agacgcagaa   5160
gggactgccg tcgcgcctcc gactgttacc ccggttccaa gcctagaggc tccttccgaa   5220
caagcaccga ctgagcaaag gcctggggtg caggagtgct accatggtaa tggacagagt   5280
tatcgaggca catactccac cactgtcaca ggaagaacct gccaagcttg gtcatctatg   5340
acaccacact cgcatagtcg gaccccagaa tactacccaa atgctggctt gatcatgaac   5400
tactgcagga atccagatgc tgtggcagct ccttattgtt atacgaggga tcccggtgtc   5460
aggtgggagt actgcaacct gacgcaatgc tcagacgcag aagggactgc cgtcgcgcct   5520
ccgactgtta ccccggttcc aagcctagag gctccttccg aacaagcacc gactgagcaa   5580
aggcctgggg tgcaggagtg ctaccatggt aatggacaga gttatcgagg cacatactcc   5640
accactgtca caggaagaac ctgccaagct tggtcatcta tgacaccaca ctcgcatagt   5700
cggaccccag aatactaccc aaatgctggc ttgatcatga actactgcag gaatccagat   5760
gctgtggcag ctccttattg ttatacgagg gatcccggtg tcaggtggga gtactgcaac   5820
ctgacgcaat gctcagacgc agaagggact gccgtcgcgc ctccgactgt taccccggtt   5880
ccaagcctag aggctccttc cgaacaagca ccgactgagc aaaggcctgg ggtgcaggag   5940
tgctaccatg gtaatggaca gagttatcga ggcacatact ccaccactgt cacaggaaga   6000
```

acctgccaag cttggtcatc tatgacacca cactcgcata gtcggacccc agaatactac 6060
ccaaatgctg gcttgatcat gaactactgc aggaatccag atgctgtggc agctccttat 6120
tgttatacga gggatcccgg tgtcaggtgg gagtactgca acctgacgca atgctcagac 6180
gcagaaggga ctgccgtcgc gcctccgact gttaccccgg ttccaagcct agaggctcct 6240
tccgaacaag caccgactga gcaaaggcct ggggtgcagg agtgctacca tggtaatgga 6300
cagagttatc gaggcacata ctccaccact gtcacaggaa gaacctgcca agcttggtca 6360
tctatgacac cacactcgca tagtcggacc ccagaatact acccaaatgc tggcttgatc 6420
atgaactact gcaggaatcc agatgctgtg gcagctcctt attgttatac gagggatccc 6480
ggtgtcaggt gggagtactg caacctgacg caatgctcag acgcagaagg gactgccgtc 6540
gcgcctccga ctgttacccc ggttccaagc ctagaggctc cttccgaaca agcaccgact 6600
gagcaaaggc ctggggtgca ggagtgctac catggtaatg gacagagtta tcgaggcaca 6660
tactccacca ctgtcacagg aagaacctgc caagcttggt catctatgac accacactcg 6720
catagtcgga ccccagaata ctacccaaat gctggcttga tcatgaacta ctgcaggaat 6780
ccagatgctg tggcagctcc ttattgttat acgagggatc ccggtgtcag gtgggagtac 6840
tgcaacctga cgcaatgctc agacgcagaa gggactgccg tcgcgcctcc gactgttacc 6900
ccggttccaa gcctagaggc tccttccgaa caagcaccga ctgagcaaag gcctggggtg 6960
caggagtgct accatggtaa tggacagagt tatcgaggca catactccac cactgtcaca 7020
ggaagaacct gccaagcttg gtcatctatg acaccacact cgcatagtcg gaccccagaa 7080
tactacccaa atgctggctt gatcatgaac tactgcagga atccagatgc tgtggcagct 7140
ccttattgtt atacgaggga tcccggtgtc aggtgggagt actgcaacct gacgcaatgc 7200
tcagacgcag aagggactgc cgtcgcgcct ccgactgtta ccccggttcc aagcctagag 7260
gctccttccg aacaagcacc gactgagcaa aggcctgggg tgcaggagtg ctaccatggt 7320
aatggacaga gttatcgagg cacatactcc accactgtca caggaagaac ctgccaagct 7380
tggtcatcta tgacaccaca ctcgcatagt cggaccccag aatactaccc aaatgctggc 7440
ttgatcatga actactgcag gaatccagat gctgtggcag ctccttattg ttatacgagg 7500
gatcccggtg tcaggtggga gtactgcaac ctgacgcaat gctcagacgc agaagggact 7560
gccgtcgcgc ctccgactgt taccccggtt ccaagcctag aggctccttc cgaacaagca 7620
ccgactgagc aaaggcctgg ggtgcaggag tgctaccatg gtaatggaca gagttatcga 7680
ggcacatact ccaccactgt cacaggaaga acctgccaag cttggtcatc tatgacacca 7740
cactcgcata gtcggacccc agaatactac ccaaatgctg gcttgatcat gaactactgc 7800
aggaatccag atgctgtggc agctccttat tgttatacga gggatcccgg tgtcaggtgg 7860
gagtactgca acctgacgca atgctcagac gcagaaggga ctgccgtcgc gcctccgact 7920
gttaccccgg ttccaagcct agaggctcct tccgaacaag caccgactga gcagaggcct 7980
ggggtgcagg agtgctacca cggtaatgga cagagttatc gaggcacata ctccaccact 8040
gtcactggaa gaacctgcca agcttggtca tctatgacac cacactcgca tagtcggacc 8100
ccagaatact acccaaatgc tggcttgatc atgaactact gcaggaatcc agatgctgtg 8160
gcagctcctt attgttatac gagggatccc ggtgtcaggt gggagtactg caacctgacg 8220
caatgctcag acgcagaagg gactgccgtc gcgcctccga ctgttacccc ggttccaagc 8280
ctagaggctc cttccgaaca agcaccgact gagcaaaggc ctggggtgca ggagtgctac 8340

-continued

```
catggtaatg gacagagtta tcgaggcaca tactccacca ctgtcacagg aagaacctgc   8400
caagcttggt catctatgac accacactcg catagtcgga ccccagaata ctacccaaat   8460
gctggcttga tcatgaacta ctgcaggaat ccagatgctg tggcagctcc ttattgttat   8520
acgagggatc ccggtgtcag gtgggagtac tgcaacctga cgcaatgctc agacgcagaa   8580
gggactgccg tcgcgcctcc gactgttacc ccggttccaa gcctagaggc tccttccgaa   8640
caagcaccga ctgagcaaag gcctggggtg caggagtgct accatggtaa tggacagagt   8700
tatcgaggca catactccac cactgtcaca ggaagaacct gccaagcttg gtcatctatg   8760
acaccacact cgcatagtcg gaccccagaa tactacccaa atgctggctt gatcatgaac   8820
tactgcagga atccagatgc tgtggcagct ccttattgtt atacgaggga tcccggtgtc   8880
aggtgggagt actgcaacct gacgcaatgc tcagacgcag aagggactgc cgtcgcgcct   8940
ccgactgtta ccccggttcc aagcctagag gctccttccg aacaagcacc gactgagcag   9000
aggcctgggg tgcaggagtg ctaccacggt aatggacaga gttatcgagg cacatactcc   9060
accactgtca ctggaagaac ctgccaagct tggtcatcta tgacaccaca ctcgcatagt   9120
cggaccccag aatactaccc aaatgctggc ttgatcatga actactgcag gaatccagat   9180
gctgtggcag ctccttattg ttatacgagg gatcccggtg tcaggtggga gtactgcaac   9240
ctgacgcaat gctcagacgc agaagggact gccgtcgcgc ctccgactgt taccccggtt   9300
ccaagcctag aggctccttc cgaacaagca ccgactgagc agaggcctgg ggtgcaggag   9360
tgctaccacg gtaatggaca gagttatcga ggcacatact ccaccactgt cactggaaga   9420
acctgccaag cttggtcatc tatgacacca cactcgcata gtcggacccc agaatactac   9480
ccaaatgctg gcttgatcat gaactactgc aggaatccag atgctgtggc agctccttat   9540
tgttatacga gggatcccgg tgtcaggtgg gagtactgca acctgacgca atgctcagac   9600
gcagaaggga ctgccgtcgc gcctccgact gttaccccgg ttccaagcct agaggctcct   9660
tccgaacaag caccgactga gcagaggcct ggggtgcagg agtgctacca cggtaatgga   9720
cagagttatc gaggcacata ctccaccact gtcactggaa gaacctgcca agcttggtca   9780
tctatgacac cacactcgca tagtcggacc ccagaatact acccaaatgc tggcttgatc   9840
atgaactact gcaggaatcc agatgctgtg gcagctcctt attgttatac gagggatccc   9900
ggtgtcaggt gggagtactg caacctgacg caatgctcag acgcagaagg gactgccgtc   9960
gcgcctccga ctgttacccc ggttccaagc ctagaggctc cttccgaaca agcaccgact  10020
gagcagaggc ctggggtgca ggagtgctac cacggtaatg gacagagtta tcgaggcaca  10080
tactccacca ctgtcactgg aagaacctgc caagcttggt catctatgac accacactcg  10140
catagtcgga ccccagaata ctacccaaat gctggcttga tcatgaacta ctgcaggaat  10200
ccagatcctg tggcagcccc ttattgttat acgagggatc ccagtgtcag gtgggagtac  10260
tgcaacctga cacaatgctc agacgcagaa gggactgccg tcgcgcctcc aactattacc  10320
ccgattccaa gcctagaggc tccttctgaa caagcaccaa ctgagcaaag gcctggggtg  10380
caggagtgct accacggaaa tggacagagt tatcaaggca catacttcat tactgtcaca  10440
ggaagaacct gccaagcttg gtcatctatg acaccacact cgcatagtcg gaccccagca  10500
tactacccaa atgctggctt gatcaagaac tactgccgaa atccagatcc tgtggcagcc  10560
ccttggtgtt atacaacaga tcccagtgtc aggtgggagt actgcaacct gacacgatgc  10620
tcagatgcag aatggactgc cttcgtccct ccgaatgtta ttctggctcc aagcctagag  10680
gctttttttg aacaagcact gactgaggaa acccccgggg tacaggactg ctactaccat  10740
```

```
tatggacaga gttaccgagg cacatactcc accactgtca caggaagaac ttgccaagct  10800
tggtcatcta tgacaccaca ccagcatagt cggaccccag aaaactaccc aaatgctggc  10860
ctgaccagga actactgcag gaatccagat gctgagattc gcccttggtg ttacaccatg  10920
gatcccagtg tcaggtggga gtactgcaac ctgacacaat gcctggtgac agaatcaagt  10980
gtccttgcaa ctctcacggt ggtcccagat ccaagcacag aggcttcttc tgaagaagca  11040
ccaacggagc aaagccccgg ggtccaggat tgctaccatg gtgatggaca gagttatcga  11100
ggctcattct ctaccactgt cacaggaagg acatgtcagt cttggtcctc tatgacacca  11160
cactggcatc agaggacaac agaatattat ccaaatggtg gcctgaccag gaactactgc  11220
aggaatccag atgctgagat tagtccttgg tgttatacca tggatcccaa tgtcagatgg  11280
gagtactgca acctgacaca atgtccagtg acagaatcaa gtgtccttgc gacgtccacg  11340
gctgtttctg aacaagcacc aacggagcaa agccccacag tccaggactg ctaccatggt  11400
gatggacaga gttatcgagg ctcattctcc accactgtta caggaaggac atgtcagtct  11460
tggtcctcta tgacaccaca ctggcatcag agaaccacag aatactaccc aaatggtggc  11520
ctgaccagga actactgcag gaatccagat gctgagattc gcccttggtg ttataccatg  11580
gatcccagtg tcagatggga gtactgcaac ctgacgcaat gtccagtgat ggaatcaact  11640
ctcctcacaa ctcccacggt ggtcccagtt ccaagcacag agcttccttc tgaagaagca  11700
ccaactgaaa acagcactgg ggtccaggac tgctaccgag gtgatggaca gagttatcga  11760
ggcacactct ccaccactat cacaggaaga acatgtcagt cttggtcgtc tatgacacca  11820
cattggcatc ggaggatccc attatactat ccaaatgctg gcctgaccag gaactactgc  11880
aggaatccag atgctgagat tcgcccttgg tgttacacca tggatcccag tgtcaggtgg  11940
gagtactgca acctgacacg atgtccagtg acagaatcga gtgtcctcac aactcccaca  12000
gtggccccgg ttccaagcac agaggctcct tctgaacaag caccacctga gaaaagccct  12060
gtggtccagg attgctacca tggtgatgga cggagttatc gaggcatatc ctccaccact  12120
gtcacaggaa ggacctgtca atcttggtca tctatgatac cacactggca tcagaggacc  12180
ccagaaaact acccaaatgc tggcctgacc gagaactact gcaggaatcc agattctggg  12240
aaacaaccct ggtgttacac aaccgatccg tgtgtgaggt gggagtactg caatctgaca  12300
caatgctcag aaacagaatc aggtgtccta gagactccca ctgttgttcc agttccaagc  12360
atggaggctc attctgaagc agcaccaact gagcaaaccc ctgtggtccg gcagtgctac  12420
catggtaatg gccagagtta tcgaggcaca ttctccacca ctgtcacagg aaggacatgt  12480
caatcttggt catccatgac accacaccgg catcagagga ccccagaaaa ctacccaaat  12540
gatggcctga caatgaacta ctgcaggaat ccagatgccg atacaggccc ttggtgtttt  12600
accatggacc ccagcatcag gtgggagtac tgcaacctga cgcgatgctc agacacagaa  12660
gggactgtgg tcgctcctcc gactgtcatc caggttccaa gcctagggcc tccttctgaa  12720
caagactgta tgtttgggaa tgggaaagga taccggggca agaaggcaac cactgttact  12780
gggacgccat gccaggaatg ggctgcccag gagccccata gacacagcac gttcattcca  12840
gggacaaata aatgggcagg tctggaaaaa aattactgcc gtaaccctga tggtgacatc  12900
aatggtccct ggtgctacac aatgaatcca agaaaacttt ttgactactg tgatatccct  12960
ctctgtgcat cctcttcatt tgattgtggg aagcctcaag tggagccgaa gaaatgtcct  13020
ggaagcattg taggggggtg tgtggcccac ccacattcct ggccctggca agtcagtctc  13080
```

-continued agaacaaggt ttggaaagca cttctgtgga ggcaccttaa tatccccaga gtgggtgctg 13140
actgctgctc actgcttgaa gaagtcctca aggccttcat cctacaaggt catcctgggt 13200
gcacaccaag aagtgaacct cgaatctcat gttcaggaaa tagaagtgtc taggctgttc 13260
ttggagccca cacaagcaga tattgccttg ctaaagctaa gcaggcctgc cgtcatcact 13320
gacaaagtaa tgccagcttg tctgccatcc ccagactaca tggtcaccgc caggactgaa 13380
tgttacatca ctggctgggg agaaacccaa ggtacctttg ggactggcct tctcaaggaa 13440
gcccagctcc ttgttattga gaatgaagtg tgcaatcact ataagtatat ttgtgctgag 13500
catttggcca gaggcactga cagttgccag ggtgacagtg gagggcctct ggtttgcttc 13560
gagaaggaca aatacatttt acaaggagtc acttcttggg gtcttggctg tgcacgcccc 13620
aataagcctg gtgtctatgc tcgtgtttca aggtttgtta cttggattga gggaatgatg 13680
agaaataatt aattggacgg gagacagagt gaagcatcaa cctacttaga agctgaaacg 13740
tgggtaagga tttagcatgc tggaaataat agacagcaat caaacgaaga cactgttccc 13800
agctaccagc tatgccaaac cttggcattt ttggtatttt tgtgtataag cttttaaggt 13860
ctgactgaca aattctgtat taaggtgtca tagctatgac atttgttaaa aataaactct 13920
gcacttattt tgatttga 13938

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
acagcaatca aacgaagaca ctg 23

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6
agcttataca caaaaatacc aaaaatgc 28

<210> SEQ ID NO 7
<211> LENGTH: 27
<212> TYPE: DNA
<213> ORGANISM: Artificial sequence
<220> FEATURE:
<223> OTHER INFORMATION: Probe

<400> SEQUENCE: 7
tcccagctac cagctatgcc aaacctt 27

<210> SEQ ID NO 8
<211> LENGTH: 16
<212> TYPE: DNA
<213> ORGANISM: Artificial sequence
<220> FEATURE:
<223> OTHER INFORMATION: Primer

<400> SEQUENCE: 8
ccacagtggc cccggt 16

```
<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9

acagggcttt tctcaggtgg t                                              21


<210> SEQ ID NO 10
<211> LENGTH: 28
<212> TYPE: DNA
<213> ORGANISM: Artificial sequence
<220> FEATURE:
<223> OTHER INFORMATION: Probe

<400> SEQUENCE: 10

ccaagcacag aggctccttc tgaacaag                                       28


<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11

ggcaggtcct tcctgtgaca                                                20


<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12

cctgtgacag tggtggagta                                                20


<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13

tcctgtgaca gtggtggagt                                                20


<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14

cttcctgtga cagtggtgga                                                20


<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 15
ccttcctgtg acagtggtgg 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tccttcctgt gacagtggtg 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gtccttcctg tgacagtggt 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ggtccttcct gtgacagtgg 20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
aggtccttcc tgtgacagtg 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
caggtccttc ctgtgacagt 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gcaggtcctt cctgtgacag 20

<210> SEQ ID NO 22
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 22
tggcaggtcc ttcctgtgac 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ttggcaggtc cttcctgtga 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
cttggcaggt ccttcctgtg 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
gcttggcagg tccttcctgt 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tcttcctgtg acagtggtgg 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ttcttcctgt gacagtggtg 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gttcttcctg tgacagtggt 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ggttcttcct gtgacagtgg 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
aggttcttcc tgtgacagtg 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
caggttcttc ctgtgacagt 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tggcaggttc ttcctgtgac 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
ttggcaggtt cttcctgtga 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
cttggcaggt tcttcctgtg 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
agcttggcag gttcttcctg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
actatgcgag tgtggtgtca 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gactatgcga gtgtggtgtc 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
cgactatgcg agtgtggtgt 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ccgactatgc gagtgtggtg 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tccgactatg cgagtgtggt 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
gtccgactat gcgagtgtgg 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ggtccgacta tgcgagtgtg 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
gggtccgact atgcgagtgt 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgctcagtc ggtgcttgtt 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
cctctgctca gtcggtgctt 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gcctctgctc agtcggtgct 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cttccagtga cagtggtgga 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ttcttccagt gacagtggtg 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gttcttccag tgacagtggt 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
ggttcttcca gtgacagtgg 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gaccttaaaa gcttatacac 20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
gtcagacctt aaaagcttat 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tgtcagtcag accttaaaag 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gaatttgtca gtcagacctt 20

<210> SEQ ID NO 55

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55

agaatttgtc agtcagacct                                                20


<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56

ccttaataca gaatttgtca                                                20


<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57

gctccgttgg tgcttgttca                                                20


<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58

tgctccgttg gtgcttgttc                                                20


<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59

ttgctccgtt ggtgcttgtt                                                20


<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60

tttgctccgt tggtgcttgt                                                20


<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
```

ctttgctccg ttggtgcttg 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tcctgtaaca gtggtggaga 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
ttcctgtaac agtggtggag 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
cttcctgtaa cagtggtgga 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
ccttcctgta acagtggtgg 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
tccttcctgt aacagtggtg 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
gtccttcctg taacagtggt 20

<210> SEQ ID NO 68
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 68
tgtccttcct gtaacagtgg 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
tggagccaga ataacattcg 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
cctctaggct tggagccaga 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
agttcttcct gtgacagtgg 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gtccgactat gctggtgtgg 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ggtccgacta tgctggtgtg 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
gggtccgact atgctggtgt 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
cctctaggct tggaatcggg 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gttcagaagg agcctctagg 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tgttcagaag gagcctctag 20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
gcttgttcag aaggagcctc 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tgcttgttca gaaggagcct 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
gtgcttgttc agaaggagcc 20

<210> SEQ ID NO 81
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 81
ggtgcttgtt cagaaggagc 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
tggtgcttgt tcagaaggag 20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
gctcagttgg tgcttgttca 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
tgctcagttg gtgcttgttc 20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gcttggatct gggaccaccg 20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
gcctccatgc ttggaactgg 20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
gctcagttgg tgctgcttca 20

-continued

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
cctcgataac tctggccatt 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
tcctgtgaca gtggtggaga 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
gtaggttgat gcttcactct 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
cgtttgattg ctgtctatta 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
ctctgtgctt ggatctggga 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
cctctgtgct tggatctggg 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
gcctctgtgc ttggatctgg 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
agaagcctct gtgcttggat 20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
ttcagaagaa gcctctgtgc 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
gctccgttgg tgcttcttca 20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
tttgctccgt tggtgcttct 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
gctttgctcc gttggtgctt 20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ggctttgctc cgttggtgct 20

<210> SEQ ID NO 101
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 101
gggctttgct ccgttggtgc 20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
ccttcctgtg acagtggtag 20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
tccttcctgt gacagtggta 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tgtccttcct gtgacagtgg 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
cctctaggct tggaaccggg 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
tgcttgttcg gaaggagcct 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gtgcttgttc ggaaggagcc 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
gcttggaact gggaccaccg 20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
ctgtgcttgg aactgggacc 20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
ctctgtgctt ggaactggga 20

<210> SEQ ID NO 111
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 111
cctgtgacag tggtgga 17

<210> SEQ ID NO 112
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 112
tcctgtgaca gtggtgg 17

<210> SEQ ID NO 113
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 113
ttcctgtgac agtggtg 17

<210> SEQ ID NO 114
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 114
cttcctgtga cagtggt 17

<210> SEQ ID NO 115
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 115
ccttcctgtg acagtgg 17

<210> SEQ ID NO 116
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 116
tccttcctgt gacagtg 17

<210> SEQ ID NO 117
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 117
gtccttcctg tgacagt 17

<210> SEQ ID NO 118
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 118
ggtccttcct gtgacag 17

<210> SEQ ID NO 119
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 119
ccgactatgc gagtgtg 17

<210> SEQ ID NO 120
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 120
gtccgactat gcgagtg 17

<210> SEQ ID NO 121
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 121
ggtccgacta tgcgagt 17

<210> SEQ ID NO 122
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 122
gtcagacctt aaaagct 17

<210> SEQ ID NO 123
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 123
aagcctctgt gcttgga 17

<210> SEQ ID NO 124
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 124
agcctctgtg cttggat 17

<210> SEQ ID NO 125
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 125
gcctctgtgc ttggatc 17

<210> SEQ ID NO 126
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 126
gctccgttgg tgcttct 17

<210> SEQ ID NO 127
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 127
ctctgtgctt ggaactg 17

<210> SEQ ID NO 128
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 128
tgcctcgata actctgt 17

<210> SEQ ID NO 129
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 129
tgtgcctcga taactct 17

<210> SEQ ID NO 130
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 130
gctcagttgg tgctgct 17

<210> SEQ ID NO 131
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 131
gcgtttgctc ttcttcttgc gtttttt 27

<210> SEQ ID NO 132
<211> LENGTH: 3987
<212> TYPE: DNA
<213> ORGANISM: Macaca mulatta

<400> SEQUENCE: 132
atgtatcgtt ttggaatttc cagtggcttg atcaggaact actgcaggaa tccagatcct 60
gtggcagccc cttattgtta tacgatggat cccaatgtca ggtgggagta ctgcaacctg 120
acacaatgct cagatgcaga agggactgcc gtcgcacctc cgaatgtcac cctggttcca 180
agcctagagg ctccttccga acaatcaccg actgagcaaa ggcctggggt gcaggagtgc 240
taccacggta atggacagag ttatcgaggc acatacttca ccactgtgac aggaagaacc 300
tgccaagctt ggtcatctat gacaccgcac tctcatagtc ggaccccgga aaactaccca 360
aatggtggct tgatcaggaa ctactgcagg aatccagatc ctgtggcagc cccttattgt 420
tataccatgg atcccaatgt caggtgggag tactgcaacc taacacaatg ctcagacgca 480
gaagggattg ccgtcacacc tctgactgtt accccggttc caagcctaga ggctccttcc 540

```
aagcaagcac caactgagca aaggcctggt gtccaggagt gctaccatgg taatggacag    600
agttatcgag gcacatactt caccactgtg acaggaagaa cctgccaagc ttggtcatct    660
atgacaccac attctcatag tcgtacccca gaaaactacc caaatggcag tccgacctct    720
tcagatctct tagtctaccc tgccgtcttc cttgatgcca tgggtcccac tgttctttca    780
actcatccgc tttccctcag tcccggagtg gctgcgacca gcagaggata tattgagagc    840
aagagagaag caccgactga gcaaaggcct ggggtgcagg agtgctacca cggtaatgga    900
cagagttatc gaggcacata cttcaccact gtgacaggaa gaacctgcca agcttggtca    960
tctatgacac cgcactctca tagtcggacc ccggaaaact acccaaatgg tggcttgatc   1020
aggaactact gcaggaatcc agatcctgtg gcagcccctt attgttatac catggatccc   1080
agtgtcaggt gggagtactg caacctgaca caatgctcag acgcagaagg gactgccgtc   1140
gcacctccga atgtcacccc ggttccaagc ctagaggctc cttctgagca agcaccaact   1200
gagcaaaggc ttggggtgca ggagtgctac cacagtaatg gacagagtta tcgaggcaca   1260
tacttcacca ctgtgacagg aagaacctgc caagcttggt catctatgac accacactct   1320
catagtcgga ccccagaaaa ctacccaaat gctggcttgg tcaagaacta ctgccgaaat   1380
ccagatcctg tggcagcccc ttggtgttat acaacggatc ccagtgtcag gtgggagtac   1440
tgcaacctga cacgatgctc agatgcagaa gggactgctg tcgtgcctcc aaatattatt   1500
ccggttccaa gcctagaggc ttttcttgaa caagaaccga ctgaggaaac cccgggggta   1560
caggagtgct actaccatta tggacagagt tatagaggca catactccac cactgttaca   1620
ggaagaactt gccaagcttg gtcatctatg acaccacacc agcatagtcg gaccccaaaa   1680
aactatccaa atgctggcct gaccaggaac tactgcagga atccagatgc tgagattcgc   1740
ccttggtgtt ataccatgga tcccagtgtc aggtgggagt actgcaacct gacacaatgt   1800
ctggtgacag aatcaagtgt ccttgaaact ctcacagtgg tcccagatcc aagcacacag   1860
gcttcttctg aagaagcacc aacggagcaa agtcccgagg tccaggactg ctaccatggt   1920
gatggacaga gttatcgagg ctcattctcc accactgtca caggaaggac atgtcagtct   1980
tggtcctcta tgacaccaca ctggcatcag aggacaacag aatattatcc agatggtggc   2040
ctgaccagga actactgcag gaatccagat gctgagattc gcccttggtg ttataccatg   2100
gatcccagtg tcaggtggga gtactgcaac ctgacacaat gtccagtgac agaatcaagt   2160
gtcctcgcaa cgtccatggc tgtttctgaa caagcaccaa tggagcaaag ccccggggtc   2220
caggactgct accatggtga tggacagagt tatcgaggtt cattctccac cactgtcaca   2280
ggaaggacat gtcagtcttg gtcctctatg acaccacact ggcatcagag gaccatagaa   2340
tactacccaa atggtggcct gaccaagaac tactgcagga atccagatgc tgagattcgc   2400
ccttggtgtt ataccatgga tcccagagtc agatgggagt actgcaacct gacacaatgt   2460
gtggtgatgg aatcaagtgt ccttgcaact cccatggtgg tcccagttcc aagcagagag   2520
gttccttctg aagaagcacc aactgaaaac agccctgggg tccaggactg ctaccaaggt   2580
gatggacaga gttatcgagg cacattctcc accactatca caggaagaac atgtcagtct   2640
tggttgtcta tgacaccaca tcggcatcgg aggatcccat tacgctatcc aaatgctggc   2700
ctgaccagga actattgcag aaatccagat gctgagattc gcccttggtg ttacaccatg   2760
gatcccagtg tcaggtggga gtactgcaac ctgacacaat gtccagtgac agaatcaagt   2820
gtcctcacaa ctcccacggt ggtcccggtt ccaagcacag aggctccttc tgaacaagca   2880
ccacctgaga aaagccctgt ggtccaggat tgctaccatg gtgatggaca gagttatcga   2940
```

```
ggcacatcct ccaccactgt cacaggaagg aactgtcagt cttggtcatc tatgatacca   3000

cactggcatc agaggacccc agaaaactac ccaaatgctg gcctgaccag gaactactgc   3060

aggaatccag attctgggaa acaaccctgg tgttacacga ctgatccatg tgtgaggtgg   3120

gagtactgca acctgacaca atgctcagaa acagaatcag gtgtcctaga gactcccact   3180

gttgttccgg ttccaagcat ggaagctcat tctgaagcag caccaactga gcaaacccct   3240

gtggtccagc agtgctacca tggtaatgga cagagttatc gaggcacatt ctccaccact   3300

gtcacaggaa ggacatgtca atcttggtca tccatgacac cacaccagca taagaggacc   3360

ccggaaaacc acccaaatga tggcttgaca atgaactact gcaggaatcc agatgctgac   3420

acaggccctt ggtgttttac catggacccc agcgtcaggc gggagtactg caacctgacg   3480

cgatgctcag acacagaagg gactgtggtc acacctccga ctgttatccc ggttccaagc   3540

ctagaggctc cttctgaaca agtgcttgga attcatcctg aattaaacga cacaattgct   3600

aacttggact caaaggtgaa ttctttccca ccttgtgcca cagcatcctc ttcatttgat   3660

tgtgggaagc ctcaagtgga gccaaagaaa tgtcctggaa gcattgtagg tgggtgtgtg   3720

gcccacccac attcctggcc ctggcaagtc agtcttagaa caaggtttgg aaagcacttc   3780

tgtggaggca ccttaatatc cccagagtgg gtgctgactg ctgcttgctg cttggagacg   3840

ttctcaaggc cttccttcta caaggtcatc ctgggtgcac accaagaagt gaatctcgaa   3900

tctcatgttc aagaaataga agtgtctagg ttgttcttgg agcccatagg agcagatatt   3960

gccttgctaa agctaagcag gtactaa                                       3987


<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133

ggttcttcca gtgacagtgg                                                 20


<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134

atgcctcgat aactccgtcc                                                 20


<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135

agcttcttgt ccagctttat                                                 20


<210> SEQ ID NO 136
<211> LENGTH: 21
<212> TYPE: DNA
<213> ORGANISM: Artificial sequence
<220> FEATURE:
```

<223> OTHER INFORMATION: Synthetic oligonucleotide

<400> SEQUENCE: 136
agcttcttgt ccagctttat a 21

<210> SEQ ID NO 137
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 137
tcagtcatga cttc 14

<210> SEQ ID NO 138
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 138
tcagtcatga cttca 15

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
gctgattaga gagaggtccc 20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
tcccatttca ggagacctgg 20

<210> SEQ ID NO 141
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 141
atcagtcatg acttc 15

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
cggtgcaagg cttaggaatt 20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
gcttcagtca tgacttcctt 20

<210> SEQ ID NO 144
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 144
gcttcagtca tgacttcctt a 21

<210> SEQ ID NO 145
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 145
agcttcagtc atgacttcct t 21

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tggtaatcca ctttcagagg 20

<210> SEQ ID NO 147
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 147
tggtaatcca ctttcagagg a 21

<210> SEQ ID NO 148
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 148
tgcttcagtc atgacttcct t 21

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
cactgatttt tgcccaggat 20

<210> SEQ ID NO 150
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 150
cactgatttt tgcccaggat a 21

<210> SEQ ID NO 151
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 151
aagcttcttg tccagcttta t 21

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
acccaattca gaaggaagga 20

<210> SEQ ID NO 153
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 153
acccaattca gaaggaagga a 21

<210> SEQ ID NO 154
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 154
aacccaattc agaaggaagg a 21

<210> SEQ ID NO 155
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 155
atggtaatcc actttcagag g 21

<210> SEQ ID NO 156
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 156
tcttggttac atgaaatccc 20

<210> SEQ ID NO 157
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 157
tcttggttac atgaaatccc a 21

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
attcactttc ataatgctgg 20

<210> SEQ ID NO 159
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 159
attcactttc ataatgctgg a 21

<210> SEQ ID NO 160
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 160
atcttggtta catgaaatcc c 21

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
atgcatggtg atgcttctga 20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162

-continued

```
cagctttatt agggacagca                                              20


<210> SEQ ID NO 163
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 163

cagctttatt agggacagca a                                            21


<210> SEQ ID NO 164
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 164

acagctttat tagggacagc a                                            21


<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165

ttcagtcatg acttcc                                                  16


<210> SEQ ID NO 166
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: bases at these positions are RNA
<220> FEATURE:
<221> NAME/KEY: misc_feature
<222> LOCATION: (15)..(18)
<223> OTHER INFORMATION: bases at these positions are RNA

<400> SEQUENCE: 166

gcuucagtca tgactucc                                                18


<210> SEQ ID NO 167
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 167

tgctccgttg gtgcttgttc a                                            21
```

COMPOSITIONS AND METHODS FOR MODULATING APOLIPOPROTEIN (A) EXPRESSION

RELATED APPLICATIONS

This application is a continuation of U.S. application Ser. No. 15/891,156, filed on Feb. 7, 2018, now allowed, which is a continuation of U.S. application Ser. No. 14/839,580, filed on Aug. 28, 2015, now U.S. Pat. No. 9,957,504, which is a continuation of U.S. application Ser. No. 14/588,061, filed on Dec. 31, 2014, now U.S. Pat. No. 9,181,550, which is a continuation of International Application No. PCT/US2014/036460 with an international filing date of May 1, 2014, which claims the benefit of and priority to U.S. Provisional Application Nos: 61/818,442, filed on May 1, 2013; 61/823,826, filed May 15, 2013; 61/843,887, filed Jul. 8, 2013; 61/871,673, filed Aug. 29, 2013; 61/880,790, filed Sep. 20, 2013; 61/976,991, filed Apr. 8, 2014; 61/986,867, filed Apr. 30, 2014; the entire contents of each of which are incorporated herein by reference in their entireties.

SEQUENCE LISTING

The present application is being filed along with a Sequence Listing in electronic format. The Sequence Listing is provided as a file entitled "PAT058755-US-CNT04 Sequence listing as filed (BIOL0250USC4) SEQ_ST25.txt", created on May 8, 2020, which is 432 Kb in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, CA) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009)361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; WO2013/177468; US20040242516; U.S. Pat. Nos. 8,138,328, 8,673,632 and 7,259,150; Merki et al., J Am Coll Cardiol 2011; 57:1611-1621; each publication incorporated by reference in its entirely) have been developed but none have been approved for commercial use.

Thus, there remains a clear unmet medical need for novel agents which can potently and selectively reduce apo(a) levels in patients at enhanced risk for cardiovascular events due to chronically elevated plasma Lp(a) levels.

SUMMARY OF THE INVENTION

Provided herein are compositions and methods for modulating expression of apo(a) mRNA and protein. In certain embodiments, the apo(a) specific inhibitor decreases expression of apo(a) mRNA and protein. Provided herein are compositions and methods for modulating expression of Lp(a) levels.

In certain embodiments, the composition is an apo(a) specific inhibitor. In certain embodiments, the apo(a) specific inhibitor is a nucleic acid, protein, or small molecule. In certain embodiments, the apo(a) specific inhibitor is an antisense oligonucleotide targeting apo(a) with a conjugate. In certain embodiments, the apo(a) specific inhibitor is a modified oligonucleotide and a conjugate, wherein the modified oligonucleotide consists of 12 to 30 linked nucleosides and comprises a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide and a conjugate, wherein the modified oligonucleotide consists of 12 to 30 linked nucleosides and has a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 1-130, 133, 134. In certain embodiments, the apo(a) specific inhibitor is a modified oligonucleotide and a conjugate, wherein the modified oligonucleotide consists of 20 linked nucleosides and has a nucleobase sequence comprising at least 8 contiguous nucleobases of any of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a composition comprising a conjugated antisense compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

Certain embodiments provide conjugated antisense compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide. In certain embodiments, the antisense compound is a modified oligonucleotide with a conjugate.

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., PNAS vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022. Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc3-10 in Example 46 and GalNAc3-7 in Example 48 are much simpler than previously described conjugates such as those described in U.S. Pat. No. 8,106,022 or 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

$$A\text{-}B\text{-}C\text{-}D\text{-}(E\text{-}F)_q$$

wherein

A is the antisense oligonucleotide;

B is the cleavable moiety

C is the conjugate linker

D is the branching group each E is a tether;

each F is a ligand; and q is an integer between 1 and 5.

In the above diagram and in similar diagrams herein, the branching group "D" branches as many times as is necessary to accommodate the number of (E-F) groups as indicated by "q". Thus, where q=1, the formula is:

A-B-C-D-E-F where q=2, the formula is:

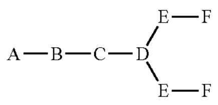

where q=3, the formula is:

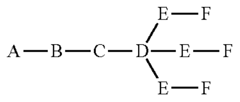

where q=4, the formula is:

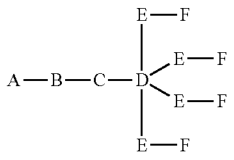

where q=5, the formula is:

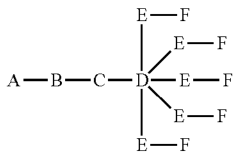

In certain embodiments, conjugated antisense compounds are provided having the structure:

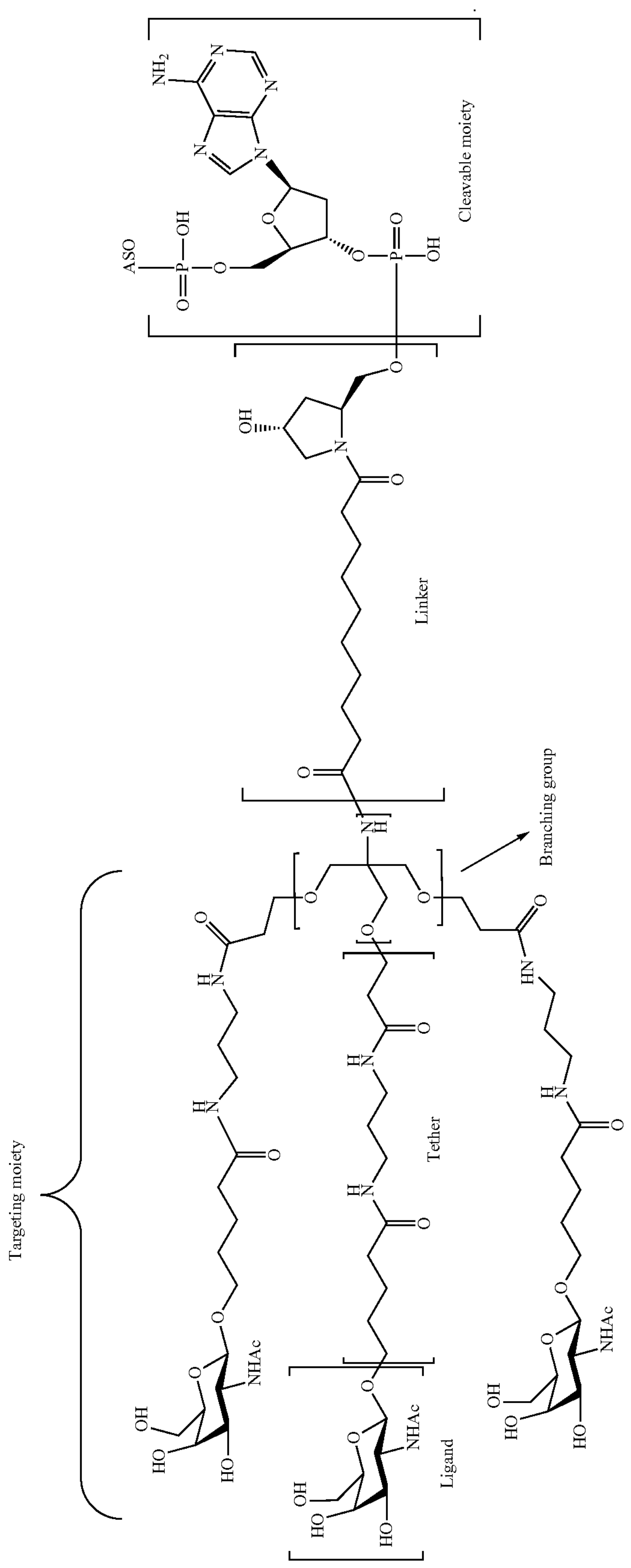
Cleavable moiety
Linker
Branching group
Targeting moiety
Tether
Ligand In certain embodiments, conjugated antisense compounds are provided having the structure:
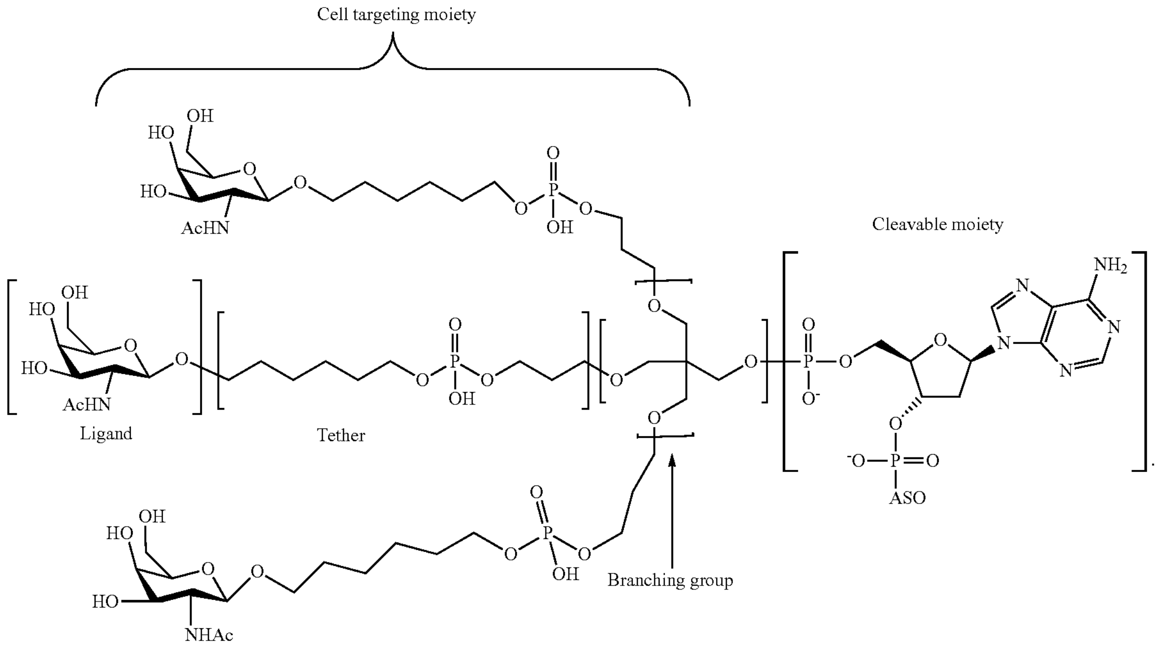
In certain embodiments, conjugated antisense compounds are provided having the structure:
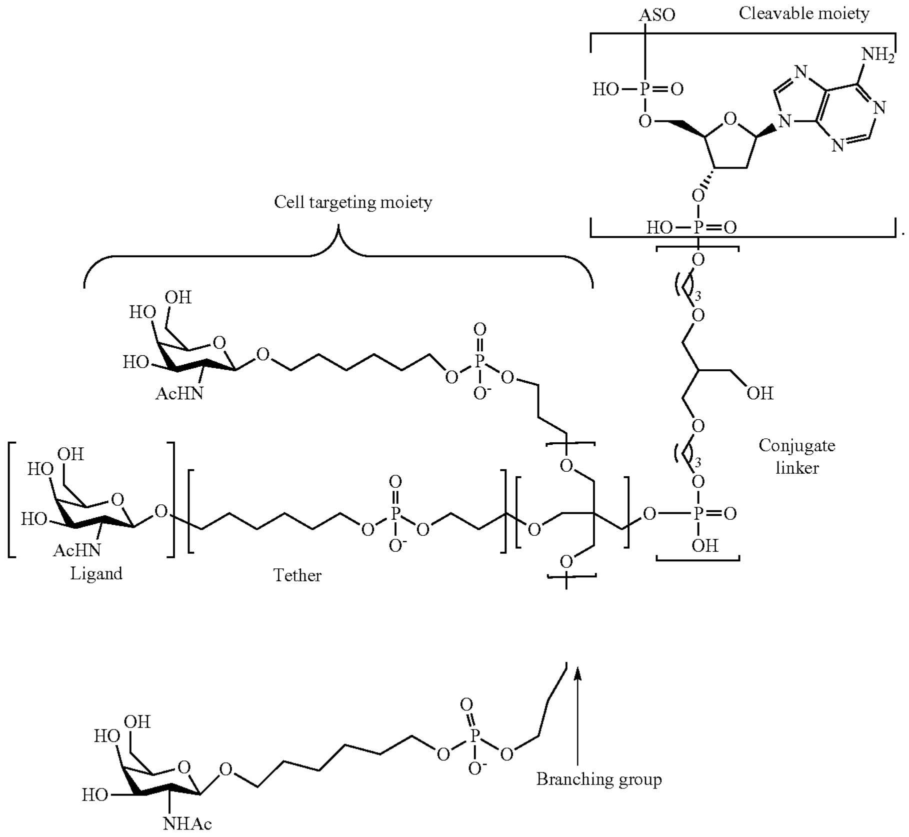

In certain embodiments, conjugated antisense compounds are provided having the structure:

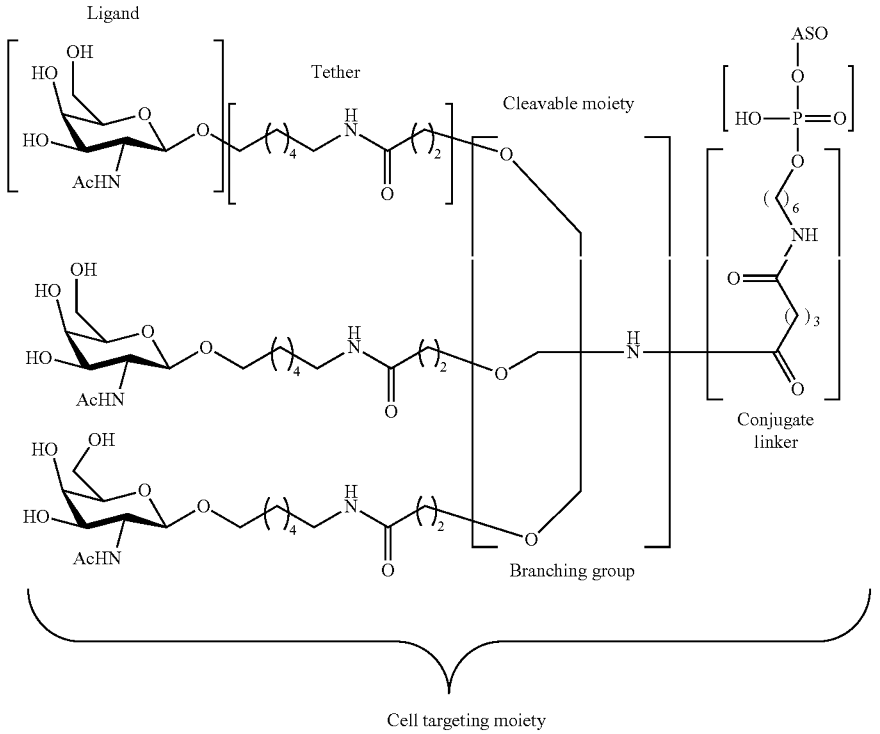

The present disclosure provides the following non-limiting numbered embodiments:

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

In certain embodiments, the present disclosure provides conjugated antisense compounds represented by the following structure. In certain embodiments, the antisense compound comprises modified oligonucleotide ISIS 494372 with a 5'-X, wherein X is a conjugate group comprising GalNAc. In certain embodiments, the antisense compound consists of modified oligonucleotide ISIS 494372 with a 5'-X, wherein X is a conjugate group comprising GalNAc.

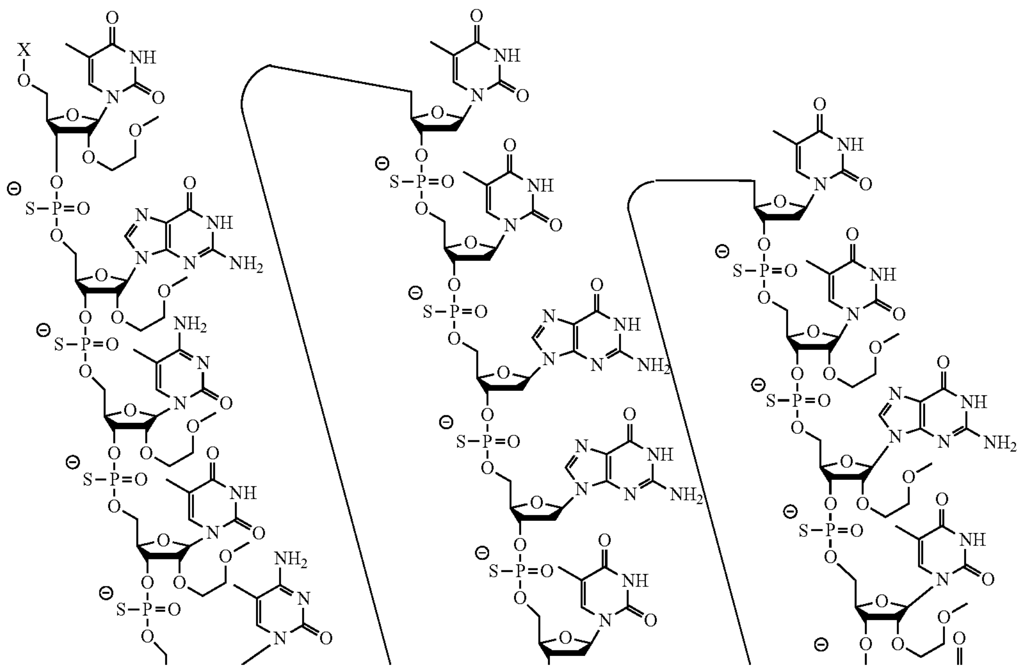

-continued
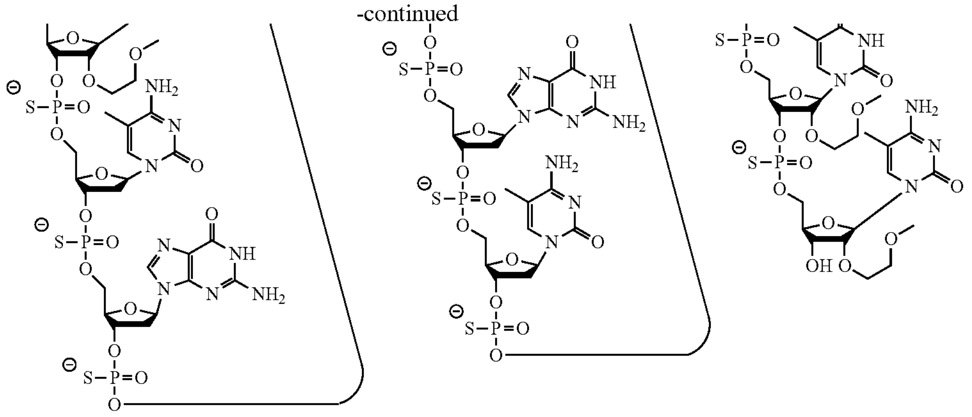
In certain embodiments, the present disclosure provides conjugated antisense compounds represented by the following structure. In certain embodiments, the antisense compound comprises the conjugated modified oligonucleotide ISIS 681251. In certain embodiments, the antisense compound consists of the conjugated modified oligonucleotide ISIS 681251.
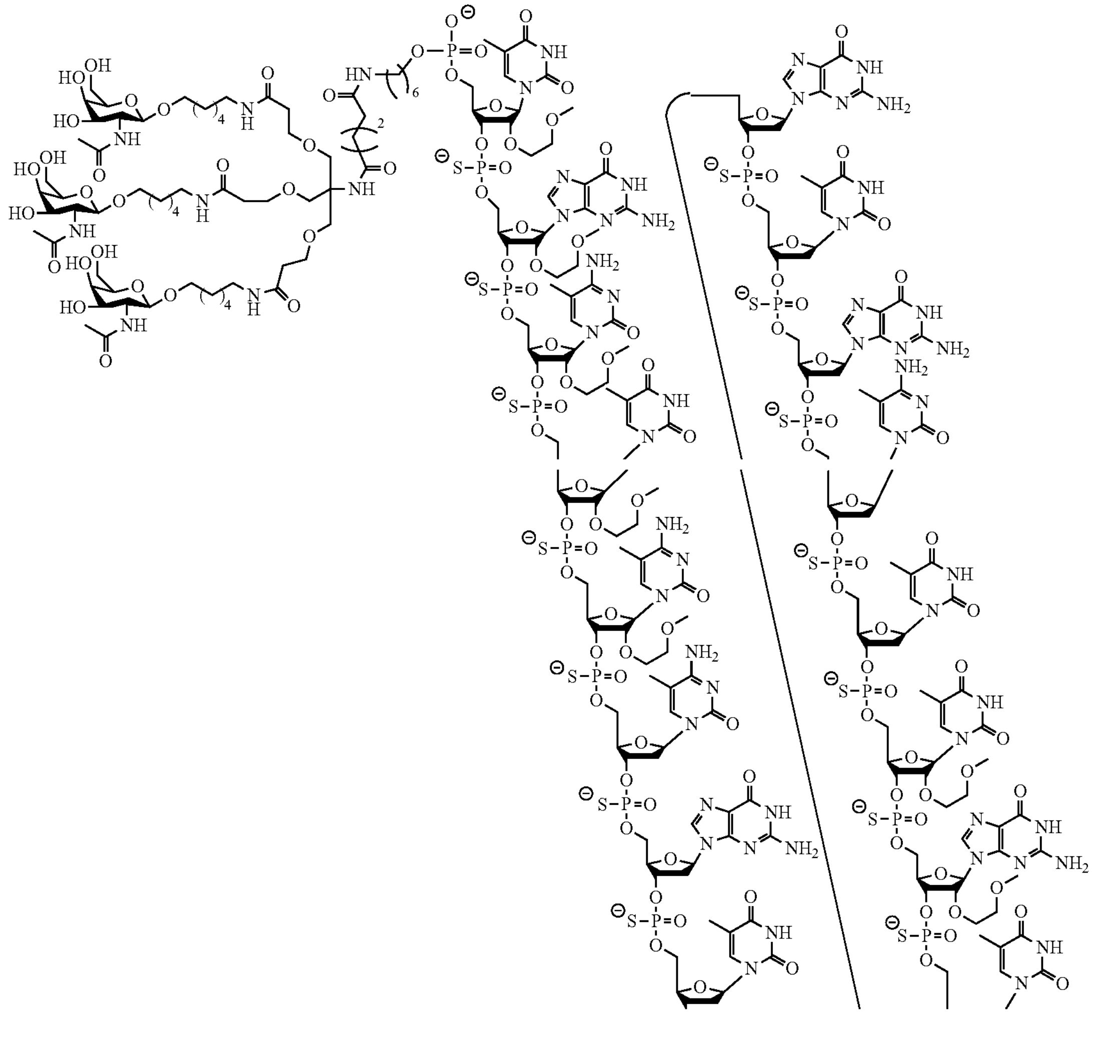

-continued
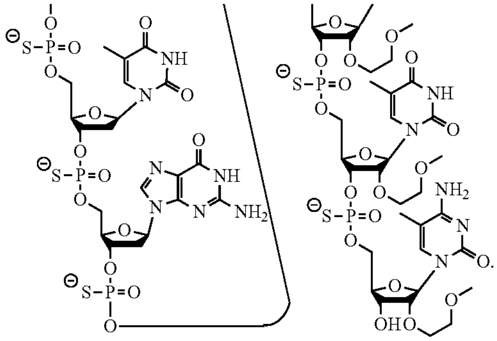
In certain embodiments, the present disclosure provides conjugated antisense compounds represented by the following structure. In certain embodiments, the antisense compound comprises the conjugated modified oligonucleotide ISIS 681257. In certain embodiments, the antisense compound consists of the conjugated modified oligonucleotide ISIS 681257.
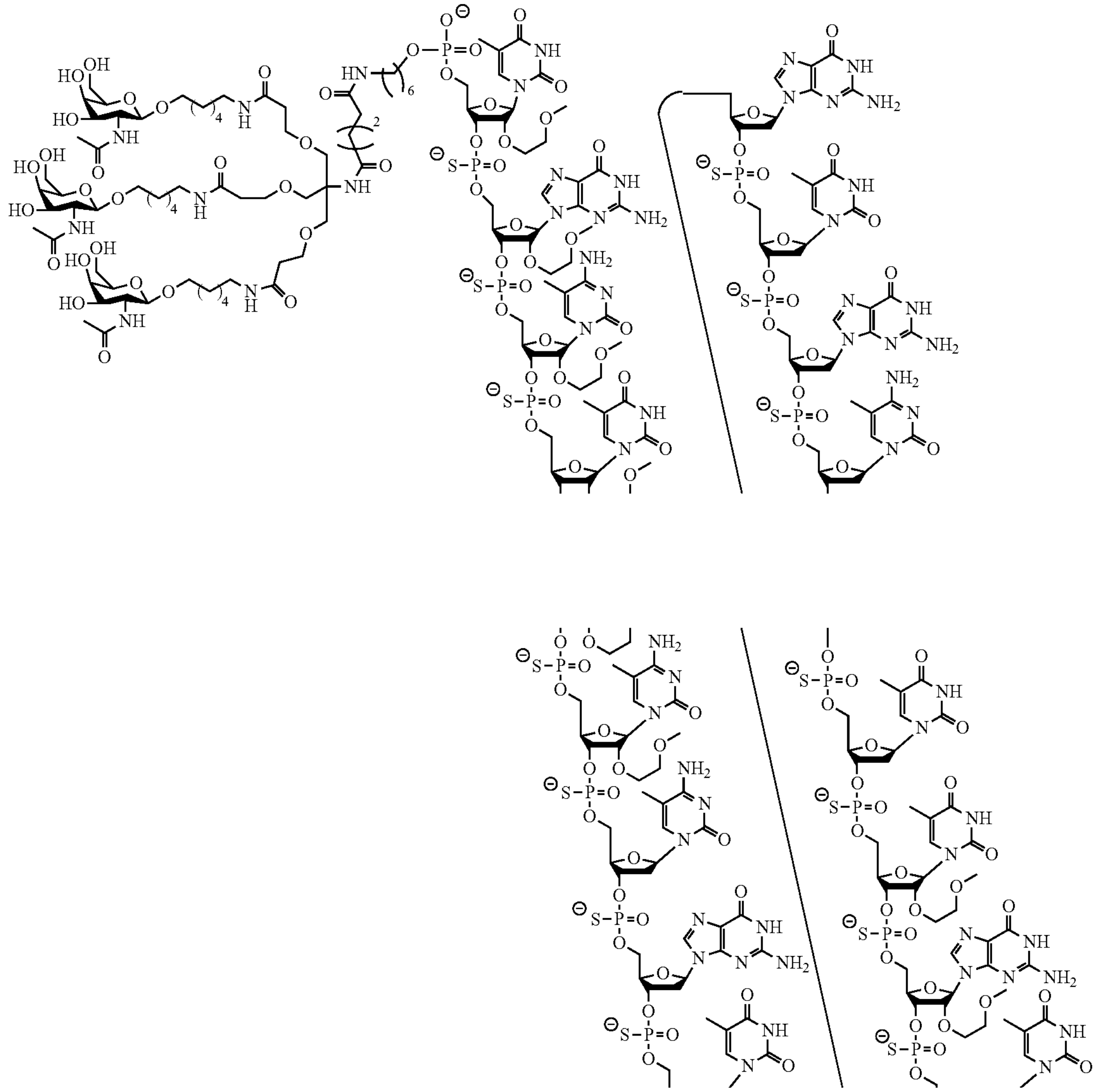

-continued

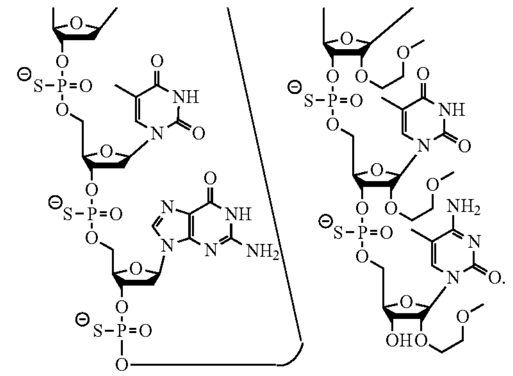

In certain embodiments, the present disclosure provides conjugated antisense compounds represented by the following structure. In certain embodiments, the antisense compound comprises a modified oligonucleotide with SEQ ID NO: 58 with a 5'-GalNAc with variability in the sugar mods of the wings. In certain embodiments, the antisense compound consists of a modified oligonucleotide with SEQ ID NO: 58 with a 5'-GalNAc with variability in the sugar mods of the wings.

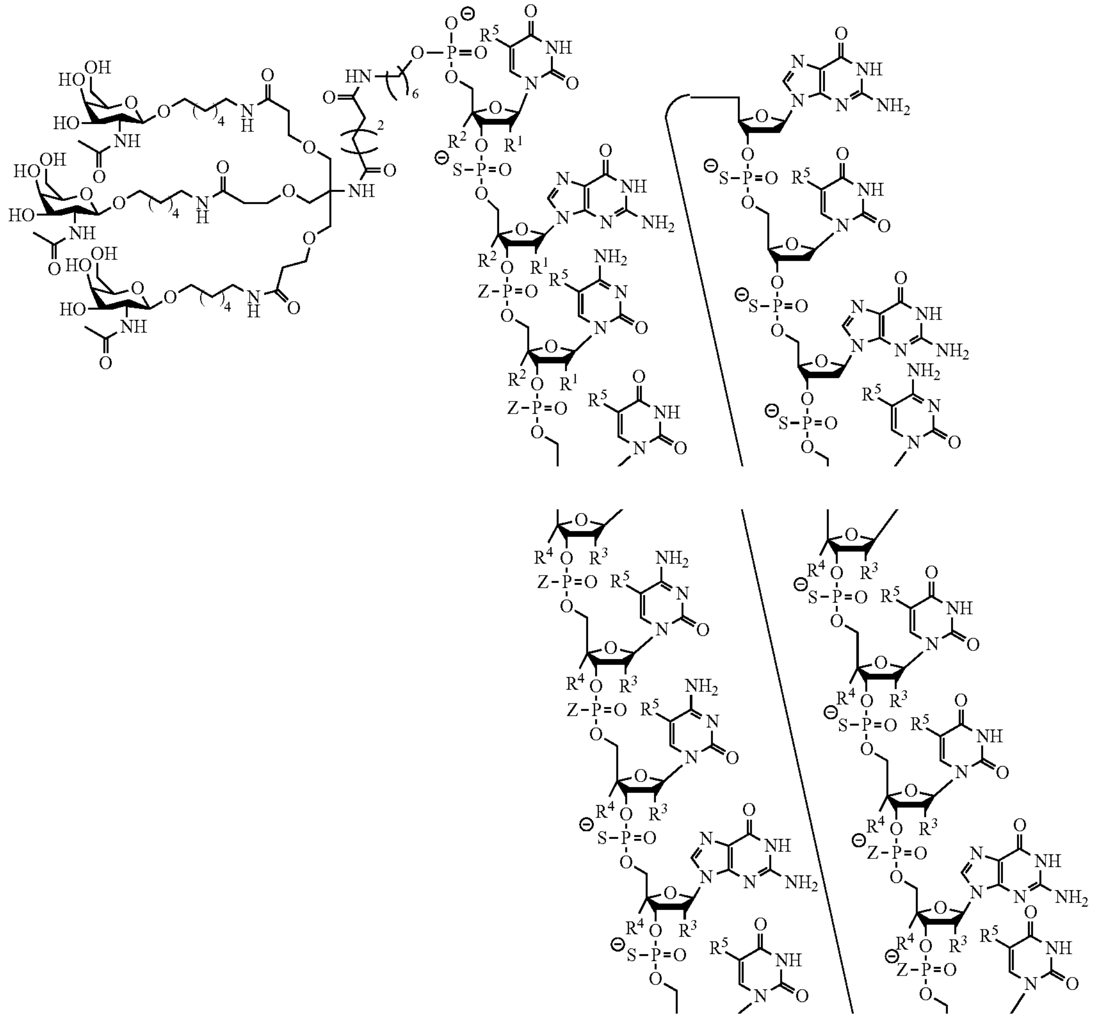

-continued

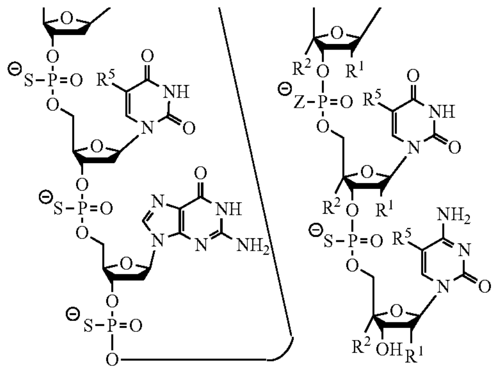

Wherein either $R^1$ is —$OCH_2CH_2OCH_3$ (MOE) and $R^2$ is H; or $R^1$ and $R^2$ together form a bridge, wherein $R^1$ is —O— and $R^2$ is —$CH_2$—, —$CH(CH_3)$—, or —$CH_2CH_2$—, and $R^1$ and $R^2$ are directly connected such that the resulting bridge is selected from: —O—$CH_2$—, —O—$CH(CH_3)$—, and —O—$CH_2CH_2$—;

And for each pair of $R^3$ and $R^4$ on the same ring, independently for each ring: either $R^3$ is selected from H and —$OCH_2CH_2OCH_3$ and $R^4$ is H; or $R^3$ and $R^4$ together form a bridge, wherein $R^3$ is —O—, and $R^4$ is —$CH_2$—, —$CH(CH_3)$—, or —$CH_2CH_2$— and $R^3$ and $R^4$ are directly connected such that the resulting bridge is selected from: —O—$CH_2$—, —O—$CH(CH_3)$—, and —O—$CH_2CH_2$—;

And $R^5$ is selected from H and —$CH_3$;

And Z is selected from $S^-$ and $O^-$.

The present disclosure provides the following non-limiting numbered embodiments:

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21st edition, 2005; and "Antisense Drug Technology, Principles, Strategies, and Applications" Edited by Stanley T. Crooke, CRC Press, Boca Raton, Florida; and Sambrook et al., "Molecular Cloning, A laboratory Manual," 2nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —$OCH_2CH_2OCH_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid.

Nucleobases may be naturally occurring or may be modified. As used herein, "nucleobase sequence" means the order of contiguous nucleobases independent of any sugar, linkage, or nucleobase modification.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2'bridge.

As used herein, "locked nucleic acid nucleoside" or "LNA" means a nucleoside comprising a bicyclic sugar moiety comprising a 4'-$CH_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

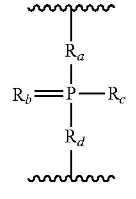

wherein:

$R_a$ and $R_d$ are each, independently, O, S, $CH_2$, NH, or $NJ_1$ wherein $J_1$ is $C_1$-$C_6$ alkyl or substituted $C_1$-$C_6$ alkyl;

$R_b$ is O or S;

$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI ($—CH_2—N(CH_3)—O—$), amide-3 ($—CH_2—C(═O)—N(H)—$), amide-4 ($—CH_2—N(H)—C(═O)—$), formacetal ($—O—CH_2—O—$), and thioformacetal ($—S—CH_2—O—$). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "$GalNAc_3$". In certain embodiments, the carbohydrate cluster portion comprises 4 GalNAc groups and is designated "$GalNAc_4$". Specific carbohydrate cluster portions (having specific tether, branching and conjugate linker groups) are described herein and designated by Roman numeral followed by subscript "a". Accordingly "GalNac3-$1_a$" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, "cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry,* 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "double stranded" means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "RISC based antisense compound" means an antisense compound wherein at least some of the antisense activity of the antisense compound is attributable to the RNA Induced Silencing Complex (RISC).

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "prodrug" means an inactive or less active form of a compound which, when administered to a subject, is metabolized to form the active, or more active, compound (e.g., drug).

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($-C(O)R_{aa}$), carboxyl ($-C(O)O-R_{aa}$), aliphatic groups, alicyclic groups, alkoxy, substituted oxy ($-O-R_{aa}$), aryl, aralkyl, heterocyclic radical, heteroaryl, heteroarylalkyl, amino ($-N(R_{bb})(R_{cc})$), imino($=NR_{bb}$), amido ($-C(O)N-(R_{bb})(R_{cc})$ or $-N(R_{bb})C(O)R_{aa}$), azido ($-N_3$), nitro ($-NO_2$), cyano ($-CN$), carbamido ($-OC(O)N(R_{bb})(R_{cc})$ or $-N(R_{bb})C(O)OR_{aa}$), ureido ($-N(R_{bb})C(O)N(R_{bb})(R_{cc})$), thioureido ($-N(R_{bb})C(S)N(R_{bb})(R_{cc})$), guanidinyl ($-N(R_{bb})C(=NR_{bb})N(R_{bb})(R_{cc})$), amidinyl ($-C(=NR_{bb})N(R_{bb})(R_{cc})$ or $-N(R_{bb})C(=NR_{bb})(R_{aa})$), thiol ($-SR_{bb}$), sulfinyl ($-S(O)R_{bb}$), sulfonyl ($-S(O)_2R_{bb}$) and sulfonamidyl ($-S(O)_2N(R_{bb})(R_{cc})$ or $-N(R_{bb})S(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula $-C(O)-X$ where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, "5' target site" refers to the nucleotide of a target nucleic acid which is complementary to the 5'-most nucleotide of a particular antisense compound.

As used herein, "About" means within ±10% of a value. For example, if it is stated, "a marker may be increased by about 50%", it is implied that the marker may be increased between 45%-55%.

As used herein, "administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

As used herein, "agent" means an active substance that can provide a therapeutic benefit when administered to an animal. "First agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo (a) therapeutic compound.

As used herein, "amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

As used herein, "animal" refers to a human or non-human animal, including, but not limited to, mice, rats, rabbits, dogs, cats, pigs, and non-human primates, including, but not limited to, monkeys and chimpanzees.

As used herein, "apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

As used herein, "apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

As used herein, "apo(a) mRNA" means a mRNA encoding an apo(a) protein.

As used herein, "apo(a) protein" means any protein sequence encoding Apo(a).

As used herein, "apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

As used herein, "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

As used herein, "coronary heart disease (CHD)" means a narrowing of the small blood vessels that supply blood and oxygen to the heart, which is often a result of atherosclerosis.

As used herein, "diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

As used herein, "diabetic dyslipidemia" or "type 2 diabetes with dyslipidemia" means a condition characterized by Type 2 diabetes, reduced HDL-C, elevated triglycerides (TG), and elevated small, dense LDL particles.

As used herein, "diluent" means an ingredient in a composition that lacks pharmacological activity, but is pharmaceutically necessary or desirable. For example, the diluent in an injected composition can be a liquid, e.g. saline solution.

As used herein, "dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

As used herein, "dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

As used herein, "dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

As used herein, "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

As used herein, "glucose" is a monosaccharide used by cells as a source of energy and inflammatory intermediate. "Plasma glucose" refers to glucose present in the plasma.

As used herein, "high density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

As used herein, "HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

As used herein, "hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

As used herein, "hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

As used herein, "hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ,* 2007, 176:1113-1120).

As used herein, "identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

As used herein, "improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

As used herein, "immediately adjacent" means there are no intervening elements between the immediately adjacent elements, for example, between regions, segments, nucleotides and/or nucleosides.

As used herein, "increasing HDL" or "raising HDL" means increasing the level of HDL in an animal after administration of at least one compound of the invention, compared to the HDL level in an animal not administered any compound.

As used herein, "individual" or "subject" or "animal" means a human or non-human animal selected for treatment or therapy.

As used herein, "individual in need thereof" refers to a human or non-human animal selected for treatment or therapy that is in need of such treatment or therapy.

As used herein, "induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

As used herein, "inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

As used herein, "inhibiting the expression or activity" refers to a reduction or blockade of the expression or activity of a RNA or protein and does not necessarily indicate a total elimination of expression or activity.

As used herein, "insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

As used herein, "insulin sensitivity" is a measure of how effectively an individual processes glucose. An individual having high insulin sensitivity effectively processes glucose whereas an individual with low insulin sensitivity does not effectively process glucose.

As used herein, "lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

As used herein, "lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

As used herein, "lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

As used herein, "Lp(a)" comprises apo(a) and a LDL like particle containing apoB. The apo(a) is linked to the apoB by a disulfide bond.

As used herein, "low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

As used herein, "major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

As used herein, "metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

As used herein, "metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

As used herein, "peptide" means a molecule formed by linking at least two amino acids by amide bonds. Peptide refers to polypeptides and proteins.

As used herein, "pharmaceutical agent" means a substance that provides a therapeutic benefit when administered to an individual. For example, in certain embodiments, an antisense oligonucleotide targeted to apo(a) is a pharmaceutical agent.

As used herein, "pharmaceutical composition" or "composition" means a mixture of substances suitable for administering to an individual. For example, a pharmaceutical composition can comprise one or more active agents and a pharmaceutical carrier e.g., a sterile aqueous solution.

As used herein, "pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

As used herein, "pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

As used herein, "portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

As used herein, "prevent" or "preventing" refers to delaying or forestalling the onset or development of a disease, disorder, or condition for a period of time from minutes to indefinitely. Prevent also means reducing risk of developing a disease, disorder, or condition.

As used herein, "raise" means to increase in amount. For example, to raise plasma HDL levels means to increase the amount of HDL in the plasma.

As used herein, "reduce" means to bring down to a smaller extent, size, amount, or number. For example, to reduce plasma triglyceride levels means to bring down the amount of triglyceride in the plasma.

As used herein, "region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

As used herein, "second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

As used herein, "segments" are defined as smaller, subportions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

As used herein, "statin" means an agent that inhibits the activity of HMG-CoA reductase.

As used herein, "subcutaneous administration" means administration just below the skin.

As used herein, "subject" means a human or non-human animal selected for treatment or therapy.

As used herein, "symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

As used herein, "targeting" or "targeted" means the process of design and selection of an antisense compound that will specifically hybridize to a target nucleic acid and induce a desired effect.

As used herein, "therapeutically effective amount" means an amount of a pharmaceutical agent that provides a therapeutic benefit to an individual.

As used herein, "therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

As used herein, "treat" or "treating" refers to administering a compound described herein to effect an alteration or improvement of a disease, disorder, or condition.

As used herein, "triglyceride" or "TG" means a lipid or neutral fat consisting of glycerol combined with three fatty acid molecules.

As used herein, "type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

Certain Embodiments

In certain embodiments, a compound comprises a siRNA or antisense oligonucleotide targeted to apolipoprotein(a) (apo(a)) known in the art and a conjugate group described herein. Examples of antisense oligonucleotides targeted to apo(a) suitable for conjugation include but are not limited to those disclosed in WO 2013/177468; U.S. Pat. Nos. 8,673,632; 7,259,150; and US Patent Application Publication No. US 2004/0242516; which are incorporated by reference in their entireties herein. In certain embodiments, a compound comprises an antisense oligonucleotide having a nucleobase sequence of any of SEQ ID NOs 12-130, 133, 134 disclosed in WO 2013/177468 and a conjugate group described herein. In certain embodiments, a compound comprises an antisense oligonucleotide having a nucleobase sequence of any of SEQ ID NOs 11-45 and 85-96 disclosed in U.S. Pat. No. 8,673,632 and a conjugate group described herein. In certain embodiments, a compound comprises an antisense oligonucleotide having a nucleobase sequence of any of SEQ ID NOs 11-45 disclosed in U.S. Pat. No. 7,259,150 and a conjugate group described herein. In certain embodiments, a compound comprises an antisense oligonucleotide having a nucleobase sequence of any of SEQ ID NOs 7-41 disclosed in US Patent Application Publication No. US 2004/0242516 and a conjugate group described herein. The nucleobase sequences of all of the aforementioned referenced SEQ ID NOs are incorporated by reference herein.

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a). In certain embodiments, the compound is an antisense oligonucleotide targeting apo(a) and a conjugate group.

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a). In certain embodiments, the compound is an antisense oligonucleotide targeting apo(a) and a conjugate group.

Certain embodiments provide a compound comprising a modified oligonucleotide targeting apo(a) and a conjugate group, wherein the modified oligonucleotide consists of 12 to 30 linked nucleosides. In certain embodiments, the modified oligonucleotide with the conjugate group consists of 15 to 30, 18 to 24, 19 to 22, 13 to 25, 14 to 25, 15 to 25 linked nucleosides. In certain embodiments, the modified oligonucleotide with the conjugate group comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide with the conjugate group consists of 20 linked nucleosides.

Certain embodiments provide a compound comprising a modified oligonucleotide targeting apo(a) and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4.

Certain embodiments provide a compound comprising a modified oligonucleotide targeting an apo(a) segment and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in, for example, Examples 114 and 117. In the tables, the “Start Site” refers to the 5'-most nucleotide of a target segment and “Stop Site” refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 125, a target segment can range from 3901-3920, the start site to the stop site of SEQ ID NO: 58. In another example, as shown in Table 125, a target segment can range from 3900-3923, the start site of SEQ ID NO: 57 to the stop site of SEQ ID NO: 61.

Certain embodiments provide a compound comprising a modified oligonucleotide targeting apo(a) and a conjugate group, wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a) and a conjugate group, wherein the nucleobase sequence of the modified oligonucleotide is at least 80%, at least 85%, at least 90%, at least 95%, or 100% complementary to any of the target segments shown in, for example, Examples 114 and 117.

Certain embodiments provide a compound comprising a modified oligonucleotide targeting apo(a) and a conjugate group, wherein the modified oligonucleotide consists of 12 to 30 linked nucleosides and comprises a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) and a conjugate group, wherein the modified oligonucleotide consists of 12 to 30 linked nucleosides and comprises a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134. In certain embodiments, the compound consists of any one of SEQ ID NOs: 12-130, 133, 134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134. In certain embodiments, the compound consists of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110. In certain embodiments, the compound consists of any of the nucleobase sequences of SEQ ID NOs: 12-19, 26-30, 32, 35, 38-44, 46-47, 50, 57-58, 61, 64-66, 68, 72-74, 76-77, 92-94, 103-110 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 111, 114-121, 123-129. In certain embodiments, the compound consists of any of the nucleobase sequences of SEQ ID NOs: 111, 114-121, 123-129 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 17, 18, 26-28, 39, 71, 106-107. In certain embodiments, the compound consists of any of the nucleobase sequences of SEQ ID NOs: 14, 17, 18, 26-28, 39, 71, 106-107 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 26-29, 39-40, 82. In certain embodiments, the compound consists of any of the nucleobase sequences of SEQ ID NOs: 14, 26-29, 39-40, 82 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 16-18. In certain embodiments, the compound consists of any of the nucleobase sequences of SEQ ID NOs: 14, 16-18 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 26-27, 107. In certain embodiments, the compound consists of any of the nucleobase sequences of SEQ ID NOs: 26-27, 107 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 28-29, 39-40, 47. In certain embodiments, the compound consists of any of the nucleobase sequences of SEQ ID NOs: 28-29, 39-40, 47 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 28, 93, 104, 134. In certain embodiments, the compound consists of any of the nucleobase sequences of SEQ ID NOs: 28, 93, 104, 134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of the nucleobase sequence of SEQ ID NO: 58. In certain embodiments, the modified oligonucleotide with the conjugate group has a nucleobase sequence comprising at least 8 contiguous nucleobases of the nucleobase sequence of SEQ ID NO: 58. In certain embodiments, the compound consists of SEQ ID NO: 58 and a conjugate group.

In certain embodiments, the present disclosure provides conjugated antisense compounds represented by the following structure. In certain embodiments, the antisense compound comprises the modified oligonucleotide ISIS 494372 with a 5'-X, wherein X is a conjugate group comprising GalNAc. In certain embodiments, the antisense compound consists of the modified oligonucleotide ISIS 494372 with a 5'-X, wherein X is a conjugate group comprising GalNAc.

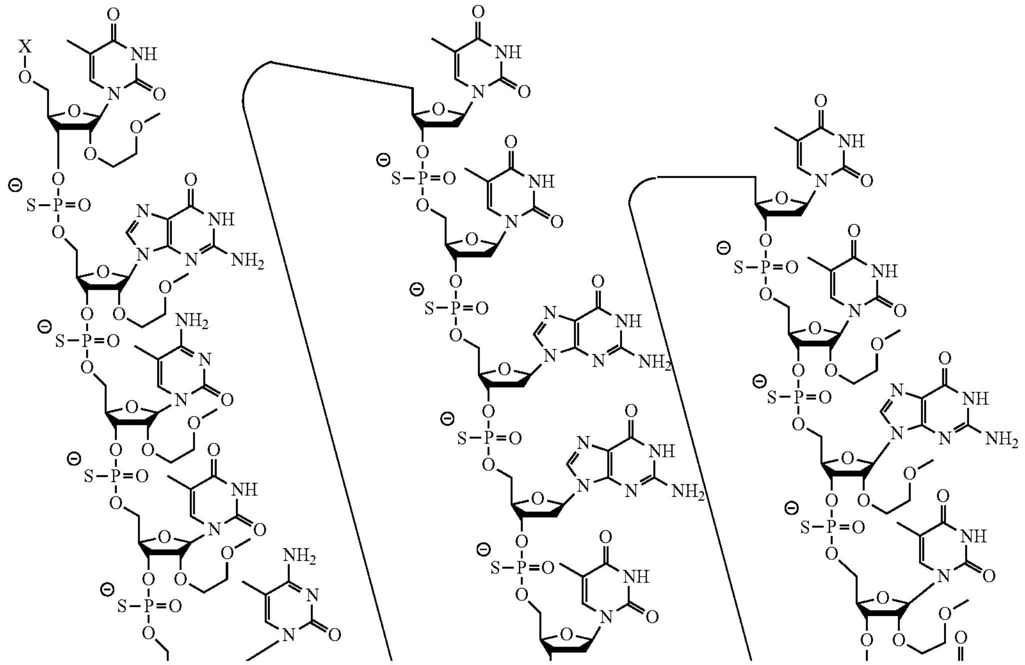
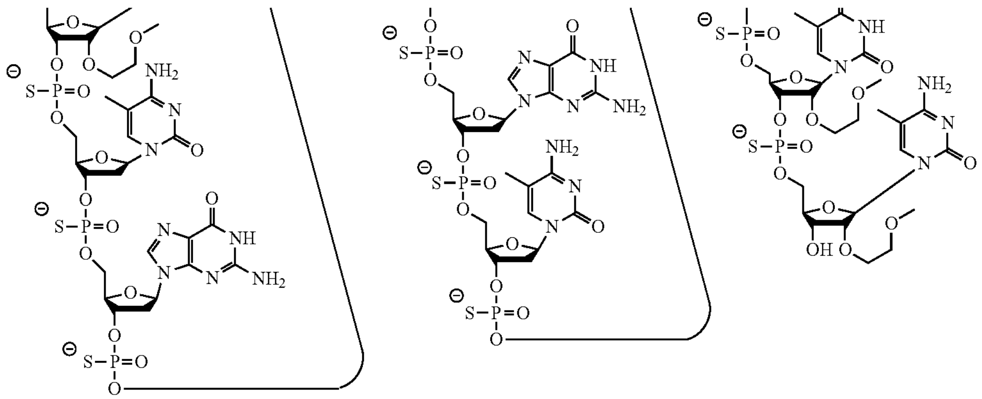
In certain embodiments, the present disclosure provides conjugated antisense compounds represented by the following structure. In certain embodiments, the antisense compound comprises the conjugated modified oligonucleotide ISIS 681251. In certain embodiments, the antisense compound consists of the conjugated modified oligonucleotide ISIS 681251.

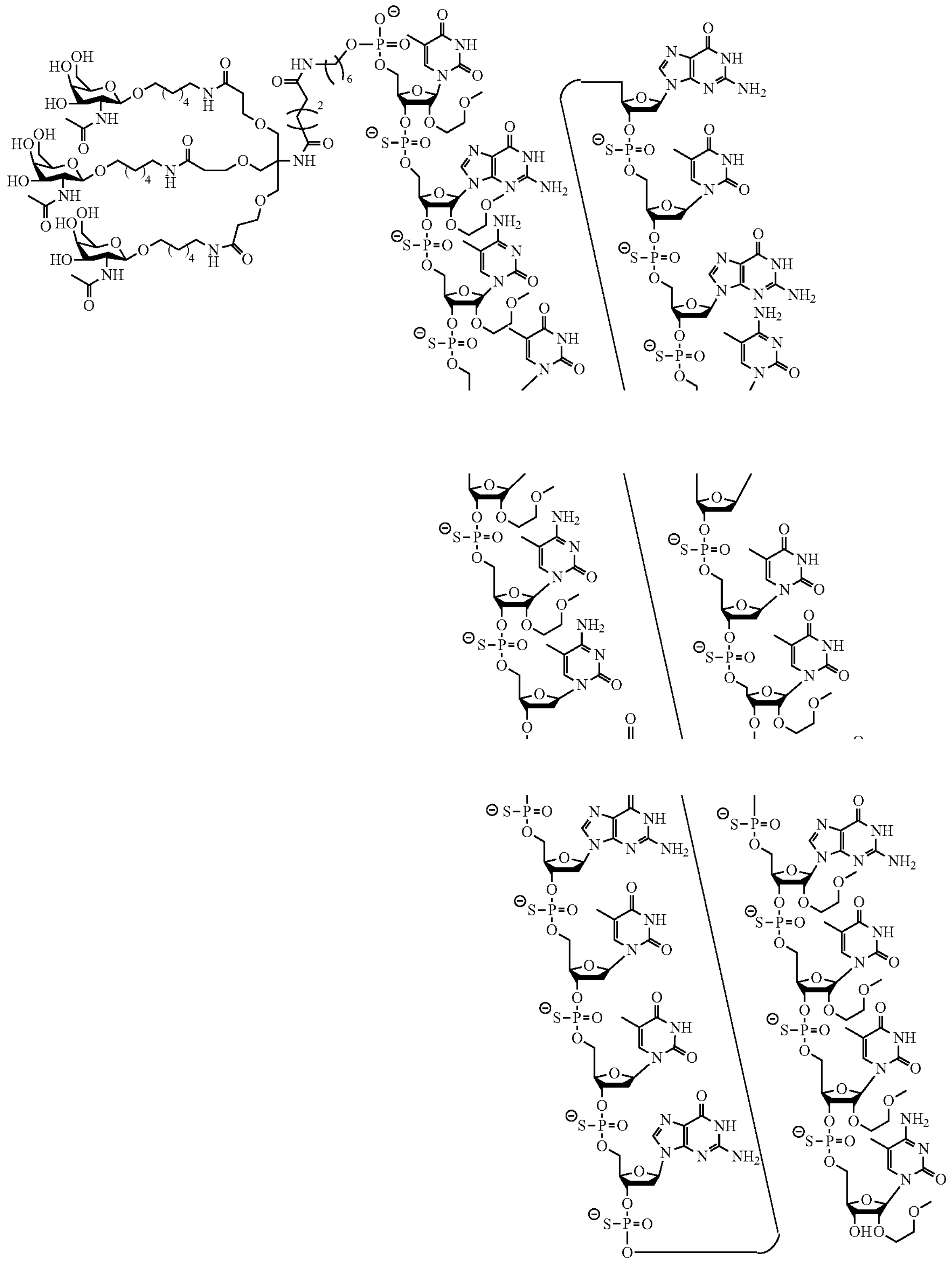
In certain embodiments, the present disclosure provides conjugated antisense compounds represented by the following structure. In certain embodiments, the antisense compound comprises the conjugated modified oligonucleotide ISIS 681257. In certain embodiments, the antisense compound consists of the conjugated modified oligonucleotide ISIS 681257.

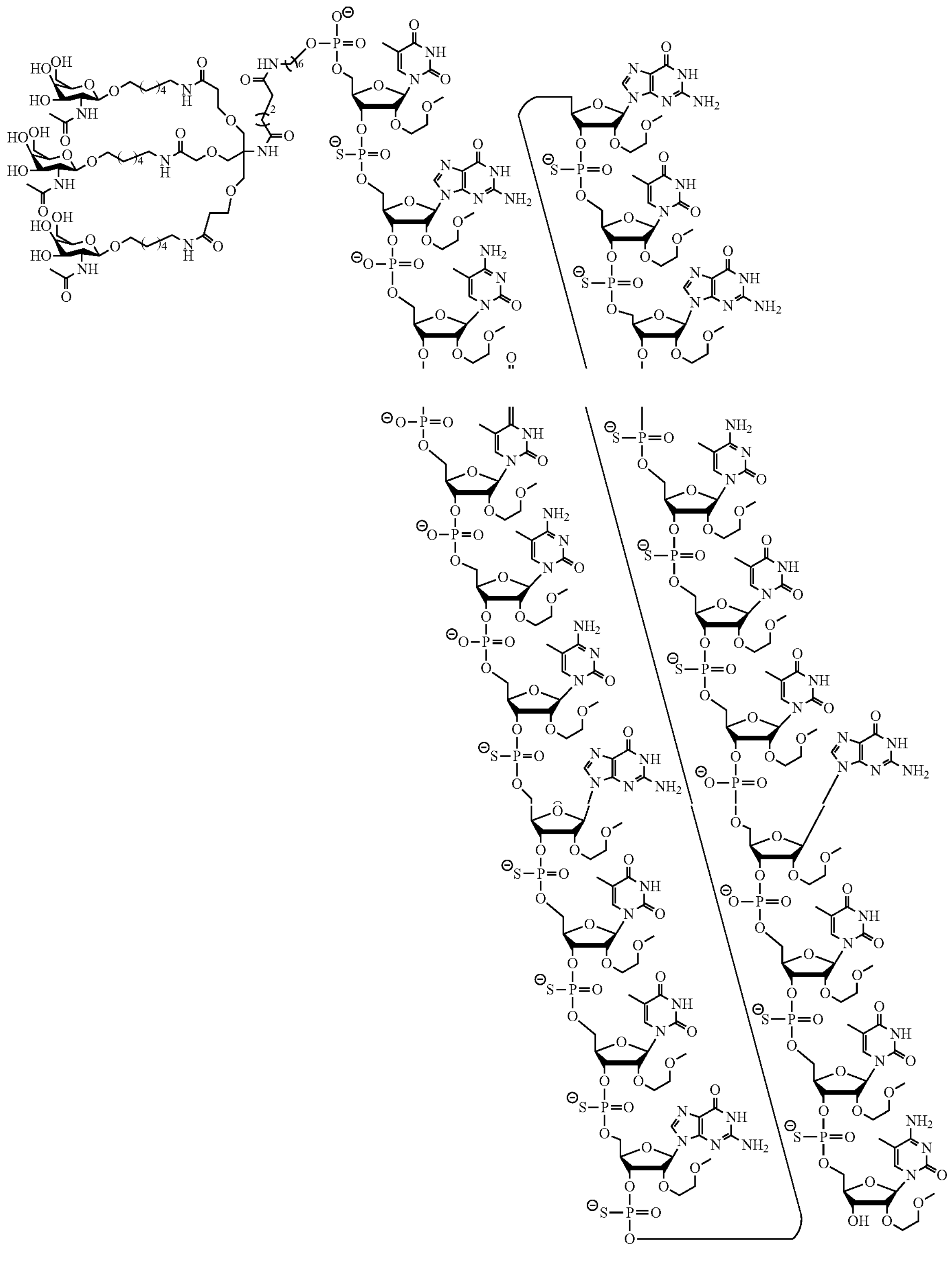

In certain embodiments, the present disclosure provides conjugated antisense compounds represented by the following structure. In certain embodiments, the antisense compound comprises a modified oligonucleotide with the nucleobase sequence of SEQ ID NO: 58 with a 5'-GalNAc with variability in the sugar mods of the wings. In certain embodiments, the antisense compound consists of a modified oligonucleotide with the nucleobase sequence of SEQ ID NO: 58 with a 5'-GalNAc with variability in the sugar mods of the wings.

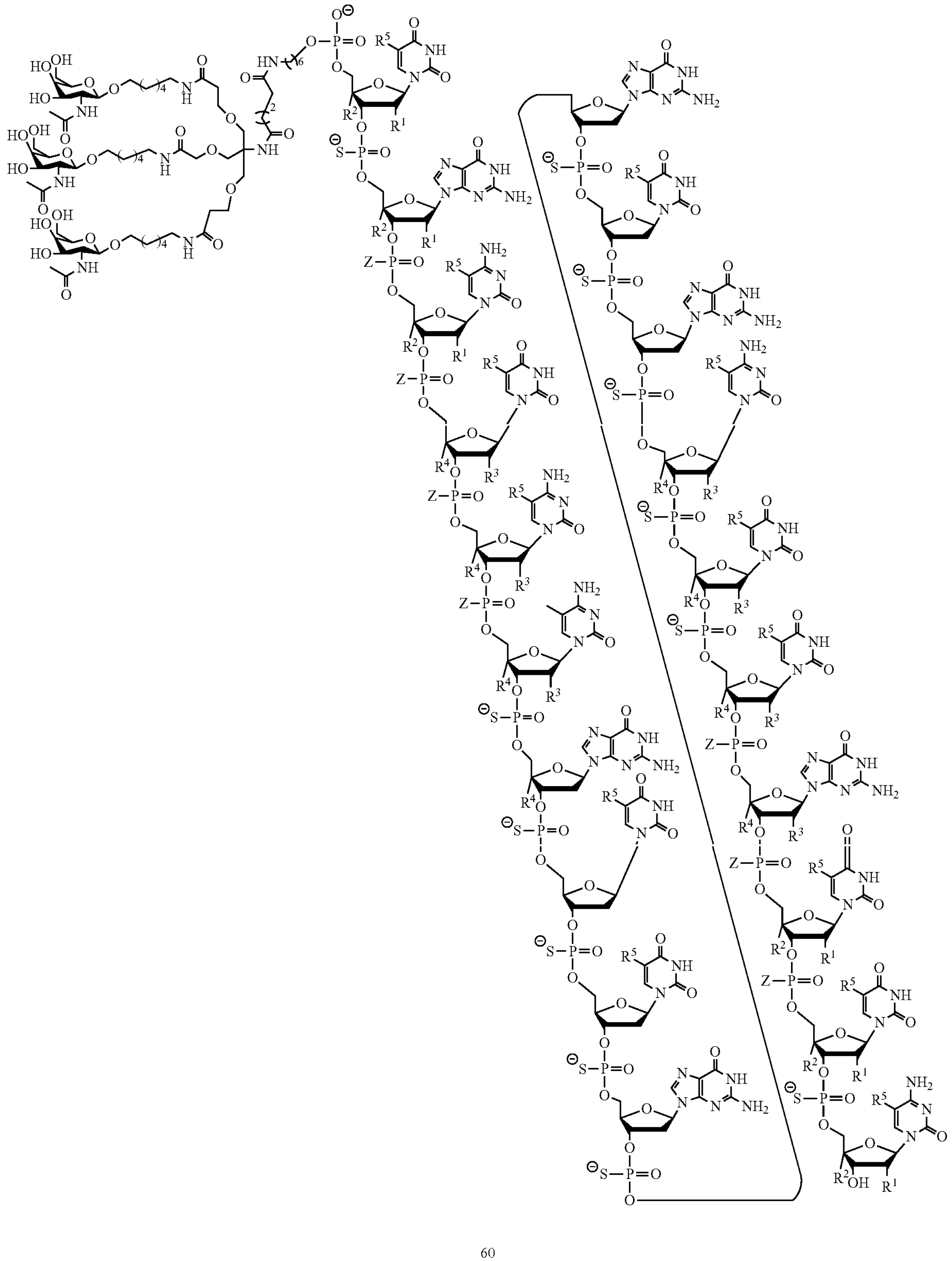

Wherein either $R^1$ is $-OCH_2CH_2OCH_3$ (MOE) and $R^2$ is H; or $R^1$ and $R^2$ together form a bridge, wherein $R^1$ is $-O-$ and $R^2$ is $-CH_2-$, $-CH(CH_3)-$, or $-CH_2CH_2-$, and $R^1$ and $R^2$ are directly connected such that the resulting bridge is selected from: $-O-CH_2-$, $-O-CH(CH_3)-$, and $-O-CH_2CH_2-$;

And for each pair of $R^3$ and $R^4$ on the same ring, independently for each ring: either $R^3$ is selected from H and $-OCH_2CH_2OCH_3$ and $R^4$ is H; or $R^3$ and $R^4$ together form a bridge, wherein $R^3$ is $-O-$, and $R^4$ is $-CH_2-$, $-CH(CH_3)-$, or $-CH_2CH_2-$ and $R^3$ and $R^4$ are directly connected such that the resulting bridge is selected from: $-O-CH_2-$, $-O-CH(CH_3)-$, and $-O-CH_2CH_2-$;

And $R^5$ is selected from H and —$CH_3$;

And Z is selected from $S^-$ and $O^-$.

Certain embodiments provide a compound comprising a modified oligonucleotide targeting apo(a) and a conjugate group, wherein the modified oligonucleotide is single-stranded.

Certain embodiments provide a compound comprising a modified oligonucleotide targeting apo(a) and a conjugate group, wherein at least one internucleoside linkage is a modified internucleoside linkage. In certain embodiments, the modified internucleoside linkage is a phosphorothioate internucleoside linkage. In certain embodiments, at least 1, at least 2, at least 3, at least 4, at least 5, at least 6, at least 7, at least 8, at least 9 or at least 10 internucleoside linkages of said modified oligonucleotide are phosphorothioate internucleoside linkages. In certain embodiments, each internucleoside linkage is a phosphorothioate internucleoside linkage. In certain embodiments, the modified oligonucleotide comprises at least 1, at least 2, at least 3, at least 4, at least 5, at least 6, at least 7, at least 8, at least 9 or at least 10 phosphodiester internucleoside linkages. In certain embodiments, each internucleoside linkage of the modified oligonucleotide is selected from a phosphodiester internucleoside linkage and a phosphorothioate internucleoside linkage.

Certain embodiments provide a compound comprising a modified oligonucleotide targeting apo(a) and a conjugate group, wherein at least one nucleoside comprises a modified nucleobase. In certain embodiments, the modified nucleobase is a 5-methylcytosine.

Certain embodiments provide a compound comprising a modified oligonucleotide targeting apo(a) and a conjugate group, wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-$(CH_2)_n$—O-2' bridge, wherein n is 1 or 2.

Certain embodiments provide a compound comprising a modified oligonucleotide targeting apo(a) and a conjugate group, wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a) and a conjugate group, wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting apo(a) and a conjugate group, wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting apo(a) and a conjugate group, wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a modified oligonucleotide targeting apo(a) and a conjugate group, wherein the modified oligonucleotide consists of 20 linked nucleosides with the nucleobase sequence of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide.

In certain embodiments, the conjugate group comprises one or more ligands. In certain embodiments, the conjugate group comprises two or more ligands. In certain embodiments, the conjugate group comprises three or more ligands. In certain embodiments, the conjugate group comprises three ligands. In certain embodiments, each ligand is selected from among: a polysaccharide, modified polysaccharide, mannose, galactose, a mannose derivative, a galactose derivative, D-mannopyranose, L-Mannopyranose, D-Arabinose, L-Galactose, D-xylofuranose, L-xylofuranose, D-glucose, L-glucose, D-Galactose, L-Galactose, α-D-Mannofuranose, β-D-Mannofuranose, α-D-Mannopyranose, β-D-Mannopyranose, α-D-Glucopyranose, β-D-Glucopyranose, α-D-Glucofuranose, β-D-Glucofuranose, α-D-fructofuranose, α-D-fructopyranose, α-D-Galactopyranose, β-D-Galactopyranose, α-D-Galactofuranose, βD-Galactofuranose, glucosamine, sialic acid, α-D-galactosamine, N-Acetylgalactosamine, 2-Amino-3-O—[(R)-1-carboxyethyl]-2-deoxy-β-D-glucopyranose, 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose, N-Glycoloyl-α-neuraminic acid, 5-thio-β-D-glucopyranose, methyl 2,3,4-tri-O-acetyl-1-thio-6-O-trityl-α-D-glucopyranoside, 4-Thio-β-D-galactopyranose, ethyl 3,4,6,7-tetra-O-acetyl-2-deoxy-1,5-dithio-α-D-gluco-heptopyranoside, 2,5-Anhydro-D-allononitrile, ribose, D-ribose, D-4-thioribose, L-ribose, L-4-thioribose. In certain embodiments, each ligand is N-acetyl galactosamine.

In certain embodiments, each ligand is N-acetyl galactosamine.

In certain embodiments, the conjugate group comprises:

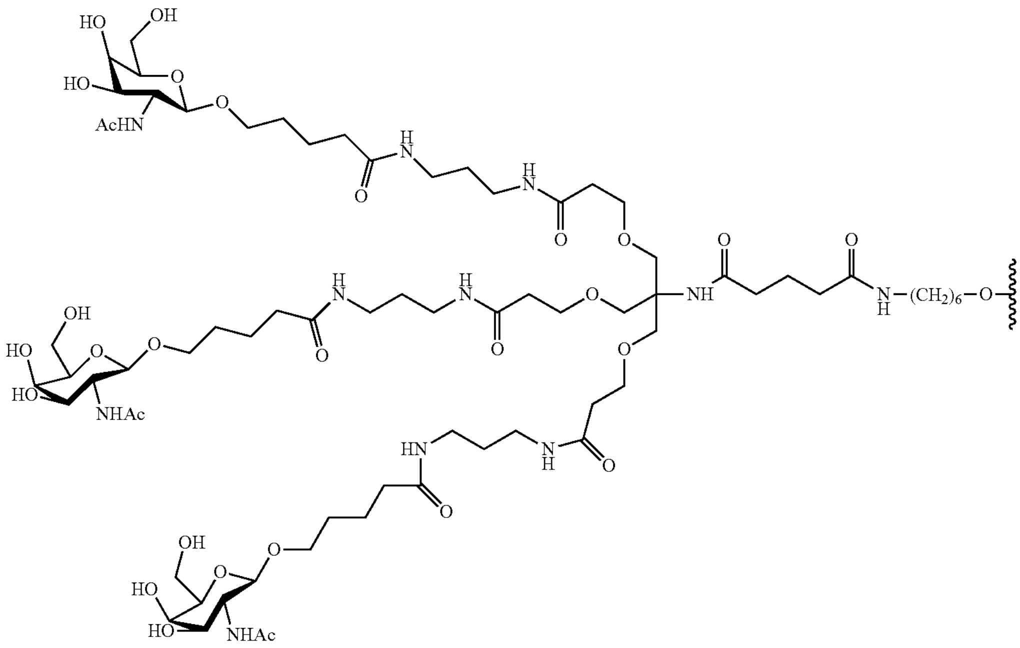

In certain embodiments, the conjugate group comprises:

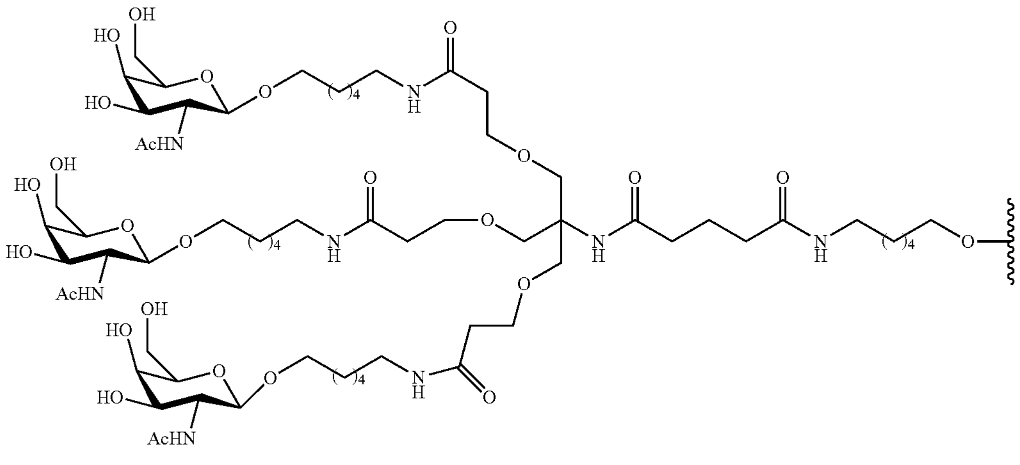

In certain embodiments, the conjugate group comprises:
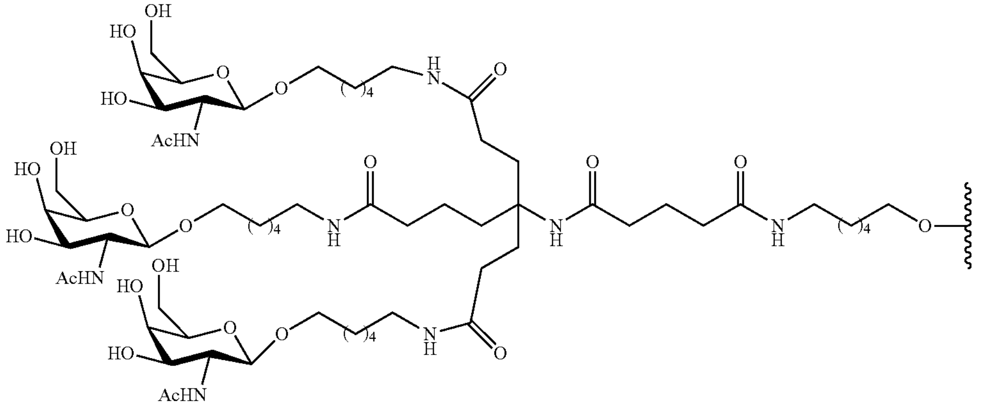
In certain embodiments, the conjugate group comprises:
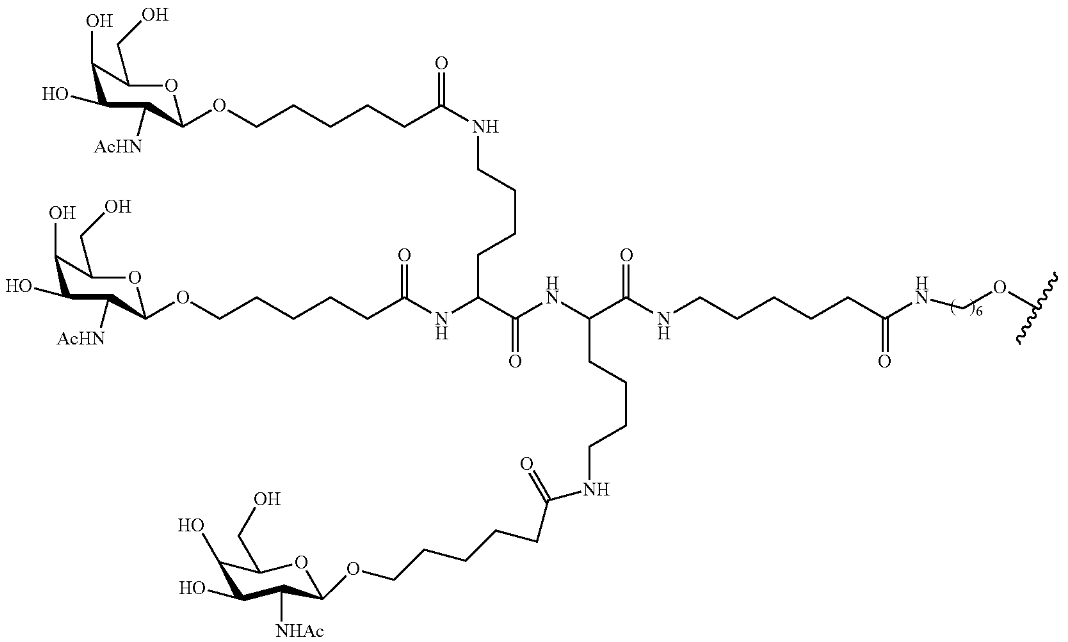

In certain embodiments, the conjugate group comprises:

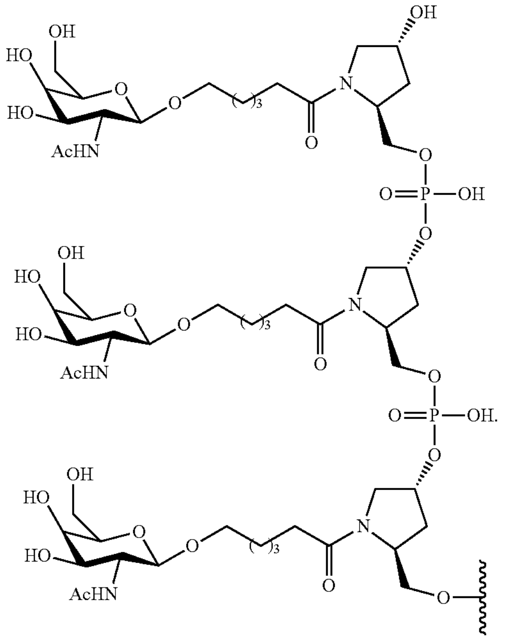

In certain embodiments, the conjugate group comprises at least one phosphorus linking group or neutral linking group.

In certain embodiments, the conjugate group comprises a structure selected from among:

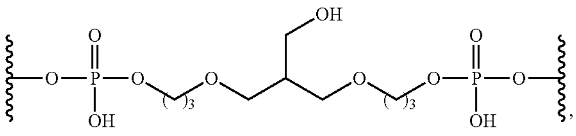
,

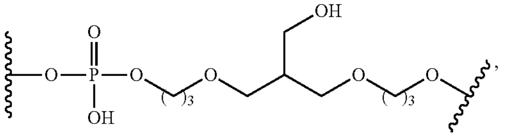
,

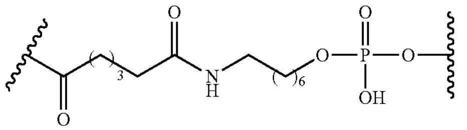
and

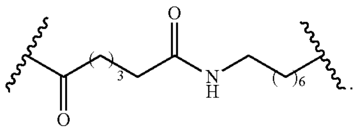
.

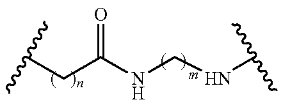
;

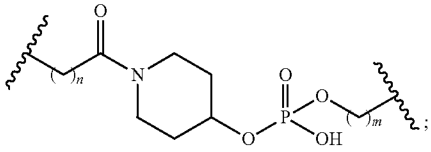
;

-continued

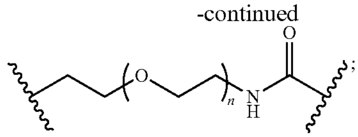
;

wherein n is from 1 to 12; and wherein m is from 1 to 12.

In certain embodiments, the conjugate group has a tether having a structure selected from among:

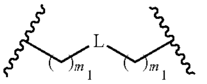
and

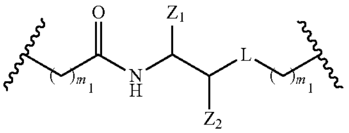

wherein L is either a phosphorus linking group or a neutral linking group;

Z1 is C(=O)O—R2;

Z2 is H, C1-C6 alkyl or substituted C1-C6 alky;

R2 is H, C1-C6 alkyl or substituted C1-C6 alky; and each m1 is, independently, from 0 to 20 wherein at least one m1 is greater than 0 for each tether.

In certain embodiments, conjugate group has a tether having a structure selected from among:

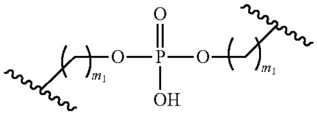
and

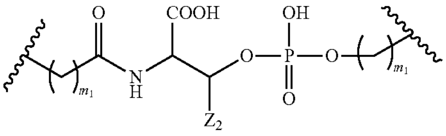

wherein Z2 is H or CH3; and each m1 is, independently, from 0 to 20 wherein at least one m1 is greater than 0 for each tether.

In certain embodiments, the conjugate group has tether having a structure selected from among:

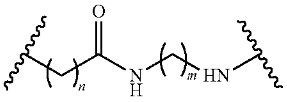
;

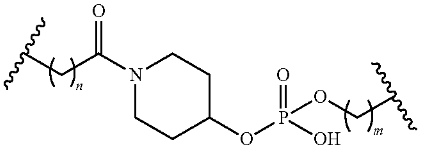
;

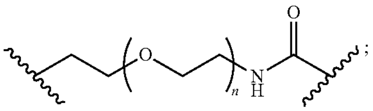
;

wherein n is from 1 to 12; and wherein m is from 1 to 12.

In certain embodiments, the conjugate group is covalently attached to the modified oligonucleotide.

In certain embodiments, the compound has a structure represented by the formula:

$A\text{-}B\text{-}C\text{-}D\text{-}(E\text{-}F)_q$ wherein

A is the modified oligonucleotide;

B is the cleavable moiety

C is the conjugate linker

D is the branching group each E is a tether;

each F is a ligand; and q is an integer between 1 and 5.

In certain embodiments, the compound has a structure represented by the formula:

$A\text{-}(B)_{n_2}\text{-}(C)_{n_1}\text{-}(D)_{n_3}\text{-}(E\text{—}F)_q$ wherein:

A is the modified oligonucleotide;

B is the cleavable moiety

C is the conjugate linker

D is the branching group each E is a tether;

each F is a ligand;

each n is independently 0 or 1; and q is an integer between 1 and 5.

In certain embodiments, the compound has a structure represented by the formula:

$A\text{-}B\text{-}C\text{-}(E\text{-}F)_q$ wherein

A is the modified oligonucleotide;

B is the cleavable moiety;

C is the conjugate linker;

each E is a tether;

each F is a ligand; and q is an integer between 1 and 5.

In certain embodiments, the compound has a structure represented by the formula:

$A\text{-}C\text{-}D\text{-}(E\text{-}F)_q$ wherein

A is the modified oligonucleotide;

C is the conjugate linker;

D is the branching group;

each E is a tether;

each F is a ligand; and q is an integer between 1 and 5.

In certain embodiments, the compound has a structure represented by the formula:

$A\text{-}C\text{-}(E\text{-}F)_q$ wherein

A is the modified oligonucleotide;

C is the conjugate linker;

each E is a tether;

each F is a ligand; and q is an integer between 1 and 5.

In certain embodiments, the compound has a structure represented by the formula:

$A\text{-}B\text{-}D\text{-}(E\text{-}F)_q$ wherein

A is the modified oligonucleotide;

B is the cleavable moiety;

D is the branching group;

each E is a tether;

each F is a ligand; and q is an integer between 1 and 5.

In certain embodiments, the compound has a structure represented by the formula:

$A\text{-}B\text{-}(E\text{-}F)_q$ wherein

A is the modified oligonucleotide;

B is the cleavable moiety;

each E is a tether;

each F is a ligand; and q is an integer between 1 and 5.

In certain embodiments, the compound has a structure represented by the formula:

$A\text{-}D\text{-}(E\text{-}F)_q$ wherein

A is the modified oligonucleotide;

D is the branching group;

each E is a tether;

each F is a ligand; and q is an integer between 1 and 5.

In certain embodiments, the conjugate linker has a structure selected from among:

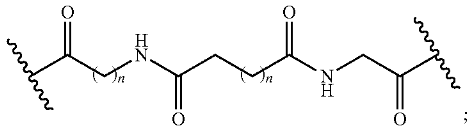
;

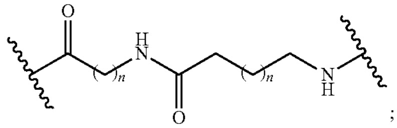
;

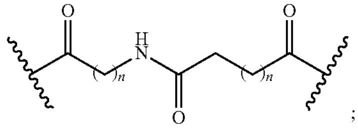
;

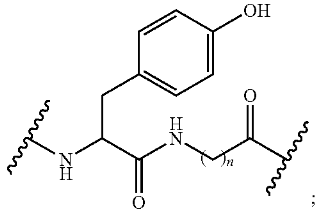
;

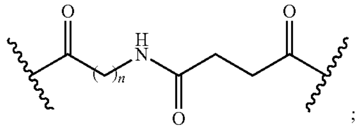
;

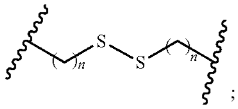
;

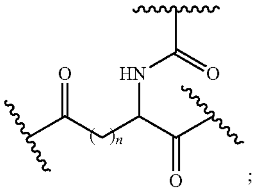
;

-continued
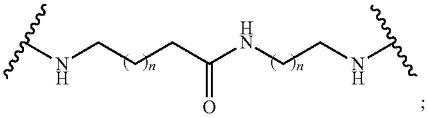
;
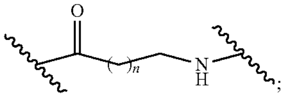
;
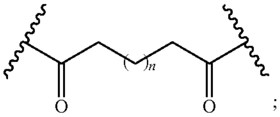
;
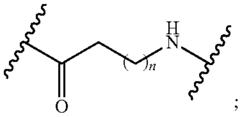
;
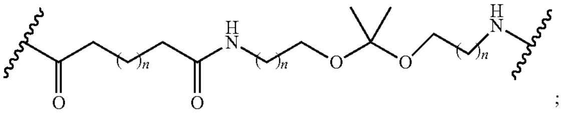
;
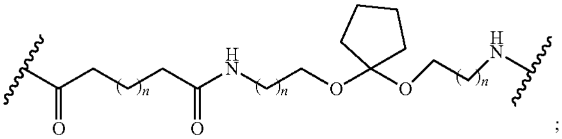
;
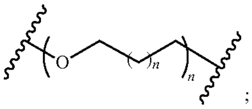
;
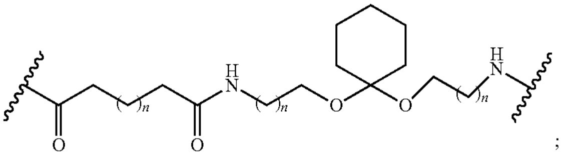
;
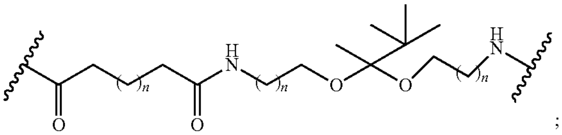
;
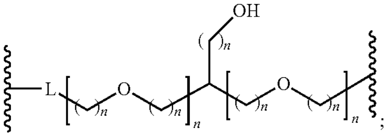
;
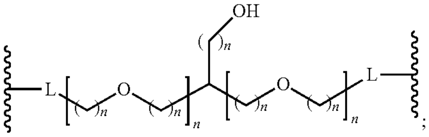
;
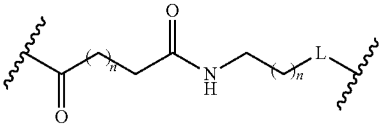
and
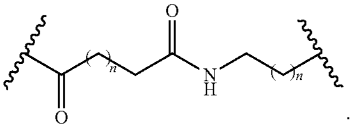
.
wherein each L is, independently, a phosphorus linking group or a neutral linking group; and
each n is, independently, from 1 to 20.
In certain embodiments, the conjugate linker has a structure selected from among:
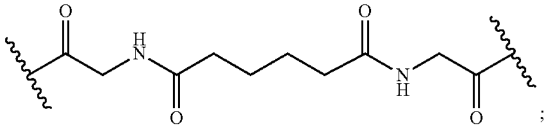
;
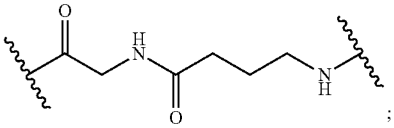
;
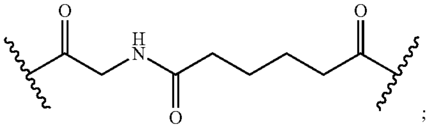
;
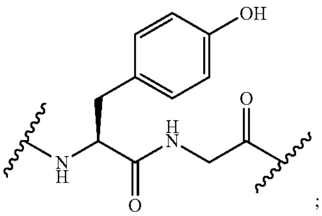
;
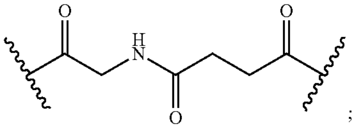
;
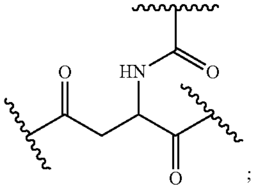
;
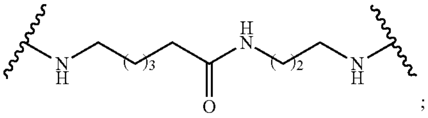
;
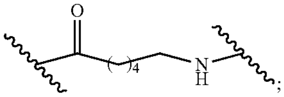
;
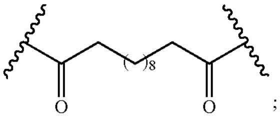
;
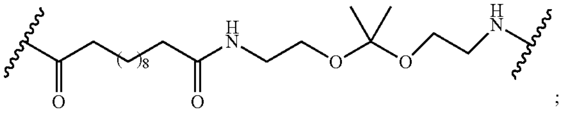
;
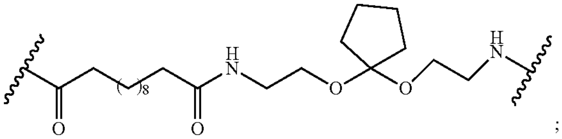
;
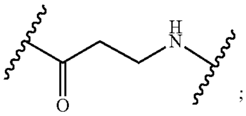
;

-continued

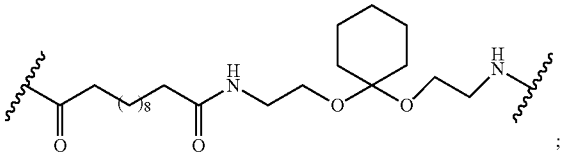

;

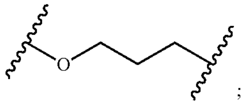

;

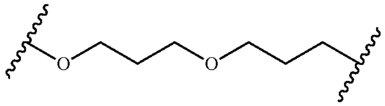

;

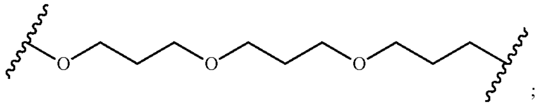

;

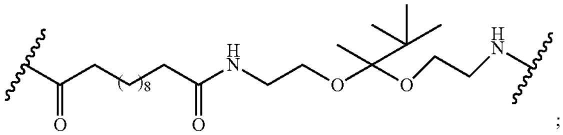

;

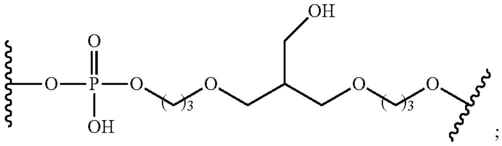

;

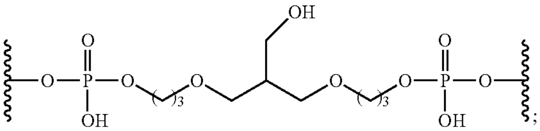

;

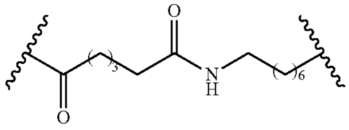

and

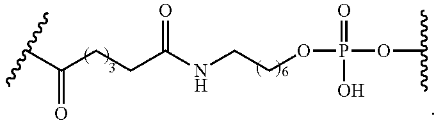

.

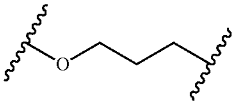

;

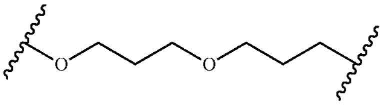

;

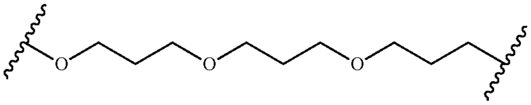

.

In certain embodiments, the conjugate linker has a structure selected from among:

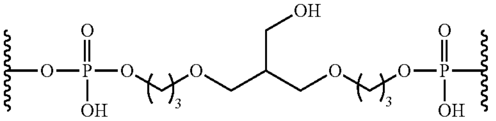

and

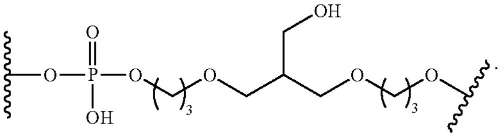

.

In certain embodiments, the conjugate linker has a structure selected from among:

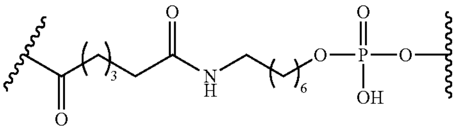

;

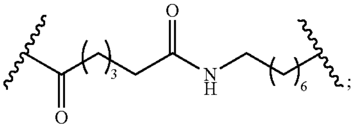

; and

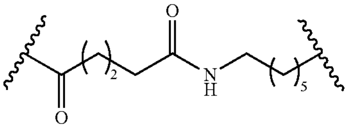

In certain embodiments, the conjugate linker has the following structure:

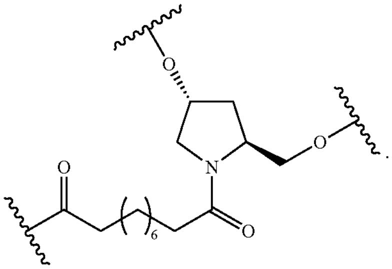

.

In certain embodiments, the conjugate linker has a structure selected from among:

In certain embodiments, the conjugate linker comprises a pyrrolidine. In certain embodiments, the conjugate linker does not comprise a pyrrolidine. In certain embodiments, the conjugate linker comprises PEG. In certain embodiments, the conjugate linker comprises an amide. In certain embodiments, the conjugate linker comprises at least two amides. In certain embodiments, the conjugate linker does not comprise an amide. In certain embodiments, the conjugate linker comprises a polyamide. In certain embodiments, the conjugate linker comprises an amine. In certain embodiments, the conjugate linker comprises one or more disulfide bonds. In certain embodiments, the conjugate linker comprises a protein binding moiety. In certain embodiments, the protein binding moiety comprises a lipid.

In certain embodiments, the protein binding moiety is selected from among: cholesterol, cholic acid, adamantane acetic acid, 1-pyrene butyric acid, dihydrotestosterone, 1,3-

Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid.

In certain embodiments, the protein binding moiety is selected from among: a C16 to C22 long chain saturated or unsaturated fatty acid, cholesterol, cholic acid, vitamin E, adamantane or 1-pentafluoropropyl.

In certain embodiments, the conjugate linker has a structure selected from among:

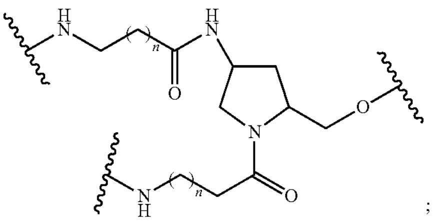
;

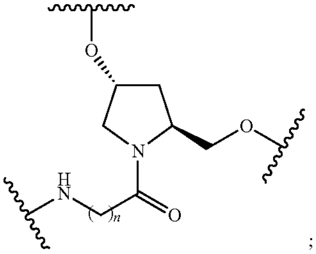
;

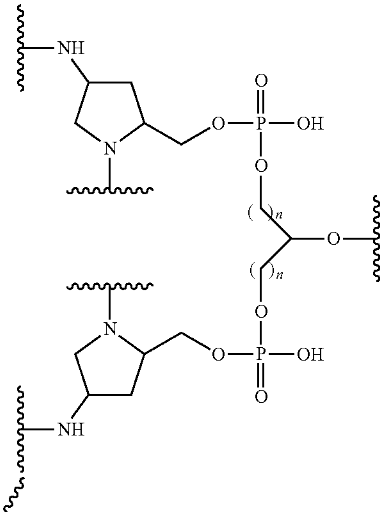
;

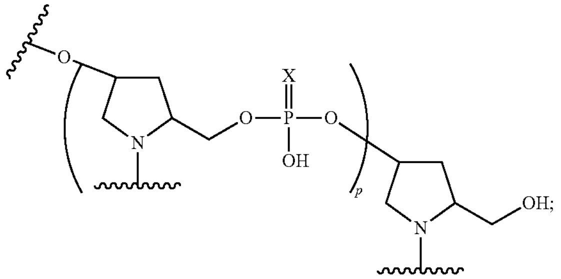

-continued

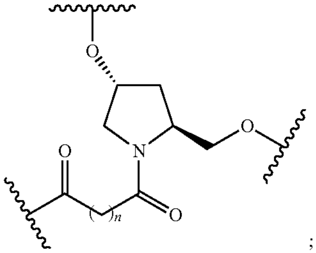
;

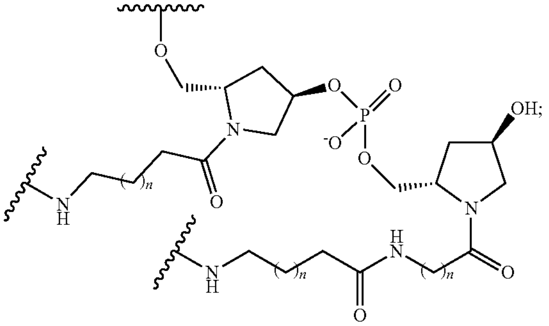

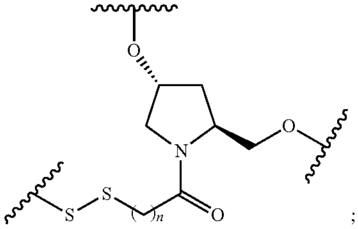
;

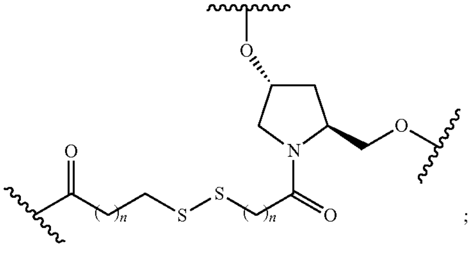
;

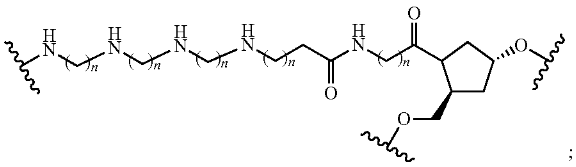
;

-continued
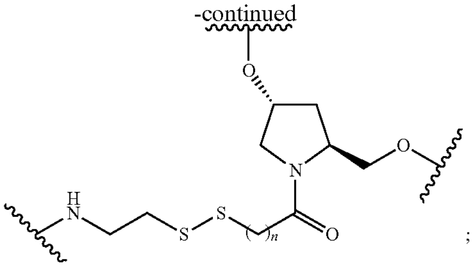
;
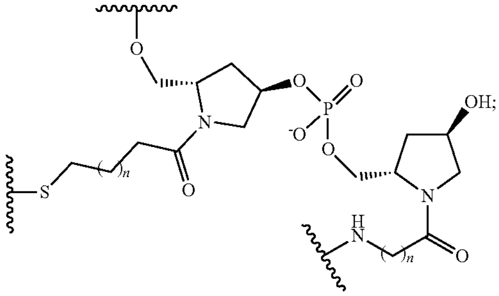
and
-continued
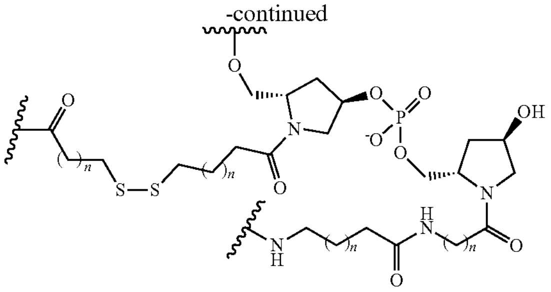
wherein each n is, independently, is from 1 to 20; and p is from 1 to 6.
In certain embodiments, the conjugate linker has a structure selected from among:
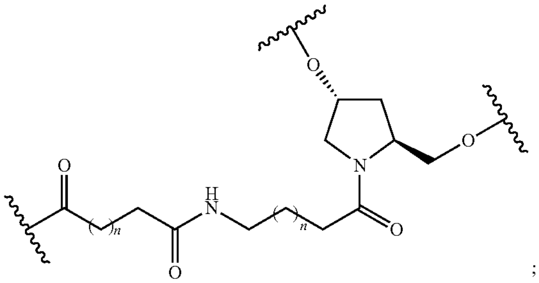
;
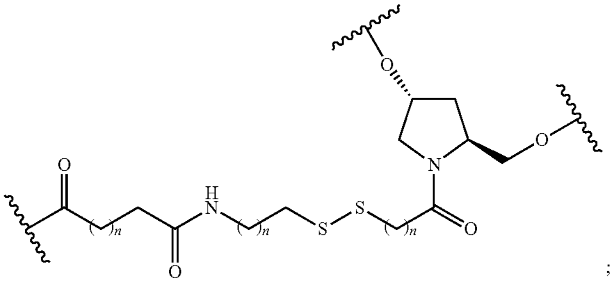
;
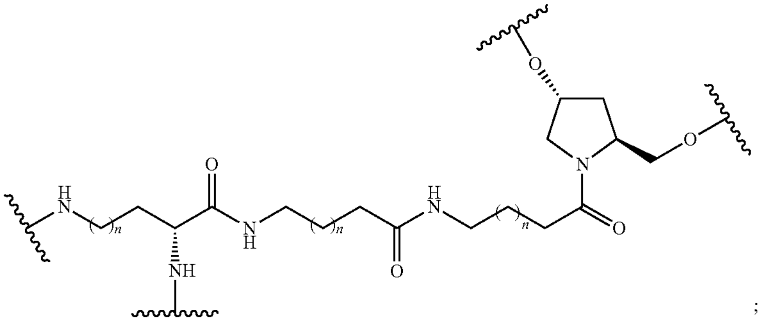
;

-continued
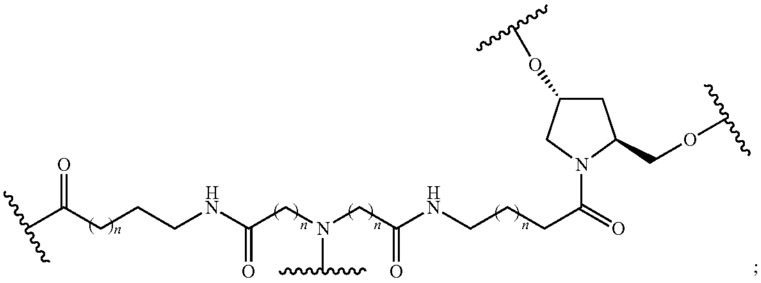
;
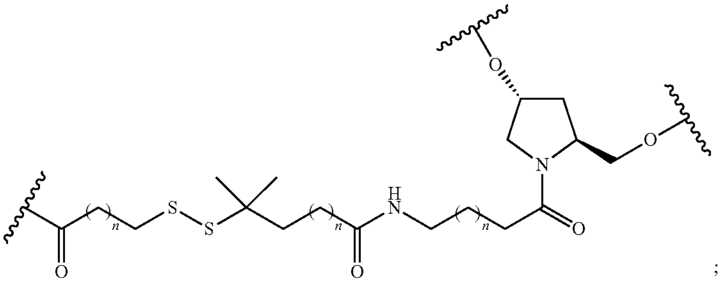
;
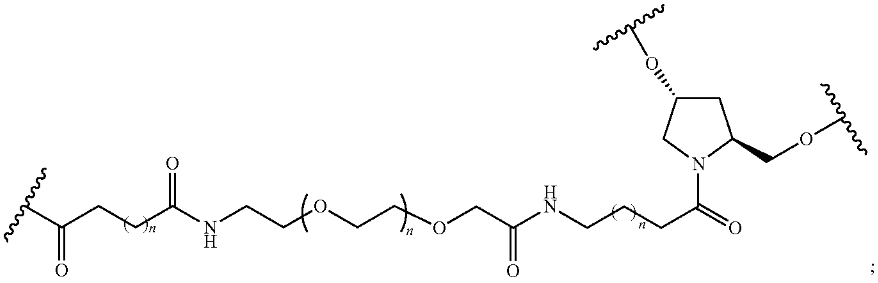
;
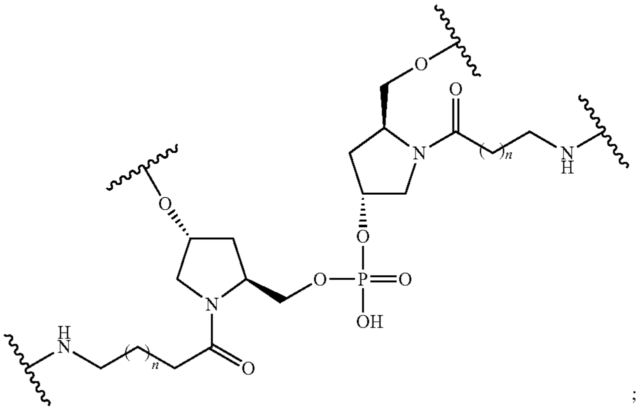
;
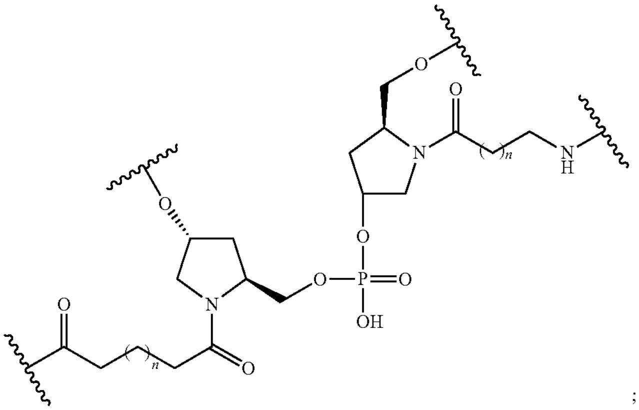
; and -continued
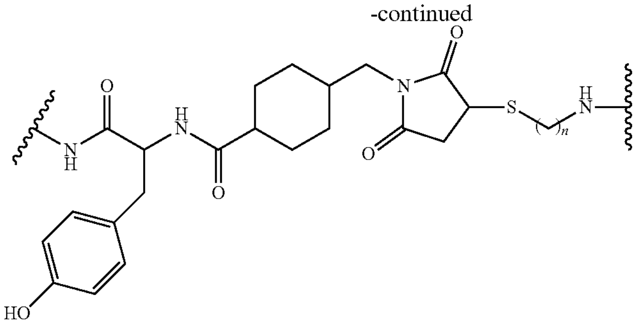
wherein each n is, independently, from 1 to 20.
In certain embodiments, the conjugate linker has a structure selected from among:
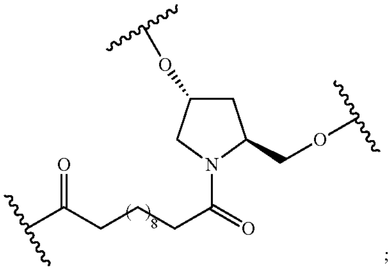
;
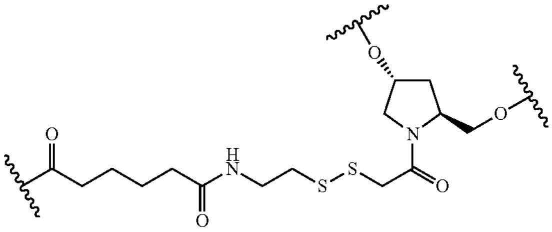
;
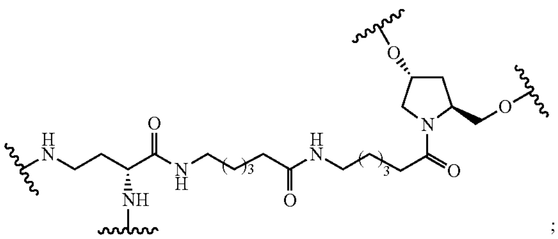
;
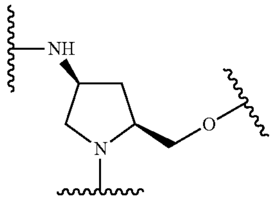
-continued
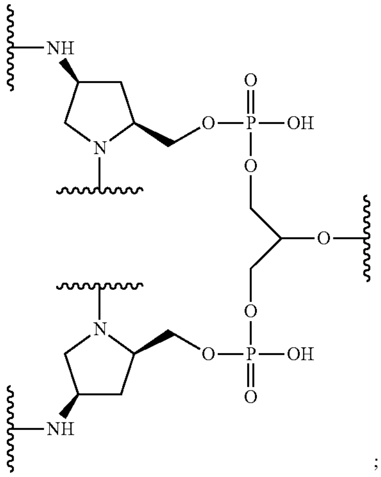
;
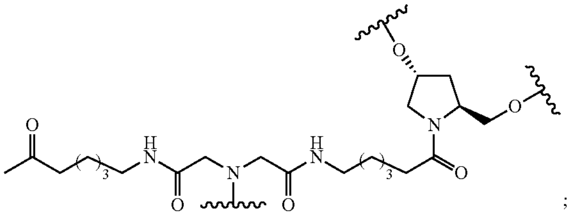
;
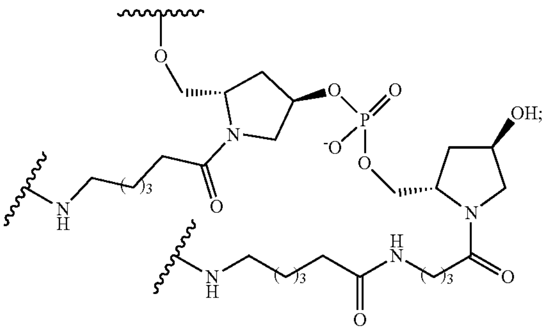

-continued
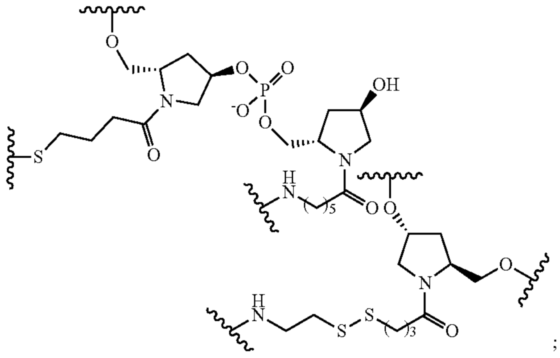
;
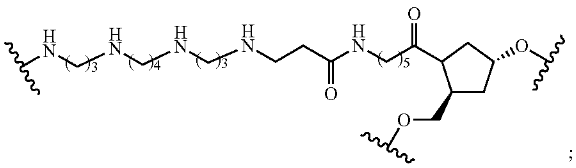
;
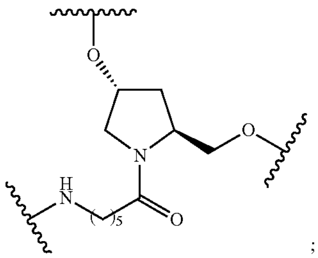
;
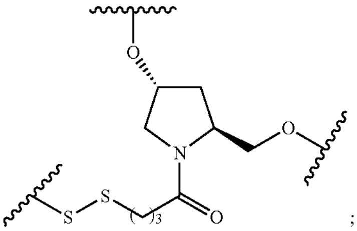
;
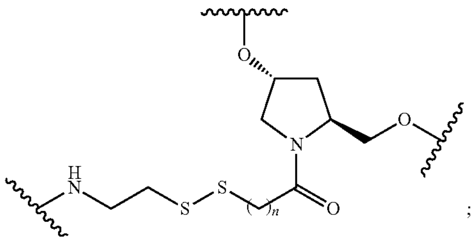
;
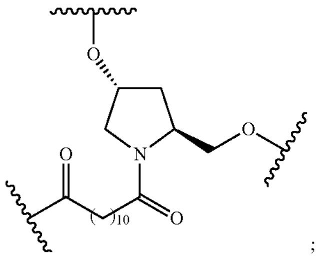
; and
-continued
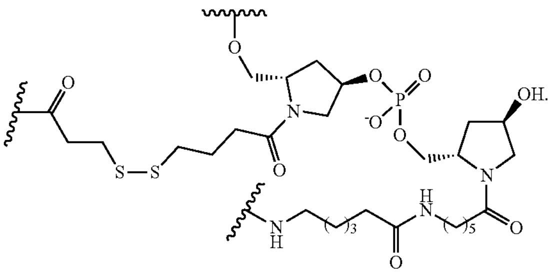
In certain embodiments, the conjugate linker has a structure selected from among:
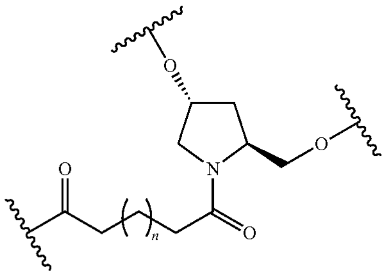
and
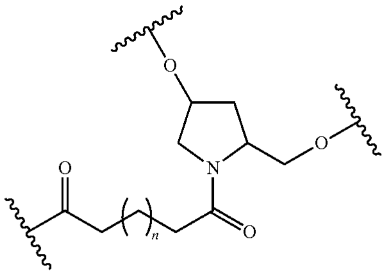
wherein n is from 1 to 20.
In certain embodiments, the conjugate linker has a structure selected from among:
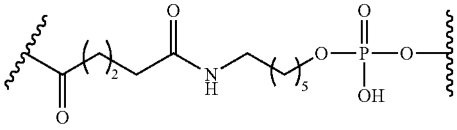
and
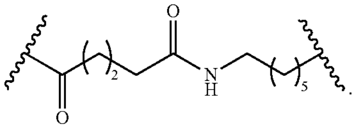
In certain embodiments, the conjugate linker has a structure selected from among:
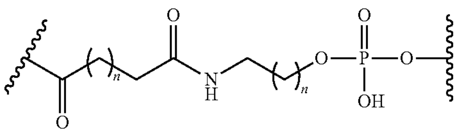
and -continued

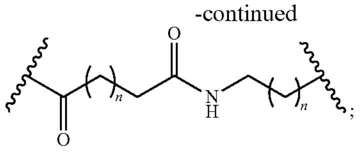

wherein each n is independently, 0, 1, 2, 3, 4, 5, 6, or 7.

In certain embodiments, the conjugate linker has the following structure:

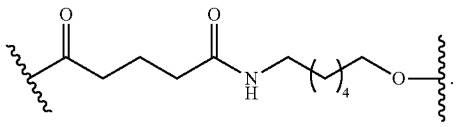

In certain embodiments, the branching group has one of the following structures:

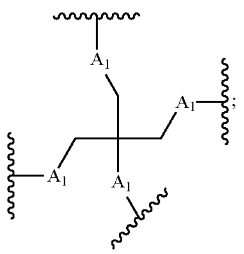

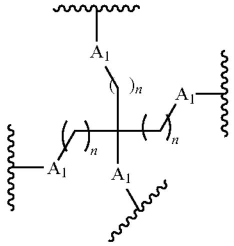

and

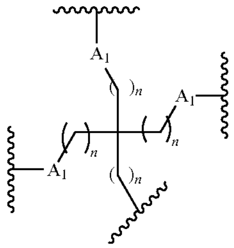

wherein each A1 is independently, O, S, C═O or NH; and each n is, independently, from 1 to 20.

In certain embodiments, the branching group has one of the following structures:

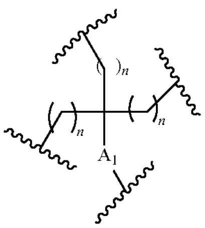

and

-continued

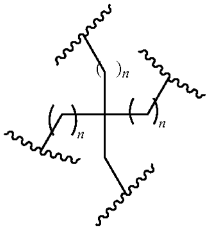

wherein each A1 is independently, O, S, C═O or NH; and each n is, independently, from 1 to 20.

In certain embodiments, the branching group has the following structure:

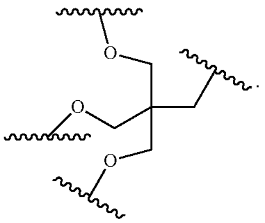 [SMILES: *CC(CO*)(CO*)CO*]

In certain embodiments, the branching group has the following structure:

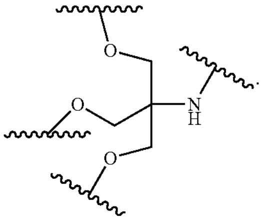 [SMILES: *NC(CO*)(CO*)CO*]

In certain embodiments, the branching group has the following structure:

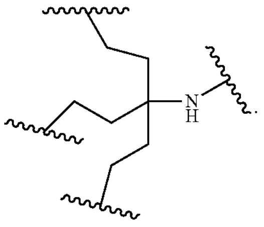 [SMILES: *CCC(CC*)(CC*)N*]

In certain embodiments, the branching group has the following structure:

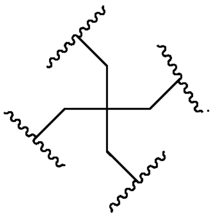 [SMILES: *CC(C*)(C*)C*]

In certain embodiments, the branching group comprises an ether.
In certain embodiments, the branching group has the following structure:
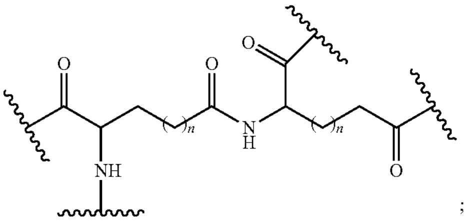
;
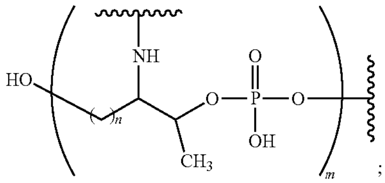
;
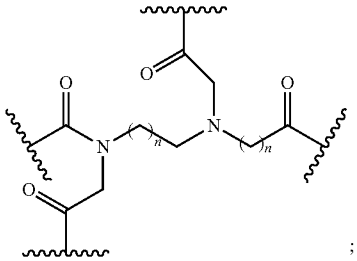
;
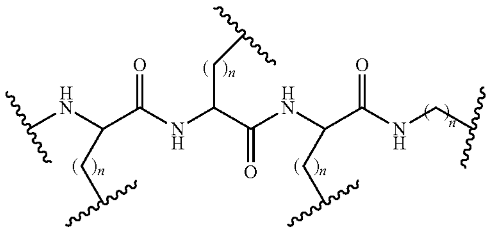
;
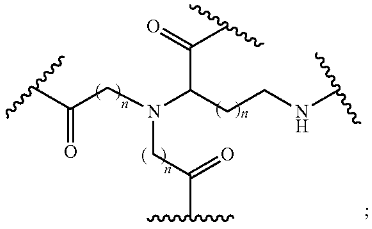
;
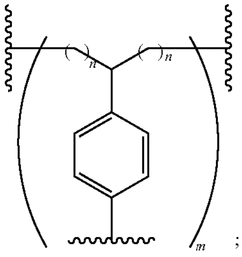
;
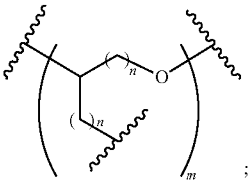
;
-continued
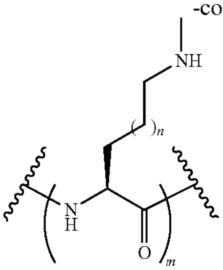
;
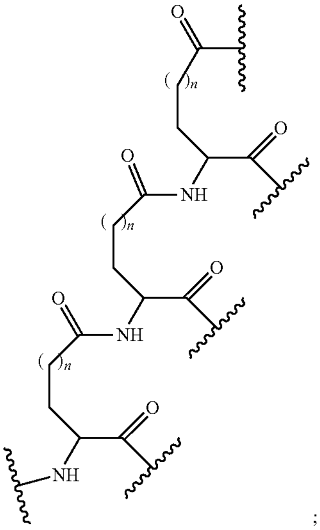
;
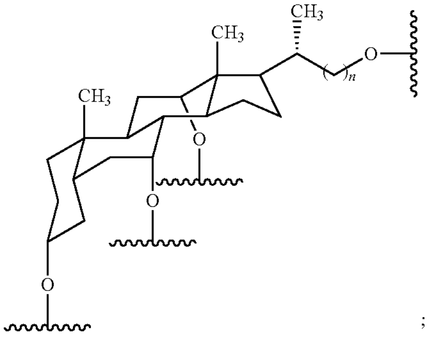
; and
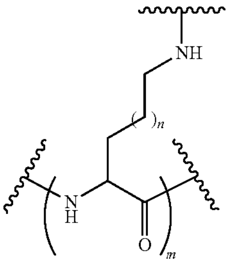
each n is, independently, from 1 to 20; and
m is from 2 to 6.

In certain embodiments, the branching group has the following structure:
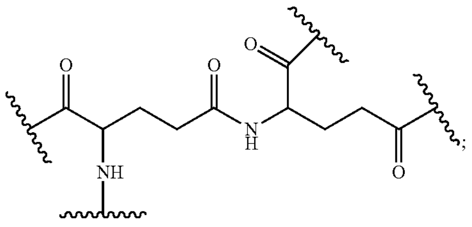
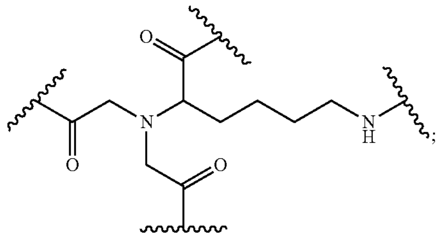
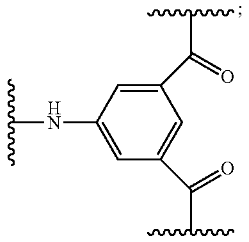
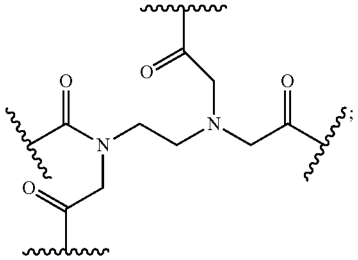
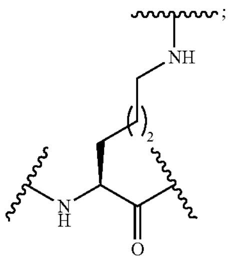
; and
-continued
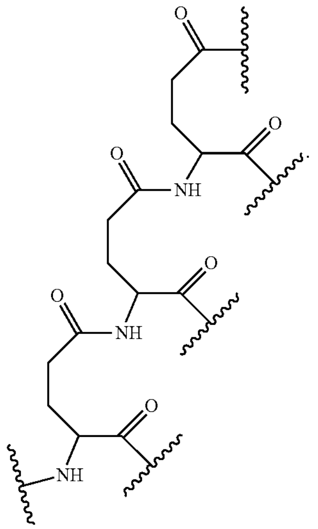
In certain embodiments, the branching group has the following structure:
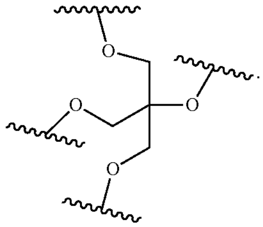 [SMILES: *OCC(CO*)(CO*)O*]
In certain embodiments, the branching group comprises:
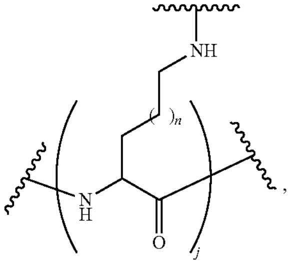
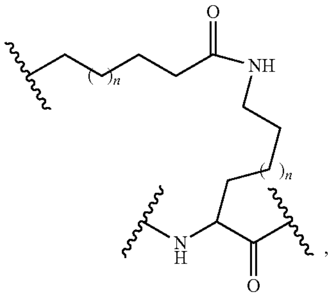

-continued
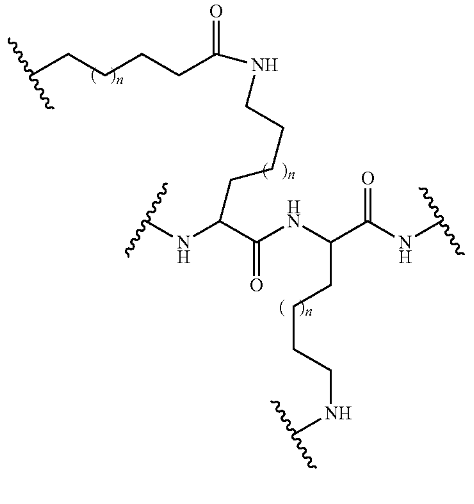
,
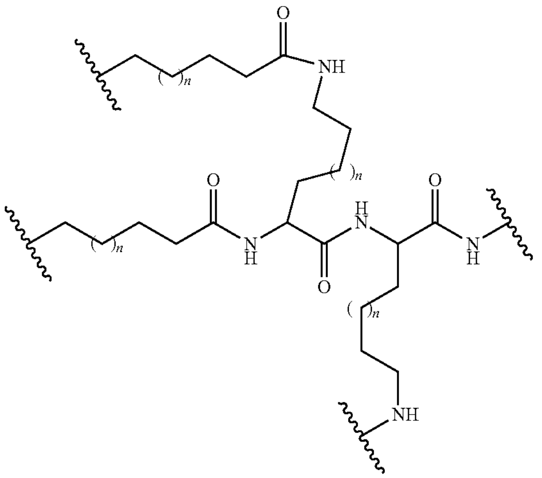
, or
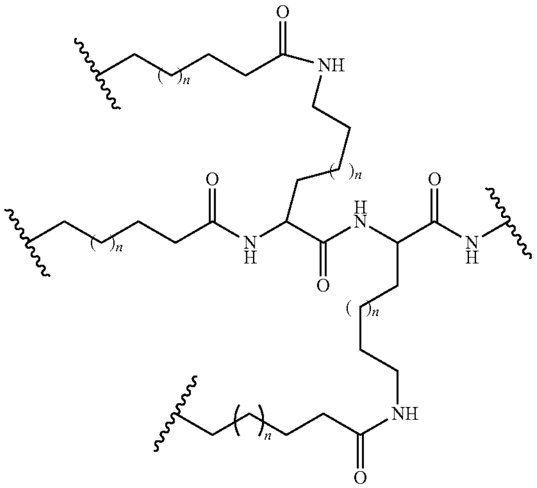
;
wherein each j is an integer from 1 to 3; and wherein each n is an integer from 1 to 20.
In certain embodiments, the branching group comprises:
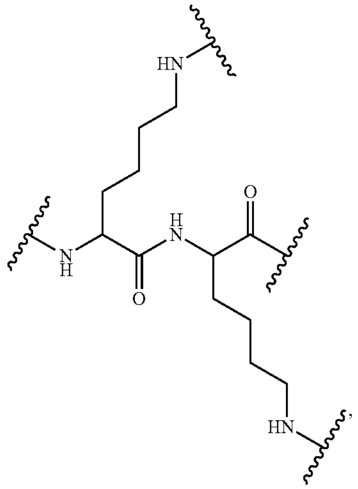
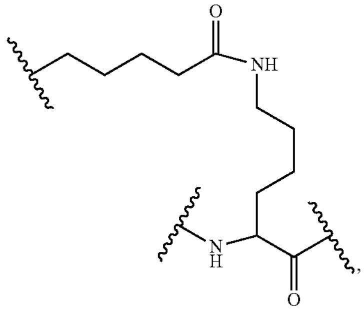
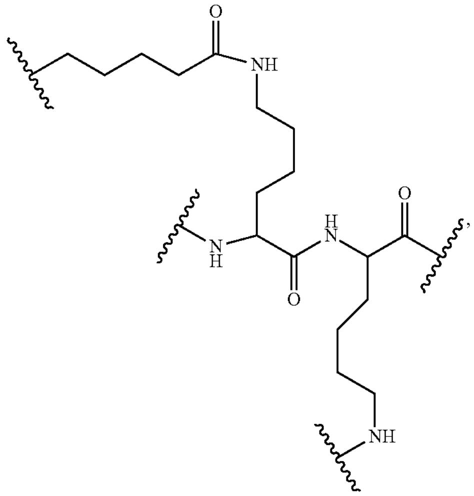

-continued

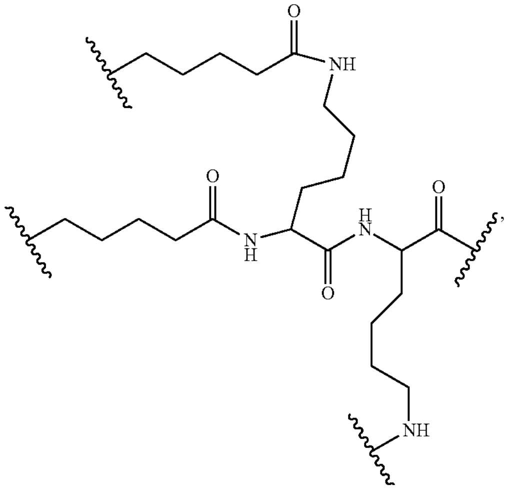

, or

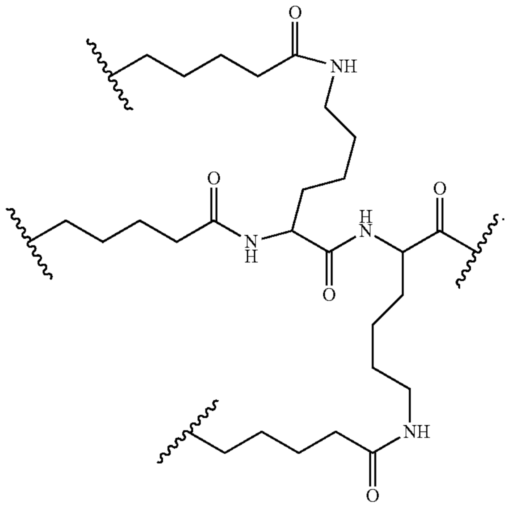 [SMILES: *CCCCC(=O)NCCCCC(NC(=O)C(CCCCNC(=O)CCCC*)NC(=O)CCCC*)C(*)=O]

.

In certain embodiments, each tether is selected from among:

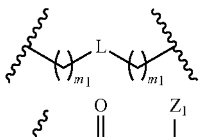

and

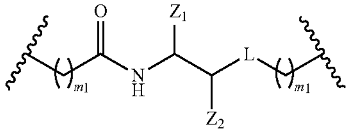

wherein L is selected from a phosphorus linking group and a neutral linking group;

Z1 is C(═O)O—R2;

Z2 is H, C1-C6 alkyl or substituted C1-C6 alky;

R2 is H, C1-C6 alkyl or substituted C1-C6 alky; and each m1 is, independently, from 0 to 20 wherein at least one m1 is greater than 0 for each tether.

In certain embodiments, each tether is selected from among:

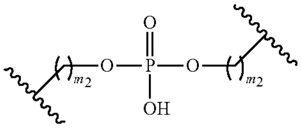

and

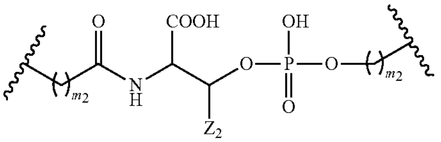

wherein Z2 is H or CH3; and each m2 is, independently, from 0 to 20 wherein at least one m2 is greater than 0 for each tether.

In certain embodiments, each tether is selected from among:

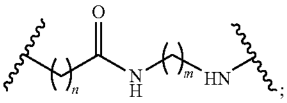

;

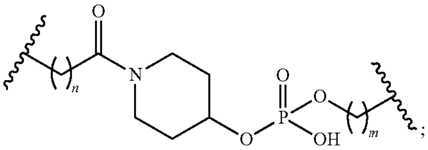

;

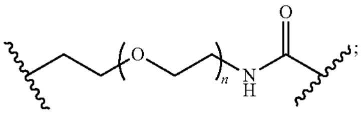

;

wherein n is from 1 to 12; and wherein m is from 1 to 12.

In certain embodiments, at least one tether comprises ethylene glycol. In certain embodiments, at least one tether comprises an amide. In certain embodiments, at least one tether comprises a polyamide. In certain embodiments, at least one tether comprises an amine. In certain embodiments, at least two tethers are different from one another. In certain embodiments, all of the tethers are the same as one another. In certain embodiments, each tether is selected from among:

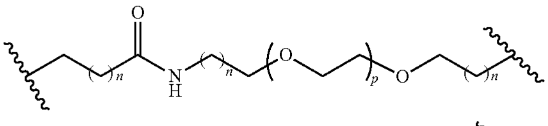

;

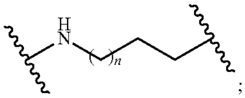

;

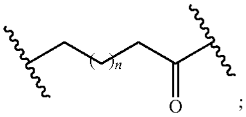

;

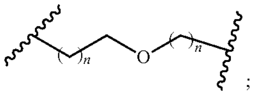

;

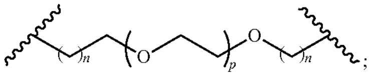

;

-continued

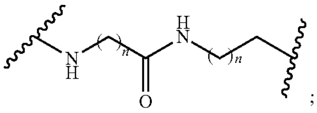
;
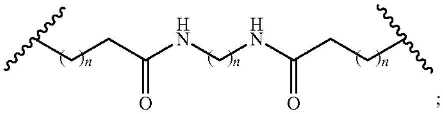
;
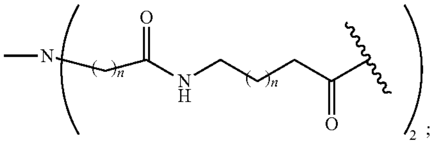
;
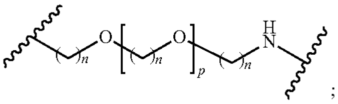
;
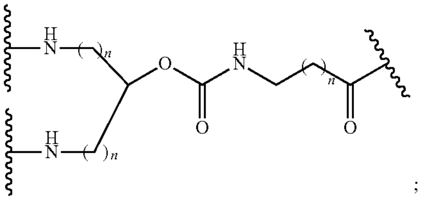
;
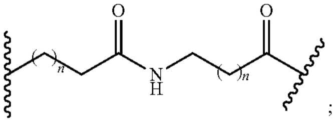
;
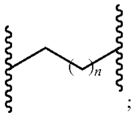
; and
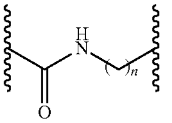

wherein each n is, independently, from 1 to 20; and each p is from 1 to about 6.

In certain embodiments, each tether is selected from among:

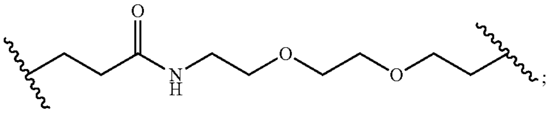
;
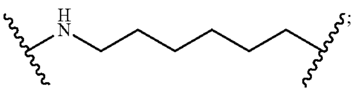
;
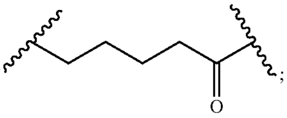
;
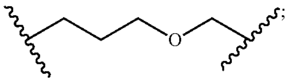
;
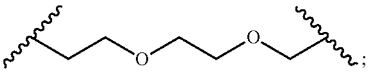
;
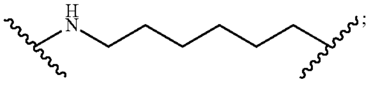
; and -continued

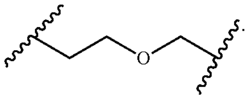

In certain embodiments, each tether has the following structure:

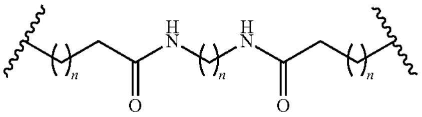

wherein each n is, independently, from 1 to 20.

In certain embodiments, each tether has the following structure:

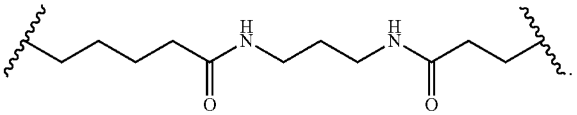 [SMILES: *CCCCC(=O)NCCCNC(=O)CC*]

In certain embodiments, the tether has a structure selected from among:

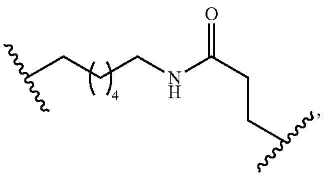
, or

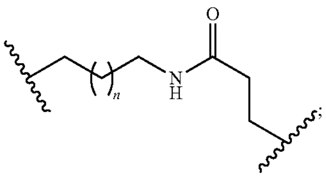
;

wherein each n is independently, 0, 1, 2, 3, 4, 5, 6, or 7.

In certain embodiments, the tether has a structure selected from among:

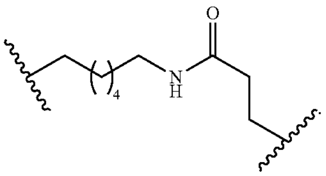

In certain embodiments, the ligand is galactose. In certain embodiments, the ligand is mannose-6-phosphate.

In certain embodiments, each ligand is selected from among:

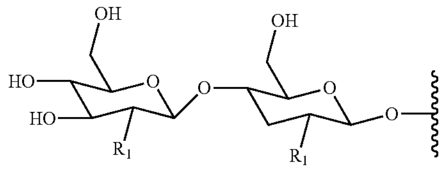

and

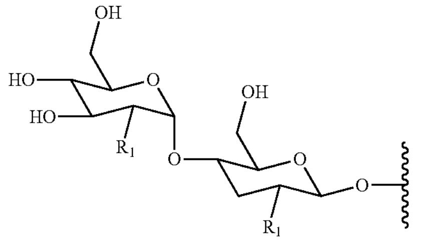

wherein each R1 is selected from OH and NHCOOH.

In certain embodiments, each ligand is selected from among:

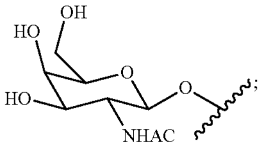

;

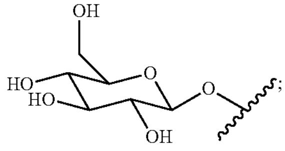

;

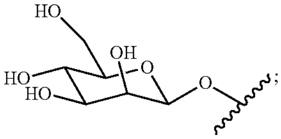

;

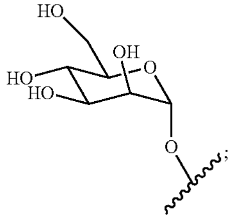

;

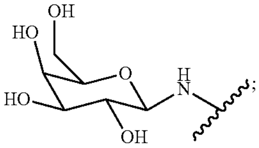

;

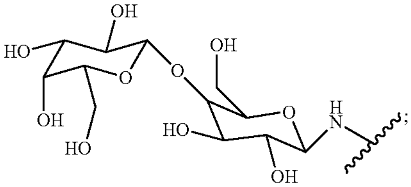

;

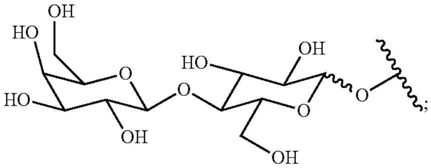

; and

-continued

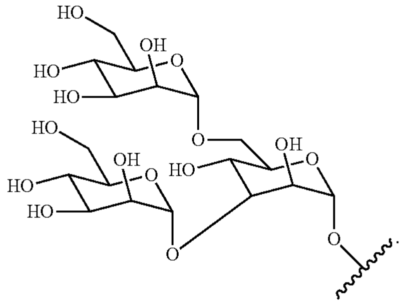

.

In certain embodiments, each ligand has the following structure:

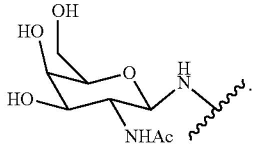 [SMILES: *NC1OC(CO)C(O)C(O)C1NC(C)=O]

.

In certain embodiments, each ligand has the following structure:

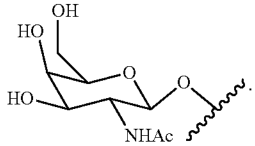 [SMILES: *OC1OC(CO)C(O)C(O)C1NC(C)=O]

.

In certain embodiments, the conjugate group comprises a cell-targeting moiety.

In certain embodiments, the conjugate group comprises a cell-targeting moiety having the following structure:

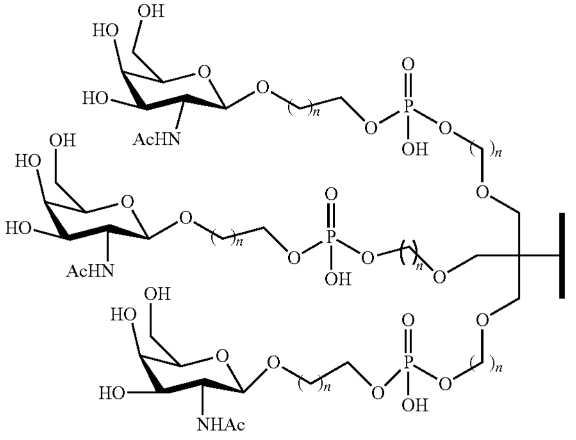

wherein each n is, independently, from 1 to 20.

In certain embodiments, the cell-targeting moiety has the following structure:

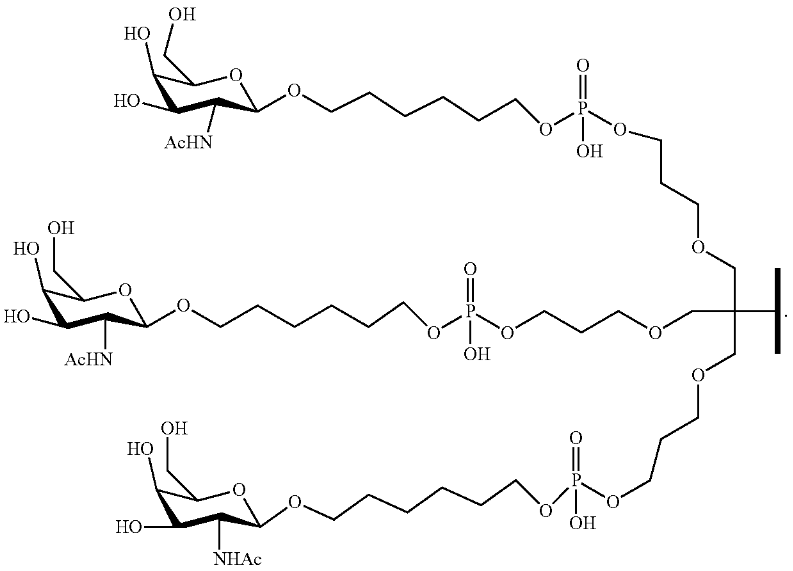

In certain embodiments, the cell-targeting moiety has the following structure:

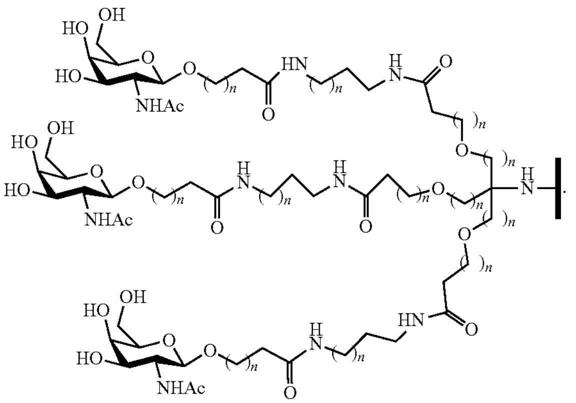

wherein each n is, independently, from 1 to 20.

In certain embodiments, the cell-targeting moiety has the following structure:

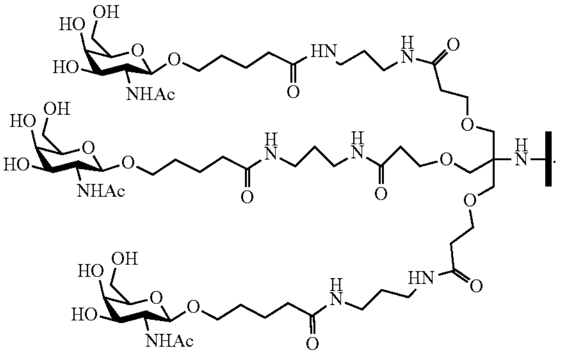

In certain embodiments, the cell-targeting moiety comprises:

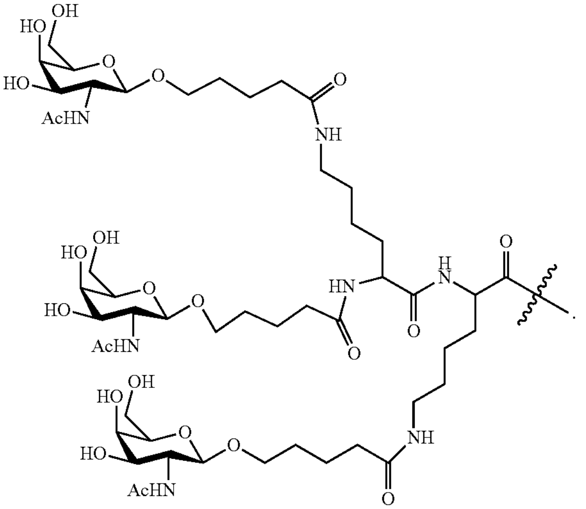

In certain embodiments, the cell-targeting moiety comprises:

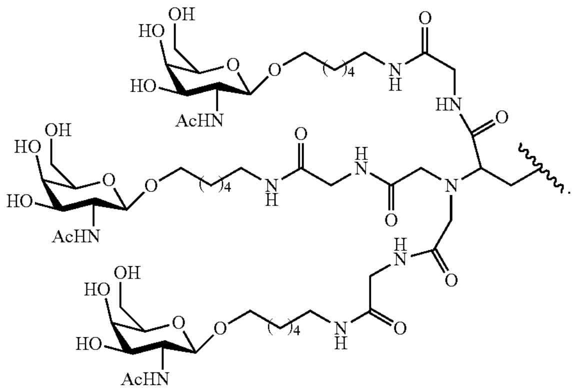

In certain embodiments, the cell-targeting moiety comprises:
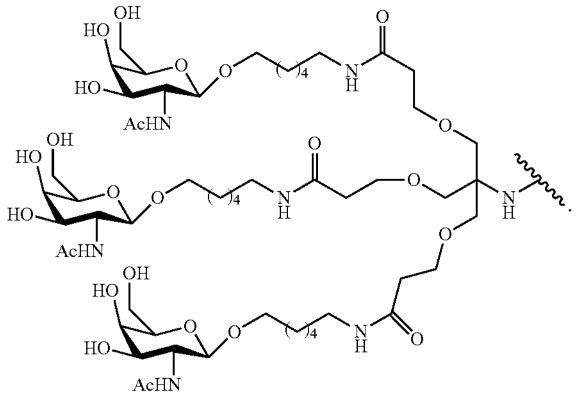
In certain embodiments, the cell-targeting moiety comprises:
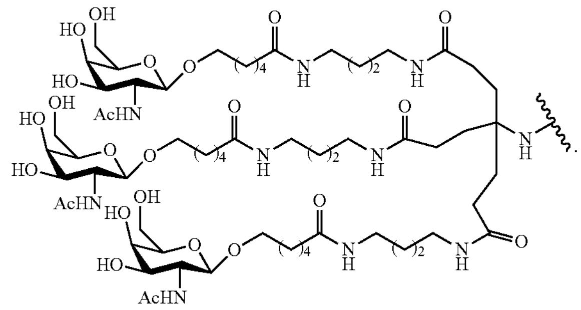
In certain embodiments, the cell-targeting moiety comprises:
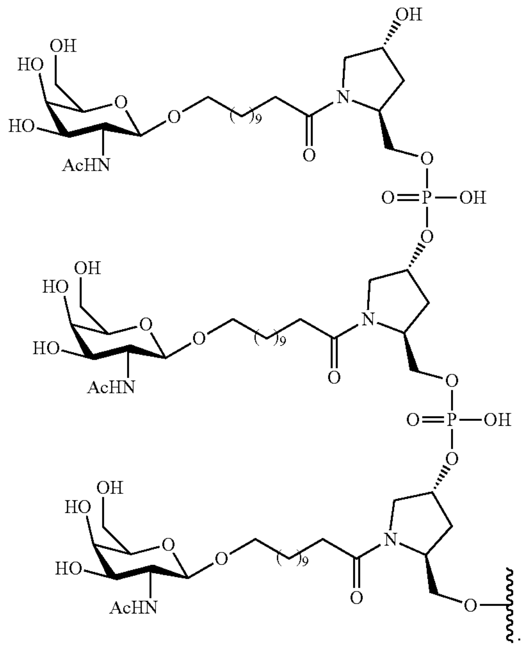
In certain embodiments, the cell-targeting moiety comprises:
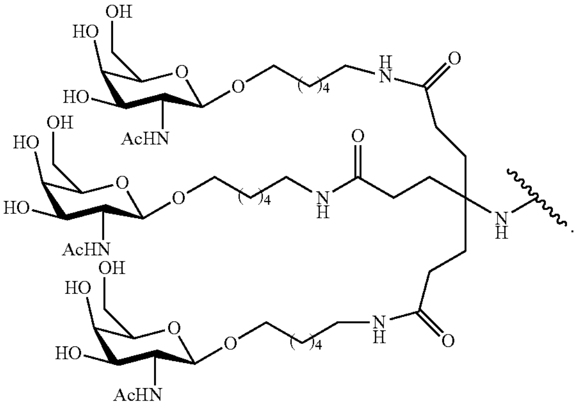
In certain embodiments, the cell-targeting moiety comprises:
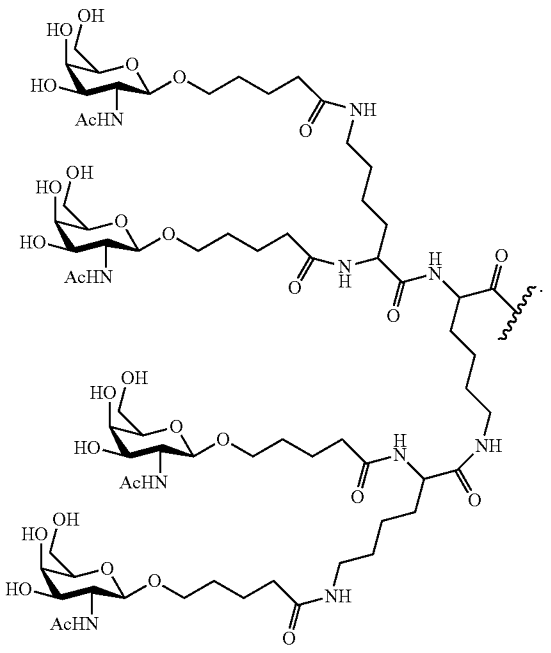

In certain embodiments, the cell-targeting moiety comprises:
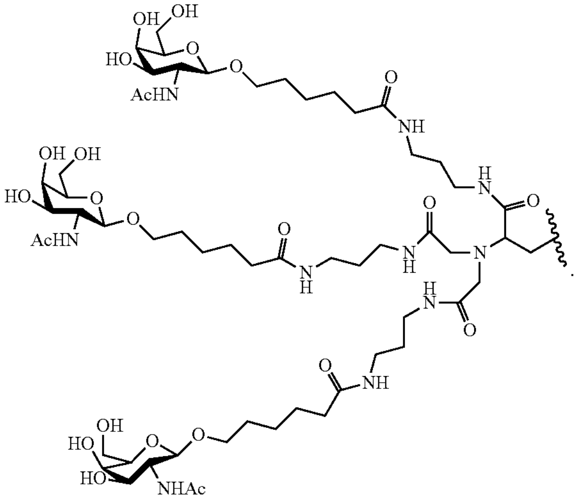
In certain embodiments, the cell-targeting moiety comprises:
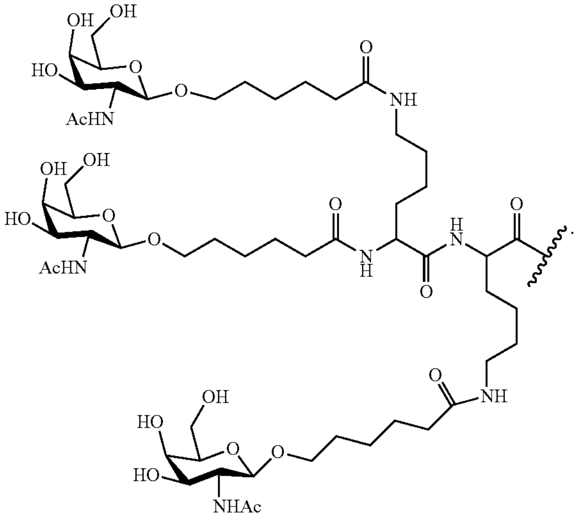
In certain embodiments, the cell-targeting moiety comprises:
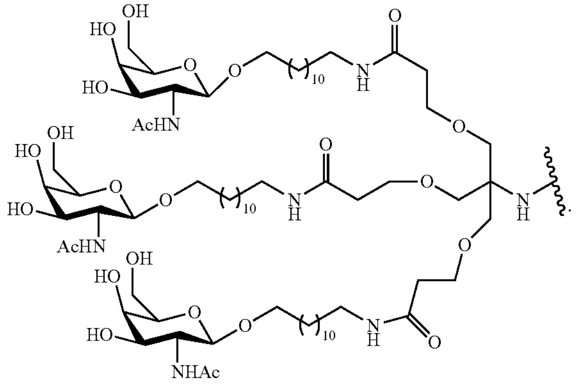

In certain embodiments, the cell-targeting moiety comprises:
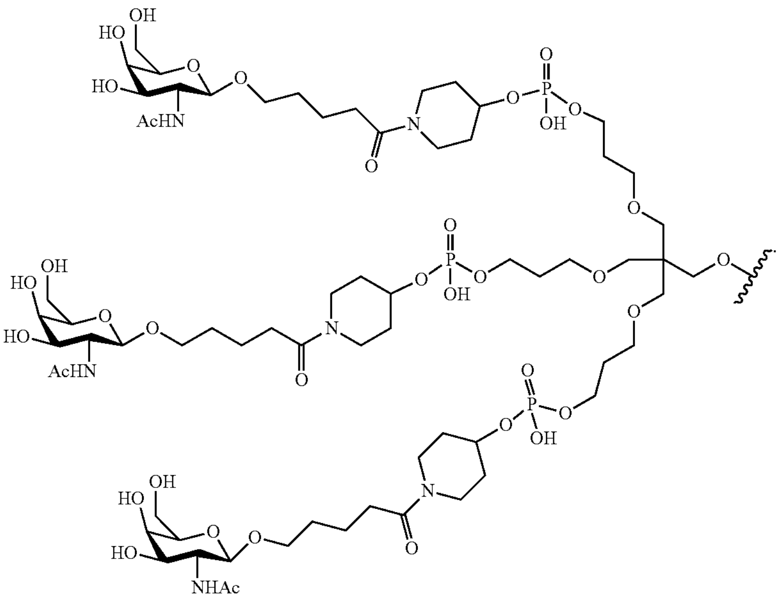
In certain embodiments, the cell-targeting moiety comprises:
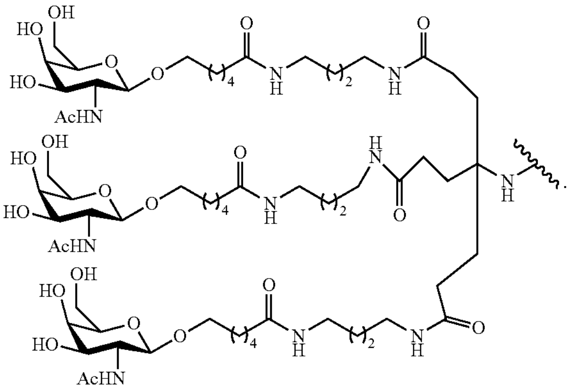
In certain embodiments, the cell-targeting moiety comprises:
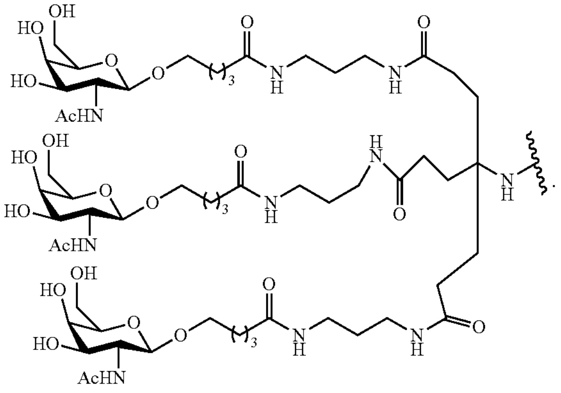
In certain embodiments, the cell-targeting moiety comprises:
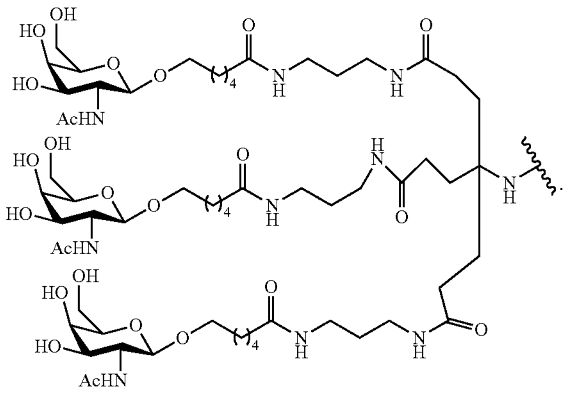

In certain embodiments, the cell-targeting moiety comprises:
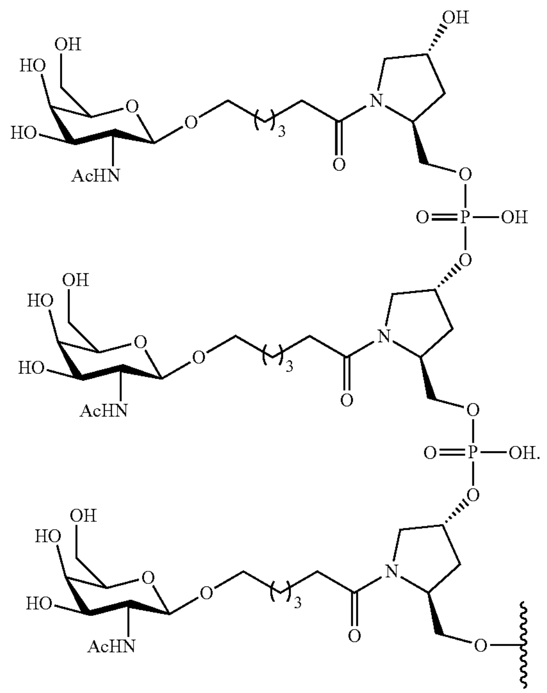
In certain embodiments, the cell-targeting moiety comprises:
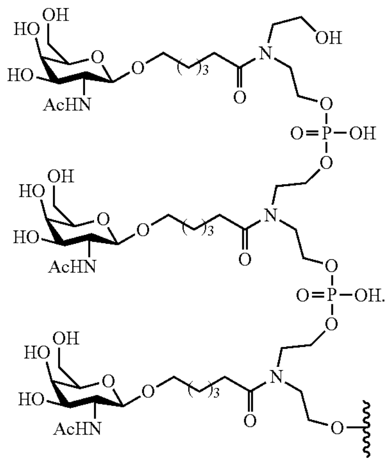
In certain embodiments, the cell-targeting moiety comprises:
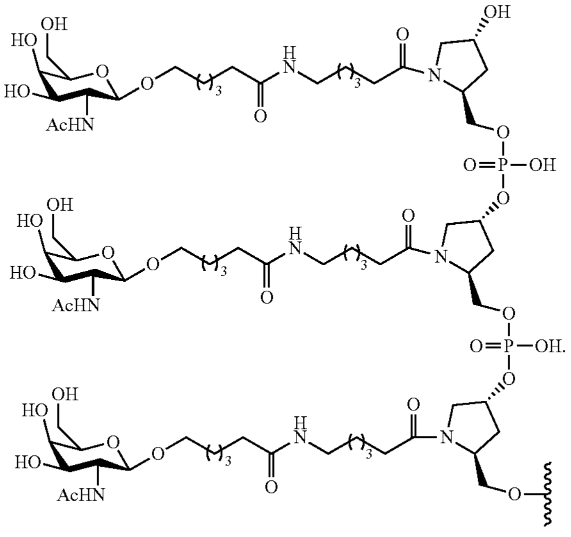
In certain embodiments, the cell-targeting moiety comprises:
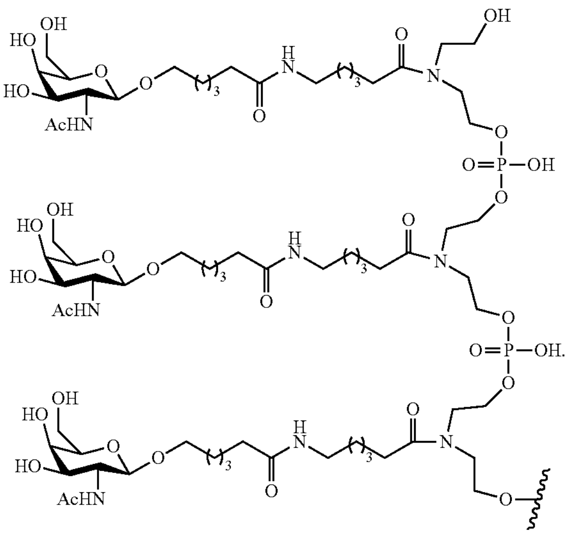

In certain embodiments, the cell-targeting moiety comprises:

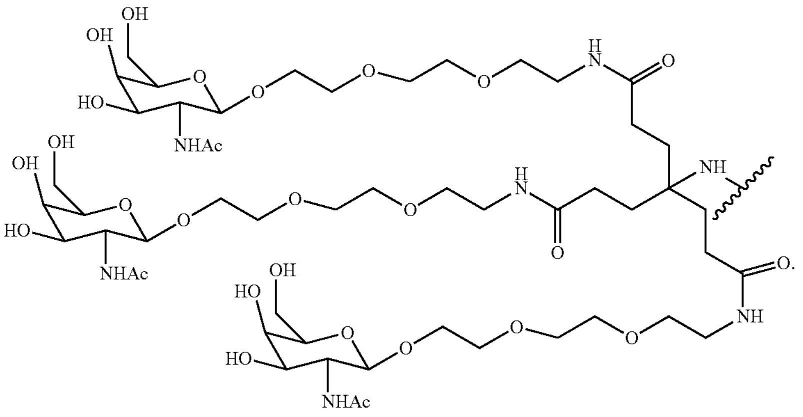 [SMILES: *NC(CCC(=O)NCCOCCOCCOC1OC(CO)C(O)C(O)C1NC(C)=O)(CCC(=O)NCCOCCOCCOC1OC(CO)C(O)C(O)C1NC(C)=O)CCC(=O)NCCOCCOCCOC1OC(CO)C(O)C(O)C1NC(C)=O]

In certain embodiments, the cell-targeting moiety comprises:

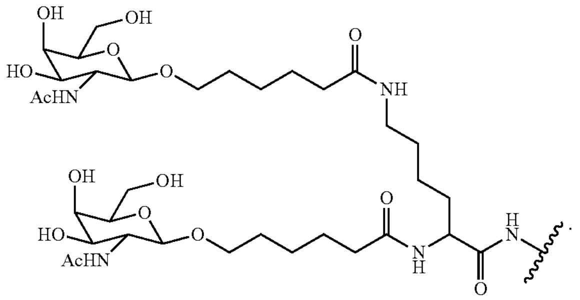 [SMILES: *NC(=O)C(CCCCNC(=O)CCCCCOC1OC(CO)C(O)C(O)C1NC(C)=O)NC(=O)CCCCCOC1OC(CO)C(O)C(O)C1NC(C)=O]

In certain embodiments, the cell-targeting moiety comprises:

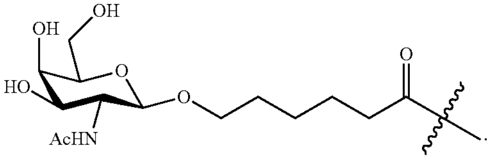

In certain embodiments, the cell-targeting moiety comprises:

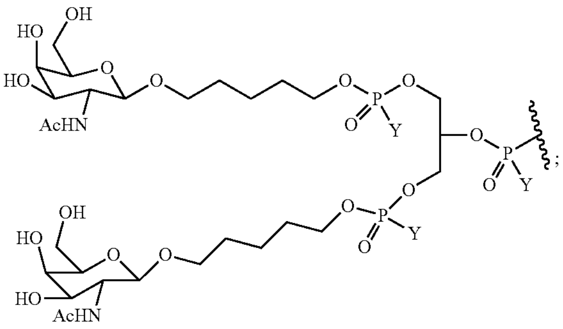

wherein each Y is selected from O, S, a substituted or unsubstituted C1-C10 alkyl, amino, substituted amino, azido, alkenyl or alkynyl.

In certain embodiments, the conjugate group comprises:

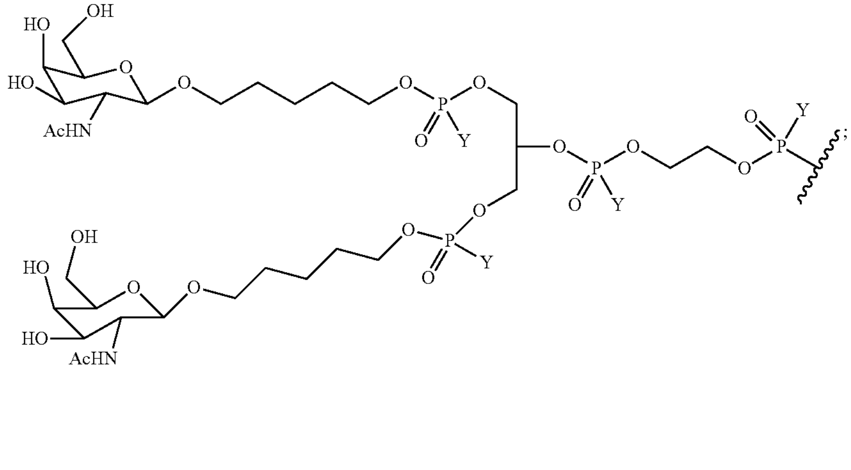

wherein each Y is selected from O, S, a substituted or unsubstituted C1-C10 alkyl, amino, substituted amino, azido, alkenyl or alkynyl.

In certain embodiments, the conjugate group comprises:

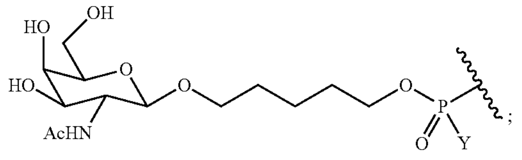

wherein each Y is selected from O, S, a substituted or unsubstituted C1-C10 alkyl, amino, substituted amino, azido, alkenyl or alkynyl.

In certain embodiments, the conjugate group comprises:

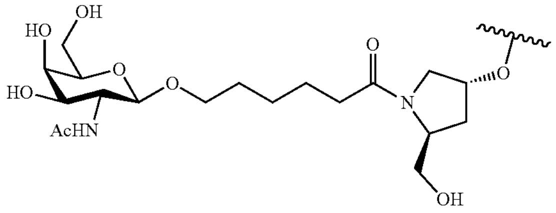

In certain embodiments, the conjugate group comprises:

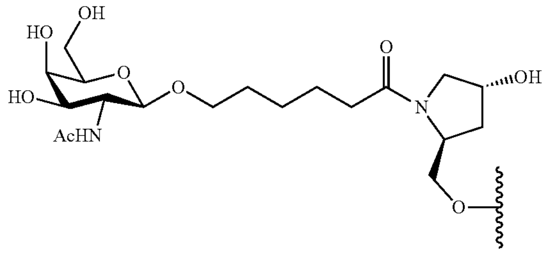

In certain embodiments, the conjugate group comprises:

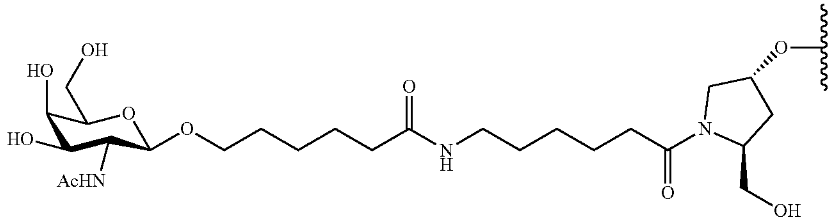

In certain embodiments, the conjugate group comprises:

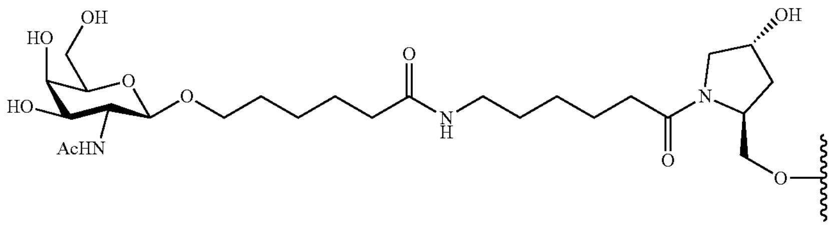

In certain embodiments, the conjugate group comprises a cleavable moiety selected from among: a phosphodiester, an amide, or an ester.

In certain embodiments, the conjugate group comprises a phosphodiester cleavable moiety.

In certain embodiments, the conjugate group does not comprise a cleavable moiety, and wherein the conjugate group comprises a phosphorothioate linkage between the conjugate group and the oligonucleotide. In certain embodiments, the conjugate group comprises an amide cleavable moiety. In certain embodiments, the conjugate group comprises an ester cleavable moiety.

In certain embodiments, the compound has the following structure:

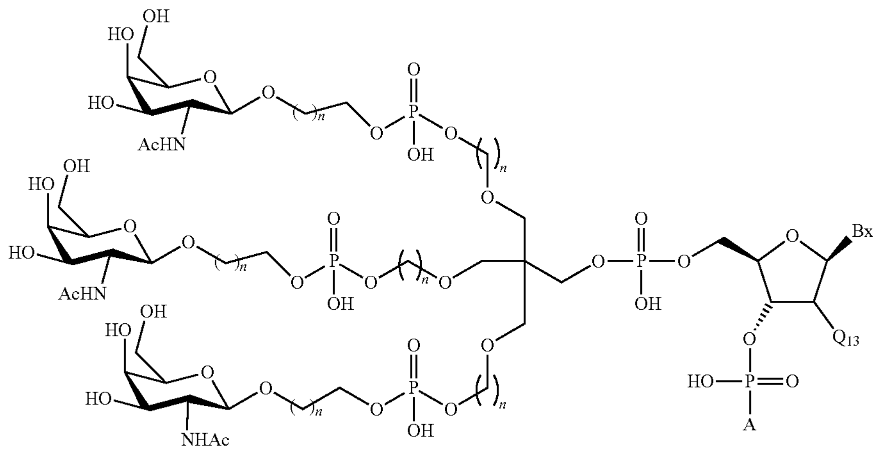

wherein each n is, independently, from 1 to 20;

Q13 is H or O(CH2)2-OCH3;

A is the modified oligonucleotide; and

Bx is a heterocyclic base moiety.

In certain embodiments, the compound has the following structure:

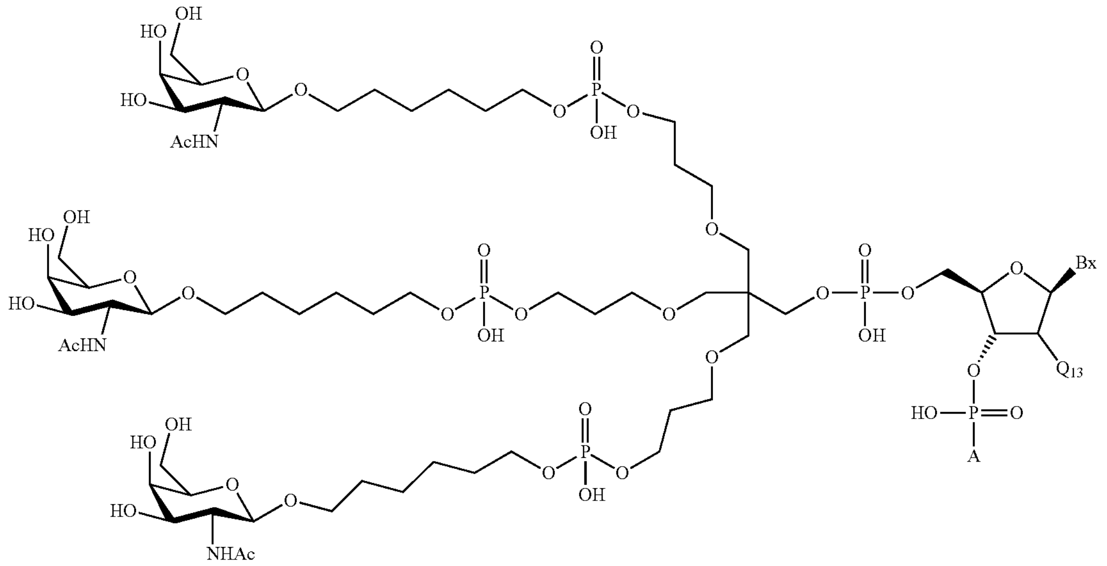

wherein each n is, independently, from 1 to 20;

Q13 is H or O(CH2)2-OCH3;

A is the modified oligonucleotide; and

Bx is a heterocyclic base moiety.

In certain embodiments, the compound has the following structure:

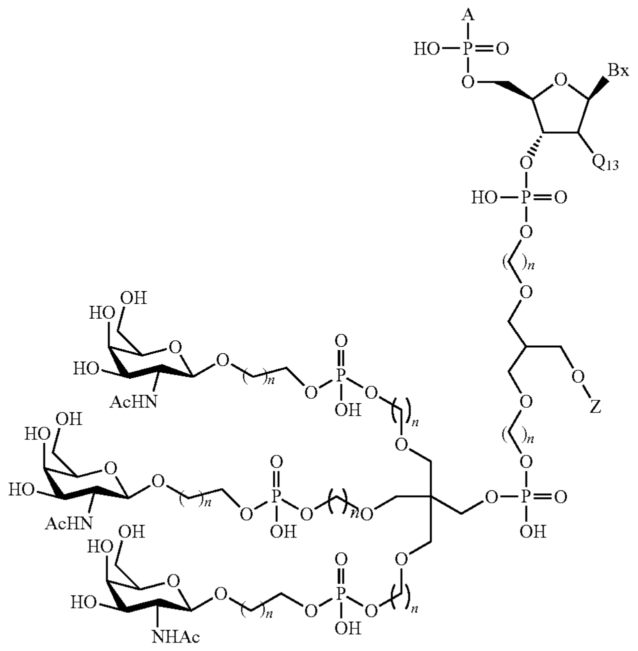

wherein each n is, independently, from 1 to 20;
Q13 is H or O(CH2)2-OCH3;
A is the modified oligonucleotide;
Z is H or a linked solid support; and
Bx is a heterocyclic base moiety.

In certain embodiments, the compound has the following structure:

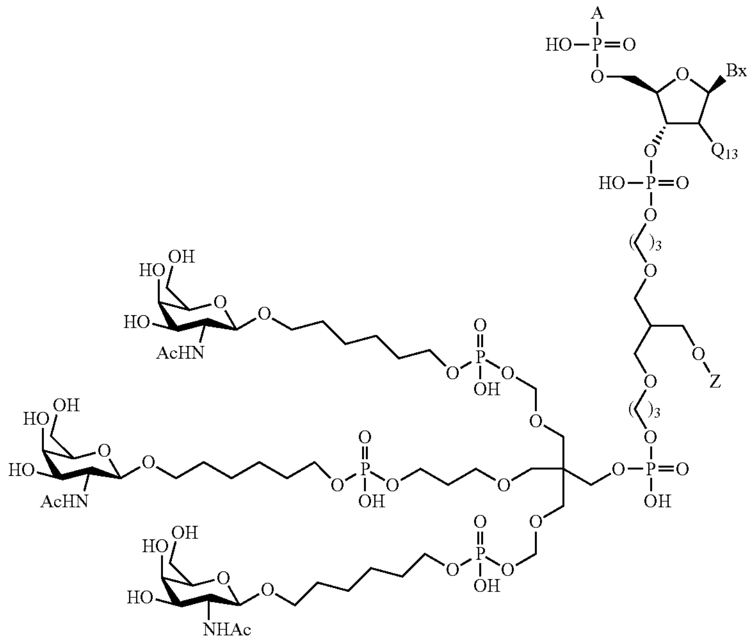

wherein each n is, independently, from 1 to 20;
Q13 is H or O(CH2)2-OCH3;
A is the modified oligonucleotide;
Z is H or a linked solid support; and
Bx is a heterocyclic base moiety.

In certain embodiments, the compound has the following structure:
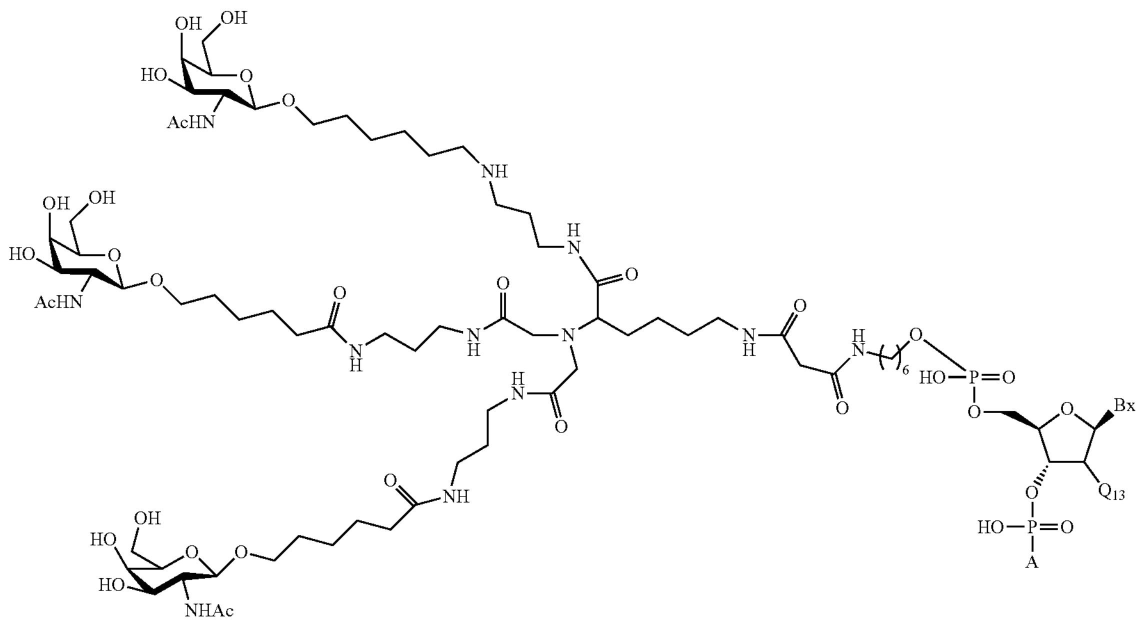
wherein Q13 is H or O(CH2)2-OCH3;
A is the modified oligonucleotide; and
Bx is a heterocyclic base moiety.
In certain embodiments, the compound has the following structure:
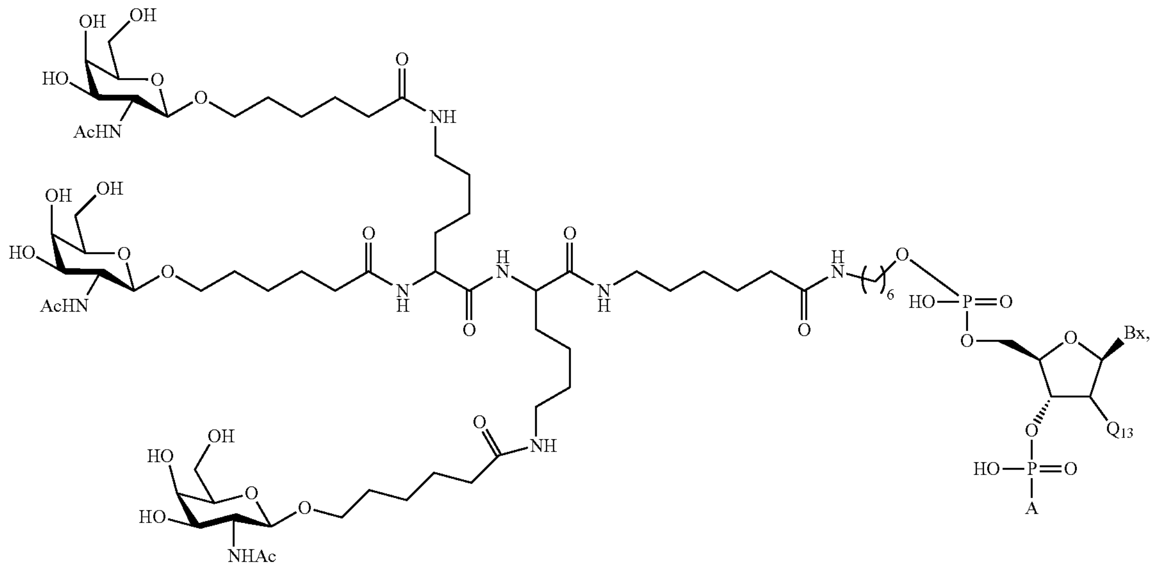
wherein Q13 is H or O(CH2)2-OCH3;
A is the modified oligonucleotide; and
Bx is a heterocyclic base moiety.

In certain embodiments, the compound has the following structure:
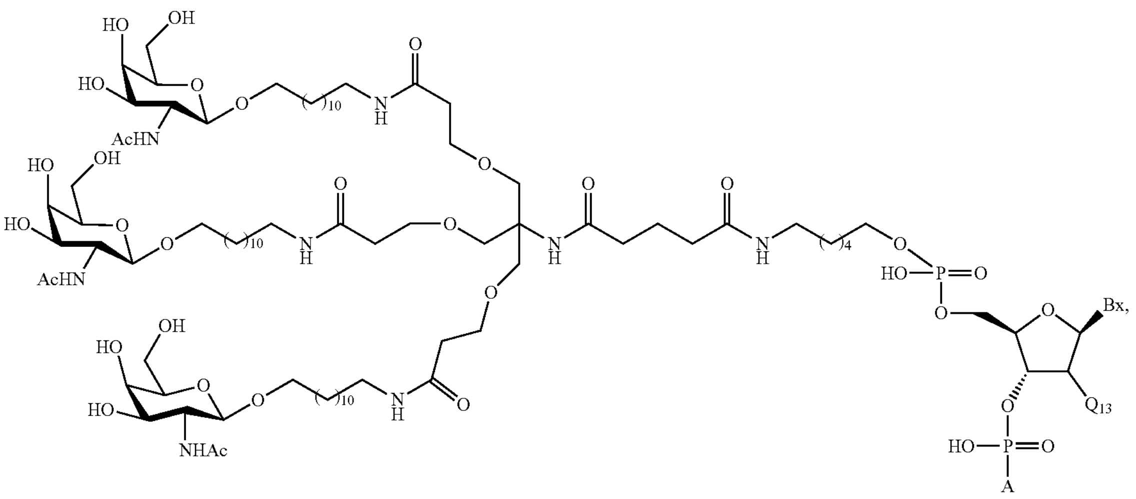
wherein Q13 is H or O(CH2)2-OCH3;
A is the modified oligonucleotide; and
Bx is a heterocyclic base moiety.
In certain embodiments, the compound has the following structure:
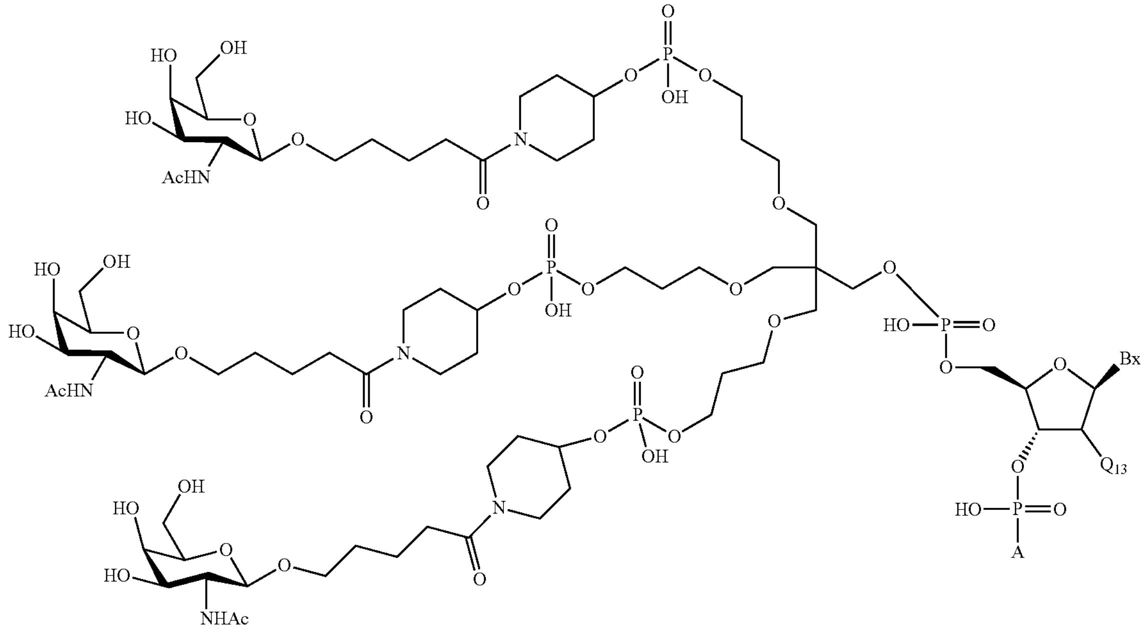
wherein Q13 is H or O(CH2)2-OCH3;
A is the modified oligonucleotide; and
Bx is a heterocyclic base moiety.

In certain embodiments, the compound has the following structure:
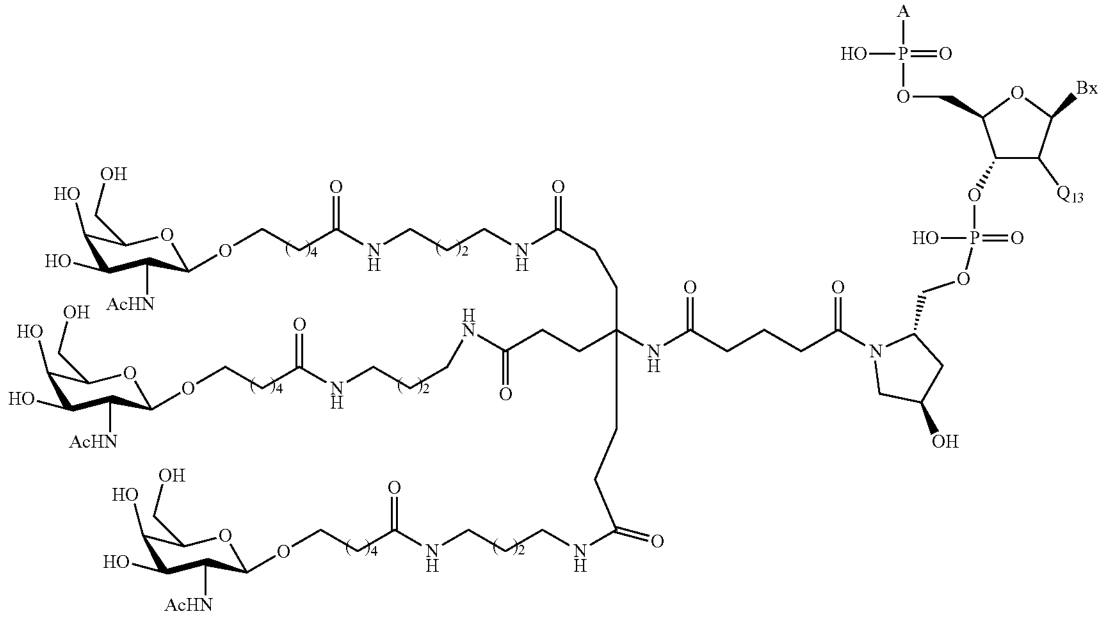
wherein Q13 is H or O(CH2)2-OCH3;
A is the modified oligonucleotide; and
Bx is a heterocyclic base moiety.
In certain embodiments, the compound has the following structure:
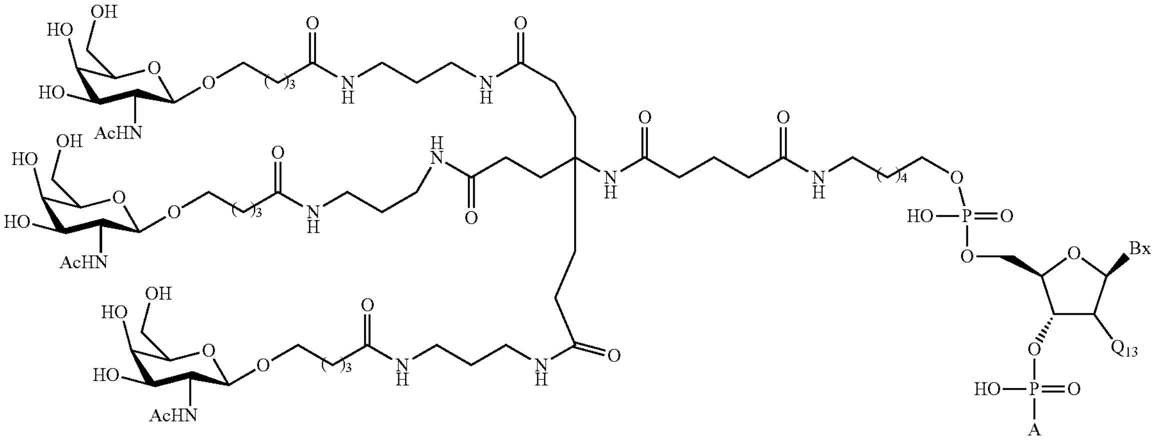
wherein Q13 is H or O(CH2)2-OCH3;
A is the modified oligonucleotide; and
Bx is a heterocyclic base moiety.

In certain embodiments, the compound has the following structure:
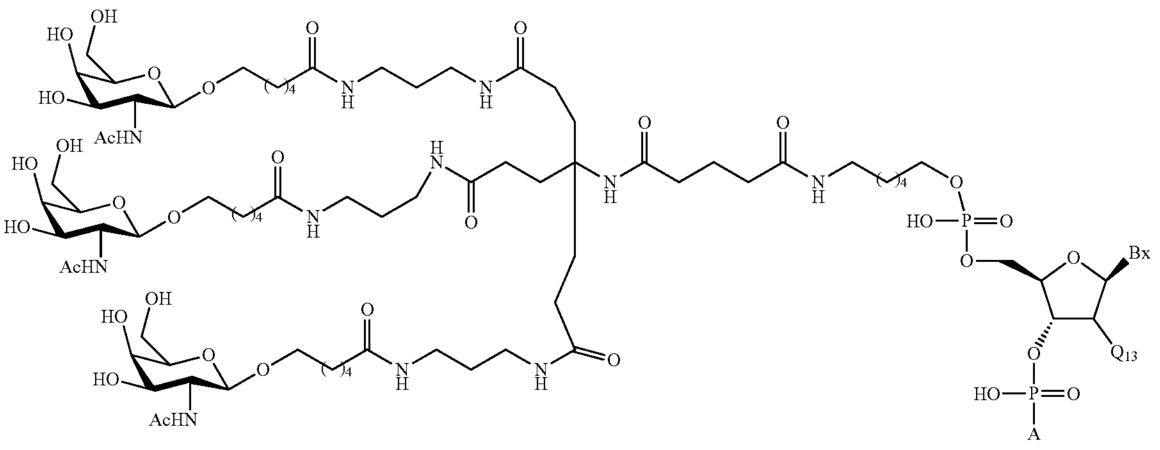
wherein Q13 is H or O(CH2)2-OCH3;
A is the modified oligonucleotide; and
Bx is a heterocyclic base moiety.
In certain embodiments, the compound has the following structure:
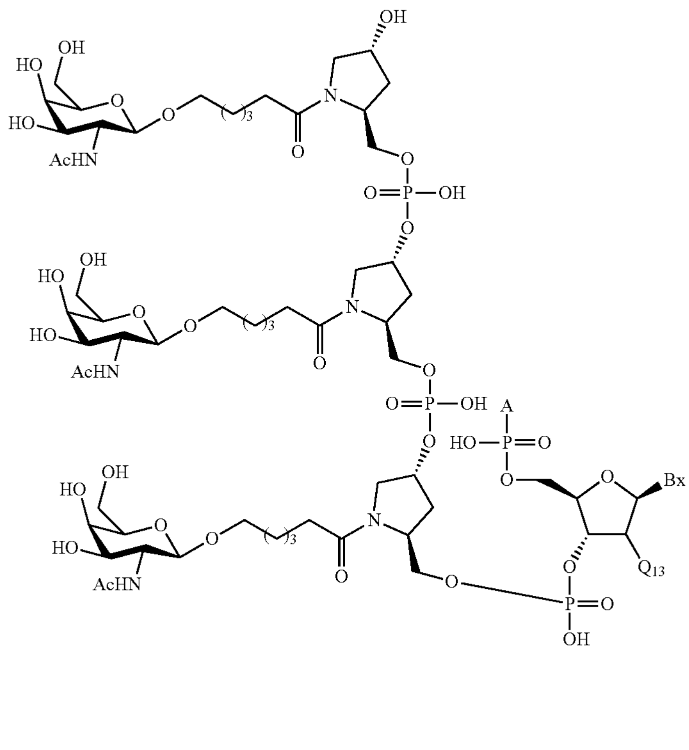
wherein Q13 is H or O(CH2)2-OCH3;
A is the modified oligonucleotide; and
Bx is a heterocyclic base moiety.

In certain embodiments, the compound has the following structure:
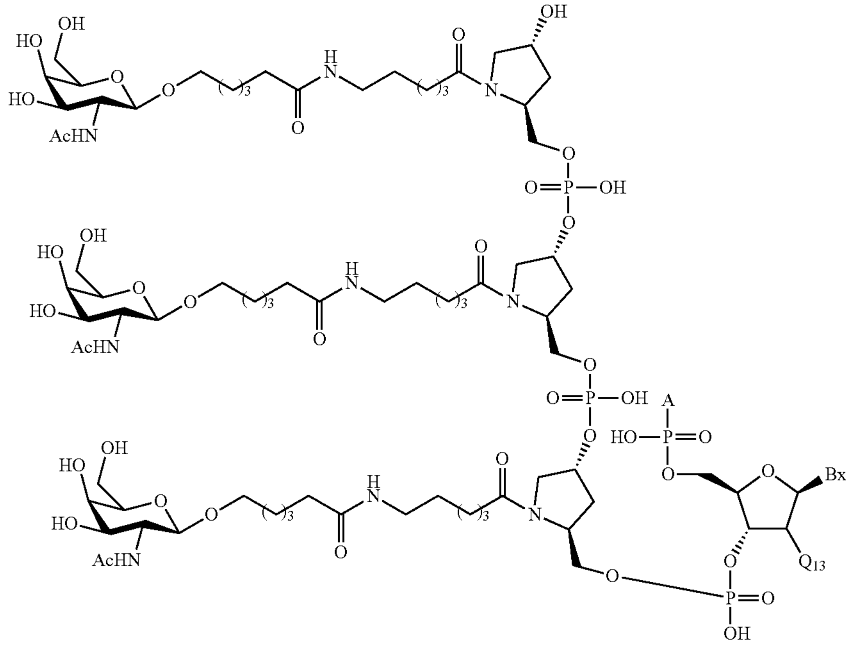
wherein Q13 is H or O(CH2)2-OCH3;
A is the modified oligonucleotide; and
Bx is a heterocyclic base moiety.
In certain embodiments, the compound has the following structure:
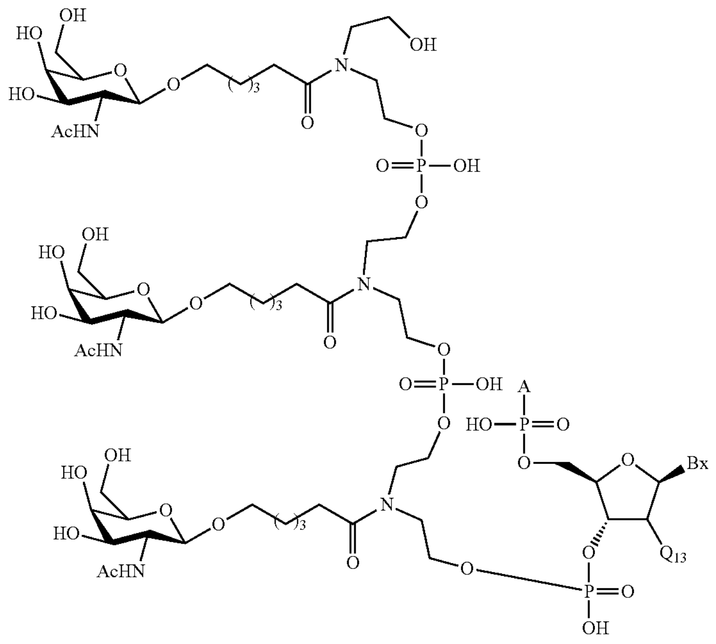
wherein Q13 is H or O(CH2)2-OCH3;
A is the modified oligonucleotide; and
Bx is a heterocyclic base moiety.

In certain embodiments, the compound has the following structure:
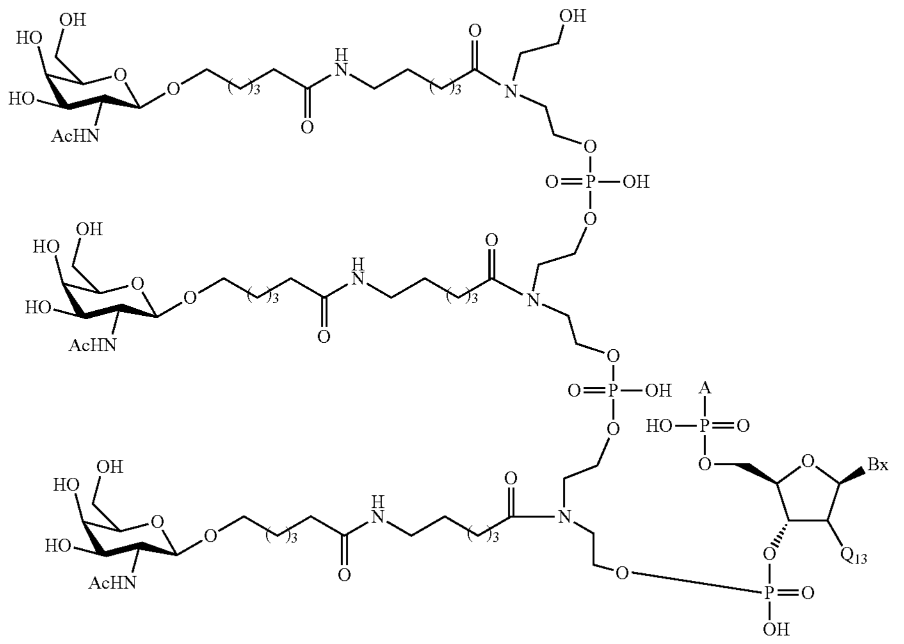
wherein Q13 is H or O(CH2)2-OCH3;
A is the modified oligonucleotide; and
Bx is a heterocyclic base moiety.
In certain embodiments, the conjugate group comprises:
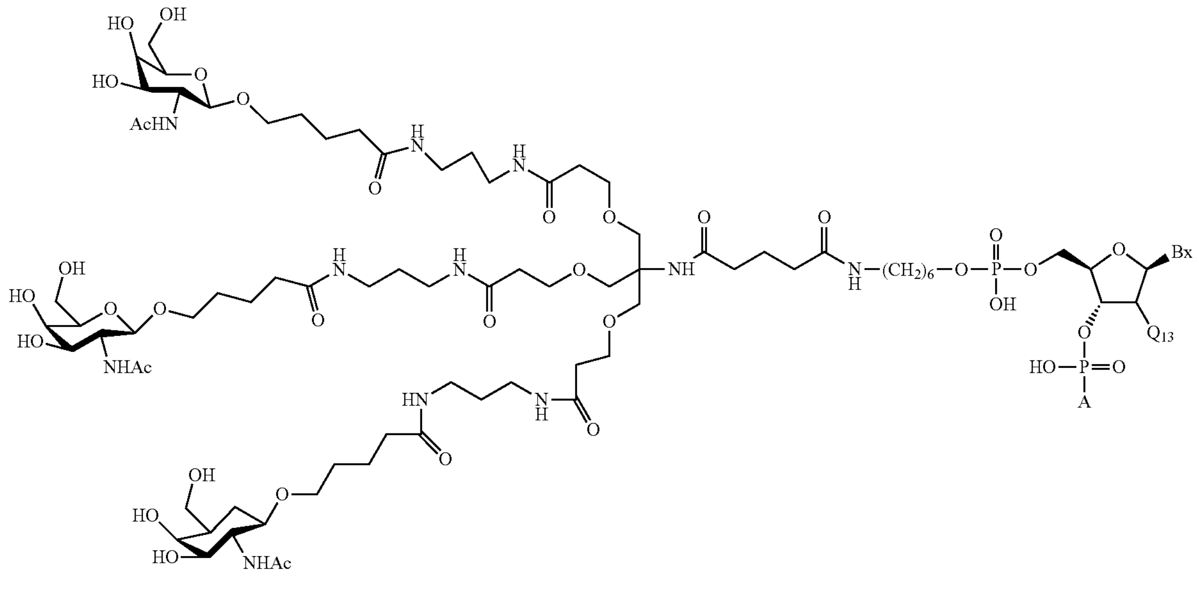
wherein Q13 is H or O(CH2)2-OCH3;
A is the modified oligonucleotide; and
Bx is a heterocyclic base moiety.

In certain embodiments, the conjugate group comprises:

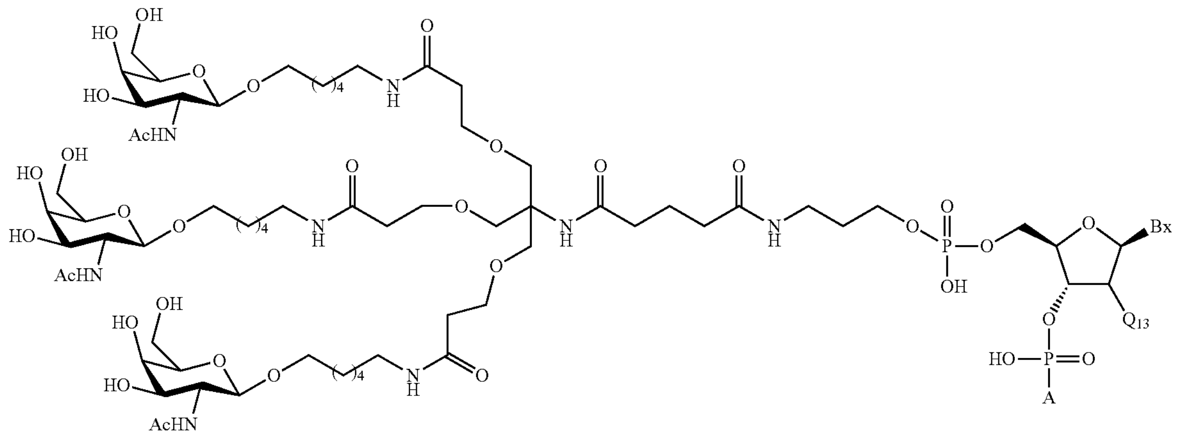

wherein Q13 is H or O(CH2)2-OCH3;

A is the modified oligonucleotide; and

Bx is a heterocyclic base moiety.

In certain embodiments, the conjugate group comprises:

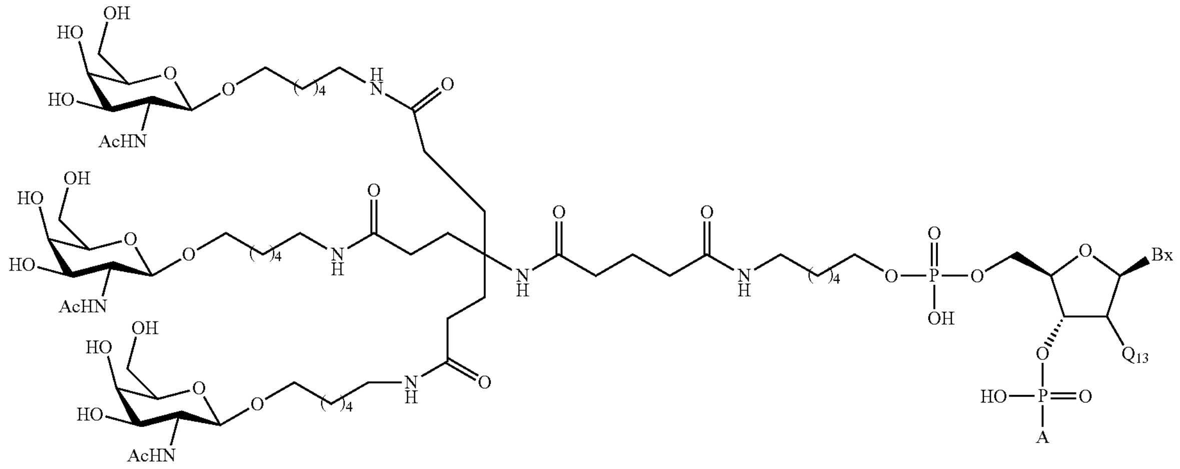

wherein Q13 is H or O(CH2)2-OCH3;

A is the modified oligonucleotide; and

Bx is a heterocyclic base moiety.

In certain embodiments, Bx is selected from among from adenine, guanine, thymine, uracil, or cytosine, or 5-methyl cytosine. In certain embodiments, Bx is adenine. In certain embodiments, Bx is thymine. In certain embodiments, Q13 is O(CH2)2-OCH3. In certain embodiments, Q13 is H.

In certain embodiments, the compound is in a salt form. In further embodiments, the compound further comprises of a pharmaceutically acceptable carrier or diluent. In certain embodiments, the compound comprises a modified oligonucleotide targeting apo(a) and a conjugate group, or a salt thereof, and a pharmaceutically acceptable carrier or diluent.

Certain embodiments provide a composition comprising a conjugated antisense compound as described herein, wherein the viscosity level of the compound is less than 40 centipoise (cP). In certain embodiments, the conjugated antisense compounds as described herein are efficacious by virtue of having a viscosity of less than 40 cP, less than 35 cP, less than 30 cP, less than 25 cP, less than 20 cP or less than 15 cP when measured by the parameters as described in Example 125.

Certain embodiments provide compositions and methods comprising administering to an animal a conjugated antisense compound or composition disclosed herein. In certain embodiments, administering the conjugated antisense compound prevents, treats, ameliorates, or slows progression of a cardiovascular, metabolic and/or inflammatory disease Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, apo(a) and/or Lp(a) levels are elevated in an animal. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the antisense compound is a modified oligonucleotide targeting apo(a) and a conjugate group. In certain embodiments, the modified oligonucleotide targeting apo(a) with the conjugate group, is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL. Certain embodiments provide compositions and methods to reduce apo(a) mRNA or protein expression in an animal comprising administering to the animal a conjugated antisense compound or composition disclosed herein to reduce apo(a) mRNA or protein expression in the animal. Certain embodiments provide compositions and methods to reduce Lp(a) levels in an animal comprising administering to the animal a conjugated antisense compound or composition disclosed herein to reduce apo(a) mRNA or protein expression in the animal.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include inflammatory, cardiovascular and/or metabolic diseases, disorders, and conditions. Certain such cardiovascular diseases, disorders or conditions include, but are not limited to, aortic stenosis, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, aortic stenosis, coronary artery disease (CAD), Alzheimer's Disease and thromboembolic diseases, disorder or conditions. Certain thromboembolic diseases, disorders or conditions include, but are not limited to, stroke, thrombosis (e.g., venous thromboembolism), myocardial infarction and peripheral vascular disease. Certain embodiments provide compositions and methods for preventing, treating, delaying, slowing the progression and/or ameliorating aortic stenosis. Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever. Certain embodiments provide a method of reducing at least one symptom of aortic stenosis.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the conjugated antisense compound is parenterally administered. In further embodiments, the parenteral administration is subcutaneous.

In certain embodiments, the conjugated antisense compound or composition is co-administered with a second agent or therapy. In certain embodiments, the conjugated antisense compound or composition and the second agent are administered concomitantly.

In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a conjugated antisense compound targeted to apo(a) for decreasing apo(a) levels in an animal. Certain embodiments provide use of a conjugated antisense compound targeted to apo(a) for decreasing Lp(a) levels in an animal. Certain embodiments provide use of a conjugated antisense compounds targeted to apo(a) for the treatment, prevention, or amelioration of a disease, disorder, or condition associated with apo(a). Certain embodiments provide use of a conjugated antisense compounds targeted to apo(a) for the treatment, prevention, or amelioration of a disease, disorder, or condition associated with Lp(a).

Certain embodiments provide use of a conjugated antisense compound targeted to apo(a) in the preparation of a medicament for decreasing apo(a) levels in an animal. Certain embodiments provide use of a conjugated antisense compound targeted to apo(a) in the preparation of a medicament for decreasing Lp(a) levels in an animal. Certain embodiments provide use of a conjugated antisense compound for the preparation of a medicament for the treatment, prevention, or amelioration of a disease, disorder, or condition associated with apo(a). Certain embodiments provide use of a conjugated antisense compound for the preparation of a medicament for the treatment, prevention, or amelioration of a disease, disorder, or condition associated with Lp(a).

Certain embodiments provide the use of a conjugated antisense compound as described herein in the manufacture of a medicament for treating, ameliorating, delaying or preventing one or more of a disease related to apo(a) and/or Lp(a).

Certain embodiments provide a kit for treating, preventing, or ameliorating a disease, disorder or condition as described herein wherein the kit comprises: (i) an apo(a)

specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

B. Certain Compounds

In certain embodiments, the invention provides conjugated antisense compounds comprising antisense oligonucleotides and a conjugate.

a. Certain Antisense Oligonucleotides

In certain embodiments, the invention provides antisense oligonucleotides. Such antisense oligonucleotides comprise linked nucleosides, each nucleoside comprising a sugar moiety and a nucleobase. The structure of such antisense oligonucleotides may be considered in terms of chemical features (e.g., modifications and patterns of modifications) and nucleobase sequence (e.g., sequence of antisense oligonucleotide, identity and sequence of target nucleic acid).

i. Certain Chemistry Features

In certain embodiments, antisense oligonucleotide comprise one or more modification. In certain such embodiments, antisense oligonucleotides comprise one or more modified nucleosides and/or modified internucleoside linkages. In certain embodiments, modified nucleosides comprise a modified sugar moiety and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; $OCF_3$, $O(CH_2)_2SCH_3$, $O(CH_2)_2$—O—N(Rm)(Rn), and O—$CH_2$—C(═O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or N($R_m$)-alkyl; O, S, or N($R_m$)-alkenyl; O, S or N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)2SCH_3$, $(CH_2)_2$—O—N($R_m$)($R_n$), $O(CH_2)_2O(CH_2)_2N(CH_3)_2$, and N-substituted acetamide (O—$CH_2$—C(═O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O(CH_2)_2N(CH_3)_2$, and O—$CH_2$—C(═O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'-$CH_2$-2', 4'-$(CH_2)_2$-2', 4'-$(CH_2)_3$-2'; 4'-$(CH_2)$—O-2' (LNA); 4'-$(CH_2)$—S-2; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.,* 2009, 74, 118-134); and 4'-$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)═C($R_b$)—, —C($R_a$)═N—, —C(═N$R_a$)—, —C(═O)—, —C(═S)—, —O—, —Si$(R_a)_2$—, —S(═O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-$(CH_2)$3-2') BNA as depicted below.

(A)

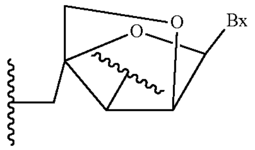

(B)

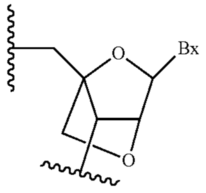

(C)

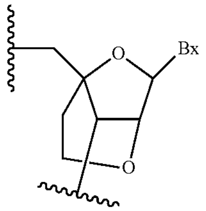

(D)

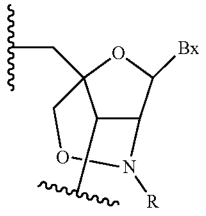

(E)

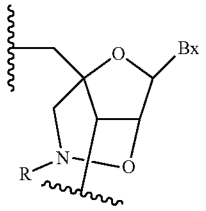

-continued (F)

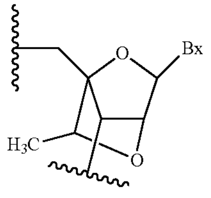

(G)

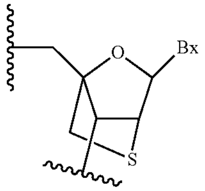

(H)

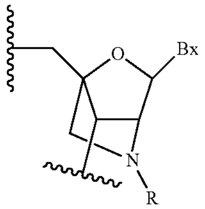

(I)

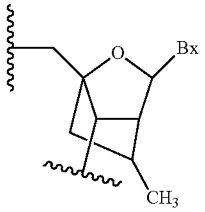

(J)

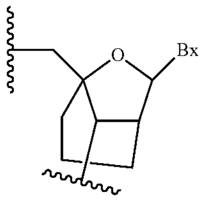

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a morpholino. Morpholino compounds and their use in oligomeric compounds has been reported in numerous patents and published articles (see for example: Braasch et al., *Biochemistry,* 2002, 41, 4503-4510; and U.S. Pat. Nos. 5,698,685; 5,166,315; 5,185,444; and 5,034,506). As used here, the term "morpholino" means a sugar surrogate having the following structure:

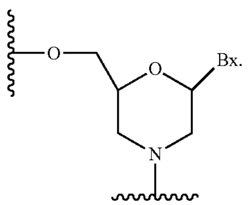

In certain embodiments, morpholinos may be modified, for example by adding or altering various substituent groups from the above morpholino structure. Such sugar surrogates are referred to herein as "modified morpholinos."

For another example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VI:

VI

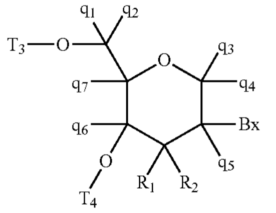

wherein independently for each of said at least one tetrahydropyran nucleoside analog of Formula VI:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379). In certain embodiments, the present disclosure provides oligonucleotides comprising modified nucleosides. Those modified nucleotides may include modified sugars, modified nucleobases, and/or modified linkages.

The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C≡C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cyto-sines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino ($—CH_2—N(CH_3)—O—CH_2—$), thiodiester (—O—C(O)—S—), thionocarbamate (—O—C(O)(NH)—S—); siloxane ($—O—Si(H)_2—O—$); and N,N'-dimethylhydrazine ($—CH_2—N(CH_3)—N(CH_3)—$). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), a or b such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—$N(CH_3)$—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

4. Certain Motifs

In certain embodiments, antisense oligonucleotides comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides.

In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides.

In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me.

In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Oligonucleotide Chemistry Motifs

In certain embodiments, the chemical structural features of antisense oligonucleotides are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

In certain embodiments, a conjugate group comprises a cleavable moiety. In certain embodiments, a conjugate group comprises one or more cleavable bond. In certain embodiments, a conjugate group comprises a linker. In certain embodiments, a linker comprises a protein binding moiety. In certain embodiments, a conjugate group comprises a cell-targeting moiety (also referred to as a cell-targeting group). In certain embodiments a cell-targeting moiety comprises a branching group. In certain embodiments, a cell-targeting moiety comprises one or more tethers. In certain embodiments, a cell-targeting moiety comprises a carbohydrate or carbohydrate cluster.

ii. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

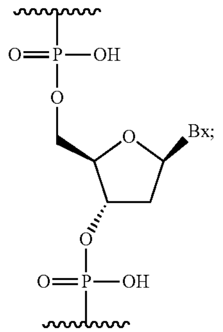

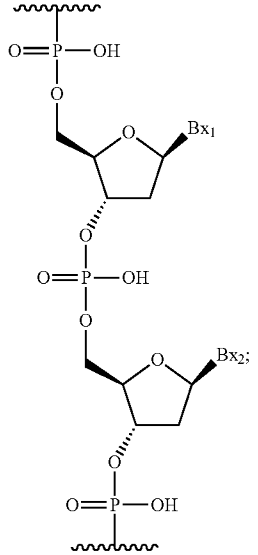

and

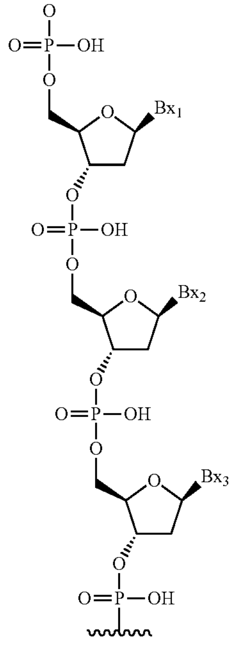

wherein each of Bx, $Bx_1$, $Bx_2$, and $Bx_3$ is independently a heterocyclic base moiety. In certain embodiments, the cleavable moiety has a structure selected from among the following:

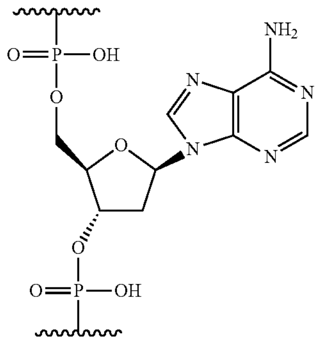 [SMILES: *P(=O)(O)OC[C@H]1O[C@@H](n2cnc3c(N)ncnc32)C[C@@H]1OP(*)(=O)O]

iii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a linker has a structure selected from among:

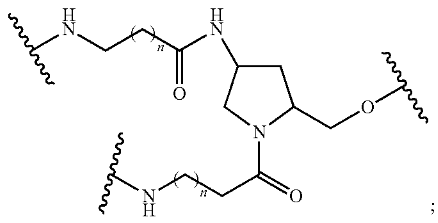

;

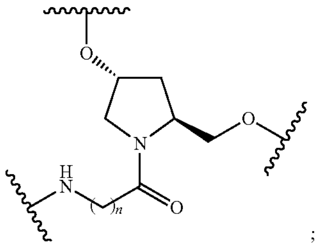

;

-continued

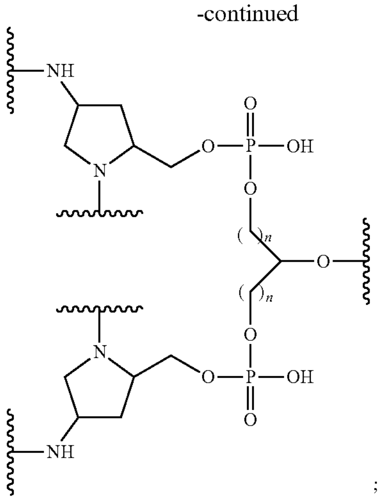

;

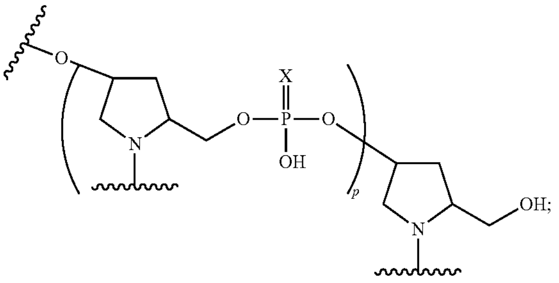

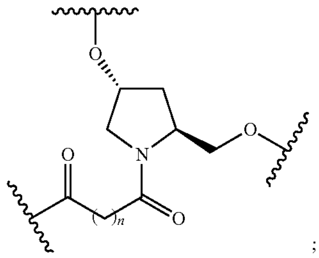

;

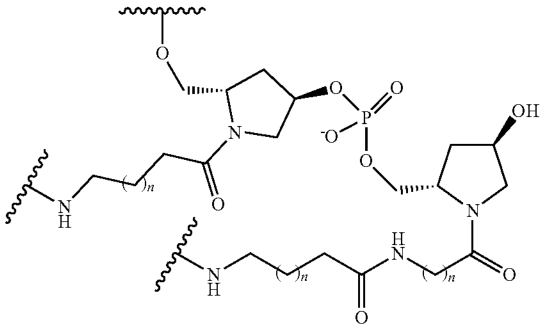

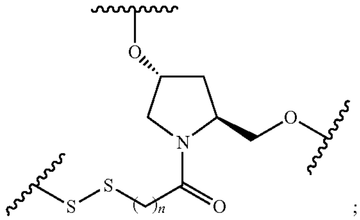

;

-continued
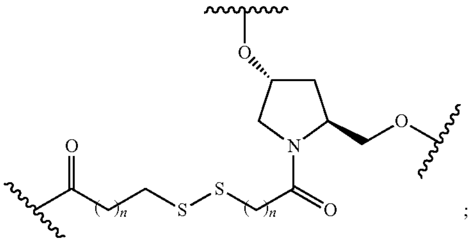
;
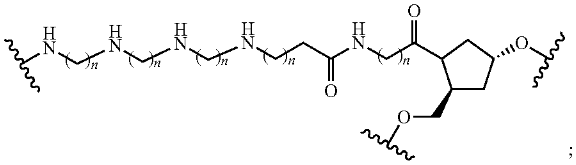
;
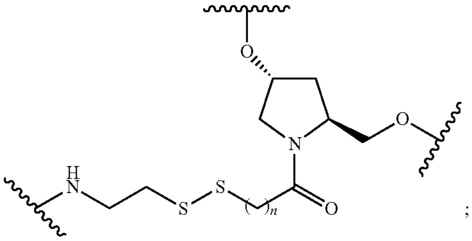
;
-continued
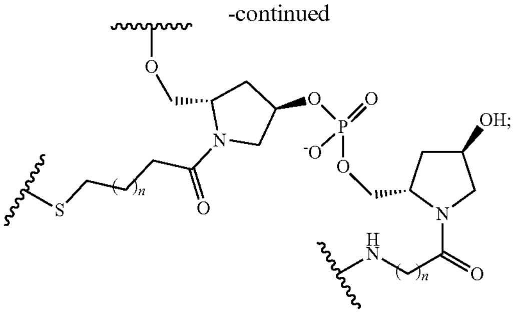
; and
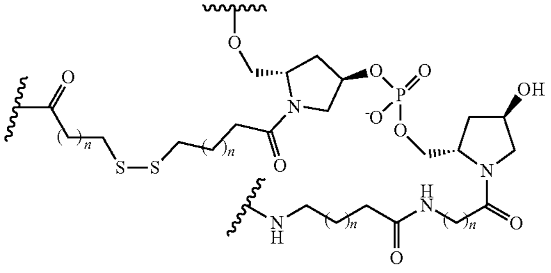
wherein each n is, independently, from 1 to 20; and p is from 1 to 6.
In certain embodiments, a linker has a structure selected from among:
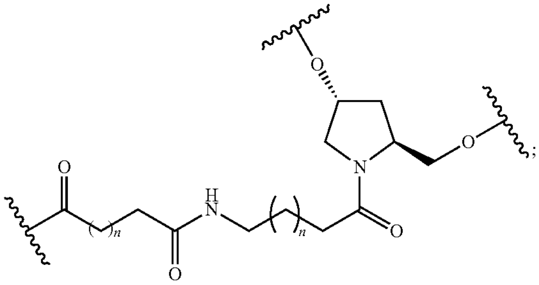
;
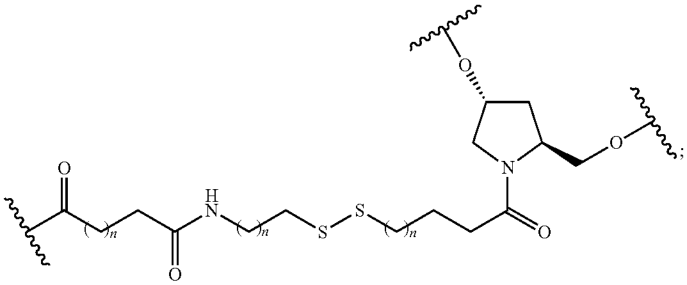
;
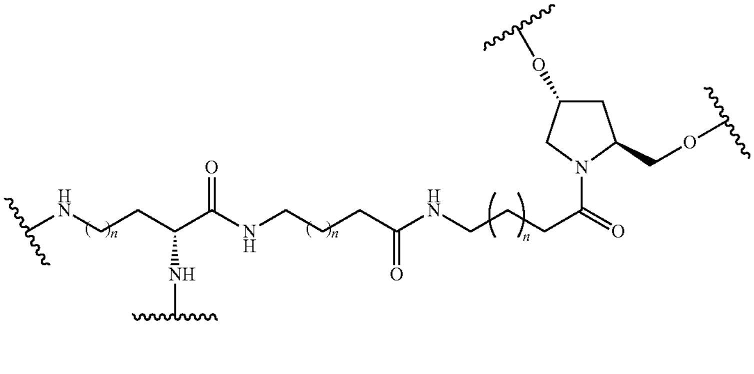
;

-continued
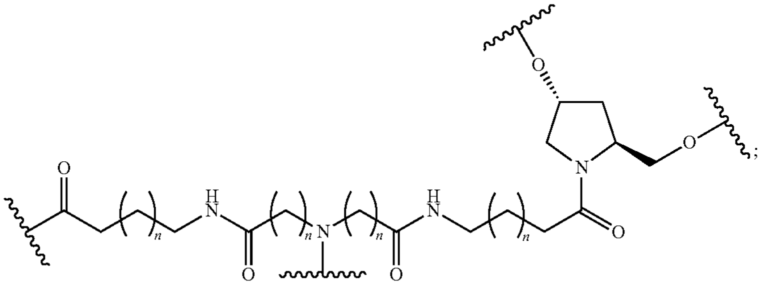
;
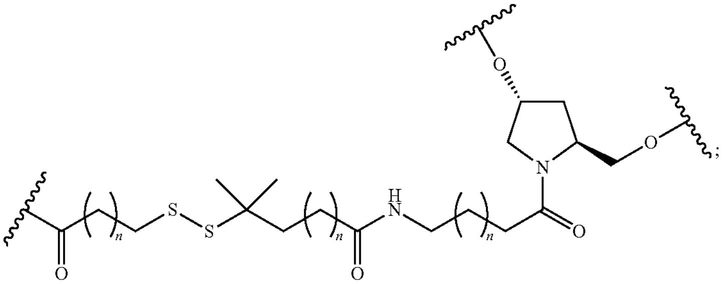
;
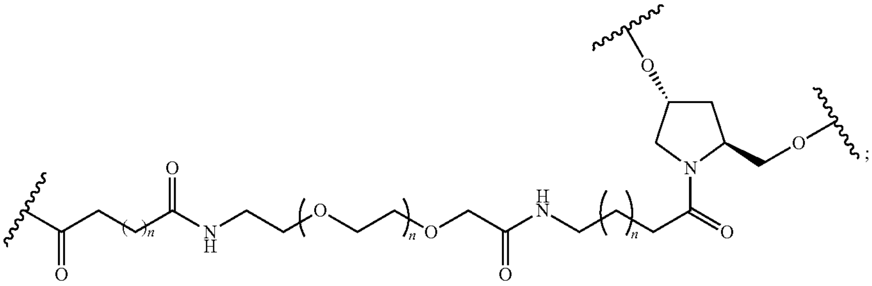
;
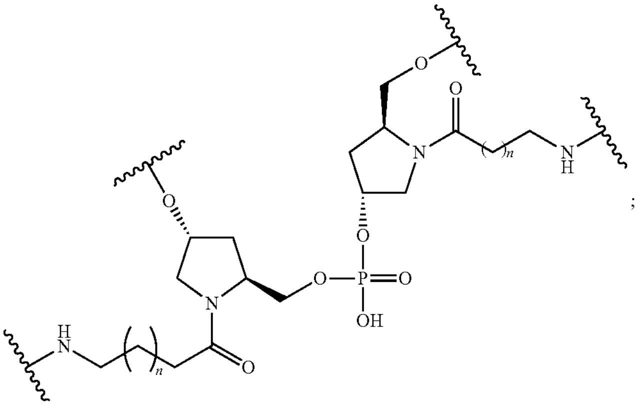
;
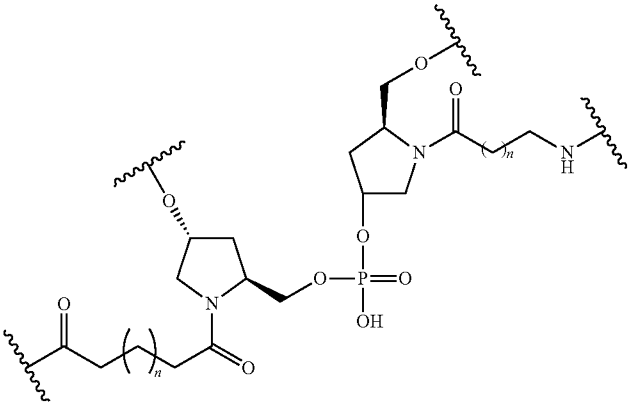
; and -continued
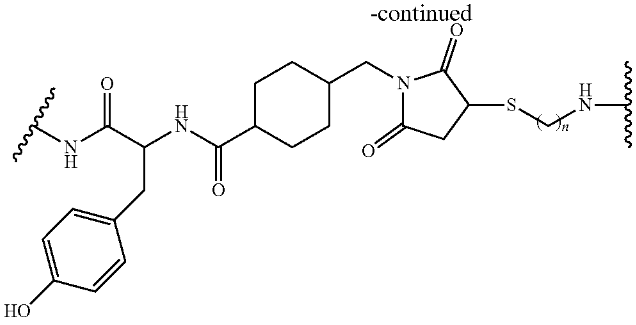
wherein each n is, independently, from 1 to 20.
In certain embodiments, a linker has a structure selected from among:
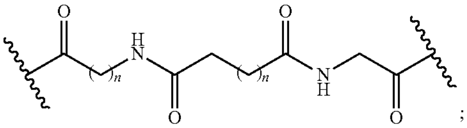
;
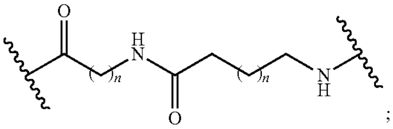
;
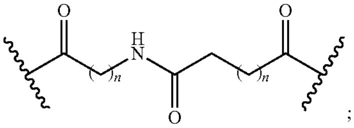
;
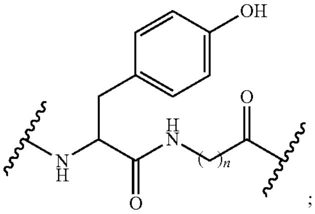
;
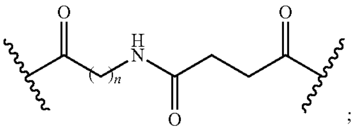
;
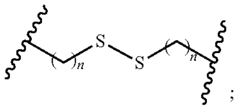
;
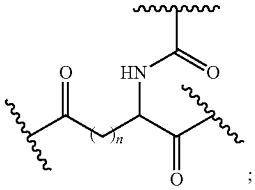
;
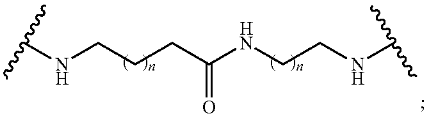
;
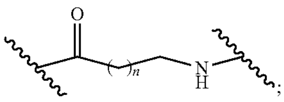
;
-continued
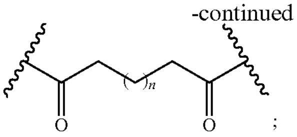
;
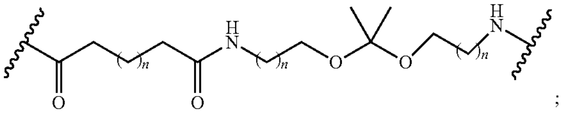
;
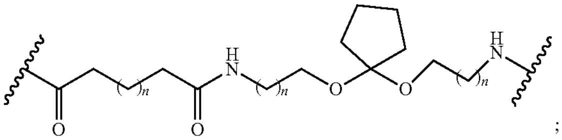
;
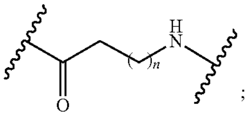
;
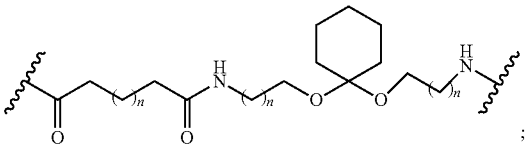
; and
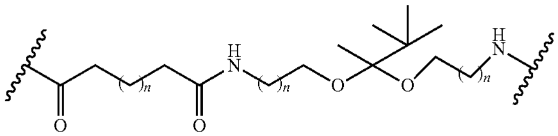
wherein n is from 1 to 20.
In certain embodiments, a linker has a structure selected from among:
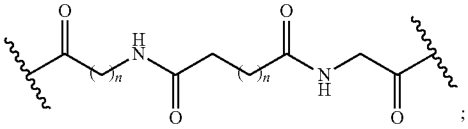
;
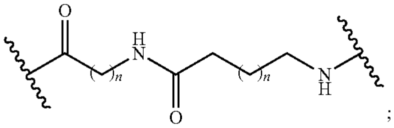
;
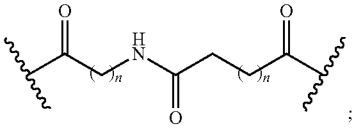
;

-continued
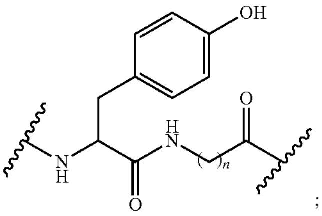
;
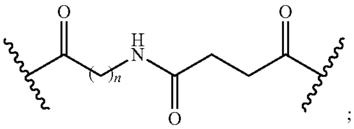
;
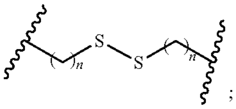
;
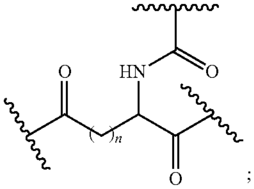
;
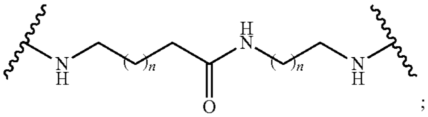
;
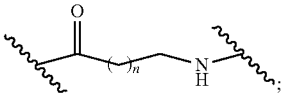
;
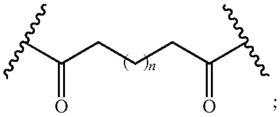
;
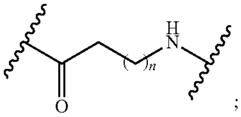
;
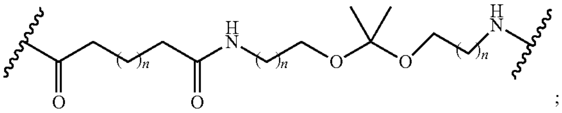
;
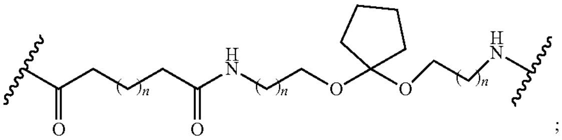
;
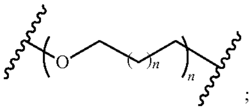
;
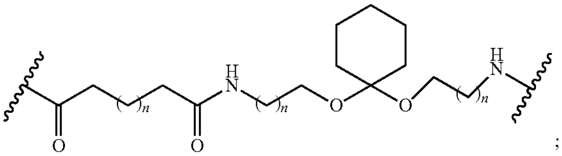
;
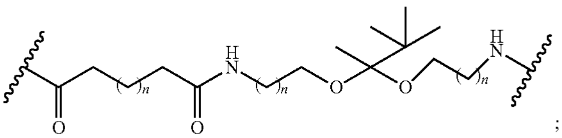
;
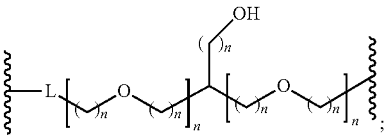
;
-continued
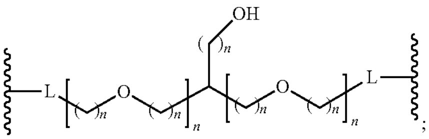
;
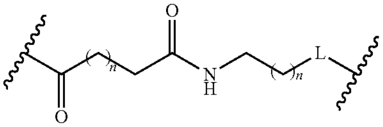
and
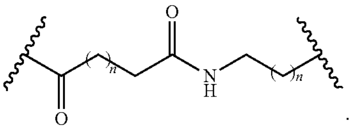
.
wherein each L is, independently, a phosphorus linking group or a neutral linking group; and
each n is, independently, from 1 to 20.
In certain embodiments, a linker has a structure selected from among:
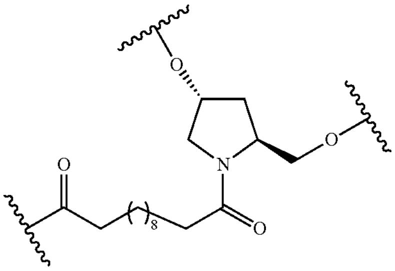
;
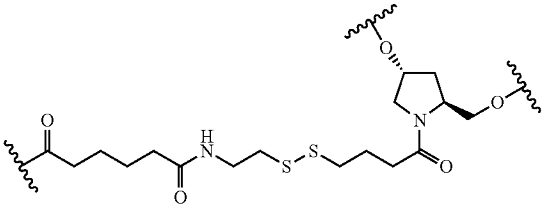
;
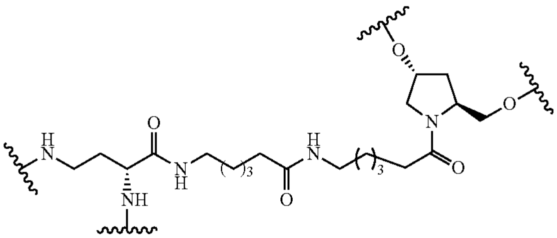
;
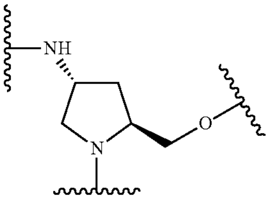

-continued
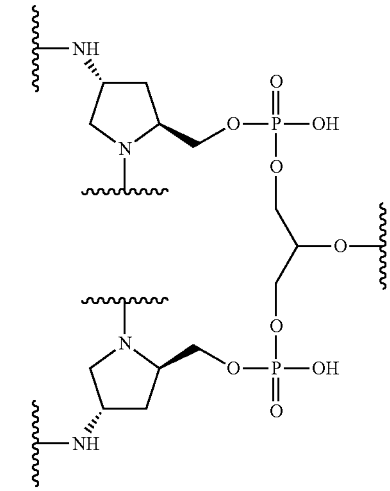
;
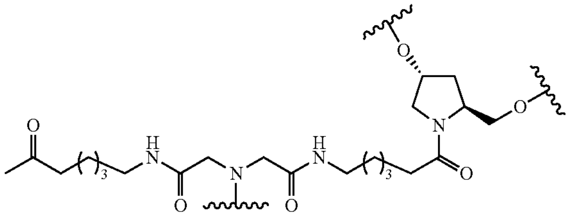
;
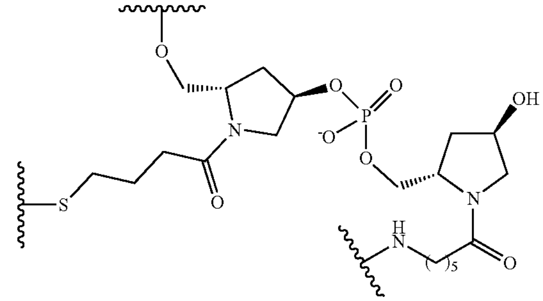
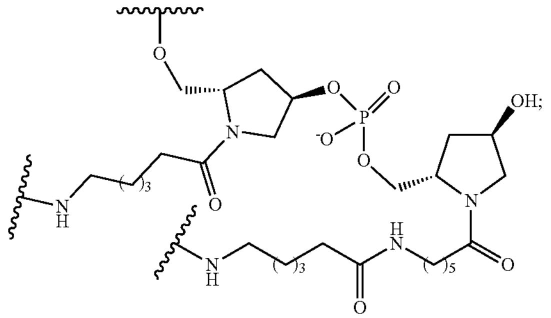
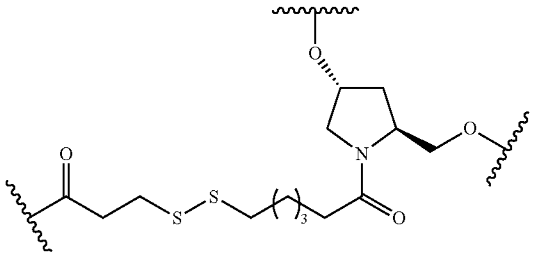
;
-continued
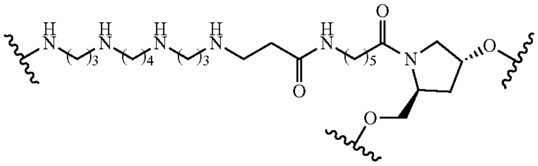
;
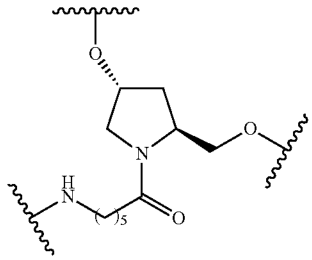
;
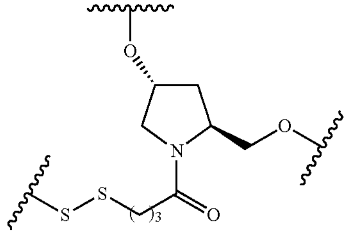
;
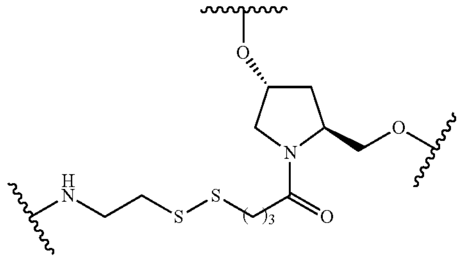
;
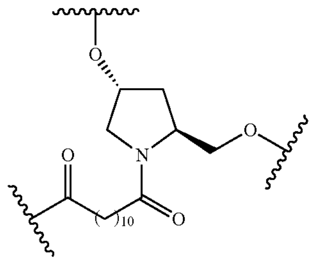
;
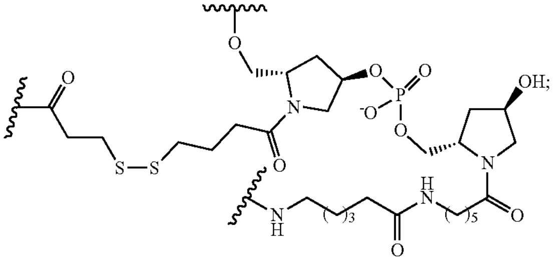

-continued
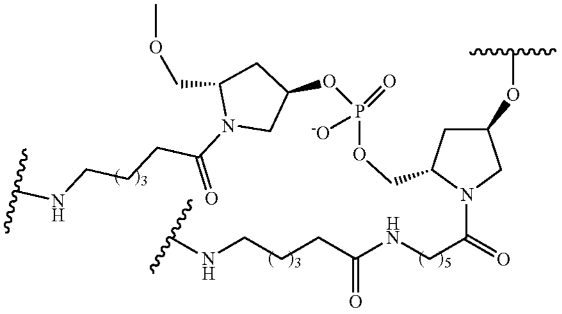
;
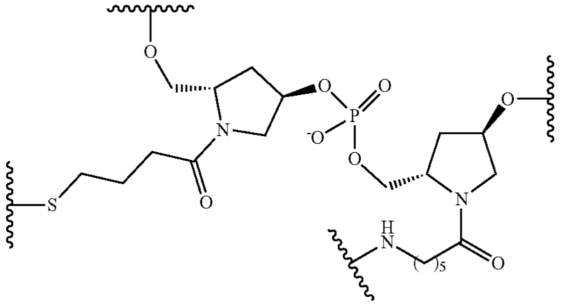
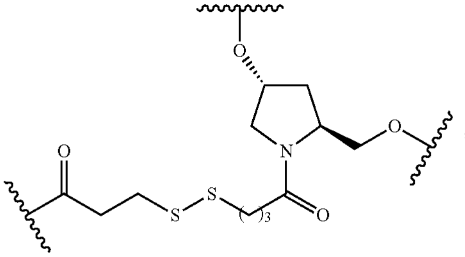
; and
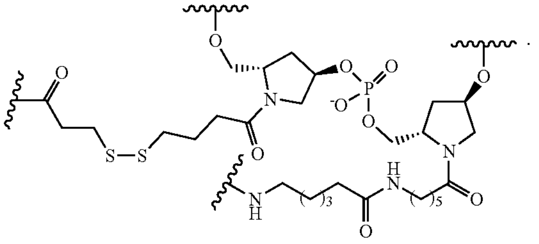
.
In certain embodiments, a linker has a structure selected from among:
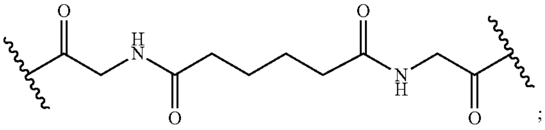
;
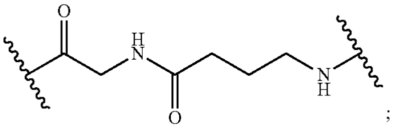
;
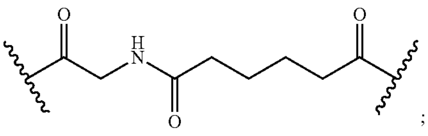
;
-continued
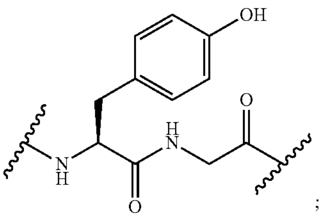
;
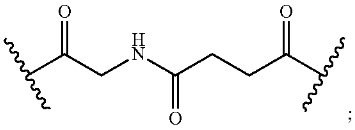
;
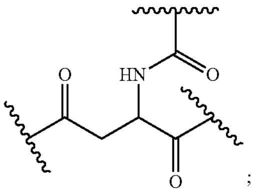
;
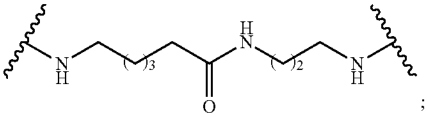
;
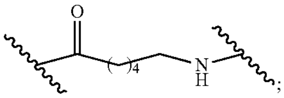
;
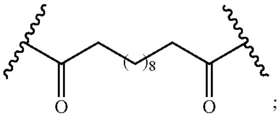
;
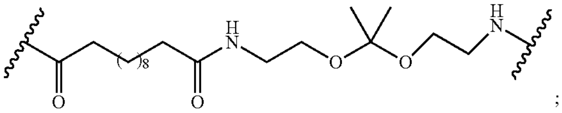
;
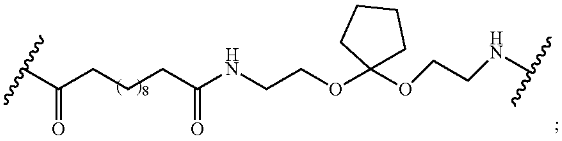
;
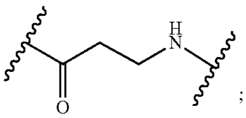
;
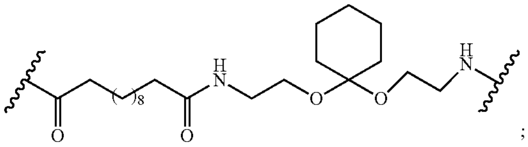
; and
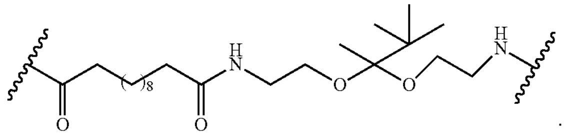
.

In certain embodiments, a linker has a structure selected from among:
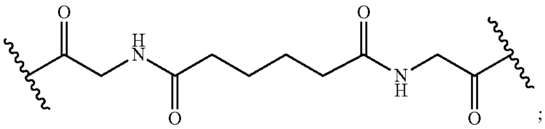
;
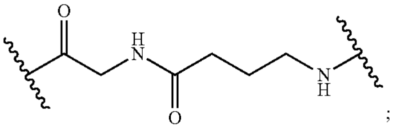
;
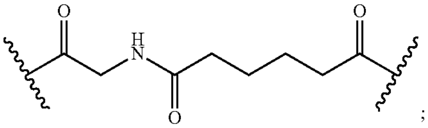
;
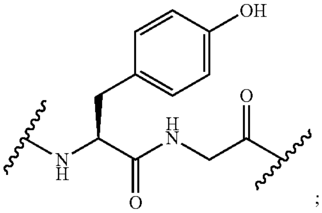
;
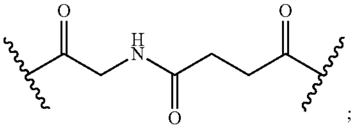
;
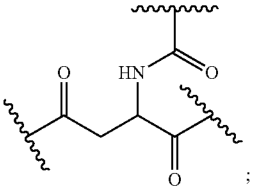
;
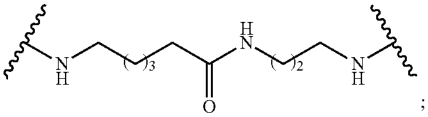
;
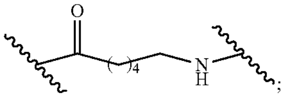
;
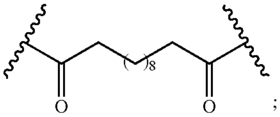
;
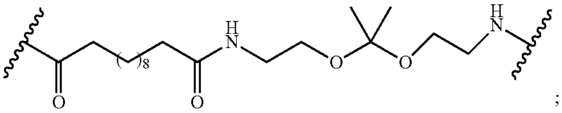
;
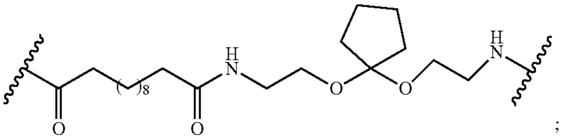
;
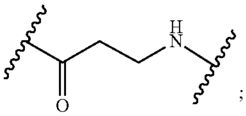
;
-continued
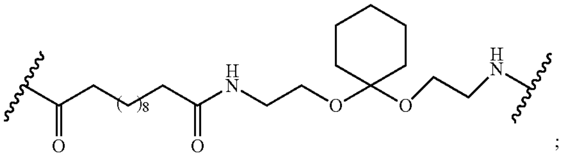
;
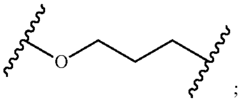
;
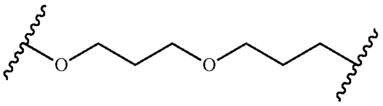
;
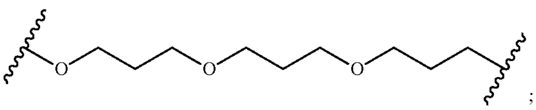
;
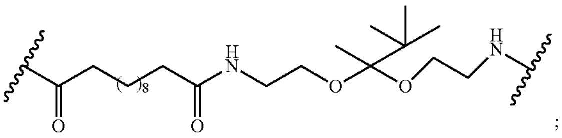
;
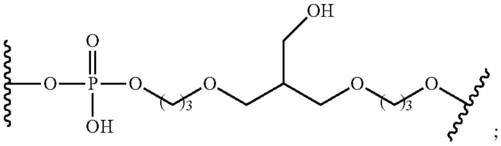
;
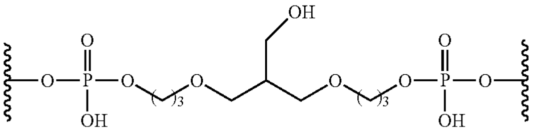
;
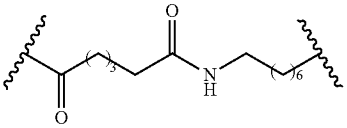
and
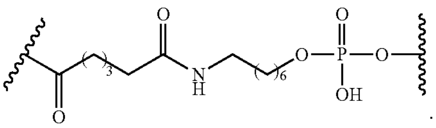
.
In certain embodiments, a linker has a structure selected from among:
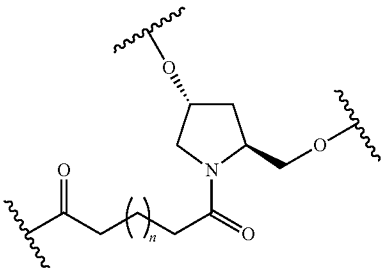
and -continued

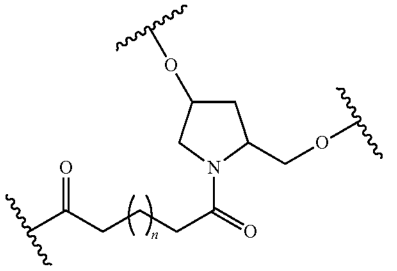

wherein n is from 1 to 20.

In certain embodiments, a linker has a structure selected from among:

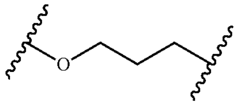

;

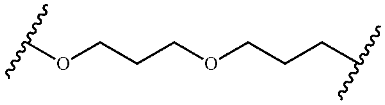

; and

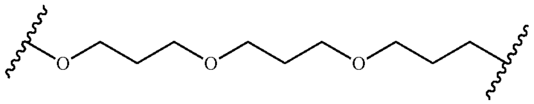

.

In certain embodiments, a linker has a structure selected from among:

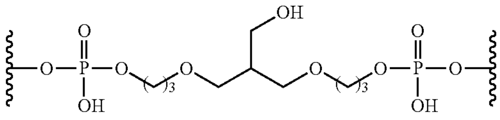

and

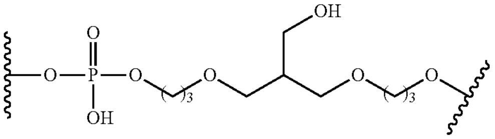

.

In certain embodiments, a linker has a structure selected from among:

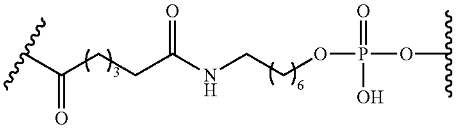

and

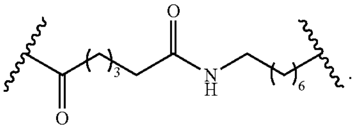

.

In certain embodiments, the conjugate linker has the structure:

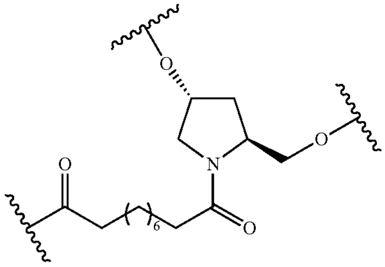

.

In certain embodiments, the conjugate linker has the structure:

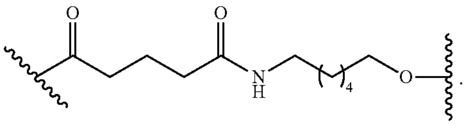

.

In certain embodiments, a linker has a structure selected from among:

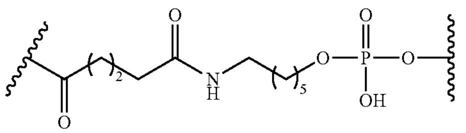

and

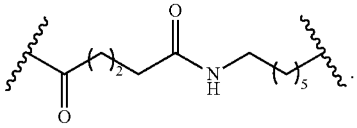

.

In certain embodiments, a linker has a structure selected from among:

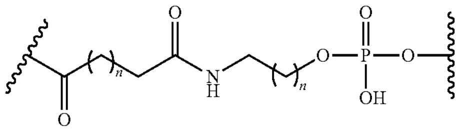

and

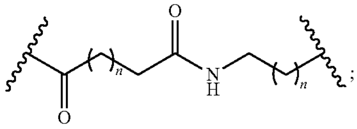

;

wherein each n is independently, 0, 1, 2, 3, 4, 5, 6, or 7.

iv. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

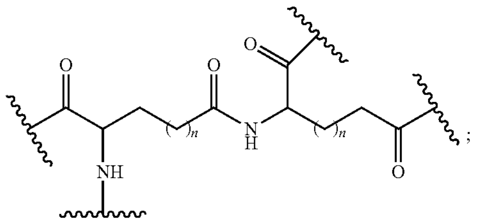

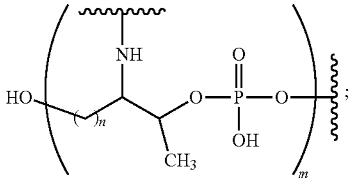

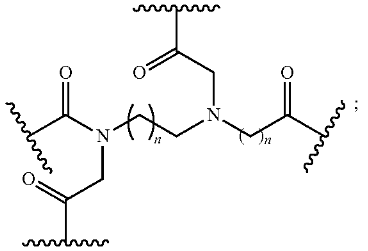

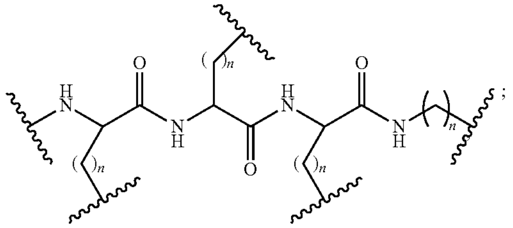

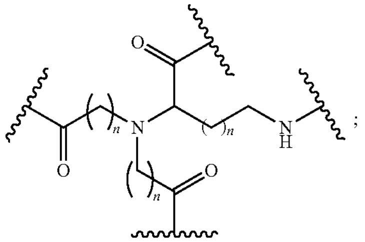

-continued

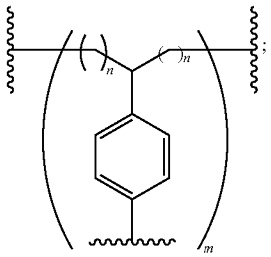

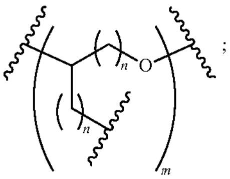

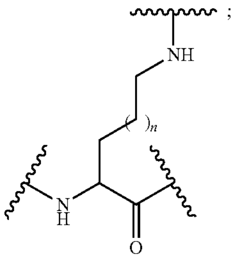

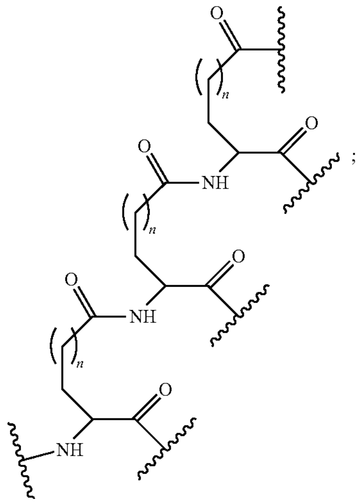

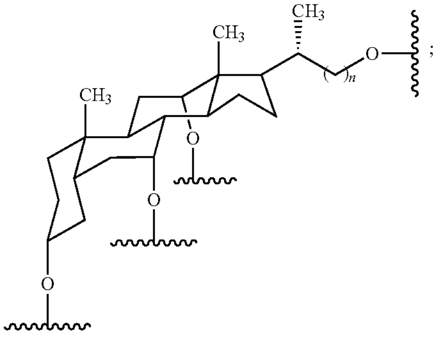

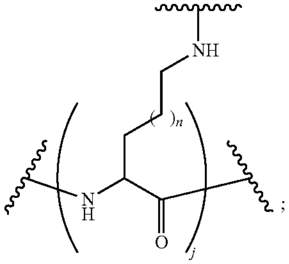

-continued
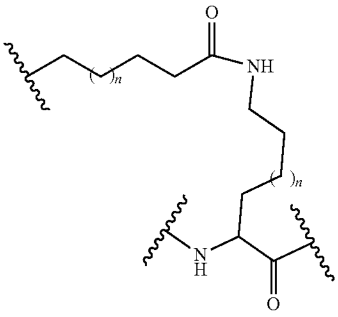
;
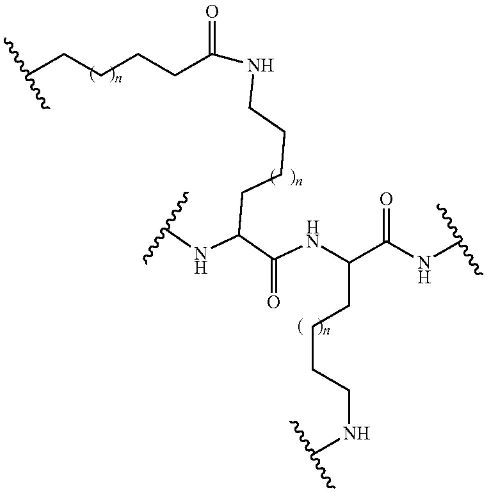
;
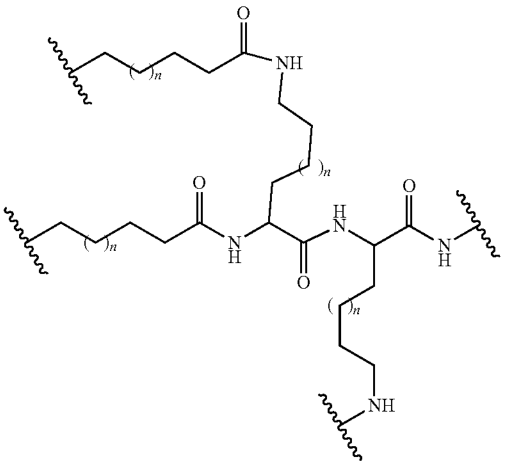
; and
-continued
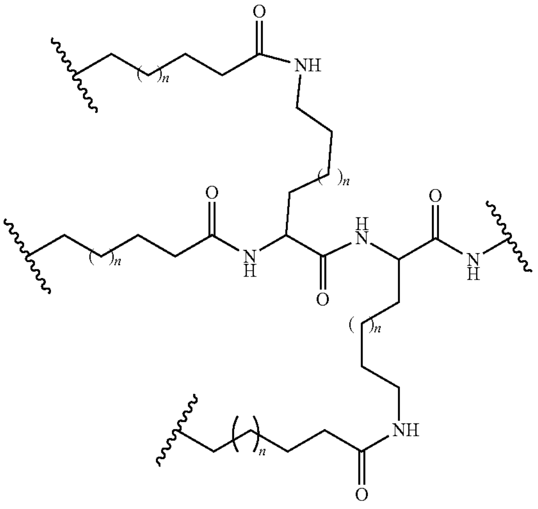
.
wherein each n is, independently, from 1 to 20;
j is from 1 to 3; and
m is from 2 to 6.
In certain embodiments, a branching group has a structure selected from among:
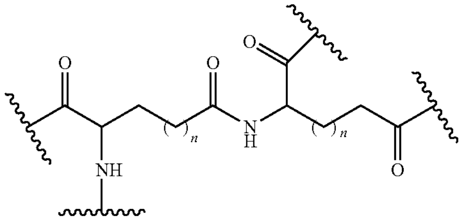
;
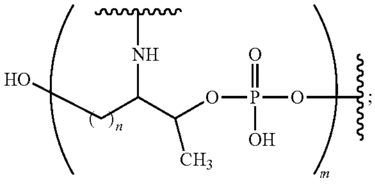
;
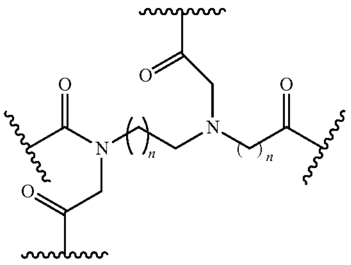
;
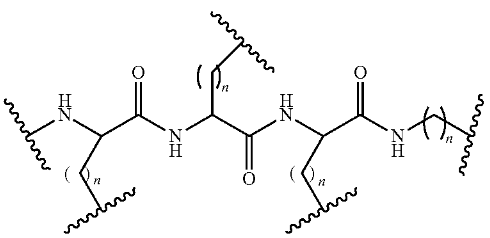
;

-continued
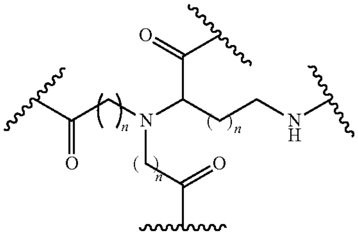
;
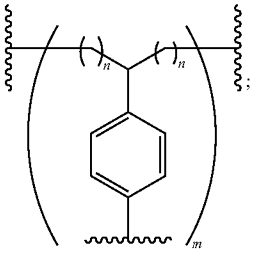
;
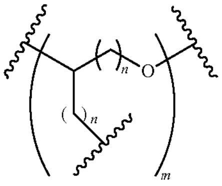
;
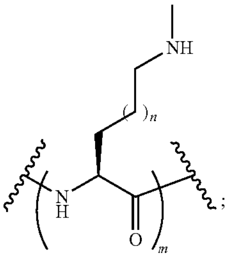
;
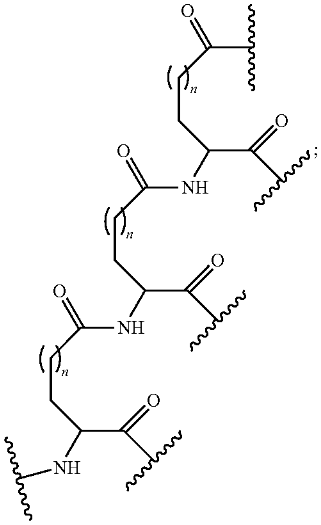
;
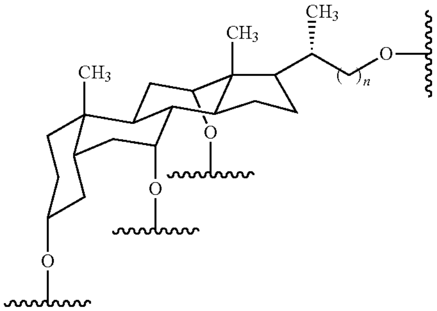
; and
-continued
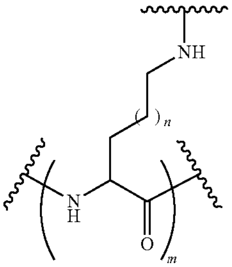
wherein each n is, independently, from 1 to 20; and m is from 2 to 6.
In certain embodiments, a branching group has a structure selected from among:
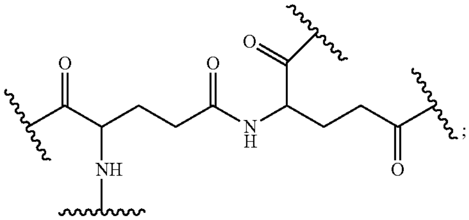
;
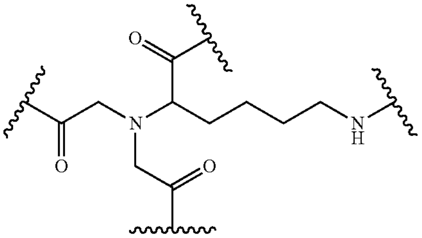
;
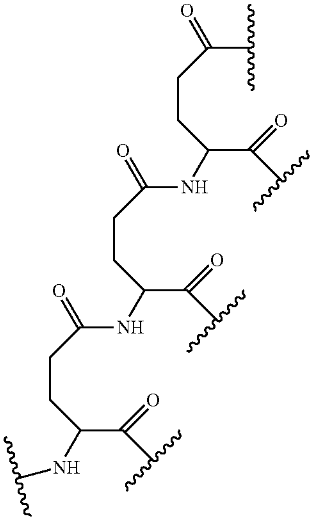
;
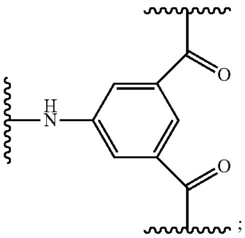
;

-continued
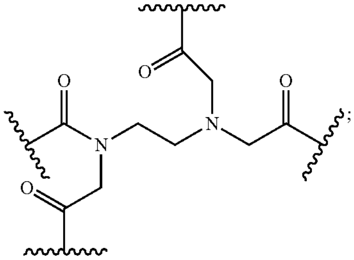
;
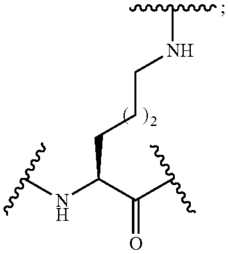
;
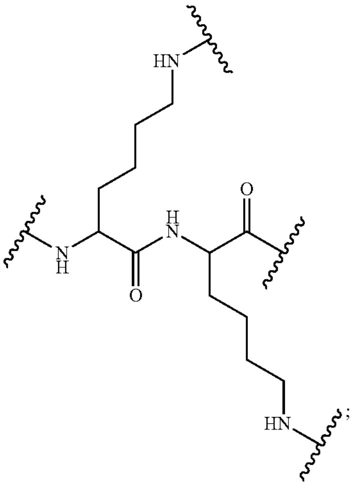
;
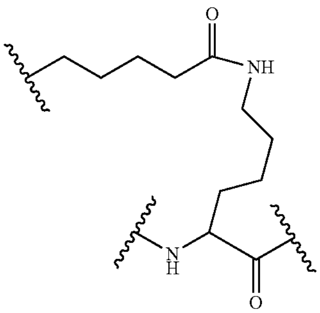
;
-continued
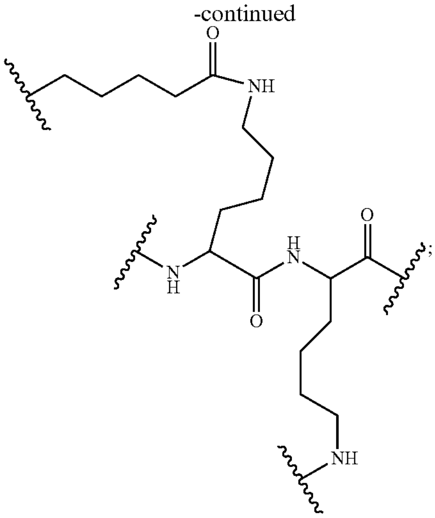
;
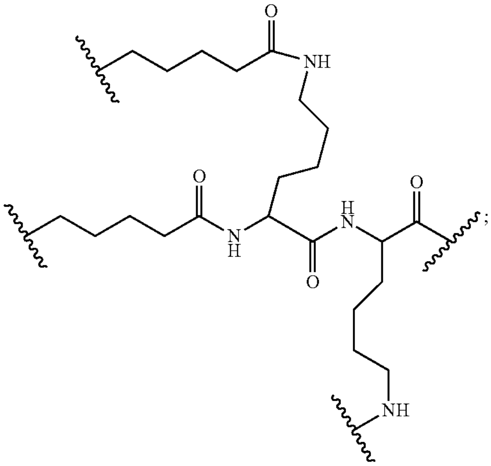
; and
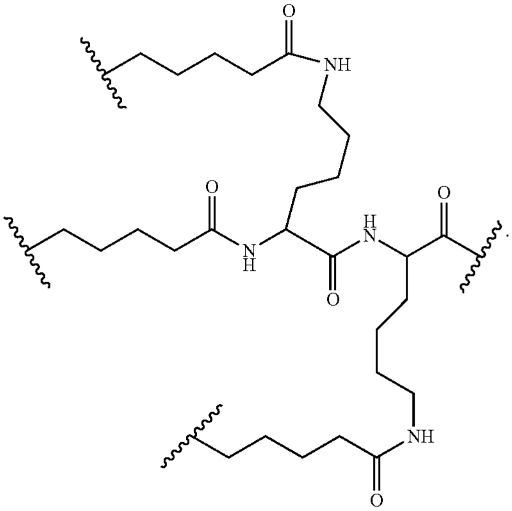
.

In certain embodiments, a branching group has a structure selected from among:

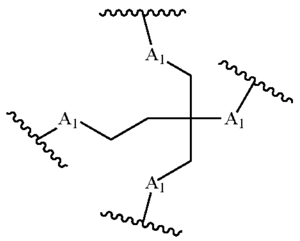

and

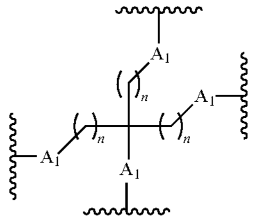

wherein each $A_1$ is independently, O, S, C═O or NH; and each n is, independently, from 1 to 20.

In certain embodiments, a branching group has a structure selected from among:

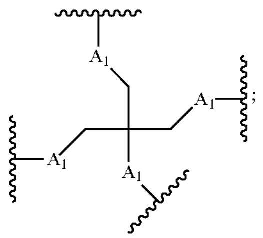

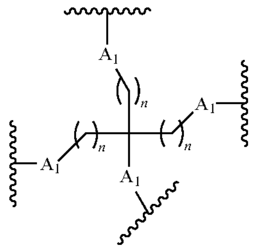

and

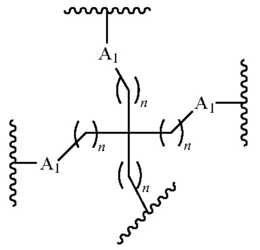

wherein each $A_1$ is independently, O, S, C═O or NH; and each n is, independently, from 1 to 20.

In certain embodiments, a branching group has a structure selected from among:

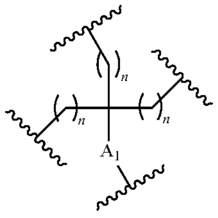

and

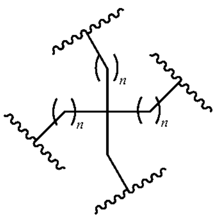

wherein $A_1$ is O, S, C═O or NH; and each n is, independently, from 1 to 20.

In certain embodiments, a branching group has a structure selected from among:

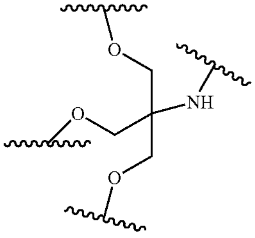

.

In certain embodiments, a branching group has a structure selected from among:

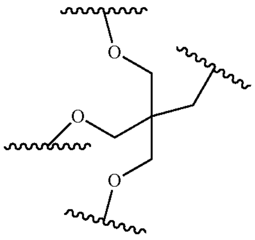

.

In certain embodiments, a branching group has a structure selected from among:

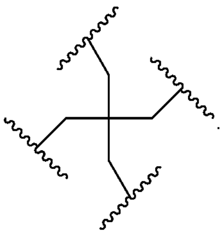 [SMILES: *CC(C*)(C*)C*]

.

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

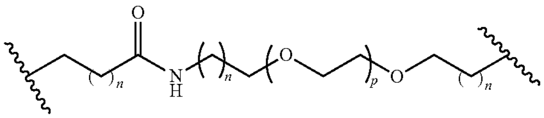
;

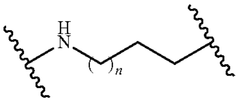
;
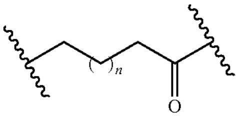
;

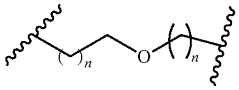
;

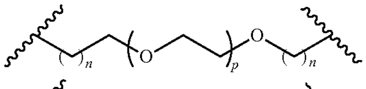
;

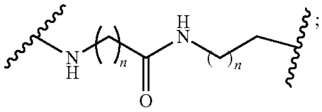
;

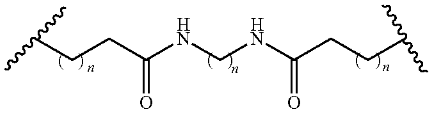
;

-continued

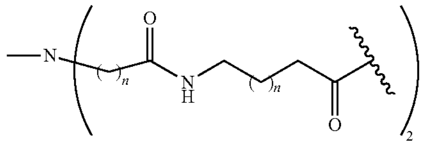
;

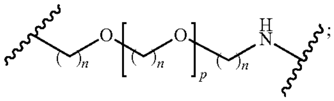
;

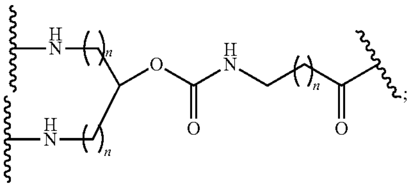
;

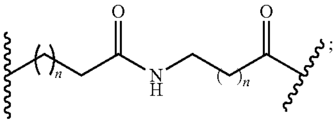
;

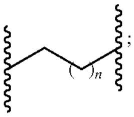
; and
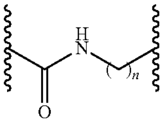

wherein each n is, independently, from 1 to 20; and each p is from 1 to about 6.

In certain embodiments, a tether has a structure selected from among:

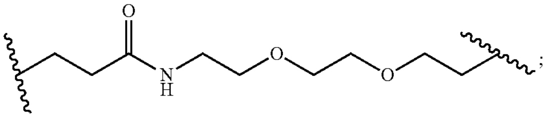
;

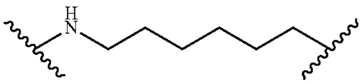
;

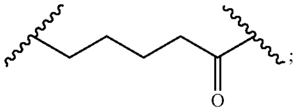
;

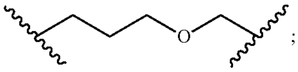
;

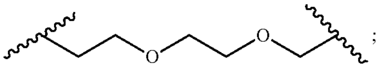
;

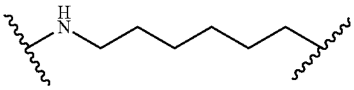
; and

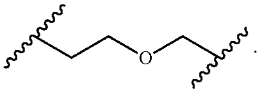
.

In certain embodiments, a tether has a structure selected from among:

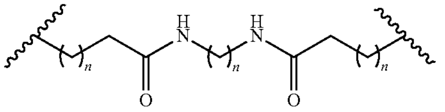

wherein each n is, independently, from 1 to 20.

In certain embodiments, a tether has a structure selected from among:

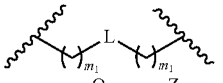

and

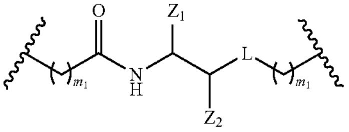

wherein L is either a phosphorus linking group or a neutral linking group;

$Z_1$ is C(=O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

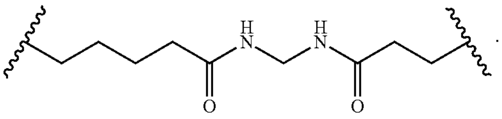 [SMILES: *CCCCC(=O)NCNC(=O)CC*]

.

In certain embodiments, a tether has a structure selected from among:

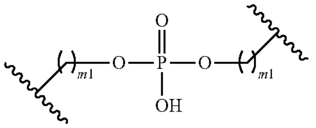

and

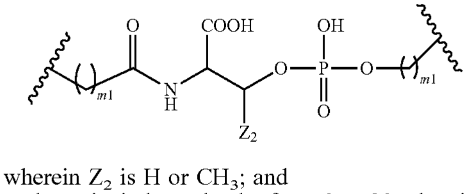

wherein $Z_2$ is H or $CH_3$; and each $m_1$ is, independently, from 0 to 20 wherein at least one $m_1$ is greater than 0 for each tether.

In certain embodiments, a tether has a structure selected from among:

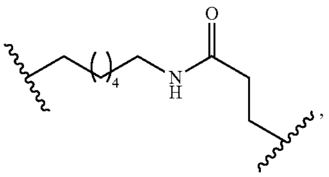

, or

-continued

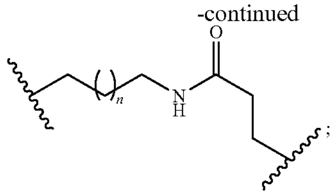

;

wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-2-deoxy-D-galactopyranose may be used interchangeably.

Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

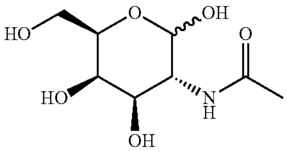

2-(Acetylamino)-2-deoxy-D-galactopyranose

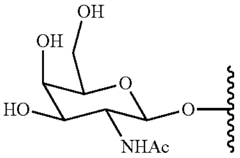

2-(Acetylamino)-2-deoxy-β-D-galactopyranose

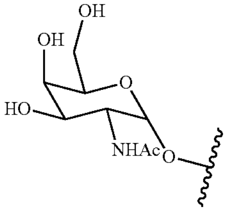

2-(Acetylamino)-2-deoxy-α-D-galactopyranose

In certain embodiments one or more ligand has a structure selected from among:

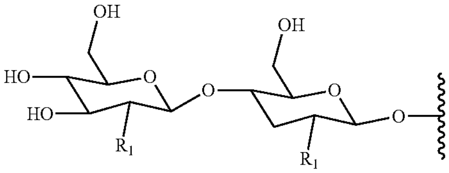

and

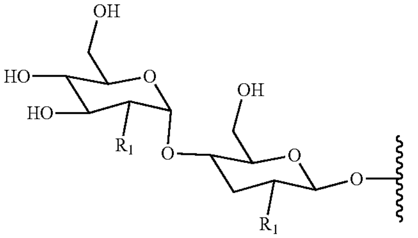

wherein each $R_1$ is selected from OH and NHCOOH.

In certain embodiments one or more ligand has a structure selected from among:

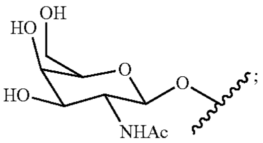

-continued

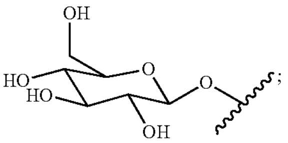

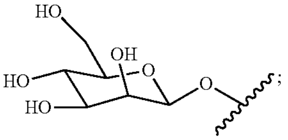

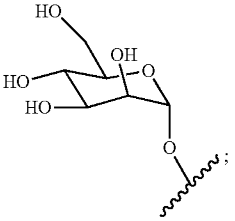

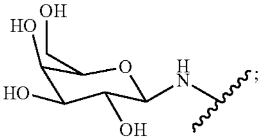

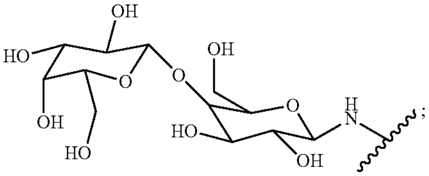

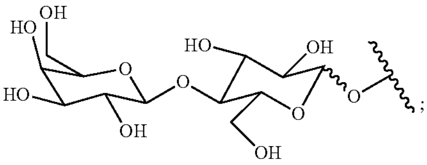

and

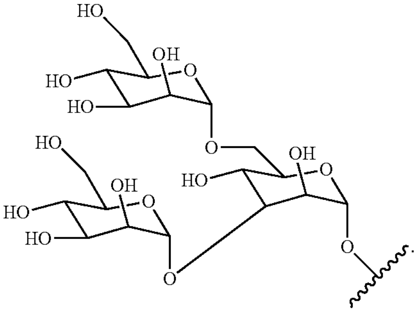

In certain embodiments one or more ligand has a structure selected from among:

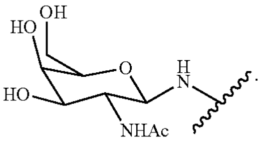 [SMILES: *NC1OC(CO)C(O)C(O)C1NC(C)=O]

In certain embodiments one or more ligand has a structure selected from among:

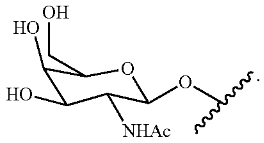 [SMILES: *OC1OC(CO)C(O)C(O)C1NC(C)=O]

i. Certain Conjugates

In certain embodiments, conjugate groups comprise the structural features above. In certain such embodiments, conjugate groups have the following structure:

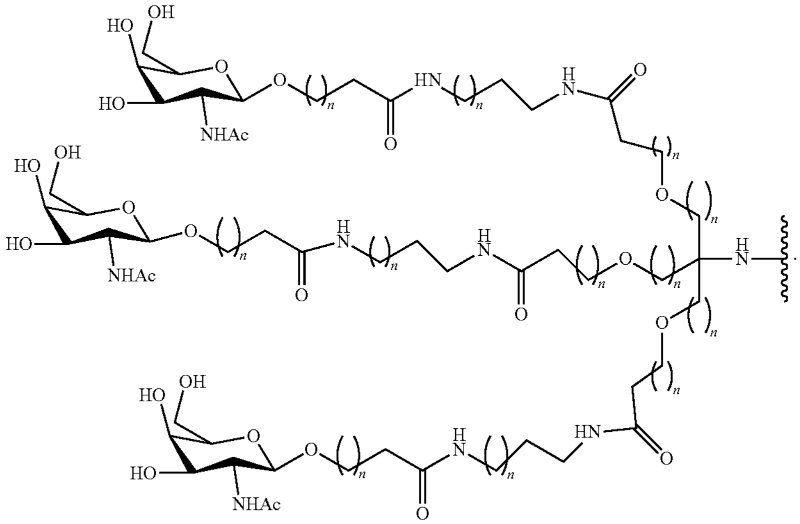

wherein each n is, independently, from 1 to 20.

In certain such embodiments, conjugate groups have the following structure:

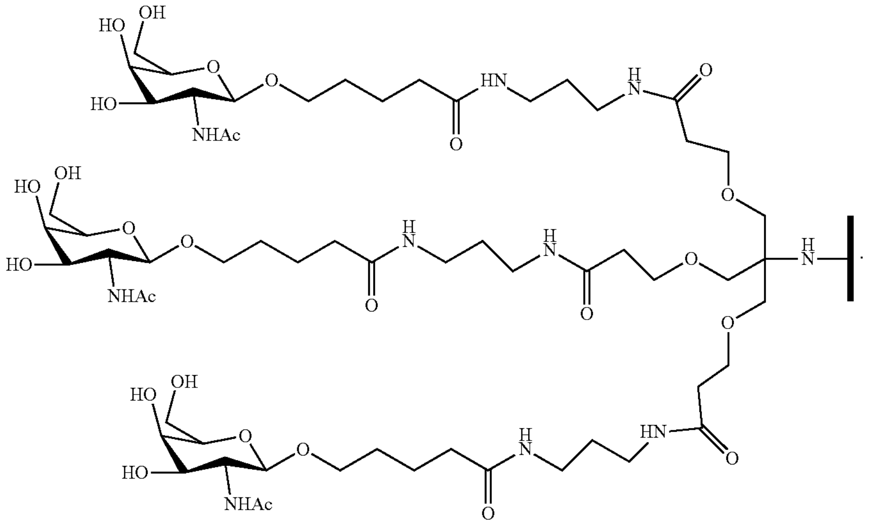

In certain such embodiments, conjugate groups have the following structure:
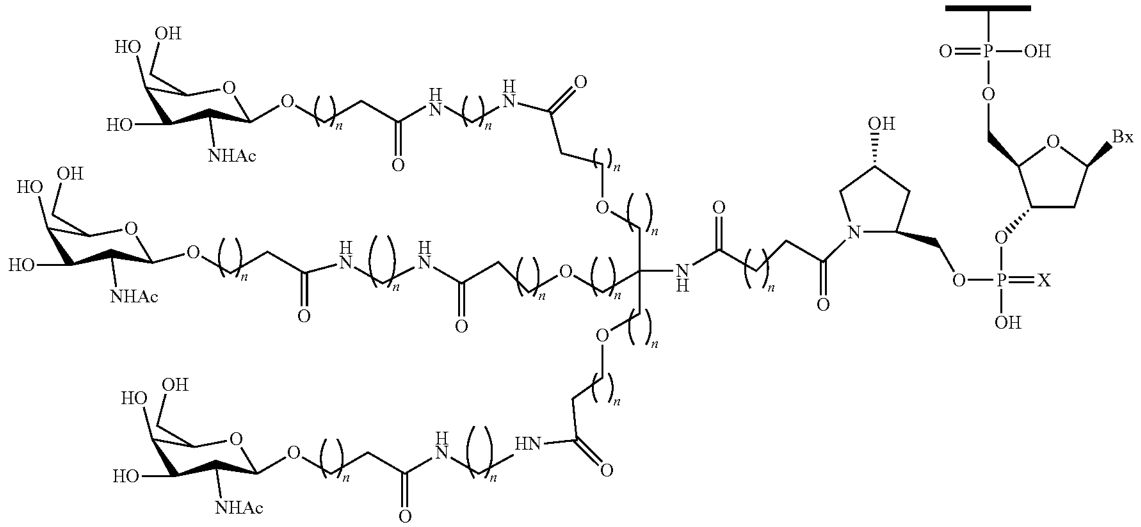
wherein each n is, independently, from 1 to 20;
Z is H or a linked solid support;
Q is an antisense compound;
X is O or S; and
Bx is a heterocyclic base moiety.
In certain such embodiments, conjugate groups have the following structure:
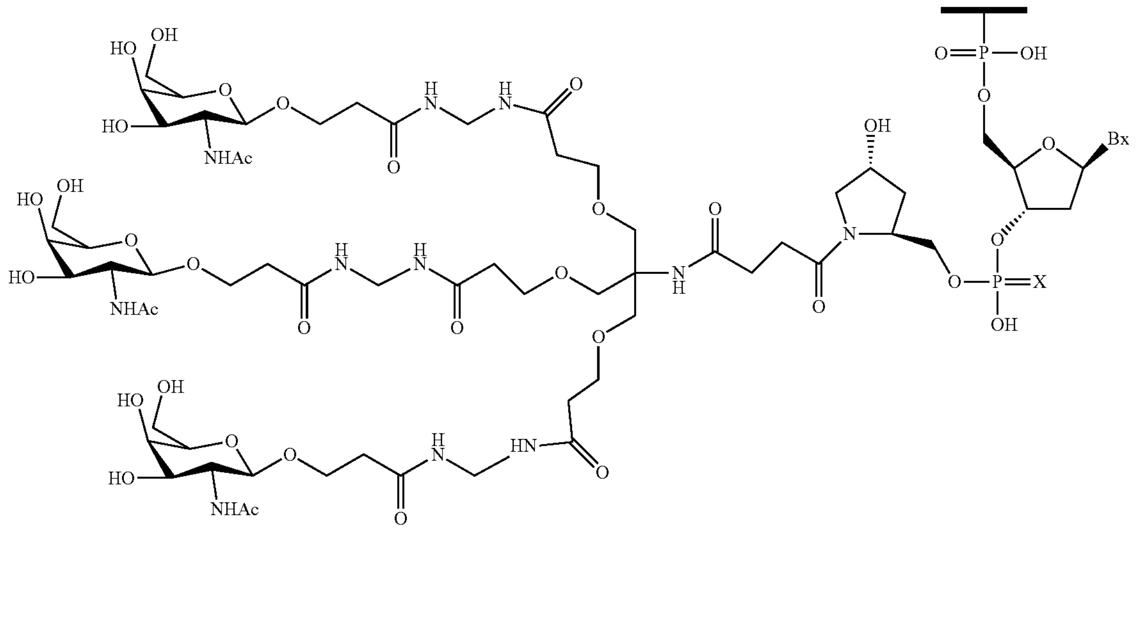

In certain such embodiments, conjugate groups have the following structure:
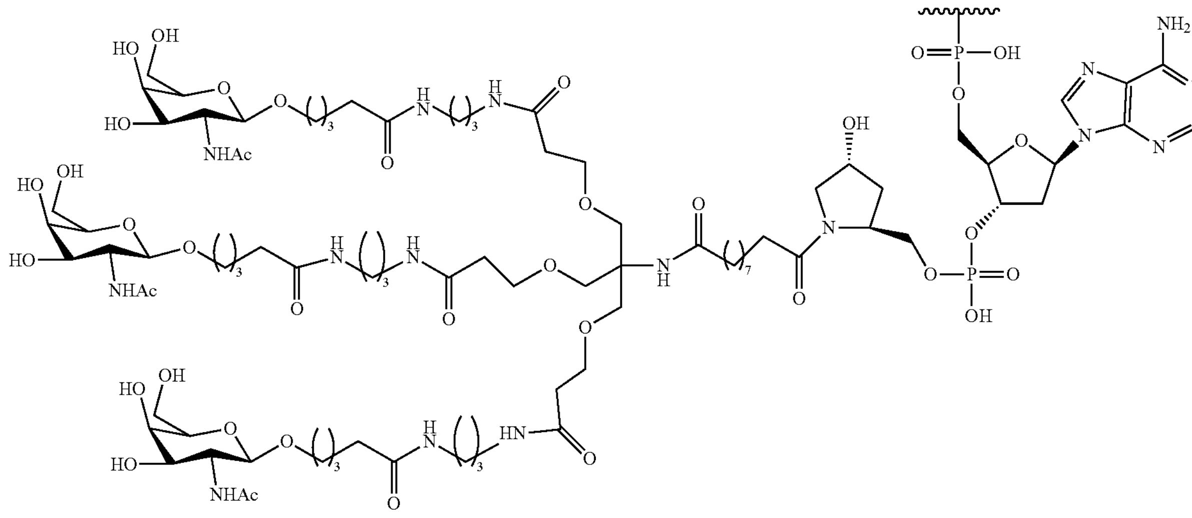
In certain such embodiments, conjugate groups have the following structure:
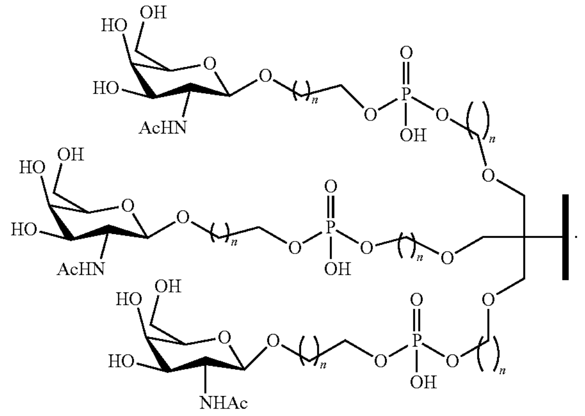
In certain such embodiments, conjugate groups have the following structure:
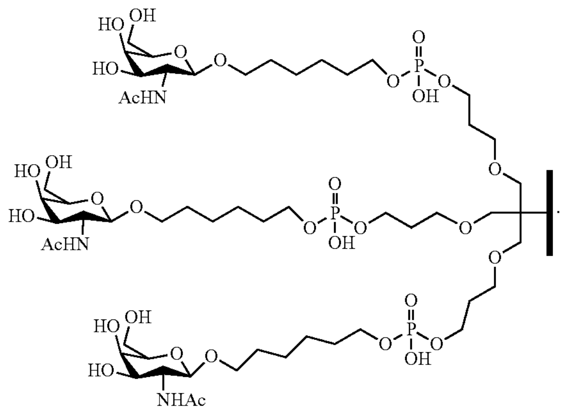
In certain such embodiments, conjugate groups have the following structure:
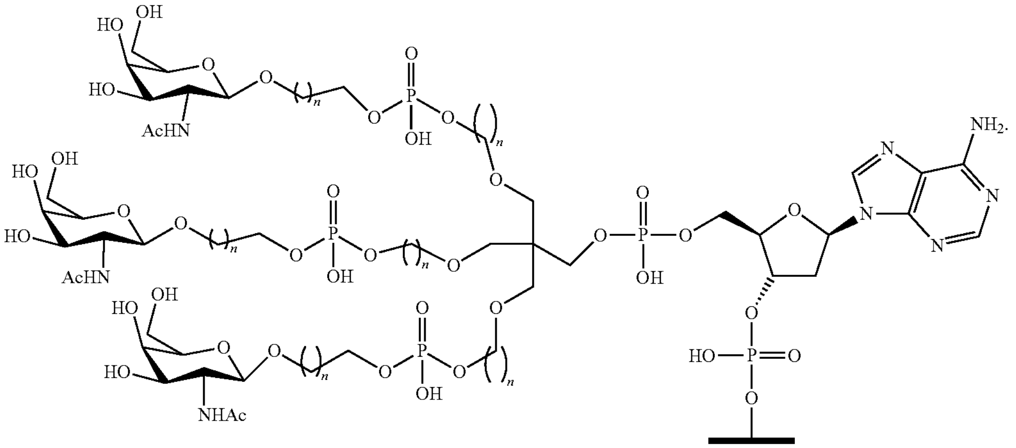

In certain such embodiments, conjugate groups have the following structure:
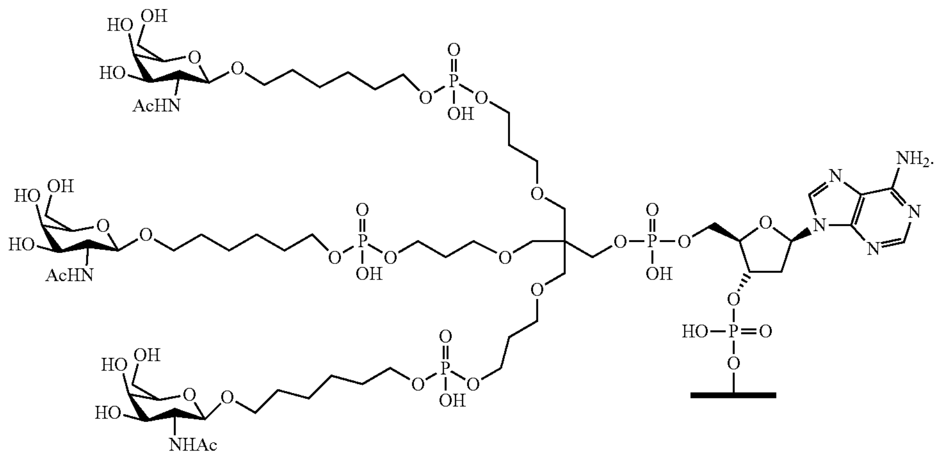
In certain such embodiments, conjugate groups have the following structure:
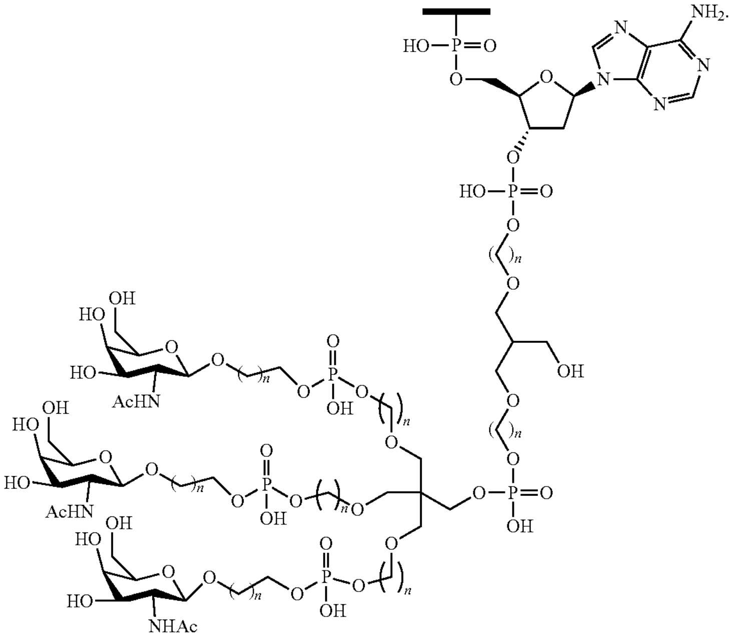

In certain such embodiments, conjugate groups have the following structure:
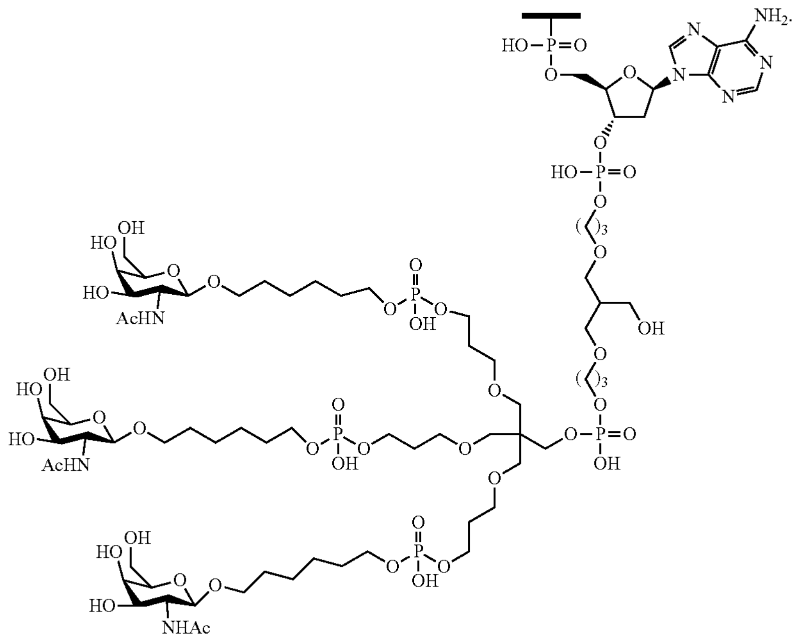
In certain embodiments, conjugates do not comprise a pyrrolidine.
In certain such embodiments, conjugate groups have the following structure:
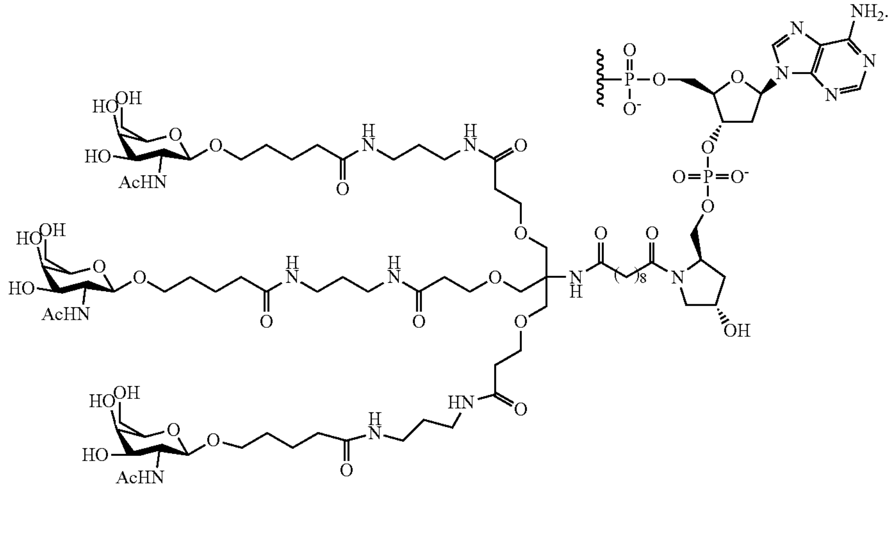

In certain such embodiments, conjugate groups have the following structure:
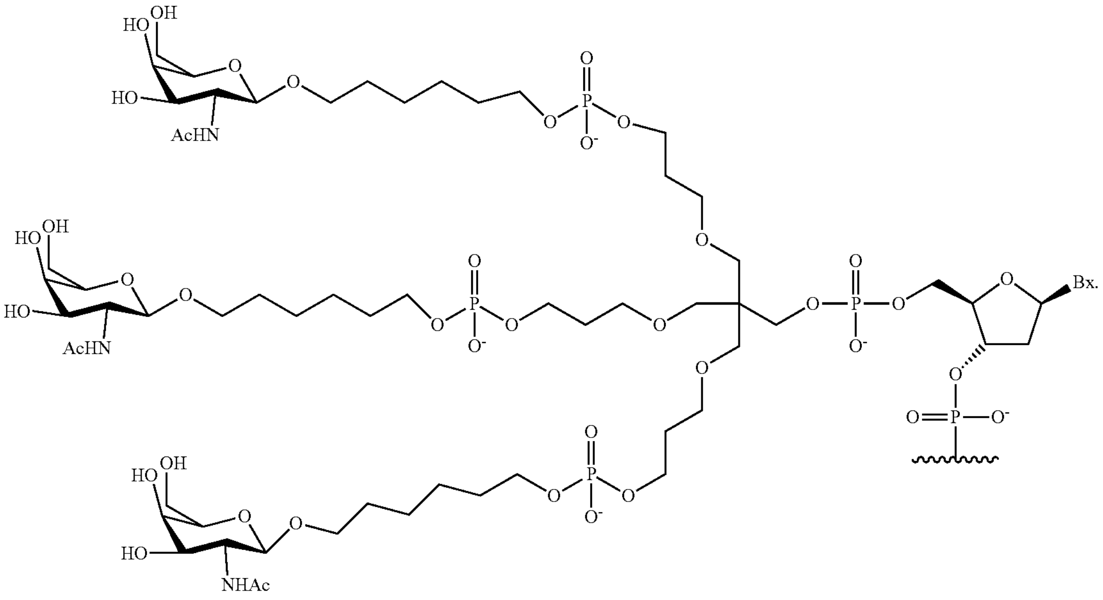
In certain such embodiments, conjugate groups have the following structure:
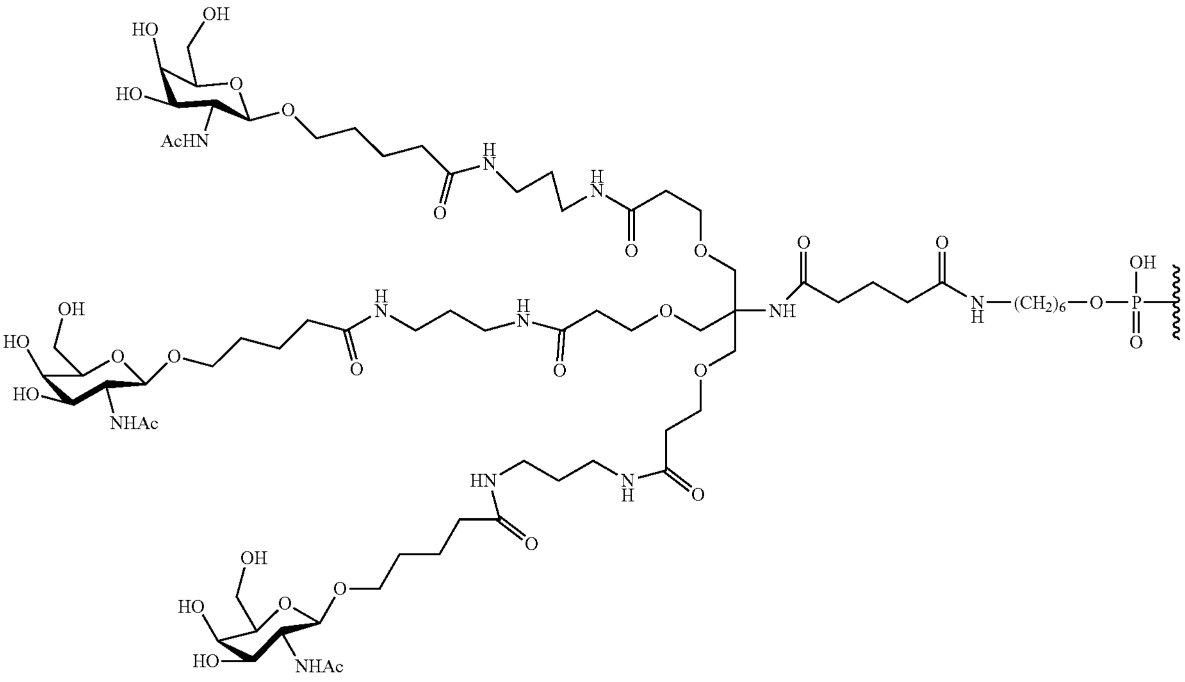

In certain such embodiments, conjugate groups have the following structure:
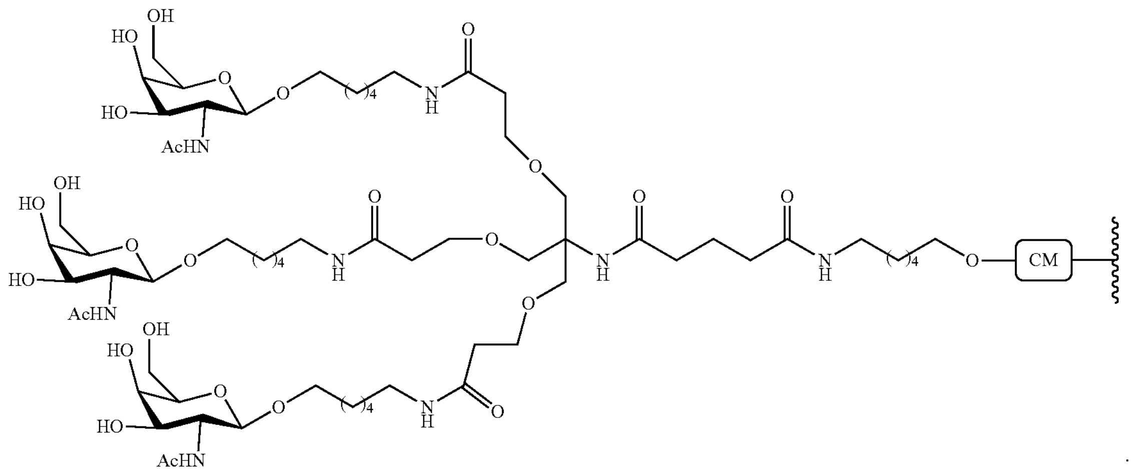
In certain such embodiments, conjugate groups have the following structure:
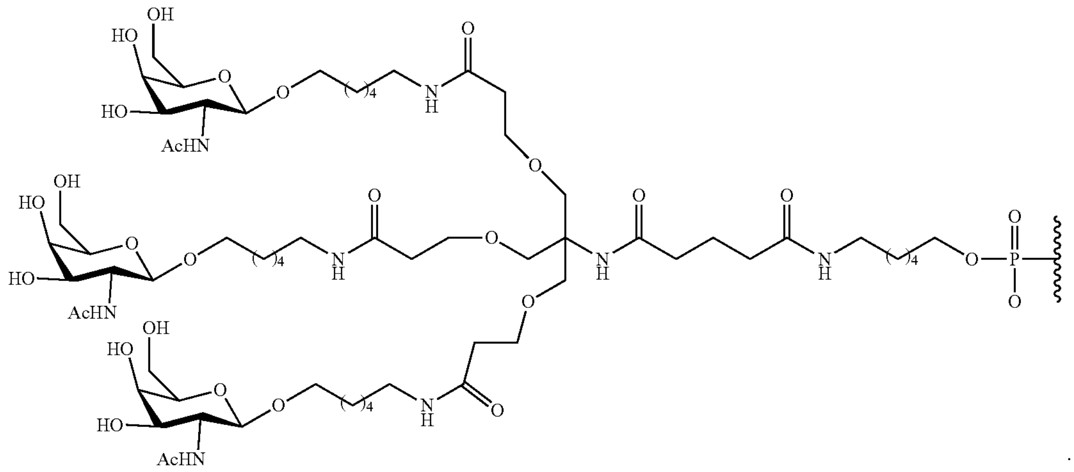
In certain such embodiments, conjugate groups have the following structure:
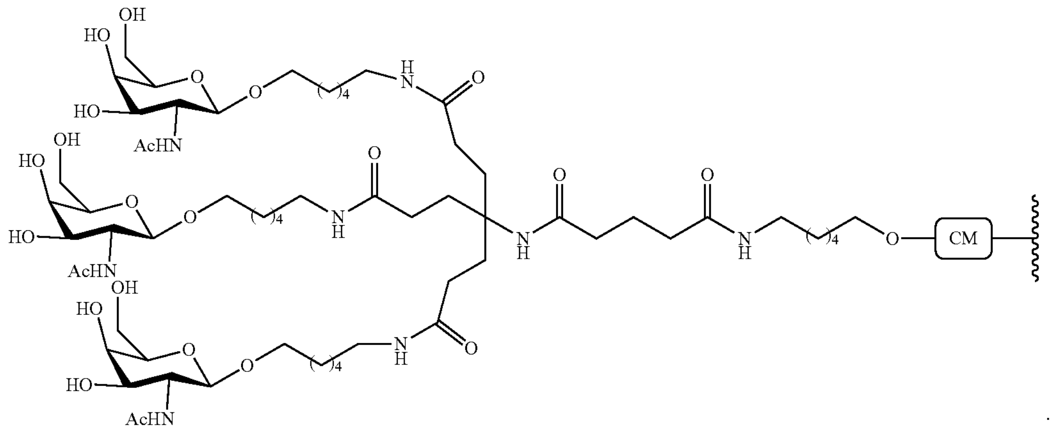

In certain such embodiments, conjugate groups have the following structure:
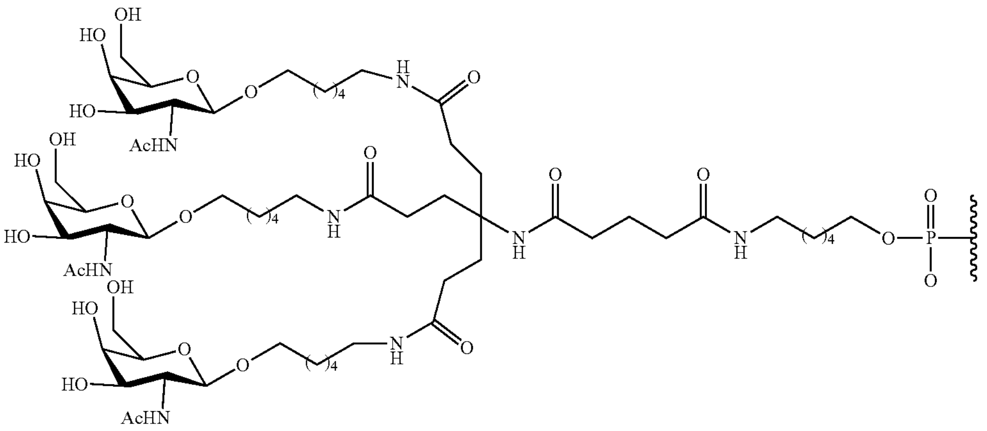
In certain such embodiments, conjugate groups have the following structure:
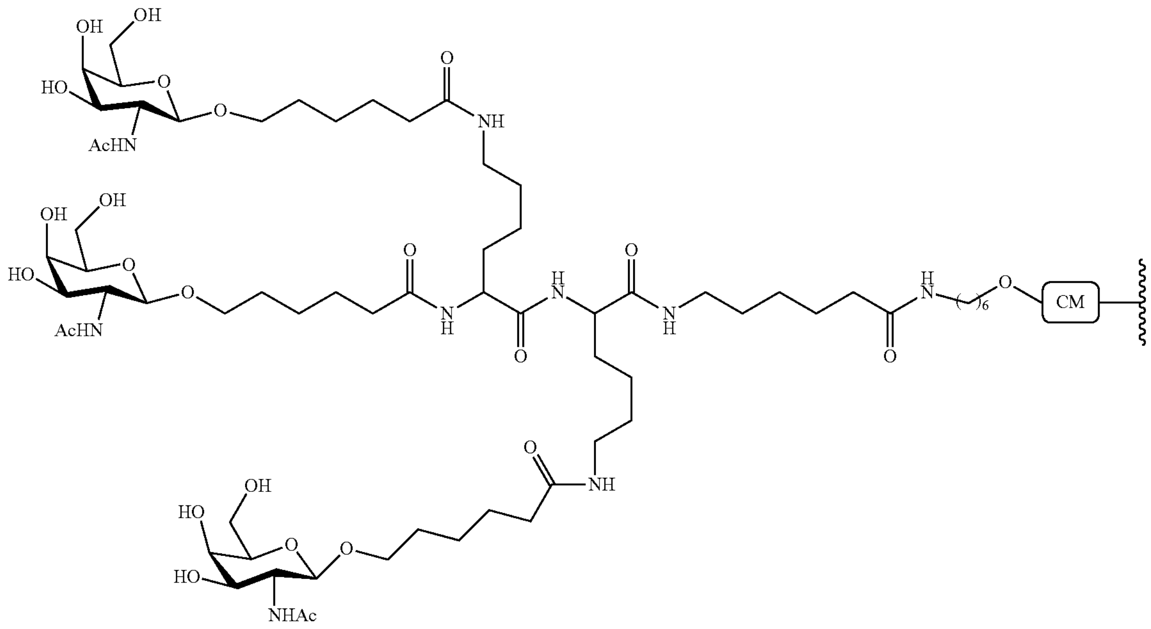

In certain such embodiments, conjugate groups have the following structure:
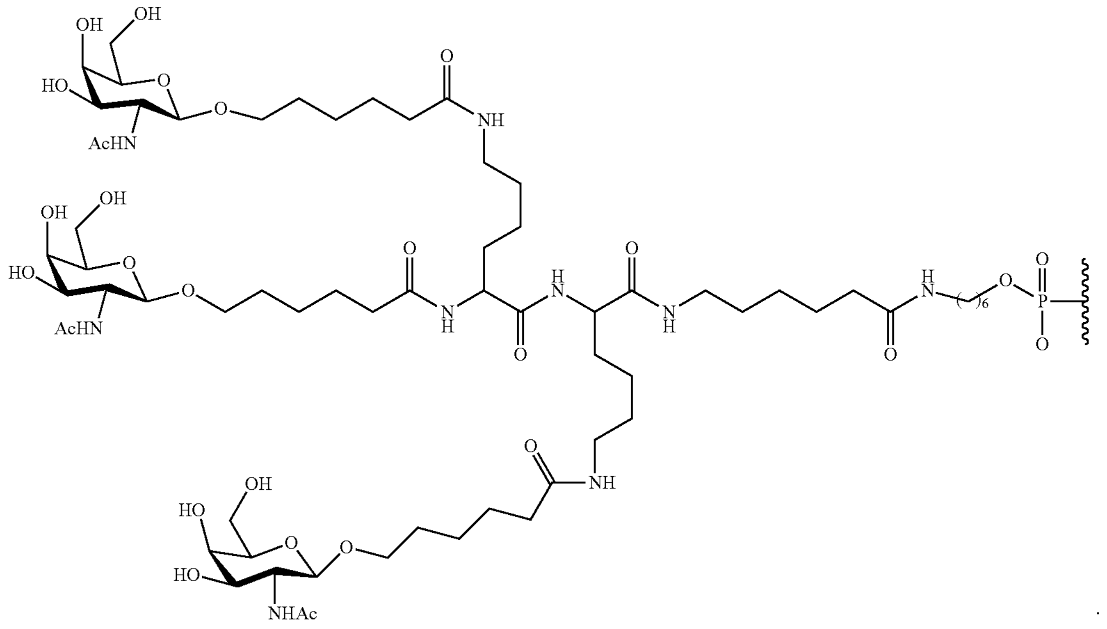
In certain such embodiments, conjugate groups have the following structure:
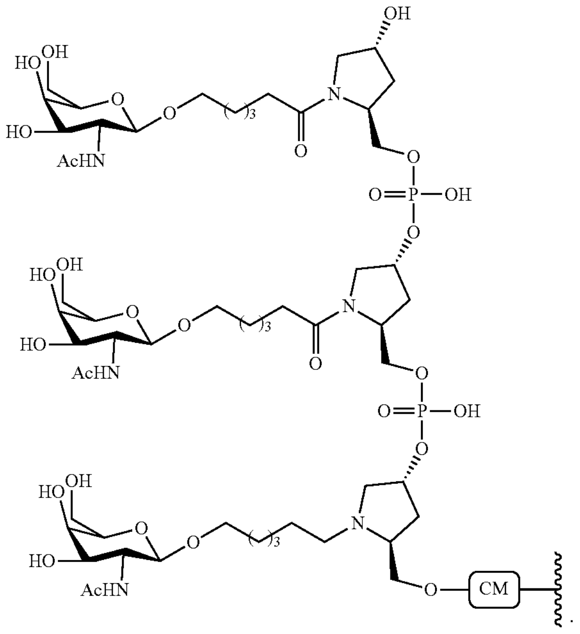
In certain such embodiments, conjugate groups have the following structure:
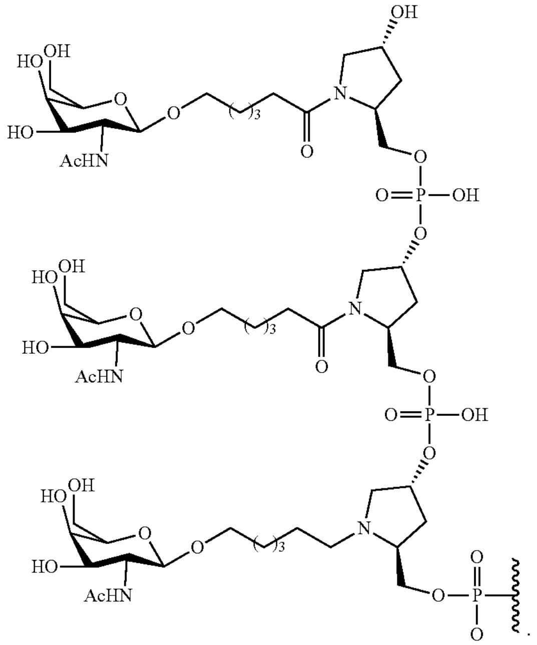

In certain embodiments, the cell-targeting moiety of the conjugate group has the following structure:

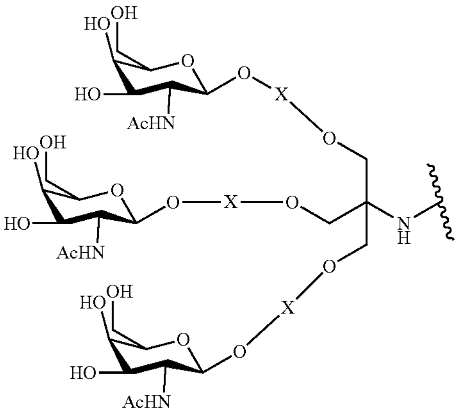

wherein X is a substituted or unsubstituted tether of six to eleven consecutively bonded atoms.

In certain embodiments, the cell-targeting moiety of the conjugate group has the following structure:

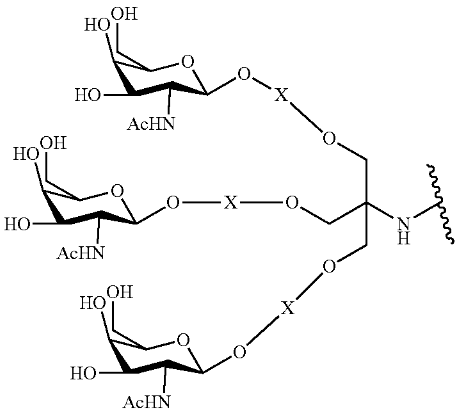

wherein X is a substituted or unsubstituted tether of ten consecutively bonded atoms.

In certain embodiments, the cell-targeting moiety of the conjugate group has the following structure:

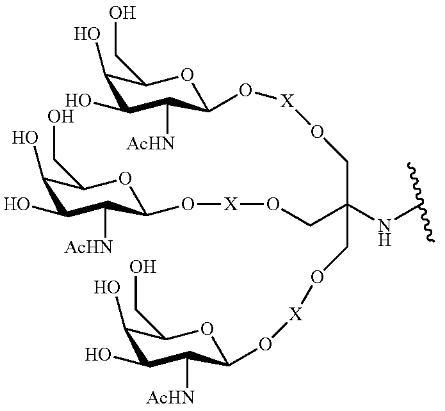

wherein X is a substituted or unsubstituted tether of four to eleven consecutively bonded atoms and wherein the tether comprises exactly one amide bond.

In certain embodiments, the cell-targeting moiety of the conjugate group has the following structure:

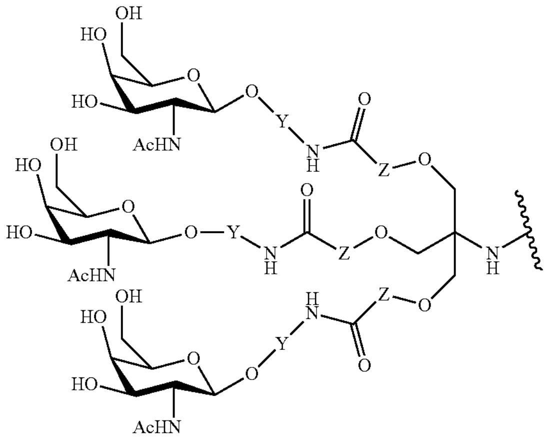

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

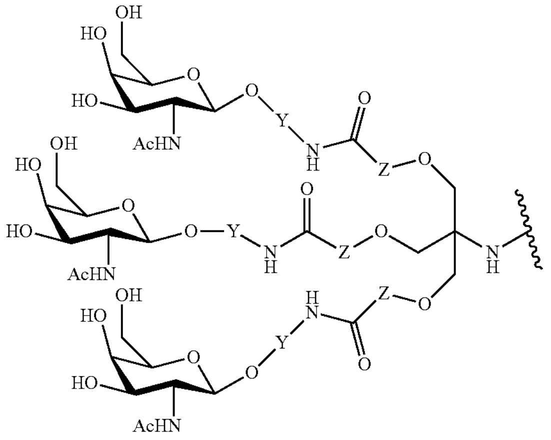

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

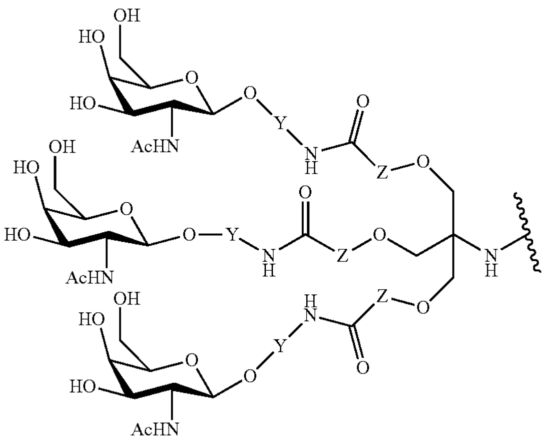

wherein Y and Z are independently selected from a $C_1$-$C_{12}$ substituted or unsubstituted alkyl group.

In certain such embodiments, the cell-targeting moiety of the conjugate group has the following structure:

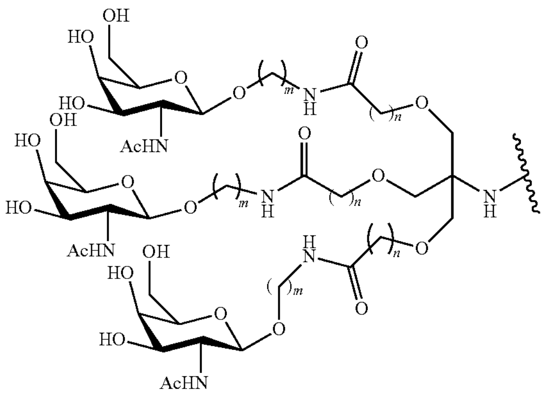

wherein m and n are independently selected from 1, 2, 3, 4, 5, 6, 7, 8, 9, 10, 11, and 12.

In certain such embodiments, the cell-targeting moiety of the conjugate group has the following structure:

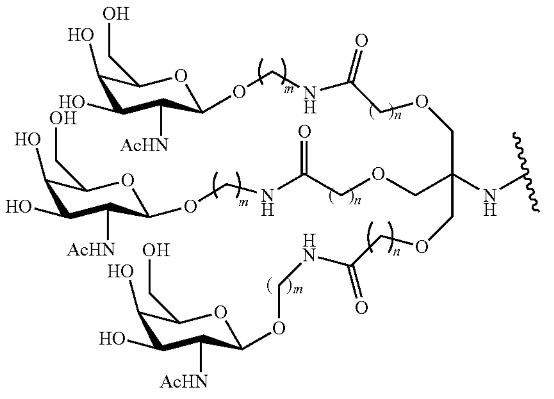

wherein m is 4, 5, 6, 7, or 8, and n is 1, 2, 3, or 4.

In certain embodiments, the cell-targeting moiety of the conjugate group has the following structure:

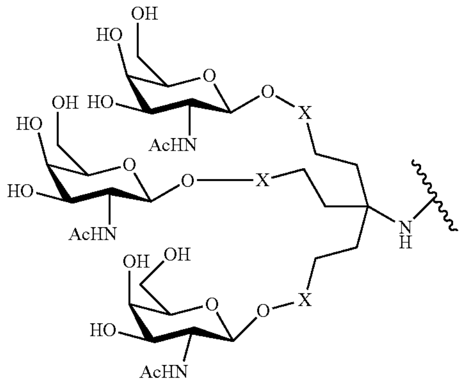

wherein X is a substituted or unsubstituted tether of four to thirteen consecutively bonded atoms, and wherein X does not comprise an ether group.

In certain embodiments, the cell-targeting moiety of the conjugate group has the following structure:

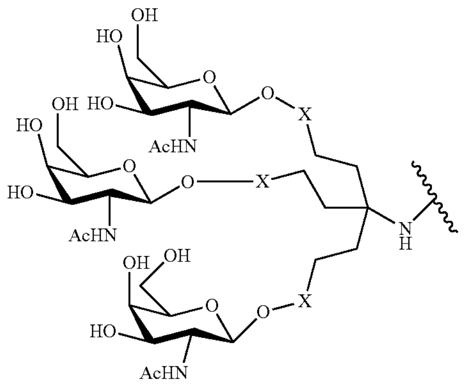

wherein X is a substituted or unsubstituted tether of eight consecutively bonded atoms, and wherein X does not comprise an ether group.

In certain embodiments, the cell-targeting moiety of the conjugate group has the following structure:

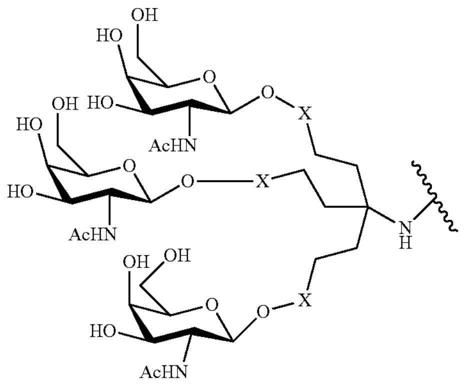

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

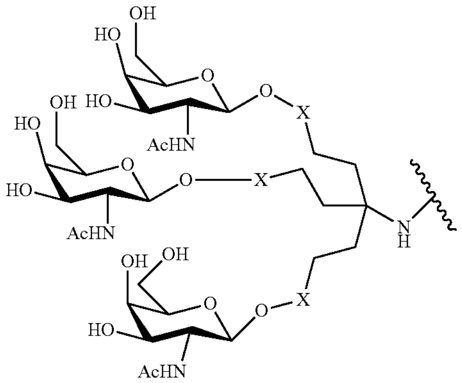

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

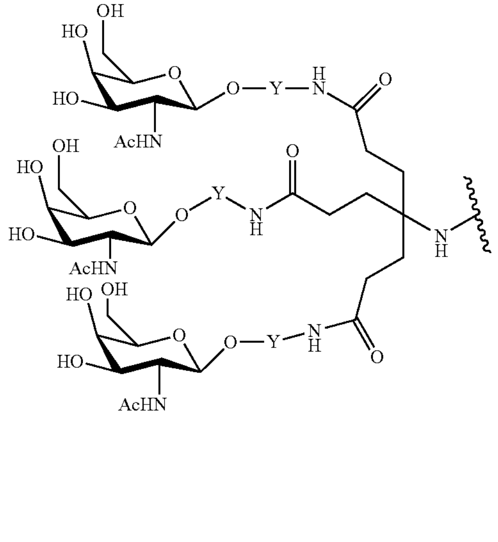

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

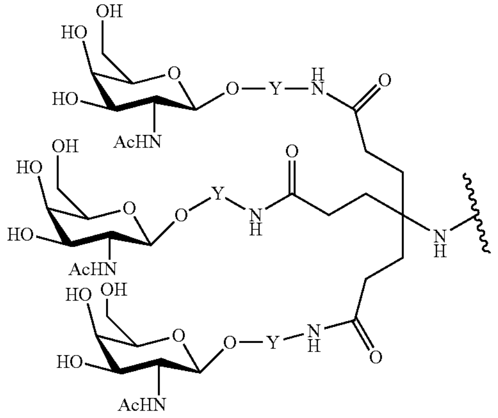

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

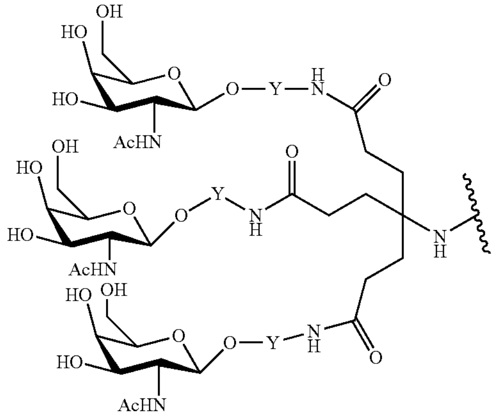

wherein Y is selected from a $C_1$-$C_{12}$ substituted or unsubstituted alkyl group.

In certain such embodiments, the cell-targeting moiety of the conjugate group has the following structure:

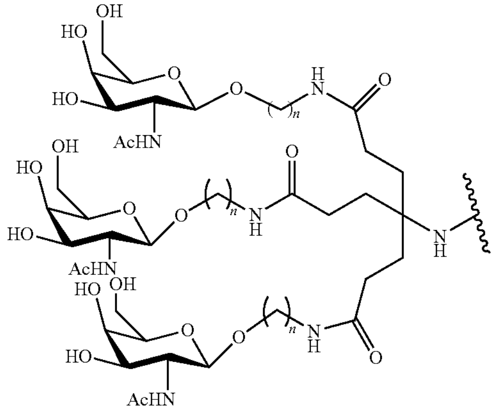

Wherein n is 1, 2, 3, 4, 5, 6, 7, 8, 9, 10, 11, or 12.

In certain such embodiments, the cell-targeting moiety of the conjugate group has the following structure:

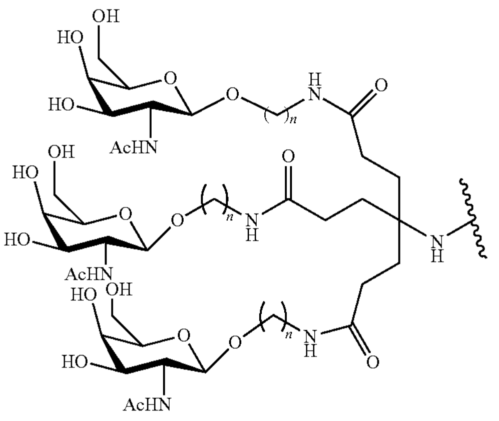

wherein n is 4, 5, 6, 7, or 8.

b. Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

A-B-C-D-(-E-F)$_q$ wherein
A is the antisense oligonucleotide;
B is the cleavable moiety
C is the conjugate linker
D is the branching group
each E is a tether;
each F is a ligand; and
q is an integer between 1 and 5.

In certain embodiments, a conjugated antisense compound has the following structure:

A-C-D-(-E-F)$_q$ wherein
A is the antisense oligonucleotide;
C is the conjugate linker
D is the branching group
each E is a tether;
each F is a ligand; and
q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

A-B-C-(-E-F)$_q$ wherein
A is the antisense oligonucleotide;
B is the cleavable moiety
C is the conjugate linker
each E is a tether;
each F is a ligand; and
q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

A-C-(-E-F)$_q$ wherein
A is the antisense oligonucleotide;
C is the conjugate linker
each E is a tether;
each F is a ligand; and
q is an integer between 1 and 5.

In certain embodiments, a conjugated antisense compound has the following structure:

A-B-D-(-E-F)$_q$ wherein
A is the antisense oligonucleotide;
B is the cleavable moiety
D is the branching group
each E is a tether;
each F is a ligand; and
q is an integer between 1 and 5.

In certain embodiments, a conjugated antisense compound has the following structure:

A-D-(-E-F)$_q$ wherein
A is the antisense oligonucleotide;
D is the branching group
each E is a tether;
each F is a ligand; and
q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:

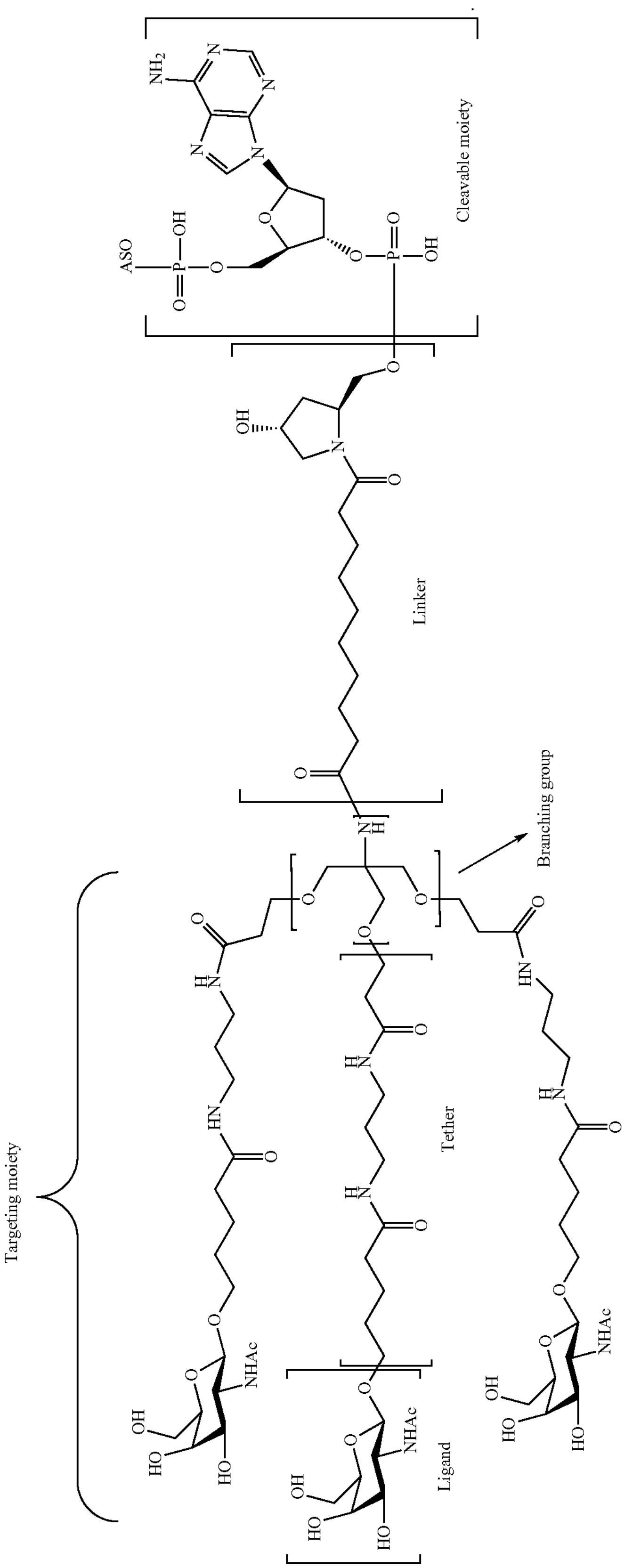
Cleavable moiety
Linker
Branching group
Targeting moiety
Tether
Ligand In certain embodiments, a conjugated antisense compound has a structure selected from among the following:
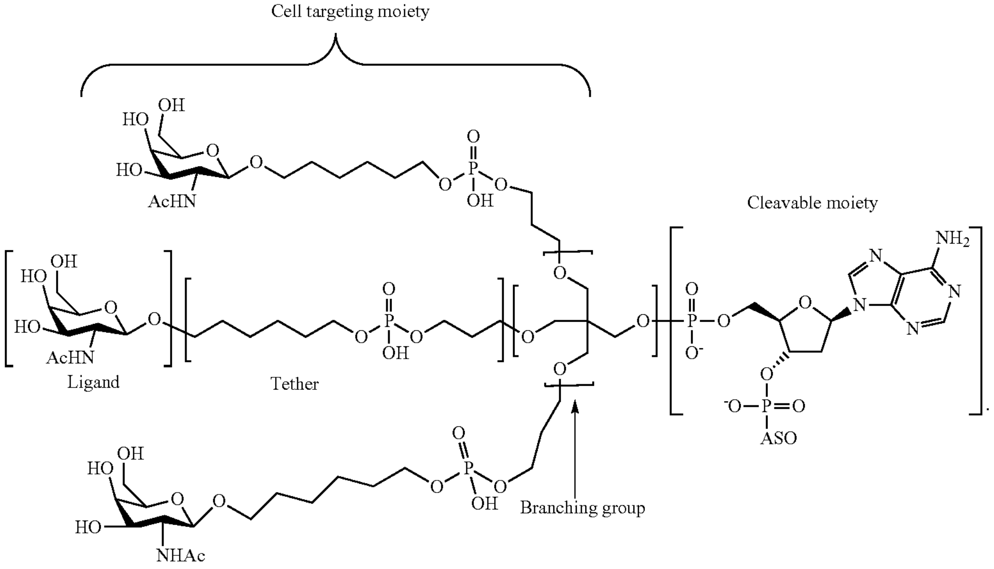
In certain embodiments, a conjugated antisense compound has a structure selected from among the following:
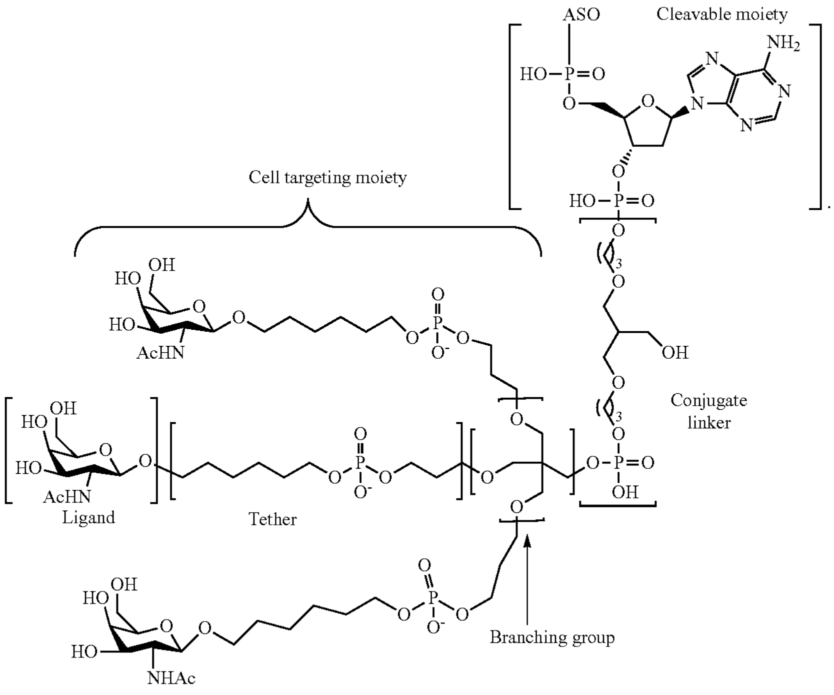

In certain embodiments, the conjugated antisense compound has the following structure:

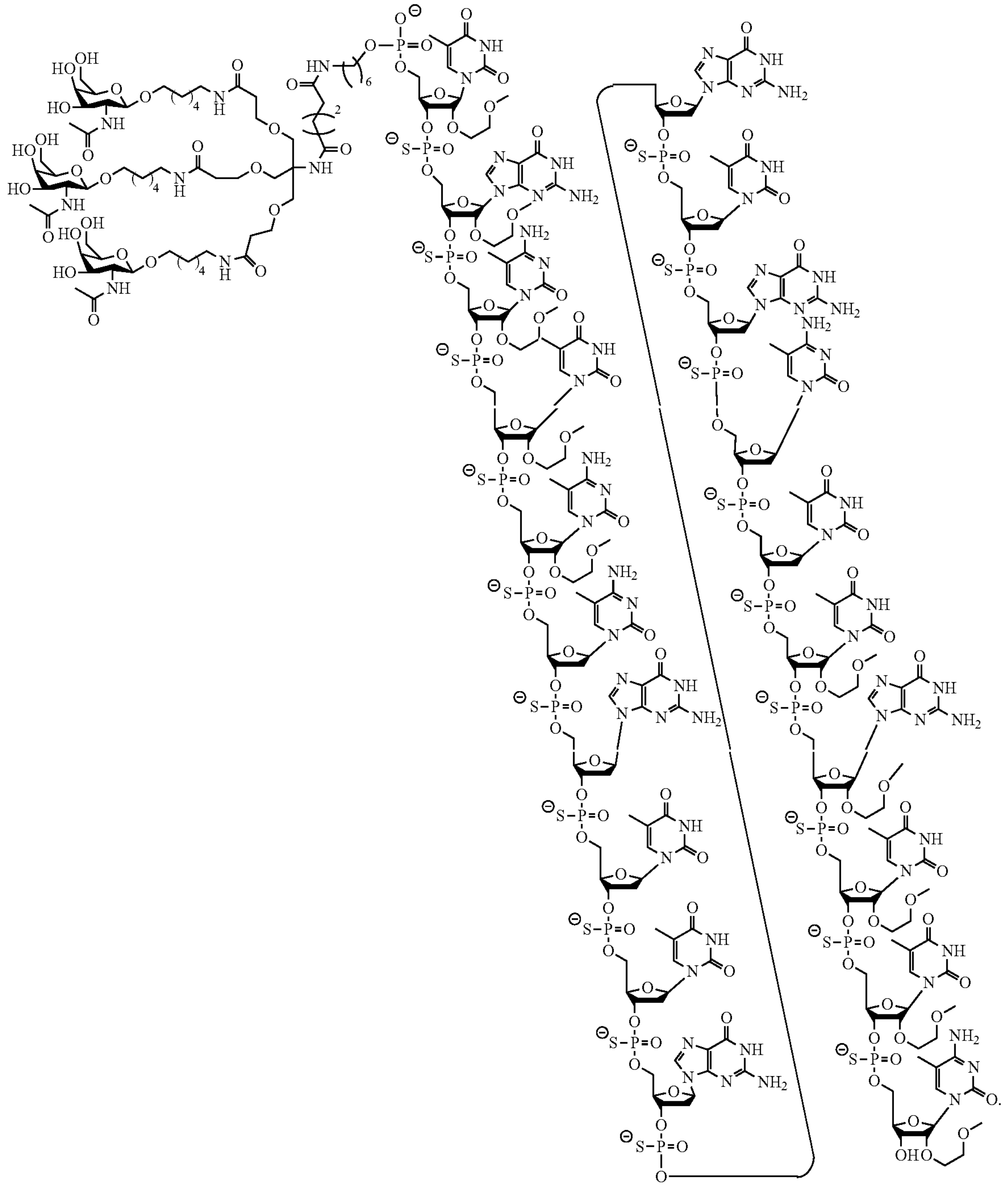

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioor ganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" *Tetrahedron,* 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., Analyt Biochem, 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, *Antisense Nucleic Acid Drug Dev,* 2002, 12, 103-128; Merwin et al., *Bioconjug Chem,* 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; U52003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

C. Certain Uses and Features

In certain embodiments, conjugated antisense compounds exhibit potent target RNA reduction in vivo. In certain embodiments, unconjugated antisense compounds accumulate in the kidney. In certain embodiments, conjugated antisense compounds accumulate in the liver. In certain embodiments, conjugated antisense compounds are well tolerated. Such properties render conjugated antisense compounds particularly useful for inhibition of many target RNAs, including, but not limited to those involved in metabolic, cardiovascular and other diseases, disorders or conditions. Thus, provided herein are methods of treating such diseases, disorders or conditions by contacting liver tissues with the conjugated antisense compounds targeted to RNAs associated with such diseases, disorders or conditions. Thus, also provided are methods for ameliorating any of a variety of metabolic, cardiovascular and other diseases, disorders or conditions with the conjugated antisense compounds of the present invention.

In certain embodiments, conjugated antisense compounds are more potent than unconjugated counterpart at a particular tissue concentration. Without wishing to be bound by any theory or mechanism, in certain embodiments, the conjugate may allow the conjugated antisense compound to enter the cell more efficiently or to enter the cell more productively. For example, in certain embodiments conjugated antisense compounds may exhibit greater target reduction as compared to its unconjugated counterpart wherein both the conjugated antisense compound and its unconjugated counterpart are present in the tissue at the same concentrations. For example, in certain embodiments conjugated antisense compounds may exhibit greater target reduction as compared to its unconjugated counterpart wherein both the conjugated antisense compound and its unconjugated counterpart are present in the liver at the same concentrations.

Productive and non-productive uptake of oligonucleotides has been discussed previously (See e.g. Geary, R. S., E. Wancewicz, et al. (2009). "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. 78(3): 284-91; & Koller, E., T. M. Vincent, et al. (2011). "Mechanisms of single-stranded phosphorothioate modified antisense oligonucleotide accumulation in hepatocytes." Nucleic Acids Res. 39(11): 4795-807). Conjugate groups described herein may improve productive uptake.

In certain embodiments, the conjugate groups described herein may further improve potency by increasing the affinity of the conjugated antisense compound for a particular type of cell or tissue. In certain embodiments, the conjugate groups described herein may further improve potency by increasing recognition of the conjugated antisense compound by one or more cell-surface receptors. In certain embodiments, the conjugate groups described herein may further improve potency by facilitating endocytosis of the conjugated antisense compound.

In certain embodiments, the cleavable moiety may further improve potency by allowing the conjugate to be cleaved from the antisense oligonucleotide after the conjugated antisense compound has entered the cell. Accordingly, in certain embodiments, conjugated antisense compounds can be administered at doses lower than would be necessary for unconjugated antisense oligonucleotides.

Phosphorothioate linkages have been incorporated into antisense oligonucleotides previously. Such phosphorothioate linkages are resistant to nucleases and so improve stability of the oligonucleotide. Further, phosphorothioate linkages also bind certain proteins, which results in accumulation of antisense oligonucleotide in the liver. Oligonucleotides with fewer phosphorothioate linkages accumulate less in the liver and more in the kidney (see, for example, Geary, R., "Pharmacokinetic Properties of 2'-O-(2-Methoxyethyl)-Modified Oligonucleotide Analogs in Rats," *Journal of Pharmacology and Experimental Therapeutics*, Vol. 296, No. 3, 890-897; & *Pharmacological Properties of* 2'-*O-Methoxyethyl Modified Oligonucleotides* in Antisense a Drug Technology, Chapter 10, Crooke, S. T., ed., 2008) In certain embodiments, oligonucleotides with fewer phosphorothioate internucleoside linkages and more phosphodiester internucleoside linkages accumulate less in the liver and more in the kidney. When treating diseases in the liver, this is undesirable for several reasons (1) less drug is getting to the site of desired action (liver); (2) drug is escaping into the urine; and (3) the kidney is exposed to relatively high concentration of drug which can result in toxicities in the kidney. Thus, for liver diseases, phosphorothioate linkages provide important benefits.

In certain embodiments, however, administration of oligonucleotides uniformly linked by phosphoro-thioate internucleoside linkages induces one or more proinflammatory reactions. (see for example: *J Lab Clin Med.* 1996 September; 128(3):329-38. "Amplification of antibody production by phosphorothioate oligodeoxynucleotides". Branda et al.; and see also for example: *Toxicologic Properties* in Antisense a Drug Technology, Chapter 12, pages 342-351, Crooke, S. T., ed., 2008). In certain embodiments, administration of oligonucleotides wherein most of the internucleoside linkages comprise phosphorothioate internucleoside linkages induces one or more proinflammatory reactions.

In certain embodiments, the degree of proinflammatory effect may depend on several variables (e.g. backbone modification, off-target effects, nucleobase modifications, and/or nucleoside modifications) see for example: *Toxicologic Properties* in Antisense a Drug Technology, Chapter 12, pages 342-351, Crooke, S. T., ed., 2008). In certain embodiments, the degree of proinflammatory effect may be mitigated by adjusting one or more variables. For example the degree of proinflammatory effect of a given oligonucleotide may be mitigated by replacing any number of phosphorothioate internucleoside linkages with phosphodiester internucleoside linkages and thereby reducing the total number of phosphorothioate internucleoside linkages.

In certain embodiments, it would be desirable to reduce the number of phosphorothioate linkages, if doing so could be done without losing stability and without shifting the distribution from liver to kidney. For example, in certain embodiments, the number of phosphorothioate linkages may be reduced by replacing phosphorothioate linkages with phosphodiester linkages. In such an embodiment, the antisense compound having fewer phosphorothioate linkages and more phosphodiester linkages may induce less proinflammatory reactions or no proinflammatory reaction. Although the antisense compound having fewer phosphorothioate linkages and more phosphodiester linkages may induce fewer proinflammatory reactions, the antisense compound having fewer phosphorothioate linkages and more phosphodiester linkages may not accumulate in the liver and may be less efficacious at the same or similar dose as compared to an antisense compound having more phosphorothioate linkages. In certain embodiments, it is therefore desirable to design an antisense compound that has a plurality of phosphodiester bonds and a plurality of phosphorothioate bonds but which also possesses stability and good distribution to the liver.

In certain embodiments, conjugated antisense compounds accumulate more in the liver and less in the kidney than unconjugated counterparts, even when some of the phosporothioate linkages are replaced with less proinflammatory phosphodiester internucleoside linkages. In certain embodiments, conjugated antisense compounds accumulate more in the liver and are not excreted as much in the urine compared to its unconjugated counterparts, even when some of the phosporothioate linkages are replaced with less proinflammatory phosphodiester internucleoside linkages. In certain embodiments, the use of a conjugate allows one to design more potent and better tolerated antisense drugs. Indeed, in certain embodiments, conjugated antisense compounds have larger therapeutic indexes than unconjugated counterparts. This allows the conjugated antisense compound to be administered at a higher absolute dose, because there is less risk of proinflammatory response and less risk of kidney toxicity. This higher dose, allows one to dose less frequently, since the clearance (metabolism) is expected to be similar. Further, because the compound is more potent, as described above, one can allow the concentration to go lower before the next dose without losing therapeutic activity, allowing for even longer periods between dosing.

In certain embodiments, the inclusion of some phosphorothioate linkages remains desirable. For example, the terminal linkages are vulnerable to exonucleoases and so in certain embodiments, those linkages are phosphorothioate or other modified linkage. Internucleoside linkages linking two deoxynucleosides are vulnerable to endonucleases and so in certain embodiments those linkages are phosphorothioate or other modified linkage. Internucleoside linkages between a modified nucleoside and a deoxynucleoside where the deoxynucleoside is on the 5' side of the linkage deoxynucleosides are vulnerable to endonucleases and so in certain embodiments those linkages are phosphorothioate or other modified linkage.

Internucleoside linkages between two modified nucleosides of certain types and between a deoxynucleoside and a modified nucleoside of certain type where the modified nucleoside is at the 5' side of the linkage are sufficiently resistant to nuclease digestion, that the linkage can be phosphodiester.

In certain embodiments, the antisense oligonucleotide of a conjugated antisense compound comprises fewer than 16 phosphorthioate linkages. In certain embodiments, the antisense oligonucleotide of a conjugated antisense compound comprises fewer than 15 phosphorthioate linkages. In certain embodiments, the antisense oligonucleotide of a conjugated antisense compound comprises fewer than 14 phosphorthioate linkages. In certain embodiments, the antisense oligonucleotide of a conjugated antisense compound comprises fewer than 13 phosphorthioate linkages. In certain embodiments, the antisense oligonucleotide of a conjugated antisense compound comprises fewer than 12 phosphorthioate linkages. In certain embodiments, the antisense oligonucleotide of a conjugated antisense compound comprises fewer than 11 phosphorthioate linkages. In certain embodiments, the antisense oligonucleotide of a conjugated antisense compound comprises fewer than 10 phosphorthioate linkages. In certain embodiments, the antisense oligonucleotide of a conjugated antisense compound comprises fewer than 9 phosphorthioate linkages. In certain embodiments, the antisense oligonucleotide of a conjugated antisense compound comprises fewer than 8 phosphorthioate linkages.

In certain embodiments, antisense compounds comprising one or more conjugate group described herein has increased activity and/or potency and/or tolerability compared to a parent antisense compound lacking such one or more conjugate group. Accordingly, in certain embodiments, attachment of such conjugate groups to an oligonucleotide is desirable. Such conjugate groups may be attached at the 5'-, and/or 3'-end of an oligonucleotide. In certain instances, attachment at the 5'-end is synthetically desirable. Typically, oligonucleotides are synthesized by attachment of the 3' terminal nucleoside to a solid support and sequential coupling of nucleosides from 3' to 5' using techniques that are well known in the art. Accordingly if a conjugate group is desired at the 3'-terminus, one may (1) attach the conjugate group to the 3'-terminal nucleoside and attach that conjugated nucleoside to the solid support for subsequent preparation of the oligonucleotide or (2) attach the conjugate group to the 3'-terminal nucleoside of a completed oligonucleotide after synthesis. Neither of these approaches is very efficient and thus both are costly. In particular, attachment of the conjugated nucleoside to the solid support, while demonstrated in the Examples herein, is an inefficient process. In certain embodiments, attaching a conjugate group to the 5'-terminal nucleoside is synthetically easier than attachment at the 3'-end. One may attach a non-conjugated 3' terminal nucleoside to the solid support and prepare the oligonucleotide using standard and well characterized reactions. One then needs only to attach a 5'nucleoside having a conjugate group at the final coupling step. In certain embodiments, this is more efficient than attaching a conjugated nucleoside directly to the solid support as is typically done to prepare a 3'-conjugated oligonucleotide. The Examples herein demonstrate attachment at the 5'-end. In addition, certain conjugate groups have synthetic advantages. For Example, certain conjugate groups comprising phosphorus linkage groups are synthetically simpler and more efficiently prepared than other conjugate groups, including conjugate groups reported previously (e.g., WO/2012/037254).

In certain embodiments, conjugated antisense compounds are administered to a subject. In such embodiments, antisense compounds comprising one or more conjugate group described herein has increased activity and/or potency and/or tolerability compared to a parent antisense compound lacking such one or more conjugate group. Without being bound by mechanism, it is believed that the conjugate group helps with distribution, delivery, and/or uptake into a target cell or tissue. In certain embodiments, once inside the target cell or tissue, it is desirable that all or part of the conjugate group to be cleaved to release the active oligonucleotide. In certain embodiments, it is not necessary that the entire conjugate group be cleaved from the oligonucleotide. For example, in Example 20 a conjugated oligonucleotide was administered to mice and a number of different chemical species, each comprising a different portion of the conjugate group remaining on the oligonucleotide, were detected (Table 23a). This conjugated antisense compound demonstrated good potency (Table 23). Thus, in certain embodiments, such metabolite profile of multiple partial cleavage of the conjugate group does not interfere with activity/potency. Nevertheless, in certain embodiments it is desirable that a prodrug (conjugated oligonucleotide) yield a single active compound. In certain instances, if multiple forms of the active compound are found, it may be necessary to determine relative amounts and activities for each one. In certain embodiments where regulatory review is required (e.g., USFDA or counterpart) it is desirable to have a single (or predominantly single) active species. In certain such embodiments, it is desirable that such single active species be the antisense oligonucleotide lacking any portion of the conjugate group. In certain embodiments, conjugate groups at the 5'-end are more likely to result in complete metabolism of the conjugate group. Without being bound by mechanism it may be that endogenous enzymes responsible for metabolism at the 5' end (e.g., 5' nucleases) are more active/efficient than the 3' counterparts. In certain embodiments, the specific conjugate groups are more amenable to metabolism to a single active species. In certain embodiments, certain conjugate groups are more amenable to metabolism to the oligonucleotide.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, oligonucleotides comprising conjugates described herein are RNAi compounds. In certain embodiments, oligomeric oligonucleotides comprising conjugates described herein are ssRNA compounds. In certain embodiments, oligonucleotides comprising conjugates described herein are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligonucleotides comprising conjugates described herein is the antisense strand in an siRNA compound. In certain embodiments, the oligonucleotides comprising conjugates described herein is the sense strand in an siRNA compound. In embodiments in which the conjugated oligomeric compound is double-stranded siRnA, the conjugate may be on the sense strand, the antisense strand or both the sense strand and the antisense strand.

C. Apolipoprotein (a) (Apo(a))

In certain embodiments, conjugated antisense compounds target any apo(a) nucleic acid. In certain embodiments, the target nucleic acid encodes an apo(a) target protein that is clinically relevant. In such embodiments, modulation of the target nucleic acid results in clinical benefit.

The targeting process usually includes determination of at least one target region, segment, or site within the target nucleic acid for the antisense interaction to occur such that the desired effect will result.

In certain embodiments, a target region is a structurally defined region of the nucleic acid. For example, in certain such embodiments, a target region may encompass a 3' UTR, a 5' UTR, an exon, an intron, a coding region, a translation initiation region, translation termination region, or other defined nucleic acid region or target segment.

In certain embodiments, a target segment is at least about an 8-nucleobase portion of a target region to which a conjugated antisense compound is targeted. Target segments can include DNA or RNA sequences that comprise at least 8 consecutive nucleobases from the 5'-terminus of one of the target segments (the remaining nucleobases being a consecutive stretch of the same DNA or RNA beginning immediately upstream of the 5'-terminus of the target segment and continuing until the DNA or RNA comprises about 8 to about 30 nucleobases). Target segments are also represented by DNA or RNA sequences that comprise at least 8 consecutive nucleobases from the 3'-terminus of one of the target segments (the remaining nucleobases being a consecutive stretch of the same DNA or RNA beginning immediately downstream of the 3'-terminus of the target segment and continuing until the DNA or RNA comprises about 8 to about 30 nucleobases). Target segments can also be represented by DNA or RNA sequences that comprise at least 8 consecutive nucleobases from an internal portion of the sequence of a target segment, and may extend in either or both directions until the conjugated antisense compound comprises about 8 to about 30 nucleobases.

In certain embodiments, antisense compounds targeted to an apo(a) nucleic acid can be modified as described herein. In certain embodiments, the antisense compounds can have a modified sugar moiety, an unmodified sugar moiety or a mixture of modified and unmodified sugar moieties as described herein. In certain embodiments, the antisense compounds can have a modified internucleoside linkage, an unmodified internucleoside linkage or a mixture of modified and unmodified internucleoside linkages as described herein. In certain embodiments, the antisense compounds can have a modified nucleobase, an unmodified nucleobase or a mixture of modified and unmodified nucleobases as described herein. In certain embodiments, the antisense compounds can have a motif as described herein.

In certain embodiments, antisense compounds targeted to apo(a) nucleic acids can be conjugated as described herein.

One apo(a) protein is linked via a disulfide bond to a single apolipoprotein B (apoB) protein to form a lipoprotein (a) (Lp(a)) particle. The apo(a) protein shares a high degree of homology with plasminogen particularly within the kringle IV type 2 repetitive domain. It is thought that the kringle repeat domain in apo(a) may be responsible for its pro-thrombotic and anti-fibrinolytic properties, potentially enhancing atherosclerotic progression. Apo(a) is transcriptionally regulated by IL-6 and in studies in rheumatoid arthritis patients treated with an IL-6 inhibitor (tocilizumab), plasma levels were reduced by 30% after 3 month treatment. Apo(a) has been shown to preferentially bind oxidized phospholipids and potentiate vascular inflammation. Further, studies suggest that the Lp(a) particle may also stimulate endothelial permeability, induce plasminogen activator inhibitor type-1 expression and activate macrophage interleukin-8 secretion. Importantly, recent genetic association studies revealed that Lp(a) was an independent risk factor for myocardial infarction, stroke, peripheral vascular disease and abdominal aortic aneurysm. Further, in the Precocious Coronary Artery Disease (PROCARDIS) study, Clarke et al. described robust and independent associations between coronary heart disease and plasma Lp(a) concentrations. Additionally, Solfrizzi et al., suggested that increased serum Lp(a) may be linked to an increased risk for Alzheimer's Disease (AD). Antisense compounds targeting apo(a) have been previously disclosed in WO2005/000201 and US2010-0331390, herein incorporated by reference in its entirety. An antisense oligonucleobase targeting Apo(a), ISIS-APOA$_{Rx}$, was assessed in a Phase I clinical trial to study it's safety profile.

Certain Conjugated Antisense Compounds Targeted to an Apo(a) Nucleic Acid

In certain embodiments, conjugated antisense compounds are targeted to an Apo(a) nucleic acid having the sequence of GENBANK® Accession No. NM_005577.2, incorporated herein as SEQ ID NO: 1; GENBANK Accession No. NT_007422.12 truncated from nucleotides 3230000 to 3380000, incorporated herein as SEQ ID NO: 2; GENBANK Accession No. NT_025741.15 truncated from nucleotides 65120000 to 65258000, designated herein as SEQ ID NO: 3; and GENBANK Accession No. NM_005577.1, incorporated herein as SEQ ID NO: 4. In certain such embodiments, a conjugated antisense compound is at least 90%, at least 95%, or 100% complementary to any of the nucleobase sequences of SEQ ID NOs: 1-4.

In certain embodiments, a conjugated antisense compound targeted to any of the nucleobase sequences of SEQ ID NOs: 1-4 comprises an at least 8 consecutive nucleobase sequence selected from the nucleobase sequence of any of SEQ ID NOs: 12-130, 133, 134. In certain embodiments, a conjugated antisense compound targeted to any of SEQ ID NOs: 1-4 comprises a nucleobase sequence selected from the nucleobase sequence of any of SEQ ID NOs: 12-130, 133, 134.

TABLE A

Antisense Compounds targeted to Apo(a) SEQ ID NO: 1

| ISIS No | Target Start Site | Sequence (5'-3') | Motif | SEQ ID NO |
|---|---|---|---|---|
| 494372 | 3901 | TGCTCCGTTGGTGCTTGTTC | eeeeeddddddddddeeeee | 58 |
| 494283 | 584<br>926<br>1610<br>1952<br>2294<br>3320 | TCTTCCTGTGACAGTGGTGG | eeeeeddddddddddeeeee | 26 |
| 494284 | 585<br>927<br>1611<br>1953<br>2295<br>3321 | TTCTTCCTGTGACAGTGGTG | eeeeeddddddddddeeeee | 27 |
| 494286 | 587<br>929<br>1613<br>1955<br>2297 | GGTTCTTCCTGTGACAGTGG | eeeeeddddddddddeeeee | 29 |
| 494301 | 628<br>970<br>1312<br>1654<br>1996<br>2338<br>2680<br>3022 | CGACTATGCGAGTGTGGTGT | eeeeeddddddddddeeeee | 38 |
| 494302 | 629<br>971<br>1313<br>1655<br>1997<br>2339<br>2681<br>3023 | CCGACTATGCGAGTGTGGTG | eeeeeddddddddddeeeee | 39 |

Apo(a) Therapeutic Indications

In certain embodiments, the invention provides methods for using a conjugated antisense compound targeted to an apo(a) nucleic acid for modulating the expression of apo(a) in a subject. In certain embodiments, the expression of apo(a) is reduced.

In certain embodiments, provided herein are methods of treating a subject comprising administering one or more pharmaceutical compositions as described herein. In certain embodiments, the invention provides methods for using a conjugated antisense compound targeted to an apo(a) nucleic acid in a pharmaceutical composition for treating a subject. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the subject has an inflammatory, cardiovascular and/or metabolic disease, disorder or condition.

In certain embodiments, the cardiovascular diseases, disorders or conditions include, but are not limited to, aortic stenosis, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administration of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, aortic stenosis, coronary artery disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by at least about 5%, 10%, 15%, 20%, 25%, 30%, 35%, 40%, 45%, 50%, 55%, 60%, 65%, 70%, 75%, 80%, 85%, 90%, 95% or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, apo(a) expression is reduced to at least ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, Lp(a) expression is reduced to at least ≤200 mg/dL, ≤190 mg/dL, ≤180 mg/dL, ≤175 mg/dL, ≤170 mg/dL, ≤160 mg/dL, ≤150 mg/dL, ≤140 mg/dL, ≤130 mg/dL, ≤120 mg/dL, ≤110 mg/dL, ≤100 mg/dL, ≤90 mg/dL, ≤80 mg/dL, ≤70 mg/dL, ≤60 mg/dL, ≤55 mg/dL, ≤50 mg/dL, ≤45 mg/dL, ≤40 mg/dL, ≤35 mg/dL, ≤30 mg/dL, ≤25 mg/dL, ≤20 mg/dL, ≤15 mg/dL, or ≤10 mg/dL.

In certain embodiments, the invention provides methods for using a conjugated antisense compound targeted to an apo(a) nucleic acid in the preparation of a medicament. In certain embodiments, pharmaceutical compositions comprising a conjugated antisense compound targeted to apo(a) are used for the preparation of a medicament for treating a patient suffering or susceptible to an inflammatory, cardiovascular and/or a metabolic disease, disorder or condition.

Apo(a) Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has apo(a) levels ≥10 mg/dL, ≥20 mg/dL, ≥30 mg/dL, ≥40 mg/dL, ≥50 mg/dL, ≥60 mg/dL, ≥70 mg/dL, ≥80 mg/dL, ≥90 mg/dL or ≥100 mg/dL. In certain embodiments, the human has Lp(a) levels ≥10 mg/dL, ≥15 mg/dL, ≥20 mg/dL, ≥25 mg/dL, ≥30 mg/dL, ≥35 mg/dL, ≥40 mg/dL, ≥50 mg/dL, ≥60 mg/dL, ≥70 mg/dL, ≥80 mg/dL, ≥90 mg/dL, ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥175 mg/dL, ≥180 mg/dL, ≥190 mg/dL, ≥200 mg/dL.

D. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: General Method for the Preparation of Phosphoramidites, Compounds 1, 1a and 2

1

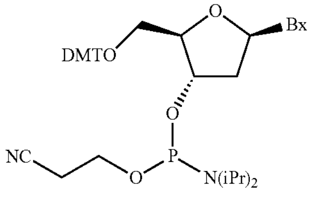

-continued

1a

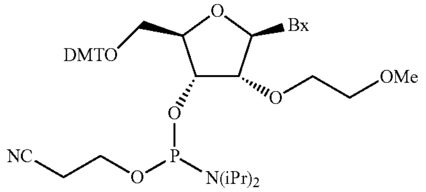

2

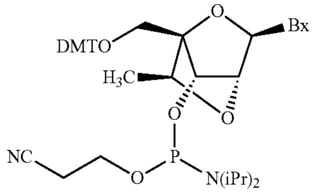

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7

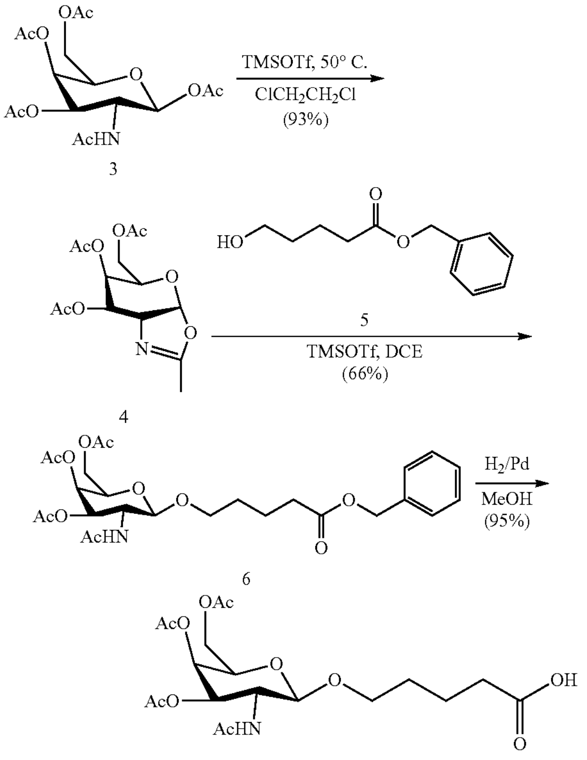

3

4

6

7

Compounds 3 (2-acetamido-1,3,4,6-tetra-O-acetyl-2-deoxy-β-Dgalactopyranose or galactosamine pentaacetate) is commercially available. Compound 5 was prepared according to published procedures (Weber et al., *J. Med. Chem.*, 1991, 34, 2692).

Example 3: Preparation of Compound 11
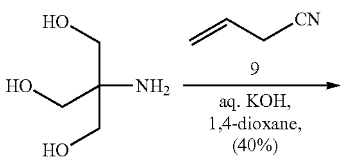
8
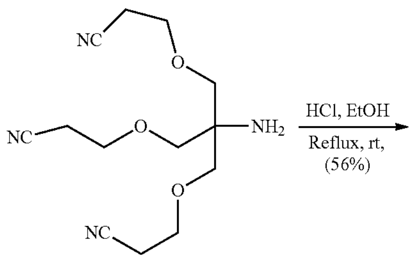
10
-continued
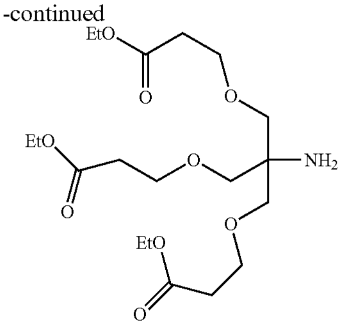
11
Compounds 8 and 9 are commercially available.
Example 4: Preparation of Compound 18
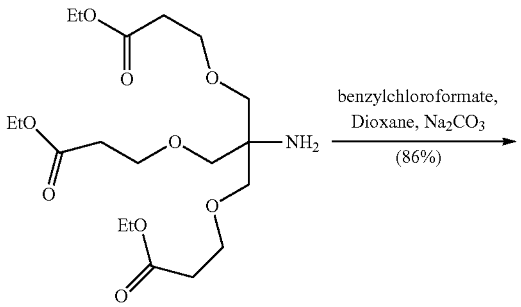
11
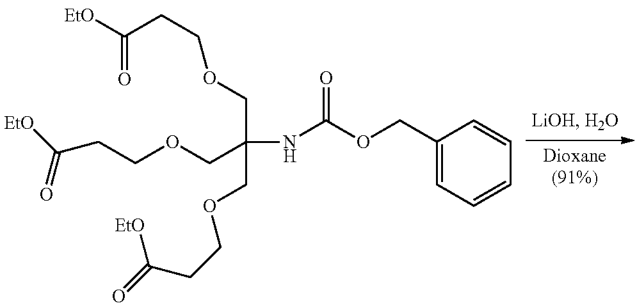
12
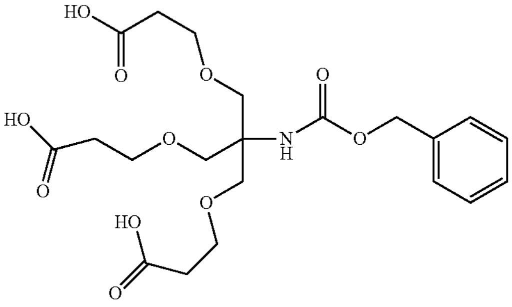
13
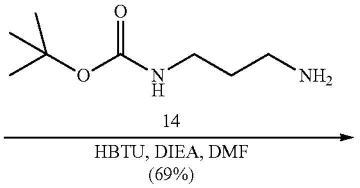
14
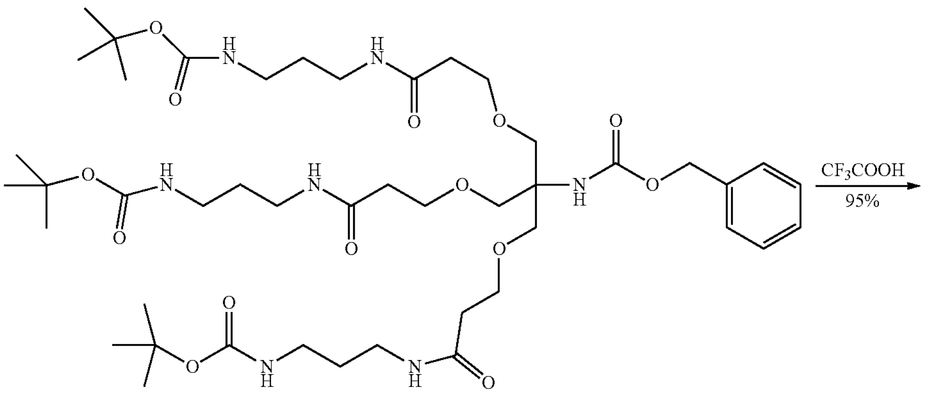
15

-continued
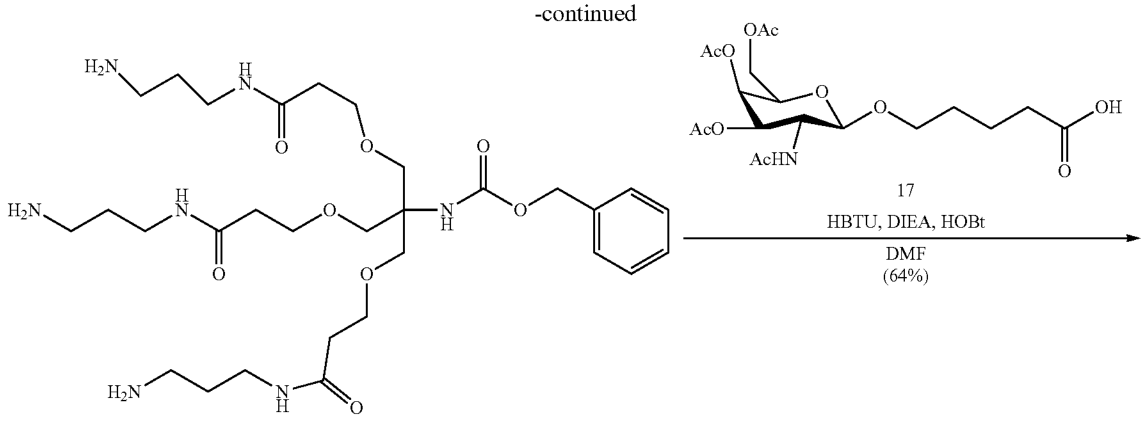
17
16
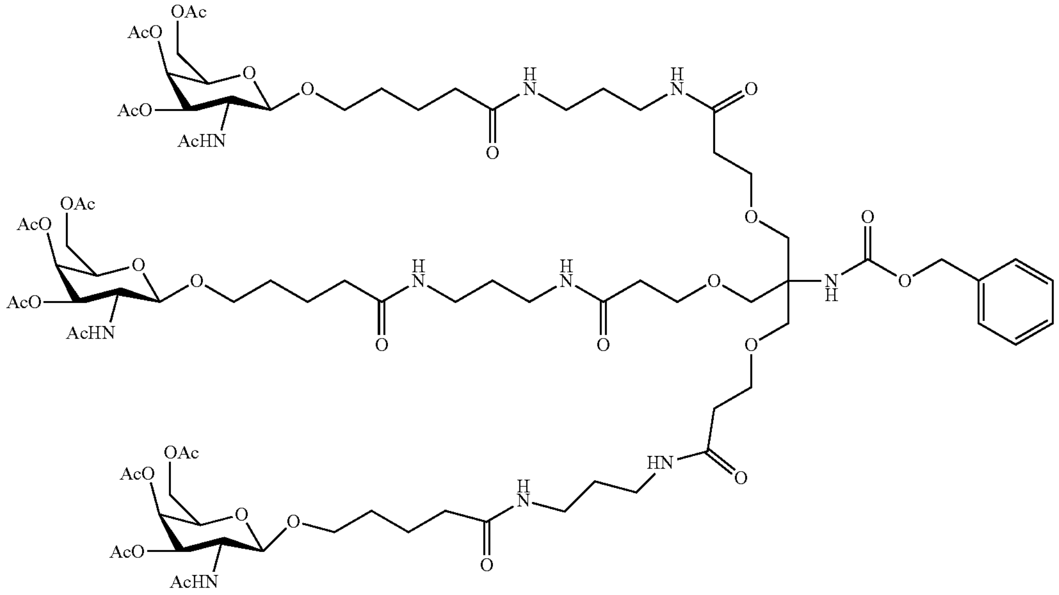
18
Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5: Preparation of Compound 23
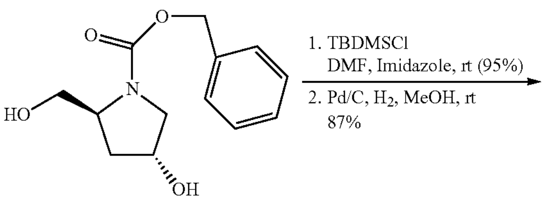
19
-continued
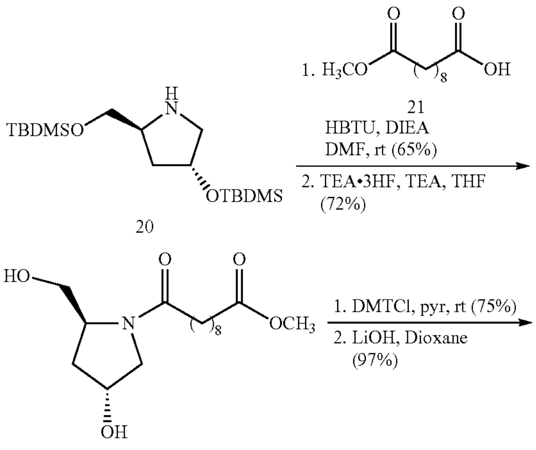
21
20
22

-continued
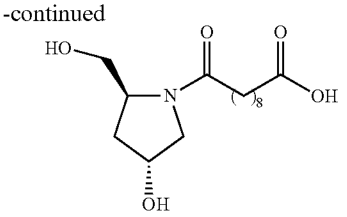
23
Compounds 19 and 21 are commercially available.
Example 6: Preparation of Compound 24
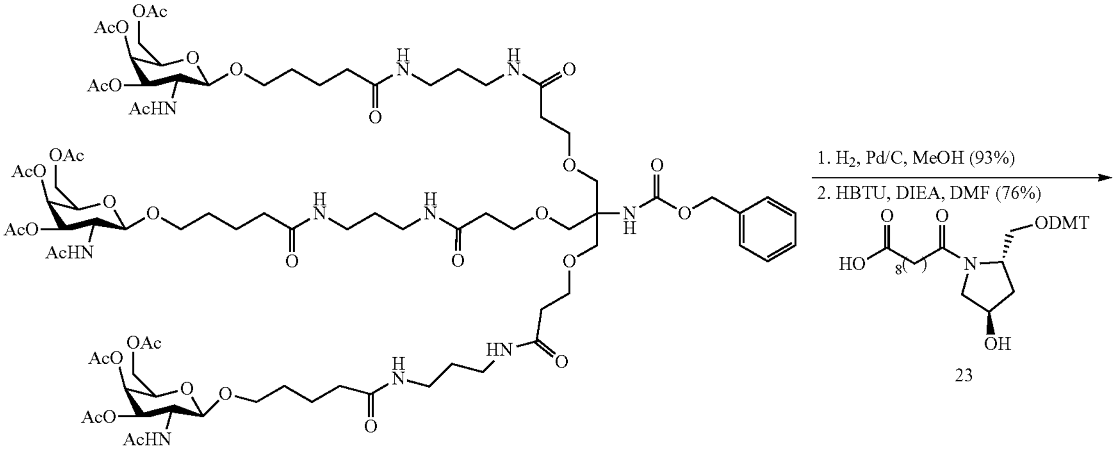
18
23
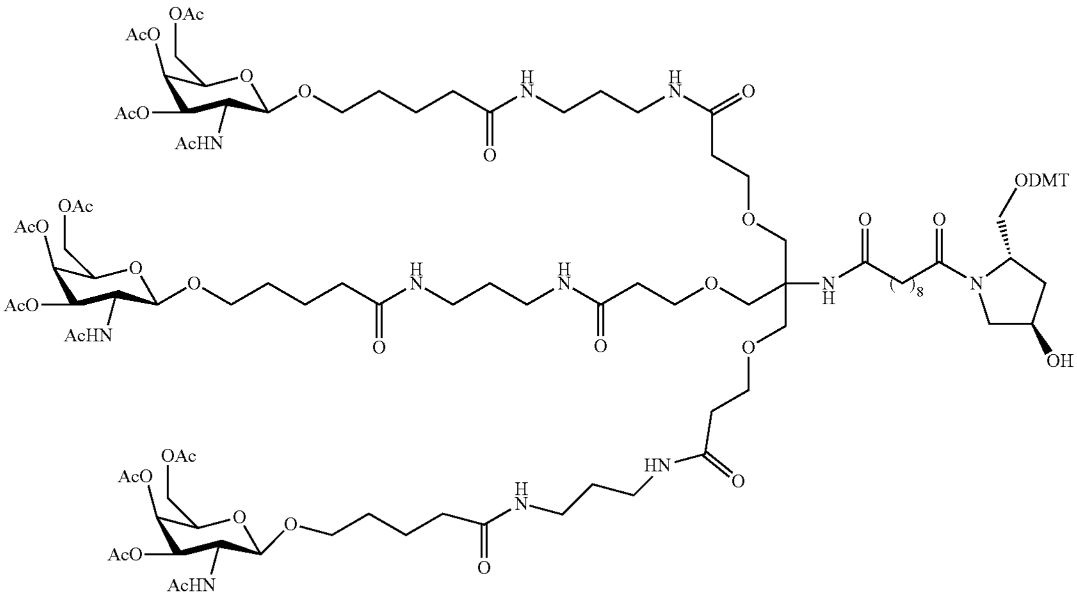
24
Compounds 18 and 23 were prepared as per the procedures illustrated in Examples 4 and 5.

Example 7: Preparation of Compound 25
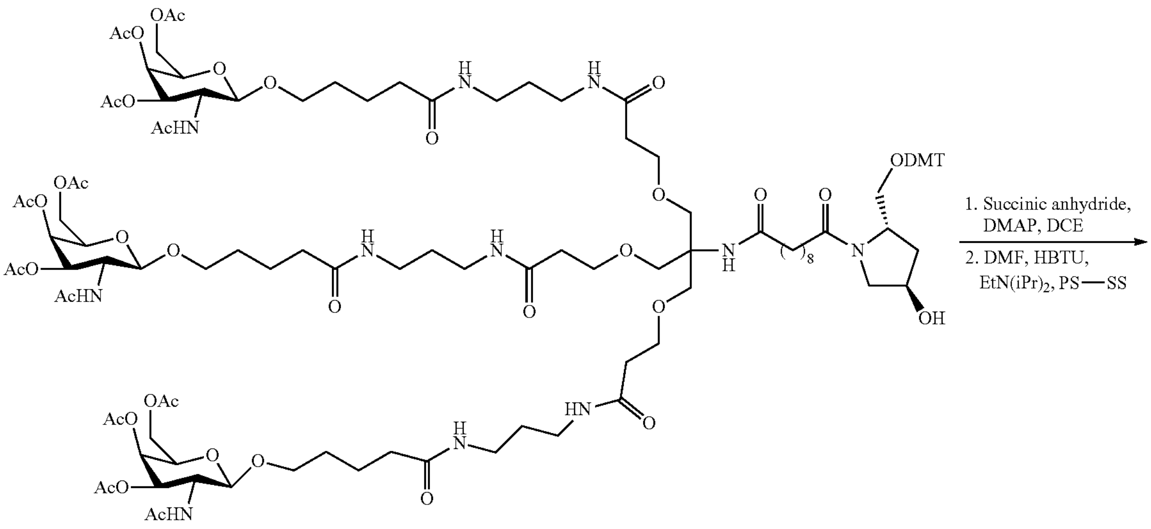
24
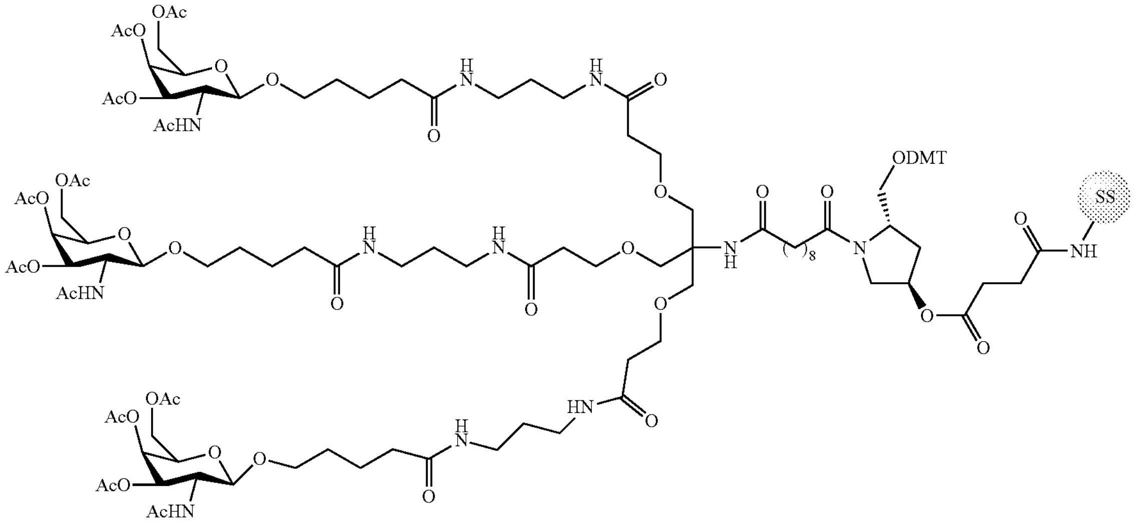
25
Compound 24 was prepared as per the procedures illustrated in Example 6.

Example 8: Preparation of Compound 26
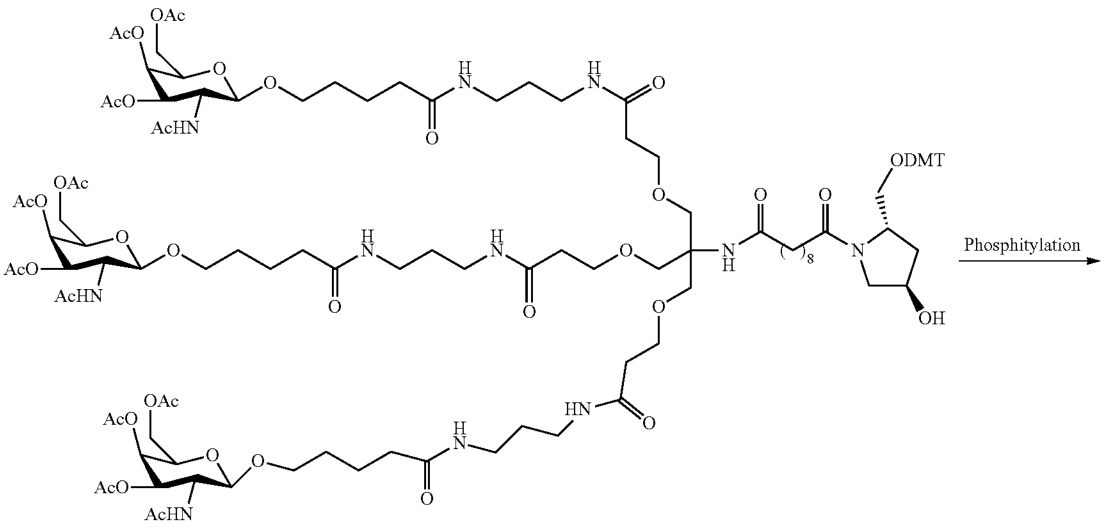
24
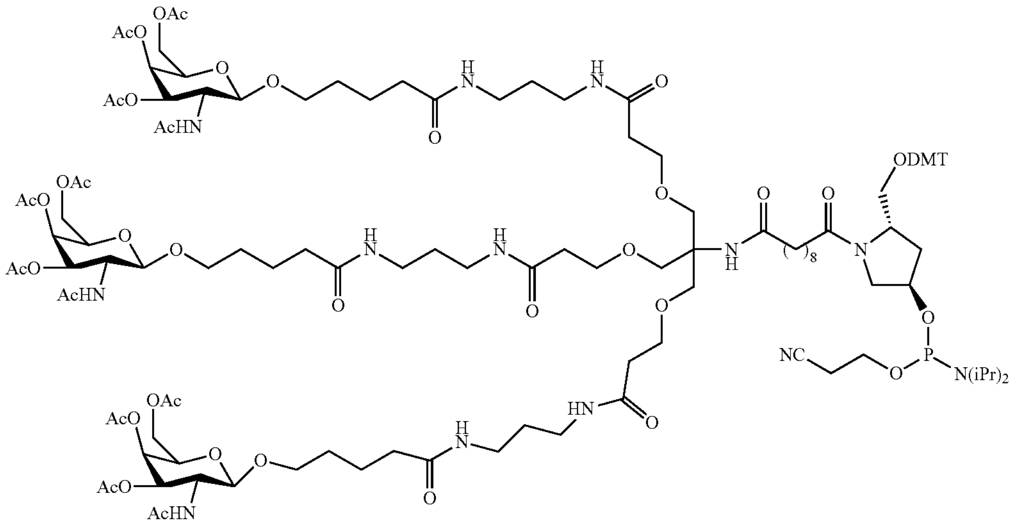
26
Compound 24 is prepared as per the procedures illustrated in Example 6.

Example 9: General Preparation of Conjugated ASOs Comprising GalNAc$_3$-1 at the 3' Terminus, Compound 29
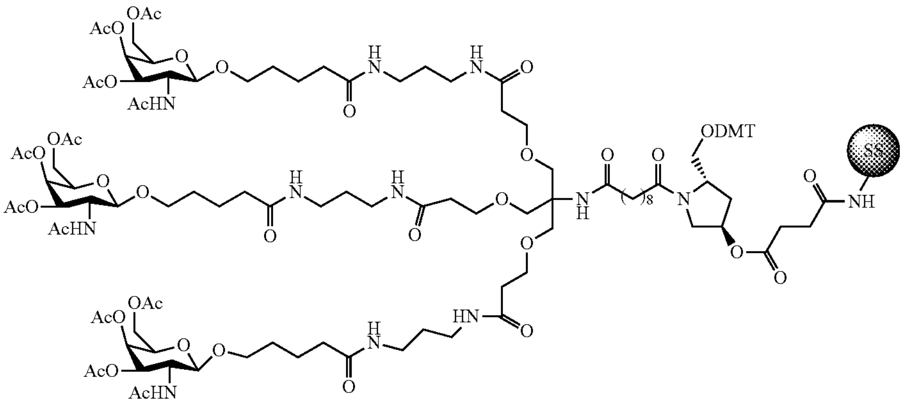
25
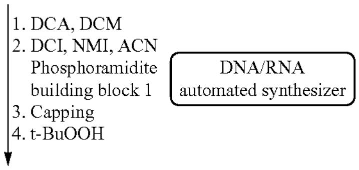
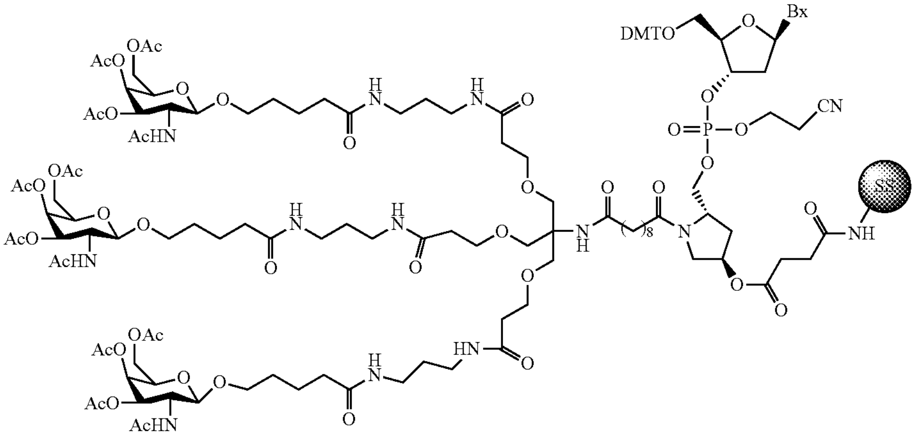
27
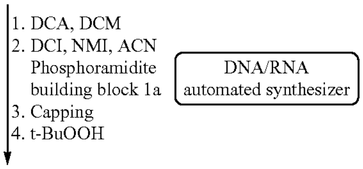

-continued
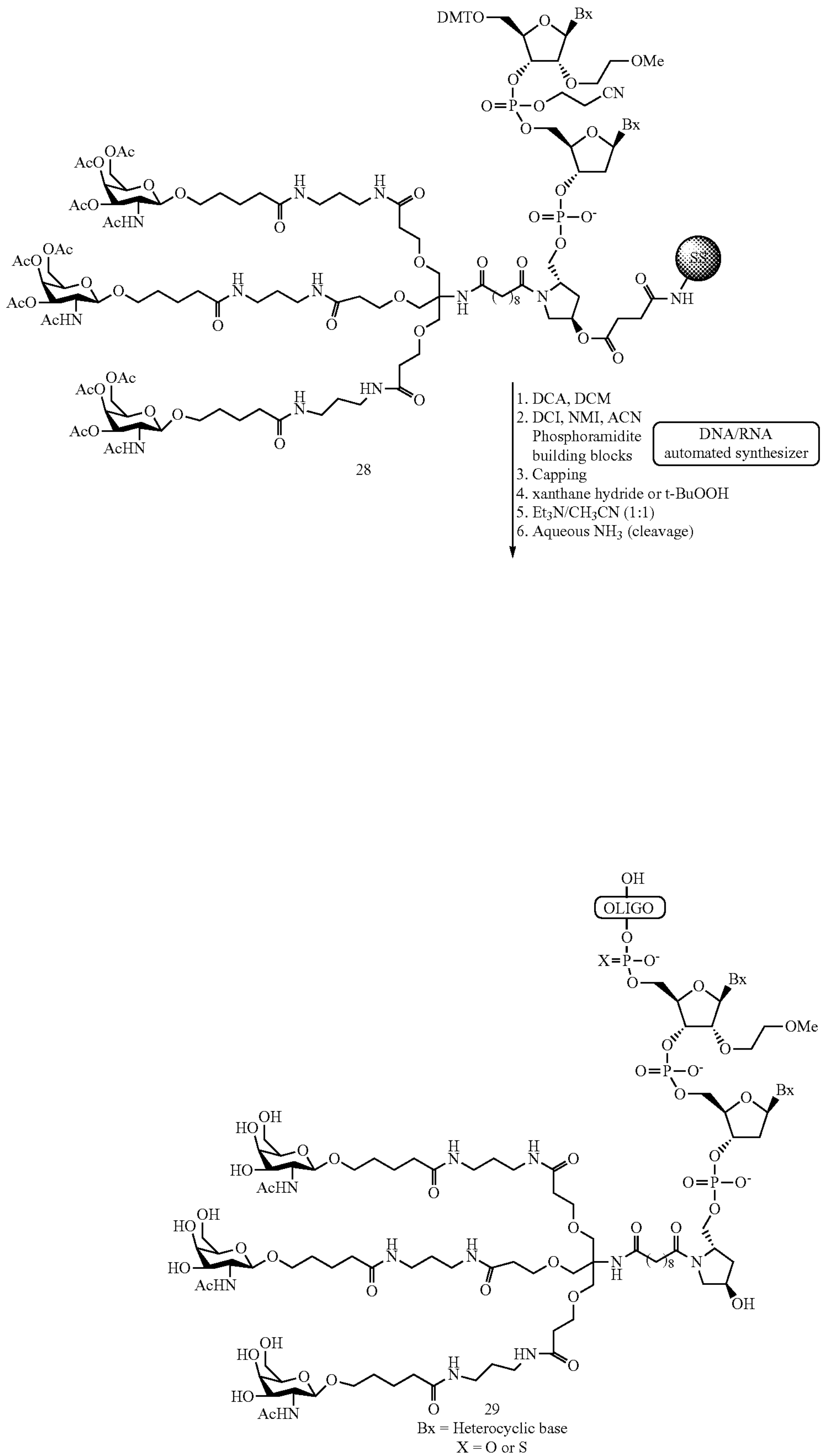
28
29
Bx = Heterocyclic base
X = O or S

Wherein the protected GalNAc$_3$-1 has the structure:

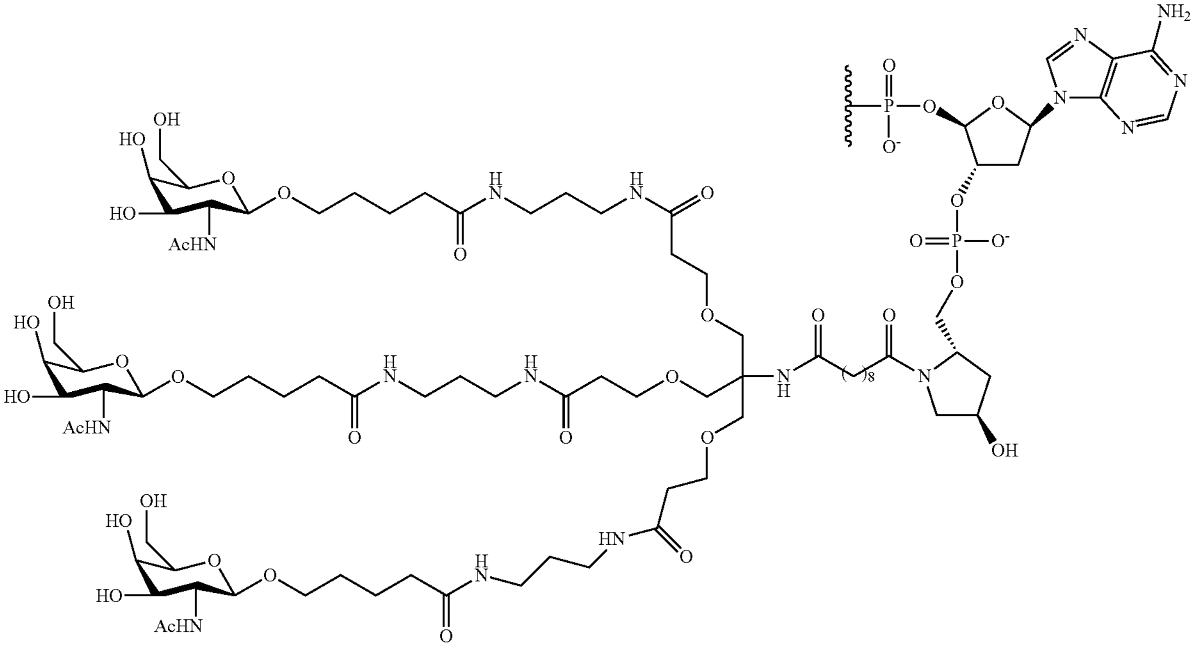

The GalNAc$_3$ cluster portion of the conjugate group GalNAc$_3$-1 (GalNAc$_3$-1$_a$) can be combined with any cleavable moiety to provide a variety of conjugate groups. Wherein GalNAc$_3$-1$_a$ has the formula:

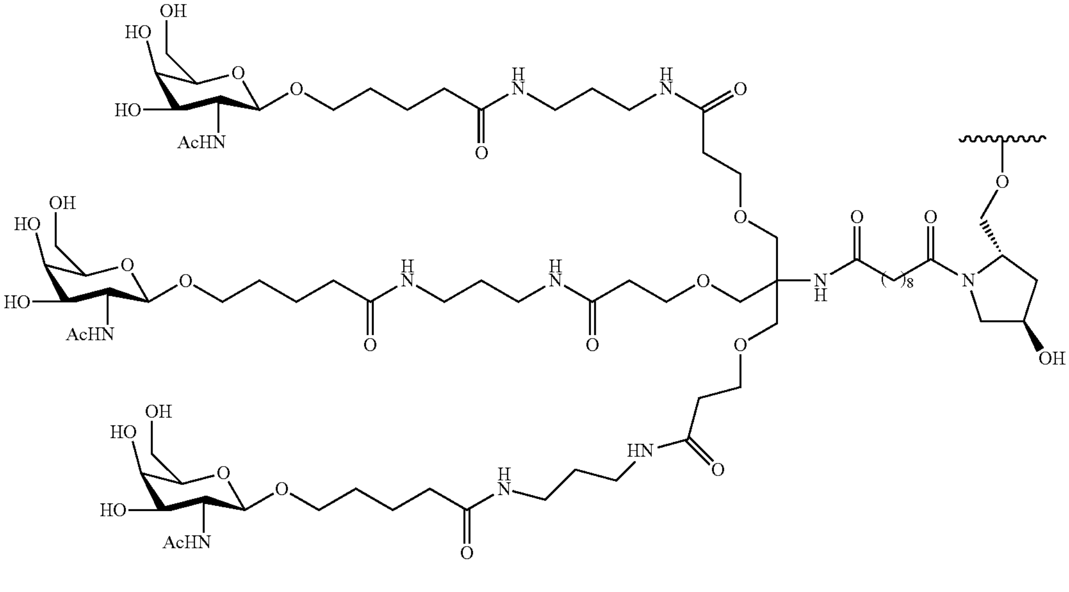

The solid support bound protected GalNAc$_3$-1, Compound 25, was prepared as per the procedures illustrated in Example 7. Oligomeric Compound 29 comprising GalNAc$_3$-1 at the 3' terminus was prepared using standard procedures in automated DNA/RNA synthesis (see Dupouy et al., *Angew. Chem. Int. Ed.,* 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: General Preparation Conjugated ASOs Comprising GalNAc$_3$-1 at the 5' Terminus, Compound 34
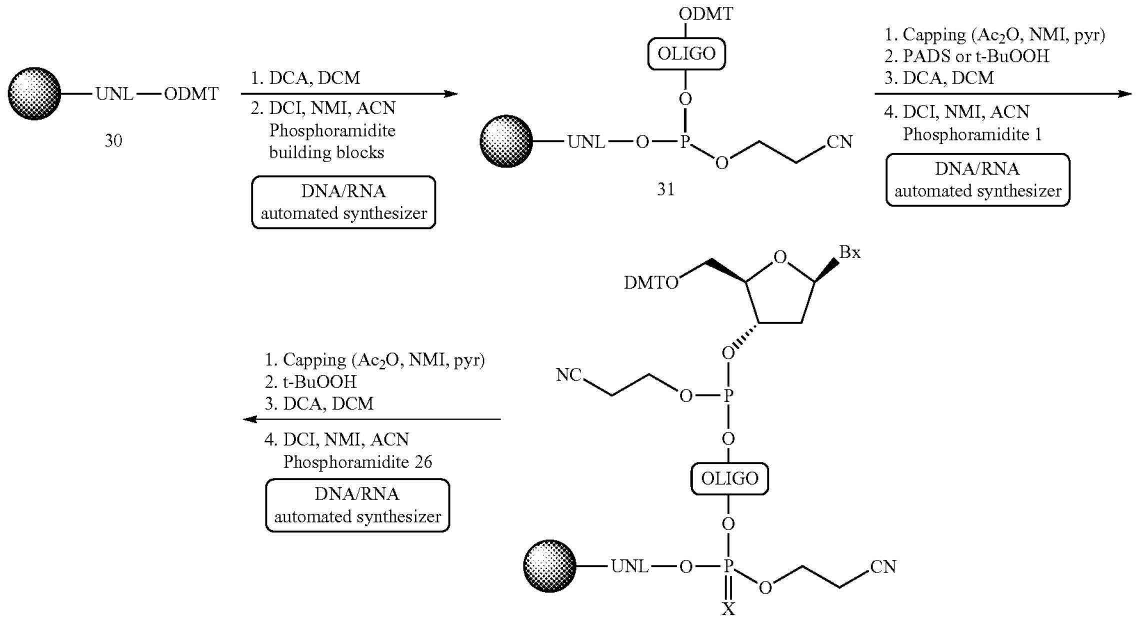
30
31
32
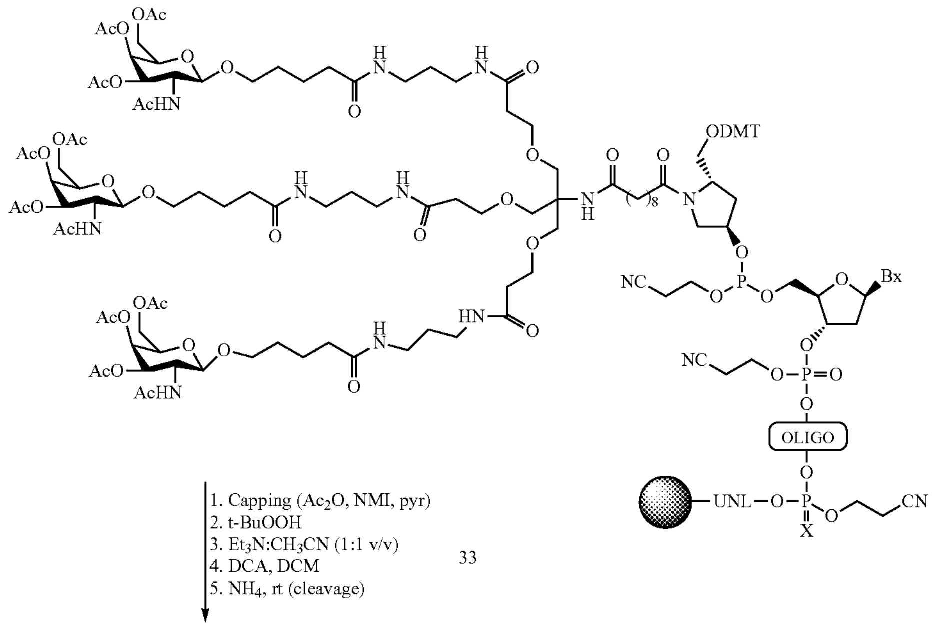
33

-continued

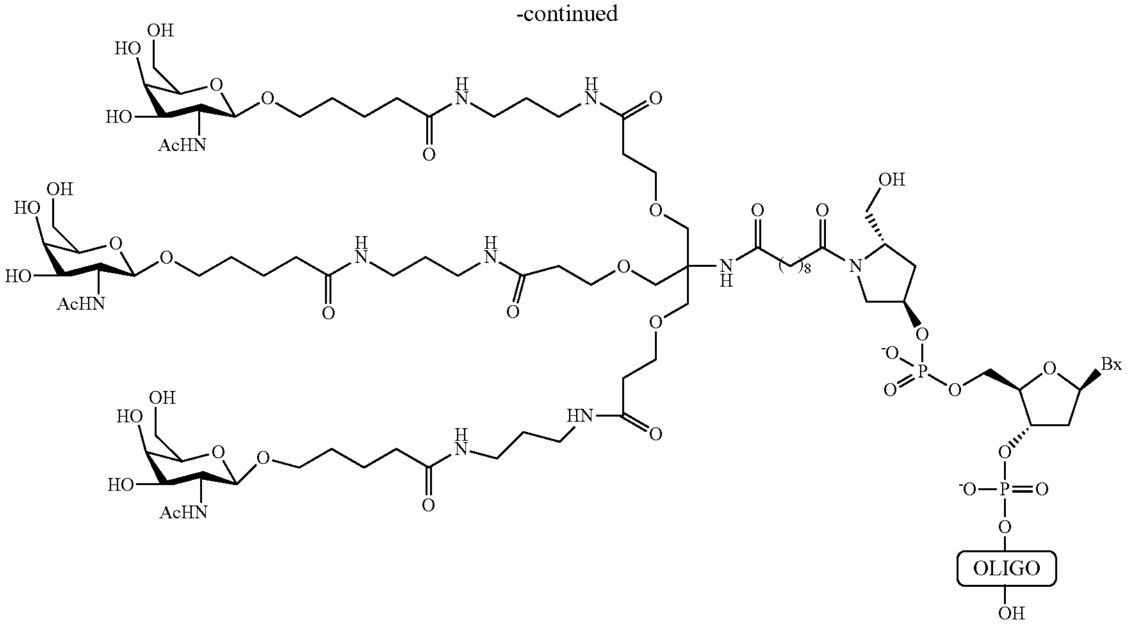

34

X = O, or S
Bx = Heterocyclic base

The Unylinker™ 30 is commercially available. Oligomeric Compound 34 comprising a GalNAc$_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11: Preparation of Compound 39

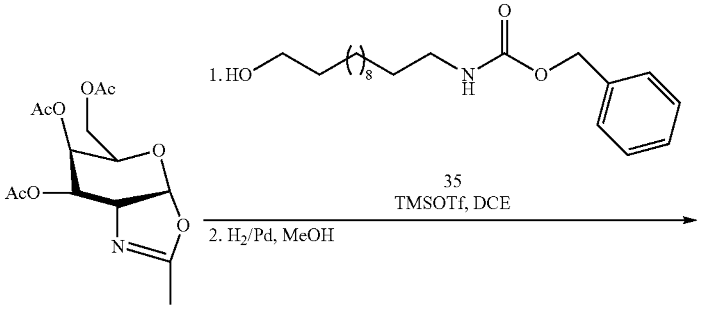

4

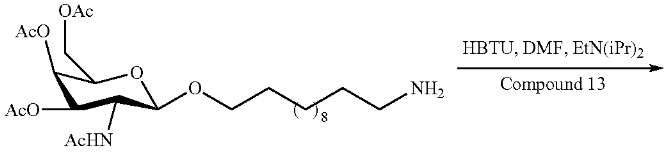

36

-continued
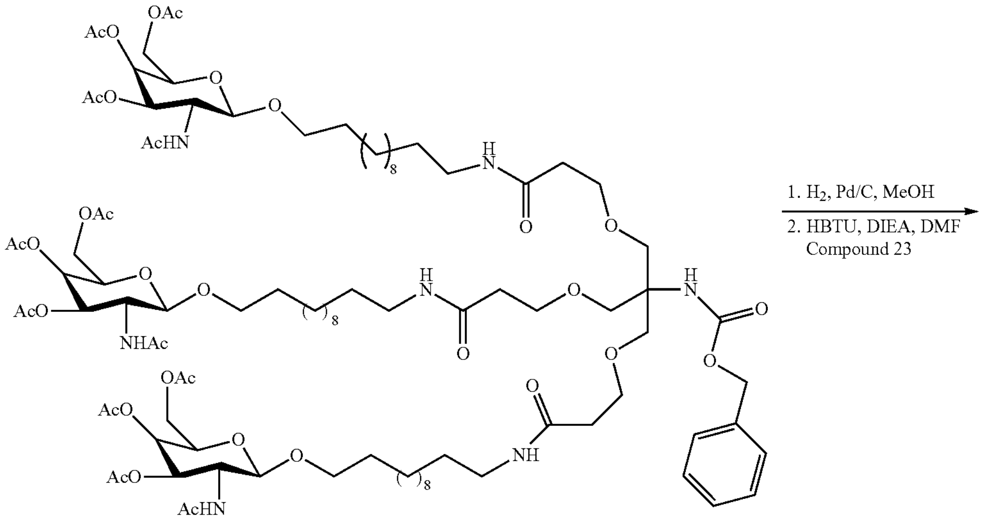
37
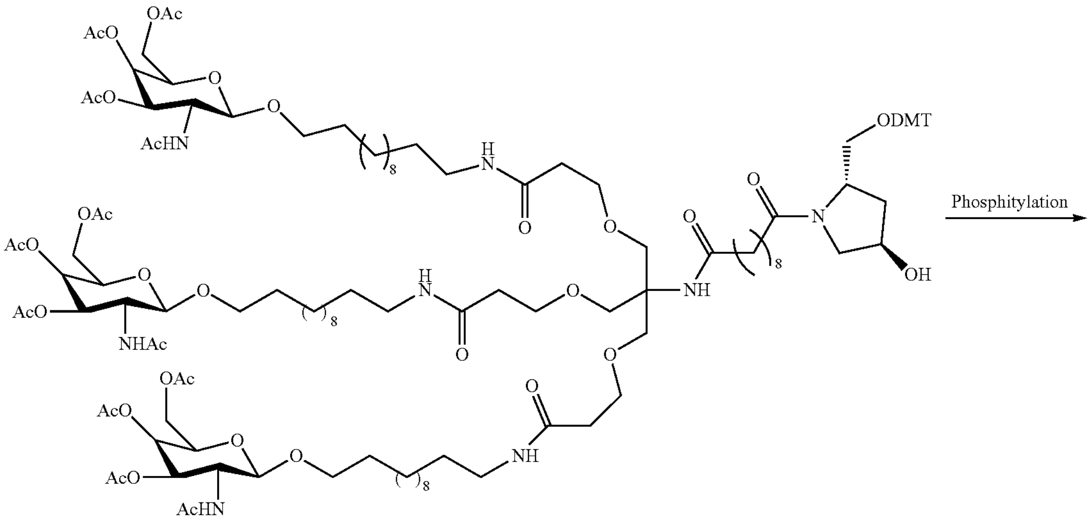
38
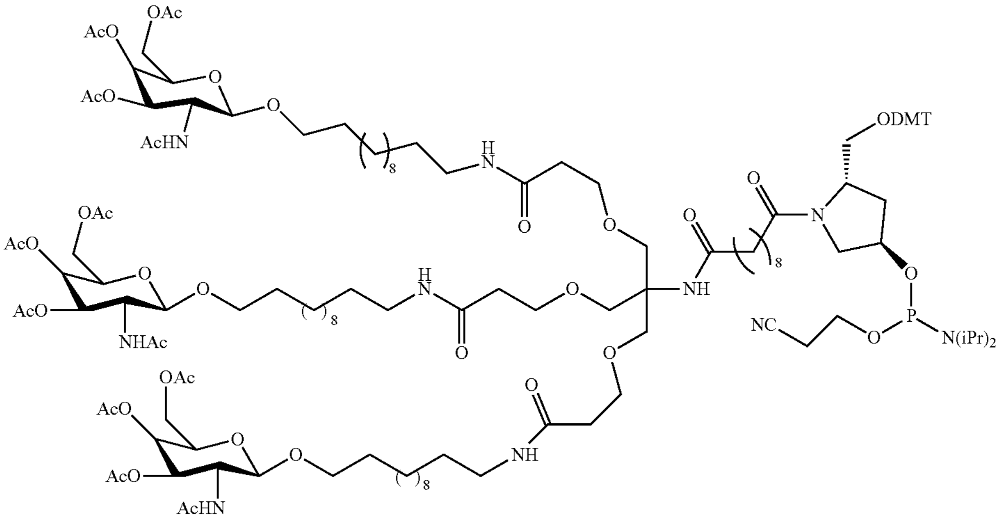
39

Compounds 4, 13 and 23 were prepared as per the procedures illustrated in Examples 2, 4, and 5. Compound 35 is prepared using similar procedures published in Rouchaud et al., *Eur. J. Org. Chem.,* 2011, 12, 2346-2353.
Example 12: Preparation of Compound 40
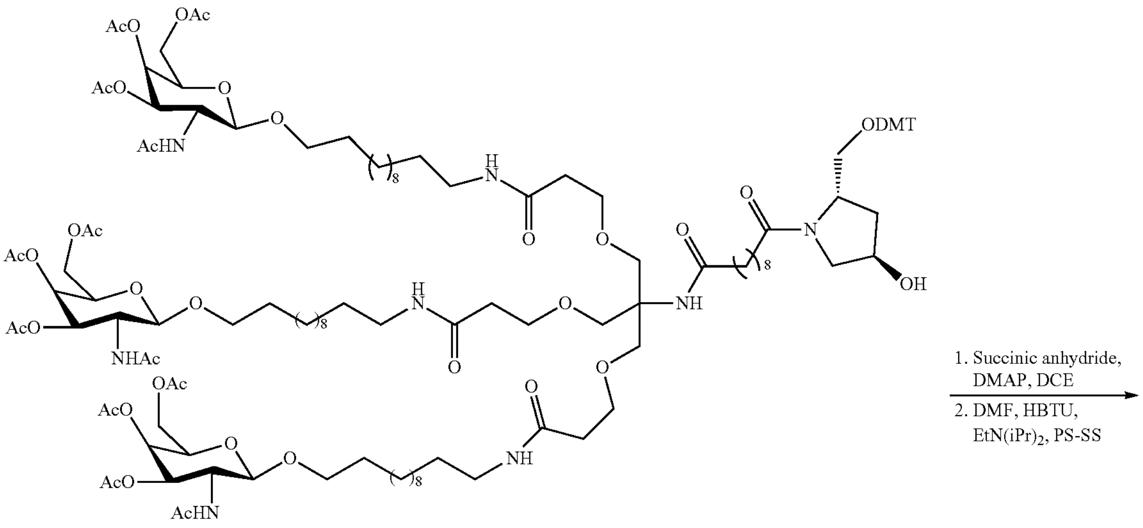
38
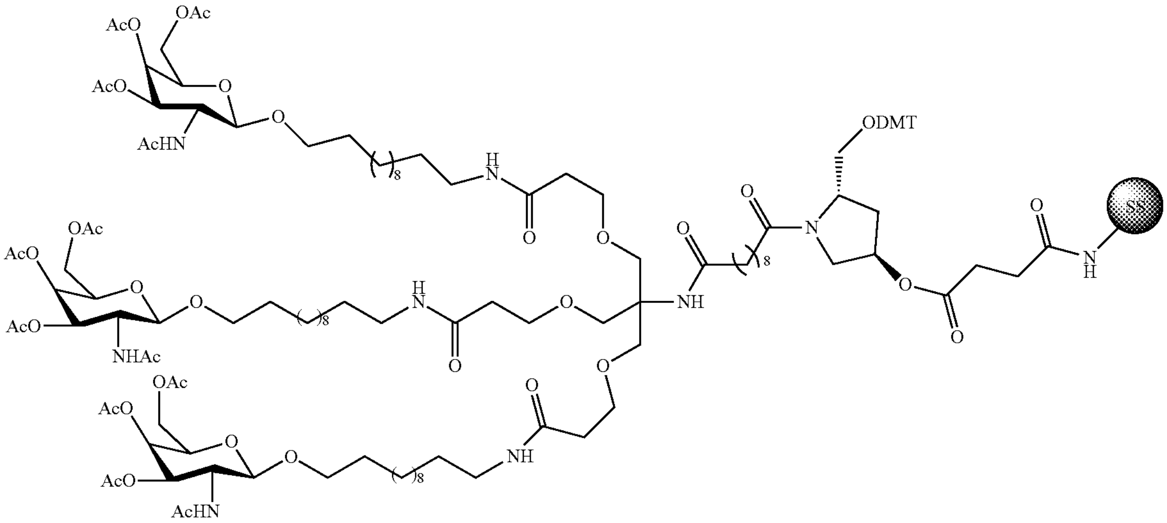
40
Compound 38 is prepared as per the procedures illustrated in Example 11.

Example 13: Preparation of Compound 44
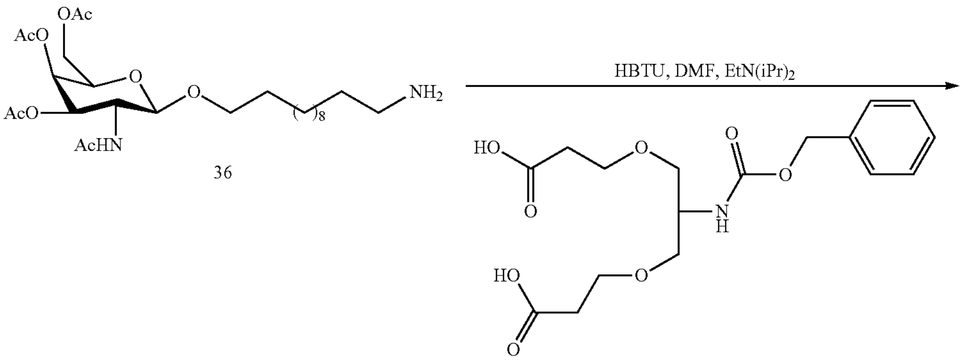
36
41
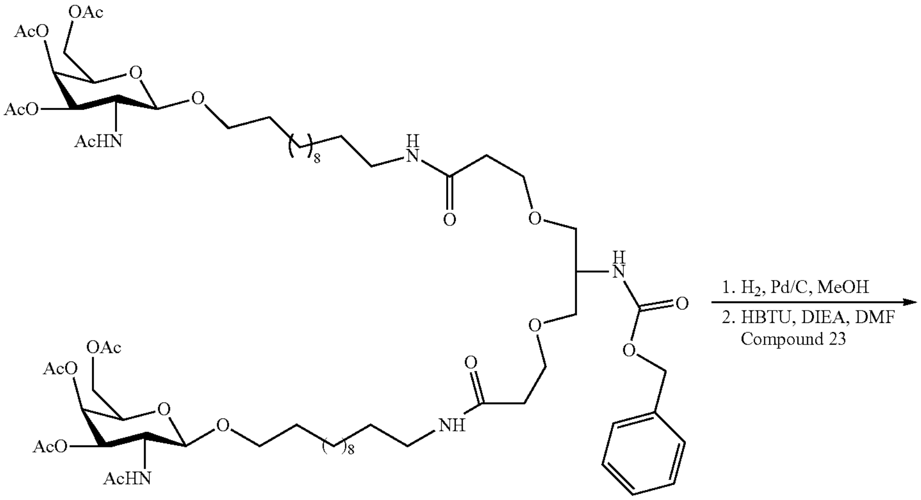
42
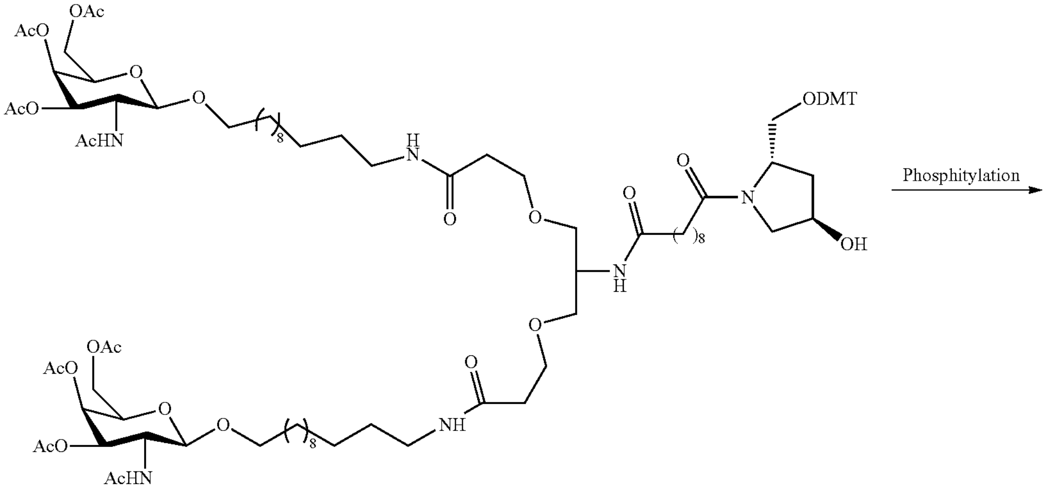
43

-continued
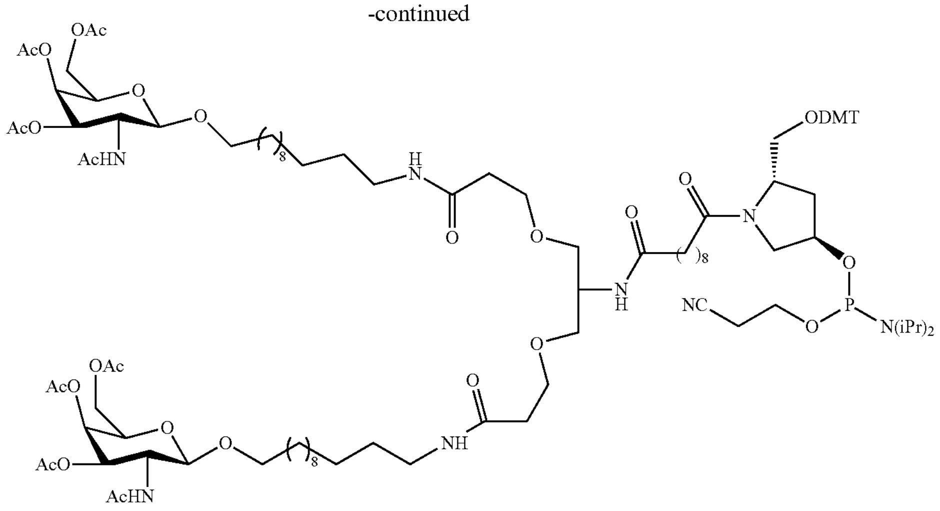
44
Compounds 23 and 36 are prepared as per the procedures illustrated in Examples 5 and 11. Compound 41 is prepared using similar procedures published in WO 2009082607.
Example 14: Preparation of Compound 45
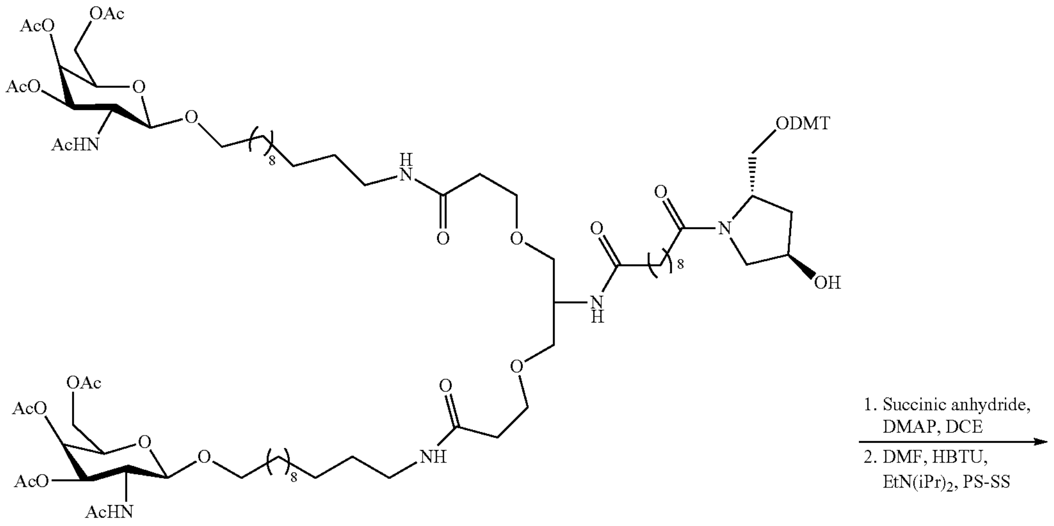
43

-continued
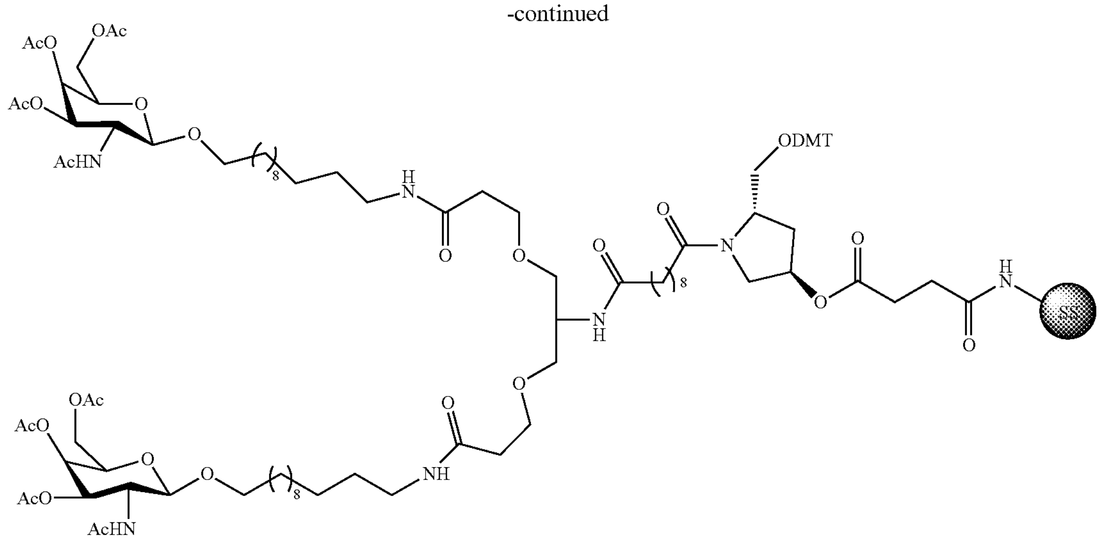
45
Compound 43 is prepared as per the procedures illustrated in Example 13.
Example 15: Preparation of Compound 47
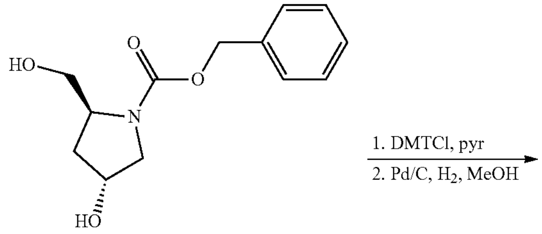
46
-continued
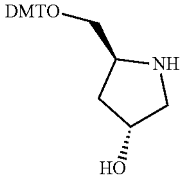
47
Compound 46 is commercially available.
Example 16: Preparation of Compound 53
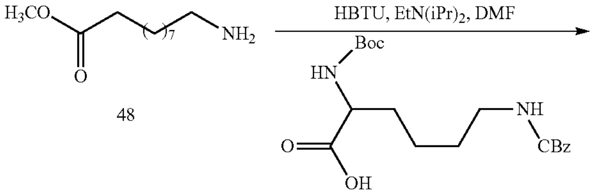
48
49
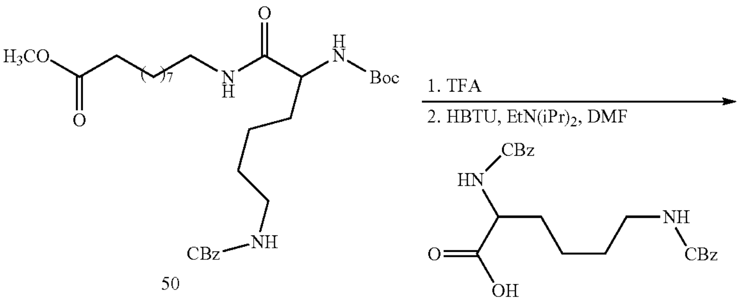
50
49

-continued
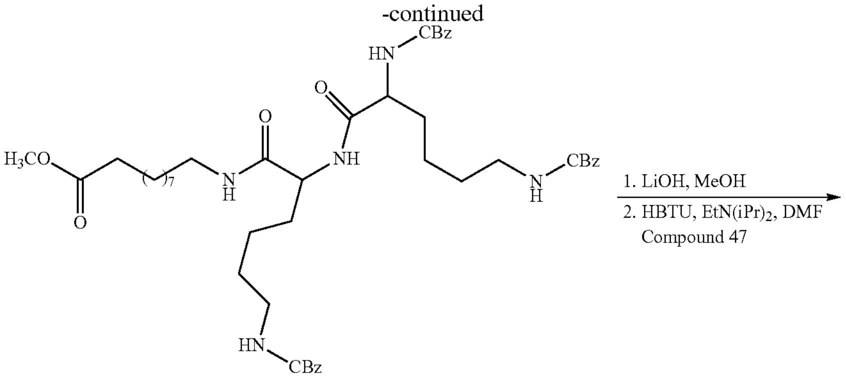
51
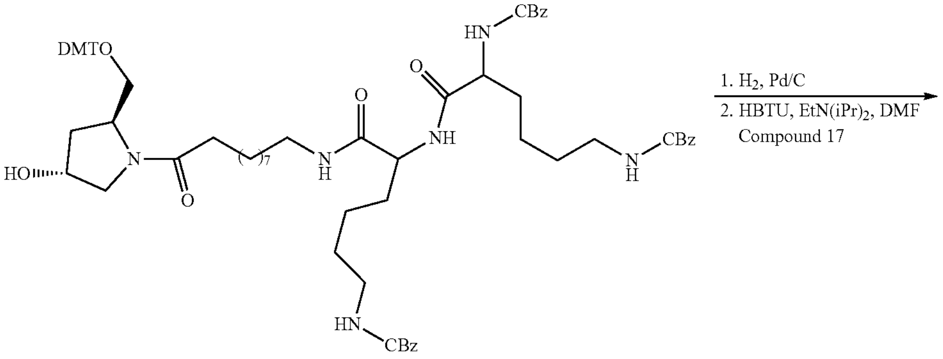
52
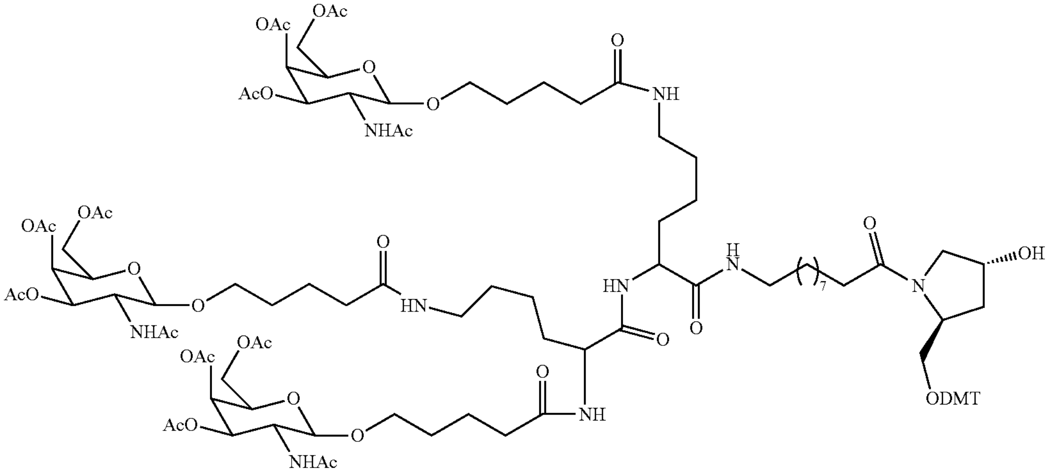
53
Compounds 48 and 49 are commercially available. Compounds 17 and 47 are prepared as per the procedures illustrated in Examples 4 and 15.

Example 17: Preparation of Compound 54
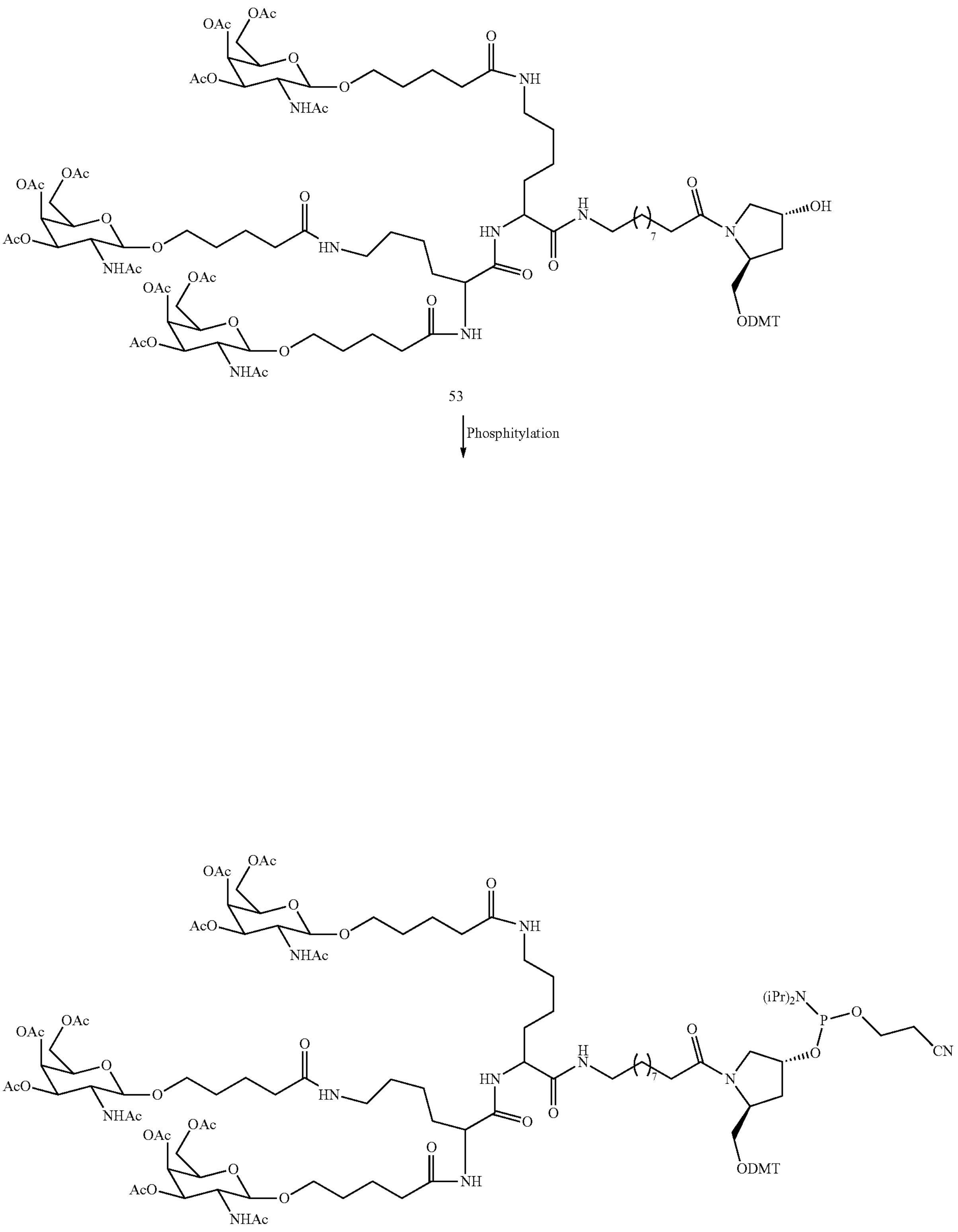
53
54
Compound 53 is prepared as per the procedures illustrated in Example 16.

Example 18: Preparation of Compound 55

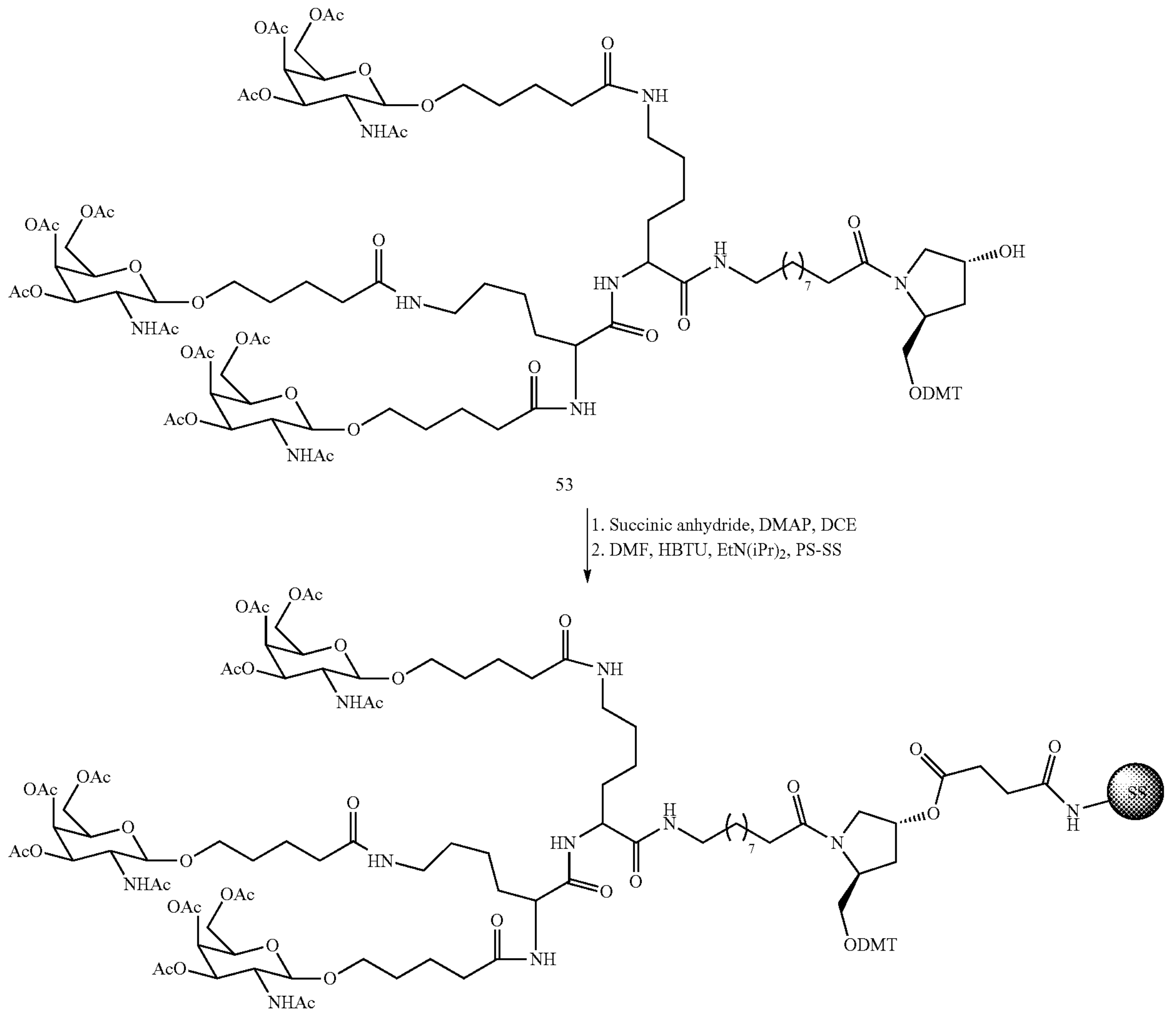

53

55

Compound 53 is prepared as per the procedures illustrated in Example 16.

Example 19: General Method for the Preparation of Conjugated ASOs Comprising GalNAc$_3$-1 at the 3' Position Via Solid Phase Techniques (Preparation of ISIS 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^{m}$C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on an GalNAc$_3$-1 loaded VIMAD solid support (110 μmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous $CH_3CN$ was used as activator during coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in $CH_3CN$ containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1, =260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 17, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a $GalNAc_3$-1 conjugated at its 3'end; and ISIS 647536 is the same as ISIS 647535 except that certain internucleoside linkages of that compound are phosphodiester linkages. As further summarized in Table 17, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a $GalNAc_3$-1 at its 3'-end.

"GalNAc3 cluster." In certain instances it is convenient to describe a conjugate group by separately providing its cluster and its cleavable moiety.

Example 20: Dose-Dependent Antisense Inhibition of Human ApoC III in huApoC III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 μmol/kg or with PBS as a control. Each treatment group consisted of 4 animals. Forty-eight hours after the administration of the last dose, blood was drawn from each mouse and the mice were sacrificed and tissues were collected.

TABLE 17

Modified ASO targeting ApoC III and SRB-1

| ASO | Sequence (5' to 3') | Target | CalCd Mass | Observed Mass | SEQ ID No. |
|---|---|---|---|---|---|
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | ApoC III | 7165.4 | 7164.4 | 135 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$**Ado.-GalNAc3-1a** | ApoC III | 9239.5 | 9237.8 | 136 |
| ISIS 647536 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}$**Ado.-GalNAc3-1a** | ApoC III | 9142.9 | 9140.8 | 136 |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | SRB-1 | 4647.0 | 4646.4 | 137 |
| ISIS 651900 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}$**Ado.-GalNAc3-1a** | SRB1-1 | 6721.1 | 6719.4 | 138 |

Subscripts: "e" indicates 2'-MOE modified nucleoside; "d" indicates β-D-2'-deoxyribonucleoside; "k" indicates 6'-(S)—CH3 bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. "$GalNAc_3$-1" indicates a conjugate group having the structure shown previously in Example 9. Note that $GalNAc_3$-1 comprises a cleavable adenosine which links the ASO to remainder of the conjugate, which is designated "$GalNAc_3$-$1_a$." This nomenclature is used in the above table to show the full nucleobase sequence, including the adenosine, which is part of the conjugate. Thus, in the above table, the sequences could also be listed as ending with "$GalNAc_3$-1" with the "$A_{do}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or ApoC III mRNA Analysis ApoC III mRNA levels in the mice's livers were determined using real-time PCR and RIBOGREEN® RNA quantification reagent (Molecular Probes, Inc. Eugene, OR) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage ($ED_{50}$) of each ASO is also presented in Table 18, below.

As illustrated, both antisense compounds reduced ApoC III RNA relative to the PBS control. Further, the antisense compound conjugated to $GalNAc_3$-1 (ISIS 647535) was substantially more potent than the antisense compound lacking the $GalNAc_3$-1 conjugate (ISIS 304801).

TABLE 18

Effect of ASO treatment on ApoC III mRNA levels in human ApoC III transgenic mice

| ASO | Dose (μmol/kg) | % PBS | $ED_{50}$ (μmol/kg) | 3' Conjugate | Internucleoside linkage/Length | SEQ ID No. |
|---|---|---|---|---|---|---|
| PBS | 0 | 100 | — | — | — | |
| ISIS 304801 | 0.08 | 95 | 0.77 | None | PS/20 | 135 |
| | 0.75 | 42 | | | | |
| | 2.25 | 32 | | | | |
| | 6.75 | 19 | | | | |
| ISIS 647535 | 0.08 | 50 | 0.074 | $GalNAc_3$-1 | PS/20 | 136 |
| | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, *Circulation Research*, published online before print Mar. 29, 2013.

Approximately 100 μl of plasma isolated from mice was analyzed without dilution using an Olympus Clinical Analyzer and a commercially available turbidometric ApoC III assay (Kamiya, Cat #KAI-006, Kamiya Biomedical, Seattle, WA). The assay protocol was performed as described by the vendor.

As shown in the Table 19 below, both antisense compounds reduced ApoC III protein relative to the PBS control. Further, the antisense compound conjugated to $GalNAc_3$-1 (ISIS 647535) was substantially more potent than the antisense compound lacking the $GalNAc_3$-1 conjugate (ISIS 304801).

TABLE 19

Effect of ASO treatment on ApoC III plasma protein levels in human ApoC III transgenic mice

| ASO | Dose (μmol/kg) | % PBS | $ED_{50}$ (μmol/kg) | 3' Conjugate | Internucleoside Linkage/Length | SEQ ID No. |
|---|---|---|---|---|---|---|
| PBS | 0 | 100 | — | — | — | |
| | 0.08 | 86 | 0.73 | None | PS/20 | 135 |
| ISIS 304801 | 0.75 | 51 | | | | |
| | 2.25 | 23 | | | | |
| | 6.75 | 13 | | | | |
| ISIS 647535 | 0.08 | 72 | 0.19 | $GalNAc_3$-1 | PS/20 | 136 |
| | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. *Can. J. Biochem. Physiol.* 37: 911-917, 1959) (Bligh, E and Dyer, W, *Can J Biochem Physiol,* 37, 911-917, 1959)(Bligh, E and Dyer, W, *Can J Biochem Physiol,* 37, 911-917, 1959) and measured by using a Beckmann Coulter clinical analyzer and commercially available reagents.

The triglyceride levels were measured relative to PBS injected mice and are denoted as "% PBS". Results are presented in Table 20. As illustrated, both antisense compounds lowered triglyceride levels. Further, the antisense compound conjugated to $GalNAc_3$-1 (ISIS 647535) was substantially more potent than the antisense compound lacking the $GalNAc_3$-1 conjugate (ISIS 304801).

TABLE 20

Effect of ASO treatment on triglyceride levels in transgenic mice

| ASO | Dose (μmol/kg) | % PBS | $ED_{50}$ (μmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 87 | 0.63 | None | PS/20 | 135 |
| | 0.75 | 46 | | | | |
| | 2.25 | 21 | | | | |
| | 6.75 | 12 | | | | |
| ISIS 647535 | 0.08 | 65 | 0.13 | $GalNAc_3$-1 | PS/20 | 136 |
| | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 21 and 22. As illustrated, both antisense compounds lowered total cholesterol levels; both lowered LDL; and both raised HDL. Further, the antisense compound conjugated to $GalNAc_3$-1 (ISIS 647535) was substantially more potent than the antisense compound lacking the $GalNAc_3$-1 conjugate (ISIS 304801). An increase in HDL and a decrease in LDL levels is a cardiovascular beneficial effect of antisense inhibition of ApoC III.

TABLE 21

Effect of ASO treatment on total cholesterol levels in transgenic mice

| ASO | Dose (μmol/kg) | Total Cholesterol (mg/dL) | 3' Conjugate | Internucleoside Linkage/Length | SEQ ID No. |
|---|---|---|---|---|---|
| PBS | 0 | 257 | — | — | |
| ISIS 304801 | 0.08 | 226 | None | PS/20 | 135 |
| | 0.75 | 164 | | | |
| | 2.25 | 110 | | | |
| | 6.75 | 82 | | | |
| ISIS 647535 | 0.08 | 230 | $GalNAc_3$-1 | PS/20 | 136 |
| | 0.75 | 82 | | | |
| | 2.25 | 86 | | | |
| | 6.75 | 99 | | | |

TABLE 22

Effect of ASO treatment on HDL and LDL cholesterol levels in transgenic mice

| ASO | Dose (μmol/kg) | HDL (mg/dL) | LDL (mg/dL) | 3' Conjugate | Internucleoside Linkage/Length | SEQ ID No. |
|---|---|---|---|---|---|---|
| PBS | 0 | 17 | 28 | — | — | |
| ISIS 304801 | 0.08 | 17 | 23 | None | PS/20 | 135 |
| | 0.75 | 27 | 12 | | | |
| | 2.25 | 50 | 4 | | | |
| | 6.75 | 45 | 2 | | | |
| ISIS 647535 | 0.08 | 21 | 21 | $GalNAc_3$-1 | PS/20 | 136 |
| | 0.75 | 44 | 2 | | | |
| | 2.25 | 50 | 2 | | | |
| | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (μg/g) of full-length ISIS 304801 and 647535 was measured and the results are provided in Table 23. As illustrated, liver concentrations of total full-length antisense compounds were similar for the two antisense compounds. Thus, even though the $GalNAc_3$-1-conjugated antisense compound is more active in the liver (as demonstrated by the RNA and protein data above), it is not present at substantially higher concentration in the liver. Indeed, the calculated $EC_{50}$ (provided in Table 23) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of $GalNAc_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that $GalNAc_3$-1 conjugation reduces kidney accumulation.

TABLE 23

PK analysis of ASO treatment in transgenic mice

| ASO | Dose (μmol/kg) | Liver (μg/g) | Kidney (μg/g) | Liver $EC_{50}$ (μg/g) | 3' Conjugate | Internucleoside Linkage/Length) | SEQ ID No. |
|---|---|---|---|---|---|---|---|
| ISIS 304801 | 0.1 | 5.2 | 2.1 | 53 | None | PS/20 | 135 |
| | 0.8 | 62.8 | 119.6 | | | | |
| | 2.3 | 142.3 | 191.5 | | | | |
| | 6.8 | 202.3 | 337.7 | | | | |
| ISIS 647535 | 0.1 | 3.8 | 0.7 | 3.8 | $GalNAc_3$-1 | PS/20 | 136 |
| | 0.8 | 72.7 | 34.3 | | | | |
| | 2.3 | 106.8 | 111.4 | | | | |
| | 6.8 | 237.2 | 179.3 | | | | |

Metabolites of ISIS 647535 were also identified and their masses were confirmed by high resolution mass spectrometry analysis. The cleavage sites and structures of the observed metabolites are shown below. The relative % of full length ASO was calculated using standard procedures and the results are presented in Table 23a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleavable bonds such as esters, peptides, disulfides, phosphoramidates or acyl-hydrazones between the $GalNAc_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 23a

Observed full length metabolites of ISIS 647535

| Metabolite | ASO | Cleavage site | Relative % |
|---|---|---|---|
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxy-pentanoic acid tether] | D | 17.6 |
| 5 | ISIS 647535 minus [2 GalNAc + 2 5-hydroxy-pentanoic acid tether] | D | 9.9 |
| 6 | ISIS 647535 minus [3 GalNAc + 3 5-hydroxy-pentanoic acid tether] | D | 9.8 |

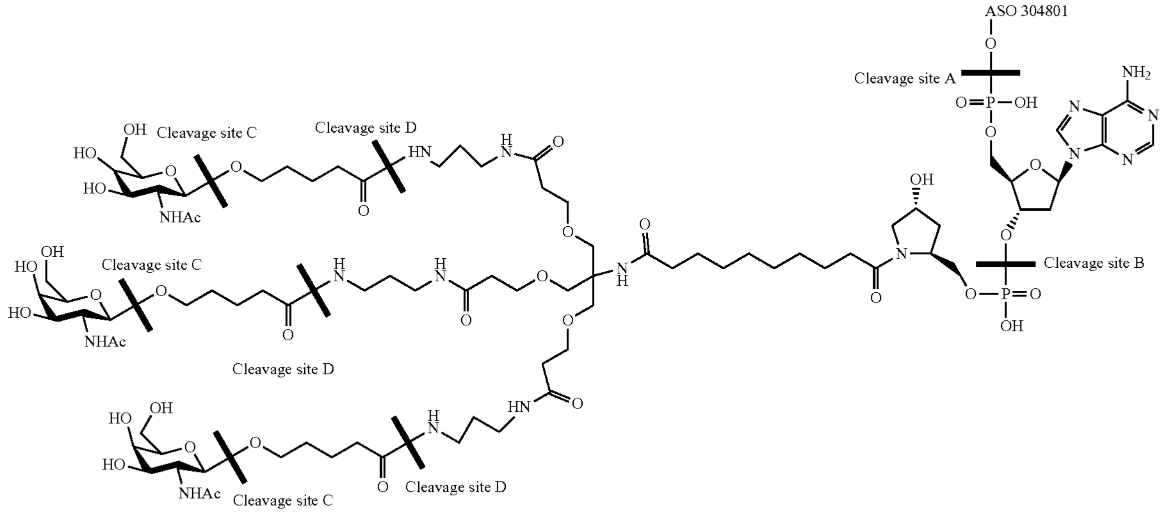

Cleavage Sites

TABLE 23a-continued
| Observed full length metabolites of ISIS 647535 | | | |
|---|---|---|---|
| Metabolite | ASO | Cleavage site | Relative % |
| 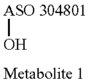 Metabolite 1 | 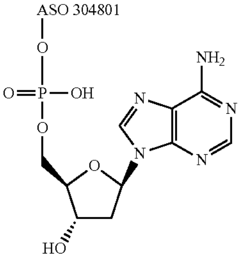 Metabolite 2 | | |
| 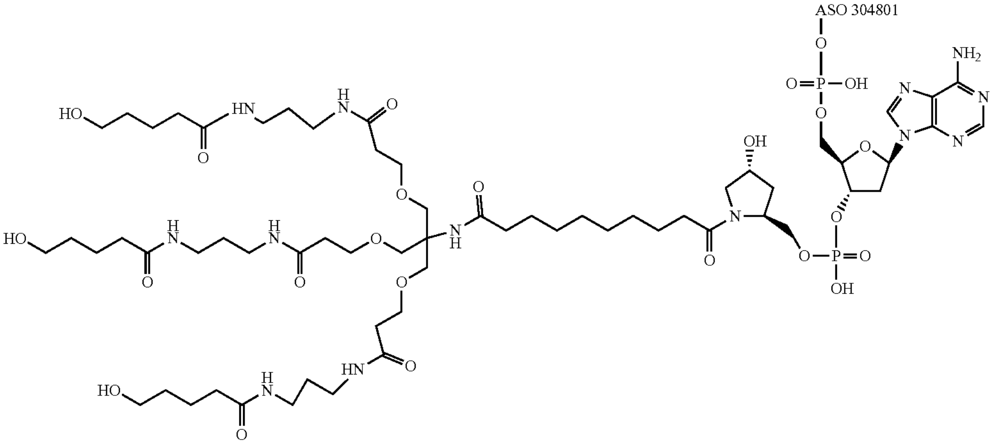 Metabolite 3 | | | |
| 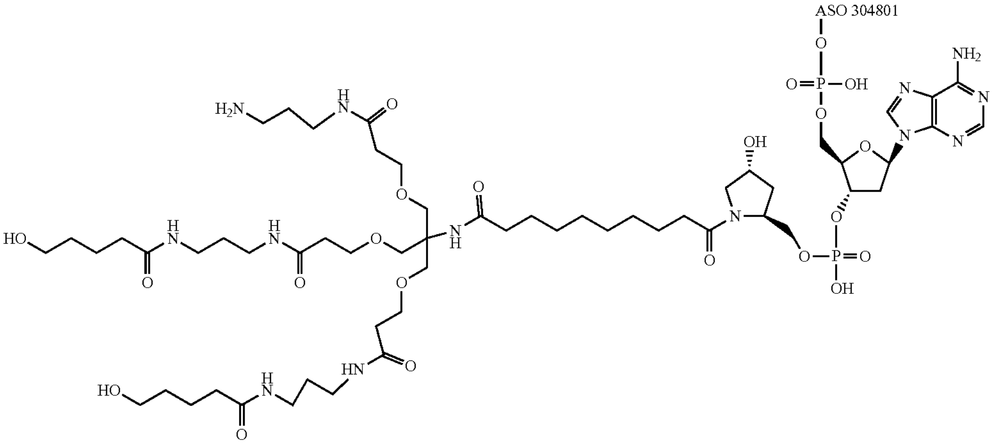 Metabolite 4 | | | |

TABLE 23a-continued

| Observed full length metabolites of ISIS 647535 | | | |
|---|---|---|---|
| Metabolite | ASO | Cleavage site | Relative % |

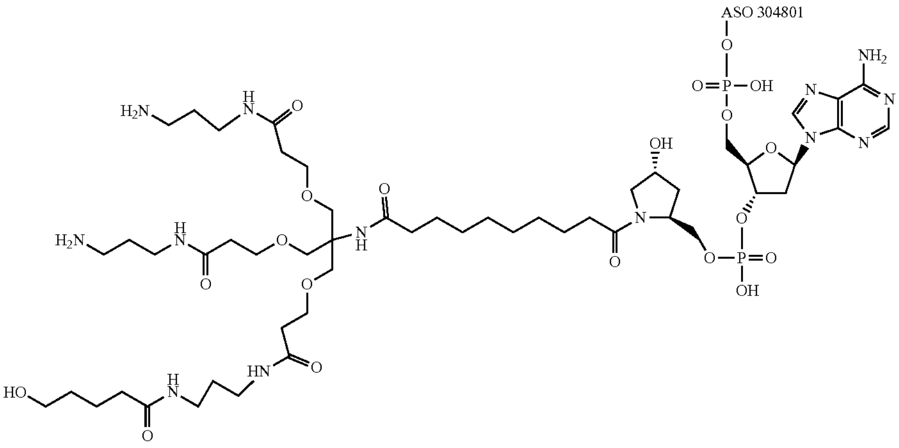

Metabolite 5

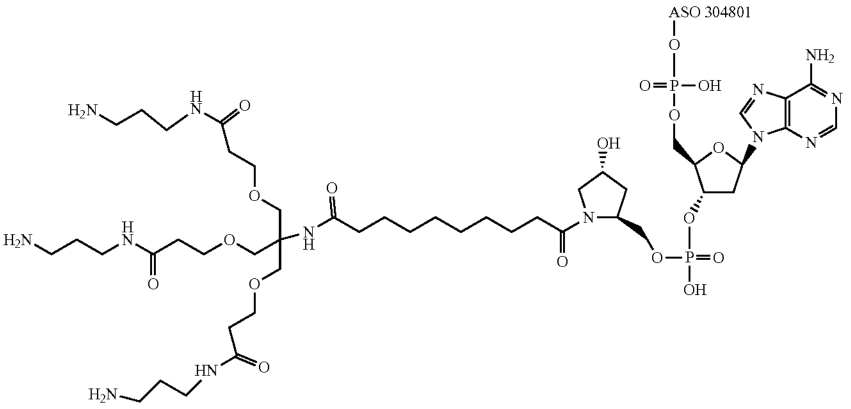

Metabolite 6

Example 21: Antisense Inhibition of Human ApoC III in Human ApoC III Transgenic Mice in Single Administration Study ISIS 304801, 647535 and 647536 each targeting human ApoC III and described in Table 17, were further evaluated in a single administration study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 24-28, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a $GalNAc_3$-1 conjugate at the 3' terminus (ISIS 647535 and 647536) compared to the antisense compound lacking a $GalNAc_3$-1 conjugate (ISIS 304801). Further, ISIS 647536, which comprises a $GalNAc_3$-1 conjugate and some phosphodiester linkages was as potent as ISIS 647535, which comprises the same conjugate and all internucleoside linkages within the ASO are phosphorothioate.

TABLE 24

Effect of ASO treatment on ApoC III mRNA levels in human ApoC III transgenic mice

| ASO | Dose (mg/kg) | % PBS | $ED_{50}$ (mg/kg) | 3' Conjugate | Inter-nucleoside Linkage/ Length) | SEQ ID No. |
|---|---|---|---|---|---|---|
| PBS | 0 | 99 | — | — | — | |
| ISIS | 1 | 104 | 13.2 | None | PS/20 | 135 |
| 304801 | 3 | 92 | | | | |
| | 10 | 71 | | | | |
| | 30 | 40 | | | | |
| ISIS | 0.3 | 98 | 1.9 | $GalNAc_3$-1 | PS/20 | 136 |
| 647535 | 1 | 70 | | | | |
| | 3 | 33 | | | | |
| | 10 | 20 | | | | |
| ISIS | 0.3 | 103 | 1.7 | $GalNAc_3$-1 | PS/PO/20 | 136 |
| 647536 | 1 | 60 | | | | |
| | 3 | 31 | | | | |
| | 10 | 21 | | | | |

TABLE 25

Effect of ASO treatment on ApoC III plasma protein levels in human ApoC III transgenic mice

| ASO | Dose (mg/kg) | % PBS | $ED_{50}$ (mg/kg) | 3' Conjugate | Inter-nucleoside Linkage/ Length) | SEQ ID No. |
|---|---|---|---|---|---|---|
| PBS | 0 | 99 | — | — | — | |
| ISIS | 1 | 104 | 23.2 | None | PS/20 | 135 |
| 304801 | 3 | 92 | | | | |
| | 10 | 71 | | | | |
| | 30 | 40 | | | | |
| ISIS | 0.3 | 98 | 2.1 | $GalNAc_3$-1 | PS/20 | 136 |
| 647535 | 1 | 70 | | | | |
| | 3 | 33 | | | | |
| | 10 | 20 | | | | |
| ISIS | 0.3 | 103 | 1.8 | $GalNAc_3$-1 | PS/PO/20 | 136 |
| 647536 | 1 | 60 | | | | |
| | 3 | 31 | | | | |
| | 10 | 21 | | | | |

TABLE 26

Effect of ASO treatment on triglyceride levels in transgenic mice

| ASO (mg/kg) | Dose (mg/kg) | % PBS | $ED_{50}$ (mg/kg) | 3' Conjugate | Inter-nucleoside Linkage/ Length | SEQ ID No. |
|---|---|---|---|---|---|---|
| PBS | 0 | 98 | — | — | — | |
| ISIS | 1 | 80 | 29.1 | None | PS/20 | 135 |
| 304801 | 3 | 92 | | | | |
| | 10 | 70 | | | | |
| | 30 | 47 | | | | |
| ISIS | 0.3 | 100 | 2.2 | $GalNAc_3$-1 | PS/20 | 136 |
| 647535 | 1 | 70 | | | | |
| | 3 | 34 | | | | |
| | 10 | 23 | | | | |
| ISIS | 0.3 | 95 | 1.9 | $GalNAc_3$-1 | PS/PO/20 | 136 |
| 647536 | 1 | 66 | | | | |
| | 3 | 31 | | | | |
| | 10 | 23 | | | | |

TABLE 27

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS | 1 | 104 | None | PS/20 | 135 |
| 304801 | 3 | 96 | | | |
| | 10 | 86 | | | |
| | 30 | 72 | | | |
| ISIS | 0.3 | 93 | $GalNAc_3$-1 | PS/20 | 136 |
| 647535 | 1 | 85 | | | |
| | 3 | 61 | | | |
| | 10 | 53 | | | |
| ISIS | 0.3 | 115 | $GalNAc_3$-1 | PS/PO/20 | 136 |
| 647536 | 1 | 79 | | | |
| | 3 | 51 | | | |
| | 10 | 54 | | | |

TABLE 28

Effect of ASO treatment on HDL and LDL cholesterol levels in transgenic mice

| ASO | Dose (mg/kg) | HDL % PBS | LDL % PBS | 3' Conjugate | Inter-nucleoside Linkage/ Length | SEQ ID No. |
|---|---|---|---|---|---|---|
| PBS | 0 | 131 | 90 | — | — | |
| ISIS | 1 | 130 | 72 | | | |
| 304801 | 3 | 186 | 79 | None | PS/20 | 135 |
| | 10 | 226 | 63 | | | |
| | 30 | 240 | 46 | | | |
| ISIS | 0.3 | 98 | 86 | | | |
| 647535 | 1 | 214 | 67 | $GalNAc_3$-1 | PS/20 | 136 |
| | 3 | 212 | 39 | | | |
| | 10 | 218 | 35 | | | |
| ISIS | 0.3 | 143 | 89 | $GalNAc_3$-1 | PS/PO/20 | 136 |
| 647536 | 1 | 187 | 56 | | | |
| | 3 | 213 | 33 | | | |
| | 10 | 221 | 34 | | | |

These results confirm that the $GalNAc_3$-1 conjugate improves potency of an antisense compound. The results also show equal potency of a $GalNAc_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a $GalNAc_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22: Effect of $GalNAc_3$-1 Conjugated Modified ASO Targeting SRB-1 In Vivo ISIS 440762 and 651900, each targeting SRB-1 and described in Table 17, were evaluated in a dose-dependent study for their ability to inhibit SRB-1 in Balb/c mice.

Treatment

Six week old male Balb/c mice (Jackson Laboratory, Bar Harbor, ME) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 29, both antisense compounds lowered SRB-1 mRNA levels. Further, the antisense compound comprising the $GalNAc_3$-1 conjugate (ISIS 651900) was substantially more potent than the antisense compound lacking the $GalNAc_3$-1 conjugate (ISIS 440762). These results demonstrate that the potency benefit of $GalNAc_3$-1 conjugates are observed using antisense oligonucleotides complementary to a different target and having different chemically modified nucleosides, in this instance modified nucleosides comprise constrained ethyl sugar moieties (a bicyclic sugar moiety).

TABLE 29

Effect of ASO treatment on SRB-1 mRNA levels in Balb/c mice

| ASO | Dose (mg/kg) | Liver % PBS | $ED_{50}$ (mg/kg) | 3' Conjugate | Internucleoside Linkage/ Length | SEQ ID No. |
|---|---|---|---|---|---|---|
| PBS | 0 | 100 | | — | — | |
| ISIS | 0.7 | 85 | 2.2 | None | PS/14 | 137 |
| 440762 | 2 | 55 | | | | |
| | 7 | 12 | | | | |
| | 20 | 3 | | | | |
| ISIS | 0.07 | 98 | 0.3 | $GalNAc_3$-1 | PS/14 | 138 |
| 651900 | 0.2 | 63 | | | | |
| | 0.7 | 20 | | | | |
| | 2 | 6 | | | | |
| | 7 | 5 | | | | |

Example 23: Human Peripheral Blood Mononuclear Cells (hPBMC) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS ($Ca^{++}$, $Mg^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 μl sample was pipette into a sample vial (Beckman Coulter) with 600 μl VersaLyse reagent (Beckman Coulter Cat #A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1\times10^7$ live PBMC/ml in RPMI+10% FBS+pen/strep.

The cells were plated at $5\times10^5$ in 50 μl/well of 96-well tissue culture plate (Falcon Microtest). 50 μl/well of 2× concentration oligos/controls diluted in RPMI+10% FBS+pen/strep. was added according to experiment template (100 μl/well total). Plates were placed on the shaker and allowed to mix for approx. 1 min. After being incubated for 24 hrs at 37° C.; 5% $CO_2$, the plates were centrifuged at 400×g for 10 minutes before removing the supernatant for MSD cytokine assay (i.e. human IL-6, IL-10, IL-8 and MCP-1).

Example 24: Evaluation of Proinflammatory Effects in hPBMC Assay for $GalNAc_3$-1 Conjugated ASOs The antisense oligonucleotides (ASOs) listed in Table 30 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 μM concentrations. After a 24 hr treatment, the cytokine levels were measured.

The levels of IL-6 were used as the primary readout. The $EC_{50}$ and $E_{max}$ was calculated using standard procedures. Results are expressed as the average ratio of $E_{max}/EC_{50}$ from two donors and is denoted as "$E_{max}/EC_{50}$." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The $GalNAc_3$-1 conjugated ASO, ISIS 647535 was slightly less proinflammatory than its non-conjugated counterpart ISIS 304801. These results indicate that incorporation of some PO linkages reduces proinflammatory reaction and addition of a $GalNAc_3$-1 conjugate does not make a compound more proinflammatory and may reduce proinflammatory response. Accordingly, one would expect that an antisense compound comprising both mixed PS/PO linkages and a $GalNAc_3$-1 conjugate would produce lower proinflammatory responses relative to full PS linked antisense compound with or without a $GalNAc_3$-1 conjugate. These results show that GalNAc3_1 conjugated antisense compounds, particularly those having reduced PS content are less proinflammatory.

Together, these results suggest that a $GalNAc_3$-1 conjugated compound, particularly one with reduced PS content, can be administered at a higher dose than a counterpart full PS antisense compound lacking a $GalNAc_3$-1 conjugate. Since half-life is not expected to be substantially different for these compounds, such higher administration would result in less frequent dosing. Indeed such administration could be even less frequent, because the $GalNAc_3$-1 conjugated compounds are more potent (See Examples 20-22) and re-dosing is necessary once the concentration of a compound has dropped below a desired level, where such desired level is based on potency.

TABLE 30

| Modified ASOs | | | |
|---|---|---|---|
| ASO | Sequence (5' to 3') | Target | SEQ ID No. |
| ISIS 104838 | $G_{es}{}^{m}C_{es}T_{es}G_{es}A_{es}T_{ds}T_{ds}A_{ds}G_{ds}A_{ds}G_{ds}A_{ds}G_{ds}A_{ds}G_{ds}G_{es}T_{es}{}^{m}C_{es}{}^{m}C_{es}{}^{m}C_{e}$ | TNFα | 139 |
| ISIS 353512 | $T_{es}{}^{m}C_{es}{}^{m}C_{es}{}^{m}C_{ds}A_{ds}T_{ds}T_{ds}T_{ds}{}^{m}C_{ds}A_{ds}G_{ds}G_{ds}A_{ds}G_{ds}A_{ds}{}^{m}C_{ds}{}^{m}C_{ds}T_{es}G_{es}G_{e}$ | CRP | 140 |
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | ApoC III | 135 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$**Ado'-GalNAC3-1a** | ApoC III | 136 |
| ISIS 616468 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$ | ApoC III | 135 |

Subscripts: "e" indicates 2'-MOE modified nucleoside; "d" indicates β-D-2'-deoxyribonucleoside; "k" indicates 6'-(S)—$CH_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. "$A_{do}$-$GalNAc_3$-$1_a$" indicates a conjugate having the structure $GalNAc_3$-1 shown in Example 9 attached to the 3'-end of the antisense oligonucleotide, as indicated.

TABLE 31

| Proinflammatory Effect of ASOs targeting ApoC III in hPBMC assay | | | | | | |
|---|---|---|---|---|---|---|
| ASO | $EC_{50}$ (μM) | $E_{max}$ (μM) | $E_{max}/EC_{50}$ | 3' Conjugate | Internucleoside Linkage/Length | SEQ ID No. |
| ISIS 353512 (high responder) | 0.01 | 265.9 | 26,590 | None | PS/20 | 140 |
| ISIS 304801 | 0.07 | 106.55 | 1,522 | None | PS/20 | 135 |
| ISIS 647535 | 0.12 | 138 | 1,150 | $GalNAc_3$-1 | PS/20 | 136 |
| ISIS 616468 | 0.32 | 71.52 | 224 | None | PS/PO/20 | 135 |

Example 25: Effect of $GalNAc_3$-1 Conjugated Modified ASO Targeting Human ApoC III In Vitro ISIS 304801 and 647535 described above were tested in vitro. Primary hepatocyte cells from transgenic mice at a density of 25,000 cells per well were treated with 0.03, 0.08, 0.24, 0.74, 2.22, 6.67 and 20 μM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The $IC_{50}$ was calculated using the standard methods and the results are presented in Table 32. As illustrated, comparable potency was observed in cells treated with ISIS 647535 as compared to the control, ISIS 304801.

TABLE 32

| Modified ASO targeting human ApoC III in primary hepatocytes | | | | |
|---|---|---|---|---|
| ASO | $IC_{50}$ (μM) | 3' Conjugate | Internucleoside linkage/Length | SEQ ID No. |
| ISIS 304801 | 0.44 | None | PS/20 | 135 |
| ISIS 647535 | 0.31 | $GalNAc_3$-1 | PS/20 | 136 |

In this experiment, the large potency benefits of $GalNAc_3$-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26: Effect of PO/PS Linkages on ApoC III ASO Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 33, below.

These results show reduction in potency for antisense compounds with PO/PS (ISIS 616468) in the wings relative to full PS (ISIS 304801).

TABLE 33

Effect of ASO treatment on ApoC III protein levels in human ApoC III transgenic mice

| ASO | Dose (mg/kg) | % PBS | 3' Conjugate | Internucleoside linkage/Length | SEQ ID No. |
|---|---|---|---|---|---|
| PBS | 0 | 99 | — | — | |
| ISIS 304801 | 25 mg/kg/wk for 2 wks | 24 | None | Full PS | 135 |
| ISIS 616468 | 25 mg/kg/wk for 2 wks | 40 | None | 14 PS/6 PO | 135 |

Example 27: Compound 56

56

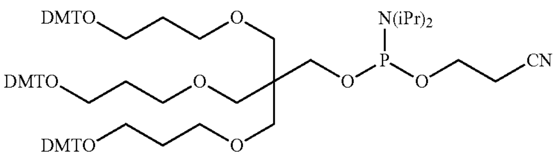

Compound 56 is commercially available from Glen Research or may be prepared according to published procedures reported by Shchepinov et al., *Nucleic Acids Research,* 1997, 25(22), 4447-4454.

Example 28: Preparation of Compound 60

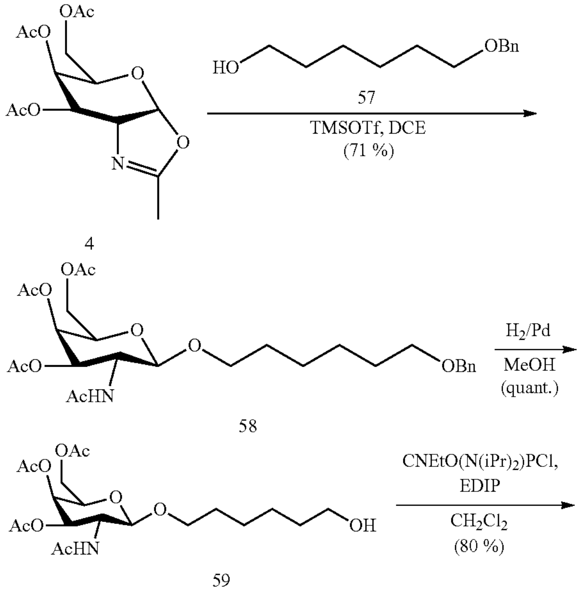

-continued

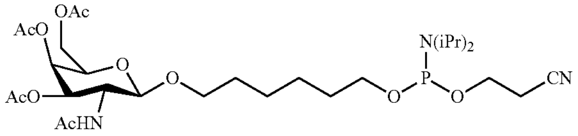

60

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 29: Preparation of Compound 63

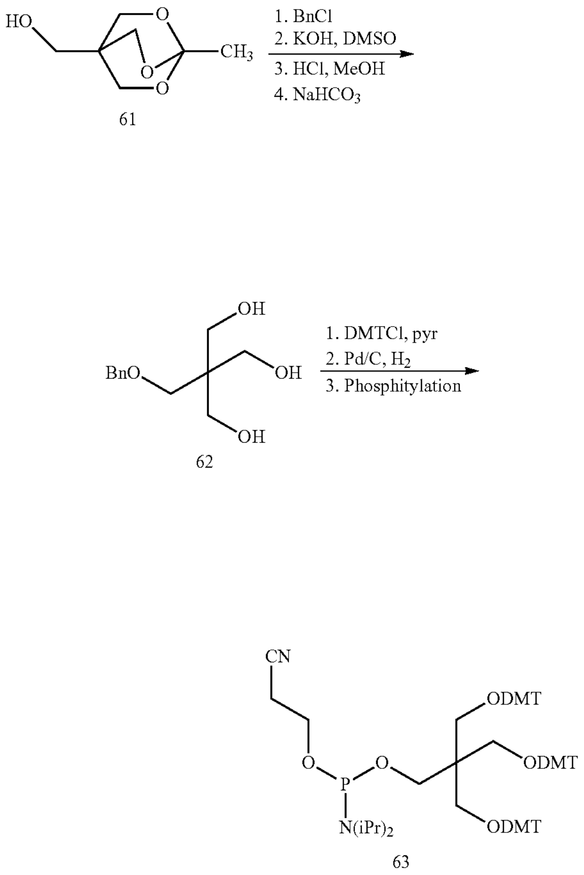

Compounds 61 and 62 are prepared using procedures similar to those reported by Tober et al., Eur. *J. Org. Chem.,* 2013, 3, 566-577; and Jiang et al., *Tetrahedron,* 2007, 63(19), 3982-3988.

Alternatively, Compound 63 is prepared using procedures similar to those reported in scientific and patent literature by Kim et al., Synlett, 2003, 12, 1838-1840; and Kim et al., published PCT International Application, WO 2004063208.

Example 30: Preparation of Compound 63b
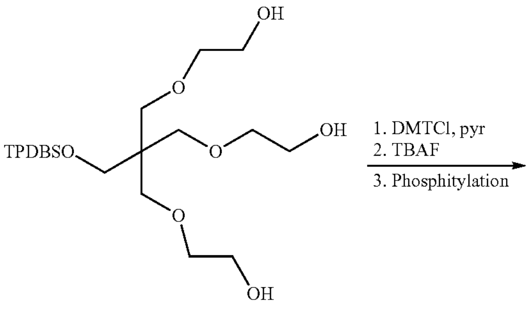
63a
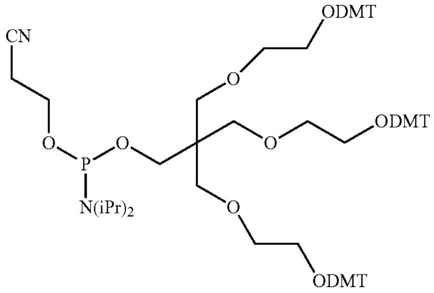
63b
Compound 63a is prepared using procedures similar to those reported by Hanessian et al., *Canadian Journal of Chemistry,* 1996, 74(9), 1731-1737.
Example 31: Preparation of Compound 63d
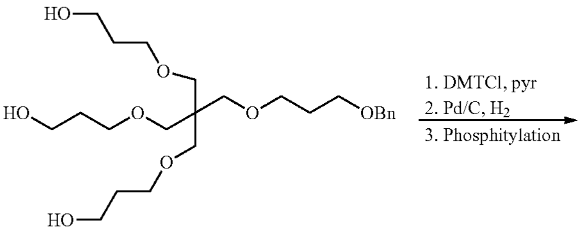
63c
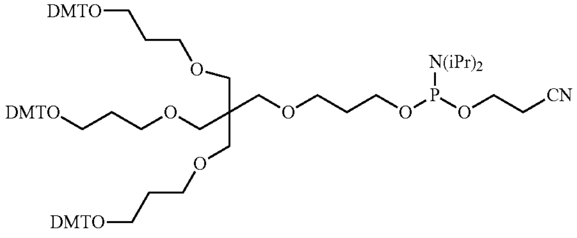
63d
Compound 63c is prepared using procedures similar to those reported by Chen et al., *Chinese Chemical Letters,* 1998, 9(5), 451-453.
Example 32: Preparation of Compound 67
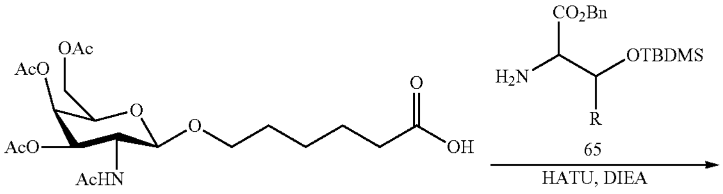
64
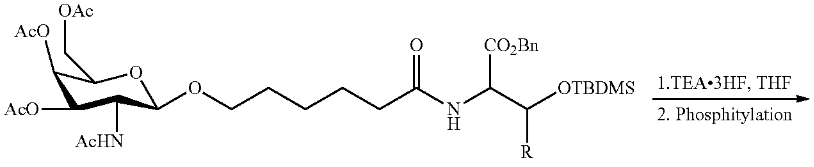
66
R = H or $CH_3$
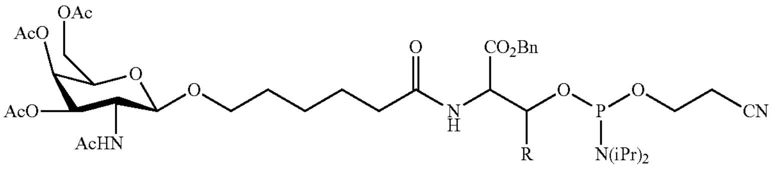
67

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33: Preparation of Compound 70

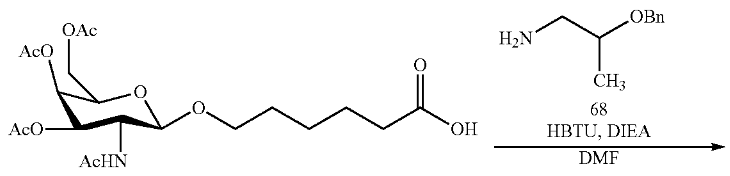

64

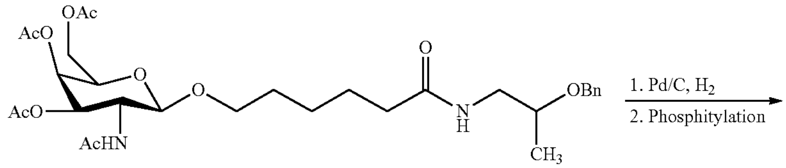

69

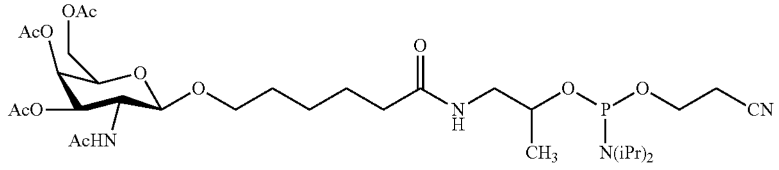

70

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34: Preparation of Compound 75a

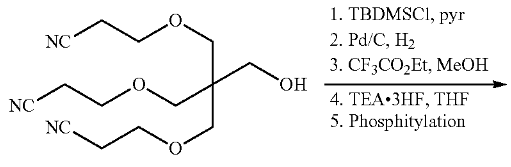

75

-continued

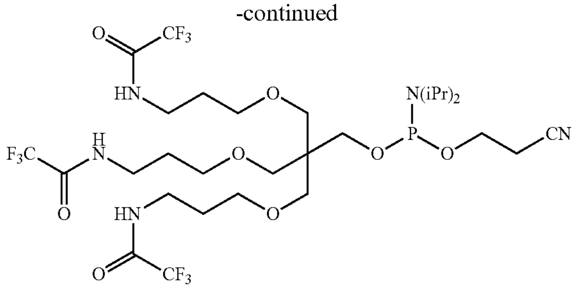

75a

Compound 75 is prepared according to published procedures reported by Shchepinov et al., *Nucleic Acids Research,* 1997, 25(22), 4447-4454.

Example 35: Preparation of Compound 79

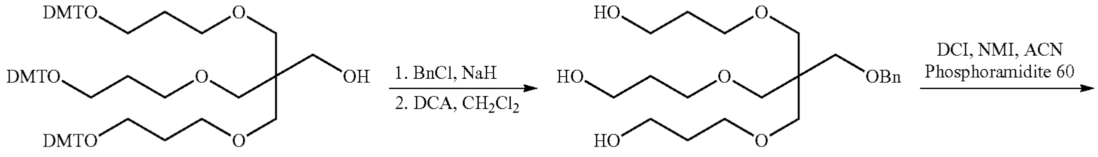

76

77

-continued
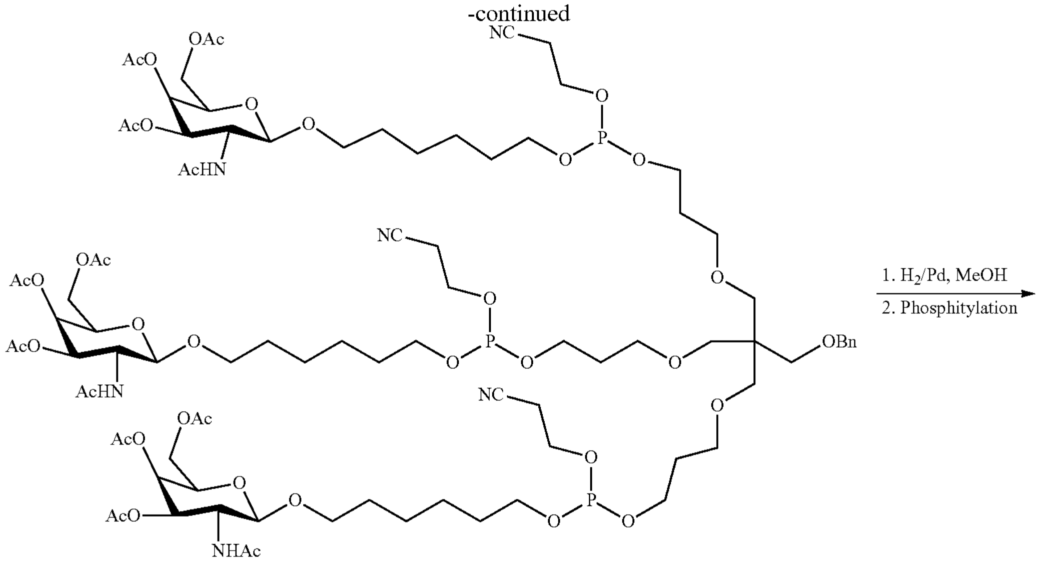
78
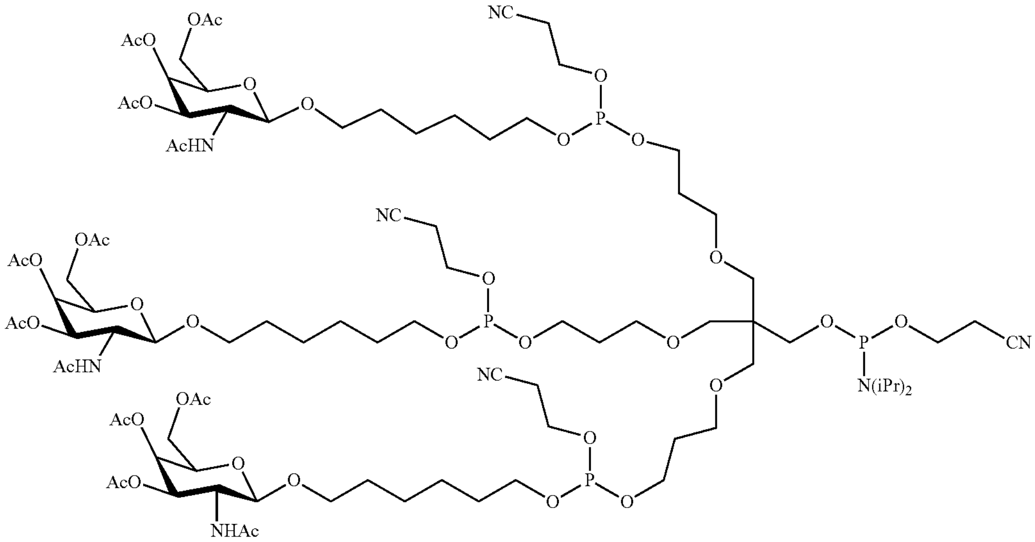
79
Compound 76 was prepared according to published procedures reported by Shchepinov et al., *Nucleic Acids Research,* 1997, 25(22), 4447-4454.
Example 36: Preparation of Compound 79a
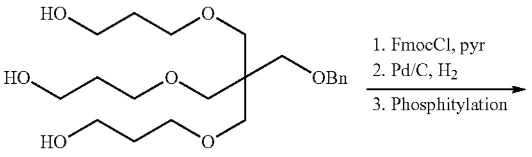
77
-continued
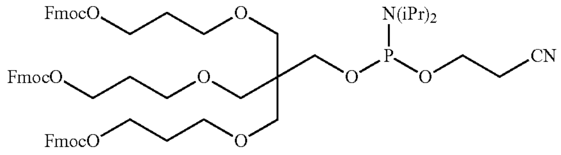
79a
Compound 77 is prepared as per the procedures illustrated in Example 35.

Example 37: General Method for the Preparation of Conjugated Oligomeric Compound 82 Comprising a Phosphodiester Linked GalNAc$_3$-2 Conjugate at 5' Terminus Via Solid Support (Method I)
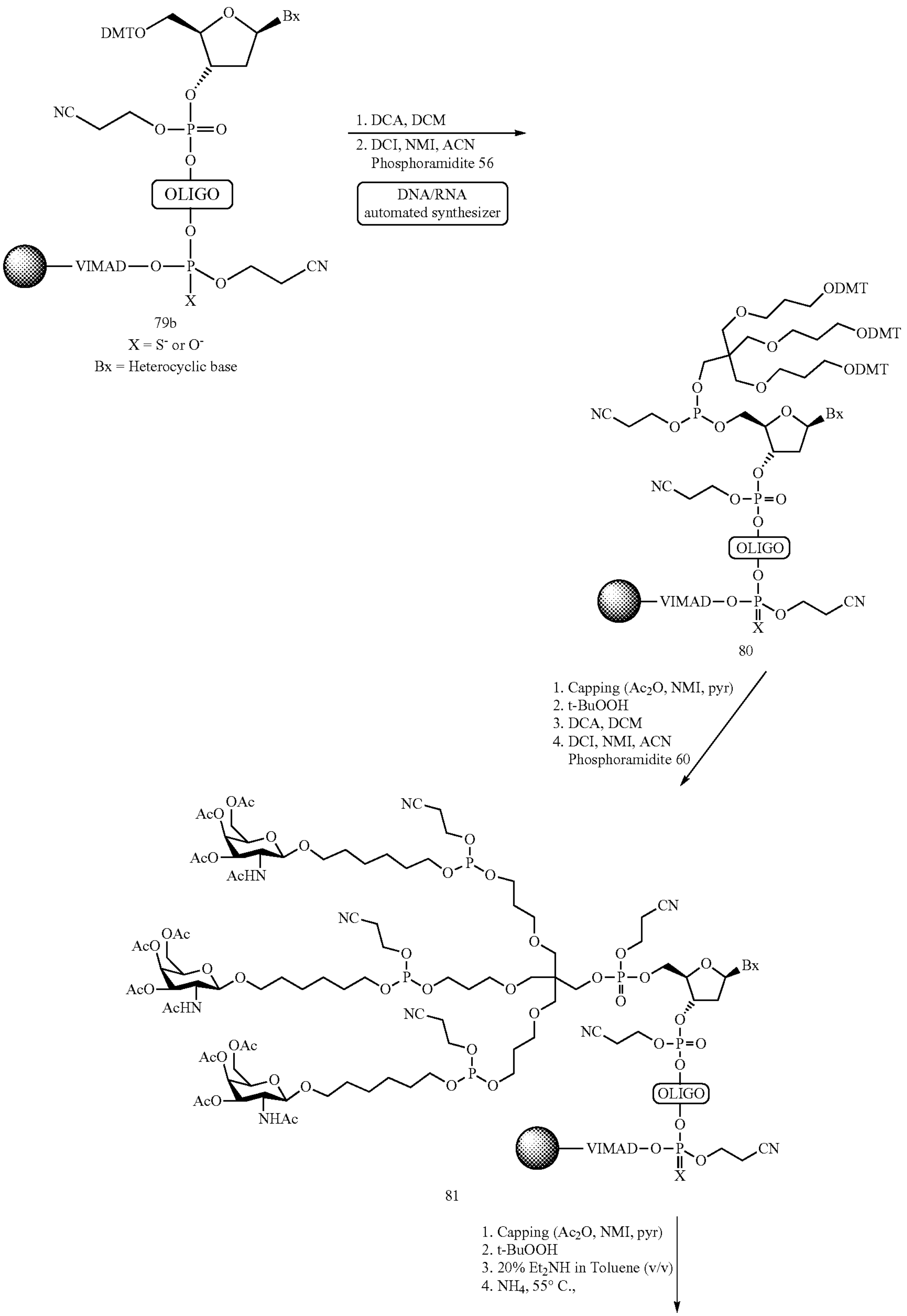
79b
X = $S^-$ or $O^-$
Bx = Heterocyclic base
80
81

-continued
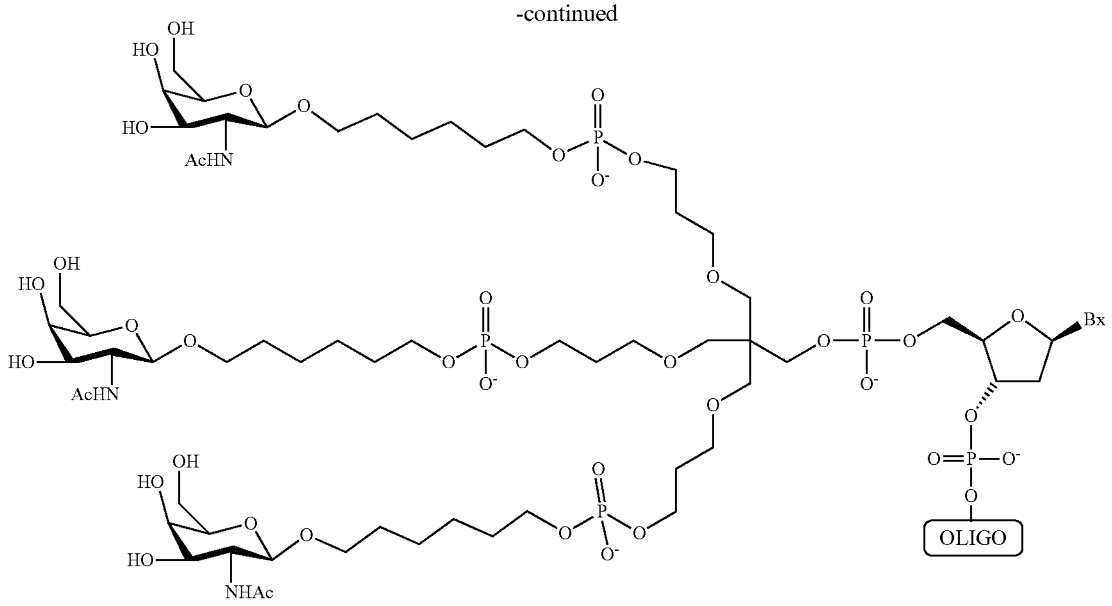
82
wherein GalNAc$_3$-2 has the structure:
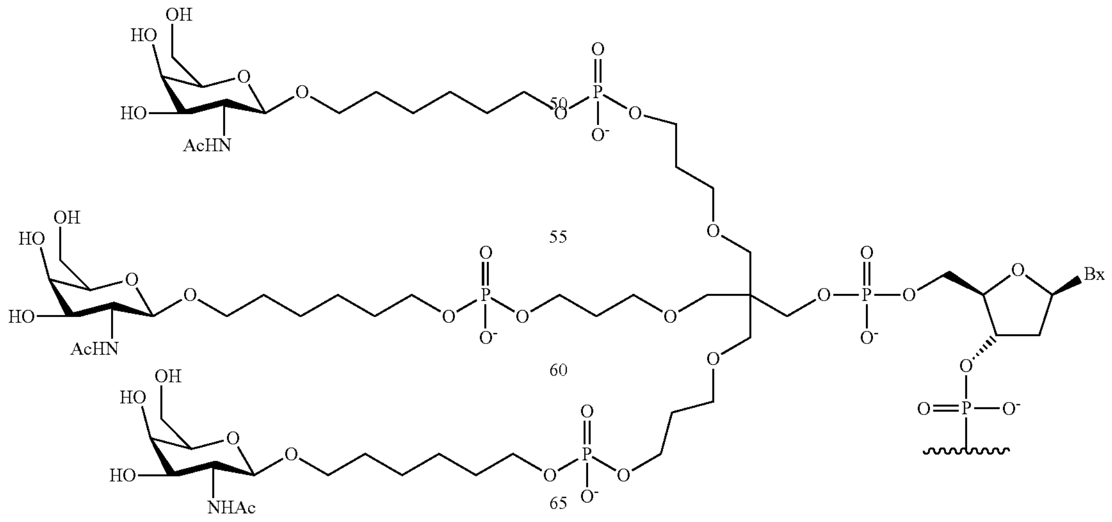

The GalNAc$_3$ cluster portion of the conjugate group GalNAc$_3$-2 (GalNAc$_3$-2$_a$) can be combined with any cleavable moiety to provide a variety of conjugate groups. Wherein GalNAc$_3$-2$_a$ has the formula:

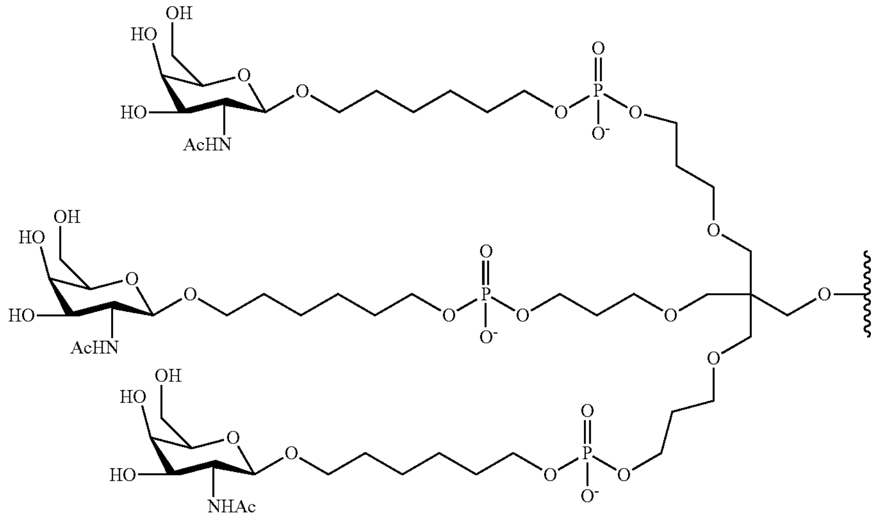

The VIMAD-bound oligomeric compound 79b was prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus. The order and quantity of phosphoramidites added to the solid support can be adjusted to prepare the oligomeric compounds as described herein having any predetermined sequence and composition.

Example 38: Alternative Method for the Preparation of Oligomeric Compound 82 Comprising a Phosphodiester Linked GalNAc$_3$-2 Conjugate at 5' Terminus (Method II)

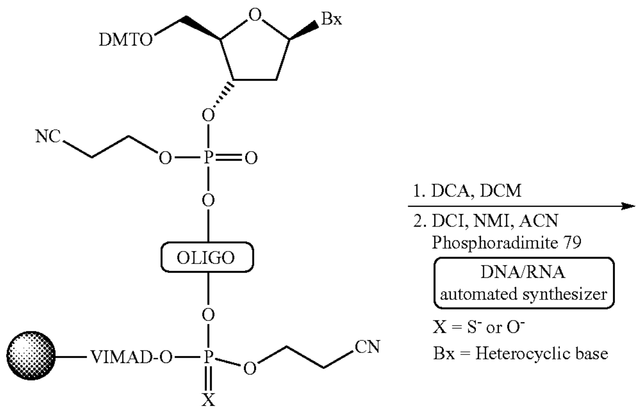

79b

-continued

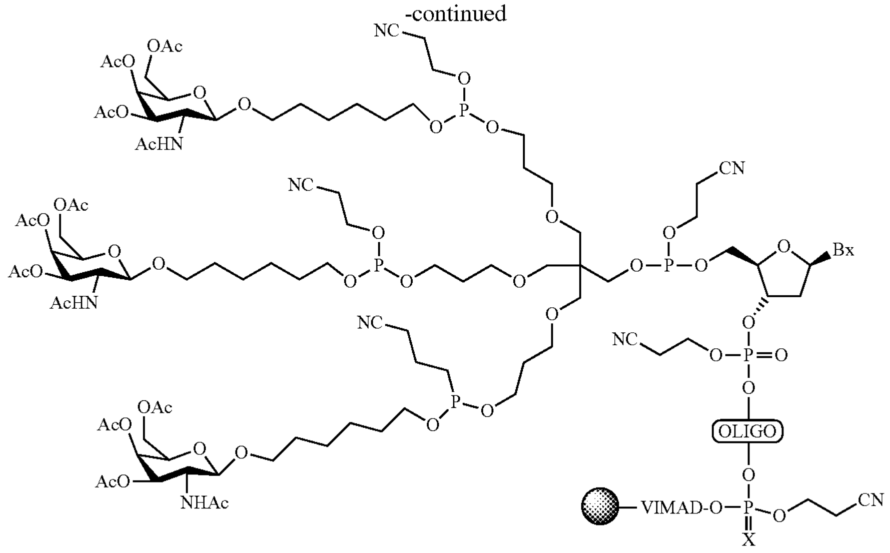

83

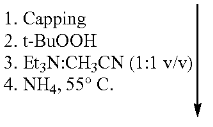

Oligomeric Compound 82

The VIMAD-bound oligomeric compound 79b was prepared using standard procedures for automated DNA/RNA synthesis (see Dupouy et al., *Angew. Chem. Int. Ed.*, 2006, 45, 3623-3627). The $GalNAc_3$-2 cluster phosphoramidite, Compound 79 was prepared as per the procedures illustrated in Example 35. This alternative method allows a one-step installation of the phosphodiester linked $GalNAc_3$-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39: General Method for the Preparation of Oligomeric Compound 83h Comprising a $GalNAc_3$-3 Conjugate at the 5' Terminus ($GalNAc_3$-1 Modified for 5' End Attachment) Via Solid Support

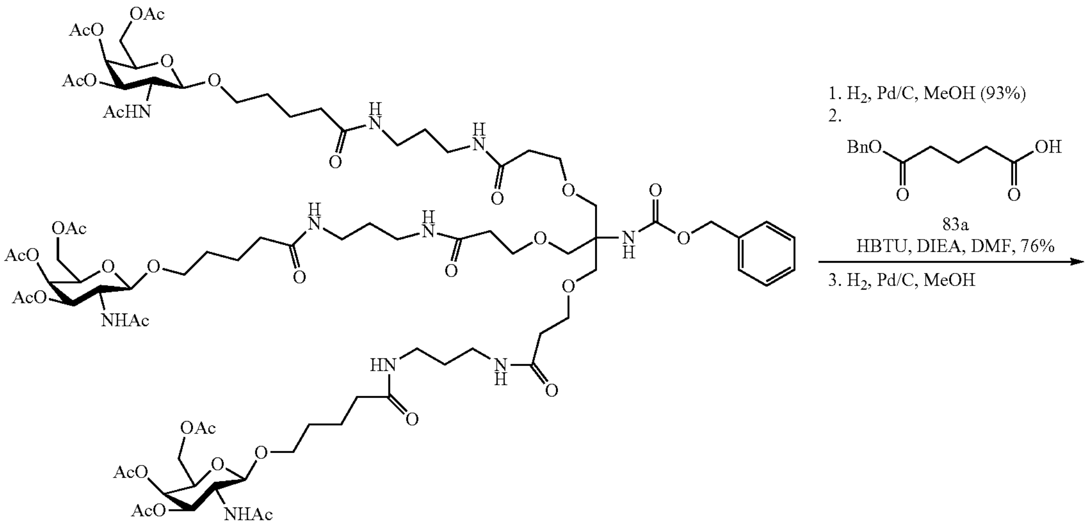

18

-continued
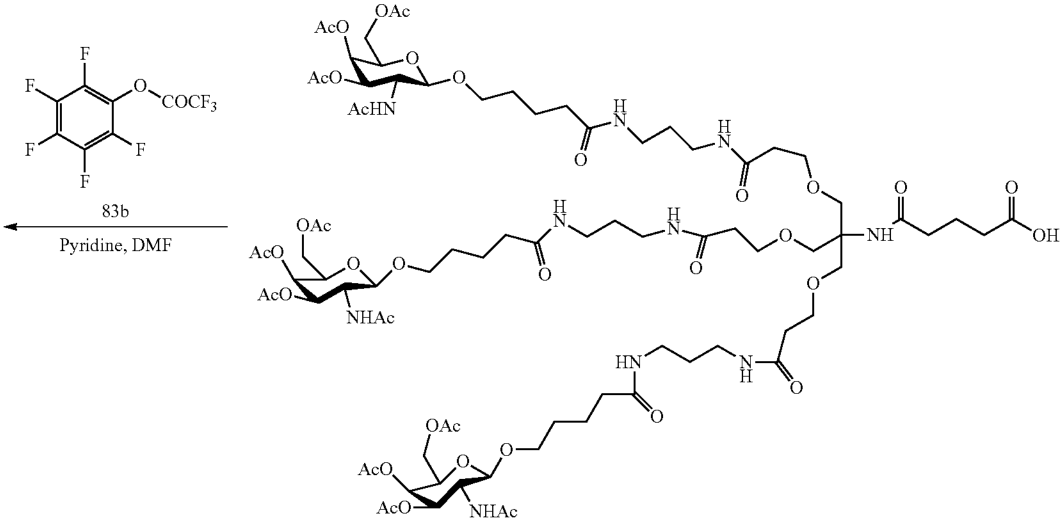
83c
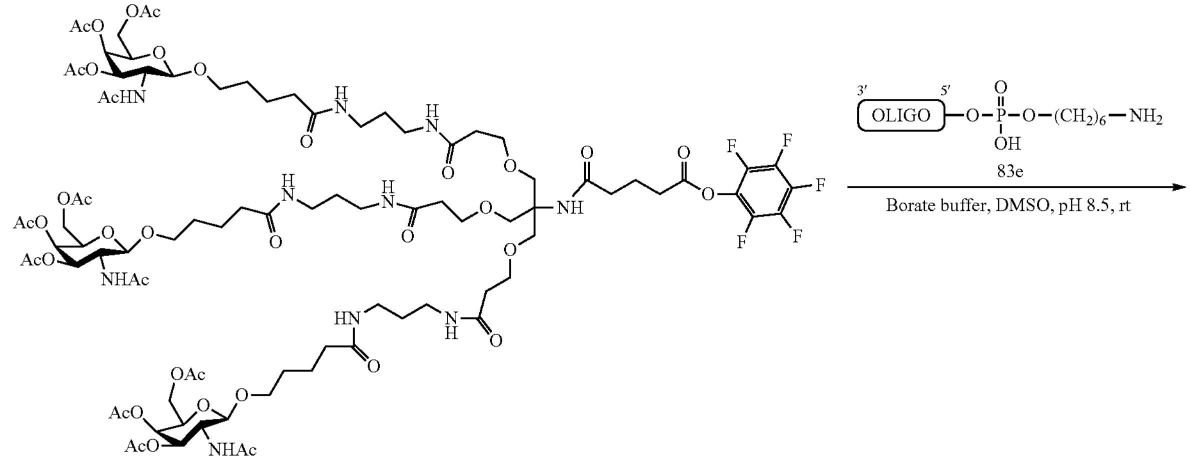
83d
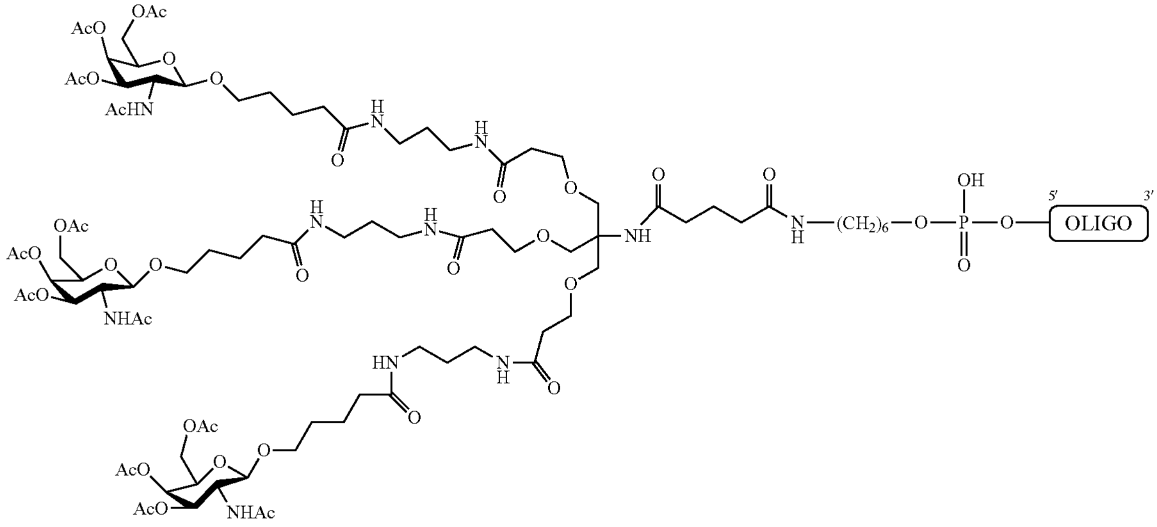
83f
Aqueous ammonia

-continued

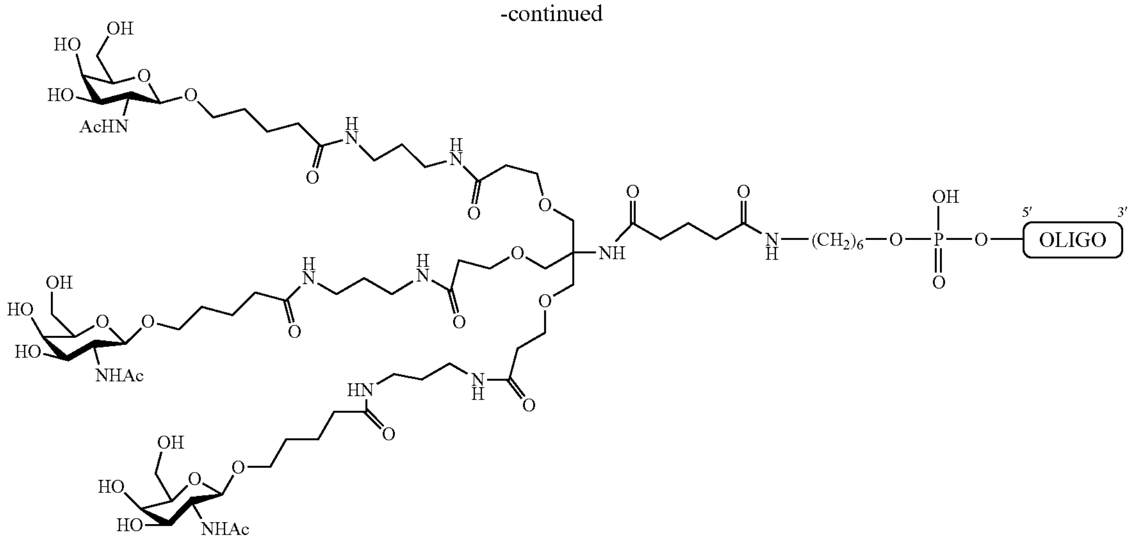

83h

Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83h).

Wherein GalNAc$_3$-3 has the structure:

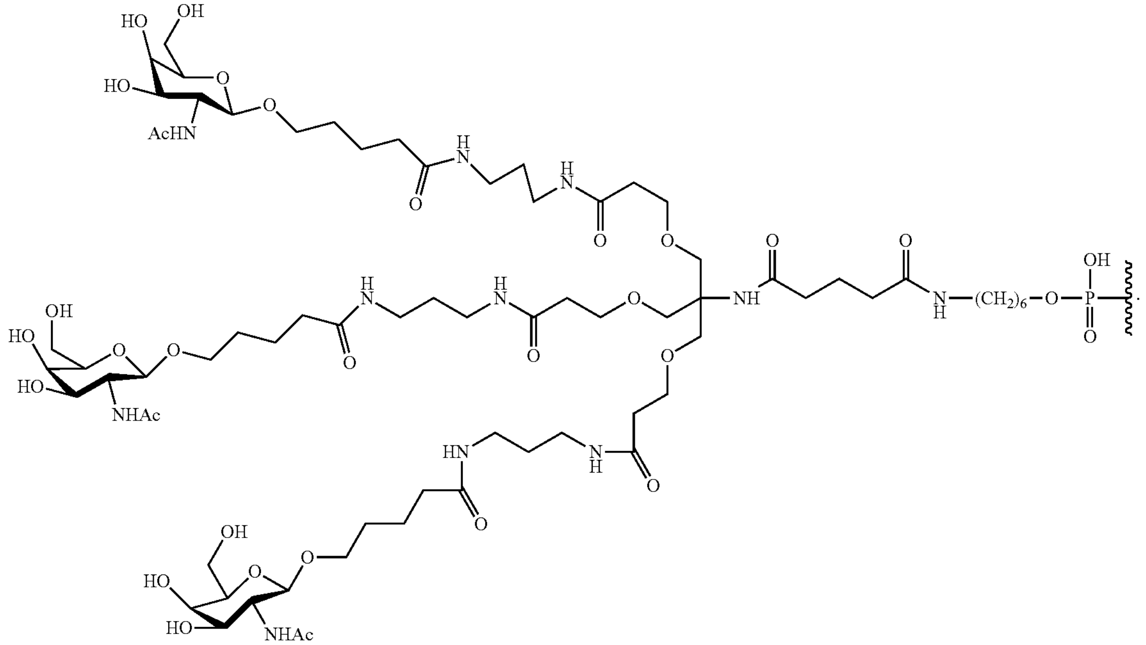

The GalNAc$_3$ cluster portion of the conjugate group GalNAc$_3$-3 (GalNAc$_3$-3$_a$) can be combined with any cleavable moiety to provide a variety of conjugate groups. Wherein GalNAc$_3$-3$_a$ has the formula:

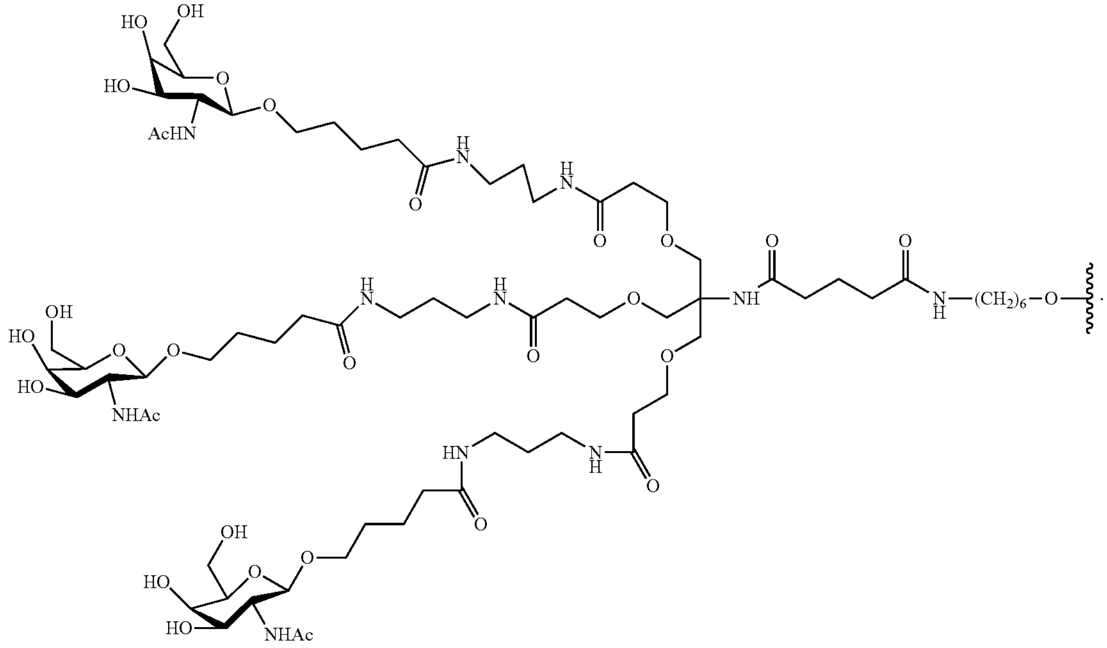
Example 40: General Method for the Preparation of Oligomeric Compound 89 Comprising a Phosphodiester Linked GalNAc$_3$-4 Conjugate at the 3' Terminus Via Solid Support
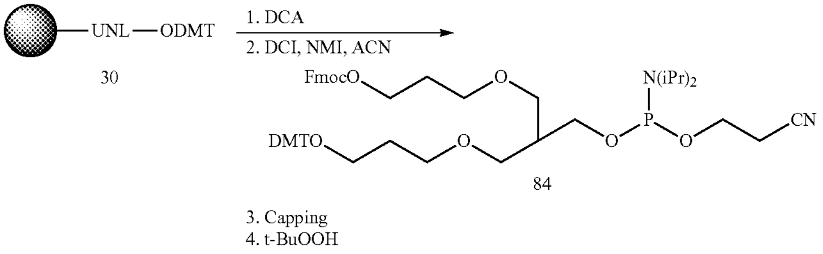
30
84
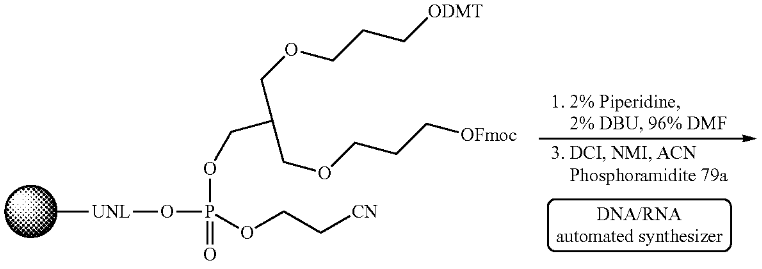
85

-continued
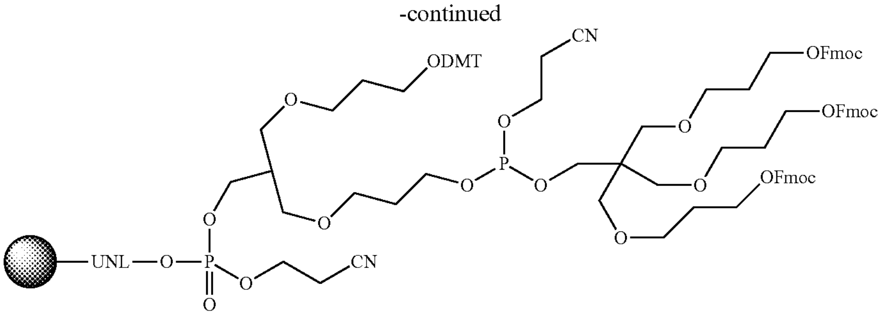
86
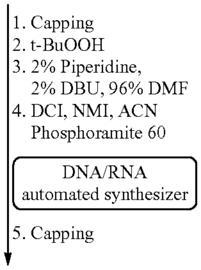
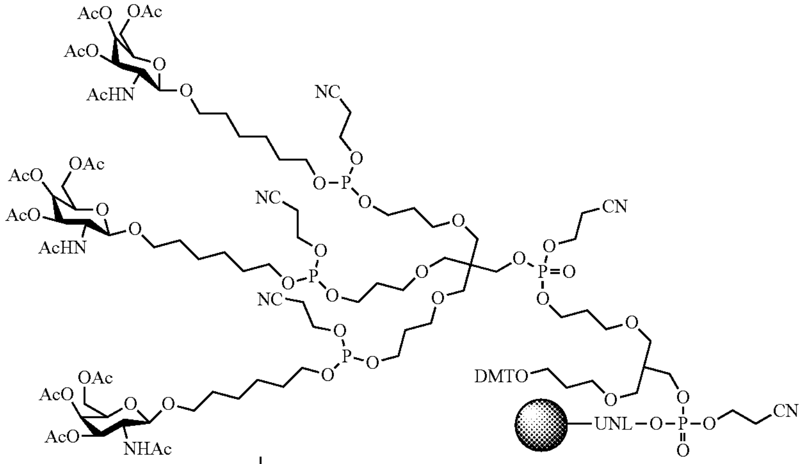
87
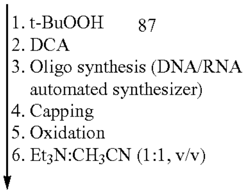

-continued
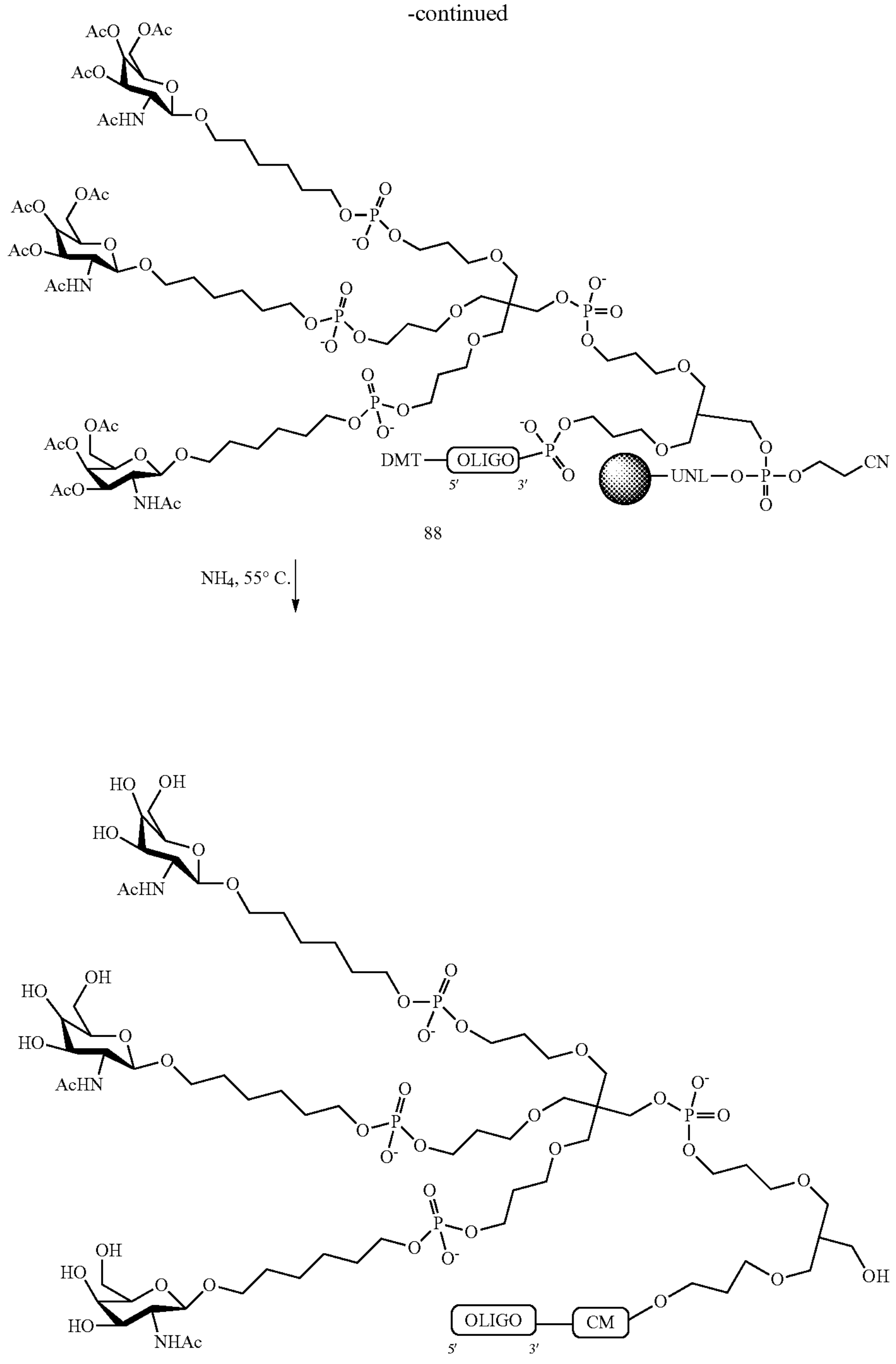
88
89
Wherein $GalNAc_3$-4 has the structure:
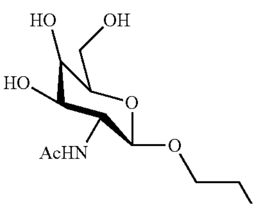

-continued
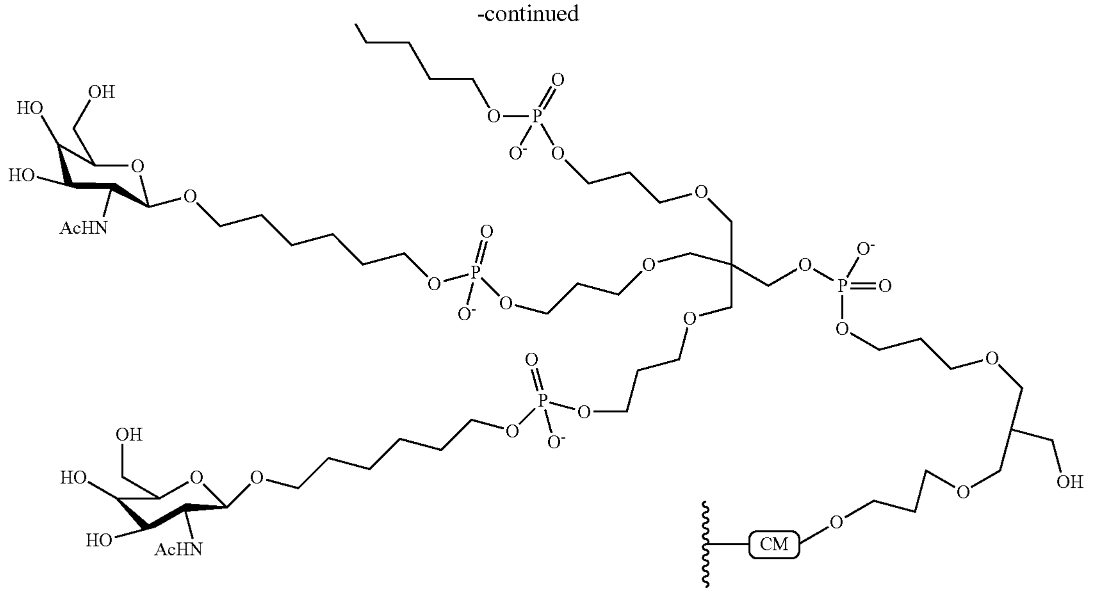
Wherein CM is a cleavable moiety. In certain embodiments, cleavable moiety is:
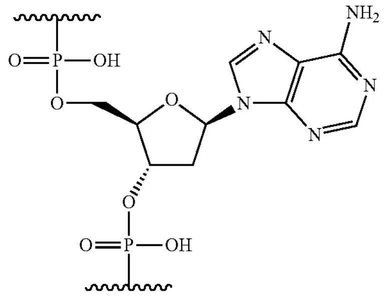 [SMILES: *P(=O)(O)OC[C@H]1O[C@@H](n2cnc3c(N)ncnc32)C[C@@H]1OP(*)(=O)O]
The $GalNAc_3$ cluster portion of the conjugate group $GalNAc_3$-4 ($GalNAc_3$-$4_a$) can be combined with any cleavable moiety to provide a variety of conjugate groups. Wherein $GalNAc_3$-$4_a$ has the formula:
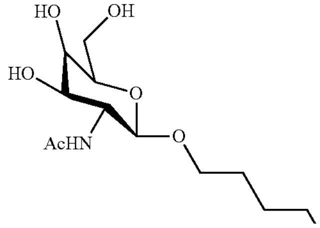

-continued

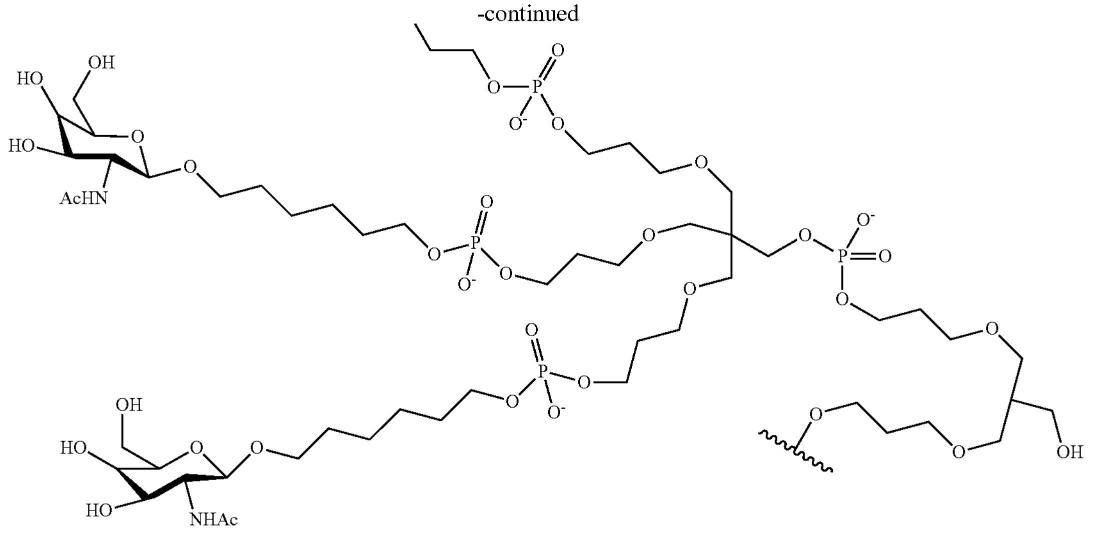

The protected Unylinker functionalized solid support Compound 30 is commercially available. Compound 84 is prepared using procedures similar to those reported in the literature (see Shchepinov et al., *Nucleic Acids Research,* 1997, 25(22), 4447-4454; Shchepinov et al., *Nucleic Acids Research,* 1999, 27, 3035-3041; and Hornet et al., *Nucleic Acids Research,* 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41: General Method for the Preparation of ASOs Comprising a Phosphodiester Linked GalNAc$_3$-2 (See Example 37, Bx is Adenine) Conjugate at the 5' Position Via Solid Phase Techniques (Preparation of ISIS 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^{m}$C residues. Phosphoramidite compounds 56 and 60 were used to synthesize the phosphodiester linked GalNAc$_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous $CH_3CN$ was used as activator during the coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in CH3CN containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min−1, =260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 34

ASO comprising a phosphodiester linked GalNAc$_3$-2 conjugate at the 5' position targeting SRB-1

| ISIS No. | Sequence (5' to 3') | CalCd Mass | Observed Mass | SEQ ID No. |
|---|---|---|---|---|
| 661134 | **GalNAc3-2$_a$-o'Ado**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | 6482.2 | 6481.6 | 141 |

Subscripts: "e" indicates 2'-MOE modified nucleoside; "d" indicates β-D-2'-deoxyribonucleoside; "k" indicates 6'-(S)—$CH_3$ bicyclic nucleoside (e.g. cEt); "s" indicates phosphorothioate internucleoside linkages (PS); "o" indicates phosphodiester internucleoside linkages (PO); and "o'" indicates —O—P(═O)(OH)—. Superscript "m" indicates 5-methylcytosines. The structure of GalNAc$_3$-2$_a$ is shown in Example 37.

Example 42: General Method for the Preparation of ASOs Comprising a GalNAc$_3$-3 Conjugate at the 5' Position Via Solid Phase Techniques (Preparation of ISIS 661166)

The synthesis for ISIS 661166 was performed using similar procedures as illustrated in Examples 39 and 41.

ISIS 661166 is a 5-10-5 MOE gapmer, wherein the 5' position comprises a GalNAc$_3$-3 conjugate. The ASO was characterized by ion-pair-HPLC coupled MS analysis with Agilent 1100 MSD system.

TABLE 34a

ASO comprising a GalNAc$_3$-3 conjugate at the 5' position via a hexylamino phosphodiester linkage targeting Malat-1

| ISIS No. | Sequence (5' to 3') | Conjugate | Calcd Mass | Observed Mass | SEQ ID No. |
|---|---|---|---|---|---|
| 661166 | 5'-**GalNAc3-3a-o'**$^{m}C_{es}G_{es}G_{es}T_{es}G_{es}$ $^{m}C_{ds}A_{ds}A_{ds}G_{ds}G_{ds}{}^{m}C_{ds}T_{ds}T_{ds}A_{ds}G_{ds}$ $G_{es}A_{es}A_{es}T_{es}T_{e}$ | **5'-GalNAc3-3** | 8992.16 | 8990.51 | 142 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(═O)(OH)—. Superscript "m" indicates 5-methylcytosines. The structure of "5'-GalNAc$_3$-3a" is shown in Example 39.

Example 43: Dose-Dependent Study of Phosphodiester Linked GalNAc$_{3-2}$ (See Examples 37 and 41, Bx is Adenine) at the 5' Terminus Targeting SRB-1 In Vivo ISIS 661134 (see Example 41) comprising a phosphodiester linked GalNAc$_3$-2 conjugate at the 5' terminus was tested in a dose-dependent study for antisense inhibition of SRB-1 in mice. Unconjugated ISIS 440762 and 651900 (GalNAc$_3$-1 conjugate at 3' terminus, see Example 9) were included in the study for comparison and are described previously in Table 17.

Treatment

Six week old male Balb/c mice (Jackson Laboratory, Bar Harbor, ME) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are presented below.

As illustrated in Table 35, treatment with antisense oligonucleotides lowered SRB-1 mRNA levels in a dose-dependent manner. Indeed, the antisense oligonucleotides comprising the phosphodiester linked GalNAc$_3$-2 conjugate at the 5' terminus (ISIS 661134) or the GalNAc$_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked GalNAc$_3$-2 conjugate at the 5' terminus was equipotent compared to ISIS 651900, which comprises the GalNAc$_3$-1 conjugate at the 3' terminus.

TABLE 35

ASOs containing GalNAc$_3$-1 or GalNAc$_3$-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| PBS | 0 | 100 | — | — | |
| 440762 | 0.2 | 116 | 2.58 | No conjugate | 137 |
| | 0.7 | 91 | | | |
| | 2 | 69 | | | |
| | 7 | 22 | | | |
| | 20 | 5 | | | |
| 651900 | 0.07 | 95 | 0.26 | 3' GalNAc$_3$-1 | 138 |
| | 0.2 | 77 | | | |
| | 0.7 | 28 | | | |
| | 2 | 11 | | | |
| | 7 | 8 | | | |
| 661134 | 0.07 | 107 | 0.25 | 5' GalNAc$_3$-2 | 141 |
| | 0.2 | 86 | | | |
| | 0.7 | 28 | | | |
| | 2 | 10 | | | |
| | 7 | 6 | | | |

Structures for 3' GalNAc$_3$-1 and 5' GalNAc$_3$-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' GalNAc$_3$-2) and ISIS 651900 (3' GalNAc$_3$-1) were identified and their masses were confirmed by high resolution mass spectrometry analysis. The results showed that the major metabolite detected for the ASO comprising a phosphodiester linked GalNAc$_3$-2 conjugate at the 5' terminus (ISIS 661134) was ISIS 440762 (data not shown). No additional metabolites, at a detectable level, were observed. Unlike its counterpart, additional metabolites similar to those reported previously in Table 23a were observed for the ASO having the GalNAc$_3$-1 conjugate at the 3' terminus (ISIS 651900). These results suggest that having the phosphodiester linked GalNAc$_3$-1 or GalNAc$_3$-2 conjugate may improve the PK profile of ASOs without compromising their potency.

Example 44: Effect of PO/PS Linkages on Antisense Inhibition of ASOs Comprising GalNAc$_3$-1 Conjugate (See Example 9) at the 3' Terminus Targeting SRB-1

ISIS 655861 and 655862 comprising a GalNAc$_3$-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table 36, below.

TABLE 36

Modified ASOs comprising GalNAc$_3$-1 conjugate at the 3' terminus targeting SRB-I

| ISIS No. | Sequence (5' to 3') | Chemistry | SEQ ID No. |
|---|---|---|---|
| 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}T_{es}T_{e}$ | Full PS no conjugate | 143 |
| 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}T_{es}T_{eo}$ **$A_{do'}$-GalNAc$_3$-1$_a$** | Full PS with **GalNAc$_3$-1** conjugate | 144 |
| 655862 | $G_{es}{}^{m}C_{es}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}T_{eo}T_{eo}$ **$A_{do'}$-GalNAc$_3$-1$_a$** | Mixed PS/PO with **GalNAc$_3$-1** conjugate | 144 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(═O)(OH)—. Superscript "m" indicates 5-methylcytosines. The structure of "GalNAc$_3$-1" is shown in Example 9.

Treatment

Six week old male Balb/c mice (Jackson Laboratory, Bar Harbor, ME) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are reported below.

As illustrated in Table 37, treatment with antisense oligonucleotides lowered SRB-1 mRNA levels in a dose-dependent manner compared to PBS treated control. Indeed, the antisense oligonucleotides comprising the GalNAc$_3$-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 37

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | ED$_{50}$ (mg/kg) | Chemistry | SEQ ID No. |
|---|---|---|---|---|---|
| PBS | 0 | 100 | — | — | |
| 353382 (parent) | 3 | 76.65 | 10.4 | Full PS without conjugate | 143 |
| | 10 | 52.40 | | | |
| | 30 | 24.95 | | | |
| 655861 | 0.5 | 81.22 | 2.2 | Full PS with GalNAc$_3$-1 conjugate | 144 |
| | 1.5 | 63.51 | | | |
| | 5 | 24.61 | | | |
| | 15 | 14.80 | | | |
| 655862 | 0.5 | 69.57 | 1.3 | Mixed PS/PO with GalNAc$_3$-1 conjugate | 144 |
| | 1.5 | 45.78 | | | |
| | 5 | 19.70 | | | |
| | 15 | 12.90 | | | |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 38) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 38

Effect of PO/PS linkages on transaminase levels of ASOs comprising GalNAc$_3$-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — | |
| 353382 (parent) | 3 | 50.25 | 89 | Full PS without conjugate | 143 |
| | 10 | 27.5 | 79.3 | | |
| | 30 | 27.3 | 97 | | |
| 655861 | 0.5 | 28 | 55.7 | Full PS with GalNAc$_3$-1 | 144 |
| | 1.5 | 30 | 78 | | |
| | 5 | 29 | 63.5 | | |
| | 15 | 28.8 | 67.8 | | |
| 655862 | 0.5 | 50 | 75.5 | Mixed PS/PO with GalNAc$_3$-1 | 144 |
| | 1.5 | 21.7 | 58.5 | | |
| | 5 | 29.3 | 69 | | |
| | 15 | 22 | 61 | | |

Example 45: Preparation of PFP Ester, Compound 110a
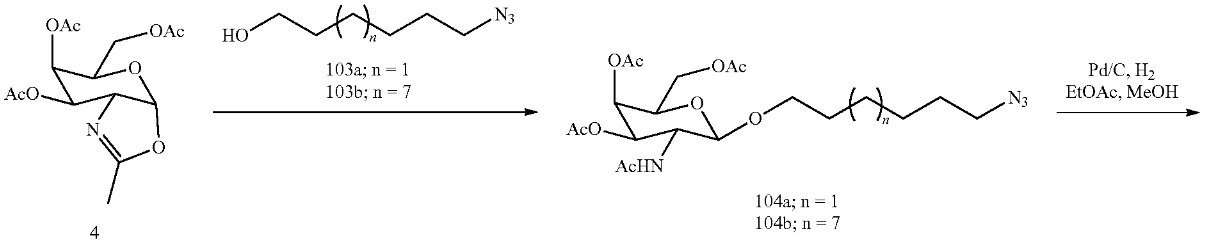
4
104a; n = 1
104b; n = 7
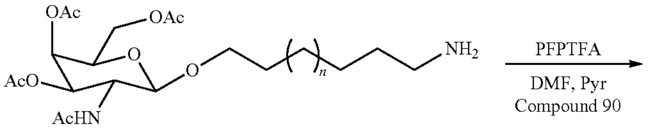
105a; n = 1
105b; n = 7
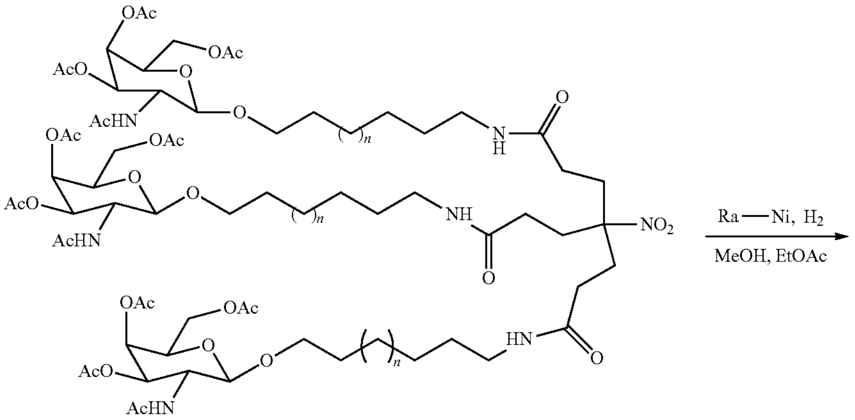
106a; n = 1
106b; n = 7
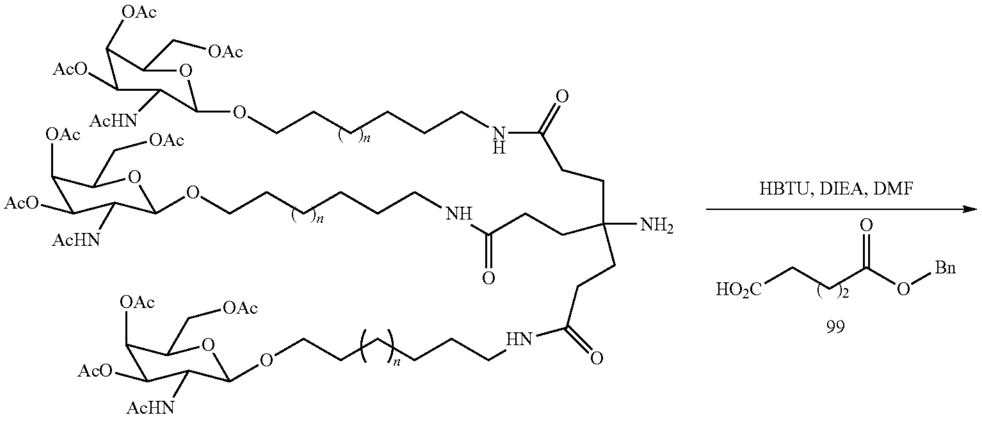
107a; n = 1
107b; n = 7

-continued
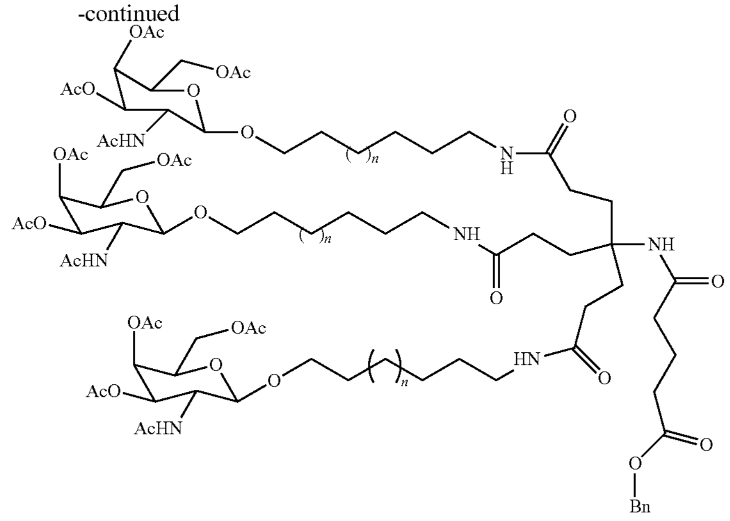
108a; n = 1
108b; n = 7
108a; n = 1
108b; n = 7
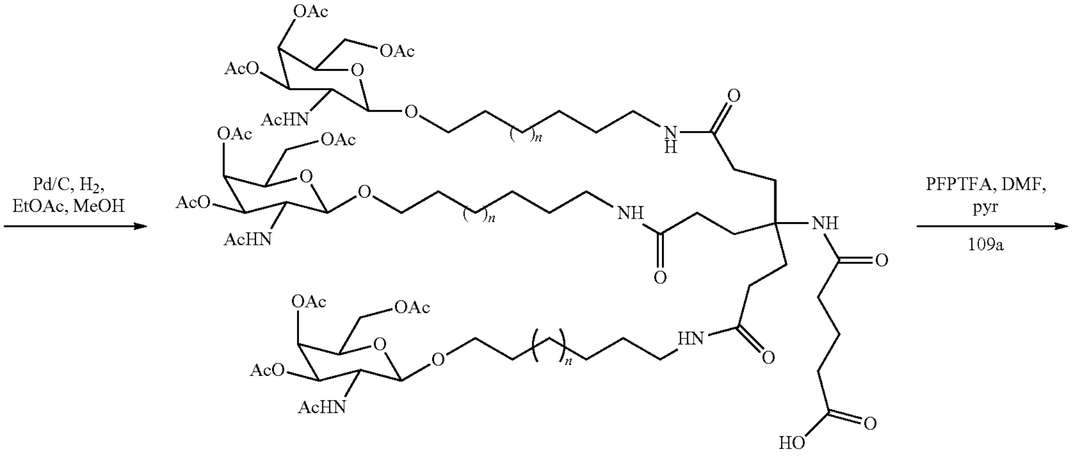
109a; n = 1
109b; n = 7
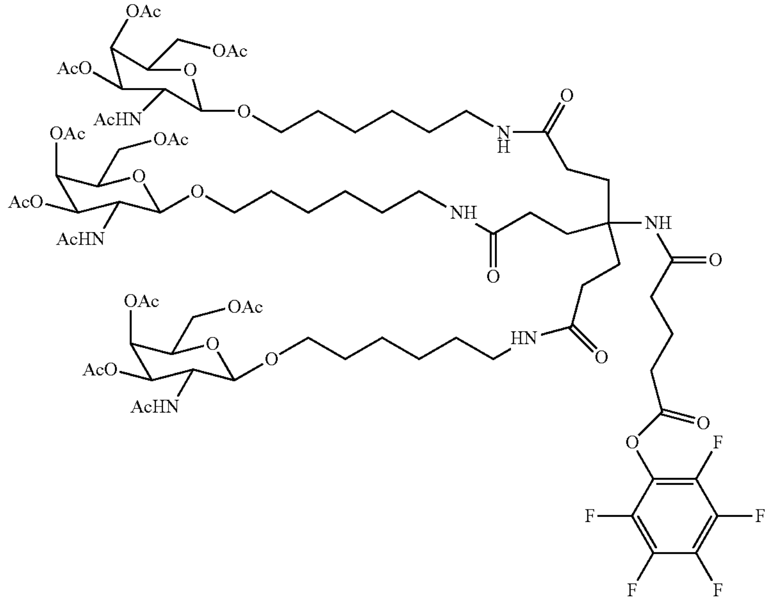
110a Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%→10% methanol/dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100a-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46: General Procedure for Conjugation with PFP Esters (Oligonucleotide 111); Preparation of ISIS 666881 (GalNAc$_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5

(200 μL) and 3 equivalents of a selected PFP esterified GalNAc3 cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the GalNAc$_3$ conjugated oligonucleotide.

110a

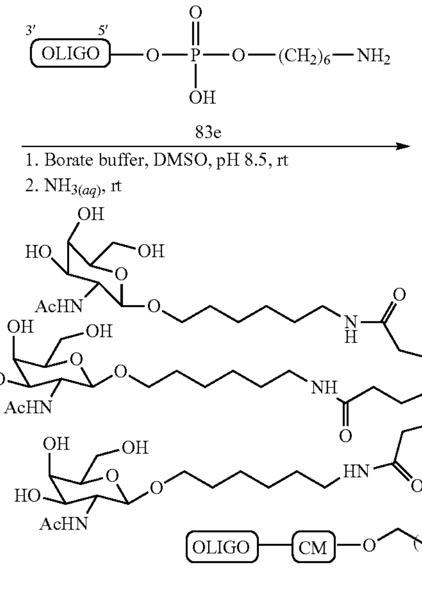

111

Oligonucleotide 111 is conjugated with GalNAc$_3$-10. The GalNAc3 cluster portion of the conjugate group GalNAc$_3$-10 (GalNAc$_3$-10$_a$) can be combined with any cleavable moiety to provide a variety of conjugate groups. In certain embodiments, the cleavable moiety is —P(═O)(OH)-A$_d$-P(═O)(OH)— as shown in the oligonucleotide (ISIS 666881) synthesized with GalNAc$_3$-10 below. The structure of GalNAc$_3$-10 (GalNAc$_3$-10$_a$-CM-) is shown below:

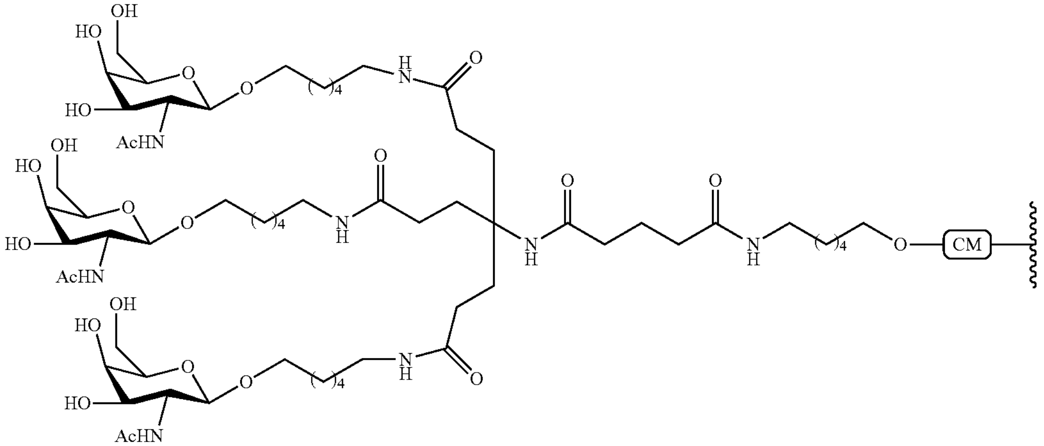

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 μmop was dissolved in 0.1 M sodium tetraborate, pH 8.5 (200 μL) and 3 equivalents PFP ester (Compound 110a) dissolved in DMSO (50 μL) was added. The PFP ester precipitated upon addition to the ASO solution requiring additional DMSO (600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 μmol).

GalNAc$_3$-10 conjugated oligonucleotide

| ASO | Sequence (5' to 3') | 5' group | SEQ ID No. |
|---|---|---|---|
| ISIS 660254 | $NH_2(CH_2)_6$-$_oA_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | Hexylamine | 145 |
| ISIS 666881 | GalNAc$_3$-10$_{a-o'}A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | **GalNAc3-10** | 145 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

Example 47: Preparation of Oligonucleotide 102 Comprising GalNAc$_3$-8

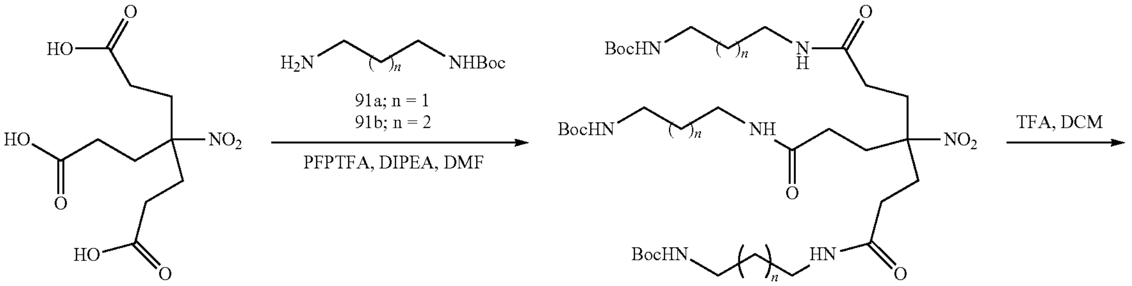

90

92a; n = 1
92b; n = 2

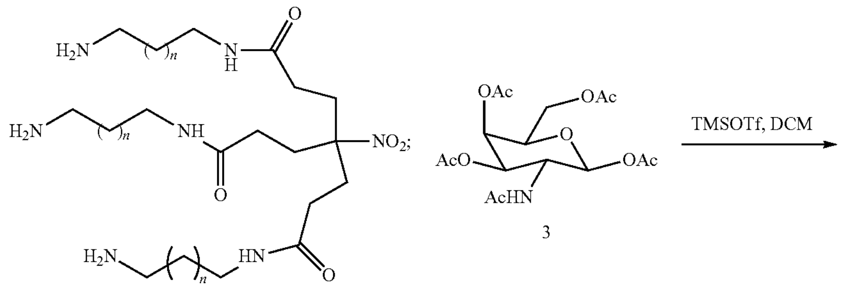

93a; n = 1
93b; n = 2

3

-continued
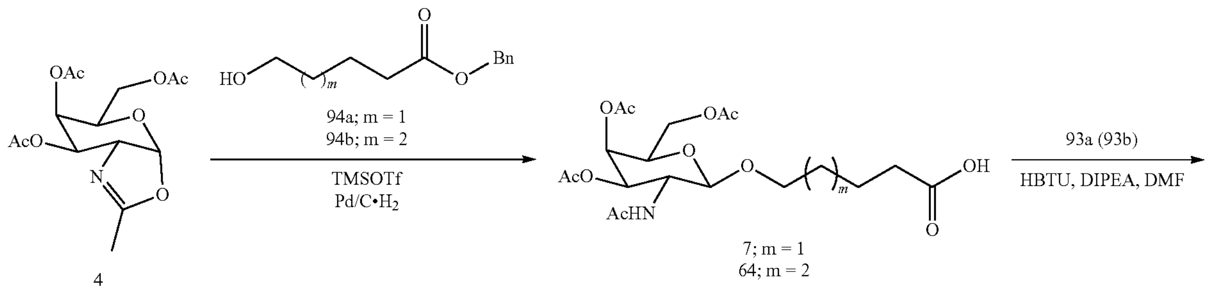
4
7; m = 1
64; m = 2
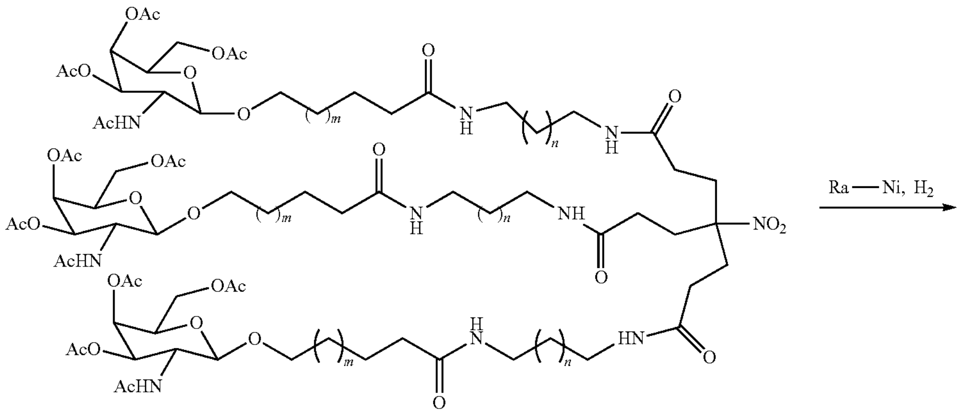
96a; n = 1, m = 1
96b; n = 1, m = 2
96c; n = 2, m = 1
96d: n = 2. m = 2
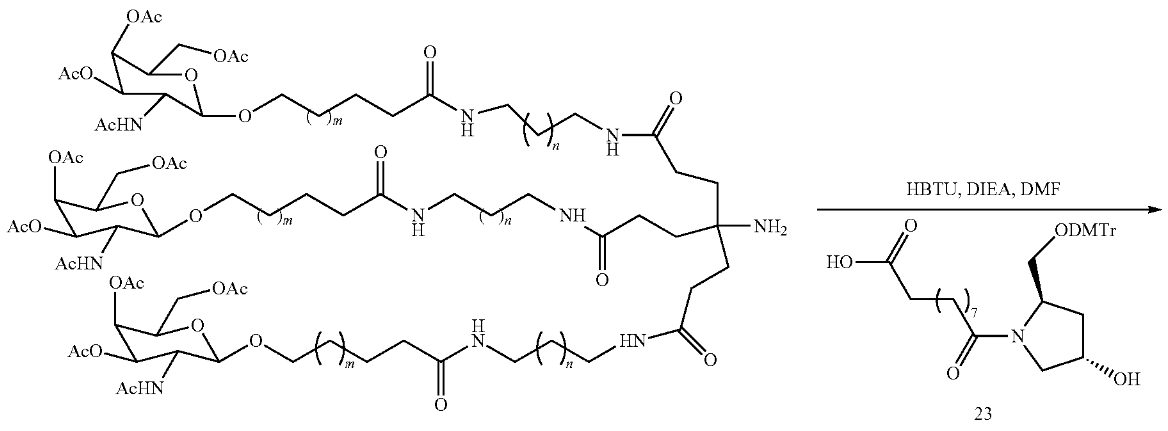
23
97a; n = 1, m = 1
97b; n = 1, m = 2
97c; n = 2, m = 1
97d; n = 2, m = 2

-continued
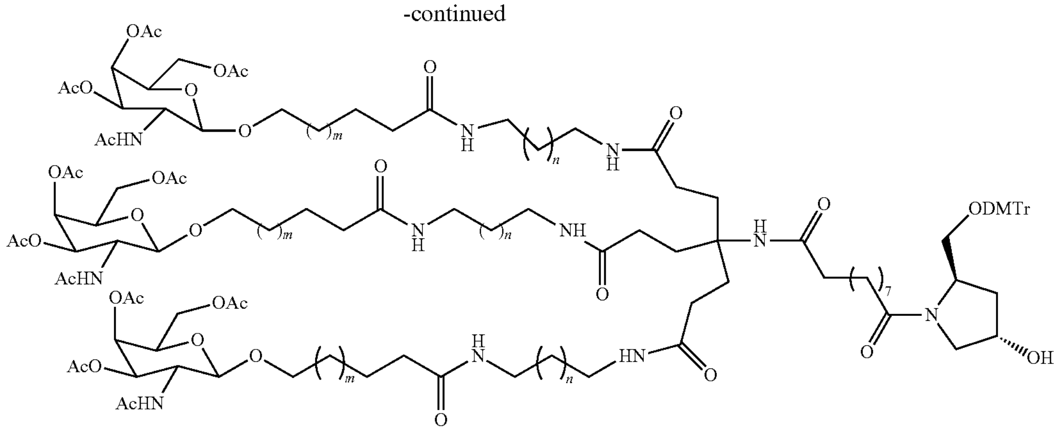
98a; n = 1, m = 1
98b; n = 1, m = 2
98c; n = 2, m = 1
98d; n = 2, m = 2
97a; n = 1, m = 1
97b; n = 1, m = 2
97c; n = 2, m = 1
97d; n = 2, m = 2
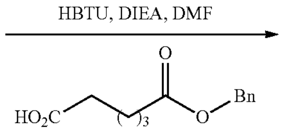
99
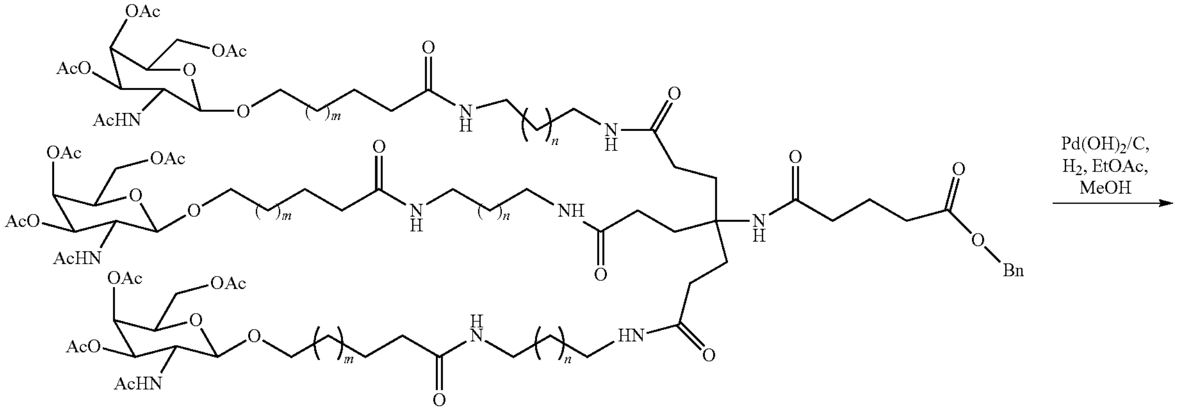
100a; n = 1, m = 1
100b; n = 1, m = 2
100c: n = 2, m = 1
100d: n = 2, m = 2
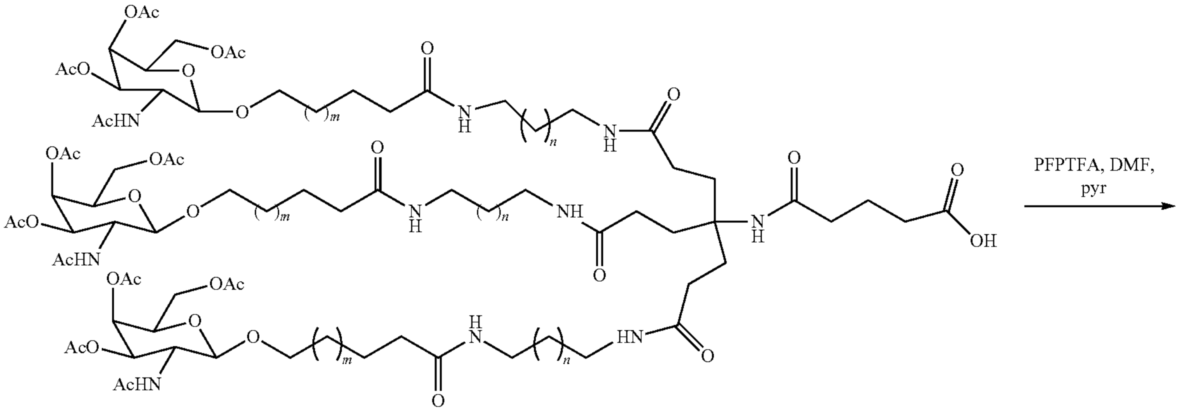
101a; n = 1, m = 1
101b; n = 1, m = 2
101c: n = 2, m = 1
101d: n = 2, m = 2

-continued

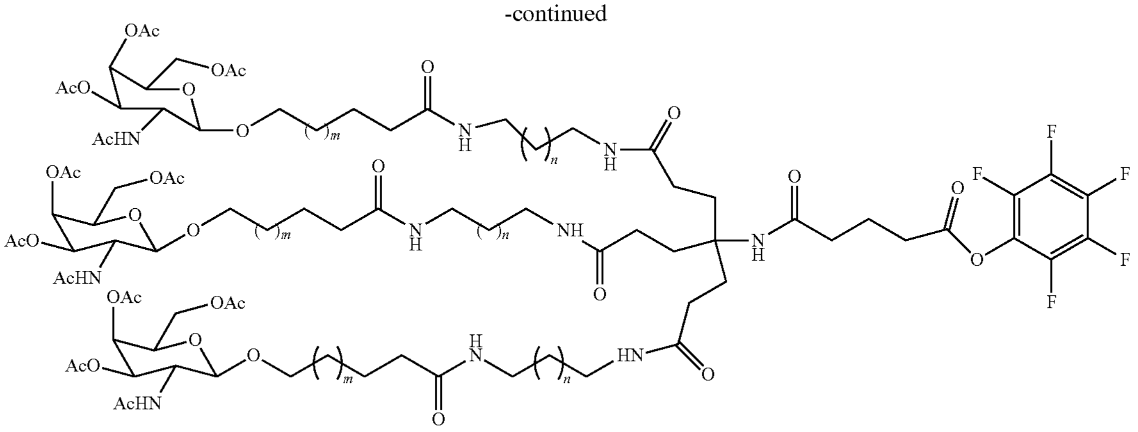

102a; n = 1, m = 1
102b; n = 1, m = 2
102c: n = 2, m = 1
102d: n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→10% methanol/dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 100a-d in 40-60% yield. LCMS and proton NMR was consistent with the structure.

Compounds 100a-d (0.16 mmoles), individually, were hydrogenated over 10% $Pd(OH)_2/C$ for 3 hours in methanol/ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol/dichloromethane) to give compounds 102a-d in an approximate 80% yield. LCMS and proton NMR were consistent with the structure.

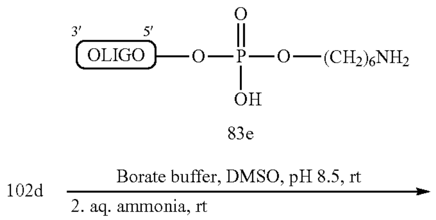

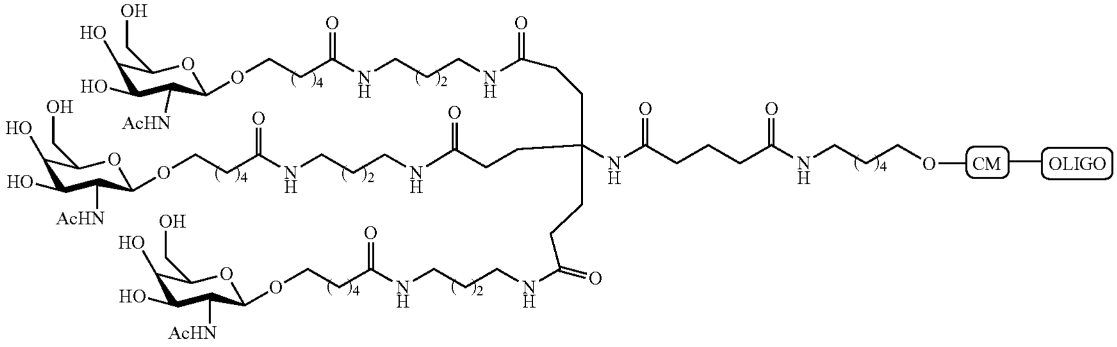

102

Oligomeric Compound 102, comprising a $GalNAc_3$-8 conjugate group, was prepared using the general procedures illustrated in Example 46. The GalNAc3 cluster portion of the conjugate group $GalNAc_3$-8 ($GalNAc_3$-$8_a$) can be combined with any cleavable moiety to provide a variety of conjugate groups. In a preferred embodiment, the cleavable moiety is —P(=O)(OH)-$A_d$-P(=O)(OH)—.

The structure of $GalNAc_3$-8 ($GalNAc_3$-$8_a$-CM-) is shown below:

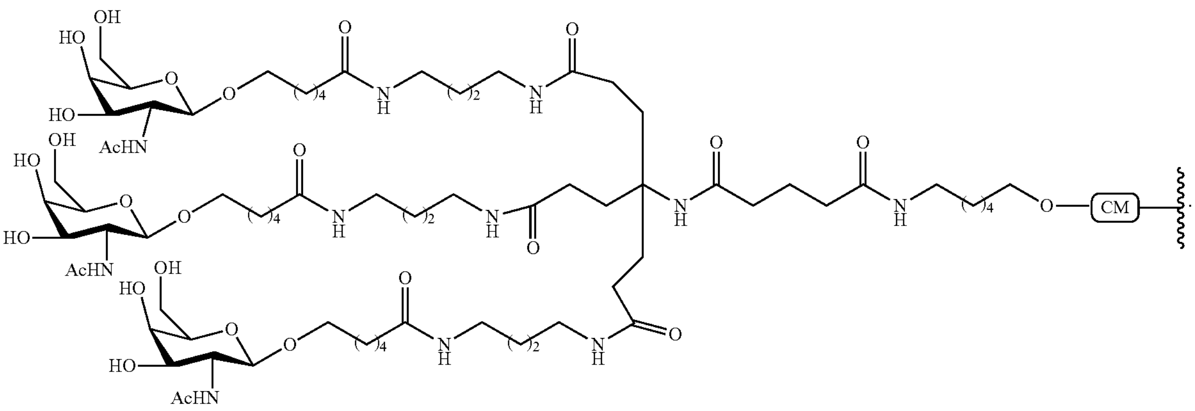

Example 48: Preparation of Oligonucleotide 119 Comprising $GalNAc_3$-7
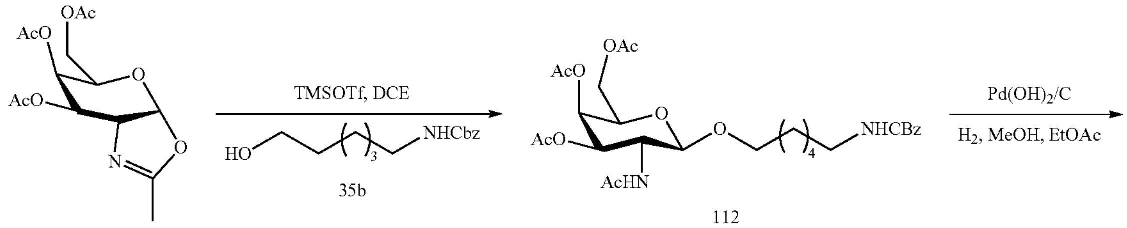
4
35b
112
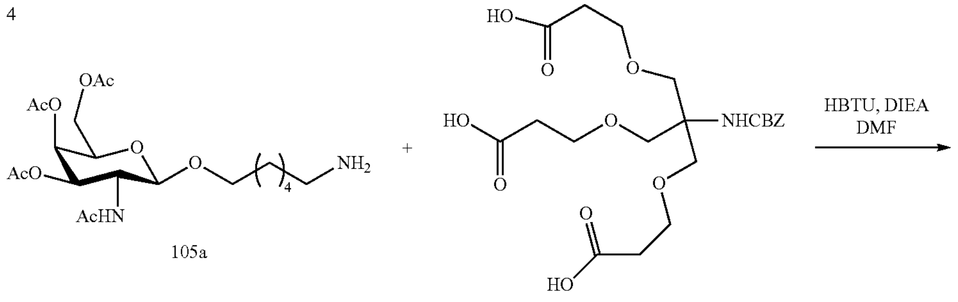
105a
113
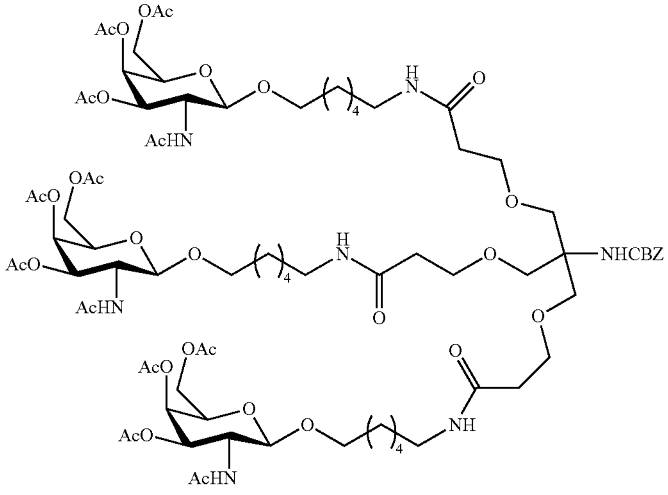
114
114
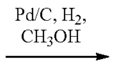
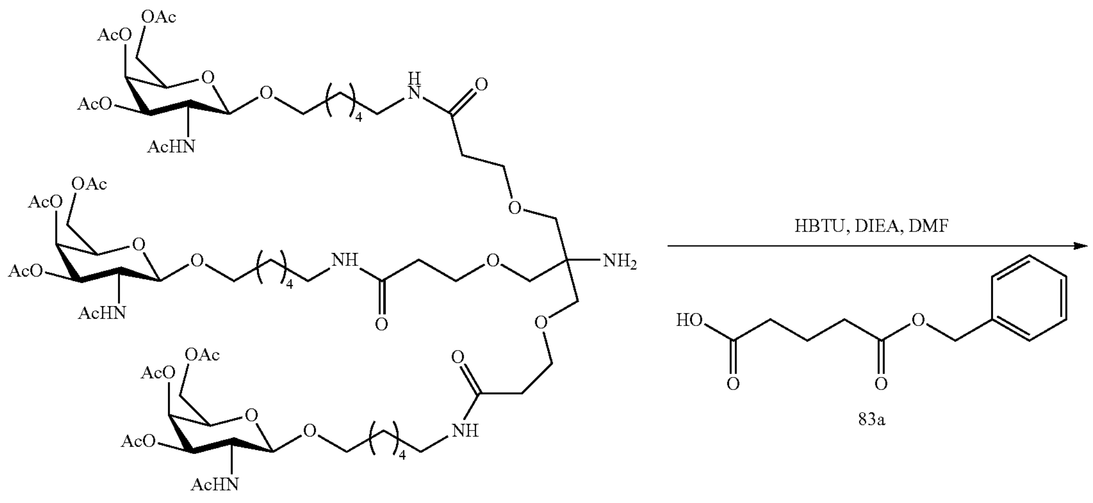
83a
115

-continued

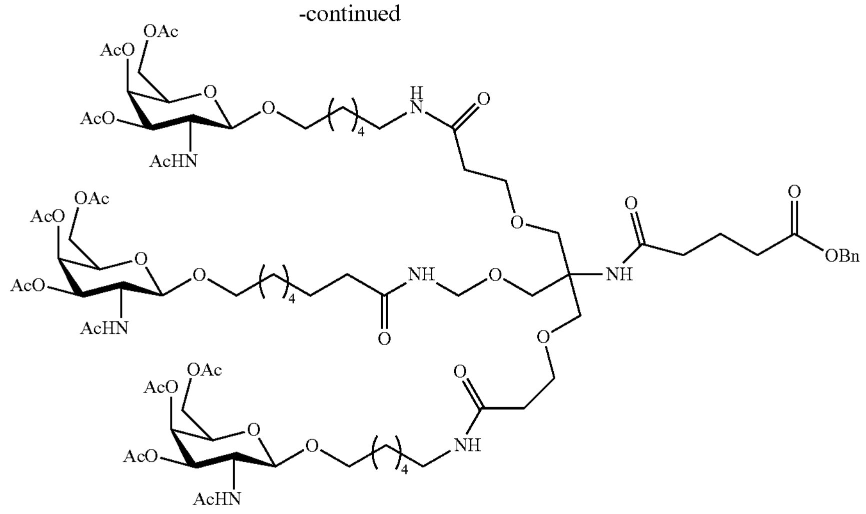

116

Compound 112 was synthesized following the procedure described in the literature (*J. Med. Chem.* 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in $CH_2Cl_2$ (100 mL) and washed with aqueous saturated $NaHCO_3$ solution (100 mL) and brine (100 mL). The organic phase was separated, dried ($Na_2SO_4$), filtered and evaporated. The residue was purified by silica gel column chromatography and eluted with 10 to 20% MeOH in dichloromethane to yield Compound 114 (1.45 g, 30%). The structure was confirmed by LCMS and $^1$H NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1$H NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in $CH_2Cl_2$. The organic layer was washed aqueous saturated $NaHCO_3$ solution and brine and dried over anhydrous $Na_2SO_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1$H NMR analysis.

116
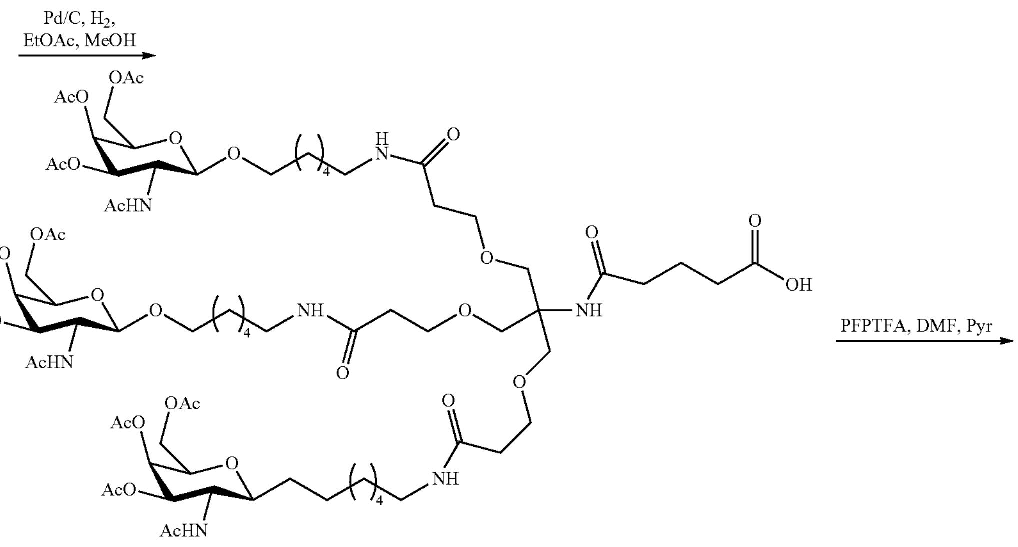

117

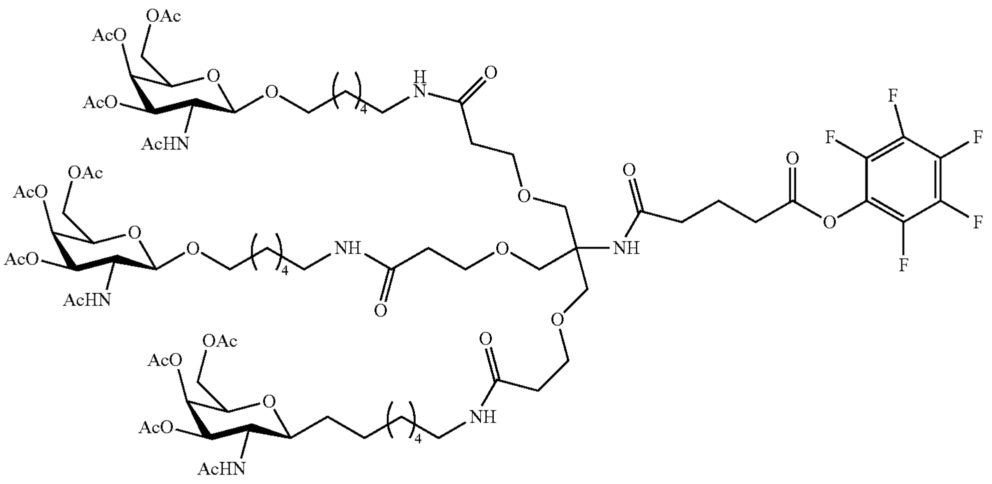

118

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^1H$ NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated $NaHCO_3$ solution. The mixture was extracted with dichloromethane, washed with brine and dried over anhydrous $Na_2SO_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1H$ and $^1H$ and $^{19}F$ NMR.

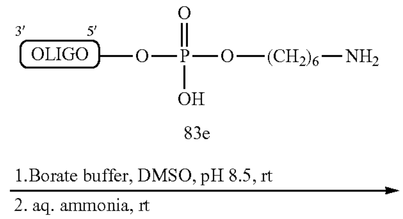

83e

118

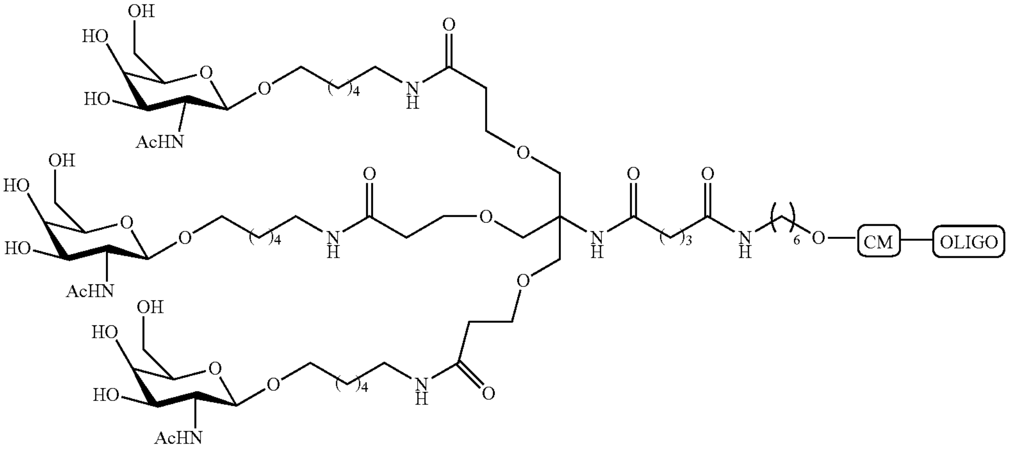

119

Oligomeric Compound 119, comprising a $GalNAc_3$-7 conjugate group, was prepared using the general procedures illustrated in Example 46. The GalNAc3 cluster portion of the conjugate group $GalNAc_3$-7 ($GalNAc_3$-$7_a$) can be combined with any cleavable moiety to provide a variety of conjugate groups. In certain embodiments, the cleavable moiety is —P(═O)(OH)-$A_d$-P(═O)(OH)—.

The structure of $GalNAc_3$-7 ($GalNAc_3$-$7_a$-CM-) is shown below:

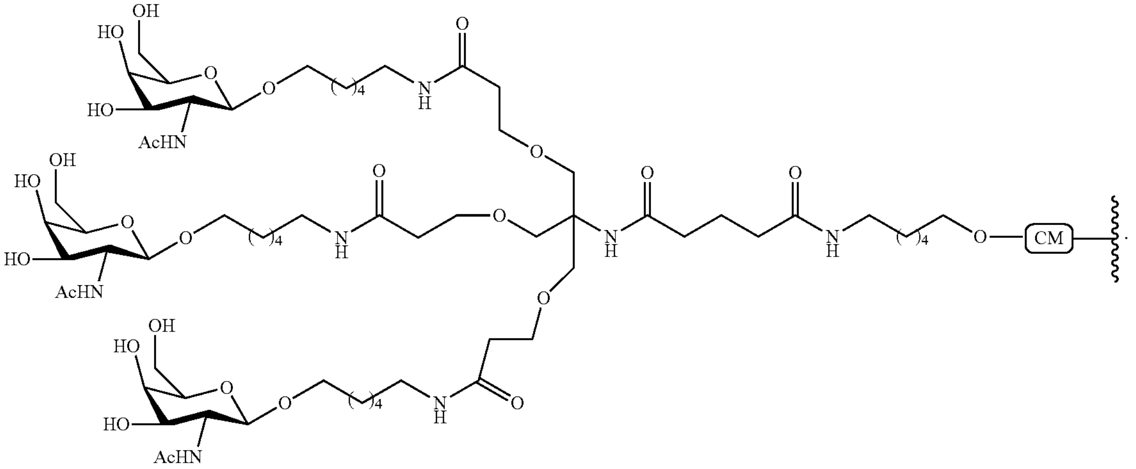

Example 49: Preparation of Oligonucleotide 132 Comprising $GalNAc_3$-5

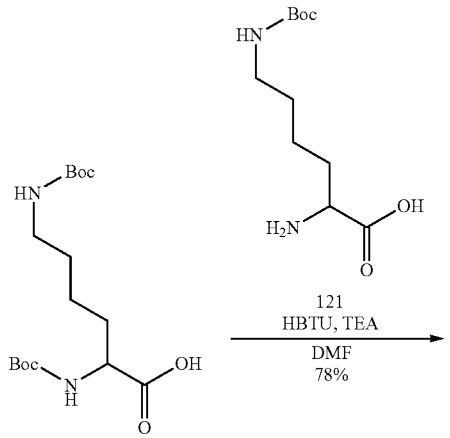

120

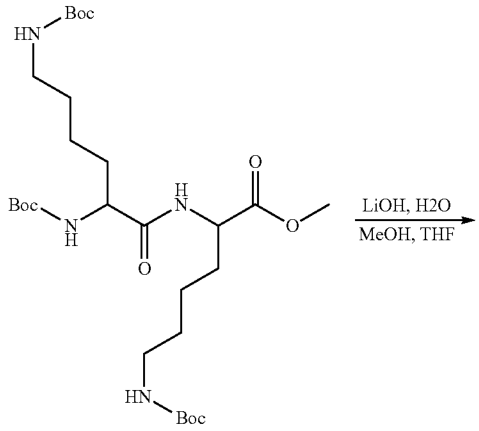

122

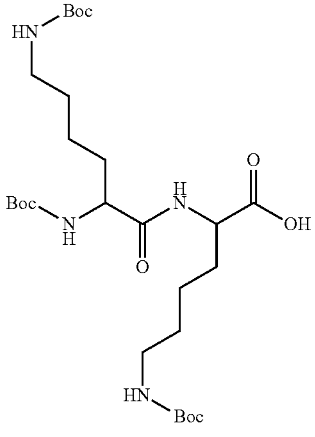

123

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M $NaHSO_4$ (3×150 mL), aqueous saturated $NaHCO_3$ solution (3×150 mL) and brine (2×100 mL). Organic layer was dried with $Na_2SO_4$. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and $^1H$ NMR analysis. Mass m/z 589.3 $[M+H]^+$.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried ($Na_2SO_4$), filtered and evaporated to yield Compound 123 (8.42 g). Residual salt is the likely cause of excess mass. LCMS is consistent with structure. Product was used without any further purification. M.W. cal: 574.36; M.W. fd: 575.3 $[M+H]^+$.

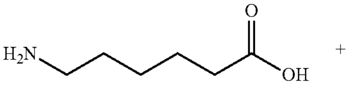

124

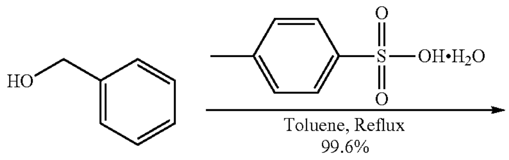

125

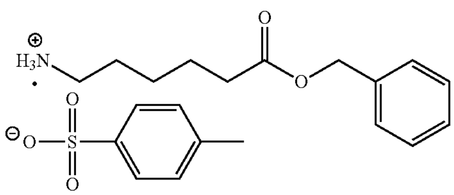

126

Compound 126 was synthesized following the procedure described in the literature (*J. Am. Chem. Soc.* 2011, 133, 958-963).

123
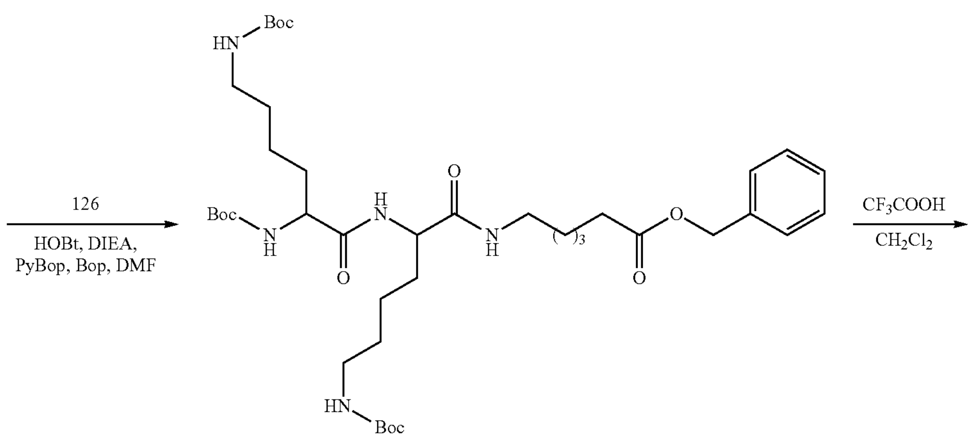
127
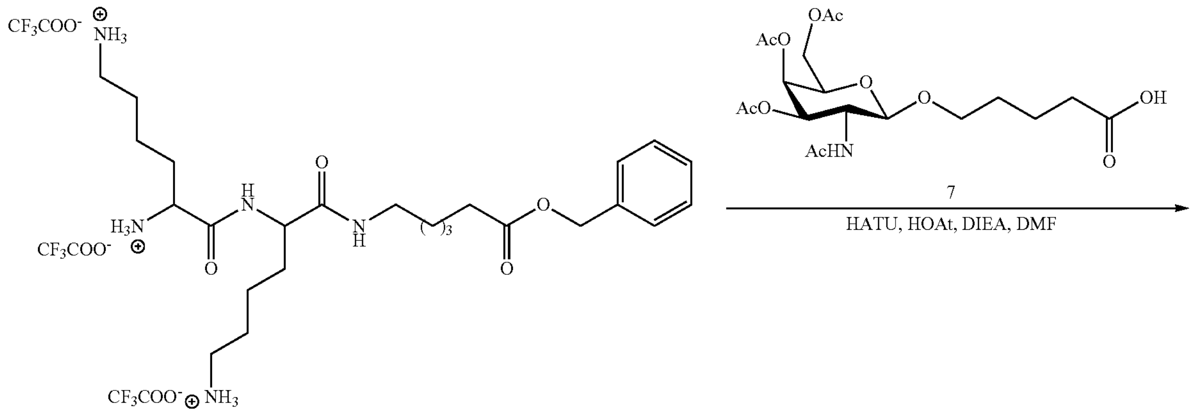
128
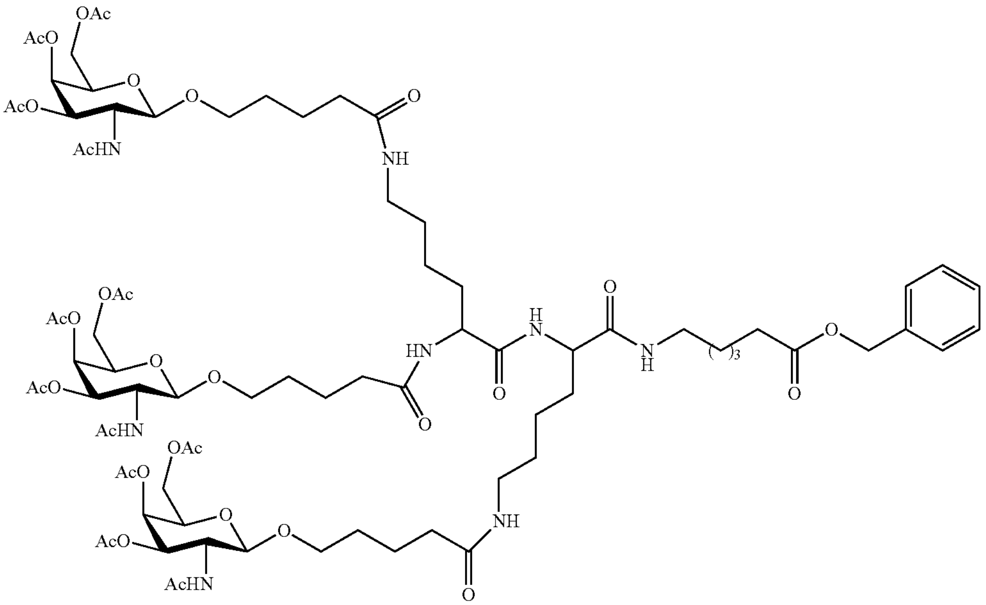
129
129
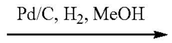

-continued

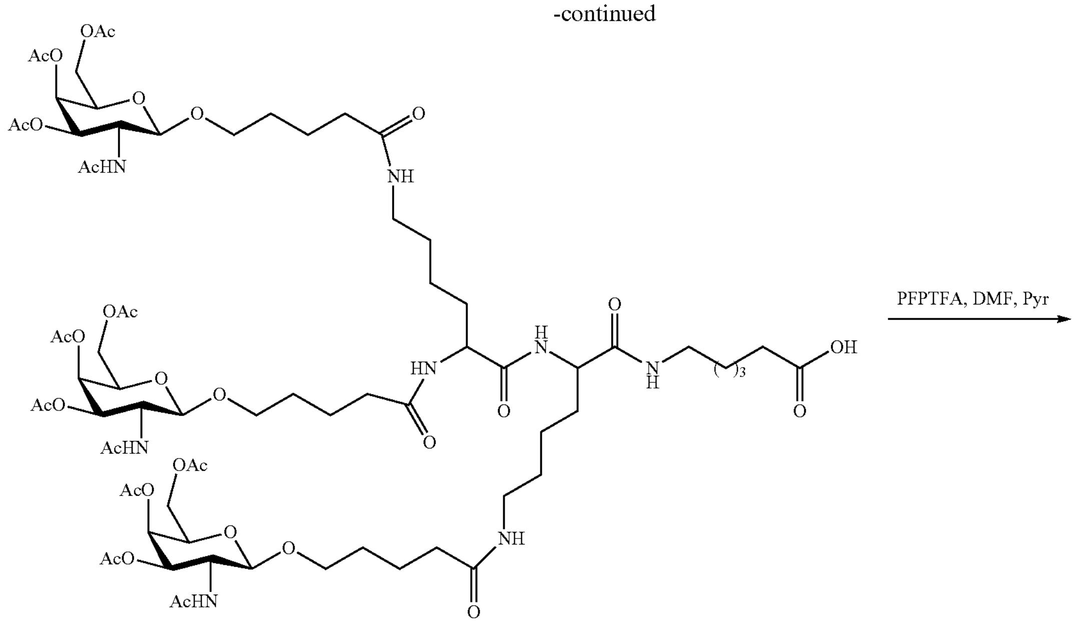

130

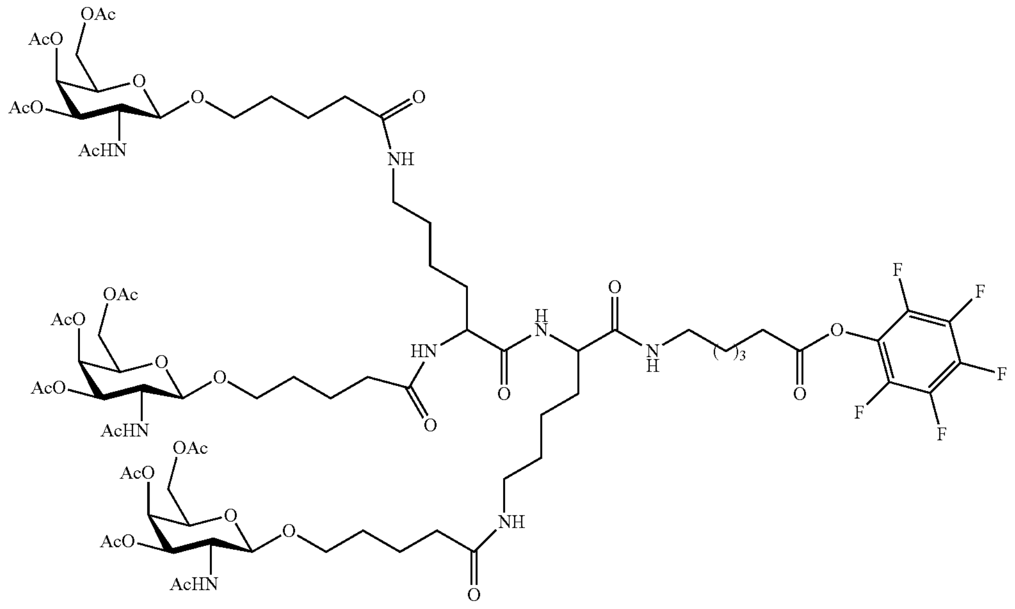

131

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M $NaHSO_4$ (3×100 mL), aqueous saturated $NaHCO_3$ (3×100 mL) and brine (2×100 mL). The organic phase separated dried ($Na_2SO_4$), filtered and concentrated. The residue was purified by silica gel column chromatography with a gradient of 50% hexanes/EtOAC to 100% EtOAc to yield Compound 127 (9.4 g) as a white foam. LCMS and $^1H$ NMR were consistent with structure. Mass m/z 778.4 $[M+H]^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1H$ NMR were consistent with structure. Mass m/z 478.2 $[M+H]^+$.

Compound 7 (0.43 g, 0.963 mmol), HATU (0.35 g, 0.91 mmol), and HOAt (0.035 g, 0.26 mmol) were combined together and dried for 4 h over $P_2O_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M $NaHSO_4$ (3×20 mL), aqueous saturated $NaHCO_3$ (3×20 mL) and brine (3×20 mL). The organic phase was separated, dried over $Na_2SO_4$, filtered and concentrated. The residue was purified by silica gel column chromatography using 5-15% MeOH in dichloromethane to yield Compound 129 (96.6 mg). LC MS and $^1H$ NMR are consistent with structure. Mass m/z 883.4 $[M+2H]^+$.

Compound 129 (0.09 g, 0.051 mmol) was dissolved in methanol (5 mL) in 20 mL scintillation vial. To this was added a small amount of 10% Pd/C (0.015 mg) and the reaction vessel was flushed with $H_2$ gas. The reaction mixture was stirred at room temperature under $H_2$ atmosphere for 18 h. The reaction mixture was filtered through a pad of Celite and the Celite pad was washed with methanol. The filtrate washings were pooled together and concentrated under reduced pressure to yield Compound 130 (0.08 g). LCMS and $^1H$ NMR were consistent with structure. The product was used without further purification. Mass m/z 838.3 $[M+2H]^+$.

To a 10 mL pointed round bottom flask were added compound 130 (75.8 mg, 0.046 mmol), 0.37 M pyridine/DMF (200 μL) and a stir bar. To this solution was added 0.7 M pentafluorophenyl trifluoroacetate/DMF (100 μL) drop wise with stirring. The reaction was completed after 1 h as determined by LC MS. The solvent was removed under reduced pressure and the residue was dissolved in $CHCl_3$ (~10 mL). The organic layer was partitioned against $NaHSO_4$ (1 M, 10 mL), aqueous saturated $NaHCO_3$ (10 mL) and brine (10 mL) three times each. The organic phase separated and dried over $Na_2SO_4$, filtered and concentrated to yield Compound 131 (77.7 mg). LCMS is consistent with structure. Used without further purification. Mass m/z 921.3 $[M+2H]^+$.

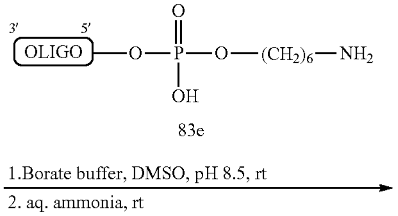

83e

131

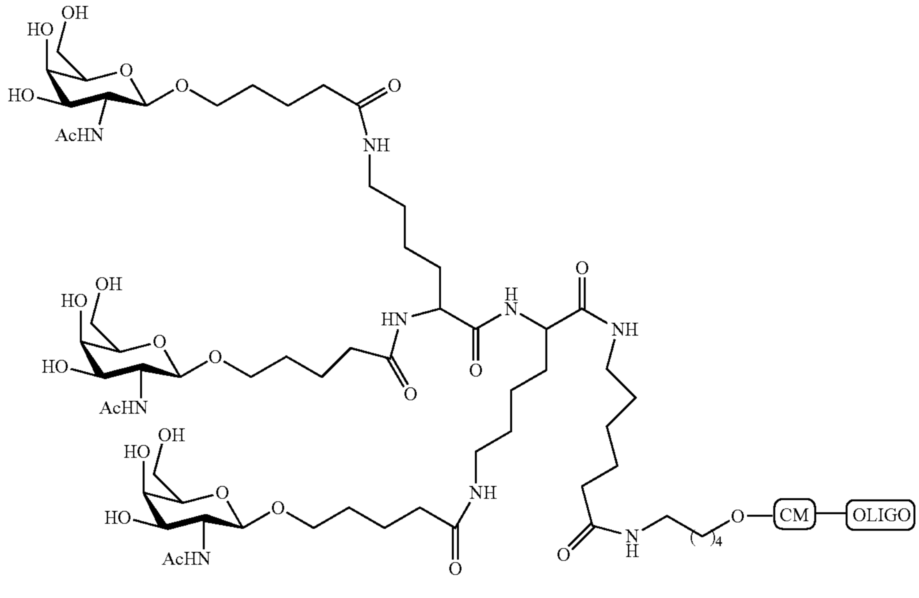

132

Oligomeric Compound 132, comprising a GalNAc$_3$-5 conjugate group, was prepared using the general procedures illustrated in Example 46. The GalNAc3 cluster portion of the conjugate group GalNAc$_3$-5 (GalNAc$_3$-5$_a$) can be combined with any cleavable moiety to provide a variety of conjugate groups. In certain embodiments, the cleavable moiety is —P(═O)(OH)-A$_d$-P(═O)(OH)—.

The structure of GalNAc$_3$-5 (GalNAc$_3$-5$_a$-CM-) is shown below:

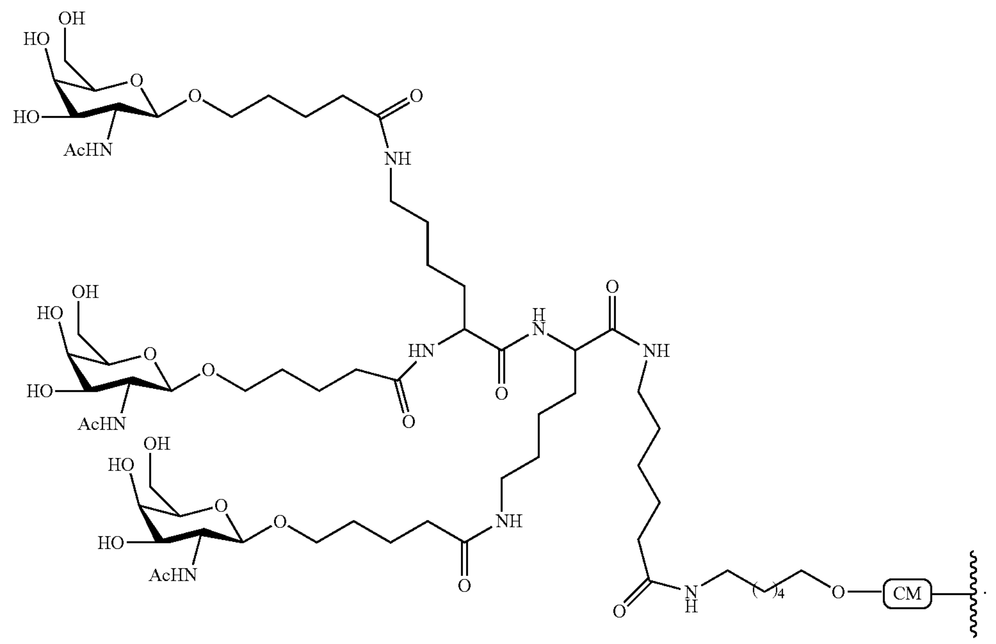

Example 50: Preparation of Oligonucleotide 144 Comprising GalNAc$_4$-11

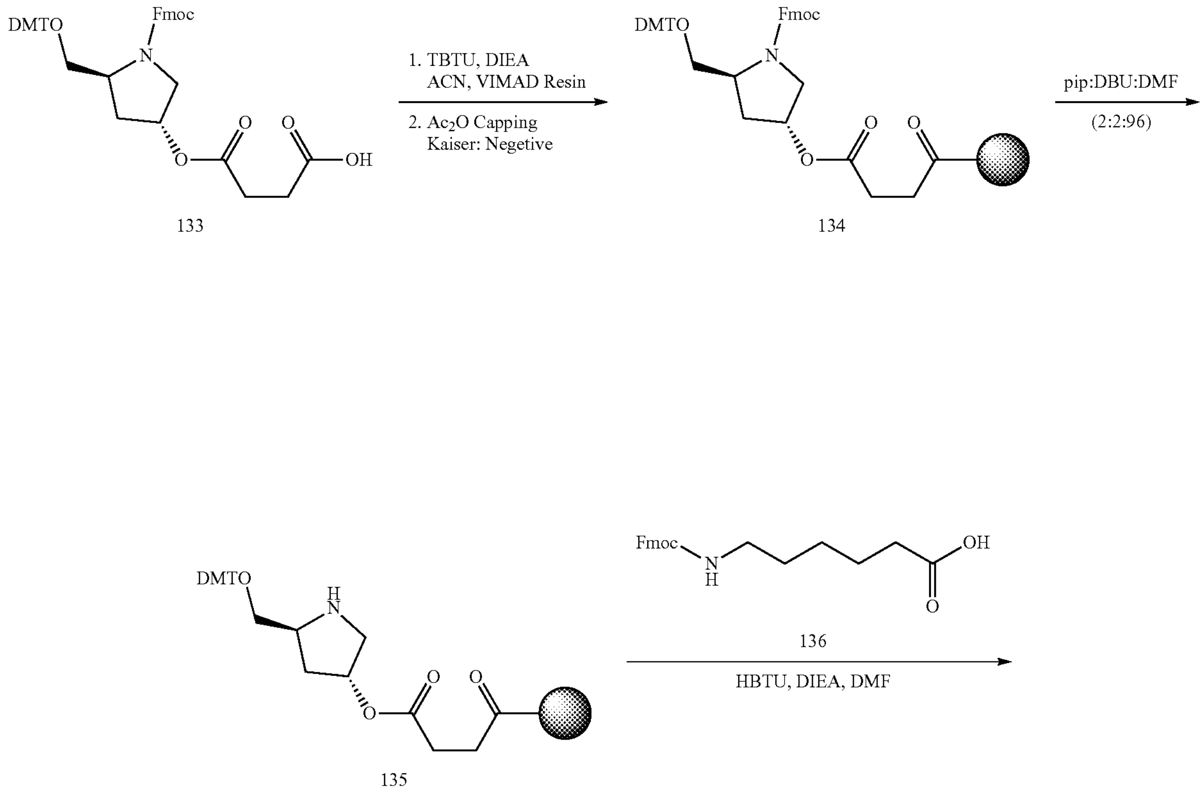

-continued
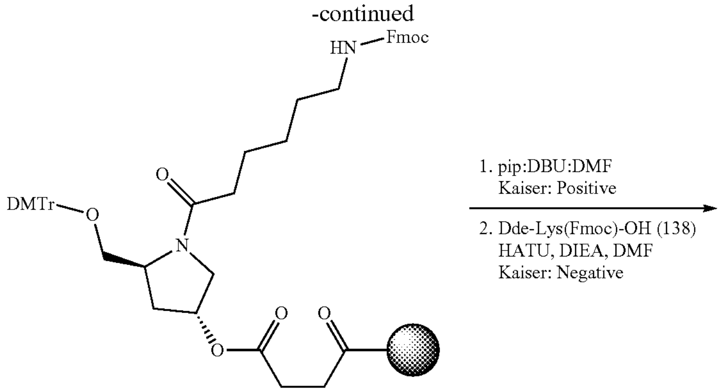
137
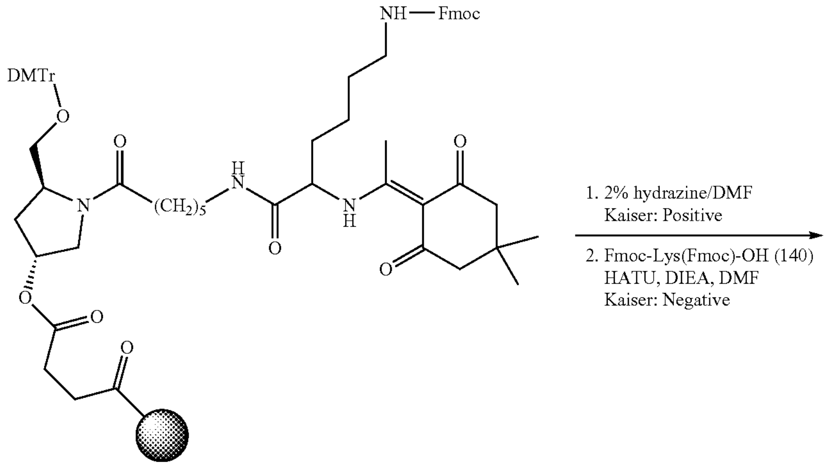
139
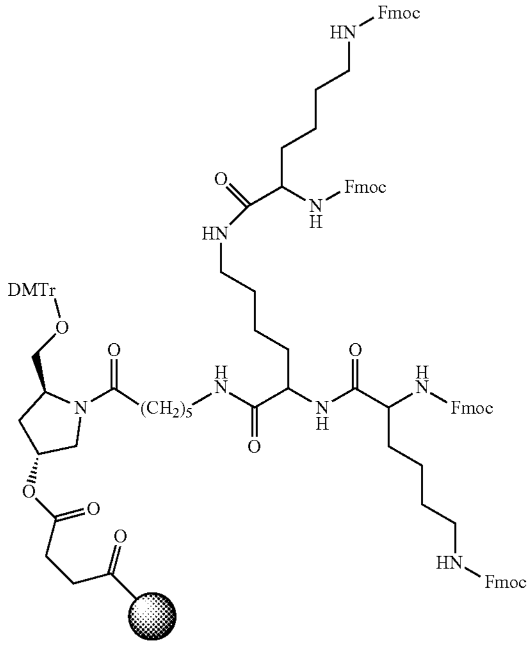
141

-continued

141
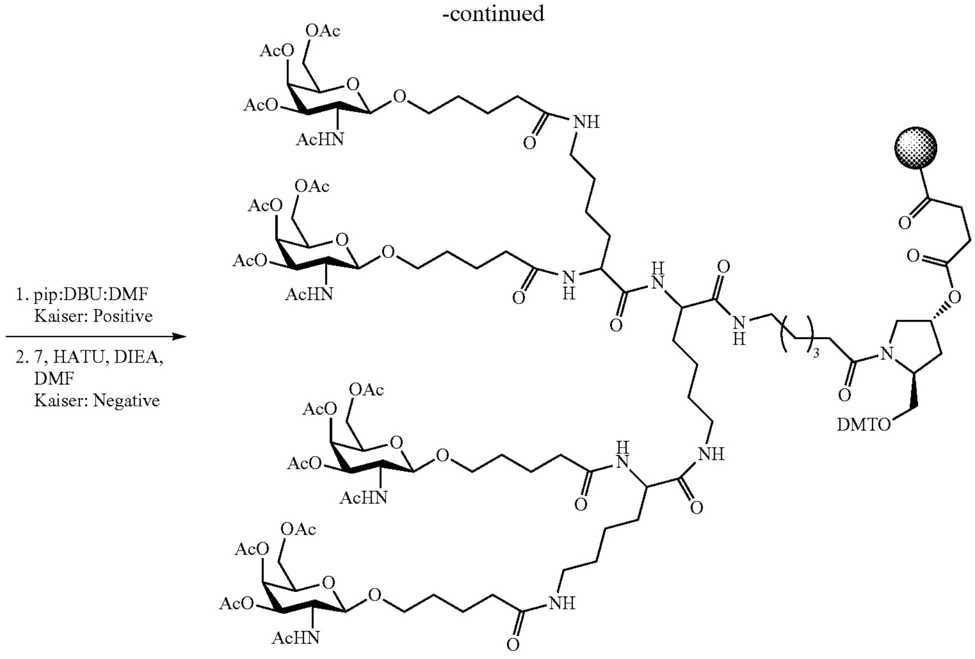

142

Synthesis of Compound 134. To a Merrifield flask was added aminomethyl VIMAD resin (2.5 g, 450 μmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 μmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 $[M+2H]^+$.

The solid support bound compound 142 was synthesized using solid phase peptide synthesis methods.

142
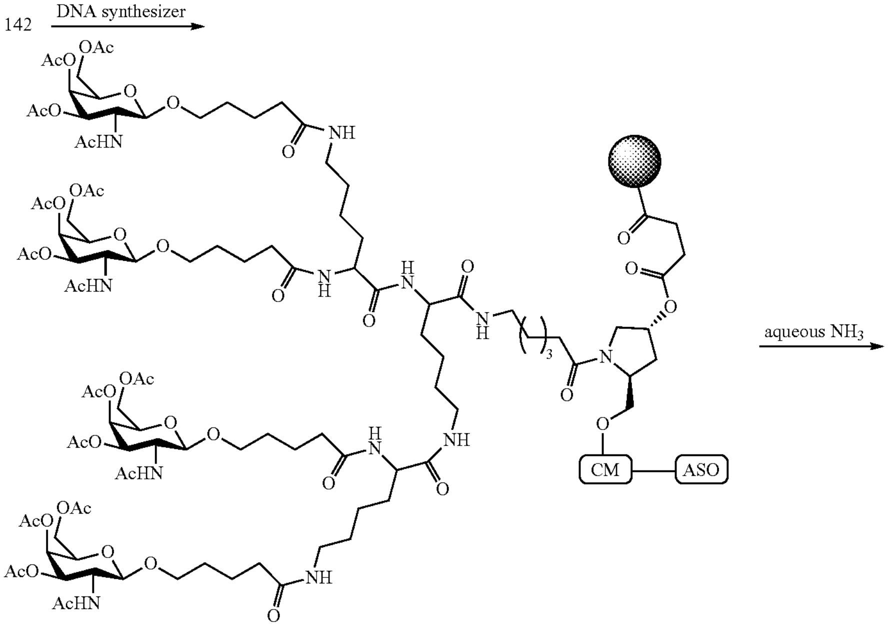

143

-continued

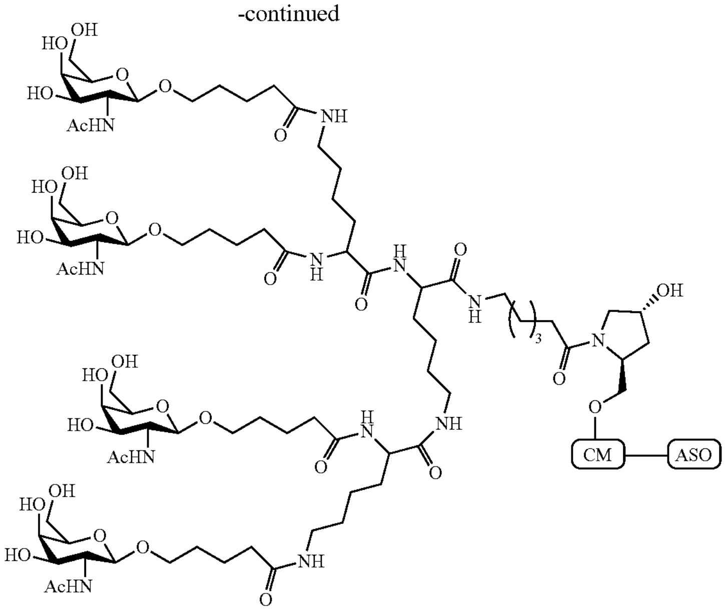

144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting $GalNAc_4$-11 conjugated oligomeric compound was analyzed by LC-MS and the observed mass was consistent with structure.

The GalNAc4 cluster portion of the conjugate group $GalNAc_4$-11 ($GalNAc_4$-$11_a$) can be combined with any cleavable moiety to provide a variety of conjugate groups. In certain embodiments, the cleavable moiety is —P(═O)(OH)-$A_d$-P(═O)(OH)—.

The structure of $GalNAc_4$-11 ($GalNAc_4$-$11_a$-CM) is shown below:

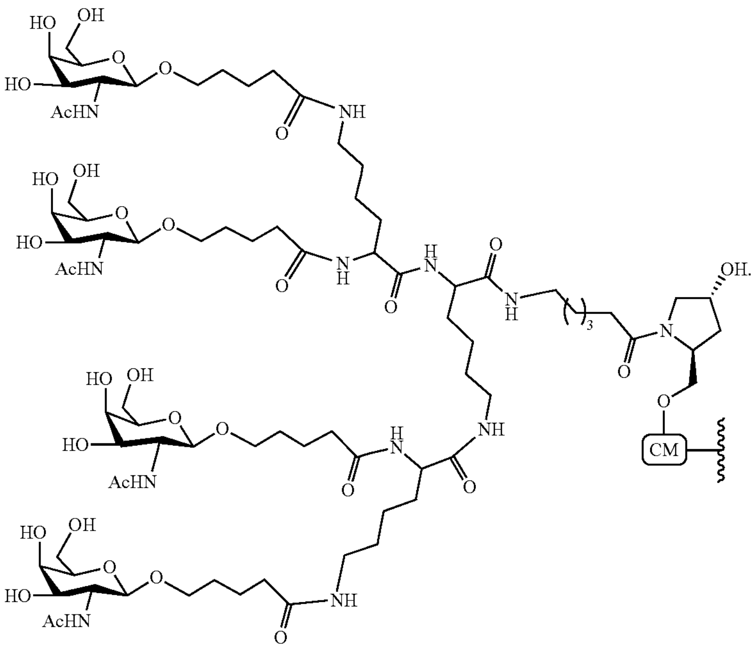

Example 51: Preparation of Oligonucleotide 155 Comprising GalNAc$_3$-6
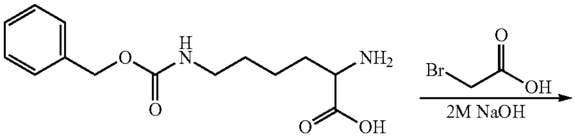
145
-continued
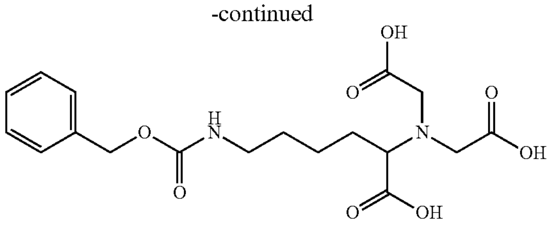
146
Compound 146 was synthesized as described in the literature (*Analytical Biochemistry* 1995, 229, 54-60).
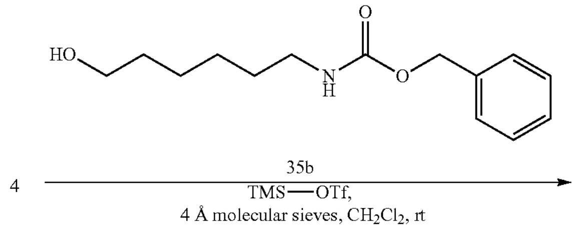
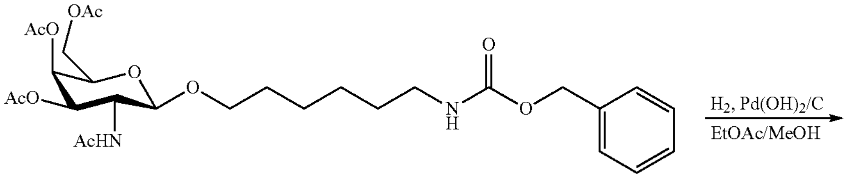
112
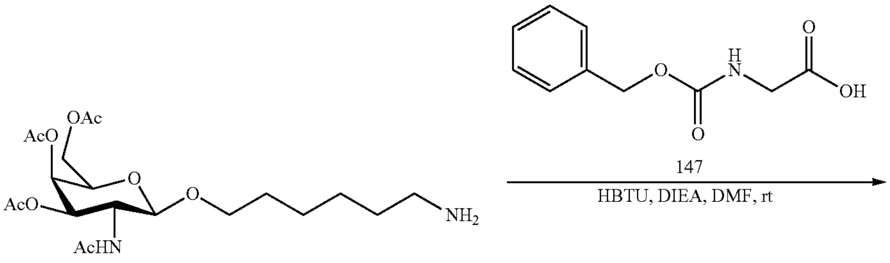
105a
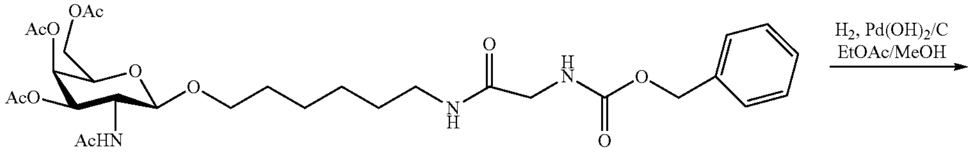
148
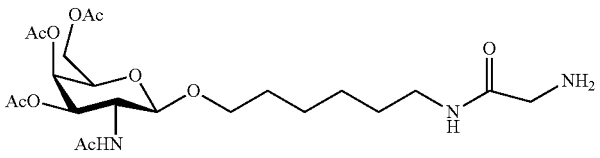
149

Compound 4 (15 g, 45.55 mmol) and compound 35b (14.3 grams, 57 mmol) were dissolved in $CH_2Cl_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous $NaHCO_3$ (500 ml) and crushed ice (~150 g). The organic layer was separated, washed with brine, dried over $MgSO_4$, filtered, and was concentrated to an orange oil under reduced pressure. The crude material was purified by silica gel column chromatography and eluted with 2-10% MeOH in $CH_2Cl_2$ to yield Compound 112 (16.53 g, 63%). LCMS and $^1H$ NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in $CH_2Cl_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous $NaHCO_3$ and brine. The organics phase was separated, dried ($MgSO_4$), filtered, and concentrated to an orange syrup. The crude material was purified by column chromatography 2-5% MeOH in $CH_2Cl_2$ to yield Compound 148 (3.44 g, 73%). LCMS and $^1H$ NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

149

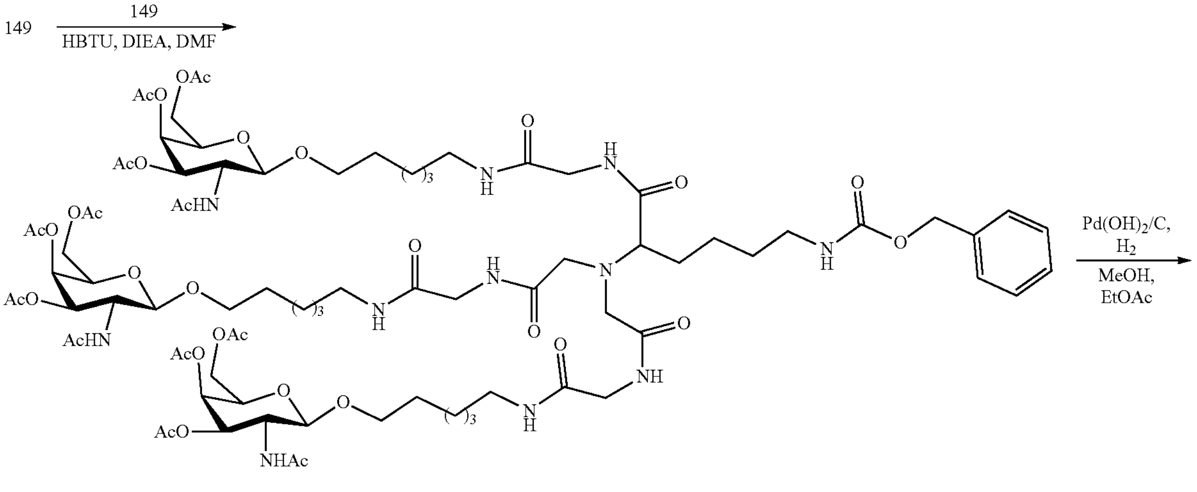

150

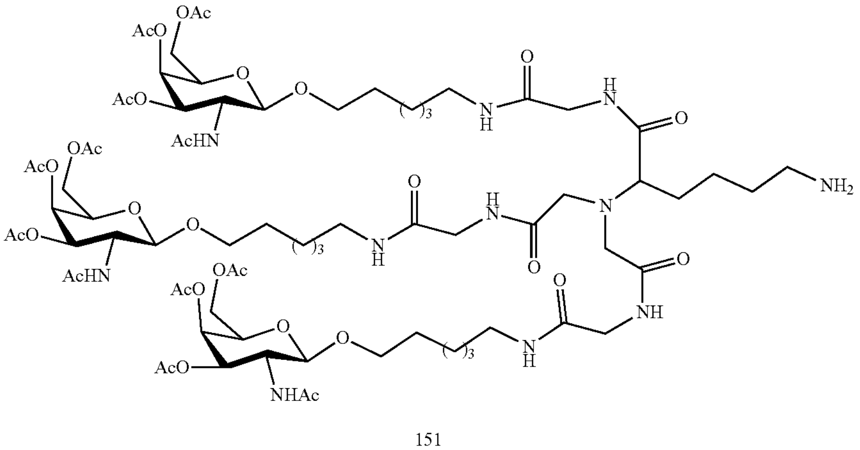

151

Compound 146 (0.68 g, 1.73 mmol) was dissolved in dry DMF (20 ml). To this DIEA (450 μL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous $NaHCO_3$, followed by brine. The organic phase was separated, dried over $MgSO_4$, filtered, and concentrated. The residue was purified by silica gel column chromatography and eluted with 2-10% MeOH in $CH_2Cl_2$ to yield Compound 150 (0.62 g, 20%). LCMS and $^1H$ NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

151

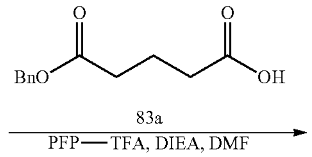

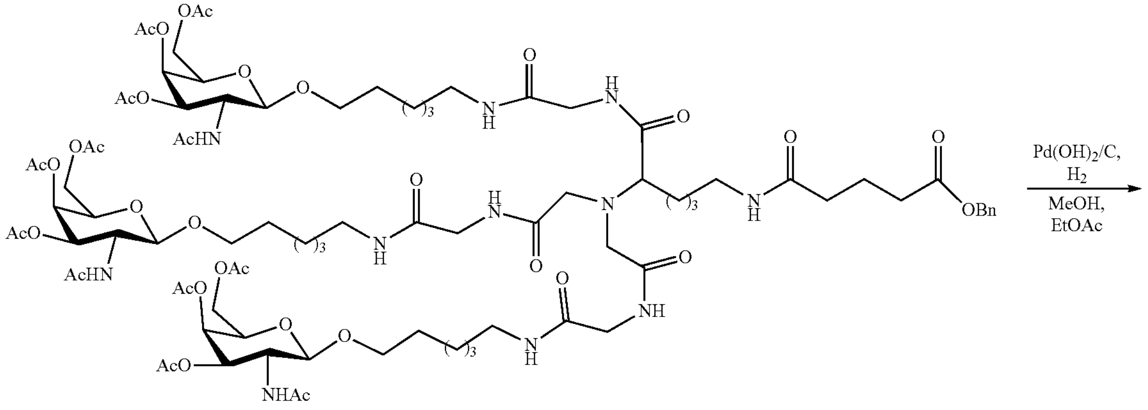

152

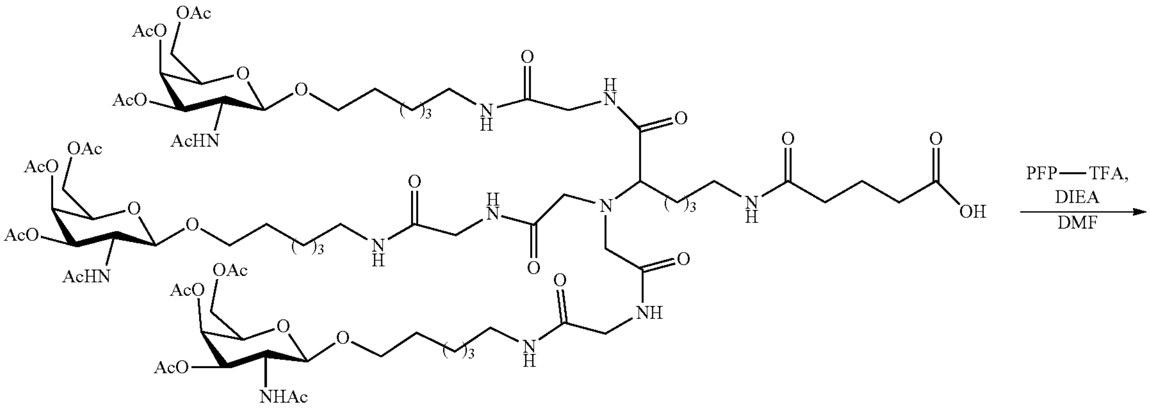

153

-continued

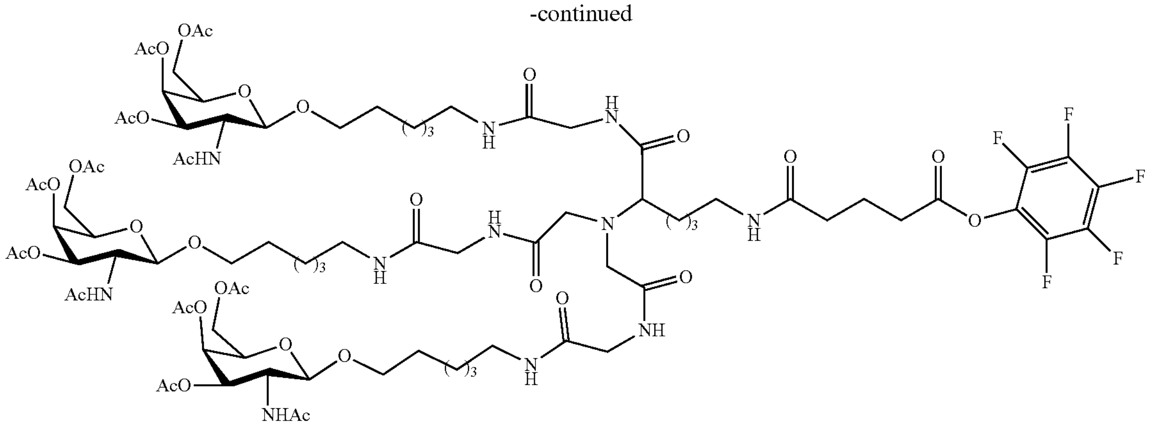

154

Compound 83a (0.11 g, 0.33 mmol) was dissolved in anhydrous DMF (5 mL) and N,N-Diisopropylethylamine (75 μL, 1 mmol) and PFP-TFA (90 μL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min. Upon completion, the majority of the solvent was removed under reduced pressure. The residue was diluted with $CH_2Cl_2$ and washed with aqueous saturated $NaHCO_3$, followed by brine. The organic phase separated, dried over $MgSO_4$, filtered, and concentrated to an orange syrup. The residue was purified by silica gel column chromatography (2-10% MeOH in $CH_2Cl_2$) to yield Compound 152 (0.35 g, 55%). LCMS and $^1H$ NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 μL, 0.37 mmol) and PFP-TFA (35 μL, 0.28 mmol) were added. The reaction mixture was stirred under nitrogen for ~30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with $CH_2Cl_2$ (50 mL), and washed with saturated aqueous $NaHCO_3$, followed by brine. The organic layer was dried over $MgSO_4$, filtered, and concentrated to an orange syrup. The residue was purified by column chromatography and eluted with 2-10% MeOH in $CH_2Cl_2$ to yield Compound 154 (0.29 g, 79%). LCMS and $^1H$ NMR were consistent with the desired product.

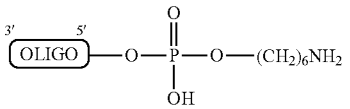

83e

154

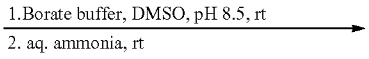

-continued

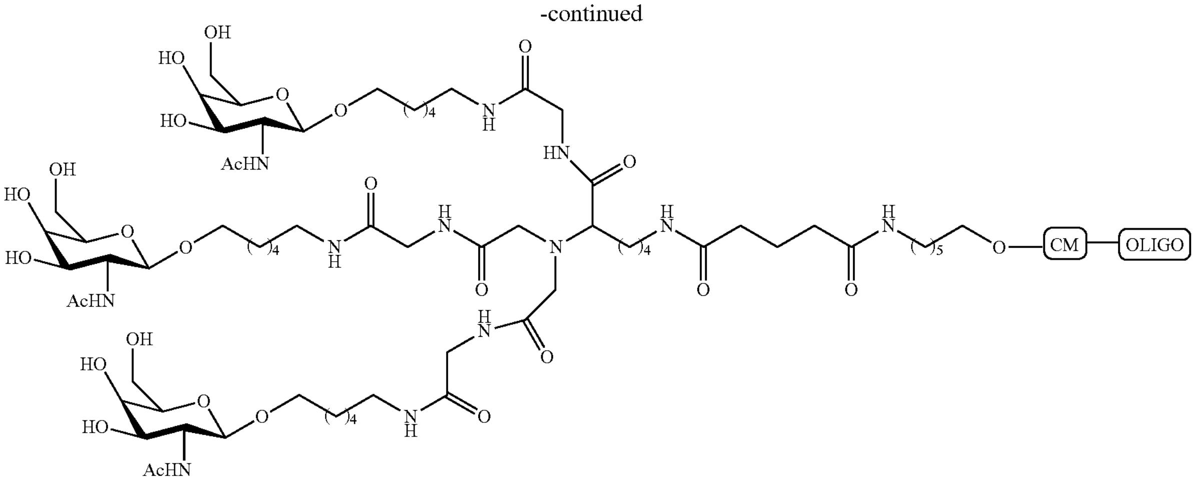

155

Oligomeric Compound 155, comprising a GalNAc$_3$-6 conjugate group, was prepared using the general procedures illustrated in Example 46. The GalNAc3 cluster portion of the conjugate group GalNAc$_3$-6 (GalNAc$_3$-6$_a$) can be combined with any cleavable moiety to provide a variety of conjugate groups. In certain embodiments, the cleavable moiety is —P(═O)(OH)-A$_d$-P(═O)(OH)—.

The structure of GalNAc$_3$-6 (GalNAc$_3$-6$_a$-CM-) is shown below:

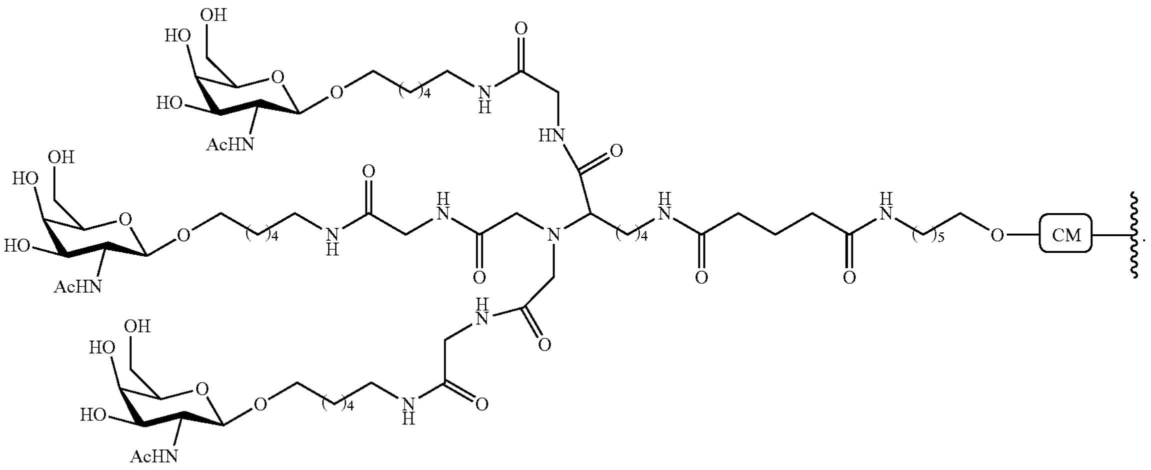

Example 52: Preparation of Oligonucleotide 160 Comprising GalNAc$_3$-9

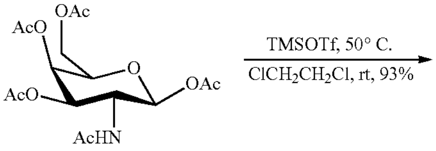

3

-continued

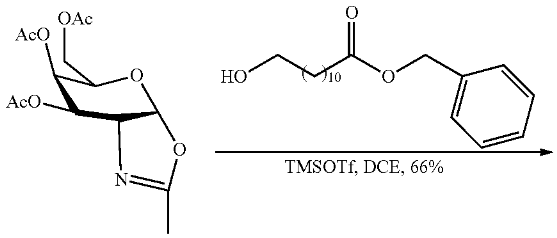

4

-continued

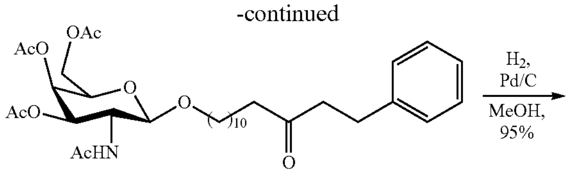

156

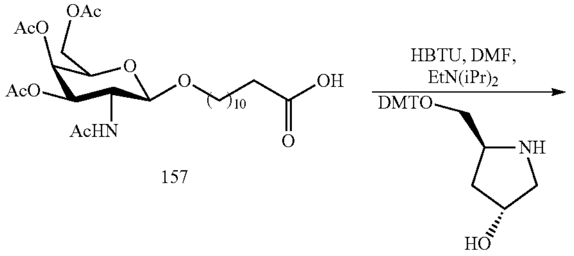

157

47

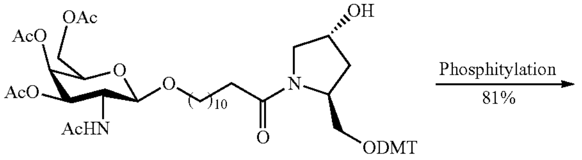

158

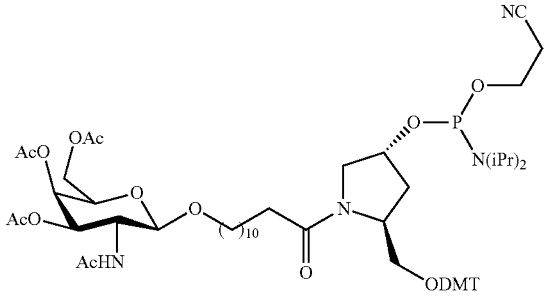

159

Compound 156 was synthesized following the procedure described in the literature (*J. Med. Chem.* 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 $[M-H]^-$.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated $NaHCO_3$ aqueous solution. The mixture was extracted with ethyl acetate and the organic layer was washed with brine and dried ($Na_2SO_4$), filtered and evaporated. The residue obtained was purified by silica gel column chromatography and eluted with 50% ethyl acetate in hexane to yield compound 158 (8.25 g, 73.3%). The structure was confirmed by MS and $^1H$ NMR analysis.

Compound 158 (7.2 g, 7.61 mmol) was dried over $P_2O_5$ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated $NaHCO_3$ and brine. The organic phase was separated, dried ($Na_2SO_4$), filtered and evaporated. The residue was purified by silica gel column chromatography and eluted with 50-90% ethyl acetate in hexane to yield Compound 159 (7.82 g, 80.5%). The structure was confirmed by LCMS and $^{31}P$ NMR analysis.

159

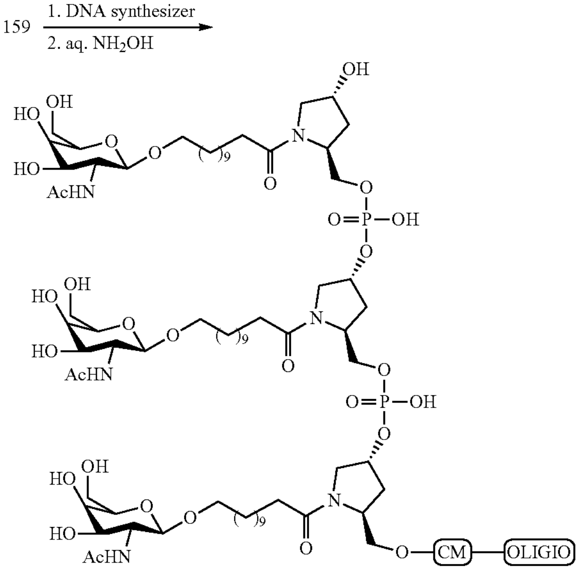

160

Oligomeric Compound 160, comprising a $GalNAc_3$-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160. The GalNAc3 cluster portion of the conjugate group $GalNAc_3$-9 ($GalNAc_3$-$9_a$) can be combined with any cleavable moiety to provide a variety of conjugate groups. In certain embodiments, the cleavable moiety is —P(=O)(OH)-$A_d$-P(=O)(OH)—. The structure of $GalNAc_3$-9 ($GalNAc_3$-$9_a$-CM) is shown below:

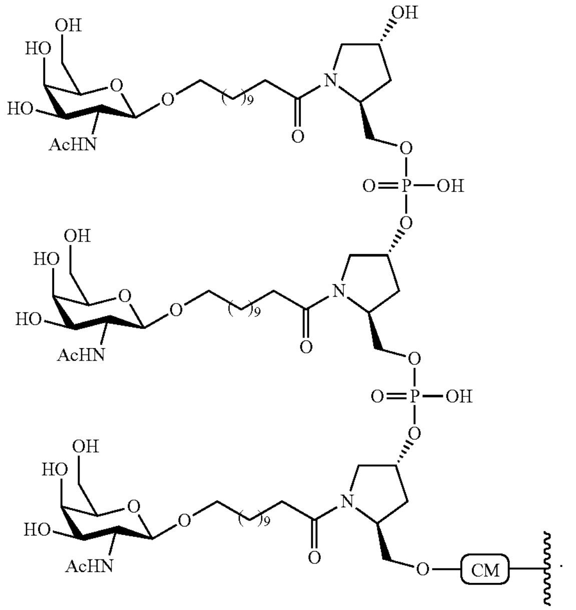
Example 53: Alternate Procedure for Preparation of Compound 18 ($GalNAc_3$-1a and $GalNAc_3$-3a)
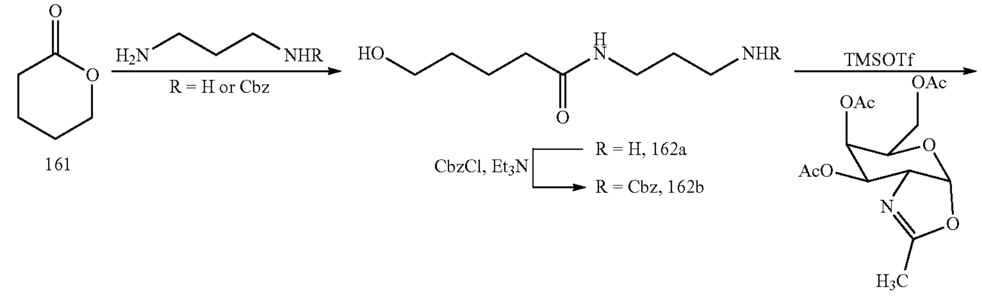
161
4
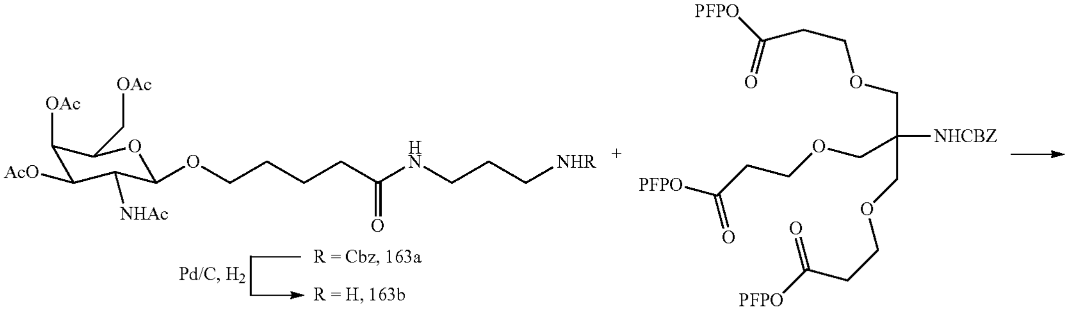
164

-continued

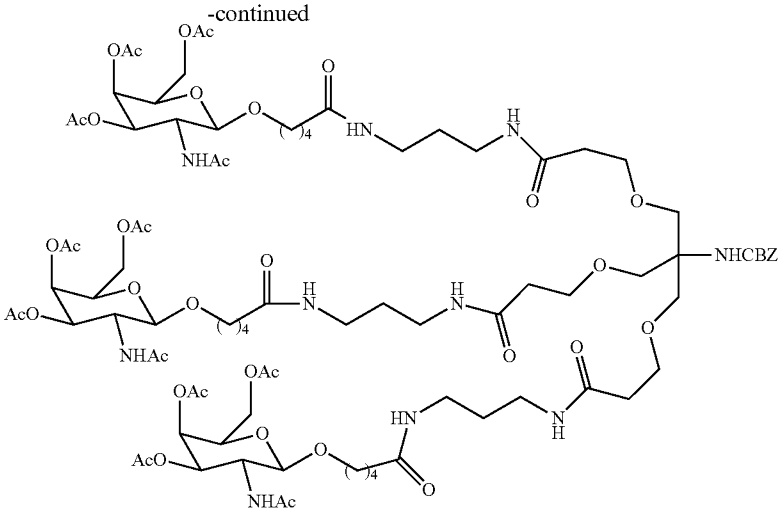

18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b was further reacted with compound 4 in the presence of TMSOTf to provide 163a which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54: Alternate Procedure for Preparation of Compound 18 (GalNAc3-1a and $GalNAc_3$-3a)

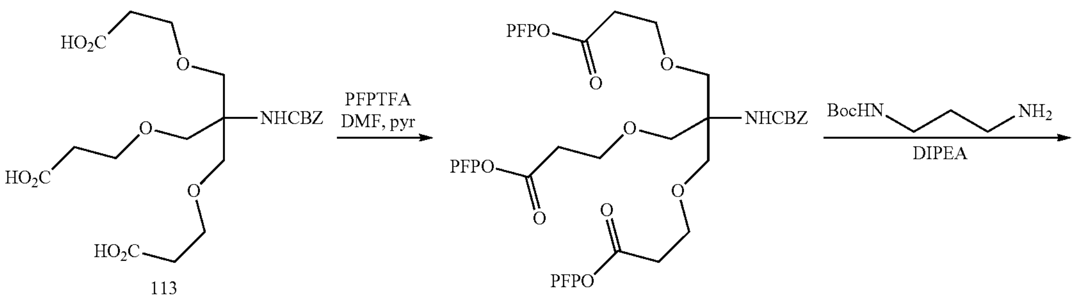

113

164

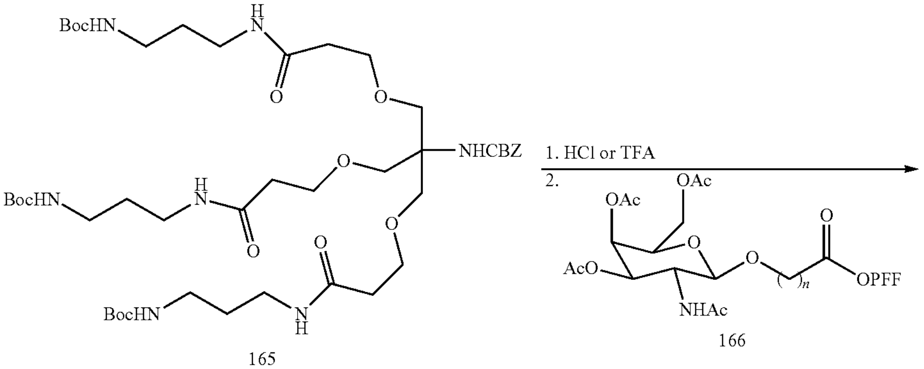

165

166

-continued

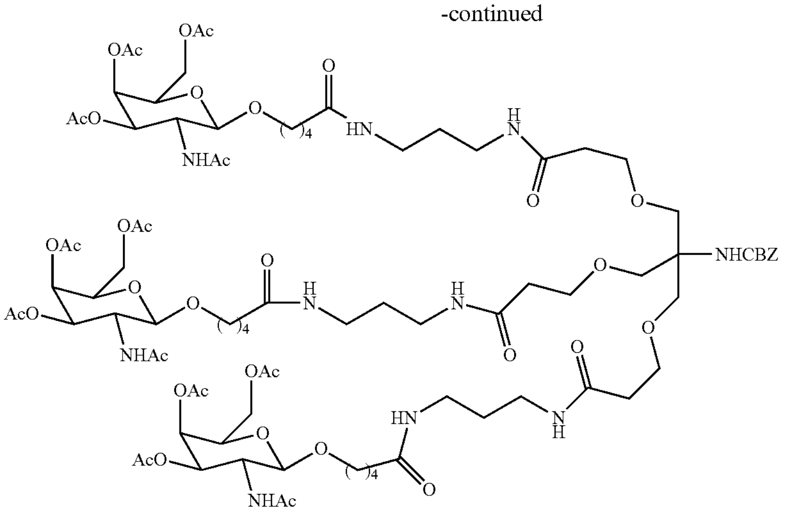

1. 1,6-hexandiol
or 1,5-pentane-diol
TMSOTf + compound 4
2. TEMPO
3. PFPTFA, pyr

18

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using conditions described previously in example 47.

Example 55: Dose-Dependent Study of Oligonucleotides Comprising Either a 3' or 5'-Conjugate Group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc3 conjugate groups was attached at either the 3' or 5' terminus of the respective oligonucleotide by a phosphodiester linked 2'-deoxyadenosine nucleoside (cleavable moiety).

TABLE 39

Modified ASO targeting SRB-1

| ASO | Sequence (5' to 3') | Motif | Conjugate | SEQ ID No. |
|---|---|---|---|---|
| ISIS 353382 (parent) | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | none | 143 |
| ISIS 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$**oAdo'-GalNAc3-1a** | 5/10/5 | **GalNAc3-1** | 144 |
| ISIS 664078 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**Ado'-GalNAc3-9a** | 5/10/5 | **GalNAc3-9** | 144 |
| ISIS 661161 | **GalNAC3-3a-o'Ado** $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | **GalNAc3-3** | 145 |
| ISIS 665001 | **GalNAc3-8a-o'Ado** $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | **GalNAc3-8** | 145 |

Capital letters indicate the nucleobase for each nucleoside and $^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-9 was shown previously in Example 52. The structure of GalNAc$_3$-3 was shown previously in Example 39. The structure of GalNAc$_3$-8 was shown previously in Example 47.

Treatment

Six week old male Balb/c mice (Jackson Laboratory, Bar Harbor, ME) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 40, treatment with antisense oligonucleotides lowered SRB-1 mRNA levels in a dose-dependent manner. Indeed, the antisense oligonucleotides comprising the phosphodiester linked GalNAc$_3$-1 and GalNAc$_3$-9 conjugates at the 3' terminus (ISIS 655861 and ISIS 664078) and the GalNAc$_3$-3 and GalNAc$_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a GalNAc$_3$-9 conjugate at the 3' terminus was essentially equipotent compared to ISIS 655861, which comprises a GalNAc$_3$-1 conjugate at the 3' terminus. The 5' conjugated antisense oligonucleotides, ISIS 661161 and ISIS 665001, comprising a GalNAc$_3$-3 or GalNAc$_3$-9, respectively, had increased potency compared to the 3' conjugated antisense oligonucleotides (ISIS 655861 and ISIS 664078).

TABLE 40

ASOs containing GalNAc$_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
| | 10 | 68 | |
| | 30 | 36 | |
| 655861 | 0.5 | 98 | GalNAc$_3$-1 (3') |
| | 1.5 | 76 | |
| | 5 | 31 | |
| | 15 | 20 | |
| 664078 | 0.5 | 88 | GalNAc$_3$-9 (3') |
| | 1.5 | 85 | |
| | 5 | 46 | |
| | 15 | 20 | |
| 661161 | 0.5 | 92 | GalNAc$_3$-3 (5') |
| | 1.5 | 59 | |
| | 5 | 19 | |
| | 15 | 11 | |
| 665001 | 0.5 | 100 | GalNAc$_3$-8 (5') |
| | 1.5 | 73 | |
| | 5 | 29 | |
| | 15 | 13 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 41

| ISIS No. | Dosage mg/kg | ALT | AST | Total Bilirubin | BUN | Conjugate |
|---|---|---|---|---|---|---|
| Saline | | 24 | 59 | 0.1 | 37.52 | |
| 353382 | 3 | 21 | 66 | 0.2 | 34.65 | none |
| | 10 | 22 | 54 | 0.2 | 34.2 | |
| | 30 | 22 | 49 | 0.2 | 33.72 | |
| 655861 | 0.5 | 25 | 62 | 0.2 | 30.65 | GalNac$_3$-1 (3') |
| | 1.5 | 23 | 48 | 0.2 | 30.97 | |
| | 5 | 28 | 49 | 0.1 | 32.92 | |
| | 15 | 40 | 97 | 0.1 | 31.62 | |
| 664078 | 0.5 | 40 | 74 | 0.1 | 35.3 | GalNac$_3$-9 (3') |
| | 1.5 | 47 | 104 | 0.1 | 32.75 | |
| | 5 | 20 | 43 | 0.1 | 30.62 | |
| | 15 | 38 | 92 | 0.1 | 26.2 | |
| 661161 | 0.5 | 101 | 162 | 0.1 | 34.17 | GalNac$_3$-3 (5') |
| | 1.5 g | 42 | 100 | 0.1 | 33.37 | |
| | 5 g | 23 | 99 | 0.1 | 34.97 | |
| | 15 | 53 | 83 | 0.1 | 34.8 | |
| 665001 | 0.5 | 28 | 54 | 0.1 | 31.32 | GalNac$_3$-8 (5') |
| | 1.5 | 42 | 75 | 0.1 | 32.32 | |
| | 5 | 24 | 42 | 0.1 | 31.85 | |
| | 15 | 32 | 67 | 0.1 | 31. | |

Example 56: Dose-Dependent Study of Oligonucleotides Comprising Either a 3' or 5'-Conjugate Group (Comparison of GalNAc$_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at the 5' terminus of the respective oligonucleotide by a phosphodiester linked 2'-deoxyadenosine nucleoside (cleavable moiety) except for ISIS 655861 which had the GalNAc$_3$ conjugate group attached at the 3' terminus.

TABLE 42

| Modified ASO targeting SRB-1 | | | | |
|---|---|---|---|---|
| ASO | Sequence (5' to 3') | Motif | Conjugate | SEQ ID No. |
| ISIS 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | no conjugate | 143 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$**oAdo'-GalNAc3-1a** | 5/10/5 | **GalNAc3-1** | 144 |
| ISIS 664507 | **GalNAc3-2a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-2** | 145 |
| ISIS 661161 | **GalNAc3-3a-o'Ado** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-3** | 145 |
| ISIS 666224 | **GalNAc3-5**$_{a-o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-5** | 145 |
| ISIS 666961 | **GalNAc3-6a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-6** | 145 |
| ISIS 666981 | **GalNAc3-7a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-7** | 145 |
| ISIS 666881 | **GalNAc3-10a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc3-10** | 145 |

Capital letters indicate the nucleobase for each nucleoside and ${}^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-1$_a$ was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, ME) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 43, treatment with antisense oligonucleotides lowered SRB-1 mRNA levels in a dose-dependent manner. Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 43

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNAc$_3$-2 (5') |
| | 1.5 | 73.2 | |
| | 5 | 31.3 | |
| | 15 | 10.8 | |
| 661161 | 0.5 | 90.7 | GalNAc$_3$-3 (5') |
| | 1.5 | 67.6 | |
| | 5 | 24.3 | |
| | 15 | 11.5 | |
| 666224 | 0.5 | 96.1 | GalNAc$_3$-5 (5') |
| | 1.5 | 61.6 | |
| | 5 | 25.6 | |
| | 15 | 11.7 | |
| 666961 | 0.5 | 85.5 | GalNAc$_3$-6 (5') |
| | 1.5 | 56.3 | |
| | 5 | 34.2 | |
| | 15 | 13.1 | |
| 666981 | 0.5 | 84.7 | GalNAc$_3$-7 (5') |
| | 1.5 | 59.9 | |
| | 5 | 24.9 | |
| | 15 | 8.5 | |
| 666881 | 0.5 | 100.0 | GalNAc$_3$-10 (5') |
| | 1.5 | 65.8 | |
| | 5 | 26.0 | |
| | 15 | 13.0 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 44 below.

TABLE 44

| ISIS No. | Dosage mg/kg | ALT | AST | Total Bilirubin | BUN | Conjugate |
|---|---|---|---|---|---|---|
| Saline | | 26 | 57 | 0.2 | 27 | |
| 353382 | 3 | 25 | 92 | 0.2 | 27 | |
| | 10 | 23 | 40 | 0.2 | 25 | none |
| | 30 | 29 | 54 | 0.1 | 28 | |
| 655861 | 0.5 | 25 | 71 | 0.2 | 34 | |
| | 1.5 | 28 | 60 | 0.2 | 26 | $GalNac_3$-1 (3') |
| | 5 | 26 | 63 | 0.2 | 28 | |
| | 15 | 25 | 61 | 0.2 | 28 | |
| 664507 | 0.5 | 25 | 62 | 0.2 | 25 | $GalNac_3$-2 (5') |
| | 1.5 | 24 | 49 | 0.2 | 26 | |
| | 5 | 21 | 50 | 0.2 | 26 | |
| | 15 | 59 | 84 | 0.1 | 22 | |
| 661161 | 0.5 | 20 | 42 | 0.2 | 29 | $GalNac_3$-3 (5') |
| | 1.5 g | 37 | 74 | 0.2 | 25 | |
| | 5 g | 28 | 61 | 0.2 | 29 | |
| | 15 | 21 | 41 | 0.2 | 25 | |
| 666224 | 0.5 | 34 | 48 | 0.2 | 21 | $GalNac_3$-5 (5') |
| | 1.5 | 23 | 46 | 0.2 | 26 | |
| | 5 | 24 | 47 | 0.2 | 23 | |
| | 15 | 32 | 49 | 0.1 | 26 | |

TABLE 44-continued

| ISIS No. | Dosage mg/kg | ALT | AST | Total Bilirubin | BUN | Conjugate |
|---|---|---|---|---|---|---|
| 666961 | 0.5 | 17 | 63 | 0.2 | 26 | $GalNAc_3$-6 (5') |
| | 1.5 | 23 | 68 | 0.2 | 26 | |
| | 5 | 25 | 66 | 0.2 | 26 | |
| | 15 | 29 | 107 | 0.2 | 28 | |
| 666981 | 0.5 | 24 | 48 | 0.2 | 26 | $GalNAc_3$-7 (5') |
| | 1.5 | 30 | 55 | 0.2 | 24 | |
| | 5 | 46 | 74 | 0.1 | 24 | |
| | 15 | 29 | 58 | 0.1 | 26 | |
| 666881 | 0.5 | 20 | 65 | 0.2 | 27 | $GalNAc_3$-10 (5') |
| | 1.5 | 23 | 59 | 0.2 | 24 | |
| | 5 | 45 | 70 | 0.2 | 26 | |
| | 15 | 21 | 57 | 0.2 | 24 | |

Example 57: Duration of Action Study of Oligonucleotides Comprising a 3'-Conjugate Group Targeting ApoC III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 45

Modified ASO targeting ApoC III

| ASO | Sequence (5' to 3') | Linkages | SEQ ID No. |
|---|---|---|---|
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | PS | 135 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$**Ado'-GalNAC3-1a** | PS | 136 |
| ISIS 647536 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$**oAdo'-GalNAC3-1a** | PO/PS | 136 |

Capital letters indicate the nucleobase for each nucleoside and ${}^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of $GalNAc_3$-$1_a$ was shown previously in Example 9.

TABLE 46

ApoC III mRNA (% Saline on Day 1) and Plasma TG Levels (% Saline on Day 1)

| ASO | Dose | Target | Day 3 | Day 7 | Day 14 | Day 35 | Day 42 |
|---|---|---|---|---|---|---|---|
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58: Dose-Dependent Study of Oligonucleotides Comprising a 3'-Conjugate Group (Comparison of $GalNAc_3$-1 and $GalNAc_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of $GalNAc_3$-$1_a$ was shown previously in Example 9. The structure of $GalNAc_3$-$11_a$ was shown previously in Example 50.

Treatment

Six week old male Balb/c mice (Jackson Laboratory, Bar Harbor, ME) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 47, treatment with antisense oligonucleotides lowered SRB-1 mRNA levels in a dose-dependent manner. The antisense oligonucleotides comprising the phosphodiester linked $GalNAc_3$-1 and $GalNAc_4$-11 conjugates at the 3' terminus (ISIS 651900 and ISIS 663748) showed substantial improvement in potency compared to the unconjugated antisense oligonucleotide (ISIS 440762). The two conjugated oligonucleotides, $GalNAc_3$-1 and $GalNAc_4$-11, were equipotent.

TABLE 47

Modified ASO targeting SRB-1

| ASO | Sequence (5' to 3') | Dose mg/kg | % Saline control | SEQ ID No. |
|---|---|---|---|---|
| Saline | | | 100 | |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | 0.6 | 73.45 | 137 |
| | | 2 | 59.66 | |
| | | 6 | 23.50 | |
| ISIS 651900 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$**oAdo'-GalNAc3-1a** | 0.2 | 62.75 | 138 |
| | | 0.6 | 29.14 | |
| | | 2 | 8.61 | |
| | | 6 | 5.62 | |
| ISIS 663748 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$**oAdo'-GalNAc4-11a** | 0.2 | 63.99 | 138 |
| | | 0.6 | 33.53 | |
| | | 2 | 7.58 | |
| | | 6 | 5.52 | |

Capital letters indicate the nucleobase for each nucleoside and $^{m}$C indicates a 5-methyl cytosine. Subscripts: "e" indicates a 2'-MOE modified nucleoside; "k" indicates 6'-(S)—$CH_3$ bicyclic nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 48 below.

TABLE 48

| ISIS No. | Dosage mg/kg | ALT | AST | Total Bilirubin | BUN | Conjugate |
|---|---|---|---|---|---|---|
| Saline | | 30 | 76 | 0.2 | 40 | none |
| 440762 | 0.60 | 32 | 70 | 0.1 | 35 | |
| | 2 | 26 | 57 | 0.1 | 35 | |
| | 6 | 31 | 48 | 0.1 | 39 | |
| 651900 | 0.2 | 32 | 115 | 0.2 | 39 | $GalNac_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | $GalNac_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59: Effects of $GalNAc_3$-1 Conjugated ASOs Targeting FXI In Vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 49

| Modified ASOs targeting FXI | | | |
|---|---|---|---|
| ASO | Sequence (5' to 3') | Linkages | SEQ ID No. |
| ISIS 404071 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$ | PS | 146 |
| ISIS 656172 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$**oAdo'-GalNAc3-1a** | PS | 147 |
| ISIS 656173 | $T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$**oAdo'-GalNAc3-1a** | PO/PS | 147 |

Capital letters indicate the nucleobase for each nucleoside and ${}^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-1$_a$ was shown previously in Example 9.

Treatment

Six week old male Balb/c mice (Jackson Laboratory, Bar Harbor, ME) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, OR) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The $ED_{50}$s were measured using similar methods as described previously and are presented below.

TABLE 50

| Factor XI mRNA (% Saline) | | | | |
|---|---|---|---|---|
| ASO | Dose mg/kg | % Control | Conjugate | Linkages |
| Saline | | 100 | none | |
| ISIS | 3 | 92 | none | PS |
| 404071 | 10 | 40 | | |
| | 30 | 15 | | |
| ISIS | 0.7 | 74 | GalNAc$_3$-1 | PS |
| 656172 | 2 | 33 | | |
| | 6 | 9 | | |
| ISIS | 0.7 | 49 | GalNAc$_3$-1 | PO/PS |
| 656173 | 2 | 22 | | |
| | 6 | 1 | | |

As illustrated in Table 50, treatment with antisense oligonucleotides lowered FXI mRNA levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

As illustrated in Table 50a, treatment with antisense oligonucleotides lowered FXI protein levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

TABLE 50a

| Factor XI protein (% Saline) | | | | |
|---|---|---|---|---|
| ASO | Dose mg/kg | Protein (% Control) | Conjugate | Linkages |
| Saline | | 100 | none | |
| ISIS | 3 | 127 | none | PS |
| 404071 | 10 | 32 | | |
| | 30 | 3 | | |
| ISIS | 0.7 | 70 | GalNAc$_3$-1 | PS |
| 656172 | 2 | 23 | | |
| | 6 | 1 | | |
| ISIS | 0.7 | 45 | GalNAc$_3$-1 | PO/PS |
| 656173 | 2 | 6 | | |
| | 6 | 0 | | |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 51

| ISIS No. | Dosage mg/kg | ALT | AST | Total Albumin | Total Bilirubin | CRE | BUN | Conjugate |
|---|---|---|---|---|---|---|---|---|
| Saline | | 71.8 | 84.0 | 3.1 | 0.2 | 0.2 | 22.9 | |
| 404071 | 3 | 152.8 | 176.0 | 3.1 | 0.3 | 0.2 | 23.0 | none |
| | 10 | 73.3 | 121.5 | 3.0 | 0.2 | 0.2 | 21.4 | |
| | 30 | 82.5 | 92.3 | 3.0 | 0.2 | 0.2 | 23.0 | |

TABLE 51-continued

| ISIS No. | Dosage mg/kg | ALT | AST | Total Albumin | Total Bilirubin | CRE | BUN | Conjugate |
|---|---|---|---|---|---|---|---|---|
| 656172 | 0.7 | 62.5 | 111.5 | 3.1 | 0.2 | 0.2 | 23.8 | GalNac$_3$-1 (3') |
| | 2 | 33.0 | 51.8 | 2.9 | 0.2 | 0.2 | 22.0 | |
| | 6 | 65.0 | 71.5 | 3.2 | 0.2 | 0.2 | 23.9 | |
| 656173 | 0.7 | 54.8 | 90.5 | 3.0 | 0.2 | 0.2 | 24.9 | GalNac$_3$-1 (3') |
| | 2 | 85.8 | 71.5 | 3.2 | 0.2 | 0.2 | 21.0 | |
| | 6 | 114.0 | 101.8 | 3.3 | 0.2 | 0.2 | 22.7 | |

Example 60: Effects of Conjugated ASOs Targeting SRB-1 In Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

TABLE 52

Modified ASO targeting SRB-1

| ASO | Sequence (5' to 3') | Motif | Conjugate | SEQ ID No. |
|---|---|---|---|---|
| ISIS 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | none | 143 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}A_{do'}$-**GalNAc$_3$-1$_a$** | 5/10/5 | **GalNAc$_3$-1** | 144 |
| ISIS 655862 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}A_{do'}$-**GalNAc$_3$-1$_a$** | 5/10/5 | **GalNAc$_3$-1** | 144 |
| ISIS 661161 | **GalNAc$_3$-3**$_{a\text{-}o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-3** | 145 |
| ISIS 665001 | **GalNAc$_3$-8**$_{a\text{-}o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-8** | 145 |
| ISIS 664078 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}A_{do'}$-GalNAc$_3$-9$_a$ | 5/10/5 | **GalNAc$_3$-9** | 144 |
| ISIS 666961 | **GalNAc$_3$-6**$_{a\text{-}o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-6** | 145 |
| ISIS 664507 | **GalNAc$_3$-2**$_{a\text{-}o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-2** | 145 |
| ISIS 666881 | **GalNAc$_3$-10**$_{a\text{-}o'}A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-10** | 145 |
| ISIS 666224 | **GalNAc$_3$-5**$_{a\text{-}o'}$**A**$_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-5** | 145 |
| ISIS 666981 | **GalNAc$_3$-7**$_{a\text{-}o'}$**A**$_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-7** | 145 |

Capital letters indicate the nucleobase for each nucleoside and $^{m}$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-1$_a$ was shown previously in Example 9. The structure of GalNAc$_3$-3a was shown previously in Example 39. The structure of GalNAc$_3$-8a was shown previously in Example 47. The structure of GalNAc$_3$-9a was shown previously in Example 52. The structure of GalNAc$_3$-6a was shown previously in Example 51. The structure of GalNAc$_3$-2a was shown previously in Example 37. The structure of GalNAc$_3$-10a was shown previously in Example 46. The structure of GalNAc$_3$-5a was shown previously in Example 49. The structure of GalNAc$_3$-7a was shown previously in Example 48.

Treatment

The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The $IC_{50}$ was calculated using standard methods and the results are presented in Table 53. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 53

| ASO | $IC_{50}$ (nM) | Internucleoside linkages | Conjugate | SEQ ID No. |
|---|---|---|---|---|
| ISIS 353382 | 190[a] | PS | none | 143 |
| ISIS 655861 | 11[a] | PS | $GalNAc_3$-1 | 144 |
| ISIS 655862 | 3 | PO/PS | $GalNAc_3$-1 | 144 |
| ISIS 661161 | 15[a] | PS | $GalNAc_3$-3 | 145 |
| ISIS 665001 | 20 | PS | $GalNAc_3$-8 | 145 |

TABLE 53-continued

| ASO | $IC_{50}$ (nM) | Internucleoside linkages | Conjugate | SEQ ID No. |
|---|---|---|---|---|
| ISIS 664078 | 55 | PS | $GalNAc_3$-9 | 144 |
| ISIS 666961 | 22[a] | PS | $GalNAc_3$-6 | 145 |
| ISIS 664507 | 30 | PS | $GalNAc_3$-2 | 145 |
| ISIS 666881 | 30 | PS | $GalNAc_3$-10 | 145 |
| ISIS 666224 | 30[a] | PS | $GalNAc_3$-5 | 145 |
| ISIS 666981 | 40 | PS | $GalNAc_3$-7 | 145 |

[a]Average of multiple runs.

Example 61: Preparation of Oligomeric Compound 175 Comprising $GalNAc_3$-12

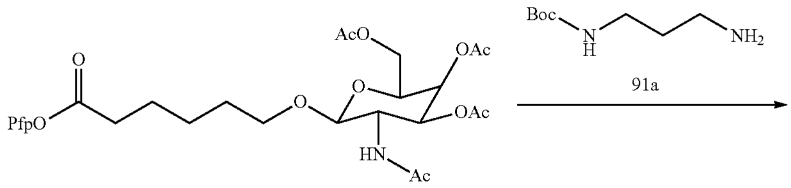

91a

166

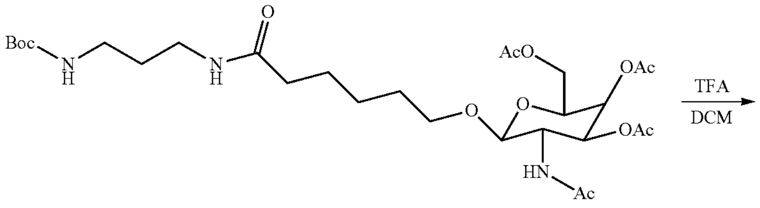

167

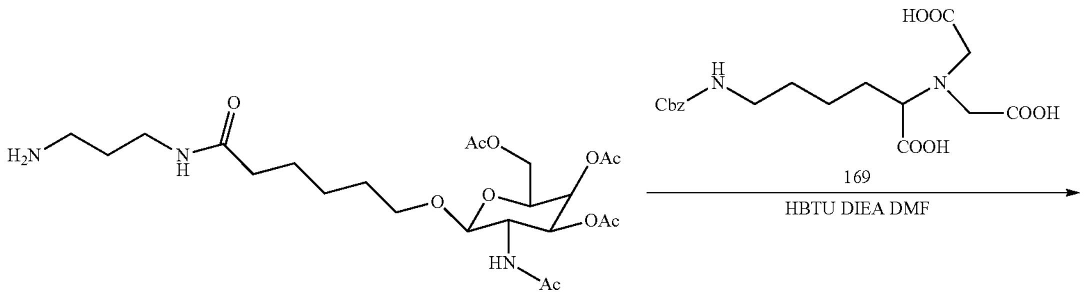

169

168

-continued
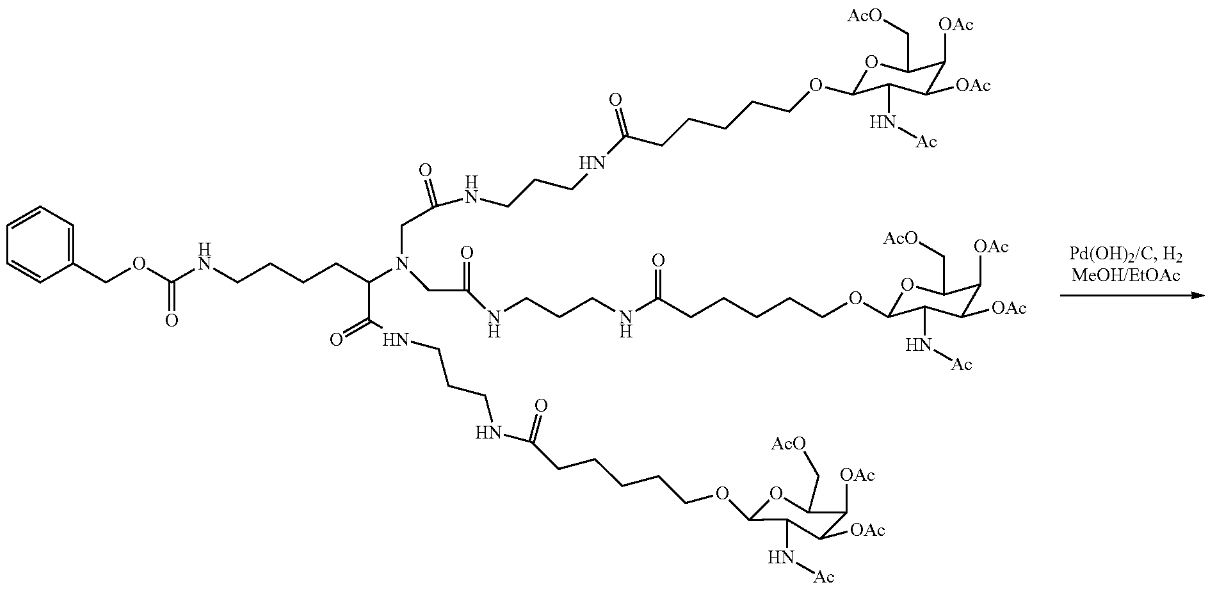
170
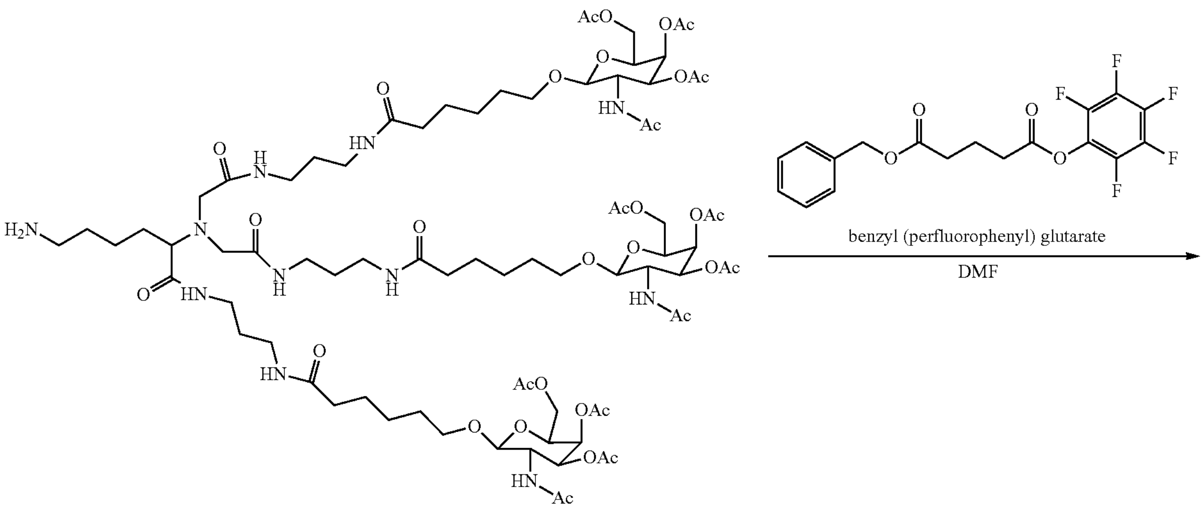
171

-continued
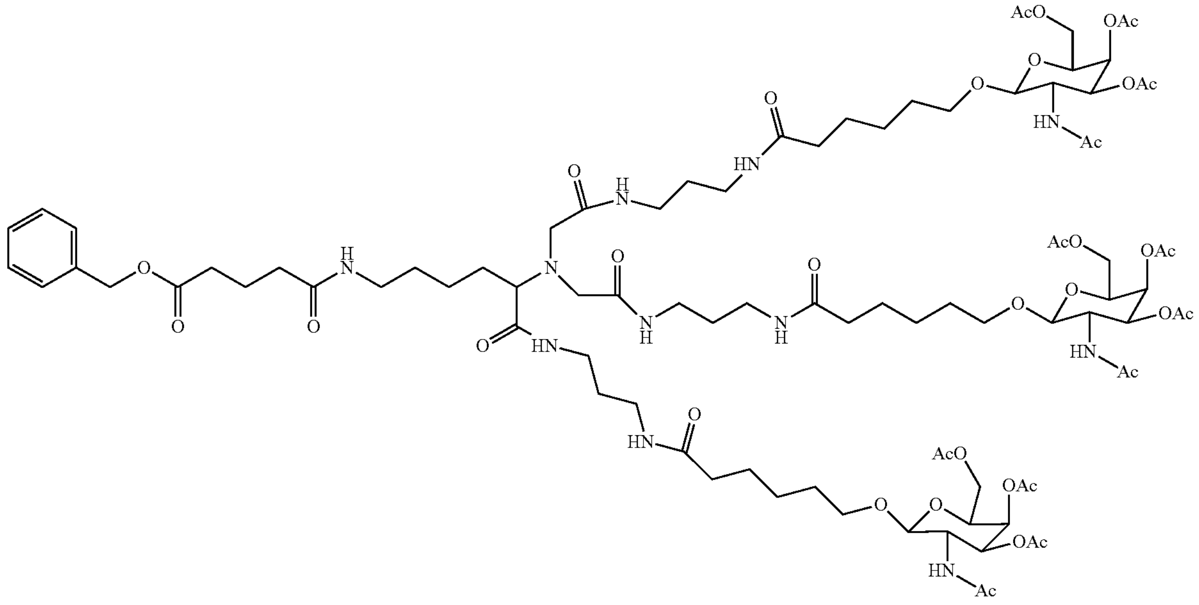
172
172 Pd(OH)$_2$/C, $H_2$ MeOH/EtOAc
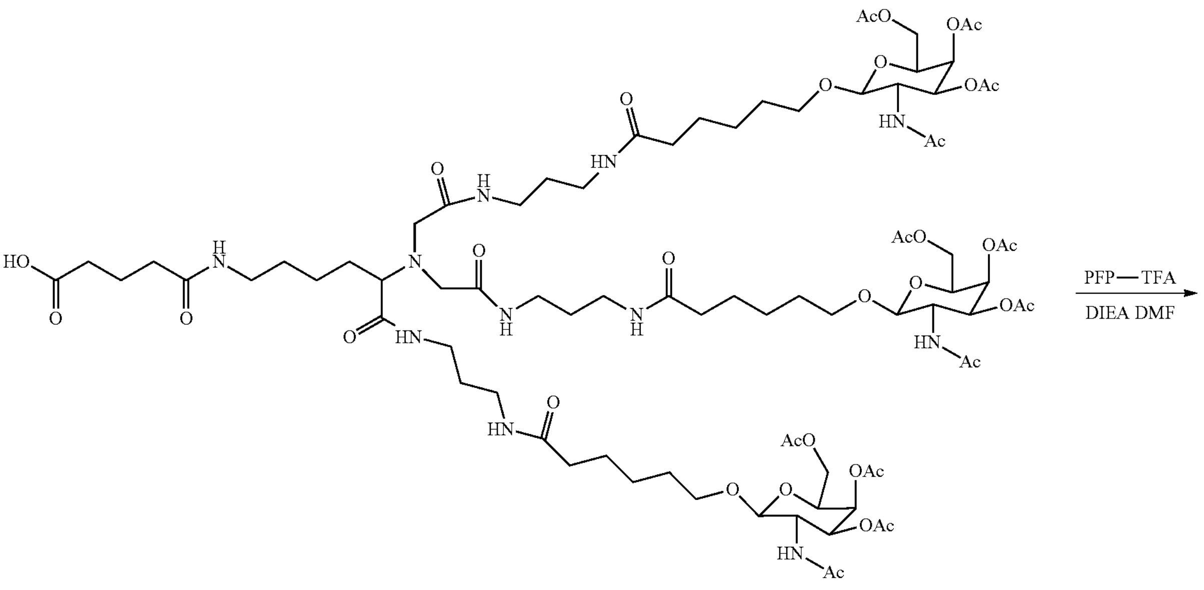
173

-continued

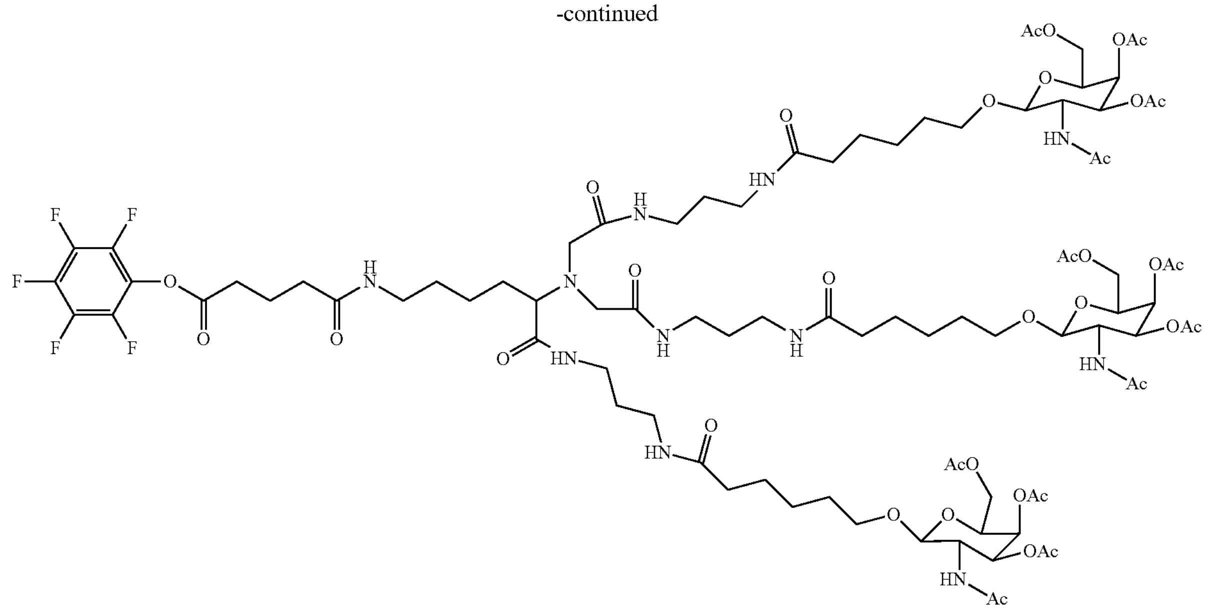

174

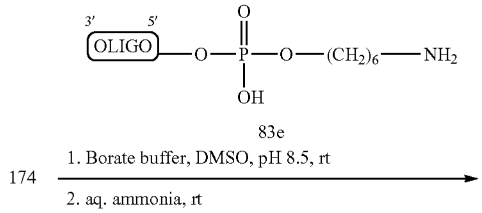

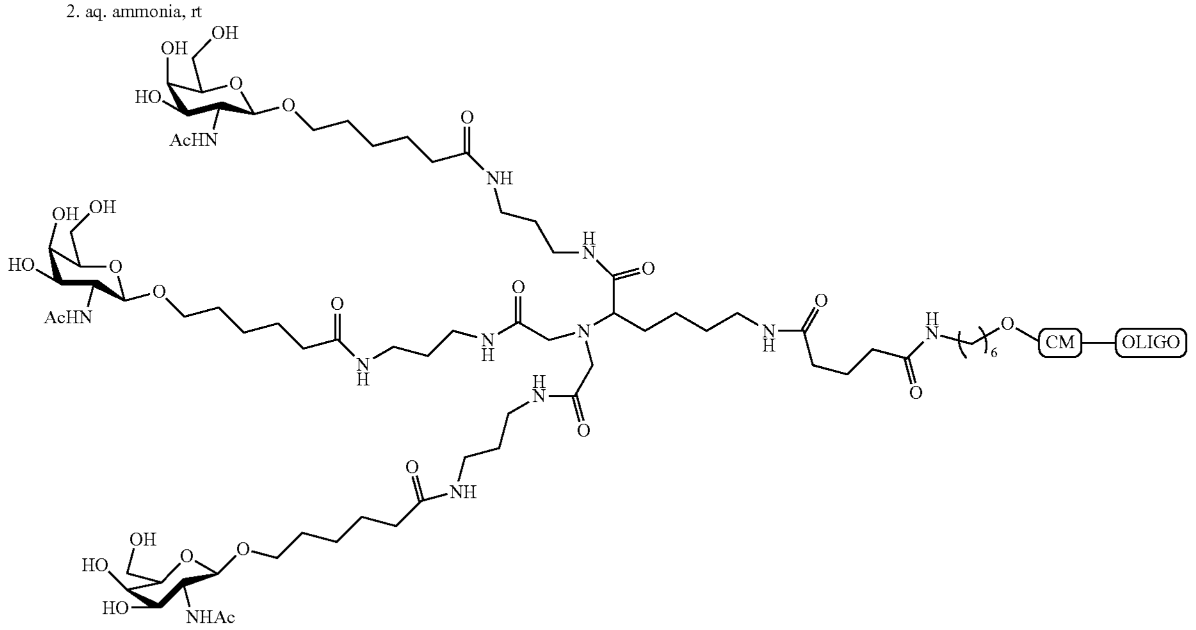

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(═O)(OH)-A$_d$-P(═O)(OH)—. The structure of GalNAc$_3$-12 (GalNAc$_3$-12$_a$-CM-) is shown below:

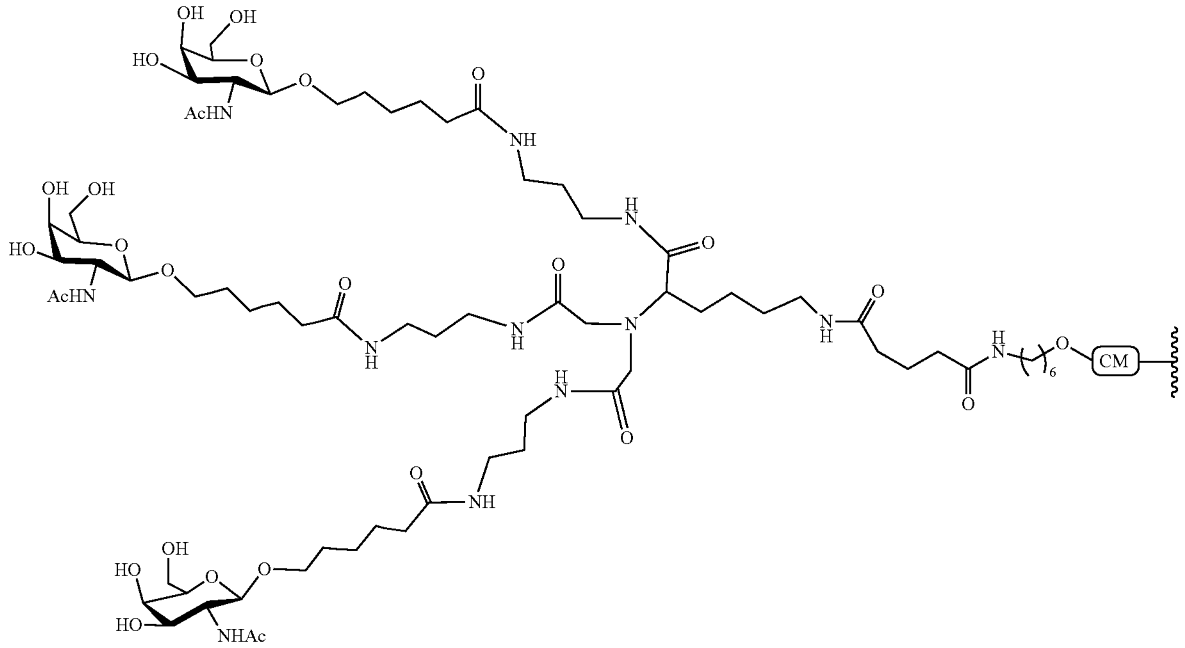
Example 62: Preparation of Oligomeric Compound 180 Comprising $GalNAc_3$-13
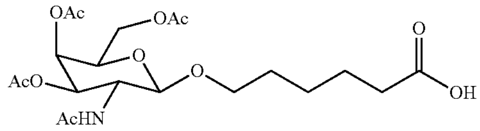
176
+
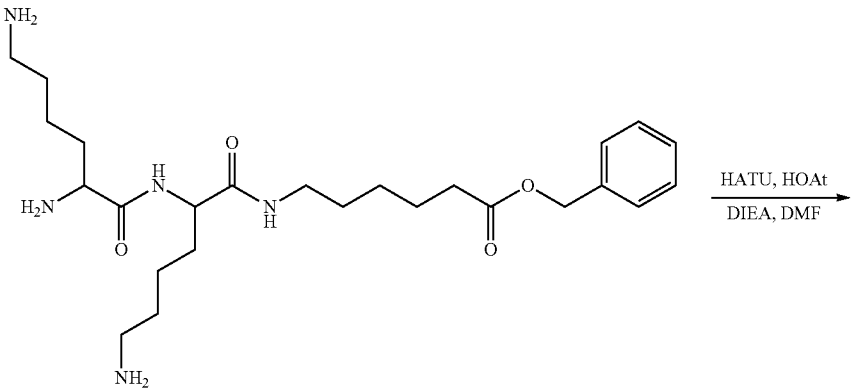
128

-continued
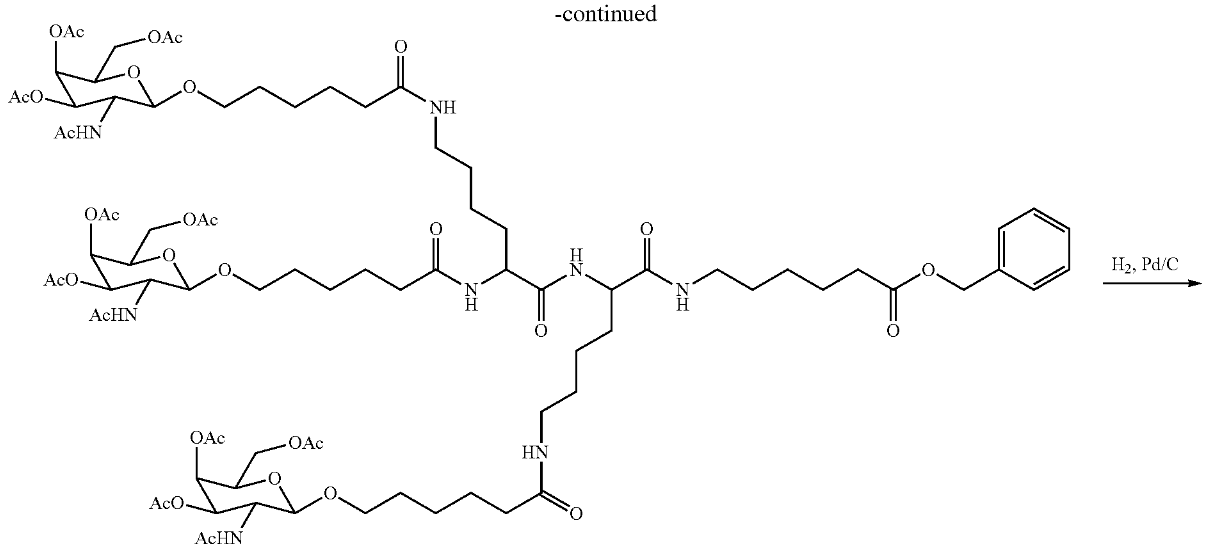
177
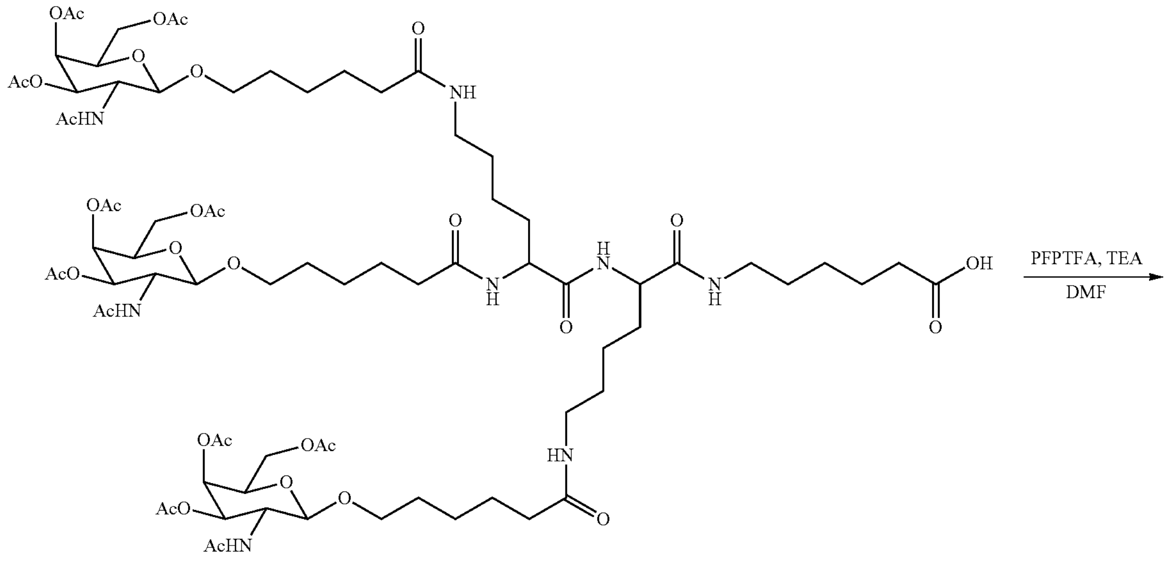
178
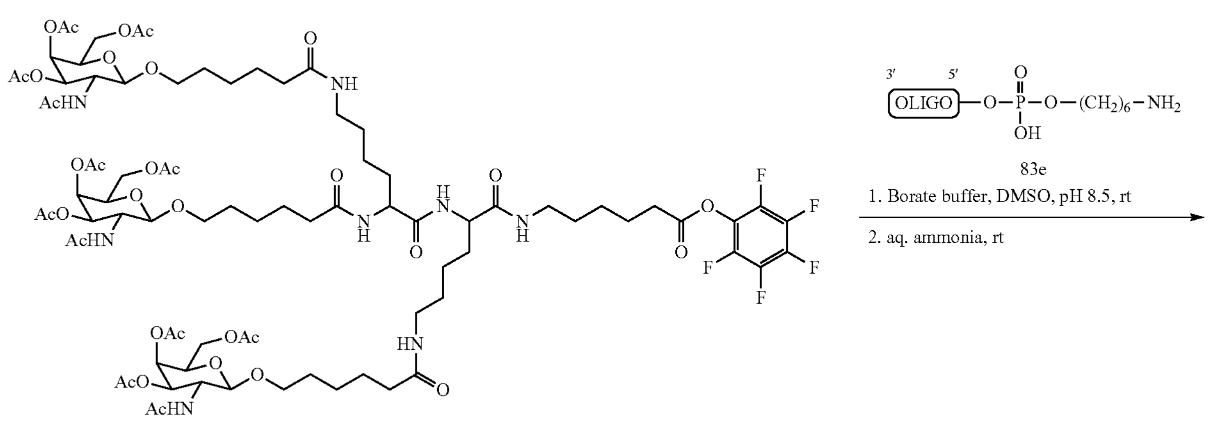
179

-continued

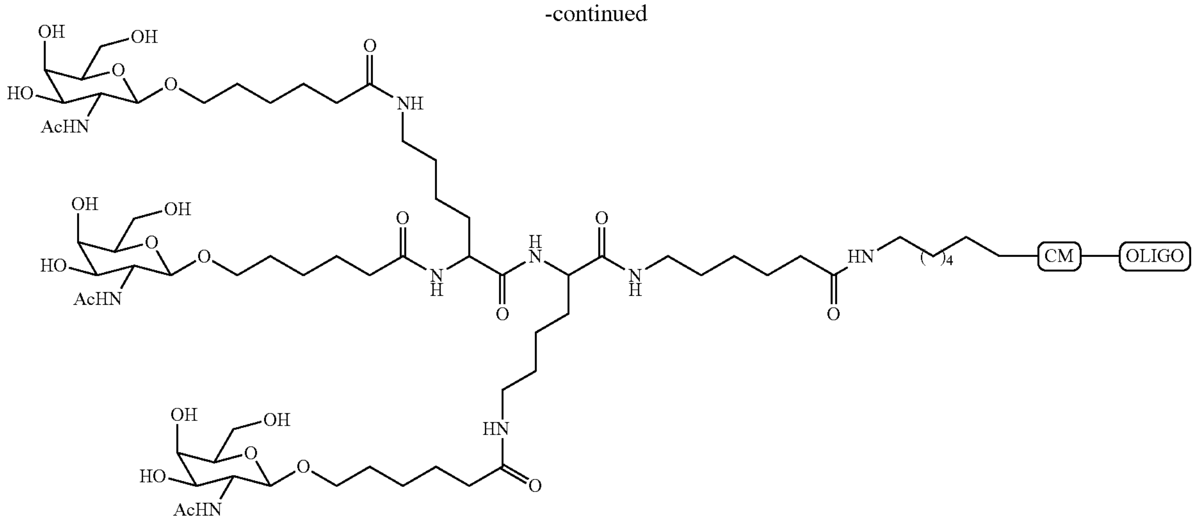

180

Compound 176 was prepared using the general procedure shown in Example 2. Oligomeric compound 180, comprising a GalNAc$_3$-13 conjugate group, was prepared from compound 177 using the general procedures illustrated in Example 49. The GalNAc3 cluster portion of the conjugate group GalNAc$_3$-13 (GalNAc$_3$-13$_a$) can be combined with any cleavable moiety to provide a variety of conjugate groups. In a certain embodiments, the cleavable moiety is —P(═O)(OH)-A$_d$-P(═O)(OH)—. The structure of GalNAc$_3$-13 (GalNAc$_3$-13$_a$-CM-) is shown below:

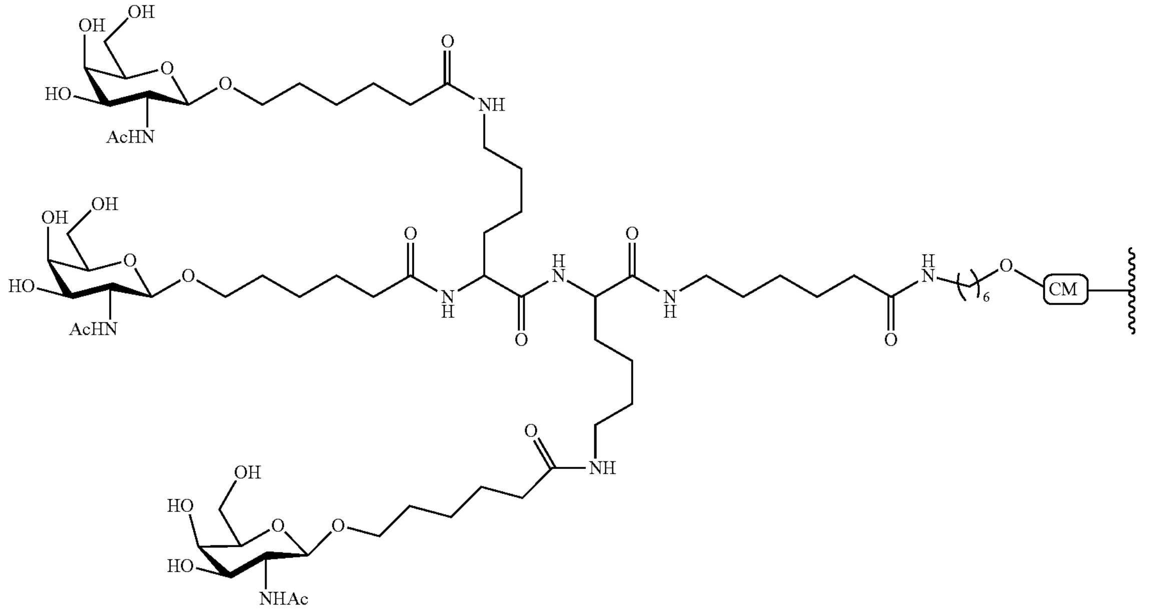

Example 63: Preparation of Oligomeric Compound 188 Comprising GalNAc$_3$-14
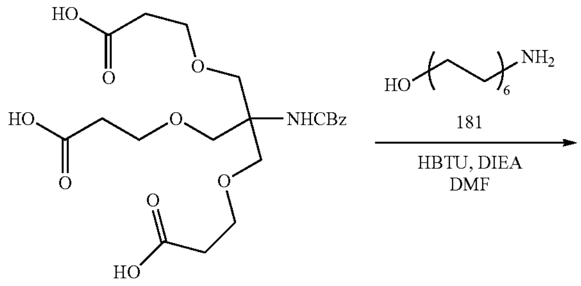
13
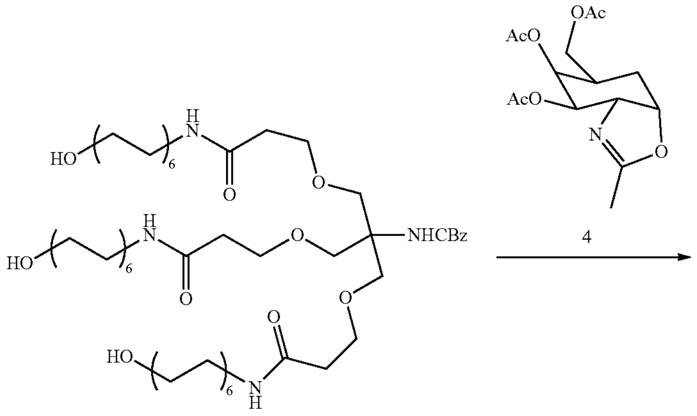
182
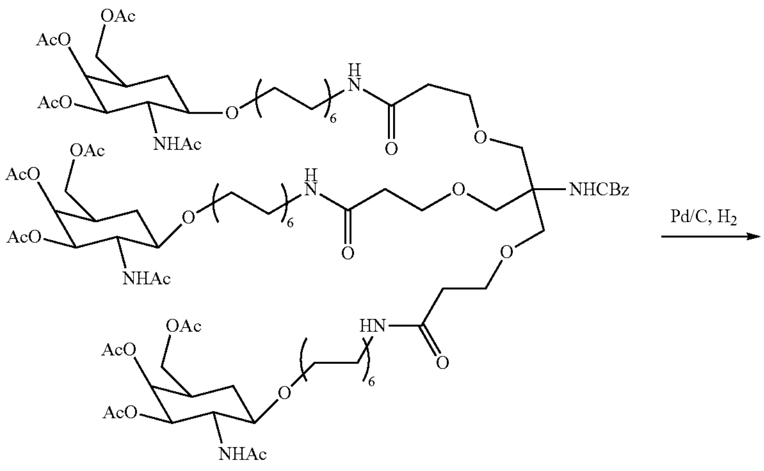
183

-continued
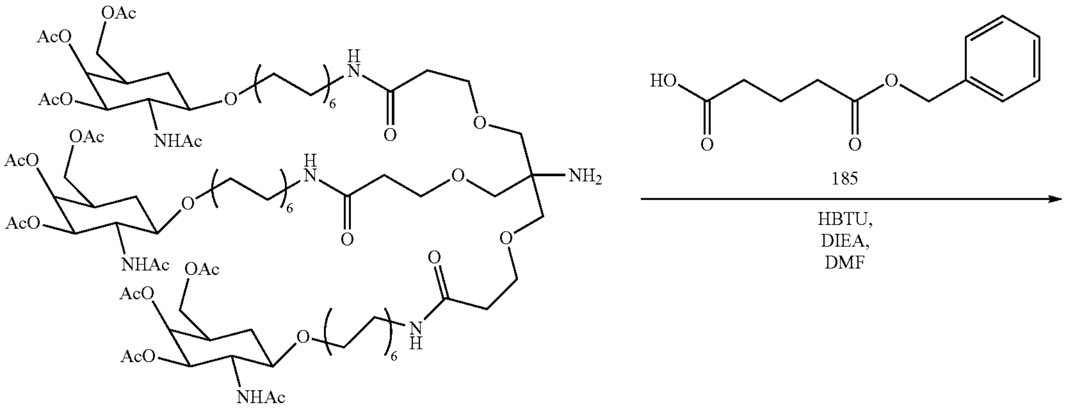
184
185
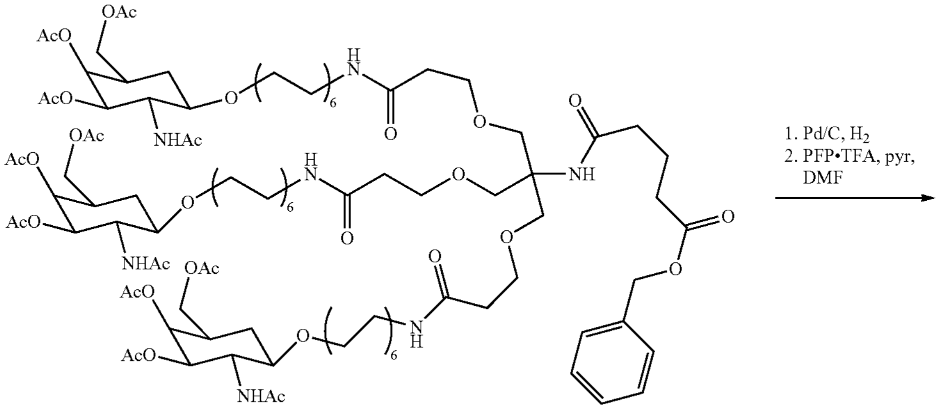
186
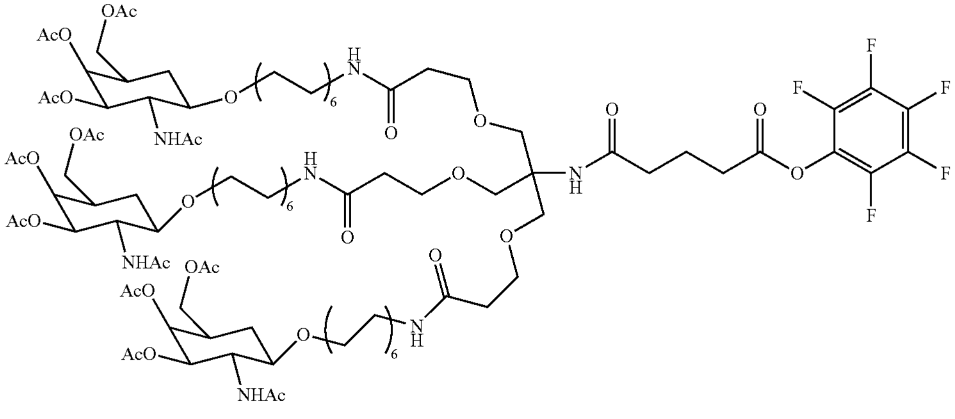
187
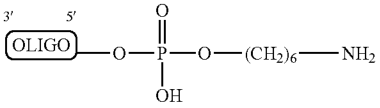
83e
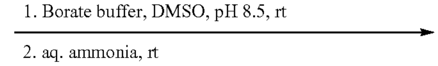
187

-continued

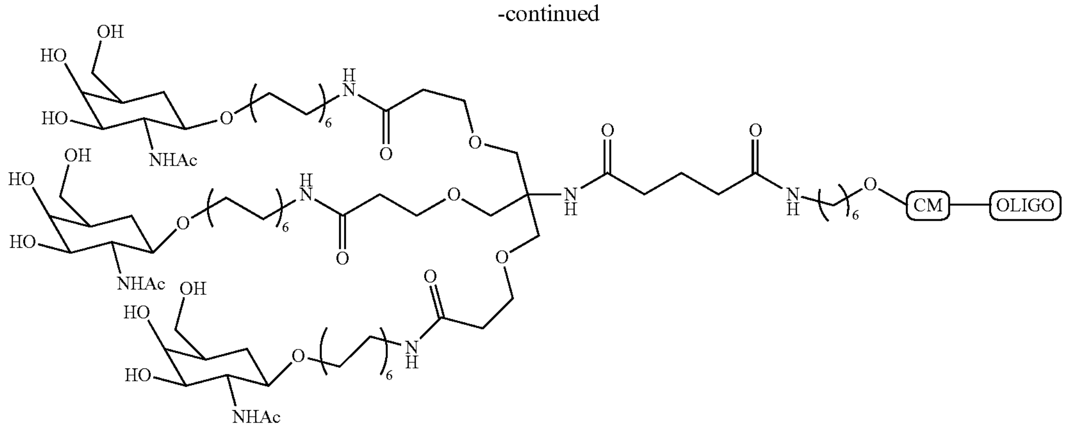

188

Compounds 181 and 185 are commercially available. Oligomeric compound 188, comprising a GalNA$c_3$-14 conjugate group, was prepared from compound 187 using the general procedures illustrated in Example 46. The GalNA$c_3$ cluster portion of the conjugate group GalNA$c_3$-14 (GalNA$c_3$-$14_a$) can be combined with any cleavable moiety to provide a variety of conjugate groups. In certain embodiments, the cleavable moiety is —P(═O)(OH)-$A_d$-P(═O)(OH)—. The structure of GalNA$c_3$-14 (GalNA$c_3$-$14_a$-CM-) is shown below:

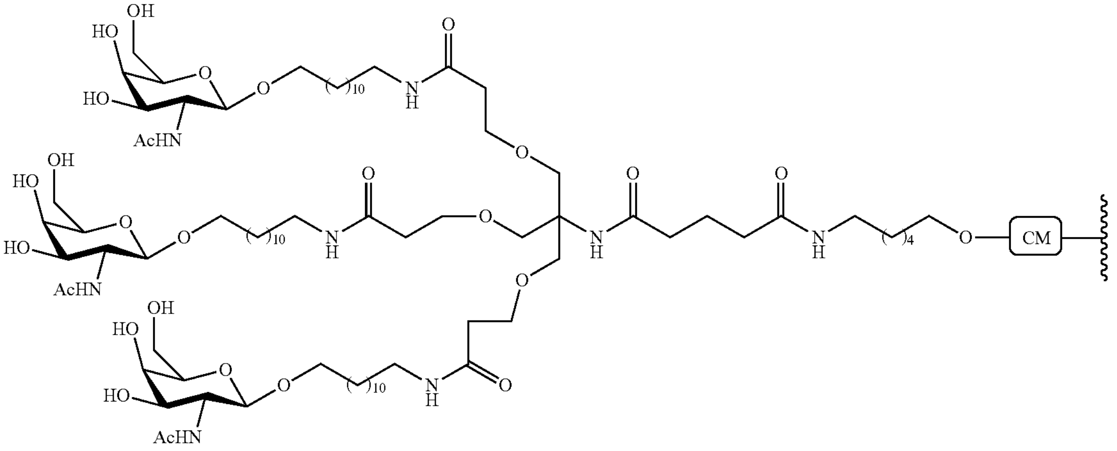

Example 64: Preparation of Oligomeric Compound 197 Comprising GalNA$c_3$-15

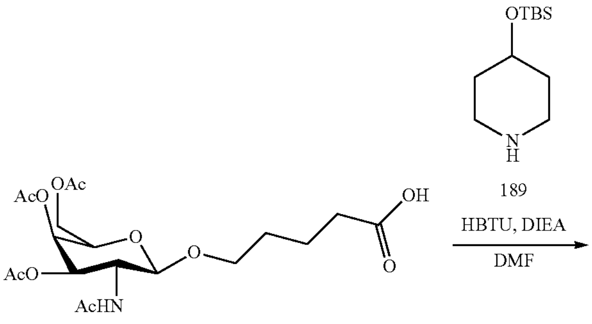

7

189

-continued
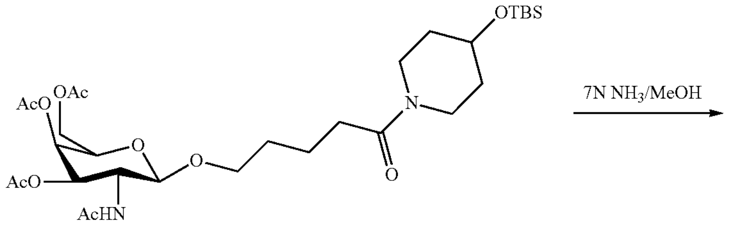
190
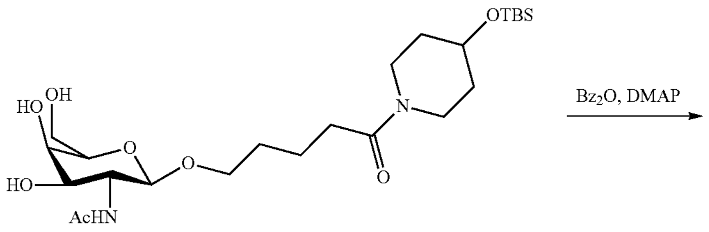
191
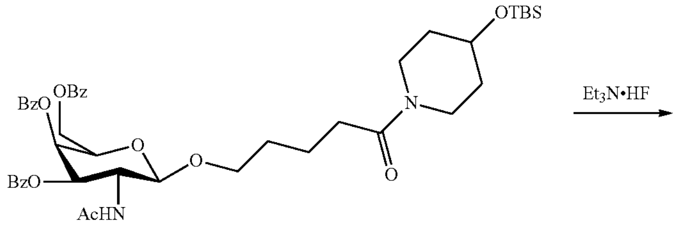
192
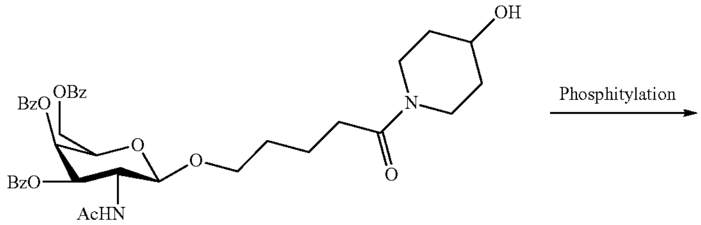
193
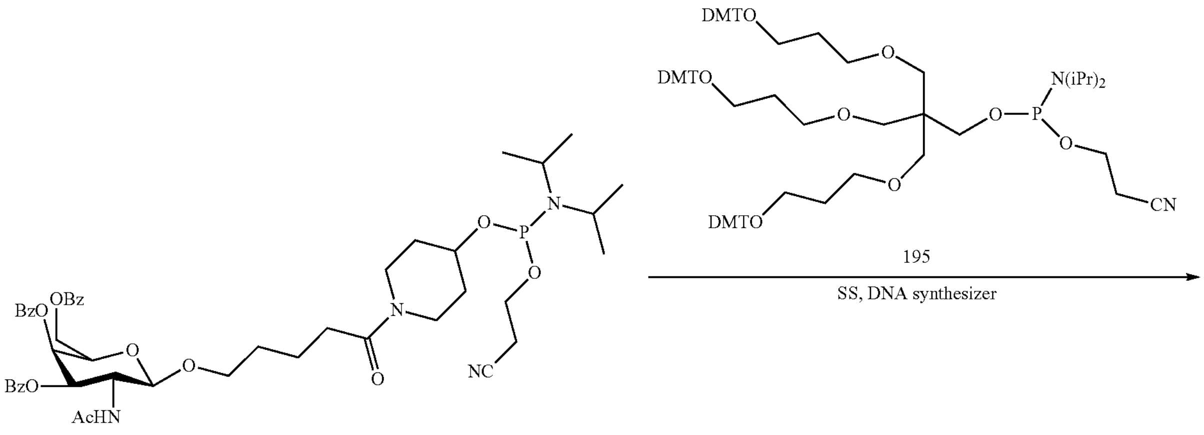
194

-continued

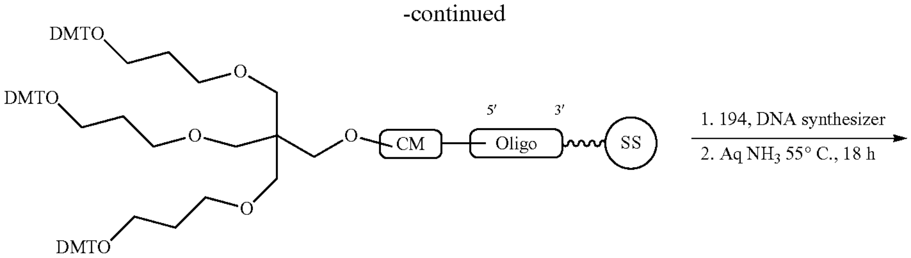

196

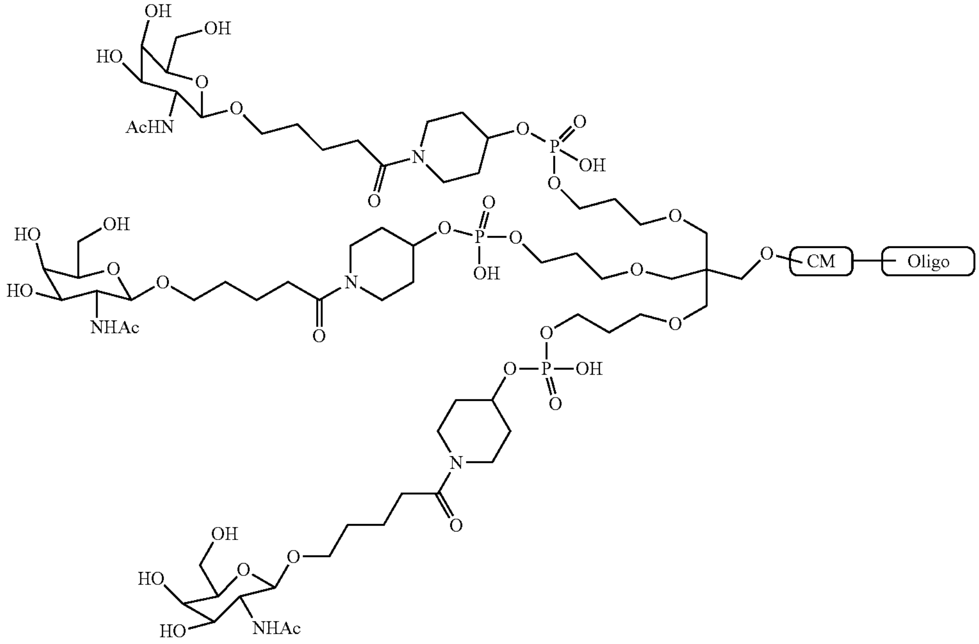

197

Compound 189 is commercially available. Compound 195 was prepared using the general procedure shown in Example 31. Oligomeric compound 197, comprising a GalNAc$_3$-15 conjugate group, was prepared from compounds 194 and 195 using standard oligonucleotide synthesis procedures. The GalNAc$_3$ cluster portion of the conjugate group GalNAc$_3$-15 (GalNAc$_3$-15$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-15 (GalNAc$_3$-15$_a$-CM-) is shown below:

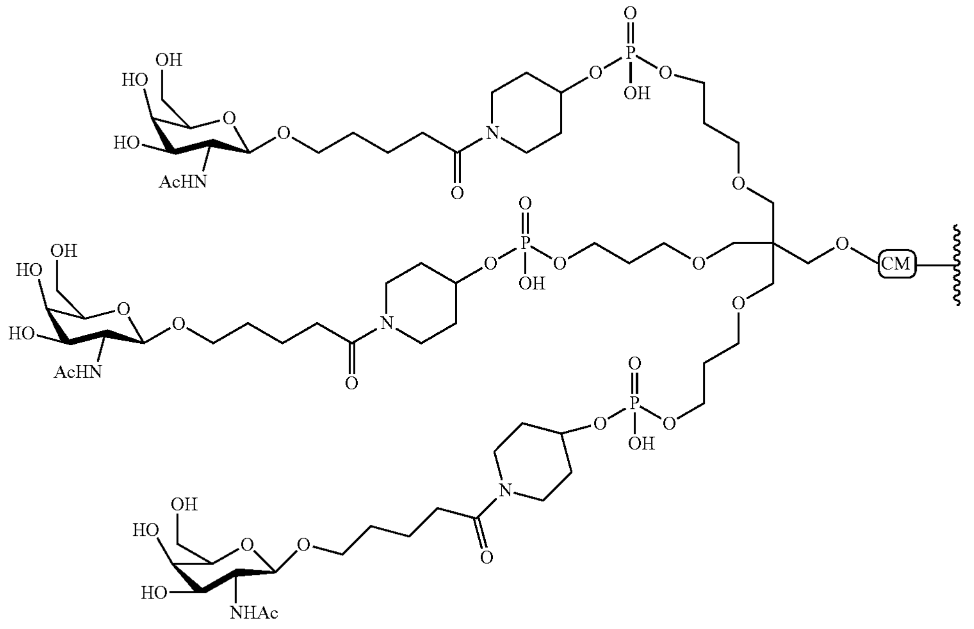

Example 65: Dose-Dependent Study of Oligonucleotides Comprising a 5'-Conjugate Group (Comparison of GalNAc$_3$-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the GalNAc3 conjugate groups was attached at the 5' terminus of the respective oligonucleotide by a phosphodiester linked 2'-deoxyadenosine nucleoside (cleavable moiety).

The structure of GalNAc$_3$-3$_a$ was shown previously in Example 39. The structure of GalNAc$_3$-12a was shown previously in Example 61. The structure of GalNAc$_3$-13a was shown previously in Example 62. The structure of GalNAc$_3$-14a was shown previously in Example 63. The structure of GalNAc$_3$-15a was shown previously in Example 64.

Treatment

Six to eight week old C57bl6 mice (Jackson Laboratory, Bar Harbor, ME) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the

TABLE 54

Modified ASOs targeting SRB-1

| ISIS No. | Sequences (5' to 3') | Conjugate | SEQ ID No. |
|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | none | 143 |
| 661161 | **GalNAc3-3a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-3 | 145 |
| 671144 | **GalNAc3-12a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-12 | 145 |
| 670061 | **GalNAc3-13a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-13 | 145 |
| 671261 | **GalNAc3-14a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-14 | 145 |
| 671262 | **GalNAc3-15a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-15 | 145 |

Capital letters indicate the nucleobase for each nucleoside and $^{m}$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

average percent of SRB-1 mRNA levels for each treatment group, normalized to the saline control.

As illustrated in Table 55, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked $GalNAc_3$-3, 12, 13, 14, and 15 conjugates showed substantial improvement in potency compared to the unconjugated antisense oligonucleotide (ISIS 335382).

TABLE 55

| SRB-1 mRNA (% Saline) | | | | |
|---|---|---|---|---|
| ISIS No. | Dosage (mg/kg) | SRB-1 mRNA (% Saline) | $ED_{50}$ (mg/kg) | Conjugate |
| Saline | n/a | 100.0 | n/a | n/a |
| 353382 | 3 | 85.0 | 22.4 | none |
| | 10 | 69.2 | | |
| | 30 | 34.2 | | |
| | 2 × 15 | 36.0 | | |
| 661161 | 0.5 | 87.4 | 2.2 | $GalNAc_3$-3 |
| | 1.5 | 59.0 | | |
| | 5 | 25.6 | | |
| | 2 × 2.5 | 27.5 | | |
| | 15 | 17.4 | | |
| 671144 | 0.5 | 101.2 | 3.4 | $GalNAc_3$-12 |
| | 1.5 | 76.1 | | |
| | 5 | 32.0 | | |
| | 15 | 17.6 | | |
| 670061 | 0.5 | 94.8 | 2.1 | $GalNAc_3$-13 |
| | 1.5 | 57.8 | | |
| | 5 | 20.7 | | |
| | 15 | 13.3 | | |
| 671261 | 0.5 | 110.7 | 4.1 | $GalNAc_3$-14 |
| | 1.5 | 81.9 | | |
| | 5 | 39.8 | | |
| | 15 | 14.1 | | |
| 671262 | 0.5 | 109.4 | 9.8 | $GalNAc_3$-15 |
| | 1.5 | 99.5 | | |
| | 5 | 69.2 | | |
| | 15 | 36.1 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 56

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
| | 10 | 25 | 78 | 0.2 | 36 | |
| | 30 | 28 | 62 | 0.2 | 35 | |
| | 2 × 15 | 22 | 59 | 0.2 | 33 | |
| 661161 | 0.5 | 39 | 72 | 0.2 | 34 | $GalNAc_3$-3 |
| | 1.5 | 26 | 50 | 0.2 | 33 | |
| | 5 | 41 | 80 | 0.2 | 32 | |
| | 2 × 2.5 | 24 | 72 | 0.2 | 28 | |
| | 15 | 32 | 69 | 0.2 | 36 | |
| 671144 | 0.5 | 25 | 39 | 0.2 | 34 | $GalNAc_3$-12 |
| | 1.5 | 26 | 55 | 0.2 | 28 | |
| | 5 | 48 | 82 | 0.2 | 34 | |
| | 15 | 23 | 46 | 0.2 | 32 | |
| 670061 | 0.5 | 27 | 53 | 0.2 | 33 | $GalNAc_3$-13 |
| | 1.5 | 24 | 45 | 0.2 | 35 | |
| | 5 | 23 | 58 | 0.1 | 34 | |
| | 15 | 24 | 72 | 0.1 | 31 | |
| 671261 | 0.5 | 69 | 99 | 0.1 | 33 | $GalNAc_3$-14 |
| | 1.5 | 34 | 62 | 0.1 | 33 | |
| | 5 | 43 | 73 | 0.1 | 32 | |
| | 15 | 32 | 53 | 0.2 | 30 | |
| 671262 | 0.5 | 24 | 51 | 0.2 | 29 | $GalNAc_3$-15 |
| | 1.5 | 32 | 62 | 0.1 | 31 | |
| | 5 | 30 | 76 | 0.2 | 32 | |
| | 15 | 31 | 64 | 0.1 | 32 | |

Example 66: Effect of Various Cleavable Moieties on Antisense Inhibition In Vivo by Oligonucleotides Targeting SRB-1 Comprising a 5'-$GalNAc_3$ Cluster The oligonucleotides listed below were tested in a dose-dependent study for antisense inhibition of SRB-1 in mice. Each of the GalNAc3 conjugate groups was attached at the 5' terminus of the respective oligonucleotide by a phosphodiester linked nucleoside (cleavable moiety (CM)).

TABLE 57

| Modified ASOs targeting SRB-1 | | | | |
|---|---|---|---|---|
| ISIS No. | Sequences (5' to 3') | $GalNAc_3$ Cluster | CM | SEQ ID No. |
| 661161 | **GalNAc3-3a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 145 |
| 670699 | **GalNAc3-3a-o'Tdo**$G_{es}{}^{m}C_{eo}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_3$-3a | $T_d$ | 148 |
| 670700 | **GalNAc3-3a-o'Aeo**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_3$-3a | $A_e$ | 145 |

TABLE 57-continued

| Modified ASOs targeting SRB-1 | | | | |
|---|---|---|---|---|
| ISIS No. | Sequences (5' to 3') | GalNAc$_3$ Cluster | CM | SEQ ID No. |
| 670701 | **GalNAc3-3a-o'Teo**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_3$-3a | $T_e$ | 148 |
| 671165 | **GalNAc3-13a-o'Ad-**o$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_3$-13a | $A_d$ | 145 |

Capital letters indicate the nucleobase for each nucleoside and $^{m}$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-3$_a$ was shown previously in Example 39. The structure of GalNAc$_3$-13a was shown previously in Example 62.

Treatment

Six to eight week old C57bl6 mice (Jackson Laboratory, Bar Harbor, ME) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 58, treatment with antisense oligonucleotides lowered SRB-1 mRNA levels in a dose-dependent manner. The antisense oligonucleotides comprising various cleavable moieties all showed similar potencies.

TABLE 58

| SRB-1 mRNA (% Saline) | | | | |
|---|---|---|---|---|
| ISIS No. | Dosage (mg/kg) | SRB-1 mRNA (% Saline) | GalNAc$_3$ Cluster | CM |
| Saline | n/a | 100.0 | n/a | n/a |
| 661161 | 0.5 | 87.8 | GalNAc$_3$-3a | $A_d$ |
| | 1.5 | 61.3 | | |
| | 5 | 33.8 | | |
| | 15 | 14.0 | | |
| 670699 | 0.5 | 89.4 | GalNAc$_3$-3a | $T_d$ |
| | 1.5 | 59.4 | | |
| | 5 | 31.3 | | |
| | 15 | 17.1 | | |
| 670700 | 0.5 | 79.0 | GalNAc$_3$-3a | $A_e$ |
| | 1.5 | 63.3 | | |
| | 5 | 32.8 | | |
| | 15 | 17.9 | | |
| 670701 | 0.5 | 79.1 | GalNAc$_3$-3a | $T_e$ |
| | 1.5 | 59.2 | | |
| | 5 | 35.8 | | |
| | 15 | 17.7 | | |

TABLE 58-continued

| SRB-1 mRNA (% Saline) | | | | |
|---|---|---|---|---|
| ISIS No. | Dosage (mg/kg) | SRB-1 mRNA (% Saline) | GalNAc$_3$ Cluster | CM |
| 671165 | 0.5 | 76.4 | GalNAc$_3$-13a | $A_d$ |
| | 1.5 | 43.2 | | |
| | 5 | 22.6 | | |
| | 15 | 10.0 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 59

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | GalNAc$_3$-3a | $A_d$ |
| | 1.5 | 24 | 50 | 0.2 | 32 | | |
| | 5 | 26 | 55 | 0.2 | 28 | | |
| | 15 | 27 | 52 | 0.2 | 31 | | |
| 670699 | 0.5 | 42 | 83 | 0.2 | 31 | GalNAc$_3$-3a | $T_d$ |
| | 1.5 | 33 | 58 | 0.2 | 32 | | |
| | 5 | 26 | 70 | 0.2 | 29 | | |
| | 15 | 25 | 67 | 0.2 | 29 | | |
| 670700 | 0.5 | 40 | 74 | 0.2 | 27 | GalNAc$_3$-3a | $A_e$ |
| | 1.5 | 23 | 62 | 0.2 | 27 | | |
| | 5 | 24 | 49 | 0.2 | 29 | | |
| | 15 | 25 | 87 | 0.1 | 25 | | |
| 670701 | 0.5 | 30 | 77 | 0.2 | 27 | GalNAc$_3$-3a | $T_e$ |
| | 1.5 | 22 | 55 | 0.2 | 30 | | |
| | 5 | 81 | 101 | 0.2 | 25 | | |
| | 15 | 31 | 82 | 0.2 | 24 | | |
| 671165 | 0.5 | 44 | 84 | 0.2 | 26 | GalNAc$_3$-13a | $A_d$ |
| | 1.5 | 47 | 71 | 0.1 | 24 | | |
| | 5 | 33 | 91 | 0.2 | 26 | | |
| | 15 | 33 | 56 | 0.2 | 29 | | |

Example 67: Preparation of Oligomeric Compound 199 Comprising GalNAc$_3$-16
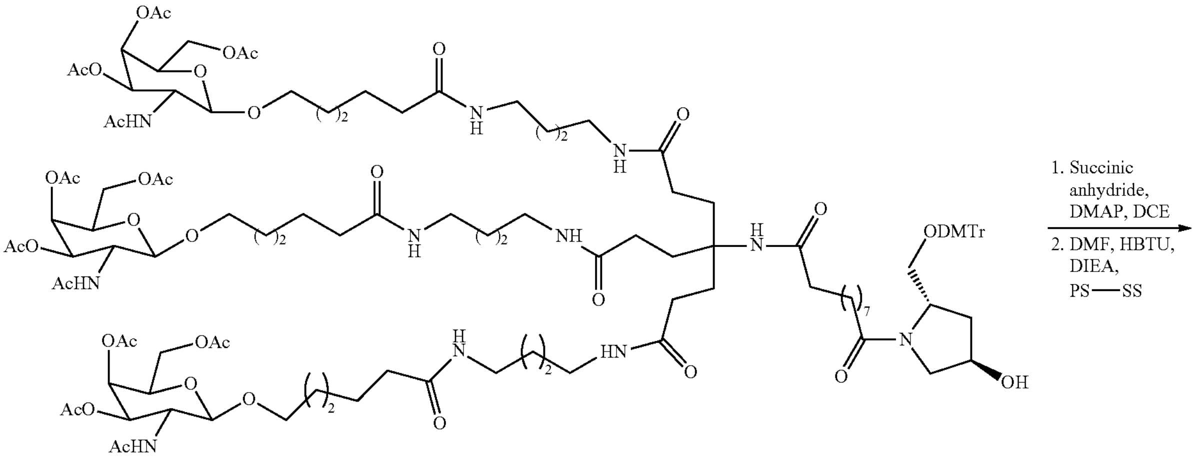
98d
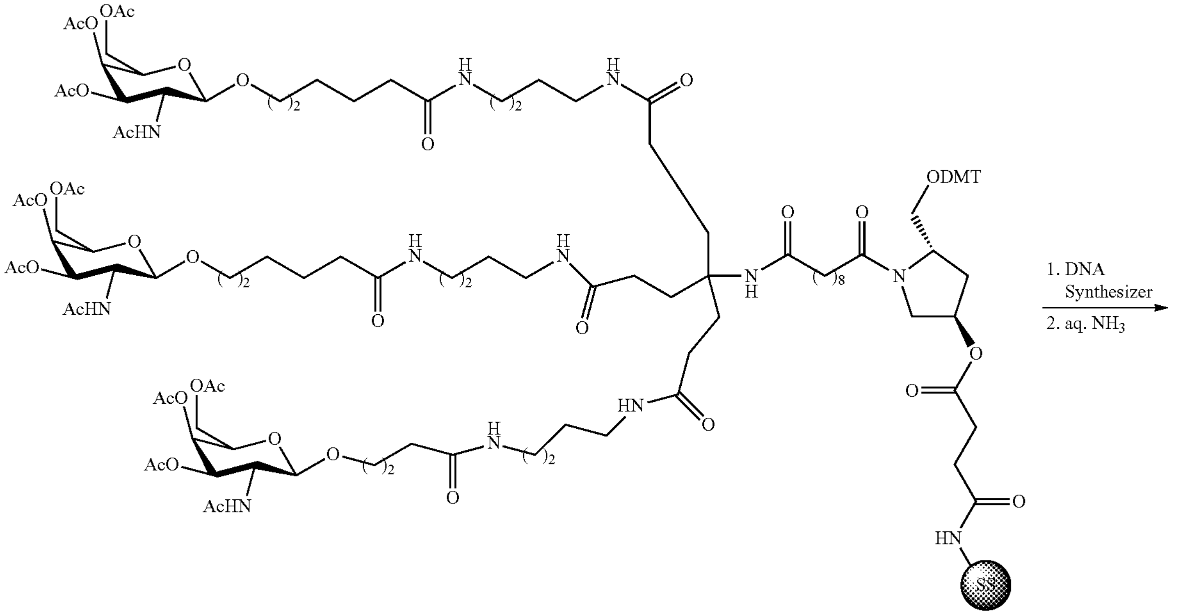
198
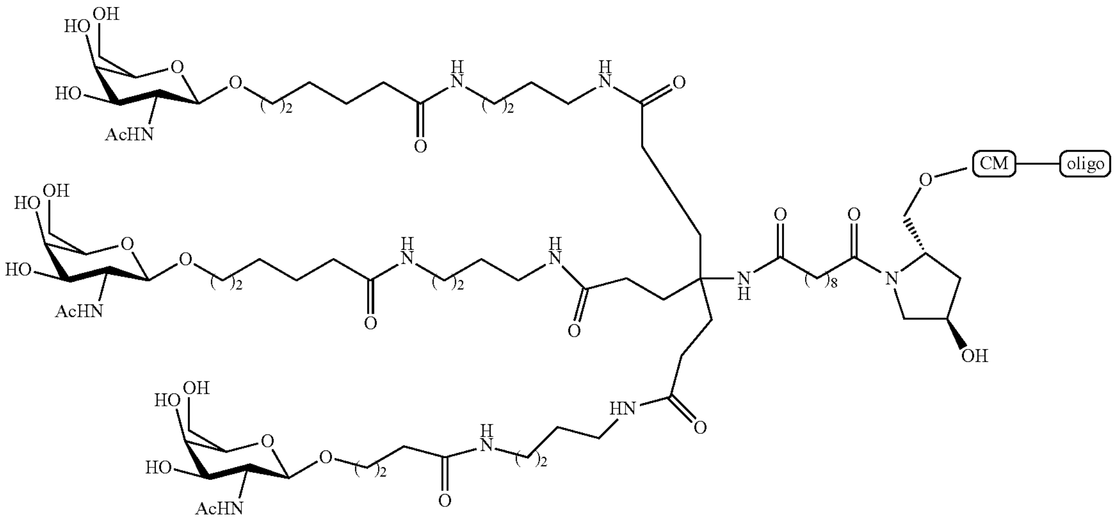
199

Oligomeric compound 199, comprising a $GalNAc_3$-16 conjugate group, is prepared using the general procedures illustrated in Examples 7 and 9. The $GalNAc_3$ cluster portion of the conjugate group $GalNAc_3$-16 ($GalNAc_3$-$16_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-16 ($GalNAc_3$-$16_a$-CM-) is shown below:

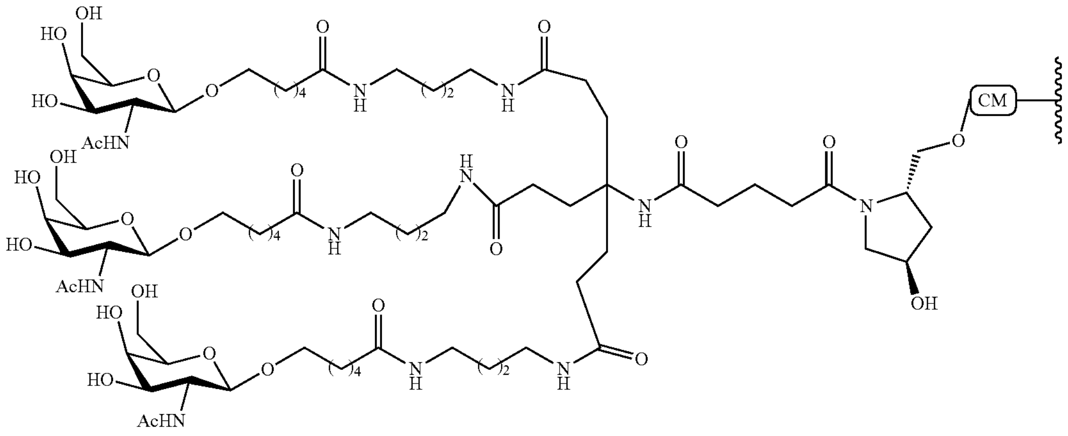

Example 68: Preparation of Oligomeric Compound 200 Comprising $GalNAc_3$-17

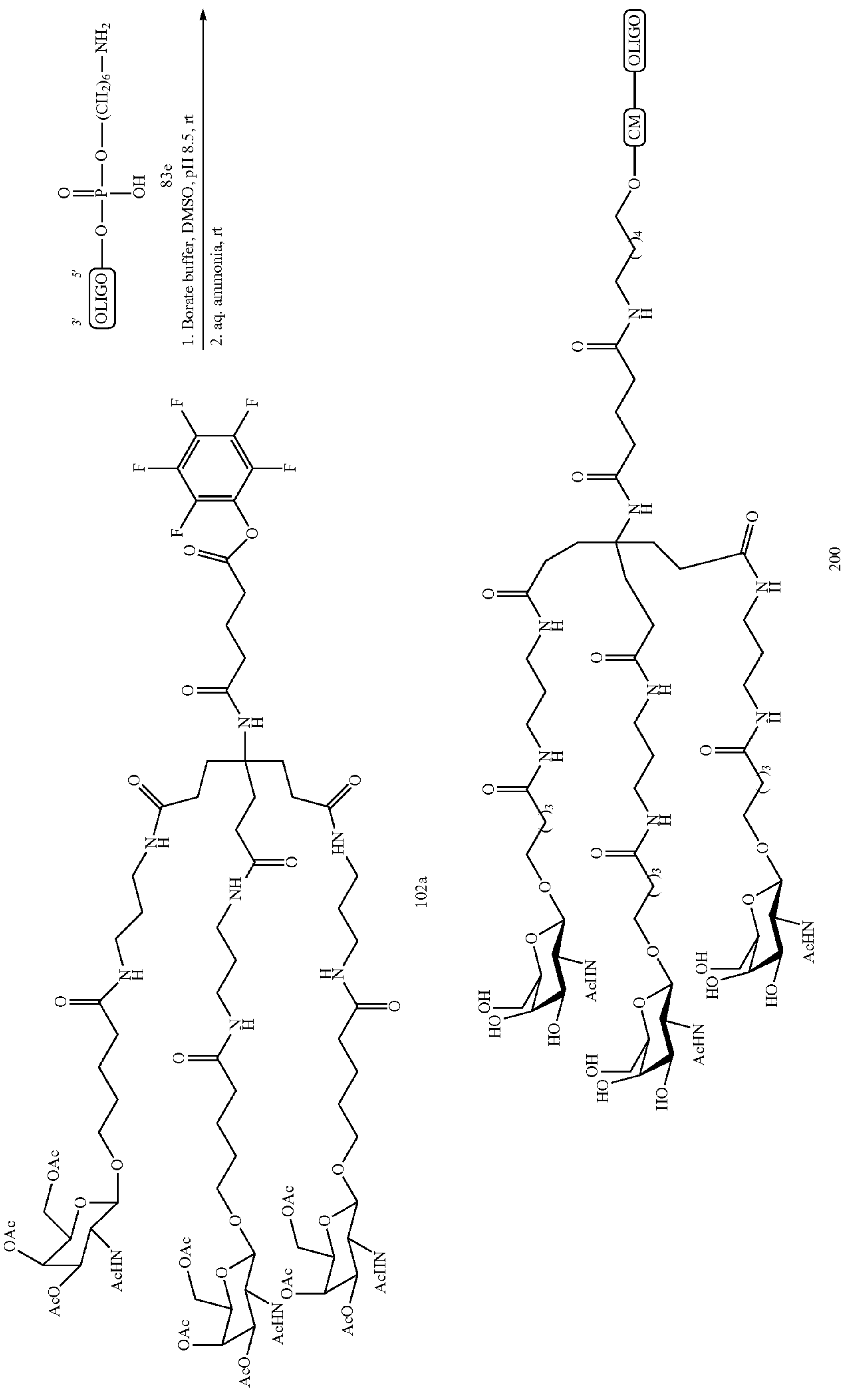
102a
200

Oligomeric compound 200, comprising a GalNAc$_3$-17 conjugate group, was prepared using the general procedures illustrated in Example 46. The GalNAc3 cluster portion of the conjugate group GalNAc$_3$-17 (GalNAc$_3$-17$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-17 (GalNAc$_3$-17$_a$-CM-) is shown below:

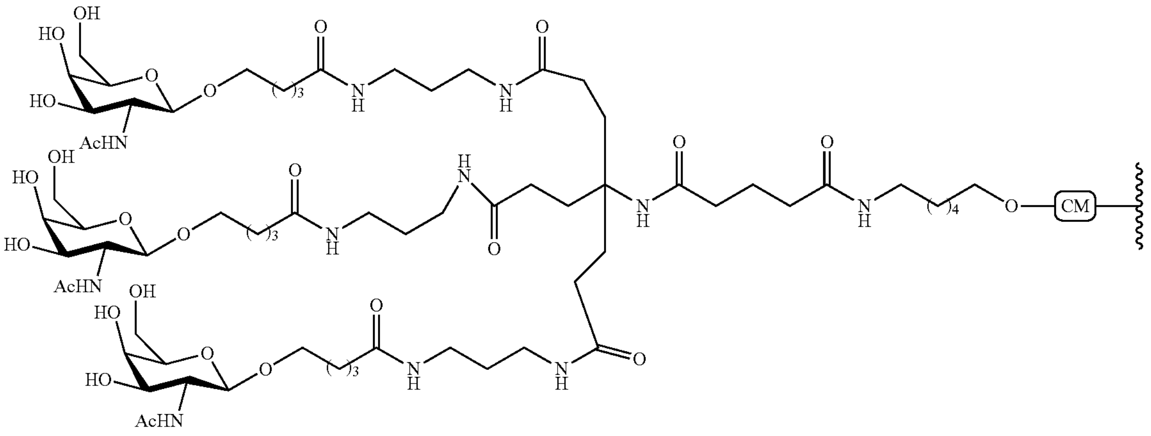

Example 69: Preparation of Oligomeric Compound 201 Comprising GalNAc$_3$-18

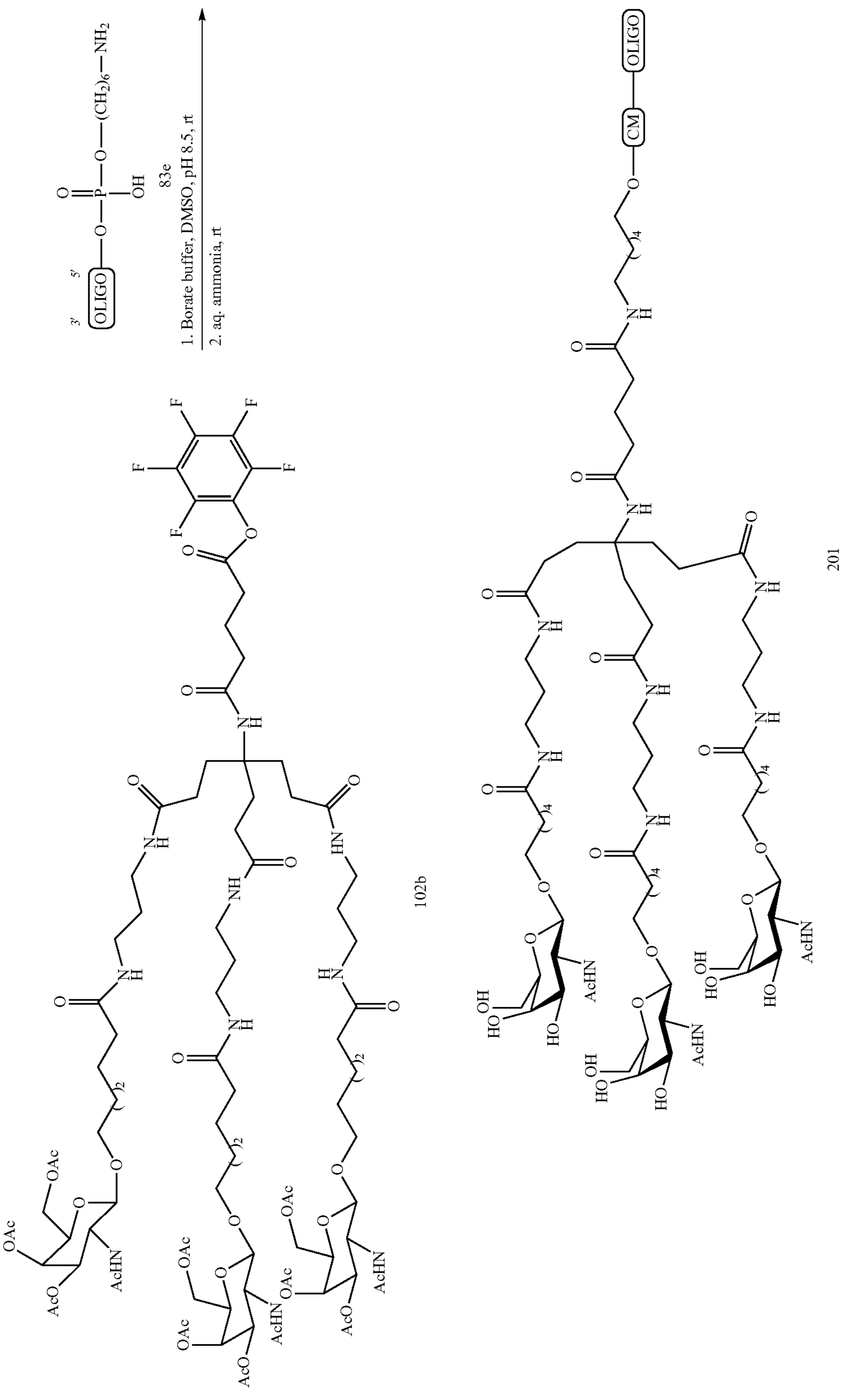
102b
83e
201

Oligomeric compound 201, comprising a $GalNAc_3$-18 conjugate group, was prepared using the general procedures illustrated in Example 46. The $GalNAc_3$ cluster portion of the conjugate group $GalNAc_3$-18 ($GalNAc_3$-$18_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-18 ($GalNAc_3$-$18_a$-CM-) is shown below:

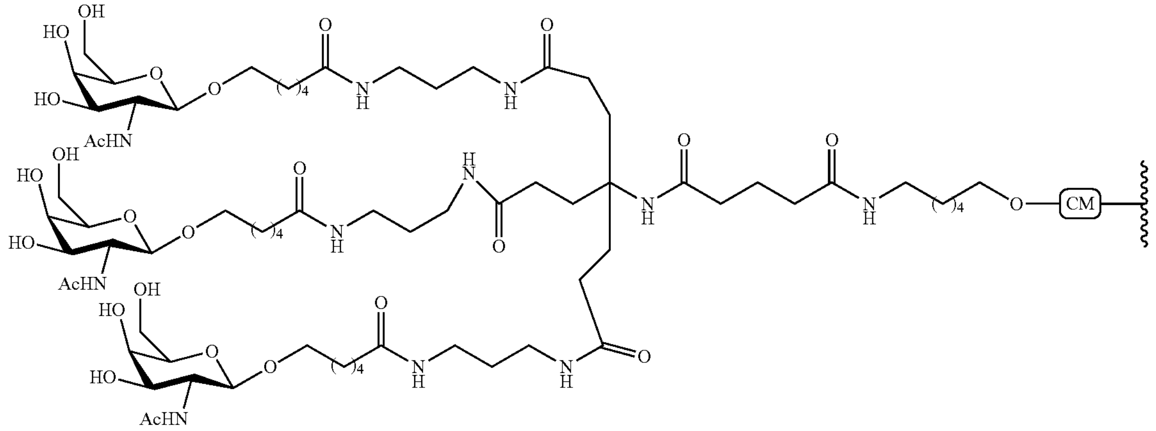

Example 70: Preparation of Oligomeric Compound 204 Comprising $GalNAc_3$-19

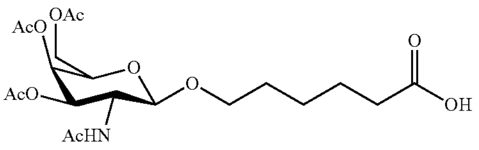

64

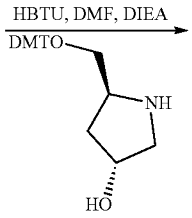

47

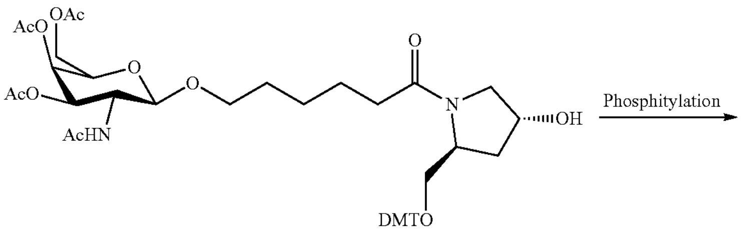

202

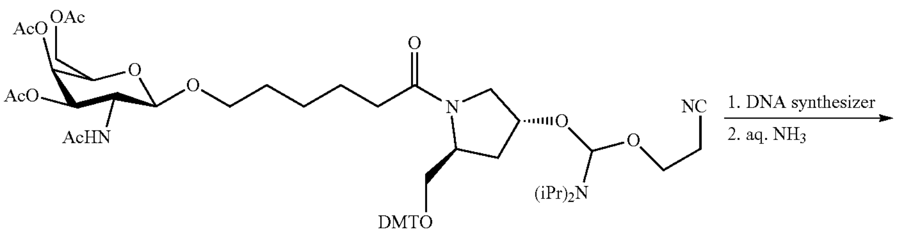

203

-continued

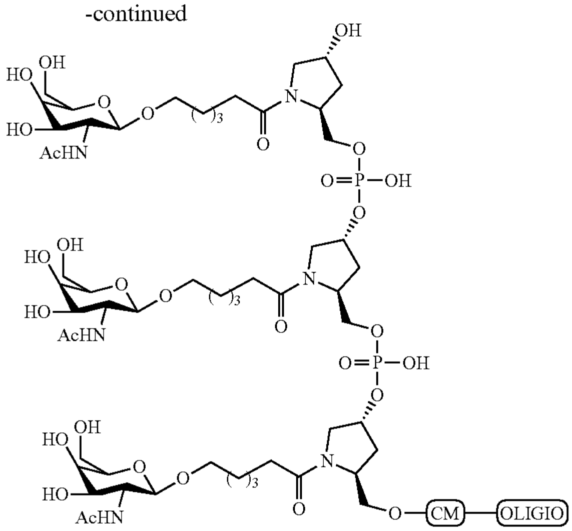

204

Oligomeric compound 204, comprising a GalNAc$_3$-19 conjugate group, was prepared from compound 64 using the general procedures illustrated in Example 52. The GalNAc$_3$ cluster portion of the conjugate group GalNAc$_3$-19 (GalNAc$_3$-19$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-19 (GalNAc$_3$-19$_a$-CM-) is shown below:

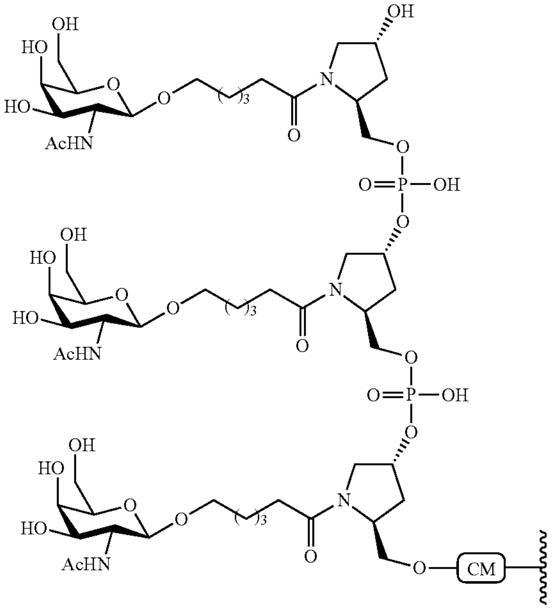

Example 71: Preparation of Oligomeric Compound 210 Comprising GalNAc$_3$-20
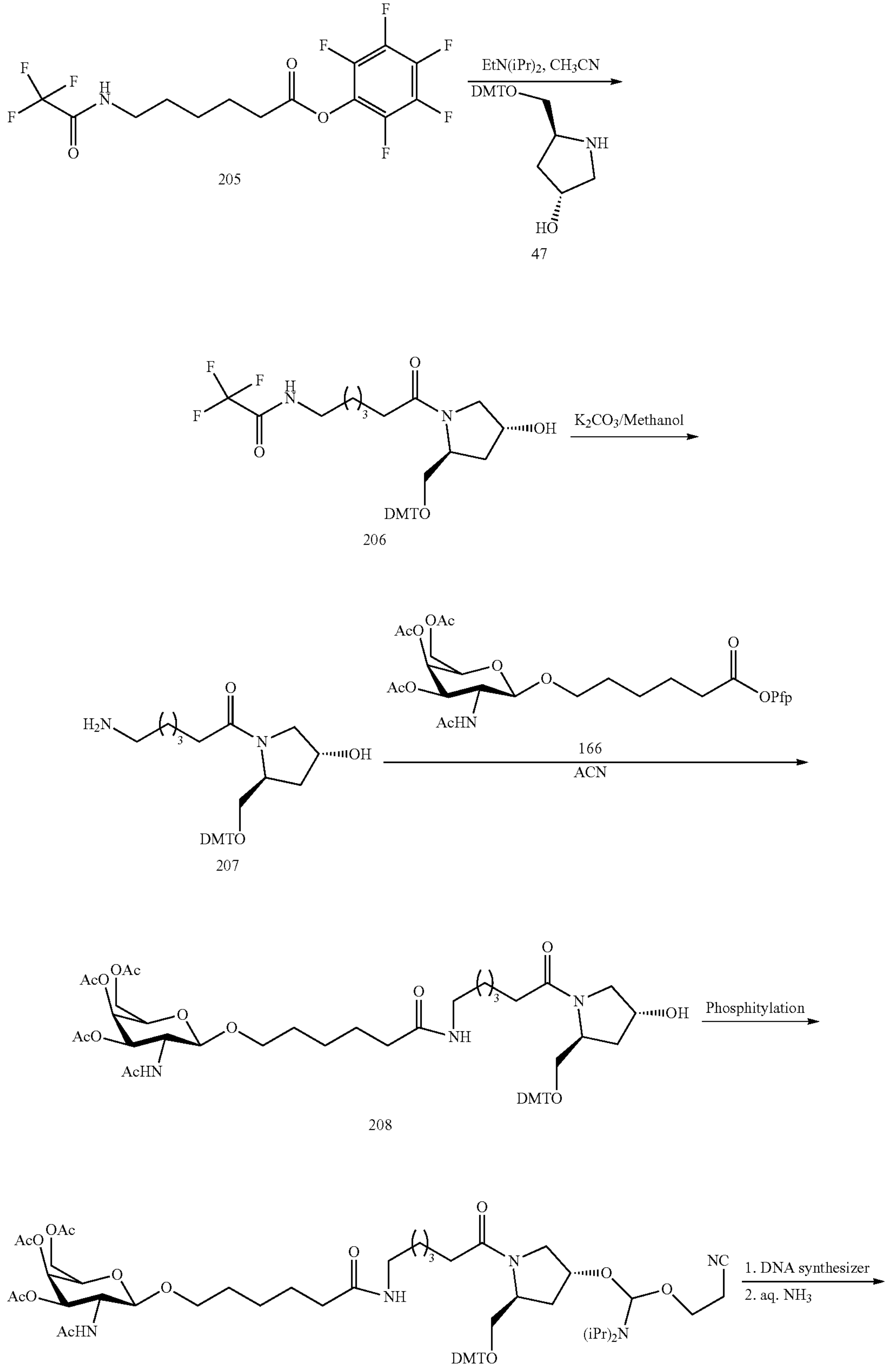
205
47
206
166
207
208
209

-continued

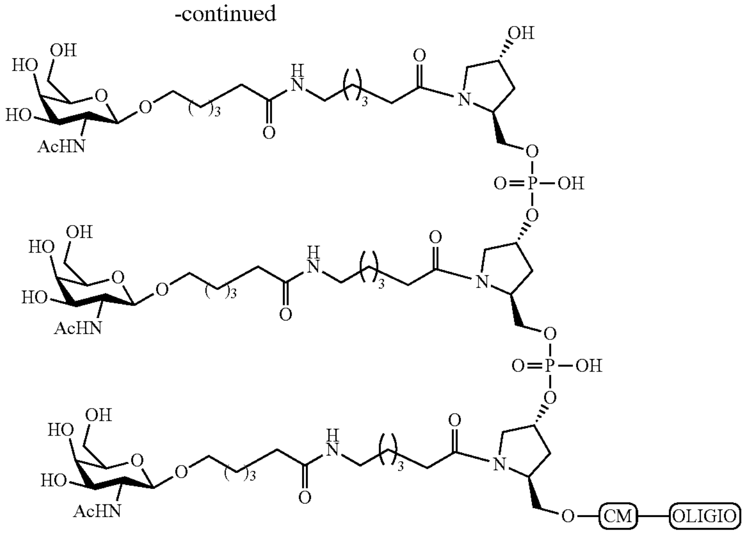

210

Compound 205 was prepared by adding PFP-TFA and DIEA to 6-(2,2,2-trifluoroacetamido)hexanoic acid in acetonitrile, which was prepared by adding triflic anhydride to 6-aminohexanoic acid. The reaction mixture was heated to 80° C., then lowered to rt. Oligomeric compound 210, comprising a GalNAc$_3$-20 conjugate group, was prepared from compound 208 using the general procedures illustrated in Example 52. The GalNAc3 cluster portion of the conjugate group GalNAc$_3$-20 (GalNAc$_3$-20$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-20 (GalNAc$_3$-20$_a$-CM-) is shown below:

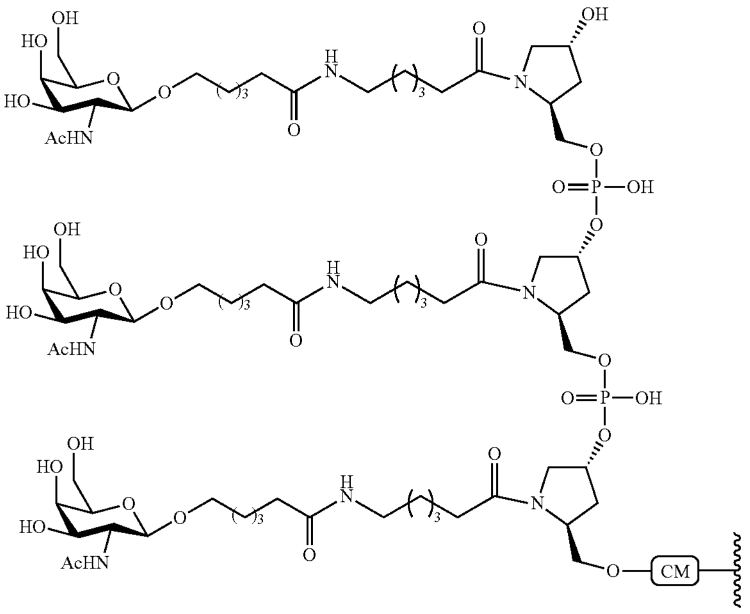

Example 72: Preparation of Oligomeric Compound 215 Comprising GalNAc$_3$-21
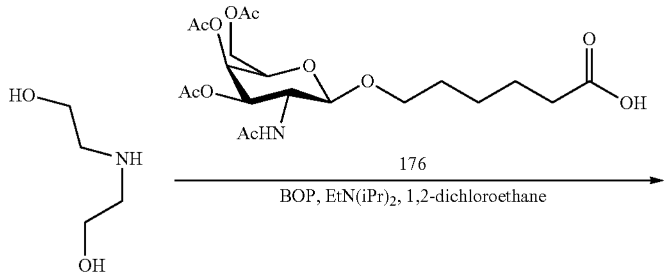
211
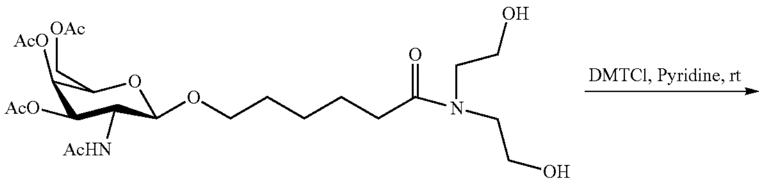
212
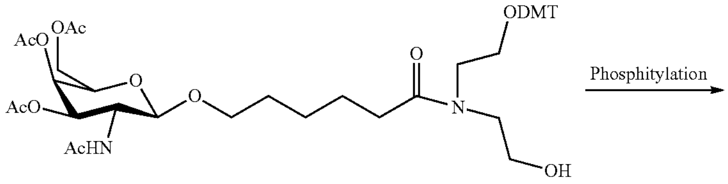
213
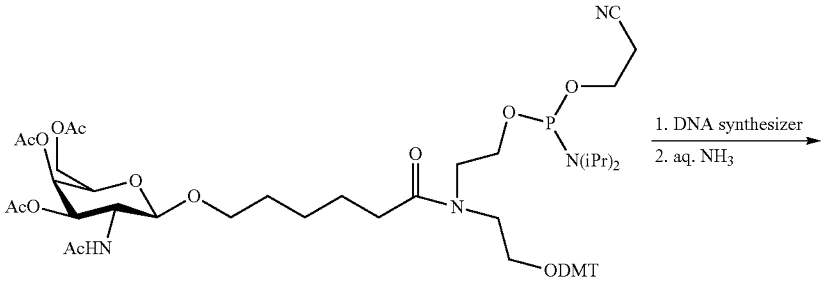
214
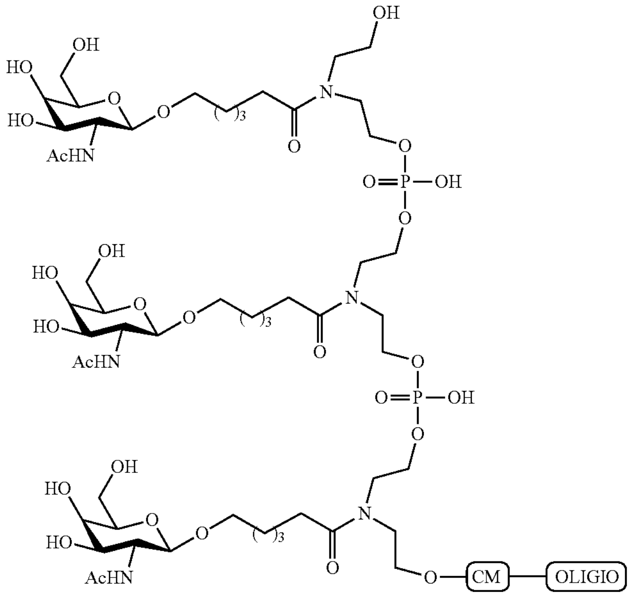
215

Compound 211 is commercially available. Oligomeric compound 215, comprising a GalNAc$_3$-21 conjugate group, was prepared from compound 213 using the general procedures illustrated in Example 52. The GalNAc$_3$ cluster portion of the conjugate group GalNAc$_3$-21 (GalNAc$_3$-21$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-21 (GalNAc$_3$-21$_a$-CM-) is shown below:

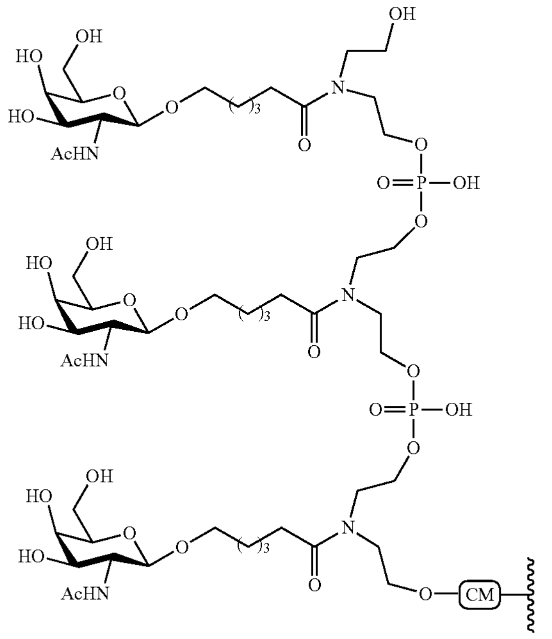

Example 73: Preparation of Oligomeric Compound 221 Comprising GalNAc$_3$-22

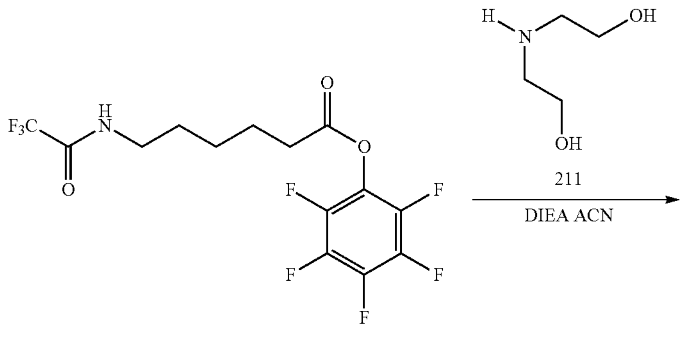

205

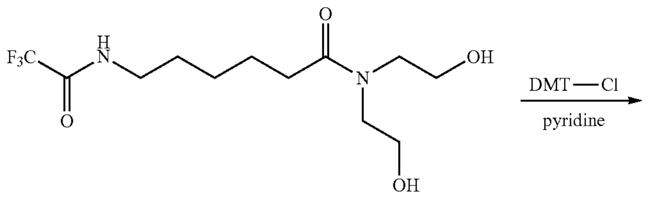

216

-continued
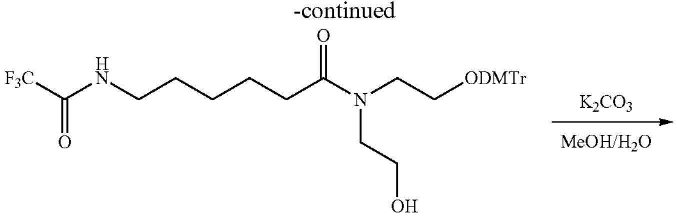
217
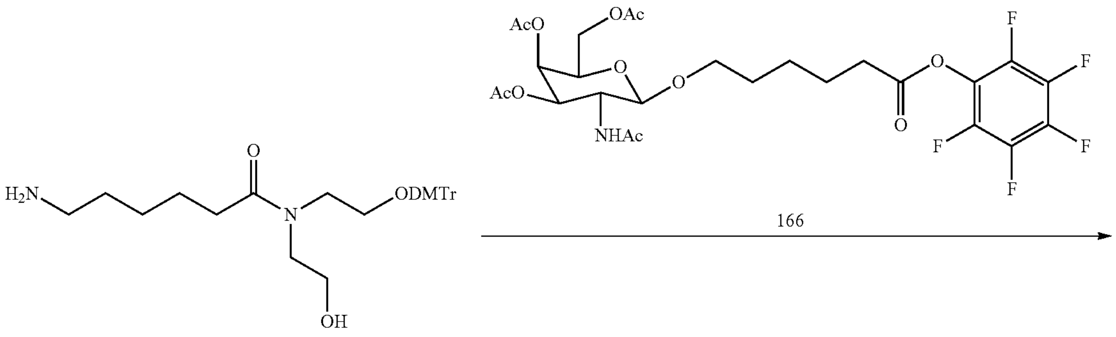
218
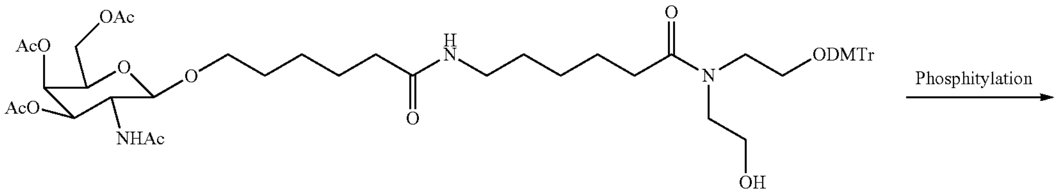
219
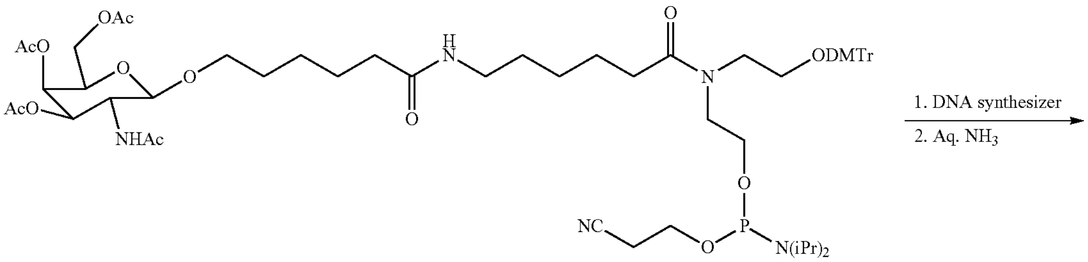
220

-continued

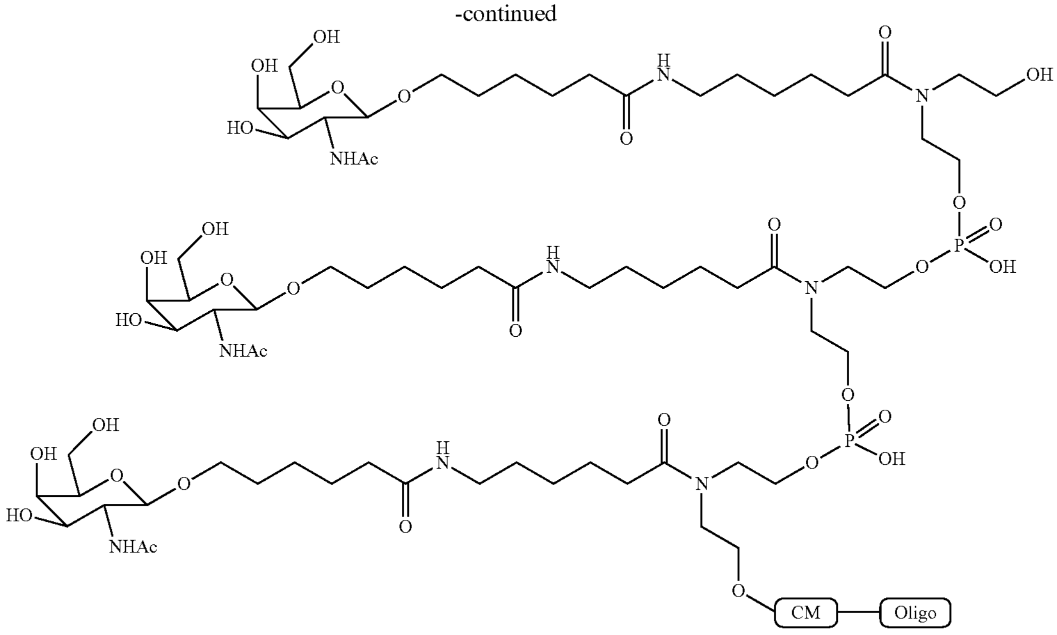

221

Compound 220 was prepared from compound 219 using diisopropylammonium tetrazolide. Oligomeric compound 221, comprising a GalNAc$_3$-21 conjugate group, is prepared from compound 220 using the general procedure illustrated in Example 52. The GalNAc3 cluster portion of the conjugate group GalNAc$_3$-22 (GalNAc$_3$-22$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-22 (GalNAc$_3$-22$_a$-CM-) is shown below:

Example 74: Effect of Various Cleavable Moieties on Antisense Inhibition In Vivo by Oligonucleotides Targeting SRB-1 Comprising a 5'-GalNAc$_3$ Conjugate The oligonucleotides listed below were tested in a dose-dependent study for antisense inhibition of SRB-1 in mice. Each of the GalNAc3 conjugate groups was attached at the 5' terminus of the respective oligonucleotide.

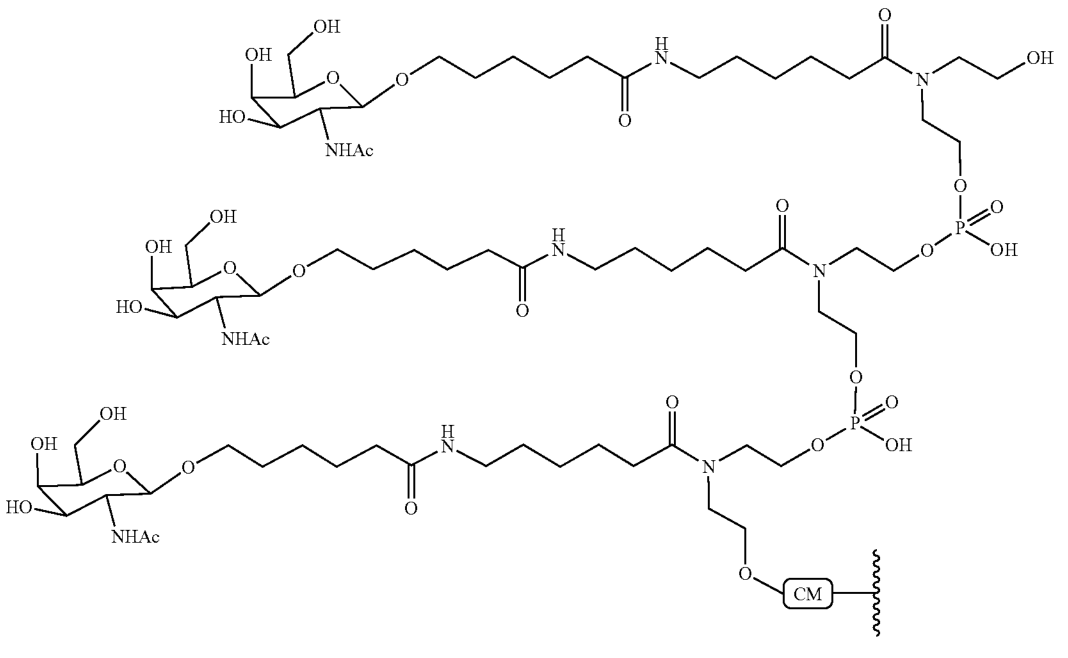

TABLE 60

| Modified ASOs targeting SRB-1 | | | | |
|---|---|---|---|---|
| ISIS No. | Sequences (5' to 3') | $GalNAc_3$ Cluster | CM | SEQ ID No. |
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | n/a | n/a | 143 |
| 661161 | **GalNAc3-3a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 145 |
| 666904 | **GalNAc3-3a-o'Ges**$^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 143 |
| 675441 | **GalNAc3-17a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-17a | $A_d$ | 145 |
| 675442 | **GalNAc3-18a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-18a | $A_d$ | 145 |

In all tables, capital letters indicate the nucleobase for each nucleoside and $^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of $GalNAc_3$-$3_a$ was shown previously in Example 39. The structure of $GalNAc_3$-17a was shown previously in Example 68, and the structure of $GalNAc_3$-18a was shown in Example 69.

Treatment

Six to eight week old C57BL/6 mice (Jackson Laboratory, Bar Harbor, ME) were injected subcutaneously once at the dosage shown below with an oligonucleotide listed in Table 60 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 61, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNAc conjugate.

TABLE 61

| SRB-1 mRNA (% Saline) | | | | |
|---|---|---|---|---|
| ISIS No. | Dosage (mg/kg) | SRB-1 mRNA (% Saline) | $GalNAc_3$ Cluster | CM |
| Saline | n/a | 100.0 | n/a | n/a |
| 353382 | 3 | 79.38 | n/a | n/a |
| | 10 | 68.67 | | |
| | 30 | 40.70 | | |
| 661161 | 0.5 | 79.18 | $GalNAc_3$-3a | $A_d$ |
| | 1.5 | 75.96 | | |
| | 5 | 30.53 | | |
| | 15 | 12.52 | | |
| 666904 | 0.5 | 91.30 | $GalNAc_3$-3a | PO |
| | 1.5 | 57.88 | | |
| | 5 | 21.22 | | |
| | 15 | 16.49 | | |

TABLE 61-continued

| SRB-1 mRNA (% Saline) | | | | |
|---|---|---|---|---|
| ISIS No. | Dosage (mg/kg) | SRB-1 mRNA (% Saline) | $GalNAc_3$ Cluster | CM |
| 675441 | 0.5 | 76.71 | $GalNAc_3$-17a | $A_d$ |
| | 1.5 | 63.63 | | |
| | 5 | 29.57 | | |
| | 15 | 13.49 | | |
| 675442 | 0.5 | 95.03 | $GalNAc_3$-18a | $A_d$ |
| | 1.5 | 60.06 | | |
| | 5 | 31.04 | | |
| | 15 | 19.40 | | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 62 below.

TABLE 62

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
| | 10 | 28 | 58 | 0.16 | 43 | | |
| | 30 | 20 | 48 | 0.12 | 34 | | |
| 661161 | 0.5 | 30 | 47 | 0.13 | 35 | $GalNAc_3$-3a | $A_d$ |
| | 1.5 | 23 | 53 | 0.14 | 37 | | |
| | 5 | 26 | 48 | 0.15 | 39 | | |
| | 15 | 32 | 57 | 0.15 | 42 | | |
| 666904 | 0.5 | 24 | 73 | 0.13 | 36 | $GalNAc_3$-3a | PO |
| | 1.5 | 21 | 48 | 0.12 | 32 | | |
| | 5 | 19 | 49 | 0.14 | 33 | | |
| | 15 | 20 | 52 | 0.15 | 26 | | |
| 675441 | 0.5 | 42 | 148 | 0.21 | 36 | $GalNAc_3$-17a | $A_d$ |
| | 1.5 | 60 | 95 | 0.16 | 34 | | |
| | 5 | 27 | 75 | 0.14 | 37 | | |
| | 15 | 24 | 61 | 0.14 | 36 | | |
| 675442 | 0.5 | 26 | 65 | 0.15 | 37 | $GalNAc_3$-18a | $A_d$ |
| | 1.5 | 25 | 64 | 0.15 | 43 | | |
| | 5 | 27 | 69 | 0.15 | 37 | | |
| | 15 | 30 | 84 | 0.14 | 37 | | |

Example 75: Pharmacokinetic Analysis of Oligonucleotides Comprising a 5'-Conjugate Group The PK of the ASOs in Tables 54, 57 and 60 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (μg/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

TABLE 63

PK Analysis in Liver

| ISIS No. | Dosage (mg/kg) | Total Tissue Level by UV (μg/g) | Parent ASO Tissue Level by EIC (μg/g) | $GalNAc_3$ Cluster | CM |
|---|---|---|---|---|---|
| 353382 | 3 | 8.9 | 8.6 | n/a | n/a |
| | 10 | 22.4 | 21.0 | | |
| | 30 | 54.2 | 44.2 | | |
| 661161 | 5 | 32.4 | 20.7 | $GalNAc_3$-3a | $A_d$ |
| | 15 | 63.2 | 44.1 | | |
| 671144 | 5 | 20.5 | 19.2 | $GalNAc_3$-12a | $A_d$ |
| | 15 | 48.6 | 41.5 | | |
| 670061 | 5 | 31.6 | 28.0 | $GalNAc_3$-13a | $A_d$ |
| | 15 | 67.6 | 55.5 | | |
| 671261 | 5 | 19.8 | 16.8 | $GalNAc_3$-14a | $A_d$ |
| | 15 | 64.7 | 49.1 | | |
| 671262 | 5 | 18.5 | 7.4 | $GalNAc_3$-15a | $A_d$ |
| | 15 | 52.3 | 24.2 | | |

TABLE 63-continued

PK Analysis in Liver

| ISIS No. | Dosage (mg/kg) | Total Tissue Level by UV (μg/g) | Parent ASO Tissue Level by EIC (μg/g) | $GalNAc_3$ Cluster | CM |
|---|---|---|---|---|---|
| 670699 | 5 | 16.4 | 10.4 | $GalNAc_3$-3a | $T_d$ |
| | 15 | 31.5 | 22.5 | | |
| 670700 | 5 | 19.3 | 10.9 | $GalNAc_3$-3a | $A_e$ |
| | 15 | 38.1 | 20.0 | | |
| 670701 | 5 | 21.8 | 8.8 | $GalNAc_3$-3a | $T_e$ |
| | 15 | 35.2 | 16.1 | | |
| 671165 | 5 | 27.1 | 26.5 | $GalNAc_3$-13a | $A_d$ |
| | 15 | 48.3 | 44.3 | | |
| 666904 | 5 | 30.8 | 24.0 | $GalNAc_3$-3a | PO |
| | 15 | 52.6 | 37.6 | | |
| 675441 | 5 | 25.4 | 19.0 | $GalNAc_3$-17a | $A_d$ |
| | 15 | 54.2 | 42.1 | | |
| 675442 | 5 | 22.2 | 20.7 | $GalNAc_3$-18a | $A_d$ |
| | 15 | 39.6 | 29.0 | | |

The results in Table 63 above show that there were greater liver tissue levels of the oligonucleotides comprising a $GalNAc_3$ conjugate group than of the parent oligonucleotide that does not comprise a $GalNAc_3$ conjugate group (ISIS 353382) 72 hours following oligonucleotide administration, particularly when taking into consideration the differences in dosing between the oligonucleotides with and without a GalNAc3 conjugate group. Furthermore, by 72 hours, 40-98% of each oligonucleotide comprising a GalNAc3 conjugate group was metabolized to the parent compound, indicating that the GalNAc3 conjugate groups were cleaved from the oligonucleotides.

Example 76: Preparation of Oligomeric Compound 230 Comprising $GalNAc_3$-23

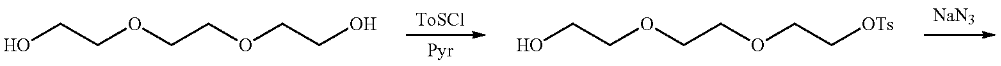

222 223

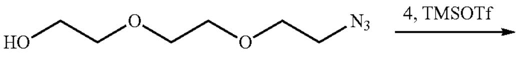

224

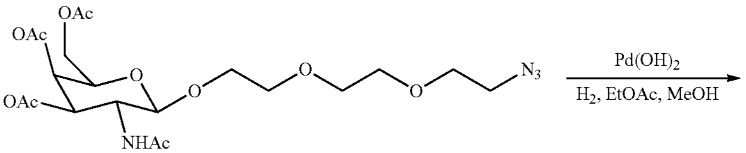

225

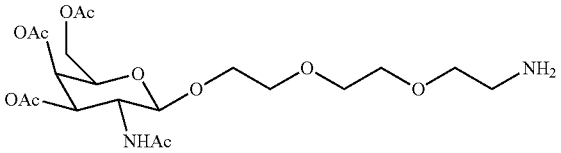

226

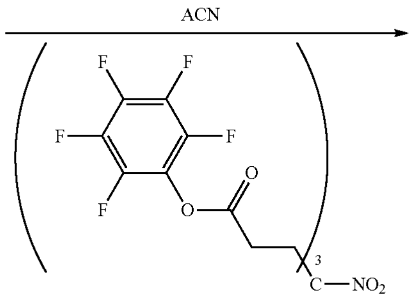

227

-continued

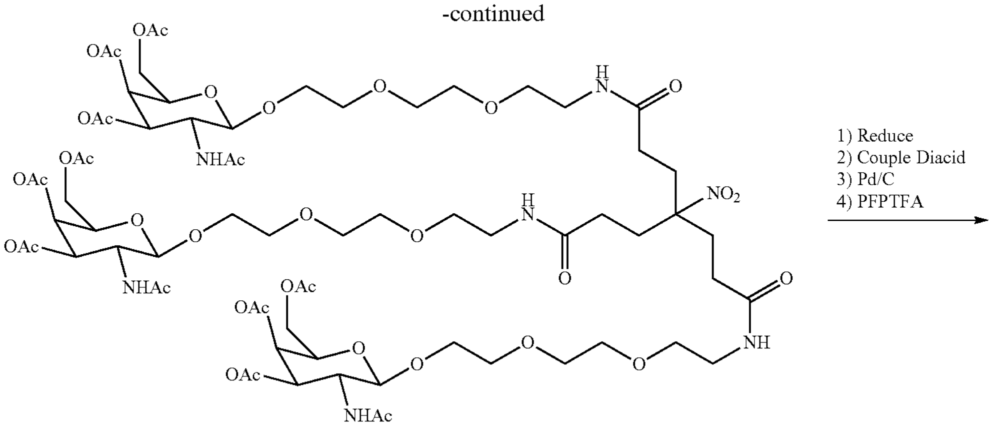

228

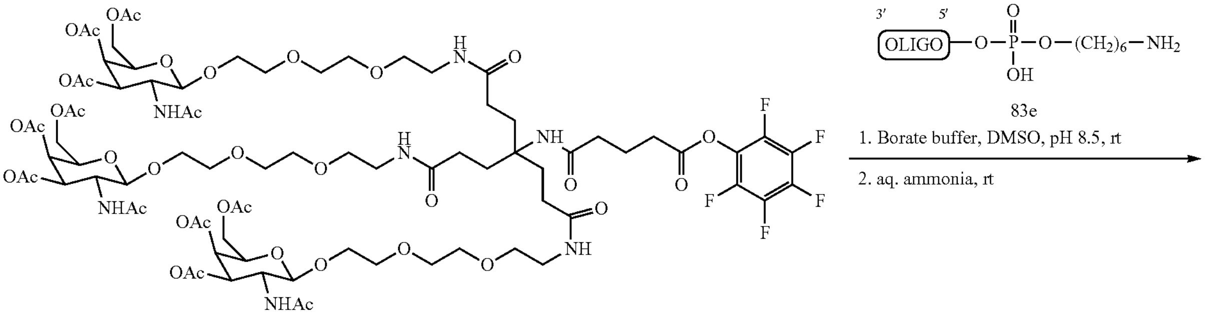

229

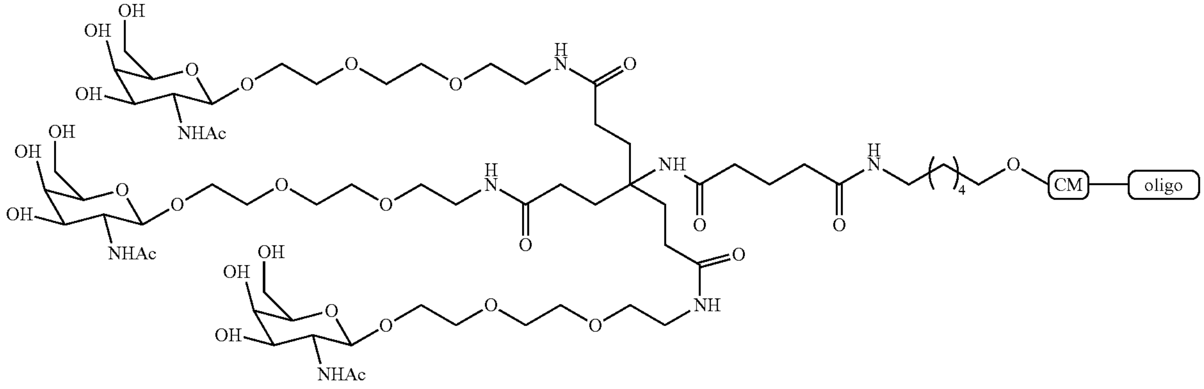

230

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. $NaHCO_3$, brine, and dried over $Na_2SO_4$. The ethyl acetate was concentrated to dryness and purified by column chromatography, eluted with EtOAc/hexanes (1:1) followed by 10% methanol in $CH_2Cl_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over $Na_2SO_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4 A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. $NaHCO_3$, water, brine, and dried over $Na_2SO_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over $Na_2SO_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 μl, 1.6 mmol) in DMF (5 mL). After 16 hours, the DMF was removed under reduced pressure at 65° C. to an oil, and the oil was dissolved in dichloromethane. The organic layer was washed with sat. $NaHCO_3$, brine, and dried over $Na_2SO_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 μl, 0.66 mmol) was added and the reaction was purged with argon. Pentaflourotriflouro acetate (46.39 μl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N $NaHSO_4$, brine, saturated sodium bicarbonate and brine again. The organics were dried over $Na_2SO_4$, filtered, and were concentrated to dryness to give 225 mg of compound 229 as a brittle yellow foam. LCMS and NMR were consistent with the structure.

Oligomeric compound 230, comprising a $GalNAc_3$-23 conjugate group, was prepared from compound 229 using the general procedure illustrated in Example 46. The $GalNAc_3$ cluster portion of the $GalNAc_3$-23 conjugate group ($GalNAc_3$-$23_a$) can be combined with any cleavable moiety to provide a variety of conjugate groups. The structure of $GalNAc_3$-23 ($GalNAc_3$-$23_a$-CM) is shown below:

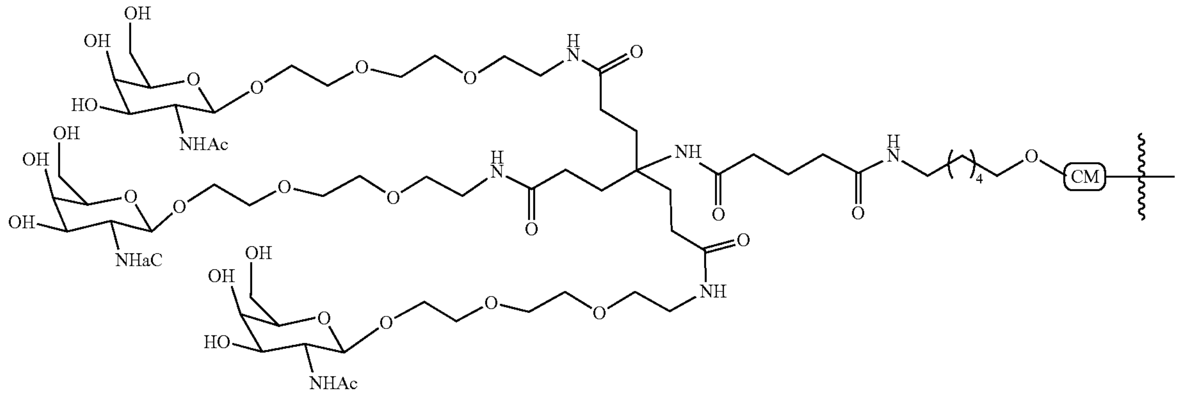

Example 77: Antisense Inhibition In Vivo by Oligonucleotides Targeting SRB-1 Comprising a GalNAc3 Conjugate The oligonucleotides listed below were tested in a dose-dependent study for antisense inhibition of SRB-1 in mice.

TABLE 64

Modified ASOs targeting SRB-1

| ISIS No. | Sequences (5' to 3') | $GalNAc_3$ Cluster | CM | SEQ ID No. |
|---|---|---|---|---|
| 661161 | **GalNAc3-3a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 145 |
| 666904 | **GalNAc3-3a-o'G**$_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 143 |
| 673502 | **GalNAc3-10a-o'Ad-o**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_3$-10a | $A_d$ | 145 |

TABLE 64-continued

| Modified ASOs targeting SRB-1 | | | | |
|---|---|---|---|---|
| ISIS No. | Sequences (5' to 3') | GalNAc$_3$ Cluster | CM | SEQ ID No. |
| 677844 | **GalNAc3-9a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-9a | $A_d$ | 145 |
| 677843 | **GalNAc3-23a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-23a | $A_d$ | 145 |
| 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**Ado'-GalNAc3-1a** | GalNAc$_3$-1a | $A_d$ | 144 |
| 677841 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**Ado'-GalNAc3-19a** | GalNAc$_3$-19a | $A_d$ | 144 |
| 677842 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**Ado'-GalNAc3-20a** | GalNAc$_3$-20a | $A_d$ | 144 |

The structure of GalNAc$_3$-1$_a$ was shown previously in Example 9, GalNAc$_3$-3$_a$ was shown in Example 39, GalNAc$_3$-9a was shown in Example 52, GalNAc$_3$-10a was shown in Example 46, GalNAc$_3$-19$_a$ was shown in Example 70, GalNAc$_3$-20$_a$ was shown in Example 71, and GalNAc$_3$-23$_a$ was shown in Example 76.

Treatment

Six to eight week old C57BL/6 mice (Jackson Laboratory, Bar Harbor, ME) were each injected subcutaneously once at a dosage shown below with an oligonucleotide listed in Table 64 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 65, treatment with antisense oligonucleotides lowered SRB-1 mRNA levels in a dose-dependent manner.

TABLE 65

| SRB-1 mRNA (% Saline) | | | | |
|---|---|---|---|---|
| ISIS No. | Dosage (mg/kg) | SRB-1 mRNA (% Saline) | GalNAc$_3$ Cluster | CM |
| Saline | n/a | 100.0 | n/a | n/a |
| 661161 | 0.5 | 89.18 | GalNAc$_3$-3a | $A_d$ |
| | 1.5 | 77.02 | | |
| | 5 | 29.10 | | |
| | 15 | 12.64 | | |
| 666904 | 0.5 | 93.11 | GalNAc$_3$-3a | PO |
| | 1.5 | 55.85 | | |
| | 5 | 21.29 | | |
| | 15 | 13.43 | | |
| 673502 | 0.5 | 77.75 | GalNAc$_3$-10a | $A_d$ |
| | 1.5 | 41.05 | | |
| | 5 | 19.27 | | |
| | 15 | 14.41 | | |
| 677844 | 0.5 | 87.65 | GalNAc$_3$-9a | $A_d$ |
| | 1.5 | 93.04 | | |
| | 5 | 40.77 | | |
| | 15 | 16.95 | | |
| 677843 | 0.5 | 102.28 | GalNAc$_3$-23a | $A_d$ |
| | 1.5 | 70.51 | | |
| | 5 | 30.68 | | |
| | 15 | 13.26 | | |

TABLE 65-continued

| SRB-1 mRNA (% Saline) | | | | |
|---|---|---|---|---|
| ISIS No. | Dosage (mg/kg) | SRB-1 mRNA (% Saline) | GalNAc$_3$ Cluster | CM |
| 655861 | 0.5 | 79.72 | GalNAc$_3$-1a | $A_d$ |
| | 1.5 | 55.48 | | |
| | 5 | 26.99 | | |
| | 15 | 17.58 | | |
| 677841 | 0.5 | 67.43 | GalNAc$_3$-19a | $A_d$ |
| | 1.5 | 45.13 | | |
| | 5 | 27.02 | | |
| | 15 | 12.41 | | |
| 677842 | 0.5 | 64.13 | GalNAc$_3$-20a | $A_d$ |
| | 1.5 | 53.56 | | |
| | 5 | 20.47 | | |
| | 15 | 10.23 | | |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 66 below.

TABLE 66

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | GalNAc$_3$-3a | $A_d$ |
| | 1.5 | 23 | 42 | 0.13 | 39 | | |
| | 5 | 22 | 59 | 0.13 | 37 | | |
| | 15 | 21 | 56 | 0.15 | 35 | | |
| 666904 | 0.5 | 24 | 56 | 0.14 | 37 | GalNAc$_3$-3a | PO |
| | 1.5 | 26 | 68 | 0.15 | 35 | | |
| | 5 | 23 | 77 | 0.14 | 34 | | |
| | 15 | 24 | 60 | 0.13 | 35 | | |
| 673502 | 0.5 | 24 | 59 | 0.16 | 34 | GalNAc$_3$-10a | $A_d$ |
| | 1.5 | 20 | 46 | 0.17 | 32 | | |
| | 5 | 24 | 45 | 0.12 | 31 | | |
| | 15 | 24 | 47 | 0.13 | 34 | | |
| 677844 | 0.5 | 25 | 61 | 0.14 | 37 | GalNAc$_3$-9a | $A_d$ |
| | 1.5 | 23 | 64 | 0.17 | 33 | | |
| | 5 | 25 | 58 | 0.13 | 35 | | |
| | 15 | 22 | 65 | 0.14 | 34 | | |
| 677843 | 0.5 | 53 | 53 | 0.13 | 35 | GalNAc$_3$-23a | $A_d$ |
| | 1.5 | 25 | 54 | 0.13 | 34 | | |
| | 5 | 21 | 60 | 0.15 | 34 | | |
| | 15 | 22 | 43 | 0.12 | 38 | | |

TABLE 66-continued

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| 655861 | 0.5 | 21 | 48 | 0.15 | 33 | $GalNAc_3$-1a | $A_d$ |
| | 1.5 | 28 | 54 | 0.12 | 35 | | |
| | 5 | 22 | 60 | 0.13 | 36 | | |
| | 15 | 21 | 55 | 0.17 | 30 | | |
| 677841 | 0.5 | 32 | 54 | 0.13 | 34 | $GalNAc_3$-19a | $A_d$ |
| | 1.5 | 24 | 56 | 0.14 | 34 | | |
| | 5 | 23 | 92 | 0.18 | 31 | | |
| | 15 | 24 | 58 | 0.15 | 31 | | |
| 677842 | 0.5 | 23 | 61 | 0.15 | 35 | $GalNAc_3$-20a | $A_d$ |
| | 1.5 | 24 | 57 | 0.14 | 34 | | |
| | 5 | 41 | 62 | 0.15 | 35 | | |
| | 15 | 24 | 37 | 0.14 | 32 | | |

Example 78: Antisense Inhibition In Vivo by Oligonucleotides Targeting Angiotensinogen Comprising a GalNAc3 Conjugate The oligonucleotides listed below were tested in a dose-dependent study for antisense inhibition of Angiotensinogen (AGT) in normotensive Sprague Dawley rats.

TABLE 67

Modified ASOs targeting AGT

| ISIS No. | Sequences (5' to 3') | $GalNAc_3$ Cluster | CM | SEQ ID No. |
|---|---|---|---|---|
| 552668 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{e}$ | n/a | n/a | 149 |
| 669509 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{e}$**oAdo'-GalNAc3-1a** | $GalNAc_3$-$1_a$ | $A_d$ | 150 |

The structure of $GalNAc_3$-$1_a$ was shown previously in Example 9.

Treatment

Six week old, male Sprague Dawley rats were each injected subcutaneously once per week at a dosage shown below, for a total of three doses, with an oligonucleotide listed in Table 67 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, OR) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 68, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 68

AGT liver mRNA and plasma protein levels

| ISIS No. | Dosage (mg/kg) | AGT liver mRNA (% PBS) | AGT plasma protein (% PBS) | $GalNAc_3$ Cluster | CM |
|---|---|---|---|---|---|
| PBS | n/a | 100 | 100 | n/a | n/a |
| 552668 | 3 | 95 | 122 | n/a | n/a |
| | 10 | 85 | 97 | | |
| | 30 | 46 | 79 | | |
| | 90 | 8 | 11 | | |
| 669509 | 0.3 | 95 | 70 | $GalNAc_3$-1a | $A_d$ |
| | 1 | 95 | 129 | | |
| | 3 | 62 | 97 | | |
| | 10 | 9 | 23 | | |

Liver transaminase levels, alanine aminotransferase (ALT) and aspartate aminotransferase (AST), in plasma and body weights were also measured at time of sacrifice using standard protocols. The results are shown in Table 69 below.

TABLE 69

Liver transaminase levels and rat body weights

| ISIS No. | Dosage (mg/kg) | ALT (U/L) | AST (U/L) | Body Weight (% of baseline) | $GalNAc_3$ Cluster | CM |
|---|---|---|---|---|---|---|
| PBS | n/a | 51 | 81 | 186 | n/a | n/a |
| 552668 | 3 | 54 | 93 | 183 | n/a | n/a |
| | 10 | 51 | 93 | 194 | | |
| | 30 | 59 | 99 | 182 | | |
| | 90 | 56 | 78 | 170 | | |
| 669509 | 0.3 | 53 | 90 | 190 | $GalNAc_3$-1a | $A_d$ |
| | 1 | 51 | 93 | 192 | | |
| | 3 | 48 | 85 | 189 | | |
| | 10 | 56 | 95 | 189 | | |

Example 79: Duration of Action In Vivo of Oligonucleotides Targeting APOC-III Comprising a GalNAc3 Conjugate The oligonucleotides listed in Table 70 below were tested in a single dose study for duration of action in mice.

TABLE 70

| Modified ASOs targeting APOC-III | | | | |
|---|---|---|---|---|
| ISIS No. | Sequences (5' to 3') | GalNAc3 Cluster | CM | SEQ ID No. |
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 135 |
| 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$**Ado'-GalNAc3-1a** | $GalNAc_3$-1a | $A_d$ | 136 |
| 663083 | **GalNAc3-3a-o'Ado**$A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-3a | $A_d$ | 151 |
| 674449 | **GalNAc3-7a-o'Ado**$A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-7a | $A_d$ | 151 |
| 674450 | **GalNAc3-10a-o'Ado**$A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-10a | $A_d$ | 151 |
| 674451 | **GalNAc3-13a-o'Ado**$A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-13a | $A_d$ | 151 |

The structure of $GalNAc_3$-$1_a$ was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six to eight week old transgenic mice that express human APOC-III were each injected subcutaneously once with an oligonucleotide listed in Table 70 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-III levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 71

Plasma triglyceride and APOC-III protein levels in transgenic mice

| ISIS No. | Dosage (mg/kg) | Time point (days post-dose) | Triglycerides (% baseline) | APOC-III protein (% baseline) | $GalNAc_3$ Cluster | CM |
|---|---|---|---|---|---|---|
| PBS | n/a | 3 | 97 | 102 | n/a | n/a |
| | | 7 | 101 | 98 | | |
| | | 14 | 108 | 98 | | |
| | | 21 | 107 | 107 | | |
| | | 28 | 94 | 91 | | |
| | | 35 | 88 | 90 | | |
| | | 42 | 91 | 105 | | |
| 304801 | 30 | 3 | 40 | 34 | n/a | n/a |
| | | 7 | 41 | 37 | | |
| | | 14 | 50 | 57 | | |
| | | 21 | 50 | 50 | | |
| | | 28 | 57 | 73 | | |
| | | 35 | 68 | 70 | | |
| | | 42 | 75 | 93 | | |
| 647535 | 10 | 3 | 36 | 37 | $GalNAc_3$-1a | $A_d$ |
| | | 7 | 39 | 47 | | |
| | | 14 | 40 | 45 | | |
| | | 21 | 41 | 41 | | |

TABLE 71-continued

Plasma triglyceride and APOC-III protein levels in transgenic mice

| ISIS No. | Dosage (mg/kg) | Time point (days post-dose) | Triglycerides (% baseline) | APOC-III protein (% baseline) | $GalNAc_3$ Cluster | CM |
|---|---|---|---|---|---|---|
| | | 28 | 42 | 62 | | |
| | | 35 | 69 | 69 | | |
| | | 42 | 85 | 102 | | |
| 663083 | 10 | 3 | 24 | 18 | | |
| | | 7 | 28 | 23 | $GalNAc_3$- | $A_d$ |
| | | 14 | 25 | 27 | | |
| | | 21 | 28 | 28 | 3a | |
| | | 28 | 37 | 44 | | |
| | | 35 | 55 | 57 | | |
| | | 42 | 60 | 78 | | |
| 674449 | 10 | 3 | 29 | 26 | $GalNAc_3$- | $A_d$ |
| | | 7 | 32 | 31 | 7a | |
| | | 14 | 38 | 41 | | |
| | | 21 | 44 | 44 | | |
| | | 28 | 53 | 63 | | |
| | | 35 | 69 | 77 | | |
| | | 42 | 78 | 99 | | |
| 674450 | 10 | 3 | 33 | 30 | | |
| | | 7 | 35 | 34 | | |
| | | 14 | 31 | 34 | | |
| | | 21 | 44 | 44 | $GalNAc_3$- | $A_d$ |
| | | 28 | 56 | 61 | 10a | |
| | | 35 | 68 | 70 | | |
| | | 42 | 83 | 95 | | |
| 674451 | 10 | 3 | 35 | 33 | | |
| | | 7 | 24 | 32 | | |
| | | 14 | 40 | 34 | | |
| | | 21 | 48 | 48 | $GalNAc_3$- | $A_d$ |
| | | 28 | 54 | 67 | 13a | |
| | | 35 | 65 | 75 | | |
| | | 42 | 74 | 97 | | |

Example 80: Antisense Inhibition In Vivo by Oligonucleotides Targeting Alpha-1 Antitrypsin (A1AT) Comprising a GalNAc3 Conjugate The oligonucleotides listed in Table 72 below were tested in a study for dose-dependent inhibition of A1AT in mice.

TABLE 72

| Modified ASOs targeting A1AT | | | | |
|---|---|---|---|---|
| ISIS No. | Sequences (5' to 3') | GalNAc3 Cluster | CM | SEQ ID No. |
| 476366 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | n/a | n/a | 152 |
| 656326 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{eo}A_{do'}$-**GalNAc3-1a** | $GalNAc_3$-1a | $A_d$ | 153 |
| 678381 | **GalNAc3-3a-o'Ado**$A_{es}{}^{m}C_{es}{}^{m}C_{es}{}^{m}C$-$_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAc_3$-3a | $A_d$ | 154 |
| 678382 | **GalNAc3-7a-o'Ado**$A_{es}{}^{m}C_{es}{}^{m}C_{es}{}^{m}C$-$_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAc_3$-7a | $A_d$ | 154 |
| 678383 | **GalNAc3-10a-o'Ado**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAc_3$-10a | $A_d$ | 154 |
| 678384 | **GalNAc3-13a-o'Ado**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAc_3$-13a | $A_d$ | 154 |

The structure of $GalNAc_3$-$1_a$ was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six week old, male C57BL/6 mice (Jackson Laboratory, Bar Harbor, ME) were each injected subcutaneously once per week at a dosage shown below, for a total of three doses, with an oligonucleotide listed in Table 72 or with PBS. Each treatment group consisted of 4 animals. The mice were sacrificed 72 hours following the final administration. A1AT liver mRNA levels were determined using real-time PCR and RIBOGREEN® RNA quantification reagent (Molecular Probes, Inc. Eugene, OR) according to standard protocols. A1AT plasma protein levels were determined using the Mouse Alpha 1-Antitrypsin ELISA (catalog #41-A1AMS-E01, Alpco, Salem, NH). The results below are presented as the average percent of A1AT liver mRNA and plasma protein levels for each treatment group, normalized to the PBS control.

As illustrated in Table 73, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 73

| A1AT liver mRNA and plasma protein levels | | | | | |
|---|---|---|---|---|---|
| ISIS No. | Dosage (mg/kg) | A1AT liver mRNA (% PBS) | A1AT plasma protein (% PBS) | GalNAc3 Cluster | CM |
| PBS | n/a | 100 | 100 | n/a | n/a |
| 476366 | 5 | 86 | 78 | n/a | n/a |
| | 15 | 73 | 61 | | |
| | 45 | 30 | 38 | | |
| 656326 | 0.6 | 99 | 90 | $GalNAc_3$-1a | $A_d$ |
| | 2 | 61 | 70 | | |
| | 6 | 15 | 30 | | |
| | 18 | 6 | 10 | | |
| 678381 | 0.6 | 105 | 90 | $GalNAc_3$-3a | $A_d$ |
| | 2 | 53 | 60 | | |
| | 6 | 16 | 20 | | |
| | 18 | 7 | 13 | | |
| 678382 | 0.6 | 90 | 79 | $GalNAc_3$-7a | $A_d$ |
| | 2 | 49 | 57 | | |
| | 6 | 21 | 27 | | |
| | 18 | 8 | 11 | | |
| 678383 | 0.6 | 94 | 84 | $GalNAc_3$-10a | $A_d$ |
| | 2 | 44 | 53 | | |
| | 6 | 13 | 24 | | |
| | 18 | 6 | 10 | | |
| 678384 | 0.6 | 106 | 91 | $GalNAc_3$-13a | $A_d$ |
| | 2 | 65 | 59 | | |
| | 6 | 26 | 31 | | |
| | 18 | 11 | 15 | | |

Liver transaminase and BUN levels in plasma were measured at time of sacrifice using standard protocols. Body weights and organ weights were also measured. The results are shown in Table 74 below. Body weight is shown as % relative to baseline. Organ weights are shown as % of body weight relative to the PBS control group.

TABLE 74

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
| | 15 | 37 | 74 | 30 | 122 | 92 | 101 | 128 |
| | 45 | 30 | 47 | 31 | 118 | 99 | 108 | 123 |
| 656326 | 0.6 | 29 | 57 | 40 | 123 | 100 | 103 | 119 |
| | 2 | 36 | 75 | 39 | 114 | 98 | 111 | 106 |
| | 6 | 32 | 67 | 39 | 125 | 99 | 97 | 122 |
| | 18 | 46 | 77 | 36 | 116 | 102 | 109 | 101 |
| 678381 | 0.6 | 26 | 57 | 32 | 117 | 93 | 109 | 110 |
| | 2 | 26 | 52 | 33 | 121 | 96 | 106 | 125 |
| | 6 | 40 | 78 | 32 | 124 | 92 | 106 | 126 |
| | 18 | 31 | 54 | 28 | 118 | 94 | 103 | 120 |
| 678382 | 0.6 | 26 | 42 | 35 | 114 | 100 | 103 | 103 |
| | 2 | 25 | 50 | 31 | 117 | 91 | 104 | 117 |
| | 6 | 30 | 79 | 29 | 117 | 89 | 102 | 107 |
| | 18 | 65 | 112 | 31 | 120 | 89 | 104 | 113 |
| 678383 | 0.6 | 30 | 67 | 38 | 121 | 91 | 100 | 123 |
| | 2 | 33 | 53 | 33 | 118 | 98 | 102 | 121 |
| | 6 | 32 | 63 | 32 | 117 | 97 | 105 | 105 |
| | 18 | 36 | 68 | 31 | 118 | 99 | 103 | 108 |
| 678384 | 0.6 | 36 | 63 | 31 | 118 | 98 | 103 | 98 |
| | 2 | 32 | 61 | 32 | 119 | 93 | 102 | 114 |
| | 6 | 34 | 69 | 34 | 122 | 100 | 100 | 96 |
| | 18 | 28 | 54 | 30 | 117 | 98 | 101 | 104 |

Example 81: Duration of Action In Vivo of Oligonucleotides Targeting A1AT Comprising a GalNAc$_3$ Cluster The oligonucleotides listed in Table 72 were tested in a single dose study for duration of action in mice.

Treatment

Six week old, male C57BL/6 mice were each injected subcutaneously once with an oligonucleotide listed in Table 72 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 75

Plasma A1AT protein levels in mice

| ISIS No. | Dosage (mg/kg) | Time point (days post-dose) | A1AT (% baseline) | GalNAc$_3$ Cluster | CM |
|---|---|---|---|---|---|
| PBS | n/a | 5 | 93 | n/a | n/a |
| | | 12 | 93 | | |
| | | 19 | 90 | | |
| | | 25 | 97 | | |
| 476366 | 100 | 5 | 38 | n/a | n/a |
| | | 12 | 46 | | |
| | | 19 | 62 | | |
| | | 25 | 77 | | |

TABLE 75-continued

Plasma A1AT protein levels in mice

| ISIS No. | Dosage (mg/kg) | Time point (days post-dose) | A1AT (% baseline) | GalNAc$_3$ Cluster | CM |
|---|---|---|---|---|---|
| 656326 | 18 | 5 | 33 | GalNAc$_3$-1a | $A_d$ |
| | | 12 | 36 | | |
| | | 19 | 51 | | |
| | | 25 | 72 | | |
| 678381 | 18 | 5 | 21 | GalNAc$_3$-3a | $A_d$ |
| | | 12 | 21 | | |
| | | 19 | 35 | | |
| | | 25 | 48 | | |
| 678382 | 18 | 5 | 21 | GalNAc$_3$-7a | $A_d$ |
| | | 12 | 21 | | |
| | | 19 | 39 | | |
| | | 25 | 60 | | |
| 678383 | 18 | 5 | 24 | GalNAc$_3$-10a | $A_d$ |
| | | 12 | 21 | | |
| | | 19 | 45 | | |
| | | 25 | 73 | | |
| 678384 | 18 | 5 | 29 | GalNAc$_3$-13a | $A_d$ |
| | | 12 | 34 | | |
| | | 19 | 57 | | |
| | | 25 | 76 | | |

Example 82: Antisense Inhibition In Vitro by Oligonucleotides Targeting SRB-1 Comprising a GalNAc3 Conjugate Primary mouse liver hepatocytes were seeded in 96 well plates at 15,000 cells/well 2 hours prior to treatment. The oligonucleotides listed in Table 76 were added at 2, 10, 50, or 250 nM in Williams E medium and cells were incubated overnight at 37° C. in 5% $CO_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, OR) according to standard protocols. $IC_{50}$ values were determined using Prism 4 software (Graph- Pad). The results show that oligonucleotides comprising a variety of different GalNAc conjugate groups and a variety of different cleavable moieties are significantly more potent in an in vitro free uptake experiment than the parent oligonucleotides lacking a GalNAc conjugate group (ISIS 353382 and 666841).

TABLE 76

Inhibition of SRB-1 expression in vitro

| ISIS No. | Sequence (5' to 3') | Linkages | GalNAc cluster | CM | $IC_{50}$ (nM) | SEQ ID No. |
|---|---|---|---|---|---|---|
| 353382 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | n/a | n/a | 250 | 143 |
| 655861 | $G_eS{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**Ado'-GalNAc3-1a** | PS | $GalNAc_3$-$1_a$ | $A_d$ | 40 | 144 |
| 661161 | **GalNAc3-3a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$3_a$ | $A_d$ | 40 | 145 |
| 661162 | **GalNAc3-3a-o'Ado**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | $GalNAc_3$-$3_a$ | $A_d$ | 8 | 145 |
| 664078 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**Ado'-GalNAc3-9a** | PS | $GalNAc_3$-$9_a$ | $A_d$ | 20 | 144 |
| 665001 | **GalNAc3-8a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$8_a$ | $A_d$ | 70 | 145 |
| 666224 | **GalNAc3-5a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$5_a$ | $A_d$ | 80 | 145 |
| 666841 | $G_{es}{}^mC_{eo}T_{eo}T_{eo}{}^mC_{es}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | n/a | n/a | >250 | 143 |
| 666881 | **GalNAc3-10a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$10_a$ | $A_d$ | 30 | 145 |
| 666904 | **GalNAc3-3a-o'G**$_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$3_a$ | PO | 9 | 143 |
| 666924 | **GalNAc3-3a-o'Tdo**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$3_a$ | $T_d$ | 15 | 148 |
| 666961 | **GalNAc3-6a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$6_a$ | $A_d$ | 150 | 145 |
| 666981 | **GalNAc3-7a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$7_a$ | $A_d$ | 20 | 145 |
| 670061 | **GalNAc3-13a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$13_a$ | $A_d$ | 30 | 145 |
| 670699 | **GalNAc3-3a-o'Tdo**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | $GalNAc_3$-$3_a$ | $T_d$ | 15 | 148 |
| 670700 | **GalNAc3-3a-o'Aeo**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T$ | PO/PS | $GalNAc_3$-$3_a$ | $A_e$ | 30 | 145 |
| 670701 | **GalNAc3-3a-o'Teo**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | $GalNAc_3$-$3_a$ | $T_e$ | 25 | 148 |
| 671144 | **GalNAc3-12a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$12_a$ | $A_d$ | 40 | 145 |
| 671165 | **GalNAc3-13a-o'Ado**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T$ | PO/PS | $GalNAc_3$-$13_a$ | $A_d$ | 8 | 145 |
| 671261 | **GalNAc3-14a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$14_a$ | $A_d$ | >250 | 145 |
| 671262 | **GalNAc3-15a-o'Ado**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | $GalNAc_3$-$15_a$ | $A_d$ | >250 | 145 |
| 673501 | **GalNAc3-7a-o'Ado**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | $GalNAc_3$-$7_a$ | $A_d$ | 30 | 145 |
| 673502 | **GalNAC3-10a-o'Ado**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | $GalNAc_3$-$10_a$ | Ad | 8 | 145 |

TABLE 76-continued

| Inhibition of SRB-1 expression in vitro | | | | | | |
|---|---|---|---|---|---|---|
| ISIS No. | Sequence (5' to 3') | Linkages | GalNAc cluster | CM | $IC_{50}$ (nM) | SEQ ID No. |
| 675441 | **GalNAc3-17a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-17$_a$ | $A_d$ | 30 | 145 |
| 675442 | **GalNAc3-18a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-18$_a$ | $A_d$ | 20 | 145 |
| 677841 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$**oAdo'-GalNAc3-19a** | PS | GalNAc$_3$-19$_a$ | $A_d$ | 40 | 144 |
| 677842 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$**oAdo'-GalNAc3-20a** | PS | GalNAc$_3$--20$_a$ | $A_d$ | 30 | 144 |
| 677843 | **GalNAc3-23a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-23$_a$ | $A_d$ | 40 | 145 |

The structure of GalNAc$_3$-1$_a$ was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-7$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17$_a$ was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83: Antisense Inhibition In Vivo by Oligonucleotides Targeting Factor XI Comprising a GalNAc3 Cluster The oligonucleotides listed in Table 77 below were tested in a study for dose-dependent inhibition of Factor XI in mice.

TABLE 77

| Modified oligonucleotides targeting Factor XI | | | | |
|---|---|---|---|---|
| ISIS No. | Sequence (5' to 3') | GalNAc cluster | CM | SEQ ID No. |
| 404071 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$ | n/a | n/a | 146 |
| 656173 | $T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{eo}$**Ado'-GalNAc3-1a** | GalNAc$_3$-1a | $A_d$ | 147 |
| 663086 | **GalNAc3-3a-o'Ad-o**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-3$_a$ | $A_d$ | 155 |
| 678347 | **GalNAc3-7a-o'Ad-o**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-7$_a$ | $A_d$ | 155 |
| 678348 | **GalNAc3-10a-o'Ado**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-10$_a$ | $A_d$ | 155 |
| 678349 | **GalNAc3-13a-o'Ado**$T_{es}G_{eo}G_{eo}$Tec$A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-13$_a$ | $A_d$ | 155 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 78, treatment with antisense oligonucleotides lowered Factor XI liver mRNA in a dose-dependent manner. The results show that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

TABLE 78

Factor XI liver mRNA, liver transaminase, BUN, and bilirubin levels

| ISIS No. | Dosage (mg/kg) | Factor XI mRNA (% PBS) | ALT (U/L) | AST (U/L) | BUN (mg/dL) | Bilirubin (mg/dL) | $GalNAc_3$ Cluster | SEQ ID No. |
|---|---|---|---|---|---|---|---|---|
| PBS | n/a | 100 | 63 | 70 | 21 | 0.18 | n/a | n/a |
| 404071 | 3 | 65 | 41 | 58 | 21 | 0.15 | n/a | 146 |
| | 10 | 33 | 49 | 53 | 23 | 0.15 | | |
| | 30 | 17 | 43 | 57 | 22 | 0.14 | | |
| 656173 | 0.7 | 43 | 90 | 89 | 21 | 0.16 | $GalNAc_3$-1a | 147 |
| | 2 | 9 | 36 | 58 | 26 | 0.17 | | |
| | 6 | 3 | 50 | 63 | 25 | 0.15 | | |
| 663086 | 0.7 | 33 | 91 | 169 | 25 | 0.16 | $GalNAc_3$-3a | 155 |
| | 2 | 7 | 38 | 55 | 21 | 0.16 | | |
| | 6 | 1 | 34 | 40 | 23 | 0.14 | | |
| 678347 | 0.7 | 35 | 28 | 49 | 20 | 0.14 | $GalNAc_3$-7a | 155 |
| | 2 | 10 | 180 | 149 | 21 | 0.18 | | |
| | 6 | 1 | 44 | 76 | 19 | 0.15 | | |
| 678348 | 0.7 | 39 | 43 | 54 | 21 | 0.16 | $GalNAc_3$-10a | 155 |
| | 2 | 5 | 38 | 55 | 22 | 0.17 | | |
| | 6 | 2 | 25 | 38 | 20 | 0.14 | | |
| 678349 | 0.7 | 34 | 39 | 46 | 20 | 0.16 | $GalNAc_3$-13a | 155 |
| | 2 | 8 | 43 | 63 | 21 | 0.14 | | |
| | 6 | 2 | 28 | 41 | 20 | 0.14 | | |

Example 84: Duration of Action In Vivo of Oligonucleotides Targeting Factor XI Comprising a $GalNAc_3$ Conjugate The oligonucleotides listed in Table 77 were tested in a single dose study for duration of action in mice.

Treatment

Six to eight week old mice were each injected subcutaneously once with an oligonucleotide listed in Table 77 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, MN (catalog #AF2460 and #BAF2460, respectively) and the OptEIA Reagent Set B (Catalog #550534, BD Biosciences, San Jose, CA). The results below are presented as the average percent of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even more potent with an even longer duration of action than the oligonucleotide comprising a 3'-GalNAc conjugate (ISIS 656173).

TABLE 79

Plasma Factor XI protein levels in mice

| ISIS No. | Dosage (mg/kg) | Time point (days post-dose) | Factor XI (% baseline) | $GalNAc_3$ Cluster | CM | SEQ ID No. |
|---|---|---|---|---|---|---|
| PBS | n/a | 3 | 123 | n/a | n/a | n/a |
| | | 10 | 56 | | | |
| | | 17 | 100 | | | |
| 404071 | 30 | 3 | 11 | n/a | n/a | 146 |
| | | 10 | 47 | | | |
| | | 17 | 52 | | | |

TABLE 79-continued

Plasma Factor XI protein levels in mice

| ISIS No. | Dosage (mg/kg) | Time point (days post-dose) | Factor XI (% baseline) | $GalNAc_3$ Cluster | CM | SEQ ID No. |
|---|---|---|---|---|---|---|
| 656173 | 6 | 3 | 1 | $GalNAc_3$-1a | $A_d$ | 147 |
| | | 10 | 3 | | | |
| | | 17 | 21 | | | |
| 663086 | 6 | 3 | 1 | $GalNAc_3$-3a | $A_d$ | 155 |
| | | 10 | 2 | | | |
| | | 17 | 9 | | | |
| 678347 | 6 | 3 | 1 | $GalNAc_3$-7a | $A_d$ | 155 |
| | | 10 | 1 | | | |
| | | 17 | 8 | | | |
| 678348 | 6 | 3 | 1 | $GalNAc_3$-10a | $A_d$ | 155 |
| | | 10 | 1 | | | |
| | | 17 | 6 | | | |
| 678349 | 6 | 3 | 1 | $GalNAc_3$-13a | $A_d$ | 155 |
| | | 10 | 1 | | | |
| | | 17 | 5 | | | |

Example 85: Antisense Inhibition In Vivo by Oligonucleotides Targeting SRB-1 Comprising a GalNAc3 Conjugate Oligonucleotides listed in Table 76 were tested in a dose-dependent study for antisense inhibition of SRB-1 in mice.

Treatment

Six to eight week old C57BL/6 mice were each injected subcutaneously once per week at a dosage shown below, for a total of three doses, with an oligonucleotide listed in Table 76 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of liver SRB-1 mRNA levels for each treatment group, normalized to the saline control.

As illustrated in Tables 80 and 81, treatment with antisense oligonucleotides lowered SRB-1 mRNA levels in a dose-dependent manner.

TABLE 80

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| Saline | n/a | 100 | n/a | n/a |
| 655861 | 0.1 | 94 | $GalNAc_3$-1a | $A_d$ |
| | 0.3 | 119 | | |
| | 1 | 68 | | |
| | 3 | 32 | | |
| 661161 | 0.1 | 120 | $GalNAc_3$-3a | $A_d$ |
| | 0.3 | 107 | | |
| | 1 | 68 | | |
| | 3 | 26 | | |
| 666881 | 0.1 | 107 | $GalNAc_3$-10a | $A_d$ |
| | 0.3 | 107 | | |
| | 1 | 69 | | |
| | 3 | 27 | | |
| 666981 | 0.1 | 120 | $GalNAc_3$-7a | $A_d$ |
| | 0.3 | 103 | | |
| | 1 | 54 | | |
| | 3 | 21 | | |
| 670061 | 0.1 | 118 | $GalNAc_3$-13a | $A_d$ |
| | 0.3 | 89 | | |
| | 1 | 52 | | |
| | 3 | 18 | | |

TABLE 80-continued

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| 677842 | 0.1 | 119 | $GalNAc_3$-20a | $A_d$ |
| | 0.3 | 96 | | |
| | 1 | 65 | | |
| | 3 | 23 | | |

TABLE 81

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| 661161 | 0.1 | 107 | $GalNAc_3$-3a | $A_d$ |
| | 0.3 | 95 | | |
| | 1 | 53 | | |
| | 3 | 18 | | |
| 677841 | 0.1 | 110 | $GalNAc_3$-19a | $A_d$ |
| | 0.3 | 88 | | |
| | 1 | 52 | | |
| | 3 | 25 | | |

Liver transaminase levels, total bilirubin, BUN, and body weights were also measured using standard protocols. Average values for each treatment group are shown in Table 82 below.

TABLE 82

| ISIS No. | Dosage (mg/kg) | ALT (U/L) | AST (U/L) | Bilirubin (mg/dL) | BUN (mg/dL) | Body Weight (% baseline) | $GalNAc_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | $GalNAc_3$-1a | $A_d$ |
| | 0.3 | 29 | 56 | 0.15 | 27 | 118 | | |
| | 1 | 20 | 32 | 0.14 | 24 | 112 | | |
| | 3 | 27 | 54 | 0.14 | 24 | 115 | | |
| 661161 | 0.1 | 35 | 83 | 0.13 | 24 | 113 | $GalNAc_3$-3a | $A_d$ |
| | 0.3 | 42 | 61 | 0.15 | 23 | 117 | | |
| | 1 | 34 | 60 | 0.18 | 22 | 116 | | |
| | 3 | 29 | 52 | 0.13 | 25 | 117 | | |
| 666881 | 0.1 | 30 | 51 | 0.15 | 23 | 118 | $GalNAc_3$-10a | $A_d$ |
| | 0.3 | 49 | 82 | 0.16 | 25 | 119 | | |
| | 1 | 23 | 45 | 0.14 | 24 | 117 | | |
| | 3 | 20 | 38 | 0.15 | 21 | 112 | | |
| 666981 | 0.1 | 21 | 41 | 0.14 | 22 | 113 | $GalNAc_3$-7a | $A_d$ |
| | 0.3 | 29 | 49 | 0.16 | 24 | 112 | | |
| | 1 | 19 | 34 | 0.15 | 22 | 111 | | |
| | 3 | 77 | 78 | 0.18 | 25 | 115 | | |
| 670061 | 0.1 | 20 | 63 | 0.18 | 24 | 111 | $GalNAc_3$-13a | $A_d$ |
| | 0.3 | 20 | 57 | 0.15 | 21 | 115 | | |
| | 1 | 20 | 35 | 0.14 | 20 | 115 | | |
| | 3 | 27 | 42 | 0.12 | 20 | 116 | | |
| 677842 | 0.1 | 20 | 38 | 0.17 | 24 | 114 | $GalNAc_3$-20a | $A_d$ |
| | 0.3 | 31 | 46 | 0.17 | 21 | 117 | | |
| | 1 | 22 | 34 | 0.15 | 21 | 119 | | |
| | 3 | 41 | 57 | 0.14 | 23 | 118 | | |

Example 86: Antisense Inhibition In Vivo by Oligonucleotides Targeting TTR Comprising a $GalNAc_3$ Cluster Oligonucleotides listed in Table 83 below were tested in a dose-dependent study for antisense inhibition of human transthyretin (TTR) in transgenic mice that express the human TTR gene.

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 85-87. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Tables 84-87 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

In Tables 84-87, "BL" indicates baseline, measurements that were taken just prior to the first dose. As illustrated in Tables 84 and 85, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PO internucleoside linkages were even more potent than the oligonucleotide comprising a GalNAc conjugate and full PS linkages.

TABLE 83

Oligonucleotides targeting human TTR

| Isis No. | Sequence 5' to 3' | Linkages | GalNAc cluster | CM | SEQ ID No. |
|---|---|---|---|---|---|
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | PS | n/a | n/a | 156 |
| 660261 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$**oAdo'-GalNAc3-1a** | PS | $GalNAc_3$-1a | $A_d$ | 157 |
| 682883 | **GalNAc3-3a-o'**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-3a | PO | 156 |
| 682884 | **GalNAc3-7a-o'**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-7a | PO | 156 |
| 682885 | **GalNAc3-10a-o'**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-10a | PO | 156 |
| 682886 | **GalNAc3-13a-o'**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-13a | PO | 156 |
| 684057 | $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}$Ad $A_{eo}T_{eo}{}^{m}C_{es}{}^{m}C_{es}{}^{m}C_{eo}$**Ado'-GalNAc3-19a** | PS/PO | $GalNAc_3$-19a | Ad | 157 |

The legend for Table 85 can be found in Example 74. The structure of $GalNAc_3$-1 was shown in Example 9. The structure of $GalNAc_3$-$3_a$ was shown in Example 39. The structure of $GalNAc_3$-$7_a$ was shown in Example 48. The structure of $GalNAc_3$-$10_a$ was shown in Example 46. The structure of $GalNAc_3$-$13_a$ was shown in Example 62. The structure of $GalNAc_3$-$19_a$ was shown in Example 70.

TABLE 84

Antisense inhibition of human TTR in vivo

| Isis No. | Dosage (mg/kg) | TTR mRNA (% PBS) | Plasma TTR protein (% PBS) | GalNAc cluster | CM | SEQ ID No. |
|---|---|---|---|---|---|---|
| PBS | n/a | 100 | 100 | n/a | n/a | |
| 420915 | 6 | 99 | 95 | n/a | n/a | 156 |
| | 20 | 48 | 65 | | | |
| | 60 | 18 | 28 | | | |

TABLE 84-continued

| Antisense inhibition of human TTR in vivo | | | | | | |
|---|---|---|---|---|---|---|
| Isis No. | Dosage (mg/kg) | TTR mRNA (% PBS) | Plasma TTR protein (% PBS) | GalNAc cluster | CM | SEQ ID No. |
| 660261 | 0.6 | 113 | 87 | GalNAc$_3$-1a | A$_d$ | 157 |
| | 2 | 40 | 56 | | | |
| | 6 | 20 | 27 | | | |
| | 20 | 9 | 11 | | | |

TABLE 85

| Antisense inhibition of human TTR in vivo | | | | | | | | | |
|---|---|---|---|---|---|---|---|---|---|
| | | | Plasma TTR protein (% PBS at BL) | | | | | | |
| Isis No. | Dosage (mg/kg) | TTR mRNA (% PBS) | BL | Day 3 | Day 10 | Day 17 (After sac) | GalNAc cluster | CM | SEQ ID No. |
| PBS | n/a | 100 | 100 | 96 | 90 | 114 | n/a | n/a | |
| 420915 | 6 | 74 | 106 | 86 | 76 | 83 | n/a | n/a | 156 |
| | 20 | 43 | 102 | 66 | 61 | 58 | | | |
| | 60 | 24 | 92 | 43 | 29 | 32 | | | |
| 682883 | 0.6 | 60 | 88 | 73 | 63 | 68 | GalNAc$_3$-3a | PO | 156 |
| | 2 | 18 | 75 | 38 | 23 | 23 | | | |
| | 6 | 10 | 80 | 35 | 11 | 9 | | | |
| 682884 | 0.6 | 56 | 88 | 78 | 63 | 67 | GalNAc$_3$-7a | PO | 156 |
| | 2 | 19 | 76 | 44 | 25 | 23 | | | |
| | 6 | 15 | 82 | 35 | 21 | 24 | | | |
| 682885 | 0.6 | 60 | 92 | 77 | 68 | 76 | GalNAc$_3$-10a | PO | 156 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | GalNAc$_3$-13a | PO | 156 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | GalNAc$_3$-19a | A$_d$ | 157 |
| | 2 | 21 | 92 | 55 | 34 | 30 | | | |
| | 6 | 11 | 82 | 50 | 18 | 13 | | | |

TABLE 86

| Transaminase levels, body weight changes, and relative organ weights | | | | | | | | | | | | | |
|---|---|---|---|---|---|---|---|---|---|---|---|---|---|
| | | ALT (U/L) | | | | AST (U/L) | | | | | | | |
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 156 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 157 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 87

| Transaminase levels, body weight changes, and relative organ weights | | | | | | | | | | | | | | |
|---|---|---|---|---|---|---|---|---|---|---|---|---|---|---|
| | | ALT (U/L) | | | | AST (U/L) | | | | | | | | |
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 156 |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |

TABLE 87-continued

Transaminase levels, body weight changes, and relative organ weights

| | | ALT (U/L) | | | | AST (U/L) | | | | | | | | |
|---|---|---|---|---|---|---|---|---|---|---|---|---|---|---|
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| 682883 | 0.6 | 32 | 35 | 38 | 40 | 53 | 81 | 74 | 76 | 104 | 101 | 112 | 95 | 156 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 156 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 156 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 156 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |
| 684057 | 0.6 | 35 | 26 | 33 | 39 | 56 | 51 | 51 | 69 | 104 | 99 | 110 | 102 | 157 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87: Duration of Action In Vivo by Single Doses of Oligonucleotides Targeting TTR Comprising a GalNAc3 Cluster ISIS numbers 420915 and 660261 (see Table 83) were tested in a single dose study for duration of action in mice. ISIS numbers 420915, 682883, and 682885 (see Table 83) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 88

Plasma TTR protein levels

| ISIS No. | Dosage (mg/kg) | Time point (days post-dose) | TTR (% baseline) | $GalNAc_3$ Cluster | CM | SEQ ID No. |
|---|---|---|---|---|---|---|
| 420915 | 100 | 3 | 30 | n/a | n/a | 156 |
| | | 7 | 23 | | | |
| | | 10 | 35 | | | |
| | | 17 | 53 | | | |
| | | 24 | 75 | | | |
| | | 39 | 100 | | | |
| 660261 | 13.5 | 3 | 27 | $GalNAc_3$-1a | $A_d$ | 157 |
| | | 7 | 21 | | | |
| | | 10 | 22 | | | |
| | | 17 | 36 | | | |
| | | 24 | 48 | | | |
| | | 39 | 69 | | | |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 89

Plasma TTR protein levels

| ISIS No. | Dosage (mg/kg) | Time point (days post-dose) | TTR (% baseline) | $GalNAc_3$ Cluster | CM | SEQ ID No. |
|---|---|---|---|---|---|---|
| 420915 | 100 | 3 | 48 | n/a | n/a | 156 |
| | | 7 | 48 | | | |
| | | 10 | 48 | | | |
| | | 17 | 66 | | | |
| | | 31 | 80 | | | |
| 682883 | 10.0 | 3 | 45 | $GalNAc_3$-3a | PO | 156 |
| | | 7 | 37 | | | |
| | | 10 | 38 | | | |
| | | 17 | 42 | | | |
| | | 31 | 65 | | | |
| 682885 | 10.0 | 3 | 40 | $GalNAc_3$-10a | PO | 156 |
| | | 7 | 33 | | | |
| | | 10 | 34 | | | |
| | | 17 | 40 | | | |
| | | 31 | 64 | | | |

The results in Tables 88 and 89 show that the oligonucleotides comprising a GalNAc conjugate are more potent with a longer duration of action than the parent oligonucleotide lacking a conjugate (ISIS 420915).

Example 88: Splicing Modulation In Vivo by Oligonucleotides Targeting SMN Comprising a $GalNAc_3$ Conjugate The oligonucleotides listed in Table 90 were tested for splicing modulation of human survival of motor neuron (SMN) in mice.

TABLE 90

| Modified ASOs targeting SMN | | | | |
|---|---|---|---|---|
| ISIS No. | Sequences (5' to 3') | GalNAc3 Cluster | CM | SEQ ID No. |
| 387954 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{e}$ | n/a | n/a | 158 |
| 699819 | **GalNAc3-7a-o'**$A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{e}$ | $GalNAc_3$-7a | PO | 158 |
| 699821 | **GalNAc3-7a-o'**$A_{es}T_{eo}T_{eo}{}^{m}C_{eo}A_{eo}{}^{m}C_{eo}T_{eo}T_{eo}T_{eo}{}^{m}C_{eo}A_{eo}T_{eo}A_{eo}A_{eo}T_{eo}G_{eo}{}^{m}C_{eo}T_{es}G_{es}G_{e}$ | $GalNAc_3$-7a | PO | 158 |
| 700000 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}C_{es}T_{es}G_{es}G_{eo}$**Ado'-GalNAc3-1a** | $GalNAc_3$-1a | Ad | 157 |
| 703421 | X-$ATT^{m}CA^{m}CTTT^{m}CATAATG^{m}CTGG$ | n/a | n/a | 158 |
| 703422 | **GalNAc3-7b**-X-$ATT^{m}CA^{m}CTTT^{m}CATAATG^{m}CTGG$ | $GalNAc_3$-7b | n/a | 158 |

The structure of $GalNAc_3$-$7_a$ was shown previously in Example 48. "X" indicates a 5' primary amine generated by Gene Tools (Philomath, OR), and $GalNAc_3$-$7_b$ indicates the structure of $GalNAc_3$-$7_a$ lacking the —NH—$C_6$—O portion of the linker as shown below:

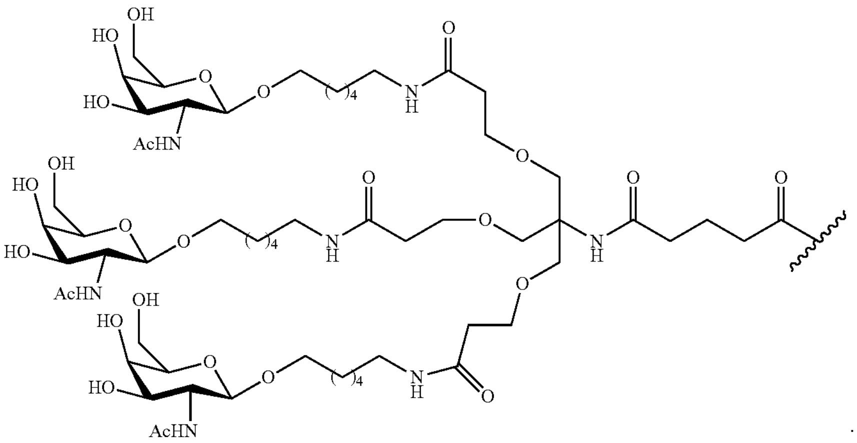

ISIS numbers 703421 and 703422 are morpholino oligonucleotides, wherein each nucleotide of the two oligonucleotides is a morpholino nucleotide.

Treatment

Six week old transgenic mice that express human SMN were injected subcutaneously once with an oligonucleotide listed in Table 91 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 91. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 91

| Effect of oligonucleotides targeting human SMN in vivo | | | | | |
|---|---|---|---|---|---|
| ISIS No. | Dose (mg/kg) | +Exon 7/ −Exon 7 | $GalNAc_3$ Cluster | CM | SEQ ID No. |
| Saline | n/a | 1.00 | n/a | n/a | n/a |
| 387954 | 32 | 1.65 | n/a | n/a | 158 |
| 387954 | 288 | 5.00 | n/a | n/a | 158 |
| 699819 | 32 | 7.84 | $GalNAc_3$-7a | PO | 158 |
| 699821 | 32 | 7.22 | $GalNAc_3$-7a | PO | 158 |
| 700000 | 32 | 6.91 | $GalNAc_3$-1a | $A_d$ | 159 |
| 703421 | 32 | 1.27 | n/a | n/a | 158 |
| 703422 | 32 | 4.12 | $GalNAc_3$-7b | n/a | 158 |

Example 89: Antisense Inhibition In Vivo by Oligonucleotides Targeting Apolipoprotein a (Apo(a)) Comprising a GalNAc3 Conjugate The oligonucleotides listed in Table 92 below were tested in a study for dose-dependent inhibition of Apo(a) in transgenic mice.

TABLE 92

| Modified ASOs targeting Apo(a) | | | | |
|---|---|---|---|---|
| ISIS No. | Sequences (5' to 3') | GalNAc3 Cluster | CM | SEQ ID No. |
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 58 |
| 681257 | **GalNAc3-7a-o'**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-7a | PO | 58 |

The structure of $GalNAc_3$-$7_a$ was shown in Example 48.

Treatment

Eight week old, female C57BL/6 mice (Jackson Laboratory, Bar Harbor, ME) were each injected subcutaneously once per week at a dosage shown below, for a total of six doses, with an oligonucleotide listed in Table 92 or with PBS. Each treatment group consisted of 3-4 animals. Tail bleeds were performed the day before the first dose and weekly following each dose to determine plasma Apo(a) protein levels. The mice were sacrificed two days following the final administration. Apo(a) liver mRNA levels were determined using real-time PCR and RIBOGREEN® RNA quantification reagent (Molecular Probes, Inc. Eugene, OR) according to standard protocols. Apo(a) plasma protein levels were determined using ELISA, and liver transaminase levels were determined. The mRNA and plasma protein results in Table 93 are presented as the treatment group average percent relative to the PBS treated group. Plasma protein levels were further normalized to the baseline (BL) value for the PBS group. Average absolute transaminase levels and body weights (% relative to baseline averages) are reported in Table 94.

As illustrated in Table 93, treatment with the oligonucleotides lowered Apo(a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 94, transaminase levels and body weights were unaffected by the oligonucleotides, indicating that the oligonucleotides were well tolerated.

TABLE 93

| Apo(a) liver mRNA and plasma protein levels | | | | | | | | | |
|---|---|---|---|---|---|---|---|---|---|
| | | Apo(a) | Apo(a) plasma protein (% PBS) | | | | | | |
| ISIS No. | Dosage (mg/kg) | mRNA (% PBS) | BL | Week 1 | Week 2 | Week 3 | Week 4 | Week 5 | Week 6 |
| PBS | n/a | 100 | 100 | 120 | 119 | 113 | 88 | 121 | 97 |
| 494372 | 3 | 80 | 84 | 89 | 91 | 98 | 87 | 87 | 79 |
| | 10 | 30 | 87 | 72 | 76 | 71 | 57 | 59 | 46 |
| | 30 | 5 | 92 | 54 | 28 | 10 | 7 | 9 | 7 |
| 681257 | 0.3 | 75 | 79 | 76 | 89 | 98 | 71 | 94 | 78 |
| | 1 | 19 | 79 | 88 | 66 | 60 | 54 | 32 | 24 |
| | 3 | 2 | 82 | 52 | 17 | 7 | 4 | 6 | 5 |
| | 10 | 2 | 79 | 17 | 6 | 3 | 2 | 4 | 5 |

TABLE 94

| ISIS No. | Dosage (mg/kg) | ALT (U/L) | AST (U/L) | Body weight (% baseline) |
|---|---|---|---|---|
| PBS | n/a | 37 | 54 | 103 |
| 494372 | 3 | 28 | 68 | 106 |
| | 10 | 22 | 55 | 102 |
| | 30 | 19 | 48 | 103 |
| 681257 | 0.3 | 30 | 80 | 104 |
| | 1 | 26 | 47 | 105 |
| | 3 | 29 | 62 | 102 |
| | 10 | 21 | 52 | 107 |

Example 90: Antisense Inhibition In Vivo by Oligonucleotides Targeting TTR Comprising a $GalNAc_3$ Cluster Oligonucleotides listed in Table 95 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 96 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Table 96 are the average values for each treatment group. The mRNA levels are the average values relative to the average for the PBS group. Plasma protein levels are the average values relative to the average value for the PBS group at baseline. "BL" indicates baseline, measurements that were taken just prior to the first dose. As illustrated in Table 96, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 95

| Oligonucleotides targeting human TTR | | | | | |
|---|---|---|---|---|---|
| Isis No. | Sequence 5' to 3' | Linkages | GalNAc cluster | CM | SEQ ID No. |
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | PS | n/a | n/a | 156 |
| 682883 | **GalNAc3-3a-o'**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-3a | PO | 156 |
| 666943 | **GalNAc3-3a-o'Ado**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-3a | $A_d$ | 160 |
| 682887 | **GalNAc3-7a-o'Ado**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-7a | $A_d$ | 160 |
| 682888 | **GalNAc3-10a-o'Ado**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-10a | $A_d$ | 160 |
| 682889 | **GalNAc3-13a-o'Ado**$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-13a | $A_d$ | 160 |

The legend for Table 95 can be found in Example 74. The structure of $GalNAc_3$-$3_a$ was shown in Example 39. The structure of $GalNAc_3$-$7_a$ was shown in Example 48. The structure of $GalNAc_3$-$10_a$ was shown in Example 46. The structure of $GalNAc_3$-$13_a$ was shown in Example 62.

TABLE 96

| Antisense inhibition of human TTR in vivo | | | | | |
|---|---|---|---|---|---|
| Isis No. | Dosage (mg/kg) | TTR mRNA (% PBS) | TTR protein (% BL) | GalNAc cluster | CM |
| PBS | n/a | 100 | 124 | n/a | n/a |
| 420915 | 6 | 69 | 114 | n/a | n/a |
| | 20 | 71 | 86 | | |
| | 60 | 21 | 36 | | |
| 682883 | 0.6 | 61 | 73 | $GalNAc_3$-3a | PO |
| | 2 | 23 | 36 | | |
| | 6 | 18 | 23 | | |
| 666943 | 0.6 | 74 | 93 | $GalNAc_3$-3a | $A_d$ |
| | 2 | 33 | 57 | | |
| | 6 | 17 | 22 | | |
| 682887 | 0.6 | 60 | 97 | $GalNAc_3$-7a | $A_d$ |
| | 2 | 36 | 49 | | |
| | 6 | 12 | 19 | | |
| 682888 | 0.6 | 65 | 92 | $GalNAc_3$-10a | $A_d$ |
| | 2 | 32 | 46 | | |
| | 6 | 17 | 22 | | |
| 682889 | 0.6 | 72 | 74 | $GalNAc_3$-13a | $A_d$ |
| | 2 | 38 | 45 | | |
| | 6 | 16 | 18 | | |

Example 91: Antisense Inhibition In Vivo by Oligonucleotides Targeting Factor VII Comprising a GalNAc3 Conjugate in Non-Human Primates Oligonucleotides listed in Table 97 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 97 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 98 are the average values for each treatment group relative to the average value for the PBS group at baseline (BL), the measurements taken just prior to the first dose. As illustrated in Table 98, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 97

| Oligonucleotides targeting Factor VII | | | | | |
|---|---|---|---|---|---|
| Isis No. | Sequence 5' to 3' | Linkages | GalNAc cluster | CM | SEQ ID No. |
| 407935 | $A_{es}T_{es}G_{es}{}^{m}C_{es}A_{es}T_{ds}G_{ds}G_{ds}T_{ds}G_{ds}A_{ds}T_{ds}G_{ds}{}^{m}C_{ds}T_{ds}T_{es}{}^{m}C_{es}T_{es}G_{es}A_{e}$ | PS | n/a | n/a | 161 |
| 686892 | **GalNAc3-10a-o'**$A_{es}T_{es}G_{es}{}^{m}C_{es}A_{es}T_{ds}G_{ds}G_{ds}T_{ds}G_{ds}A_{ds}T_{ds}G_{ds}{}^{m}C_{ds}T_{ds}T_{es}{}^{m}C_{es}T_{es}G_{es}A_{e}$ | PS | $GalNAc_3$-10a | PO | 161 |

The legend for Table 97 can be found in Example 74. The structure of GalNAc$_3$-10$_a$ was shown in Example 46.

TABLE 98

| Factor VII plasma protein levels | | | |
|---|---|---|---|
| ISIS No. | Day | Dose (mg/kg) | Factor VII (% BL) |
| 407935 | 0 | n/a | 100 |
| | 15 | 10 | 87 |
| | 22 | n/a | 92 |
| | 29 | 30 | 77 |
| | 36 | n/a | 46 |
| | 43 | n/a | 43 |
| 686892 | 0 | 3 | 100 |
| | 15 | 10 | 56 |
| | 22 | n/a | 29 |
| | 29 | 30 | 19 |
| | 36 | n/a | 15 |
| | 43 | n/a | 11 |

Example 92: Antisense Inhibition in Primary Hepatocytes by Antisense Oligonucleotides Targeting Apo-CIII Comprising a GalNAc3 Conjugate Primary mouse hepatocytes were seeded in 96-well plates at 15,000 cells per well, and the oligonucleotides listed in Table 99, targeting mouse ApoC-III, were added at 0.46, 1.37, 4.12, or 12.35, 37.04, 111.11, or 333.33 nM or 1.00 µM. After incubation with the oligonucleotides for 24 hours, the cells were lysed and total RNA was purified using RNeasy (Qiagen). ApoC-III mRNA levels were determined using real-time PCR and RIBOGREEN® RNA quantification reagent (Molecular Probes, Inc.) according to standard protocols. IC$_{50}$ values were determined using Prism 4 software (GraphPad). The results show that regardless of whether the cleavable moiety was a phosphodiester or a phosphodiester-linked deoxyadensoine, the oligonucleotides comprising a GalNAc conjugate were significantly more potent than the parent oligonucleotide lacking a conjugate.

TABLE 99

| Inhibition of mouse APOC-III expression in mouse primary hepatocytes | | | | |
|---|---|---|---|---|
| ISIS No. | Sequence (5' to 3') | CM | IC$_{50}$ (nM) | SEQ ID No. |
| 440670 | $^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a | 13.20 | 162 |
| 661180 | $^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{eo}$**Ado'-GalNAc3-1a** | $A_d$ | 1.40 | 163 |
| 680771 | **GalNAc3-3a-o'**$^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 0.70 | 162 |
| 680772 | **GalNAC3-7a-o'**$^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 1.70 | 162 |
| 680773 | **GalNAc3-10a-o'**$^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 2.00 | 162 |
| 680774 | **GalNAc3-13a-o'**$^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 1.50 | 162 |
| 681272 | **GalNAc3-3a-o'**$^{m}C_{es}A_{eo}G_{eo}{}^{m}C_{eo}T_{eo}T_{ds}T_{ds}A_{ds}T_{ds}T_{ds}A_{ds}G_{ds}G_{ds}G_{ds}A_{ds}{}^{m}C_{eo}$ $A_{eo}G_{es}{}^{m}C_{es}A_{e}$ | PO | <0.46 | 162 |
| 681273 | **GalNAc3-3a-o,A**$_{do}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}$ $^{m}C_{es}A_{es}G_{es}{}^{m}C_{es}A_{e}$ | $A_d$ | 1.10 | 164 |
| 683733 | $^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{eo}$**Ado'-GalNAc3-19a** | $A_d$ | 2.50 | 163 |

The structure of $GalNAc_3$-$1_a$ was shown previously in Example 9, $GalNAc_3$-$3_a$ was shown in Example 39, $GalNAc_3$-$7_a$ was shown in Example 48, $GalNAc_3$-$10_a$ was shown in Example 46, $GalNAc_3$-$13_a$ was shown in Example 62, and $GalNAc_3$-$19_a$ was shown in Example 70.

Example 93: Antisense Inhibition In Vivo by Oligonucleotides Targeting SRB-1 Comprising Mixed Wings and a 5'-GalNAc3 Conjugate The oligonucleotides listed in Table 100 were tested in a dose-dependent study for antisense inhibition of SRB-1 in mice.

TABLE 100

Modified ASOs targeting SRB-1

| ISIS No. | Sequences (5' to 3') | $GalNAc_3$ Cluster | CM | SEQ ID No. |
|---|---|---|---|---|
| 449093 | $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | n/a | n/a | 165 |
| 699806 | **GalNAc3-3a-o'** $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | $GalNAc_3$-3a | PO | 165 |
| 699807 | **GalNAc3-7a-o'** $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | $GalNAc_3$-7a | PO | 165 |
| 699809 | **GalNAc3-7a-o'** $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{e}$ | $GalNAc_3$-7a | PO | 165 |
| 699811 | **GalNAc3-7a-o'** $T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | $GalNAc_3$-7a | PO | 165 |
| 699813 | **GalNAc3-7a-o'** $T_{ks}T_{ds}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ds}{}^{m}C_{k}$ | $GalNAc_3$-7a | PO | 165 |
| 699815 | **GalNAc3-7a-o'** $T_{es}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{e}$ | $GalNAc_3$-7a | PO | 165 |

The structure of $GalNAc_3$-$3_a$ was shown previously in Example 39, and the structure of $GalNAc_3$-7a was shown previously in Example 48. Subscripts: "e" indicates 2'-MOE modified nucleoside; "d" indicates β-D-2'-deoxyribonucleoside; "k" indicates 6'-(S)—$CH_3$ bicyclic nucleoside (cEt); "s" indicates phosphorothioate internucleoside linkages (PS); "o" indicates phosphodiester internucleoside linkages (PO). Superscript "m" indicates 5-methylcytosines.

Treatment

Six to eight week old C57BL/6 mice (Jackson Laboratory, Bar Harbor, ME) were injected subcutaneously once at the dosage shown below with an oligonucleotide listed in Table 100 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 101, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 101. Body weight is shown as the average percent body weight relative to the baseline body weight (% BL) measured just prior to the oligonucleotide dose.

TABLE 101

SRB-1 mRNA, ALT, AST, BUN, and total bilirubin levels and body weights

| ISIS No. | Dosage (mg/kg) | SRB-1 mRNA (% PBS) | ALT (U/L) | AST (U/L) | Bil | BUN | Body weight (% BL) |
|---|---|---|---|---|---|---|---|
| PBS | n/a | 100 | 31 | 84 | 0.15 | 28 | 102 |
| 449093 | 1 | 111 | 18 | 48 | 0.17 | 31 | 104 |
| | 3 | 94 | 20 | 43 | 0.15 | 26 | 103 |
| | 10 | 36 | 19 | 50 | 0.12 | 29 | 104 |
| 699806 | 0.1 | 114 | 23 | 58 | 0.13 | 26 | 107 |
| | 0.3 | 59 | 21 | 45 | 0.12 | 27 | 108 |
| | 1 | 25 | 30 | 61 | 0.12 | 30 | 104 |
| 699807 | 0.1 | 121 | 19 | 41 | 0.14 | 25 | 100 |
| | 0.3 | 73 | 23 | 56 | 0.13 | 26 | 105 |
| | 1 | 24 | 22 | 69 | 0.14 | 25 | 102 |
| 699809 | 0.1 | 125 | 23 | 57 | 0.14 | 26 | 104 |
| | 0.3 | 70 | 20 | 49 | 0.10 | 25 | 105 |
| | 1 | 33 | 34 | 62 | 0.17 | 25 | 107 |
| 699811 | 0.1 | 123 | 48 | 77 | 0.14 | 24 | 106 |
| | 0.3 | 94 | 20 | 45 | 0.13 | 25 | 101 |
| | 1 | 66 | 57 | 104 | 0.14 | 24 | 107 |
| 699813 | 0.1 | 95 | 20 | 58 | 0.13 | 28 | 104 |
| | 0.3 | 98 | 22 | 61 | 0.17 | 28 | 105 |
| | 1 | 49 | 19 | 47 | 0.11 | 27 | 106 |
| 699815 | 0.1 | 93 | 30 | 79 | 0.17 | 25 | 105 |
| | 0.3 | 64 | 30 | 61 | 0.12 | 26 | 105 |
| | 1 | 24 | 18 | 41 | 0.14 | 25 | 106 |

Example 94: Antisense Inhibition In Vivo by Oligonucleotides Targeting SRB-1 Comprising 2'-Sugar Modifications and a 5'-GalNAc3 Conjugate The oligonucleotides listed in Table 102 were tested in a dose-dependent study for antisense inhibition of SRB-1 in mice.

TABLE 102

Modified ASOs targeting SRB-1

| ISIS No. | Sequences (5' to 3') | $GalNAc_3$ Cluster | CM | SEQ ID No. |
|---|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | n/a | n/a | 143 |
| 700989 | $G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}U_{m}$ | n/a | n/a | 166 |
| 666904 | **GalNAc3-3a-o'**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 143 |
| 700991 | **GalNAc3-7a-o'**$G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}U_{m}$ | $GalNAc_3$-7a | PO | 166 |

Subscript "m" indicates a 2'-O-methyl modified nucleoside. See Example 74 for complete table legend. The structure of $GalNAc_3$-$3_a$ was shown previously in Example 39, and the structure of $GalNAc_3$-7a was shown previously in Example 48.

Treatment

The study was completed using the protocol described in Example 93. Results are shown in Table 103 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 103

SRB-1 mRNA

| ISIS No. | Dosage (mg/kg) | SRB-1 mRNA (% PBS) |
|---|---|---|
| PBS | n/a | 100 |
| 353382 | 5 | 116 |
| | 15 | 58 |
| | 45 | 27 |
| 700989 | 5 | 120 |
| | 15 | 92 |
| | 45 | 46 |
| 666904 | 1 | 98 |
| | 3 | 45 |
| | 10 | 17 |
| 700991 | 1 | 118 |
| | 3 | 63 |
| | 10 | 14 |

Example 95: Antisense Inhibition In Vivo by Oligonucleotides Targeting SRB-1 Comprising Bicyclic Nucleosides and a 5'-GalNAc3 Conjugate The oligonucleotides listed in Table 104 were tested in a dose-dependent study for antisense inhibition of SRB-1 in mice.

TABLE 104

Modified ASOs targeting SRB-1

| ISIS No. | Sequences (5' to 3') | $GalNAc_3$ Cluster | CM | SEQ ID No. |
|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | n/a | 137 |
| 666905 | **GalNAc3-3a-o'**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$3_a$ | PO | 137 |
| 699782 | **GalNAc3-7a-o'**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$7_a$ | PO | 137 |
| 699783 | **GalNAc3-3a-o'**$T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{l}$ | $GalNAc_3$-$3_a$ | PO | 137 |
| 653621 | $T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{lo}$**Ado'-GalNAc3-1a** | $GalNAc_3$-$1_a$ | $A_d$ | 138 |

TABLE 104-continued

| Modified ASOs targeting SRB-1 | | | | |
|---|---|---|---|---|
| ISIS No. | Sequences (5' to 3') | $GalNAc_3$ Cluster | CM | SEQ ID No. |
| 439879 | $T_{gs}{}^{m}C_{gs}A_{ds}G_{ds}T_{ds}{}^{m}C_{ds}A_{ds}T_{d}G_{ds}A_{ds}{}^{m}C_{ds}T_{ds}T_{gs}{}^{m}C_{g}$ | n/a | n/a | 137 |
| 699789 | **GalNAc3-3a-o'**$T_{gs}{}^{m}C_{gs}A_{ds}G_{ds}T_{ds}{}^{m}C_{ds}A_{ds}T_{d}G_{ds}A_{ds}{}^{m}C_{ds}T_{ds}T_{gs}{}^{m}C_{g}$ | $GalNAc_3$-$3_a$ | PO | 137 |

Subscript "g" indicates a fluoro-HNA nucleoside, subscript "1" indicates a locked nucleoside comprising a 2'-O—$CH_2$-4' bridge. See the Example 74 table legend for other abbreviations. The structure of $GalNAc_3$-$1_a$ was shown previously in Example 9, the structure of $GalNAc_3$-$3_a$ was shown previously in Example 39, and the structure of $GalNAc_3$-7a was shown previously in Example 48.

Treatment

The study was completed using the protocol described in Example 93. Results are shown in Table 105 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 105

| SRB-1 mRNA, ALT, AST, BUN, and total bilirubin levels and body weights | | |
|---|---|---|
| ISIS No. | Dosage (mg/kg) | SRB-1 mRNA (% PBS) |
| PBS | n/a | 100 |
| 440762 | 1 | 104 |
| | 3 | 65 |
| | 10 | 35 |
| 666905 | 0.1 | 105 |
| | 0.3 | 56 |
| | 1 | 18 |
| 699782 | 0.1 | 93 |
| | 0.3 | 63 |
| | 1 | 15 |
| 699783 | 0.1 | 105 |
| | 0.3 | 53 |
| | 1 | 12 |
| 653621 | 0.1 | 109 |
| | 0.3 | 82 |
| | 1 | 27 |
| 439879 | 1 | 96 |
| | 3 | 77 |
| | 10 | 37 |
| 699789 | 0.1 | 82 |
| | 0.3 | 69 |
| | 1 | 26 |

Example 96: Plasma Protein Binding of Antisense Oligonucleotides Comprising a $GalNAc_3$ Conjugate Group Oligonucleotides listed in Table 70 targeting ApoC-III and oligonucleotides in Table 106 targeting Apo(a) were tested in an ultra-filtration assay in order to assess plasma protein binding.

TABLE 106

| Modified oligonucleotides targeting Apo(a) | | | | |
|---|---|---|---|---|
| ISIS No. | Sequences (5' to 3') | $GalNAc_3$ Cluster | CM | SEQ ID No. |
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 58 |
| 693401 | $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | n/a | n/a | 58 |
| 681251 | **GalNAc3-7a-o'**$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | $GalNAc_3$-$7_a$ | PO | 58 |
| 681257 | **GalNAc3-7a-o'**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-$7_a$ | PO | 58 |

See the Example 74 for table legend. The structure of $GalNAc_3$-7a was shown previously in Example 48.

Ultrafree-MC ultrafiltration units (30,000 NMWL, low-binding regenerated cellulose membrane, Millipore, Bedford, MA) were pre-conditioned with 300 µL of 0.5% Tween 80 and centrifuged at 2000 g for 10 minutes, then with 3004 of a 300 µg/mL solution of a control oligonucleotide in $H_2O$ and centrifuged at 2000 g for 16 minutes. In order to assess non-specific binding to the filters of each test oligonucleotide from Tables 70 and 106 to be used in the studies, 300 µL of a 250 ng/mL solution of oligonucleotide in $H_2O$ at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC (Westbury, NY). The test oligonucleotides were added to 1.2 mL aliquots of plasma at two concentrations (5 and 150 µg/mL). An aliquot (300 µL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 107 for the two concentrations of oligonucleotide tested (5 and 150 µg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 107

| Percent of modified oligonucleotide bound to plasma proteins | | | | | | |
|---|---|---|---|---|---|---|
| ISIS | Human plasma | | Monkey plasma | | Mouse plasma | |
| No. | 5 µg/mL | 150 µg/mL | 5 µg/mL | 150 µg/mL | 5 µg/mL | 150 µg/mL |
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97: Modified Oligonucleotides Targeting TTR Comprising a GalNAc3 Conjugate Group The oligonucleotides shown in Table 108 comprising a GalNAc conjugate were designed to target TTR.

TABLE 108

| Modified oligonucleotides targeting TTR | | | | |
|---|---|---|---|---|
| ISIS No. | Sequences (5' to 3') | $GalNAc_3$ Cluster | CM | SEQ ID No. |
| 666941 | **GalNAc3-3a-o'Ado**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-3 | $A_d$ | 160 |
| 666942 | $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{eo}$**Ado'-GalNAc3-3a** | $GalNAc_3$-1 | $A_d$ | 157 |
| 682876 | **GalNAc3-3a-o'**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | GalNAc3-3 | PO | 156 |
| 682877 | **GalNAc3-7a-o'**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-7 | PO | 156 |
| 682878 | **GalNAc3-10a-o'**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-10 | PO | 156 |
| 682879 | **GalNAc3-13a-o'**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-13 | PO | 156 |
| 682880 | **GalNAc3-7a-o'Ado**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-7 | $A_d$ | 160 |
| 682881 | **GalNAc3-10a-o'Ado**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-10 | $A_d$ | 160 |
| 682882 | **GalNAc3-13a-o'Ado**$T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-13 | $A_d$ | 160 |
| 684056 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$**Ado'-GalNAc3-19a** | $GalNAc_3$-19 | $A_d$ | 157 |

The legend for Table 108 can be found in Example 74. The structure of GalNAc$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

Example 98: Evaluation of Pro-Inflammatory Effects of Oligonucleotides Comprising a GalNAc Conjugate in hPMBC Assay The oligonucleotides listed in Table 109 and were tested for pro-inflammatory effects in an hPMBC assay as described in Examples 23 and 24. (See Tables 30, 83, 95, and 108 for descriptions of the oligonucleotides.) ISIS 353512 is a high responder used as a positive control, and the other oligonucleotides are described in Tables 83, 95, and 108. The results shown in Table 109 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 109

| ISIS No. | $E_{max}$/$EC_{50}$ | GalNAc$_3$ cluster | Linkages | CM |
|---|---|---|---|---|
| 353512 | 3630 | n/a | PS | n/a |
| 420915 | 802 | n/a | PS | n/a |
| 682881 | 1311 | GalNAc$_3$-10 | PS | A$_d$ |
| 682888 | 0.26 | GalNAc$_3$-10 | PO/PS | A$_d$ |
| 684057 | 1.03 | GalNAc$_3$-19 | PO/PS | A$_d$ |

Example 99: Binding Affinities of Oligonucleotides Comprising a GalNAc Conjugate for the Asialoglycoprotein Receptor The binding affinities of the oligonucleotides listed in Table 110 (see Table 76 for descriptions of the oligonucleotides) for the asialoglycoprotein receptor were tested in a competitive receptor binding assay. The competitor ligand, α1-acid glycoprotein (AGP), was incubated in 50 mM sodium acetate buffer (pH 5) with 1 U neuraminidase-agarose for 16 hours at 3TC, and >90% desialylation was confirmed by either sialic acid assay or size exclusion chromatography (SEC). Iodine monochloride was used to iodinate the AGP according to the procedure by Atsma et al. (see J Lipid Res. 1991 January; 32(1):173-81.) In this method, desialylated al-acid glycoprotein (de-AGP) was added to 10 mM iodine chloride, Na$^{125}$I, and 1 M glycine in 0.25 M NaOH. After incubation for 10 minutes at room temperature, $^{125}$I-labeled de-AGP was separated from free $^{125}$I by concentrating the mixture twice utilizing a 3 KDMWCO spin column. The protein was tested for labeling efficiency and purity on a HPLC system equipped with an Agilent SEC-3 column (7.8×300 mm) and a B-RAM counter. Competition experiments utilizing $^{125}$I-labeled de-AGP and various GalNAc-cluster containing ASOs were performed as follows. Human HepG2 cells ($10^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 3TC with 5% and 10% $CO_2$ respectively. Cells were washed with media without FBS prior to the experiment. Cells were incubated for 30 min @37° C. with 1 ml competition mix containing appropriate growth media with 2% FBS, $10^{-8}$ M $^{125}$I-labeled de-AGP and GalNAc-cluster containing ASOs at concentrations ranging from $10^{-11}$ to $10^{-5}$ M. Non-specific binding was determined in the presence of $10^{-2}$ M GalNAc sugar. Cells were washed twice with media without FBS to remove unbound $^{125}$I-labeled de-AGP and competitor GalNAc ASO. Cells were lysed using Qiagen's RLT buffer containing 1% ß-mercaptoethanol. Lysates were transferred to round bottom assay tubes after a brief 10 min freeze/thaw cycle and assayed on a γ-counter. Non-specific binding was subtracted before dividing $^{125}$I protein counts by the value of the lowest GalNAc-ASO concentration counts. The inhibition curves were fitted according to a single site competition binding equation using a nonlinear regression algorithm to calculate the binding affinities ($K_D$'s).

The results in Table 110 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 110

Asialoglycoprotein receptor binding assay results

| ISIS No. | GalNAc conjugate | Oligonucleotide end to which GalNAc conjugate is attached | $K_D$ (nM) |
|---|---|---|---|
| 661161[a] | GalNAc$_3$-3 | 5' | 3.7 |
| 666881[a] | GalNAc$_3$-10 | 5' | 7.6 |
| 666981 | GalNAc$_3$-7 | 5' | 6.0 |
| 670061 | GalNAc$_3$-13 | 5' | 7.4 |
| 655861[a] | GalNAc$_3$-1 | 3' | 11.6 |
| 677841[a] | GalNAc$_3$-19 | 3' | 60.8 |

Example 100: Antisense Inhibition In Vivo by Oligonucleotides Comprising a GalNAc Conjugate Group Targeting Apo(a) In Vivo The oligonucleotides listed in Table 111a below were tested in a single dose study for duration of action in mice.

TABLE 111a

Modified ASOs targeting APO(a)

| ISIS No. | Sequences (5' to 3') | GalNAc$_3$ Cluster | CM | SEQ ID No. |
|---|---|---|---|---|
| 681251 | **GalNAc3-7a-o'**$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | GalNAc$_3$-7a | PO | 58 |

TABLE 111a-continued

| Modified ASOs targeting APO(a) | | | | |
|---|---|---|---|---|
| ISIS No. | Sequences (5' to 3') | GalNAc$_3$ Cluster | CM | SEQ ID No. |
| 681257 | **GalNAc3-7a-o'**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-7a | PO | 58 |

The structure of GalNAc$_3$-7$_a$ was shown in Example 48.

Treatment

Female transgenic mice that express human Apo(a) were each injected subcutaneously once per week, for a total of 6 doses, with an oligonucleotide and dosage listed in Table 111b or with PBS. Each treatment group consisted of 3 animals. Blood was drawn the day before dosing to determine baseline levels of Apo(a) protein in plasma and at 72 hours, 1 week, and 2 weeks following the first dose. Additional blood draws will occur at 3 weeks, 4 weeks, 5 weeks, and 6 weeks following the first dose. Plasma Apo(a) protein levels were measured using an ELISA. The results in Table 111b are presented as the average percent of plasma Apo(a) protein levels for each treatment group, normalized to baseline levels (% BL), The results show that the oligonucleotides comprising a GalNAc conjugate group exhibited potent reduction in Apo(a) expression. This potent effect was observed for the oligonucleotide that comprises full PS internucleoside linkages and the oligonucleotide that comprises mixed PO and PS linkages.

TABLE 111b

| Apo(a) plasma protein levels | | | | |
|---|---|---|---|---|
| ISIS No. | Dosage (mg/kg) | Apo(a) at 72 hours (% BL) | Apo(a) at 1 week (% BL) | Apo(a) at 3 weeks (% BL) |
| PBS | n/a | 116 | 104 | 107 |
| 681251 | 0.3 | 97 | 108 | 93 |
| | 1.0 | 85 | 77 | 57 |
| | 3.0 | 54 | 49 | 11 |
| | 10.0 | 23 | 15 | 4 |

TABLE 111b-continued

| Apo(a) plasma protein levels | | | | |
|---|---|---|---|---|
| ISIS No. | Dosage (mg/kg) | Apo(a) at 72 hours (% BL) | Apo(a) at 1 week (% BL) | Apo(a) at 3 weeks (% BL) |
| 681257 | 0.3 | 114 | 138 | 104 |
| | 1.0 | 91 | 98 | 54 |
| | 3.0 | 69 | 40 | 6 |
| | 10.0 | 30 | 21 | 4 |

Example 101: Antisense Inhibition by Oligonucleotides Comprising a GalNAc Cluster Linked Via a Stable Moiety The oligonucleotides listed in Table 112 were tested for inhibition of mouse APOC-III expression in vivo. C57Bl/6 mice were each injected subcutaneously once with an oligonucleotide listed in Table 112 or with PBS. Each treatment group consisted of 4 animals. Each mouse treated with ISIS 440670 received a dose of 2, 6, 20, or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-III mRNA levels were measured using real-time PCR. APOC-III mRNA levels were normalized to cyclophilin mRNA levels according to standard protocols. The results are presented in Table 112 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

TABLE 112

| Modified oligonucleotides targeting mouse APOC-III | | | | | |
|---|---|---|---|---|---|
| ISIS No. | Sequences (5' to 3') | CM | Dosage (mg/kg) | APOC-III mRNA (% PBS) | SEQ ID No. |
| 440670 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a | 2 | 92 | 162 |
| | | | 6 | 86 | |
| | | | 20 | 59 | |
| | | | 60 | 37 | |
| 680772 | **GalNAc3-7a-o'**${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 0.6 | 79 | 162 |
| | | | 2 | 58 | |
| | | | 6 | 31 | |
| | | | 20 | 13 | |

TABLE 112-continued

| Modified oligonucleotides targeting mouse APOC-III | | | | | |
|---|---|---|---|---|---|
| ISIS No. | Sequences (5' to 3') | CM | Dosage (mg/kg) | APOC-III mRNA (% PBS) | SEQ ID No. |
| 696847 | **GalNAc3-7**$_{a-s'}$ $^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a (PS) | 0.6 | 83 | 162 |
| | | | 2 | 73 | |
| | | | 6 | 40 | |
| | | | 20 | 28 | |

The structure of GalNAc$_3$-7$_a$ was shown in Example 48.

Example 102: Distribution in Liver of Antisense Oligonucleotides Comprising a GalNAc Conjugate The liver distribution of ISIS 353382 (see Table 36) that does not comprise a GalNAc conjugate and ISIS 655861 (see Table 36) that does comprise a GalNAc conjugate was evaluated. Male balb/c mice were subcutaneously injected once with ISIS 353382 or 655861 at a dosage listed in Table 113. Each treatment group consisted of 3 animals except for the 18 mg/kg group for ISIS 655861, which consisted of 2 animals. The animals were sacrificed 48 hours following the dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 113 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 113

| ISIS No. | Dosage (mg/kg) | Concentration in whole liver (molecules* 10^6 per cell) | Concentration in hepatocytes (molecules* 10^6 per cell) | Concentration in non-parenchymal liver cells (molecules* 10^6 per cell) |
|---|---|---|---|---|
| 353382 | 3 | 9.7 | 1.2 | 37.2 |
| | 10 | 17.3 | 4.5 | 34.0 |
| | 20 | 23.6 | 6.6 | 65.6 |
| | 30 | 29.1 | 11.7 | 80.0 |
| | 60 | 73.4 | 14.8 | 98.0 |
| | 90 | 89.6 | 18.5 | 119.9 |
| 655861 | 0.5 | 2.6 | 2.9 | 3.2 |
| | 1 | 6.2 | 7.0 | 8.8 |
| | 3 | 19.1 | 25.1 | 28.5 |
| | 6 | 44.1 | 48.7 | 55.0 |
| | 18 | 76.6 | 82.3 | 77.1 |

Example 103: Duration of Action In Vivo of Oligonucleotides Targeting APOC-III Comprising a GalNAc3 Conjugate The oligonucleotides listed in Table 114 below were tested in a single dose study for duration of action in mice.

TABLE 114

| Modified ASOs targeting APOC-III | | | | |
|---|---|---|---|---|
| ISIS No. | Sequences (5' to 3') | GalNAc$_3$ Cluster | CM | SEQ ID No. |
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 135 |
| 663084 | **GalNAc3-3a-o'Ado**$A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$ | GalNAc$_3$-3a | $A_d$ | 151 |
| 679241 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}$**Ado'-GalNAc3-19a** | GalNAc$_3$-19a | $A_d$ | 136 |

The structure of GalNAc$_3$-3$_a$ was shown in Example 39, and GalNAc$_3$-19$_a$ was shown in Example 70.

Treatment

Female transgenic mice that express human APOC-III were each injected subcutaneously once with an oligonucleotide listed in Table 114 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 115 are presented as the average percent of plasma triglyceride and APOC-III levels for each treatment group, normalized to baseline levels. A comparison of the results in Table 71 of example 79 with the results in Table 115 below show that oligonucleotides comprising a mixture of phosphodiester and phosphorothioate internucleoside linkages exhibited increased duration of action than equivalent oligonucleotides comprising only phosphorothioate internucleoside linkages.

TABLE 115

Plasma triglyceride and APOC-III protein levels in transgenic mice

| ISIS No. | Dosage (mg/kg) | Time point (days post-dose) | Tri-glycerides (% baseline) | APOC-III protein (% baseline) | GalNAc$_3$ Cluster | CM |
|---|---|---|---|---|---|---|
| PBS | n/a | 3 | 96 | 101 | n/a | n/a |
| | | 7 | 88 | 98 | | |
| | | 14 | 91 | 103 | | |
| | | 21 | 69 | 92 | | |
| | | 28 | 83 | 81 | | |
| | | 35 | 65 | 86 | | |
| | | 42 | 72 | 88 | | |
| 304801 | 30 | 3 | 42 | 46 | n/a | n/a |
| | | 7 | 42 | 51 | | |
| | | 14 | 59 | 69 | | |
| | | 21 | 67 | 81 | | |
| | | 28 | 79 | 76 | | |
| | | 35 | 72 | 95 | | |
| | | 42 | 82 | 92 | | |
| 663084 | 10 | 3 | 35 | 28 | GalNAc$_3$-3a | A$_d$ |
| | | 7 | 23 | 24 | | |
| | | 14 | 23 | 26 | | |
| | | 21 | 23 | 29 | | |
| | | 28 | 30 | 22 | | |
| | | 35 | 32 | 36 | | |
| | | 42 | 37 | 47 | | |
| 679241 | 10 | 3 | 38 | 30 | GalNAc$_3$-19a | A$_d$ |
| | | 7 | 31 | 28 | | |
| | | 14 | 30 | 22 | | |
| | | 21 | 36 | 34 | | |
| | | 28 | 48 | 34 | | |
| | | 35 | 50 | 45 | | |
| | | 42 | 72 | 64 | | |

Example 104: Synthesis of Oligonucleotides Comprising a 5'-GalNAc2 Conjugate

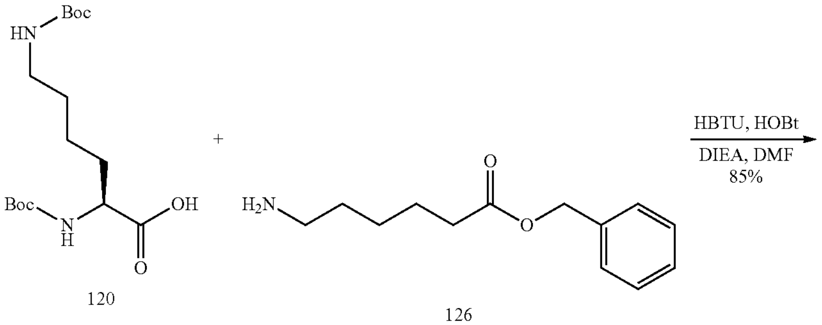

120

126

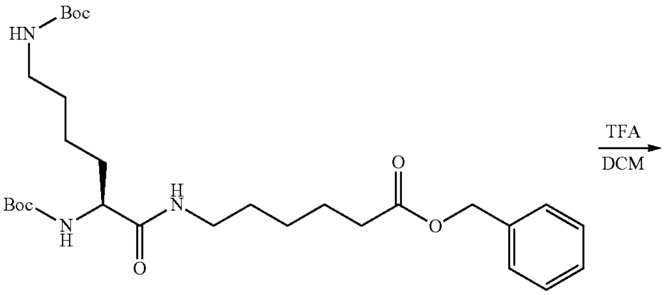

231

-continued
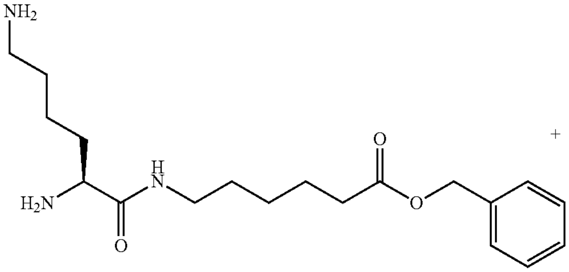
232
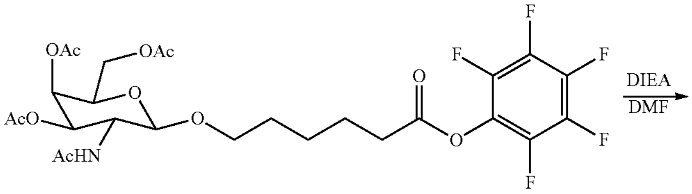
166
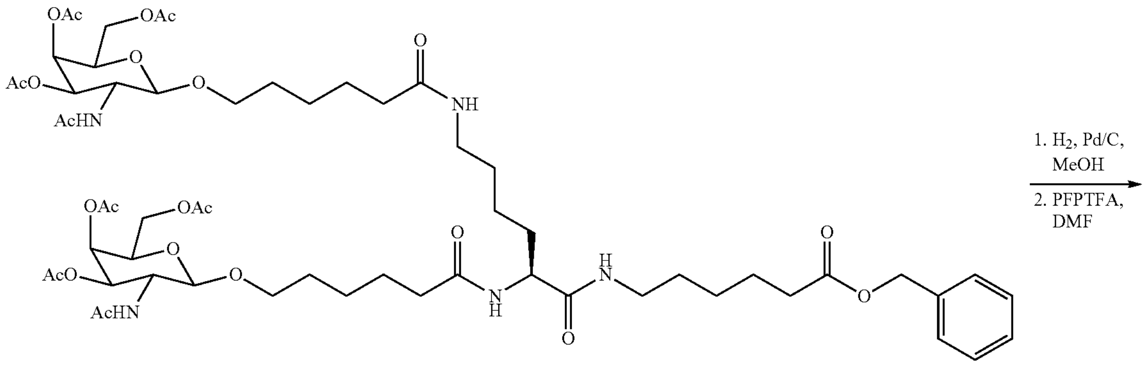
233
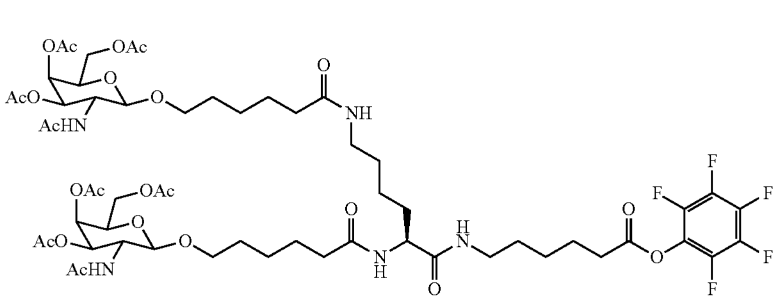
234
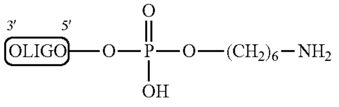
83e
1. Borate buffer, DMSO, pH 8.5, rt
2. aq. ammonia, rt
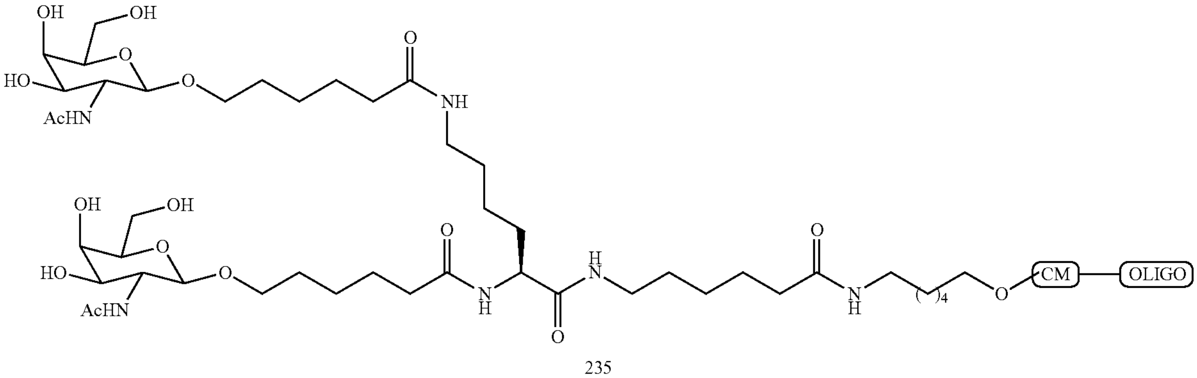
235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL. and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO4 and extracted with 2×50 mL ethyl acetate. Organic layers were combined and washed with 3×40 mL sat $NaHCO_3$ and 2× brine, dried with $Na_2SO_4$, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifluoracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat. aqueous $NaHCO_3$ (3×80 mL), 1 M $NaHSO_4$ (3×80 mL) and brine (2×80 mL), then dried ($Na_2SO_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylethylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The $GalNAc_2$ cluster portion ($GalNAc_2$-$24_a$) of the conjugate group $GalNAc_2$-24 can be combined with any cleavable moiety present on the oligonucleotide to provide a variety of conjugate groups. The structure of $GalNAc_2$-24 ($GalNAc_2$-$24_a$-CM) is shown below:

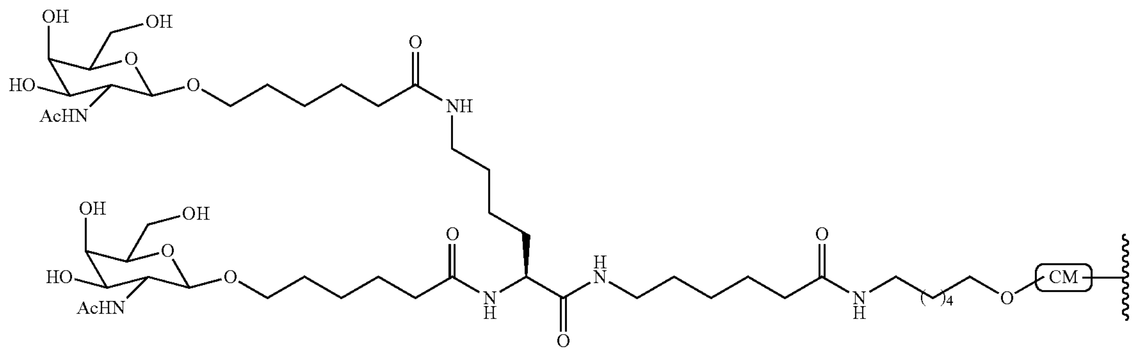

Example 105: Synthesis of Oligonucleotides Comprising a $GalNAc_1$-25 Conjugate

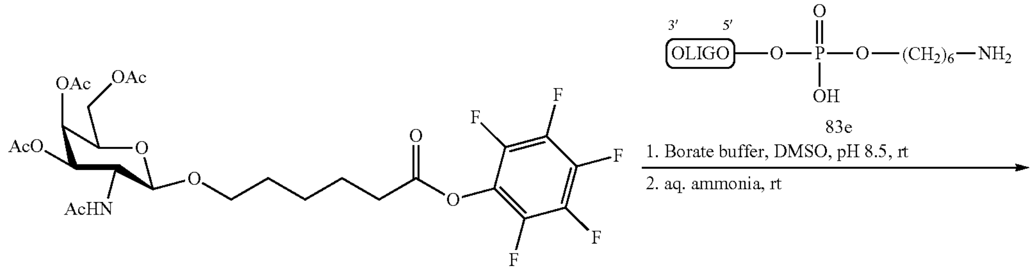

166

-continued

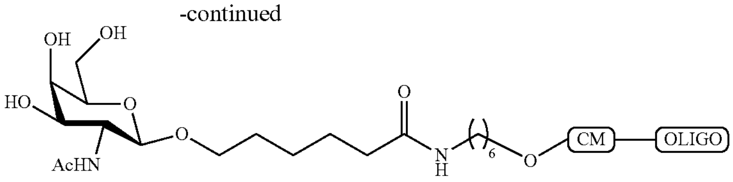

236

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

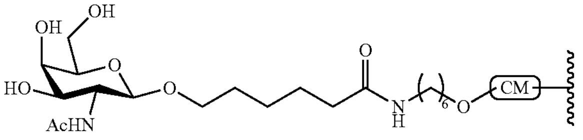

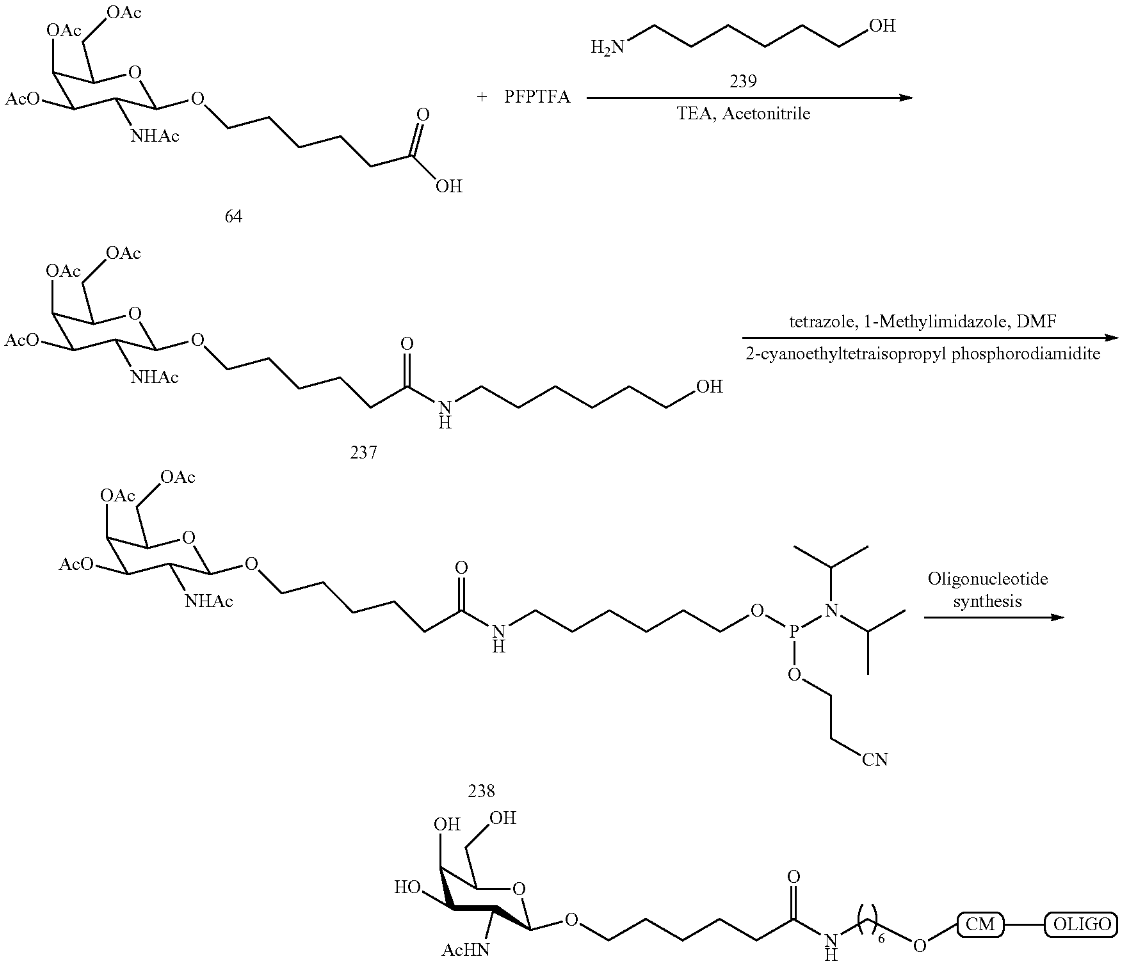

64

237

238

236

The GalNAc$_1$ cluster portion (GalNAc$_1$-25$_a$) of the conjugate group GalNAc$_1$-25 can be combined with any cleavable moiety present on the oligonucleotide to provide a variety of conjugate groups. The structure of GalNAc$_1$-25 (GalNAc$_1$-25$_a$-CM) is shown below:

Example 106: Antisense Inhibition In Vivo by Oligonucleotides Targeting SRB-1 Comprising a 5'-GalNAc$_2$ or a 5'-GalNAc$_3$ Conjugate Oligonucleotides listed in Tables 116 and 117 were tested in dose-dependent studies for antisense inhibition of SRB-1 in mice.

Treatment

Six to week old, male C57BL/6 mice (Jackson Laboratory, Bar Harbor, ME) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the $ED_{50}$ results are presented in Tables 116 and 117. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., *Bioorg. & Med. Chem.*, Vol. 16, 5216-5231 (2008)), treatment with antisense oligonucleotides comprising monovalent, divalent, and trivalent GalNAc clusters lowered SRB-1 mRNA levels with similar potencies as shown in Tables 116 and 117.

TABLE 116

Modified oligonucleotides targeting SRB-1

| ISIS No. | Sequences (5' to 3') | GalNAc Cluster | $ED_{50}$ (mg/kg) | SEQ ID No |
|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 4.7 | 137 |
| 686221 | **GalNAc2-24a-o'Ado**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_2$-$24_a$ | 0.39 | 141 |
| 686222 | **GalNAc3-13a-o'Ado**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$13_a$ | 0.41 | 141 |

See Example 93 for table legend. The structure of $GalNAc_3$-13a was shown in Example 62, and the structure of GalNAc2-24a was shown in Example 104.

TABLE 117

Modified oligonucleotides targeting SRB-1

| ISIS No. | Sequences (5' to 3') | GalNAc Cluster | $ED_{50}$ (mg/kg) | SEQ ID No |
|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 5 | 137 |
| 708561 | **GalNAc1-25a-o'**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_1$-$25_a$ | 0.4 | 137 |

See Example 93 for table legend. The structure of $GalNAc_1$-25a was shown in Example 105.

The concentrations of the oligonucleotides in Tables 116 and 117 in liver were also assessed, using procedures described in Example 75. The results shown in Tables 117a and 117b below are the average total antisense oligonucleotide tissues levels for each treatment group, as measured by UV in units of μg oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 116 and 117 above.

TABLE 117a

Liver concentrations of oligonucleotides comprising a $GalNAc_2$ or $GalNAc_3$ conjugate group

| ISIS No. | Dosage (mg/kg) | [Antisense oligonucleotide] (μg/g) | GalNAc cluster | CM |
|---|---|---|---|---|
| 440762 | 2 | 2.1 | n/a | n/a |
| | 7 | 13.1 | | |
| | 20 | 31.1 | | |
| 686221 | 0.2 | 0.9 | $GalNAc_2$-$24_a$ | $A_d$ |
| | 0.6 | 2.7 | | |
| | 2 | 12.0 | | |
| | 6 | 26.5 | | |
| 686222 | 0.2 | 0.5 | | |
| | 0.6 | 1.6 | $GalNAc_3$-$13_a$ | $A_d$ |
| | 2 | 11.6 | | |
| | 6 | 19.8 | | |

TABLE 117b

Liver concentrations of oligonucleotides comprising a $GalNAc_1$ conjugate group

| ISIS No. | Dosage (mg/kg) | [Antisense oligonucleotide] (μg/g) | GalNAc cluster | CM |
|---|---|---|---|---|
| 440762 | 2 | 2.3 | n/a | n/a |
| | 7 | 8.9 | | |
| | 20 | 23.7 | | |
| 708561 | 0.2 | 0.4 | $GalNAc_1$-$25_a$ | PO |
| | 0.6 | 1.1 | | |
| | 2 | 5.9 | | |
| | 6 | 23.7 | | |
| | 20 | 53.9 | | |

Example 107: Synthesis of Oligonucleotides Comprising a GalNAc$_1$-26 or GalNAc$_1$-27 Conjugate

239

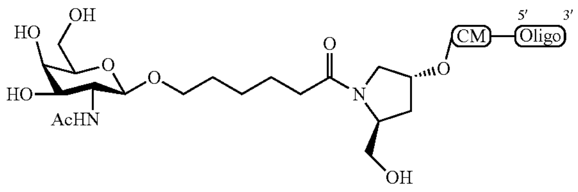

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc$_1$ cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

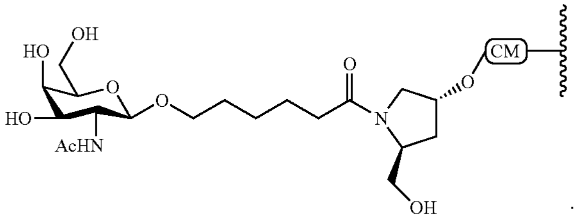

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

240

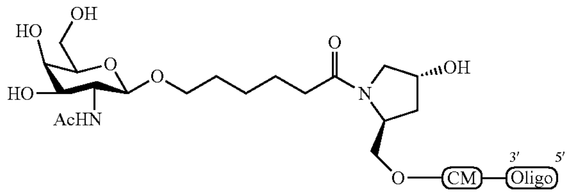

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

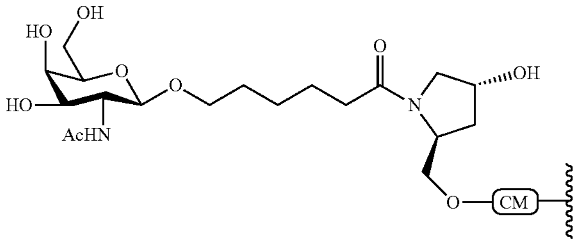

Example 108: Antisense Inhibition In Vivo by Oligonucleotides Comprising a GalNAc Conjugate Group Targeting Apo(a) In Vivo The oligonucleotides listed in Table 118 below were tested in a single dose study in mice.

TABLE 118

Modified ASOs targeting APO(a)

| ISIS No. | Sequences (5' to 3') | GalNAc$_3$ Cluster | CM | SEQ ID No. |
|---|---|---|---|---|
| 494372 | $T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}$ $T_{ds}T_{es}G_{es}T_{es}T_{es}{}^mC_e$ | n/a | n/a | 58 |
| 681251 | **GalNAc3-7a-o'**$T_{es}G_{es}{}^mC_{es}T_{es}{}^mC_{es}{}^mC_{ds}G_{ds}T_{ds}T_{ds}G_{ds}G_{ds}$ $T_{ds}G_{ds}{}^mC_{ds}T_{ds}T_{es}G_{es}T_{es}T_{es}{}^mC_e$ | GalNAc$_3$-7a | PO | 58 |
| 681255 | **GalNAc3-3a-o'**$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-3a | PO | 58 |
| 681256 | **GalNAc3-10a-o'**$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-10a | PO | 58 |
| 681257 | **GalNAc3-7a-o'**$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-7a | PO | 58 |
| 681258 | **GalNAc3-13a-o'**$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-13a | PO | 58 |
| 681260 | $T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}T_{ds}T_{eo}G_{eo}$ $T_{es}T_{es}{}^mC_{eo}$**Ado'-GalNAc3-19** | GalNAc$_3$-19a | $A_d$ | 167 |

The structure of $GalNAc_3$-$7_a$ was shown in Example 48.

Treatment

Male transgenic mice that express human Apo(a) were each injected subcutaneously once with an oligonucleotide and dosage listed in Table 119 or with PBS. Each treatment group consisted of 4 animals. Blood was drawn the day before dosing to determine baseline levels of Apo(a) protein in plasma and at 1 week following the first dose. Additional blood draws will occur weekly for approximately 8 weeks. Plasma Apo(a) protein levels were measured using an ELISA. The results in Table 119 are presented as the average percent of plasma Apo(a) protein levels for each treatment group, normalized to baseline levels (% BL), The results show that the antisense oligonucleotides reduced Apo(a) protein expression. Furthermore, the oligonucleotides comprising a GalNAc conjugate group exhibited even more potent reduction in Apo(a) expression than the oligonucleotide that does not comprise a conjugate group.

TABLE 119

Apo(a) plasma protein levels

| ISIS No. | Dosage (mg/kg) | Apo(a) at 1 week (% BL) |
|---|---|---|
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

Example 109: Synthesis of Oligonucleotides Comprising a $GalNAc_1$-28 or $GalNAc_1$-29 Conjugate

241

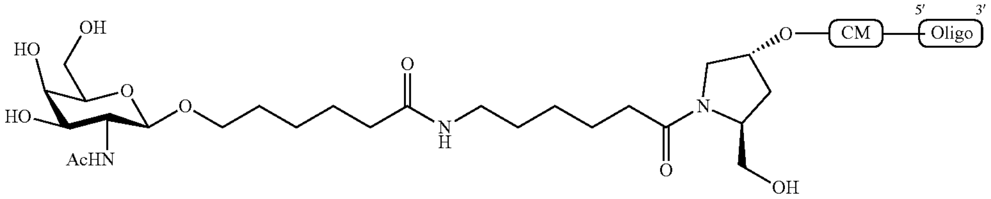

Oligonucleotide 241 is synthesized using procedures similar to those described in Example 71 to form the phosphoramidite intermediate, followed by procedures described in Example 10 to synthesize the oligonucleotide. The $GalNAc_1$ cluster portion ($GalNAc_1$-$28_a$) of the conjugate group $GalNAc_1$-28 can be combined with any cleavable moiety present on the oligonucleotide to provide a variety of conjugate groups. The structure of $GalNAc_1$-28 ($GalNAc_1$-$28_a$-CM) is shown below:

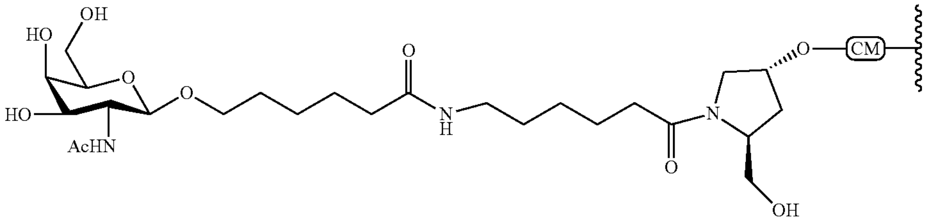

In order to add the $GalNAc_1$ conjugate group to the 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

242

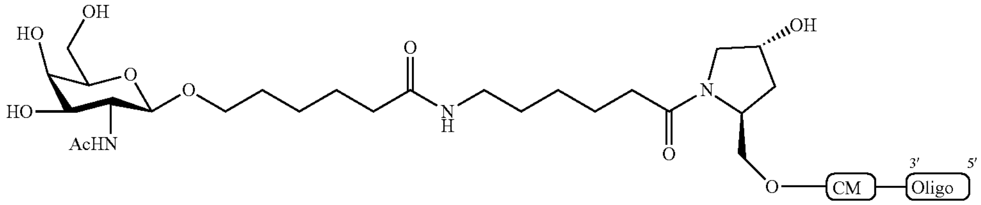

The $GalNAc_1$ cluster portion ($GalNAc_1$-$29_a$) of the conjugate group $GalNAc_1$-29 can be combined with any cleavable moiety present on the oligonucleotide to provide a variety of conjugate groups. The structure of $GalNAc_1$-29 ($GalNAc_1$-$29_a$-CM) is shown below:

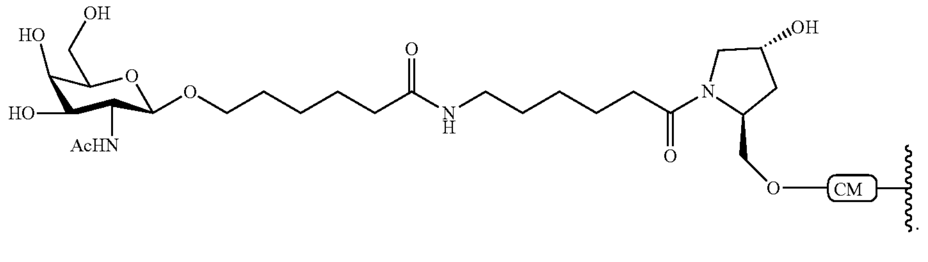

Example 110: Synthesis of Oligonucleotides Comprising a $GalNAc_1$-30 Conjugate

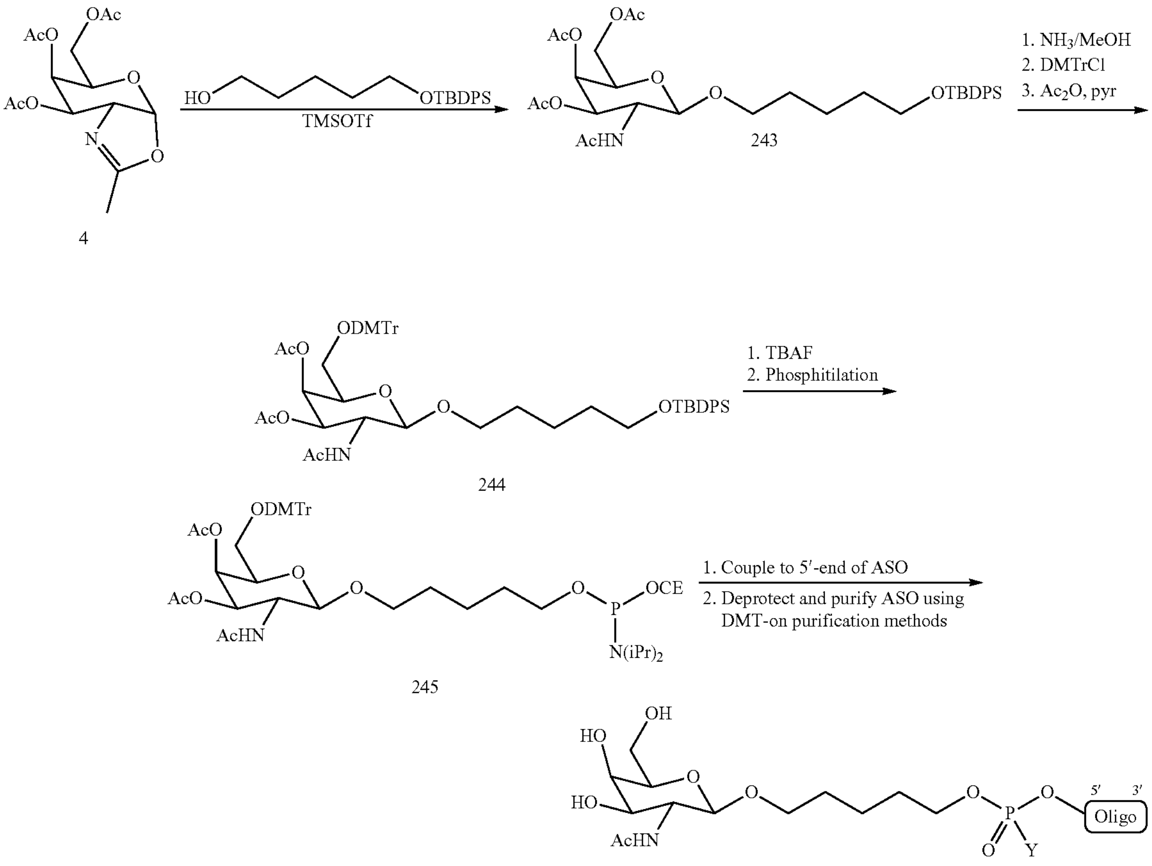

4

243

244

245

246

Oligonucleotide 246 comprising a $GalNAc_1$-30 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_1$ cluster portion ($GalNAc_1$-$30_a$) of the conjugate group $GalNAc_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of $GalNAc_1$-$30_a$ is shown below:

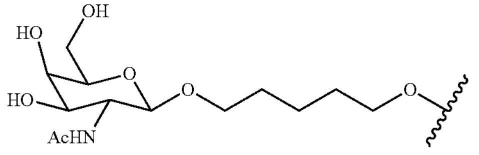 [SMILES: *OCCCCCOC1OC(CO)C(O)C(O)C1NC(C)=O]

Example 111: Synthesis of Oligonucleotides Comprising a GalNAc$_2$-31 or GalNAc$_2$-32 Conjugate

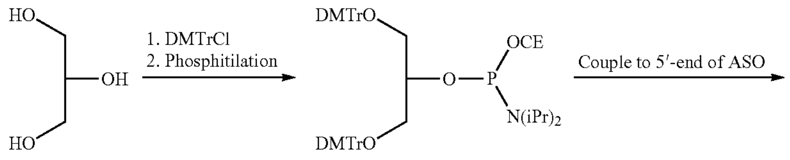

247 248

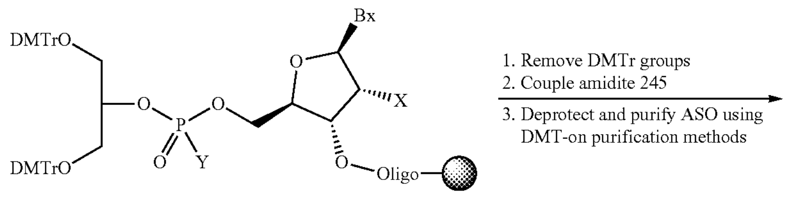

249

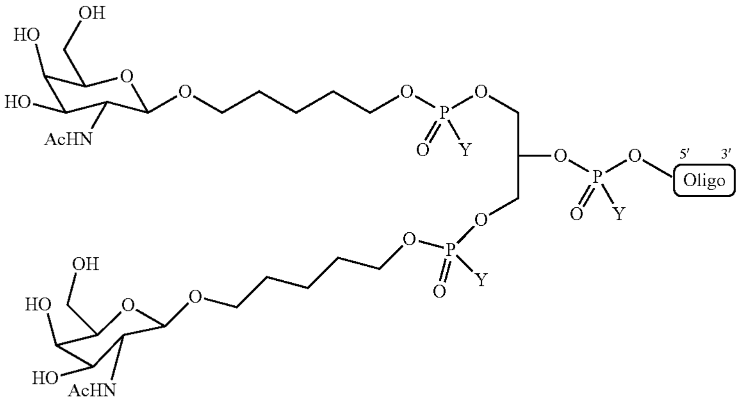

250

Oligonucleotide 250 comprising a GalNAc$_2$-31 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc$_2$ cluster portion (GalNAc$_2$-31$_a$) of the conjugate group GalNAc$_2$-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc$_2$-31$_a$ is shown below:

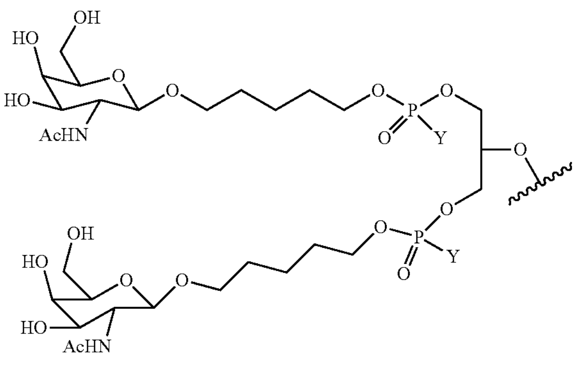

The synthesis of an oligonucleotide comprising a GalNAc$_2$-32 conjugate is shown below.

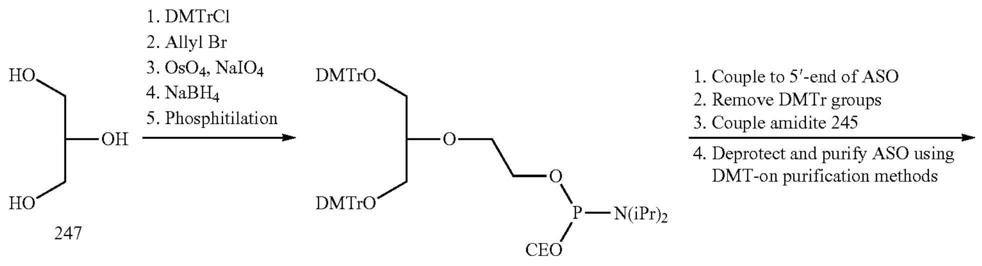

247

251

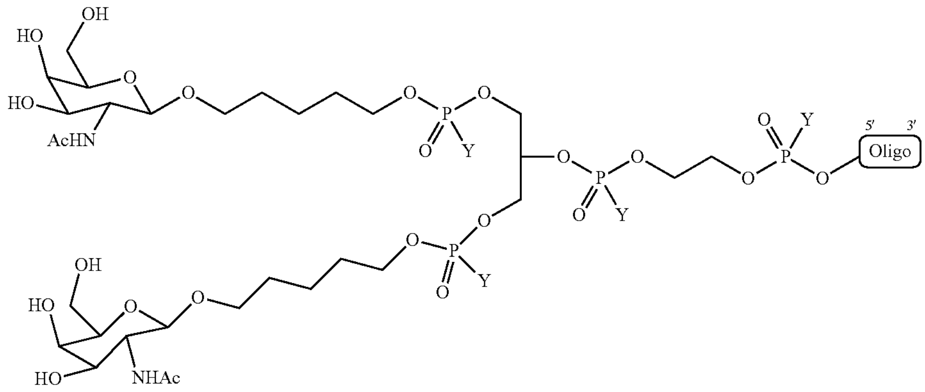

252

Oligonucleotide 252 comprising a $GalNAc_2$-32 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc2 cluster portion ($GalNAc_2$-$32_a$) of the conjugate group $GalNAc_2$-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of $GalNAc_2$-$32_a$ is shown below:

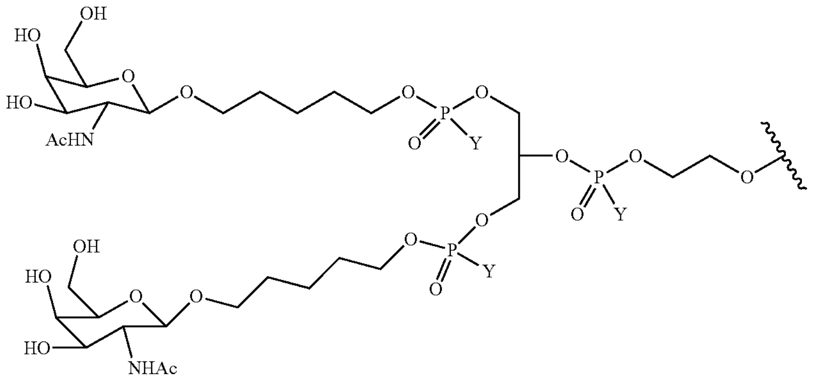

Example 112: Modified Oligonucleotides Comprising a GalNAc$_1$ Conjugate

The oligonucleotides in Table 120 targeting SRB-1 were synthesized with a GalNAc$_1$ conjugate group in order to further test the potency of oligonucleotides comprising conjugate groups that contain one GalNAc ligand.

TABLE 120

| ISIS No. | Sequences (5' to 3') | GalNAc Cluster | CM | SEQ ID NO. |
|---|---|---|---|---|
| 711461 | **GalNAc1-25a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-25$_a$ | $A_d$ | 145 |
| 711462 | **GalNAc1-25a-o'**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-25$_a$ | PO | 143 |
| 711463 | **GalNAc1-25a-o'**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_1$-25$_a$ | PO | 143 |
| 711465 | **GalNAc1-26a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-26$_a$ | $A_d$ | 145 |
| 711466 | **GalNAc1-26a-o'**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-26$_a$ | PO | 143 |
| 711467 | **GalNAc1-26a-o'**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_1$-26$_a$ | PO | 143 |
| 711468 | **GalNAc1-28a-o'Ado**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-28$_a$ | $A_d$ | 145 |
| 711469 | **GalNAc1-28a-o'**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_1$-28$_a$ | PO | 143 |
| 711470 | **GalNAc1-28a-o'**$G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_1$-28$_a$ | PO | 143 |
| 713844 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo'}$**-GalNAc1-27a** | GalNAc$_1$-27$_a$ | PO | 143 |
| 713845 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo'}$**-GalNAc1-27a** | GalNAc$_1$-27$_a$ | PO | 143 |
| 713846 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}\mathbf{A}_{do'}$**-GalNAc1-27a** | GalNAc$_1$-27$_a$ | $A_d$ | 144 |
| 713847 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo'}$**-GalNAc1-29a** | GalNAc$_1$-29$_a$ | PO | 143 |
| 713848 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo'}$**-GalNAc1-29a** | GalNAc$_1$-29$_a$ | PO | 143 |
| 713849 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**Ado'-GalNAc1-29a** | GalNAc$_1$-29$_a$ | $A_d$ | 144 |
| 713850 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}$**Ado'-GalNAc1-29a** | GalNAc$_1$-29$_a$ | $A_d$ | 144 |

Example 113: Dose-Dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, NJ) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTACCAGCTATGCCAAACCTT, designated herein as SEQ ID NO: 7) was used to measure mRNA levels. Additionally, mRNA levels were also measured using human apo(a) primer probe set hAPO(a)12 kB (forward sequence CCACAGTGGCCCCGGT, designated herein as SEQ ID NO: 8; reverse sequence ACAGGGCTTTTCTCAGGTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in the table below as percent inhibition of apo(a), relative to untreated control cells.

TABLE 121

Antisense inhibition of human apo(a) in human primary hepatocytes

| ISIS No | % inhibition (hAPO(a)3' PPset) | % inhibition (hAPO(a)12 kB PPset) |
|---|---|---|
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |
| 144383 | 63 | 79 |
| 144384 | 38 | 0 |
| 144385 | 40 | 94 |
| 144386 | 47 | 61 |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in the table below. After a treatment period of approximately 16 hours, RNA was isolated from the cells and apo(a) mRNA levels were measured by quantitative real-time PCR. Human apo(a) primer probe set hAPO(a)3' was used to measure mRNA levels. Apo(a) mRNA levels were normalized to GAPDH mRNA expression. Results are presented as percent inhibition of apo(a), relative to untreated control cells.

TABLE 122

Dose-dependent antisense inhibition of human apo(a) in human primary hepatocytes, as measured with hAPO(a)3'

| ISIS No | 25 nM | 50 nM | 150 nM | 300 nM |
|---|---|---|---|---|
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 114: Antisense Inhibition of Human Apo(a) in Transgenic Mouse Primary Hepatocytes Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12 kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. “Start site” indicates the 5'-most nucleoside to which the gapmer is targeted in the human sequence. “Stop site” indicates the 3'-most nucleoside to which the gapmer is targeted human sequence. An apo(a) antisense oligonucleotide may have more than one “Start site” or “Stop site” depending on whether or not it targets a Kringle repeat.

Most gapmers listed in the tables are targeted with 100% complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. ‘n/a’ indicates that the antisense oligonucleotide does not target that particular sequence with 100% complementarity.

TABLE 123

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTC<br>CTTCCTGT<br>GACA | 90 | 21210 | 21229 | 11 |
| 494157 | 238<br>580<br>922<br>1606<br>1948<br>2290<br>3316 | 257<br>599<br>941<br>1625<br>1967<br>2309<br>3335 | CCTGTGAC<br>AGTGGTGG<br>AGTA | 95 | 21199<br>26690<br>32237<br>43330<br>48874<br>54420<br>72037 | 21218<br>26709<br>32256<br>43349<br>48893<br>54439<br>72056 | 12 |
| 494158 | 239<br>581<br>923<br>1607<br>1949<br>2291<br>3317 | 258<br>600<br>942<br>1626<br>1968<br>2310<br>3336 | TCCTGTGA<br>CAGTGGTG<br>GAGT | 95 | 21200<br>26691<br>32238<br>43331<br>48875<br>54421<br>72038 | 21219<br>26710<br>32257<br>43350<br>48894<br>54440<br>72057 | 13 |
| 494159 | 241<br>583<br>925<br>1609<br>1951<br>2293<br>3319<br>4663<br>5005 | 260<br>602<br>944<br>1628<br>1970<br>2312<br>3338<br>4682<br>5024 | CTTCCTGT<br>GACAGTGG<br>TGGA | 97 | 21202<br>26693<br>32240<br>43333<br>48877<br>54423<br>72040<br>94404<br>115515 | 21221<br>26712<br>32259<br>43352<br>48896<br>54442<br>72059<br>94423<br>115534 | 14 |
| 494160 | 242<br>4664<br>5006 | 261<br>4683<br>5025 | CCTTCCTG<br>TGACAGTG<br>GTGG | 97 | 21203<br>94405<br>115516 | 21222<br>94424<br>115535 | 15 |
| 494161 | 243<br>4665<br>5007 | 262<br>4684<br>5026 | TCCTTCC<br>TGTGACA<br>GTGGTG | 96 | 21204<br>4406<br>115517 | 21223<br>94425<br>115536 | 16 |
| 494162 | 244<br>3664<br>4666<br>5008 | 263<br>3683<br>4685<br>5027 | GTCCTTCC<br>TGTGACAG<br>TGGT | 95 | 21205<br>77585<br>94407<br>115518 | 21224<br>77604<br>94426<br>115537 | 17 |
| 494163 | 245<br>4667 | 264<br>4686 | GGTCCTTC<br>CTGTGACA<br>GTGG | 96 | 21206<br>94408 | 21225<br>94427 | 18 |
| 494164 | 246<br>4668 | 265<br>4687 | AGGTCCTT<br>CCTGTGAC<br>AGTG | 93 | 21207<br>94409 | 21226<br>94428 | 19 |
| 494165 | 247<br>4669 | 266<br>4688 | CAGGTCCT<br>TCCTGTGA<br>CAGT | 91 | 21208<br>94410 | 21227<br>94429 | 20 |
| 494166 | 248 | 267 | GCAGGTCC<br>TTCCTGTG<br>ACAG | 89 | 21209 | 21228 | 21 |
| 494167 | 250 | 269 | TGGCAGGT<br>CCTTCCTG<br>TGAC | 92 | 21211 | 21230 | 22 |
| 494168 | 251 | 270 | TTGGCAGG<br>TCCTTCCT<br>GTGA | 89 | 21212 | 21231 | 23 |
| 494169 | 252 | 271 | CTTGGCAG<br>GTCCTTCC<br>TGTG | 92 | 21213 | 21232 | 24 |
| 494170 | 253 | 272 | GCTTGGCA<br>GGTCCTTC<br>CTGT | 88 | 21214 | 21233 | 25 |

TABLE 124

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTC<br>CTTCCTGT<br>GACA | 91<br>84 | 21210 | 21229 | 11 |
| 494283 | 584<br>926<br>1610<br>1952<br>2294<br>3320 | 603<br>945<br>1629<br>1971<br>2313<br>3339 | TCTTCCT<br>GTGACAG<br>TGGTGG | 93 | 26694<br>32241<br>43334<br>48878<br>54424<br>72041 | 26713<br>32260<br>43353<br>48897<br>54443<br>72060 | 26 |
| 494284 | 585<br>927<br>1611<br>1953<br>2295<br>3321 | 604<br>946<br>1630<br>1972<br>2314<br>3340 | TTCTTCC<br>TGTGACA<br>GTGGTG | 95 | 26695<br>32242<br>43335<br>48879<br>54425<br>72042 | 26714<br>32261<br>43354<br>48898<br>54444<br>72061 | 27 |
| 494285 | 586<br>928<br>1612<br>1954<br>2296<br>3322 | 605<br>947<br>1631<br>1973<br>2315<br>3341 | GTTCTTC<br>CTGTGAC<br>AGTGGT | 95 | 26696<br>32243<br>43336<br>48880<br>54426<br>72043 | 26715<br>32262<br>43355<br>48899<br>54445<br>72062 | 28 |
| 494286 | 587<br>929<br>1613<br>1955<br>2297 | 606<br>948<br>1632<br>1974<br>2316 | GGTTCTT<br>CCTGTGA<br>CAGTGG | 95 | 26697<br>32244<br>43337<br>48881<br>54427 | 26716<br>32263<br>43356<br>48900<br>54446 | 29 |
| 494287 | 588<br>930<br>1614<br>1956<br>2298 | 607<br>949<br>1633<br>1975<br>2317 | AGGTTCT<br>TCCTGTG<br>ACAGTG | 95 | 26698<br>32245<br>43338<br>48882<br>54428 | 26717<br>32264<br>43357<br>48901<br>54447 | 30 |
| 494288 | 589<br>931<br>1615<br>1957<br>2299<br>2983 | 608<br>950<br>1634<br>1976<br>2318<br>3002 | CAGGTTC<br>TTCCTGT<br>GACAGT | 91 | 26699<br>32246<br>43339<br>48883<br>54429<br>66500 | 26718<br>32265<br>43358<br>48902<br>54448<br>66519 | 31 |
| 494290 | 592<br>934<br>1618<br>1960<br>2302<br>2986 | 611<br>953<br>1637<br>1979<br>2321<br>3005 | TGGCAGG<br>TTCTTCC<br>TGTGAC | 90 | 26702<br>32249<br>43342<br>48886<br>54432<br>66503 | 26721<br>32268<br>43361<br>48905<br>54451<br>66522 | 32 |
| 494291 | 593<br>935<br>1619<br>1961<br>2303<br>2987 | 612<br>954<br>1638<br>1980<br>2322<br>3006 | TTGGCAG<br>GTTCTTC<br>CTGTGA | 89 | 26703<br>32250<br>43343<br>48887<br>54433<br>66504 | 26722<br>32269<br>43362<br>48906<br>54452<br>66523 | 33 |

TABLE 124-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494292 | 594 | 613 | CTTGGCA | 94 | 26704 | 26723 | 35 |
| | 936 | 955 | GGTTCTT | | 32251 | 32270 | |
| | 1620 | 1639 | CCTGTG | | 43344 | 43363 | |
| | 1962 | 1981 | | | 48888 | 48907 | |
| | 2304 | 2323 | | | 54434 | 54453 | |
| | 2988 | 3007 | | | 66505 | 66524 | |
| 494294 | 596 | 615 | AGCTTGG | 90 | 26706 | 26725 | 36 |
| | 938 | 957 | CAGGTTC | | 32253 | 32272 | |
| | 1622 | 1641 | TTCCTG | | 43346 | 43365 | |
| | 1964 | 1983 | | | 48890 | 48909 | |
| | 2306 | 2325 | | | 54436 | 54455 | |
| | 2990 | 3009 | | | 66507 | 66526 | |
| 494299 | 626 | 645 | ACTATGC | 91 | 26736 | 26755 | 37 |
| | 968 | 987 | GAGTGTG | | 32283 | 32302 | |
| | 1310 | 1329 | GTGTCA | | 37830 | 37849 | |
| | 1652 | 1671 | | | 43376 | 43395 | |
| | 1994 | 2013 | | | 48920 | 48939 | |
| | 2336 | 2355 | | | 54466 | 54485 | |
| | 2678 | 2697 | | | 60021 | 60040 | |
| | 3020 | 3039 | | | 66537 | 66556 | |
| 494300 | 627 | 646 | GACTATG | 93 | 26737 | 26756 | 38 |
| | 969 | 988 | CGAGTGT | | 32284 | 32303 | |
| | 1311 | 1330 | GGTGTC | | 37831 | 37850 | |
| | 1653 | 1672 | | | 43377 | 43396 | |
| | 1995 | 2014 | | | 48921 | 48940 | |
| | 2337 | 2356 | | | 54467 | 54486 | |
| | 2679 | 2698 | | | 60022 | 60041 | |
| | 3021 | 3040 | | | 66538 | 66557 | |
| 494301 | 628 | 647 | CGACTAT | 93 | 26738 | 26757 | 39 |
| | 970 | 989 | GCGAGTG | | 32285 | 32304 | |
| | 1312 | 1331 | TGGTGT | | 37832 | 37851 | |
| | 1654 | 1673 | | | 43378 | 43397 | |
| | 1996 | 2015 | | | 48922 | 48941 | |
| | 2338 | 2357 | | | 54468 | 54487 | |
| | 2680 | 2699 | | | 60023 | 60042 | |
| | 3022 | 3041 | | | 66539 | 66558 | |
| 494302 | 629 | 648 | CCGACTA | 94 | 26739 | 26758 | 40 |
| | 971 | 990 | TGCGAGT | | 32286 | 32305 | |
| | 1313 | 1332 | GTGGTG | | 37833 | 37852 | |
| | 1655 | 1674 | | | 43379 | 43398 | |
| | 1997 | 2016 | | | 48923 | 48942 | |
| | 2339 | 2358 | | | 54469 | 54488 | |
| | 2681 | 2700 | | | 60024 | 60043 | |
| | 3023 | 3042 | | | 66540 | 66559 | |
| 494303 | 630 | 649 | TCCGACT | 93 | 26740 | 26759 | 41 |
| | 972 | 991 | ATGCGAG | | 32287 | 32306 | |
| | 1314 | 1333 | TGTGGT | | 37834 | 37853 | |
| | 1656 | 1675 | | | 43380 | 43399 | |
| | 1998 | 2017 | | | 48924 | 48943 | |
| | 2340 | 2359 | | | 54470 | 54489 | |
| | 2682 | 2701 | | | 60025 | 60044 | |
| | 3024 | 3043 | | | 66541 | 66560 | |
| 494304 | 631 | 650 | GTCCGAC | 94 | 26741 | 26760 | 42 |
| | 973 | 992 | TATGCGA | | 32288 | 32307 | |
| | 1315 | 1334 | GTGTGG | | 37835 | 37854 | |
| | 1657 | 1676 | | | 43381 | 43400 | |
| | 1999 | 2018 | | | 48925 | 48944 | |
| | 2341 | 2360 | | | 54471 | 54490 | |
| | 2683 | 2702 | | | 60026 | 60045 | |
| | 3025 | 3044 | | | 66542 | 66561 | |
| 494305 | 632 | 651 | GGTCCGAC | 93 | 26742 | 26761 | 43 |
| | 974 | 993 | TATGCGAG | | 32289 | 32308 | |
| | 1316 | 1335 | TGTG | | 37836 | 37855 | |
| | 1658 | 1677 | | | 43382 | 43401 | |
| | 2000 | 2019 | | | 48926 | 48945 | |
| | 2342 | 2361 | | | 54472 | 54491 | |
| | 2684 | 2703 | | | 60027 | 60046 | |
| | 3026 | 3045 | | | 66543 | 66562 | |
| 494306 | 633 | 652 | GGGTCCGA | 92 | 26743 | 26762 | 44 |
| | 975 | 994 | CTATGCGA | | 32290 | 32309 | |
| | 1317 | 1336 | GTGT | | 37837 | 37856 | |
| | 1659 | 1678 | | | 43383 | 43402 | |
| | 2001 | 2020 | | | 48927 | 48946 | |
| | 2343 | 2362 | | | 54473 | 54492 | |
| | 2685 | 2704 | | | 60028 | 60047 | |
| | 3027 | 3046 | | | 66544 | 66563 | |
| 494307 | 1190 | 1209 | CTGCTCAG | 91 | n/a | n/a | 45 |
| | | | TCGGTGCT | | | | |
| | 2558 | 2577 | TGTT | | | | |
| 494310 | 1193 | 1212 | CCTCTGCT | 90 | n/a | n/a | 46 |
| | 2561 | 2580 | CAGTCGGT | | | | |
| | | | GCTT | | | | |
| 494311 | 1194 | 1213 | GCCTCTGC | 88 | 37714 | 37733 | 47 |
| | 2562 | 2581 | TCAGTCGG | | 59905 | 59924 | |
| | | | TGCT | | | | |
| 494334 | 1267 | 1286 | CTTCCAGT | 90 | 37787 | 37806 | 48 |
| | 2635 | 2654 | GACAGTGG | | 59978 | 59997 | |
| | | | TGGA | | | | |
| 494336 | 1269 | 1288 | TTCTTCCA | 90 | 37789 | 37808 | 49 |
| | 2637 | 2656 | GTGACAGT | | 59980 | 59999 | |
| | | | GGTG | | | | |
| 494337 | 1270 | 1289 | GTTCTTCC | 95 | 37790 | 37809 | 50 |
| | 2638 | 2657 | AGTGACAG | | 59981 | 60000 | |
| | | | TGGT | | | | |
| 494338 | 1271 | 1290 | GGTTCTTC | 91 | 37791 | 37810 | 133 |
| | 2639 | 2658 | CAGTGACA | | 59982 | 60001 | |
| | | | GTGG | | | | |
| 494521 | 6393 | 6412 | GACCTTAA | 82 | 140049 | 140068 | 51 |
| | | | AAGCTTAT | | | | |
| | | | ACAC | | | | |
| 494525 | 6397 | 6416 | GTCAGACC | 84 | 140053 | 140072 | 52 |
| | | | TTAAAAGC | | | | |
| | | | TTAT | | | | |
| 494530 | 6402 | 6421 | TGTCAGTC | 82 | 140058 | 140077 | 53 |
| | | | AGACCTTA | | | | |
| | | | AAAG | | | | |
| 494535 | 6407 | 6426 | GAATTTGT | 85 | 140063 | 140082 | 54 |
| | | | CAGTCAGA | | | | |
| | | | CCTT | | | | |
| 494536 | 6408 | 6427 | AGAATTTG | 83 | 140064 | 140083 | 55 |
| | | | TCAGTCAG | | | | |
| | | | ACCT | | | | |
| 494544 | 6417 | 6436 | CCTTAATA | 82 | 140073 | 140092 | 56 |
| | | | CAGAATTT | | | | |
| | | | GTCA | | | | |

TABLE 125

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 81985 | 82004 | 62 |
| 494387 | 3978 | 3997 | TTCCTGTAACAGTGGTGGAG | 82 | 81986 | 82005 | 63 |
| 494388 | 3979 | 3998 | CTTCCTGTAACAGTGGTGGA | 86 | 81987 | 82006 | 64 |
| 494389 | 3980 | 3999 | CCTTCCTGTAACAGTGGTGG | 92 | 81988 | 82007 | 65 |
| 494390 | 3981 | 4000 | TCCTTCCTGTAACAGTGGTG | 92 | 81989 | 82008 | 66 |
| 494391 | 3982 | 4001 | GTCCTTCCTGTAACAGTGGT | 84 | 81990 | 82009 | 67 |
| 494392 | 3983 | 4002 | TGTCCTTCCTGTAACAGTGG | 81 | 81991 | 82010 | 68 |

TABLE 126

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 21210 | 21229 | 11 |
| 498369 | 3203 | 3222 | TGGAGCCAGAATAACATTCG | 91 | 70667 | 70686 | 69 |

TABLE 126-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 498379 | 3213 | 3232 | CCTCTAGGCTTGGAGCCAGA | 85 | 70677 | 70696 | 70 |
| 498408 | 3323 | 3342 | AGTTCTTCCTGTGACAGTGG | 86 | 72044 | 72063 | 71 |
| 498433 | 3367 | 3386 | GTCCGACTATGCTGGTGTGG | 87 | 72088 | 72107 | 72 |
| 498434 | 3368 | 3387 | GGTCCGACTATGCTGGTGTG | 86 | 72089 | 72108 | 73 |
| 498435 | 3369 | 3388 | GGGTCCGACTATGCTGGTGT | 83 | 72090 | 72109 | 74 |

TABLE 127

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 498229 | 2871 | 2890 | CCTCTAGGCTTGGAATCGGG | 90 | 65117 | 65136 | 75 |
| 498238 | 2883 | 2902 | GTTCAGAAGGAGCCTCTAGG | 93 | 65129 | 65148 | 76 |
| 498239 | 2884 | 2903 | TGTTCAGAAGGAGCCTCTAG | 94 | 65130 | 65149 | 77 |
| 498240 | 2887 4573 | 2906 4592 | GCTTGTTCAGAAGGAGCCTC | 98 | n/a | n/a | 78 |
| 498241 | 2888 4574 | 2907 4593 | TGCTTGTTCAGAAGGAGCCT | 94 | n/a | n/a | 79 |
| 498242 | 2889 4575 | 2908 4594 | GTGCTTGTTCAGAAGGAGCC | 96 | n/a | n/a | 80 |
| 498243 | 2890 4576 | 2909 4595 | GGTGCTTGTTCAGAAGGAGC | 97 | n/a | n/a | 81 |
| 498244 | 2891 4577 | 2910 4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |

TABLE 127-continued

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 498252 | 2899 | 2918 | TGCTCAG<br>TTGGTGC<br>TTGTTC | 90 | n/a | n/a | 84 |

TABLE 128

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 144367 | 249 | 268 | GGCAGGTC<br>CTTCCTGT<br>GACA | 91 | 21210 | 21229 | 11 |
| 498517 | 3548 | 3567 | GCTTGGAT<br>CTGGGACC<br>ACCG | 89 | 76233 | 76252 | 85 |

TABLE 129

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 144367 | 249 | 268 | GGCAGGTCCT<br>TCCTGTGACA | 94 | 21210 | 21229 | 11 |
| 498833 | 4900 | 4919 | GCCTCCATGC<br>TTGGAACTGG | 94 | 114205 | 114224 | 86 |
| 498859 | 4926 | 4945 | GCTCAGTTGG<br>TGCTGCTTCA | 92 | n/a | n/a | 87 |
| 498868 | 4978 | 4997 | CCTCGATAAC<br>TCTGGCCATT | 94 | 115488 | 115507 | 88 |
| 498875 | 5003 | 5022 | TCCTGTGACA<br>GTGGTGGAGA | 94 | 115513 | 115532 | 89 |

TABLE 130

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 144367 | 249 | 268 | GGCAGGTCCT<br>TCCTGTGACA | 92 | 21210 | 21229 | 11 |
| 499020 | 6257 | 6276 | GTAGGTTGAT<br>GCTTCACTCT | 91 | 139913 | 139932 | 90 |
| 499041 | 6318 | 6337 | CGTTTGATTG<br>CTGTCTATTA | 90 | 139974 | 139993 | 91 |

TABLE 131

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 144367 | 249 | 268 | GGCAGGTC<br>CTTCCTGT<br>GACA | 91 | 21210 | 21229 | 11 |
| 498523 | 3554 | 3573 | CTCTGTGC<br>TTGGATCT<br>GGGA | 94 | 76239 | 76258 | 92 |
| 498524 | 3555 | 3574 | CCTCTGTG<br>CTTGGATC<br>TGGG | 96 | 76240 | 76259 | 93 |
| 498525 | 3556 | 3575 | GCCTCTGTG<br>CTTGGATCT<br>GG | 94 | 76241 | 76260 | 94 |
| 498529 | 3560 | 3579 | AGAAGCCTC<br>TGTGCTTGG<br>AT | 89 | 76245 | 76264 | 95 |
| 498535 | 3566 | 3585 | TTCAGAAGA<br>AGCCTCTGT<br>GC | 89 | 76251 | 76270 | 96 |
| 498550 | 3582 | 3601 | GCTCCGTTG<br>GTGCTTCTT<br>CA | 90 | n/a | n/a | 97 |
| 498553 | 3585 | 3604 | TTTGCTCC<br>GTTGGTGC<br>TTCT | 87 | n/a | n/a | 98 |
| 498555 | 3587<br>3905 | 3606<br>3924 | GCTTTGCT<br>CCGTTGGT<br>GCTT | 90 | n/a | n/a | 99 |
| 498556 | 3588<br>3906 | 3607<br>3925 | GGCTTTGC<br>TCCGTTGG<br>TGCT | 89 | 77509<br>81914 | 77528<br>81933 | 100 |
| 498557 | 3589<br>3907 | 3608<br>3926 | GGGCTTTG<br>CTCCGTTG<br>GTGC | 89 | 77510<br>81915 | 77529<br>81934 | 101 |
| 498579 | 3662 | 3681 | CCTTCCTG<br>TGACAGTG<br>GTAG | 87 | 77583 | 77602 | 102 |
| 498580 | 3663 | 3682 | TCCTTCCT<br>GTGACAGT<br>GGTA | 92 | 77584 | 77603 | 103 |
| 498581 | 3665<br>5009 | 3684<br>5028 | TGTCCTTC<br>CTGTGACA<br>GTGG | 94 | 77586<br>115519 | 77605<br>115538 | 104 |

TABLE 132

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO |
|---|---|---|---|---|---|---|---|
| 144367 | 249 | 268 | GGCAGGTC<br>CTTCCTGT<br>GACA | 100 | 21210 | 21229 | 11 |

TABLE 132-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494230 | 477<br>819<br>1161<br>1503<br>1845<br>2187<br>2529 | 496<br>838<br>1180<br>1522<br>1864<br>2206<br>2548 | CCTCTAGGCTTGGAACCGGG | 95 | 25380<br>30927<br>36471<br>42020<br>47564<br>53110<br>58662 | 25399<br>30946<br>36490<br>42039<br>47583<br>53129<br>58681 | 105 |
| 494243 | 494<br>836<br>1178<br>1520<br>1862<br>2204<br>2546 | 513<br>855<br>1197<br>1539<br>1881<br>2223<br>2565 | TGCTTGTTCGGAAGGAGCCT | 93 | n/a | n/a | 106 |
| 494244 | 495<br>837<br>1179<br>1521<br>1863<br>2205<br>2547 | 514<br>856<br>1198<br>1540<br>1882<br>2224<br>2566 | GTGCTTGTTCGGAAGGAGCC | 95 | n/a | n/a | 107 |

TABLE 133

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 96 | 21210 | 21229 | 11 |
| 494466 | 4208 | 4227 | GCTTGGAACTGGGACCACCG | 95 | 85138 | 85157 | 108 |
| 494470 | 4212 | 4231 | CTGTGCTTGGAACTGGGACC | 94 | 85142 | 85161 | 109 |
| 494472 | 4214 | 4233 | CTCTGTGCTTGGAACTGGGA | 92 | 85144 | 85163 | 110 |

Example 115: Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 μM, 0.125 μM, 0.25 μM, 0.500 μM, or 1.000 μM concentrations of antisense oligonucleotide. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each table representing a separate experiment. The half maximal inhibitory concentration ($IC_{50}$) of each oligonucleotide is also presented in the tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 134

| ISIS No | 0.0625 μM | 0.125 μM | 0.250 μM | 0.500 μM | 1.000 μM | $IC_{50}$ (μM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 135

| ISIS No | 0.0625 μM | 0.125 μM | 0.250 μM | 0.500 μM | 1.000 μM | $IC_{50}$ (μM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 136

| ISIS No | 0.0625 μM | 0.125 μM | 0.250 μM | 0.500 μM | 1.000 μM | $IC_{50}$ (μM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 137

| ISIS No | 0.0625 μM | 0.125 μM | 0.250 μM | 0.500 μM | 1.000 μM | $IC_{50}$ (μM) |
|---|---|---|---|---|---|---|
| 144367 | 0 | 29 | 45 | 73 | 92 | 0.27 |
| 494311 | 28 | 53 | 65 | 85 | 95 | 0.13 |

TABLE 137-continued

| ISIS No | 0.0625 µM | 0.125 µM | 0.250 µM | 0.500 µM | 1.000 µM | $IC_{50}$ (µM) |
|---|---|---|---|---|---|---|
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 138

| ISIS No | 0.0625 µM | 0.125 µM | 0.250 µM | 0.500 µM | 1.000 µM | $IC_{50}$ (µM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 139

| ISIS No | 0.0625 µM | 0.125 µM | 0.250 µM | 0.500 µM | 1.000 µM | $IC_{50}$ (µM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 140

| ISIS No | 0.0625 µM | 0.125 µM | 0.250 µM | 0.500 µM | 1.000 µM | $IC_{50}$ (µM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |

TABLE 140-continued

| ISIS No | 0.0625 µM | 0.125 µM | 0.250 µM | 0.500 µM | 1.000 µM | $IC_{50}$ (µM) |
|---|---|---|---|---|---|---|
| 498580 | 36 | 57 | 81 | 91 | 96 | 0.10 |
| 498581 | 34 | 64 | 75 | 93 | 97 | 0.05 |

TABLE 141

| ISIS No | 0.0625 µM | 0.125 µM | 0.250 µM | 0.500 µM | 1.000 µM | $IC_{50}$ (µM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 142

| ISIS No | 0.0625 µM | 0.125 µM | 0.250 µM | 0.500 µM | 1.000 µM | $IC_{50}$ (µM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the tables above, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO:43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO:

60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO: 85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGA-TAACTCCGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 116: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 µM, 0.148 µM, 0.444 µM, 1.333 µM, or 4.000 µM concentrations of antisense oligonucleotide, as specified in tables below. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each table representing a separate experiment. The half maximal inhibitory concentration ($IC_{50}$) of each oligonucleotide is also presented in the tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the tables below, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 143

| ISIS No | 0.049 µM | 0.148 µM | 0.444 µM | 1.333 µM | 4.000 µM | $IC_{50}$ (µM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |
| 494283 | 18 | 45 | 80 | 93 | 91 | 0.18 |
| 494284 | 9 | 53 | 80 | 95 | 94 | 0.18 |

TABLE 144

| ISIS No | 0.049 µM | 0.148 µM | 0.444 µM | 1.333 µM | 4.000 µM | $IC_{50}$ (µM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 145

| ISIS No | 0.049 µM | 0.148 µM | 0.444 µM | 1.333 µM | 4.000 µM | $IC_{50}$ (µM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 146

| ISIS No | 0.049 μM | 0.148 μM | 0.444 μM | 1.333 μM | 4.000 μM | $IC_{50}$ (μM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |
| 498408 | 1 | 38 | 63 | 79 | 80 | 0.32 |
| 498433 | 23 | 43 | 70 | 77 | 79 | 0.21 |

TABLE 147

| ISIS No | 0.049 μM | 0.148 μM | 0.444 μM | 1.333 μM | 4.000 μM | $IC_{50}$ (μM) |
|---|---|---|---|---|---|---|
| 144367 | 0 | 40 | 76 | 90 | 93 | 0.26 |
| 498434 | 32 | 44 | 64 | 78 | 84 | 0.20 |
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 117: Antisense Inhibition of Human Apo(a) in Transgenic Mouse Primary Hepatocytes Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12 kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises of ten 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. “Start site” indicates the 5'-most nucleoside to which the gapmer is targeted in the human sequence. “Stop site” indicates the 3'-most nucleoside to which the gapmer is targeted human sequence. An apo(a) antisense oligonucleotide may have more than one “Start site” or “Stop site” depending on whether or not it targets a Kringle repeat.

Most gapmers listed in the tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. ‘n/a’ indicates that the antisense oligonucleotide does not target that particular sequence with 100% complementarity.

TABLE 148

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO: |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
| | 583 | 599 | CCTGTGACAGTGGTGGA | | 26693 | 26709 | |
| | 925 | 941 | CCTGTGACAGTGGTGGA | | 32240 | 32256 | |
| | 1609 | 1625 | CCTGTGACAGTGGTGGA | | 43333 | 43349 | |
| | 1951 | 1967 | CCTGTGACAGTGGTGGA | | 48877 | 48893 | |
| | 2293 | 2309 | CCTGTGACAGTGGTGGA | | 54423 | 54439 | |
| | 3319 | 3335 | CCTGTGACAGTGGTGGA | | 72040 | 72056 | |
| | 4663 | 4679 | CCTGTGACAGTGGTGGA | | 94404 | 94420 | |
| | 5005 | 5021 | CCTGTGACAGTGGTGGA | | 115515 | 115531 | |
| 510543 | 242 | 258 | TCCTGTGACAGTGGTGG | 75 | 21203 | 21219 | 112 |
| | 584 | 600 | TCCTGTGACAGTGGTGG | | 26694 | 26710 | |
| | 926 | 942 | TCCTGTGACAGTGGTGG | | 32241 | 32257 | |
| | 1610 | 1626 | TCCTGTGACAGTGGTGG | | 43334 | 43350 | |
| | 1952 | 1968 | TCCTGTGACAGTGGTGG | | 48878 | 48894 | |
| | 2294 | 2310 | TCCTGTGACAGTGGTGG | | 54424 | 54440 | |

TABLE 148-continued

| ISIS NO | SEQ ID NO: 1 Start Site | SEQ ID NO: 1 Stop Site | Sequence | % inhi-bi-tion | SEQ ID NO: 2 Start Site | SEQ ID NO: 2 Stop Site | SEQ ID NO: |
|---|---|---|---|---|---|---|---|
| | 3320 | 3336 | TCCTGTGACAGTGGTGG | | 72041 | 72057 | |
| | 4664 | 4680 | TCCTGTGACAGTGGTGG | | 94405 | 94421 | |
| | 5006 | 5022 | TCCTGTGACAGTGGTGG | | 115516 | 115532 | |
| 510544 | 243 | 259 | TTCCTGTGACAGTGGTG | 73 | 21204 | 21220 | 113 |
| | 585 | 601 | TTCCTGTGACAGTGGTG | | 26695 | 26711 | |
| | 927 | 943 | TTCCTGTGACAGTGGTG | | 32242 | 32258 | |
| | 1611 | 1627 | TTCCTGTGACAGTGGTG | | 43335 | 43351 | |
| | 1953 | 1969 | TTCCTGTGACAGTGGTG | | 48879 | 48895 | |
| | 2295 | 2311 | TTCCTGTGACAGTGGTG | | 54425 | 54441 | |
| | 3321 | 3337 | TTCCTGTGACAGTGGTG | | 72042 | 72058 | |
| | 4665 | 4681 | TTCCTGTGACAGTGGTG | | 94406 | 94422 | |
| | 5007 | 5023 | TTCCTGTGACAGTGGTG | | 115517 | 115533 | |
| 510545 | 244 | 260 | CTTCCTGTGACAGTGGT | 65 | 21205 | 21221 | 114 |
| | 586 | 602 | CTTCCTGTGACAGTGGT | | 26696 | 26712 | |
| | 928 | 944 | CTTCCTGTGACAGTGGT | | 32243 | 32259 | |
| | 1612 | 1628 | CTTCCTGTGACAGTGGT | | 43336 | 43352 | |
| | 1954 | 1970 | CTTCCTGTGACAGTGGT | | 48880 | 48896 | |
| | 2296 | 2312 | CTTCCTGTGACAGTGGT | | 54426 | 54442 | |
| | 3322 | 3338 | CTTCCTGTGACAGTGGT | | 72043 | 72059 | |
| | 3664 | 3680 | CTTCCTGTGACAGTGGT | | 77585 | 77601 | |
| | 4666 | 4682 | CTTCCTGTGACAGTGGT | | 94407 | 94423 | |
| | 5008 | 5024 | CTTCCTGTGACAGTGGT | | 115518 | 115534 | |
| 510546 | 245 | 261 | CCTTCCTGTGACAGTGG | 74 | 21206 | 21222 | 115 |
| | 3665 | 3681 | CCTTCCTGTGACAGTGG | | 77586 | 77602 | |
| | 4667 | 4683 | CCTTCCTGTGACAGTGG | | 94408 | 94424 | |
| | 5009 | 5025 | CCTTCCTGTGACAGTGG | | 115519 | 115535 | |
| 510547 | 246 | 262 | TCCTTCCTGTGACAGTG | 77 | 21207 | 21223 | 116 |
| | 3666 | 3682 | TCCTTCCTGTGACAGTG | | 77587 | 77603 | |
| | 4668 | 4684 | TCCTTCCTGTGACAGTG | | 94409 | 94425 | |
| | 5010 | 5026 | TCCTTCCTGTGACAGTG | | 115520 | 115536 | |
| 510548 | 247 | 263 | GTCCTTCCTGTGACAGT | 73 | 21208 | 21224 | 117 |
| | 3667 | 3683 | GTCCTTCCTGTGACAGT | | 77588 | 77604 | |
| | 4669 | 4685 | GTCCTTCCTGTGACAGT | | 94410 | 94426 | |
| | 5011 | 5027 | GTCCTTCCTGTGACAGT | | 115521 | 115537 | |
| 510549 | 248 | 264 | GGTCCTTCCTGTGACAG | 67 | 21209 | 21225 | 118 |
| | 4670 | 4686 | GGTCCTTCCTGTGACAG | | 94411 | 94427 | |
| 510595 | 632 | 648 | CCGACTATGCGAGTGTG | 76 | 26742 | 26758 | 119 |
| | 974 | 990 | CCGACTATGCGAGTGTG | | 32289 | 32305 | |
| | 1316 | 1332 | CCGACTATGCGAGTGTG | | 37836 | 37852 | |
| | 1658 | 1674 | CCGACTATGCGAGTGTG | | 43382 | 43398 | |
| | 2000 | 2016 | CCGACTATGCGAGTGTG | | 48926 | 48942 | |
| | 2342 | 2358 | CCGACTATGCGAGTGTG | | 54472 | 54488 | |
| | 2684 | 2700 | CCGACTATGCGAGTGTG | | 60027 | 60043 | |
| | 3026 | 3042 | CCGACTATGCGAGTGTG | | 66543 | 66559 | |
| 510597 | 634 | 650 | GTCCGACTATGCGAGTG | 70 | 26744 | 26760 | 120 |
| | 976 | 992 | GTCCGACTATGCGAGTG | | 32291 | 32307 | |
| | 1318 | 1334 | GTCCGACTATGCGAGTG | | 37838 | 37854 | |
| | 1660 | 1676 | GTCCGACTATGCGAGTG | | 43384 | 43400 | |
| | 2002 | 2018 | GTCCGACTATGCGAGTG | | 48928 | 48944 | |
| | 2344 | 2360 | GTCCGACTATGCGAGTG | | 54474 | 54490 | |
| | 2686 | 2702 | GTCCGACTATGCGAGTG | | 60029 | 60045 | |
| | 3028 | 3044 | GTCCGACTATGCGAGTG | | 66545 | 66561 | |
| 510598 | 635 | 651 | GGTCCGACTATGCGAGT | 70 | 26745 | 26761 | 121 |
| | 977 | 993 | GGTCCGACTATGCGAGT | | 32292 | 32308 | |
| | 1319 | 1335 | GGTCCGACTATGCGAGT | | 37839 | 37855 | |
| | 1661 | 1677 | GGTCCGACTATGCGAGT | | 43385 | 43401 | |
| | 2003 | 2019 | GGTCCGACTATGCGAGT | | 48929 | 48945 | |
| | 2345 | 2361 | GGTCCGACTATGCGAGT | | 54475 | 54491 | |
| | 2687 | 2703 | GGTCCGACTATGCGAGT | | 60030 | 60046 | |
| | 3029 | 3045 | GGTCCGACTATGCGAGT | | 66546 | 66562 | |

TABLE 149

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCT TCCTGTGACA | 83 | 21210 | 21229 | 11 |
| 510783 | 6400 | 6416 | GTCAGACCTT AAAAGCT | 75 | 140056 | 140072 | 122 |
| 512944 | 3561 | 3577 | AAGCCTCTGT GCTTGGA | 81 | 76246 | 76262 | 123 |
| 512947 | 3560 | 3576 | AGCCTCTGTG CTTGGAT | 85 | 76245 | 76261 | 124 |
| 512958 | 3559 | 3575 | GCCTCTGTGC TTGGATC | 82 | 76244 | 76260 | 125 |
| 512959 | 3585 | 3601 | GCTCCGTTGG TGCTTCT | 77 | n/a | n/a | 126 |

TABLE 150

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTC CTTCCTGT GACA | 76 | 21210 | 21229 | 11 |
| 510701 | 4217 | 4233 | CTCTGTGCT TGGAACTG | 78 | 85147 | 85163 | 127 |
| 510702 | 219 | 235 | TGCCTCGA TAACTCTG T | 79 | 21180 | 21196 | 128 |
| | 561 | 577 | | | 26671 | 26687 | |
| | 903 | 919 | | | 32218 | 32234 | |
| | 1245 | 1261 | | | 37765 | 37781 | |
| | 1587 | 1603 | | | 43311 | 43327 | |
| | 1929 | 1945 | | | 48855 | 48871 | |
| | 2271 | 2287 | | | 54401 | 54417 | |
| | 2613 | 2629 | | | 59956 | 59972 | |
| | 4299 | 4315 | | | 86472 | 86488 | |
| 510704 | 563 | 579 | TGTGCCTCG ATAACTCT | 80 | 26673 | 26689 | 129 |
| | 905 | 921 | | | 32220 | 32236 | |
| | 1247 | 1263 | | | 37767 | 37783 | |
| | 1589 | 1605 | | | 43313 | 43329 | |
| | 1931 | 1947 | | | 48857 | 48873 | |
| | 2273 | 2289 | | | 54403 | 54419 | |
| | 2615 | 2631 | | | 59958 | 59974 | |
| | 4301 | 4317 | | | 86474 | 86490 | |
| | 4985 | 5001 | | | 115495 | 115511 | |
| 510757 | 4929 | 4945 | GCTCAGTTG GTGCTGCT | 74 | n/a | n/a | 130 |

Example 118: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 μM, 0.313 μM, 0.625 μM, 1.250 μM, 2.500 μM, or 5.000 μM concentrations of antisense oligonucleotide, as specified in the tables below. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each study represented in a separate table. The half maximal inhibitory concentration ($IC_{50}$) of each oligonucleotide is also presented in the tables.

TABLE 151

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 152

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 153

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 154

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |
| 510704 | 54 | 61 | 77 | 84 | 89 | 80 | 0.12 |

TABLE 154-continued

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the tables above, ISIS 510542 (SEQ ID NO: 111), ISIS 510545 (SEQ ID NO: 114), ISIS 510546 (SEQ ID NO: 115), ISIS 510547 (SEQ ID NO: 116), ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 119: Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS 494311, ISIS 494337, ISIS 494372, ISIS 498238, ISIS 498523, ISIS 498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in the table below, expressed as percent inhibition of apo(a) mRNA compared to the PBS control.

TABLE 155

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in the table below, expressed as percent inhibition of apo(a) mRNA compared to the PBS control.

TABLE 156

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |

TABLE 156-continued

| Percent inhibition of human apo(a) protein in transgenic mice | |
|---|---|
| ISIS No | % inhibition |
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control.

TABLE 157

| Dose-dependent inhibition of human apo(a) mRNA in transgenic mice | | | |
|---|---|---|---|
| ISIS No | Dose (mg/kg/wk) | % inhibition | $ED_{50}$ |
| 144367 | 100 | 71 | 31 |
| | 30 | 42 | |
| | 10 | 0 | |
| | 3 | 5 | |
| 494159 | 100 | 91 | 5 |
| | 30 | 67 | |
| | 10 | 48 | |
| | 3 | 39 | |
| 494161 | 100 | 82 | 6 |
| | 30 | 49 | |
| | 10 | 61 | |
| | 3 | 30 | |
| 494162 | 100 | 90 | 5 |
| | 30 | 67 | |
| | 10 | 58 | |
| | 3 | 25 | |
| 494163 | 100 | 83 | 5 |
| | 30 | 66 | |
| | 10 | 58 | |
| | 3 | 21 | |

TABLE 157-continued

| Dose-dependent inhibition of human apo(a) mRNA in transgenic mice | | | |
|---|---|---|---|
| ISIS No | Dose (mg/kg/wk) | % inhibition | $ED_{50}$ |
| 494243 | 100 | 80 | 32 |
| | 30 | 26 | |
| | 10 | 0 | |
| | 3 | 6 | |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO:17), and ISIS 94163 (SEQ ID NO: 18) were more efficacious than the benchmark ISIS 144367 (SEQ ID NO: 11). Reduction of human apo(a) protein levels Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control.

TABLE 158

| Dose-dependent inhibition of human apo(a) protein in transgenic mice | | | |
|---|---|---|---|
| ISIS No | Dose (mg/kg/wk) | % inhibition | $ED_{50}$ |
| 144367 | 100 | 73 | 71 |
| | 30 | 0 | |
| | 10 | 6 | |
| | 3 | 69 | |
| 494159 | 100 | 88 | 2 |
| | 30 | 88 | |
| | 10 | 85 | |
| | 3 | 36 | |
| 494161 | 100 | 90 | 2 |
| | 30 | 85 | |
| | 10 | 73 | |
| | 3 | 44 | |
| 494162 | 100 | 89 | 3 |
| | 30 | 78 | |
| | 10 | 76 | |
| | 3 | 24 | |
| 494163 | 100 | 90 | 3 |
| | 30 | 86 | |
| | 10 | 60 | |
| | 3 | 37 | |
| 494243 | 100 | 61 | 174 |
| | 30 | 0 | |
| | 10 | 0 | |
| | 3 | 0 | |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control.

TABLE 159

Dose-dependent inhibition of human apo(a) mRNA in transgenic mice

| ISIS No | Dose (mg/kg/wk) | % inhibition | $ED_{50}$ |
|---|---|---|---|
| 144367 | 50 | 75 | 22 |
| | 15 | 60 | |
| | 5 | 0 | |
| | 1.5 | 0 | |
| 494244 | 50 | 73 | 18 |
| | 15 | 41 | |
| | 5 | 34 | |
| | 1.5 | 0 | |
| 494283 | 50 | 74 | 16 |
| | 15 | 52 | |
| | 5 | 24 | |
| | 1.5 | 0 | |
| 494284 | 50 | 73 | 16 |
| | 15 | 58 | |
| | 5 | 17 | |
| | 1.5 | 2 | |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control.

TABLE 160

Dose-dependent inhibition of human apo(a) plasma protein in transgenic mice

| ISIS No | Dose (mg/kg/wk) | % inhibition | $ED_{50}$ |
|---|---|---|---|
| 144367 | 50 | 64 | 16 |
| | 15 | 14 | |
| | 5 | 0 | |
| | 1.5 | 0 | |
| 494244 | 50 | 67 | 2 |
| | 15 | 60 | |
| | 5 | 58 | |
| | 1.5 | 0 | |
| 494283 | 50 | 64 | 4 |
| | 15 | 65 | |
| | 5 | 64 | |
| | 1.5 | 69 | |
| 494284 | 50 | 66 | 4 |
| | 15 | 63 | |
| | 5 | 51 | |
| | 1.5 | 54 | |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 161

Dose-dependent inhibition of human Apo(a) mRNA in transgenic mice

| ISIS No | Dose (mg/kg/wk) | % inhibition | $ED_{50}$ |
|---|---|---|---|
| 494285 | 50 | 98 | 1 |
| | 15 | 97 | |
| | 5 | 79 | |
| 494286 | 50 | 97 | 1 |
| | 15 | 91 | |
| | 5 | 80 | |
| 494301 | 50 | 98 | 3 |
| | 15 | 96 | |
| | 5 | 59 | |
| 494302 | 50 | 98 | 2 |
| | 15 | 88 | |
| | 5 | 72 | |
| 494311 | 50 | 99 | 1 |
| | 15 | 96 | |
| | 5 | 87 | |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control. The data demonstrates significant reduction of apo (a) plasma protein levels by ISIS 494285, ISIS 494286, ISIS 494301, ISIS 494302 and ISIS 494311.

TABLE 162

Dose-dependent inhibition of human apo(a) protein in transgenic mice

| ISIS No | Dose (mg/kg/wk) | % inhibition | $ED_{50}$ |
|---|---|---|---|
| 494285 | 50 | 88 | 2 |
| | 15 | 88 | |
| | 5 | 72 | |
| 494286 | 50 | 90 | 2 |
| | 15 | 85 | |
| | 5 | 75 | |
| 494301 | 50 | 89 | 5 |
| | 15 | 86 | |
| | 5 | 38 | |
| 494302 | 50 | 90 | 3 |
| | 15 | 82 | |
| | 5 | 61 | |
| 494311 | 50 | 90 | 3 |
| | 15 | 82 | |
| | 5 | 69 | |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 163

Dose-dependent inhibition of human Apo(a) mRNA in transgenic mice

| ISIS No | Dose (mg/kg/wk) | % inhibition | $ED_{50}$ |
|---|---|---|---|
| 494372 | 50 | 88 | 18 |
| | 15 | 49 | |
| | 5 | 0 | |
| 498524 | 50 | 83 | 8 |
| | 15 | 74 | |
| | 5 | 34 | |
| 498581 | 50 | 98 | 7 |
| | 15 | 58 | |
| | 5 | 48 | |
| 498721 | 50 | 97 | 14 |
| | 15 | 68 | |
| | 5 | 0 | |
| 498833 | 50 | 61 | 155 |
| | 15 | 0 | |
| | 5 | 17 | |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control. The data demonstrates significant reduction of apo (a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 164

Dose-dependent inhibition of human apo(a) protein in transgenic mice

| ISIS No | Dose (mg/kg/wk) | % inhibition | $ED_{50}$ |
|---|---|---|---|
| 494372 | 50 | 68 | 32 |
| | 15 | 25 | |
| | 5 | 12 | |
| 498524 | 50 | 38 | 118 |
| | 15 | 0 | |
| | 5 | 0 | |
| 498581 | 50 | 79 | 9 |
| | 15 | 52 | |
| | 5 | 49 | |
| 498721 | 50 | 81 | 10 |
| | 15 | 63 | |
| | 5 | 29 | |
| 498833 | 50 | 15 | 738 |
| | 15 | 0 | |
| | 5 | 67 | |

Example 120: Tolerability of Antisense Oligonucleotides Targeting Human Apo(a) in Rodent Models Gapmer antisense oligonucleotides targeting human apo (a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 Mice: Study 1

CD1® mice (Charles River, MA) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS.

Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, NY). The results are presented in the table below. ISIS oligonucleotides that caused changes in the levels of any of the liver or kidney function markers outside the expected range for antisense oligonucleotides were excluded in further studies.

TABLE 165

| Plasma chemistry markers of CD1 mice | | | | | | |
|---|---|---|---|---|---|---|
| | ALT (IU/L | AST (IU/L) | Albumin (g/dL) | BUN (mg/dL) | Creatinine (mg/dL) | Bilirubin (mg/dL) |
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in the table below. ISIS oligonucleotides that caused any changes in organ weights outside the expected range for antisense oligonucleotides were excluded from further studies.

TABLE 166

| Organ weights of CD1 mice (g) | | | |
|---|---|---|---|
| | Kidney | Liver | Spleen |
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |
| ISIS 494337 | 0.56 | 2.3 | 0.17 |
| ISIS 494372 | 0.60 | 2.5 | 0.27 |
| ISIS 510548 | 0.55 | 3.7 | 0.20 |

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, NY). The results are presented in the table below. ISIS oligonucleotides that caused changes in the levels of any of the liver or kidney function markers outside the expected range for antisense oligonucleotides were excluded in further studies.

TABLE 167

| Plasma chemistry markers of Sprague Dawley rats | | | | | | |
|---|---|---|---|---|---|---|
| | ALT (IU/L) | AST (IU/L) | Bilirubin (mg/dL) | Albumin (mg/dL) | BUN (mg/dL) | Creatinine (mg/dL) |
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function

To evaluate the effect of ISIS oligonucleotides on kidney function, urine levels of total protein and creatinine were measured using an automated clinical chemistry analyzer (Hitachi Olympus AU400e, Melville, NY). Results are presented in the table below, expressed in mg/dL.

TABLE 168

| Kidney function markers (mg/dL) in Sprague-Dawley rats | | |
|---|---|---|
| | Creatinine | Total protein |
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in the table below. ISIS oligonucleotides that caused any changes in organ weights outside the expected range for antisense oligonucleotides were excluded from further studies.

TABLE 169

| Organ weights of Sprague Dawley rats (g) | | | |
|---|---|---|---|
| | Kidney | liver | Spleen |
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 121: Pharmacokinetics of Antisense Oligonucleotide in CD1 Mice

CD1 mice were treated with ISIS oligonucleotides and the oligonucleotide concentrations in the liver and kidney were evaluated.

Treatment

Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in the table below, expressed as µg/g liver or kidney tissue. The data indicates that ISIS 494372 was at an acceptable concentration in the liver and kidneys.

TABLE 170

| Oligonucleotide concentration (µg/g tissue) of ISIS oligonucleotides in CD1 mice | | |
|---|---|---|
| ISIS No | Liver | Kidney |
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 122: Pharmacokinetics of Antisense Oligonucleotide in Sprague Dawley Rats Male Sprague Dawley rats were treated with ISIS oligonucleotides and the oligonucleotide concentrations in the liver and kidney were evaluated.

Treatment

Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in the table below, expressed as µg/g liver or kidney tissue. The data indicates that ISIS 494372 was at an acceptable concentration in the liver and kidneys.

TABLE 171

| Oligonucleotide concentration (µg/g tissue) of ISIS oligonucleotides in Sprague Dawley rats | | |
|---|---|---|
| ISIS No | Liver | Kidney |
| 494283 | 220 | 434 |
| 494284 | 178 | 573 |
| 494286 | 234 | 448 |
| 494301 | 279 | 540 |
| 494302 | 205 | 387 |
| 494372 | 288 | 663 |

Example 123: Effect of ISIS Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in the table below. Each antisense oligonucleotide targets more than one region in SEQ ID NO:132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 172

Antisense oligonucleotides complementary to SEQ ID NO: 132

| ISIS No | Start Site | Mismatches |
|---|---|---|
| 494283 | 278 | 2 |
| | 620 | 2 |
| | 923 | 2 |
| | 1265 | 2 |
| | 1607 | 1 |
| | 1949 | 1 |
| | 2267 | 1 |
| | 2609 | 1 |
| | 2951 | 1 |
| | 3293 | 1 |
| 494284 | 279 | 1 |
| | 621 | 1 |
| | 924 | 1 |
| | 1266 | 1 |
| | 1608 | 1 |
| | 1950 | 1 |
| | 2268 | 1 |
| | 2610 | 1 |
| | 2952 | 1 |
| | 3294 | 1 |
| 494286 | 281 | 1 |
| | 623 | 1 |
| | 926 | 1 |
| | 1268 | 1 |
| | 1610 | 2 |
| | 1952 | 2 |
| | 2270 | 2 |
| | 2612 | 2 |
| | 2954 | 2 |
| | 3296 | 2 |
| 494301 | 322 | 2 |
| | 664 | 2 |
| | 967 | 2 |
| | 1309 | 1 |
| | 1651 | 2 |
| 494302 | 323 | 2 |
| | 968 | 2 |
| | 1310 | 1 |
| | 1652 | 2 |
| 494372 | 1186 | 2 |
| | 1870 | 1 |
| | 2188 | 1 |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized Scheduled euthanasia of the animals was conducted on days 86 and 87 by exsanguination under deep anesthesia. The protocols described in the Example were approved by the Institutional Animal Care and Use Committee (IACUC).

Target Reduction

RNA Analysis

On day 86, RNA was extracted from liver tissue for real-time PCR analysis of apo(a) using human primer probe set ABI Hs00916691_m1 (Applied Biosystems, Carlsbad CA). Results are presented as percent inhibition of apo(a) mRNA, relative to PBS control. As shown in the table below, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 173

Percent Inhibition of apo(a) mRNA in the cynomolgus monkey liver relative to the PBS control

| ISIS No | % inhibition |
|---|---|
| 494283 | 91 |
| 494284 | 99 |
| 494286 | 96 |
| 494301 | 88 |
| 494302 | 89 |
| 494372 | 93 |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in the table below, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 174

Apo(a) plasma protein levels (% inhibition over baseline values) in the cynomolgus monkey

| | Day 16 | Day 30 | Day 44 | Day 56 | Day 72 | Day 86 |
|---|---|---|---|---|---|---|
| PBS | 0 | 0 | 10 | 0 | 0 | 0 |
| ISIS 494283 | 78 | 79 | 81 | 66 | 66 | 70 |

TABLE 174-continued

| Apo(a) plasma protein levels (% inhibition over baseline values) in the cynomolgus monkey | | | | | | |
|---|---|---|---|---|---|---|
| | Day 16 | Day 30 | Day 44 | Day 56 | Day 72 | Day 86 |
| ISIS 494284 | 92 | 95 | 95 | 93 | 93 | 94 |
| ISIS 494286 | 92 | 95 | 96 | 94 | 94 | 94 |
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies

Body and Organ Weight Measurements

To evaluate the effect of ISIS oligonucleotides on the overall health of the animals, body and organ weights were measured at day 86. Body weights were measured and are presented in the table below. Organ weights were measured and the data is presented in the table below. The results indicate that treatment with ISIS 494372 was well tolerated in terms of the body and organ weights of the monkeys.

TABLE 175

| Body weights (g) in the cynomolgus monkey | | | | | | |
|---|---|---|---|---|---|---|
| | Day 14 | Day 35 | Day 49 | Day 56 | Day 70 | Day 84 |
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 176

| Organ weights (% body weight) in the cynomolgus monkey | | | | | |
|---|---|---|---|---|---|
| | Spleen | Kidneys | Liver | Heart | Lungs |
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in the table below, expressed in IU/L. Bilirubin, a liver function marker, was similarly measured and is presented in the table below, expressed in mg/dL. The results indicate that treatment with ISIS 494372 was well tolerated in terms of the liver function in monkeys.

TABLE 177

| Liver function markers in cynomolgus monkey plasma | | | |
|---|---|---|---|
| | ALT (IU/L) | AST (IU/L) | Bilirubin (mg/dL) |
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-Reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 178

| C-reactive protein levels (mg/L) in cynomolgus monkey plasma | |
|---|---|
| | CRP |
| PBS | 1.4 |
| ISIS 494283 | 14.7 |
| ISIS 494284 | 7.7 |
| ISIS 494286 | 4.4 |
| ISIS 494301 | 3.5 |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 179

| Complement C3 levels (mg/dL) in cynomolgus monkey plasma | | |
|---|---|---|
| | Pre-dose | Post-dose |
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing K2-EDTA. Samples were analyzed for red blood cell (RBC) count, white blood cells (WBC) count, as well as for platelet count, using an ADVIA120 hematology analyzer (Bayer, USA). The data is presented in the table below.

The data indicate that treatment with ISIS 494372 was well tolerated in terms of the hematologic parameters of the monkeys.

TABLE 180

Blood cell counts in cynomolgus monkeys

| | WBC ($\times10^3/\mu L$) | RBC ($\times10^6/\mu L$) | Platelet ($\times10^3/\mu L$) |
|---|---|---|---|
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 124: Characterization of the Pharmacological Activity of ISIS 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 181

Dosing groups in cynomolgus monkeys

| | | | Number of animals for necropsy | | |
|---|---|---|---|---|---|
| Group | Test Article | Dose | Interim | Terminal | Recovery |
| 1 | PBS | — | 4 | 6 | 4 |
| 2 | ISIS | 4 | — | 6 | — |
| 3 | 494372 | 8 | — | 6 | — |
| 4 | | 12 | 4 | 6 | 4 |
| 5 | | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns. After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_m1, Applied Biosystems, Carlsbad CA) targeting position 1512 of the rhesus monkey apo(a) mRNA transcript GENBANK Accession No XM_001098061.2 (SEQ ID NO: 132) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in the table below, treatment with ISIS 494372 resulted in a dose-dependent reduction of apo(a) mRNA in comparison to the PBS control. At day 30, hepatic apo(a) mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, $P<0.05$).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 182

Percent inhibition levels of liver apo(a) mRNA in the dosing phase in cynomolgus monkeys treated with ISIS 494372

| Day | Dose (mg/kg/wk) | % inhibition |
|---|---|---|
| 30 | 12 | 73 |
| | 40 | 99 |
| 93 | 4 | 44 |
| | 8 | 43 |
| | 12 | 53 |
| | 40 | 93 |

Protein Analysis

Approximately 20 μl of plasma was analyzed using a commercially available apo(a) ELISA kit (Mercodia 10-1106-01, Uppsala, Sweden). The assay protocol was performed as described by the manufacturer. The results are presented in the tables below as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 183

| Apo(a) plasma protein levels as a percent of Day 1 levels in the dosing phase in cynomolgus monkeys treated with ISIS 494372 | | |
|---|---|---|
| Day | Dose (mg/kg/wk) | % |
| 30 | 4 | 93 |
| | 8 | 70 |
| | 12 | 49 |
| | 40 | 15* |
| 93 | 4 | 73 |
| | 8 | 56 |
| | 12 | 32* |
| | 40 | 11* |

TABLE 184

| Apo(a) plasma protein levels as a percent of Day 1 levels in the recovery phase in cynomolgus monkeys treated with ISIS 494372 | | |
|---|---|---|
| Day | Dose (mg/kg/wk) | % |
| 121 | 12 | 38* |
| | 40 | 22* |
| 182 | 12 | 84 |
| | 40 | 93 |

Example 125: Measurement of Viscosity of ISIS Antisense Oligonucleotides Targeting Human Apo(a)

The viscosity of select antisense oligonucleotides from the studies described above was measured with the aim of screening out antisense oligonucleotides which have a viscosity more than 40 centipoise (cP). Oligonucleotides having a viscosity greater than 40 cP would have less than optimal viscosity.

ISIS oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometter was set to 25° C. and the viscosity of the sample was measured. Another part (20 μL) of the pre-heated sample was pipetted into 10 mL of water for UV reading at 260 nM at 85° C. (Cary UV instrument). The results are presented in the table below and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 185

| Viscosity and concentration of ISIS antisense oligonucleotides targeting human Apo(a) | | | |
|---|---|---|---|
| ISIS No | Motif | Viscosity (cP) | Concentration (mg/mL) |
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A compound or a salt thereof comprising a modified oligonucleotide and a conjugate group, wherein the modified oligonucleotide consists of 12 to 30 linked nucleosides and comprises a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1; and wherein the conjugate group comprises:

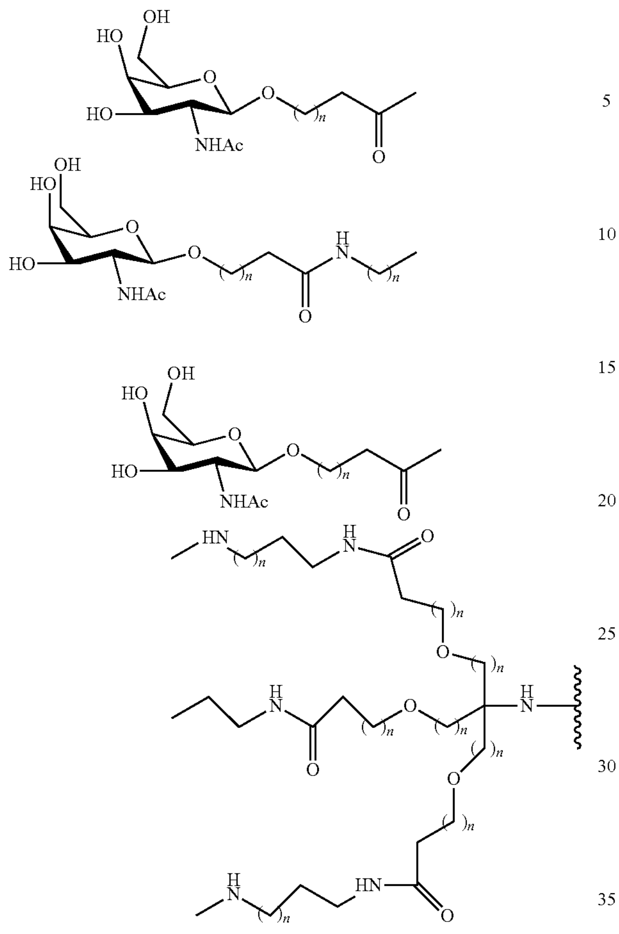

wherein each n is, independently, an integer from 1 to 20.

2. The compound of claim 1, wherein the modified oligonucleotide consists of 20 linked nucleosides.

3. The compound of claim 1, wherein the modified oligonucleotide comprises at least one modified sugar.

4. The compound of claim 3, wherein at least one modified sugar is a bicyclic sugar.

5. The compound of claim 3, wherein at least one modified sugar comprises a 2'-O-methoxyethyl, a constrained ethyl, a 3'-fluoro-HNA or a 4'-$(CH_2)_n$-O-2' bridge, wherein n is 1 or 2.

6. The compound of claim 3, wherein at least one modified sugar comprises 2'-O-methoxyethyl.

7. The compound of claim 1, wherein at least one nucleoside comprises a modified nucleobase.

8. The compound of claim 7, wherein the modified nucleobase is a 5-methylcytosine.

9. The compound of claim 1, wherein the conjugate group is linked to the modified oligonucleotide at the 5' end of the modified oligonucleotide.

10. The compound of claim 1, wherein the conjugate group is linked to the modified oligonucleotide at the 3' end of the modified oligonucleotide.

11. The compound of claim 1, wherein each internucleoside linkage of the modified oligonucleotide is selected from a phosphodiester internucleoside linkage and a phosphorothioate internucleoside linkage.

12. The compound of claim 11, wherein the modified oligonucleotide comprises at least 5 phosphodiester internucleoside linkages.

13. The compound of claim 11, wherein the modified oligonucleotide comprises at least 2 phosphorothioate internucleoside linkages.

14. The compound of claim 1, wherein the modified oligonucleotide is single-stranded.

15. The compound of claim 1, wherein the modified oligonucleotide is double stranded.

16. The compound of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

17. The compound of claim 16, wherein each internucleoside linkage in the gap segment of the modified oligonucleotide is a phosphorothioate linkage.

18. The compound of claim 17, wherein the modified oligonucleotide further comprises at least one phosphorothioate internucleoside linkage in each wing segment.

19. The compound of claim 2, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar, and wherein each cytosine residue is a 5-methylcytosine.

20. The compound of claim 19, wherein each internucleoside linkage in the gap segment of the modified oligonucleotide is a phosphorothioate linkage.

21. The compound of claim 20, wherein the modified oligonucleotide further comprises at least one phosphorothioate internucleoside linkage in each wing segment.

22. The compound of claim 2, wherein the modified oligonucleotide comprises the nucleobase sequence of SEQ ID NO: 58, and wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein each internucleoside linkage in the gap segment is a phosphorothioate linkage and wherein each cytosine residue is a 5-methylcytosine.

23. The compound of claim 22, wherein the modified oligonucleotide further comprises at least one phosphorothioate internucleoside linkage in each wing segment.

24. The compound of claim 22, wherein the internucleoside linkages are phosphorothioate linkages between nucleosides 1-2, nucleosides 6-16 and nucleosides 17-20 of the modified oligonucleotide, wherein nucleosides 1-20 are positioned 5' to 3'.

25. The compound of claim 22, wherein the $2^{nd}$, $3^{rd}$, $4^{th}$, and $5^{th}$ internucleoside linkage from the 5'-end is a phosphodiester internucleoside linkage, wherein the $3^{rd}$ and $4^{th}$ internucleoside linkage from the 3'-end is a phosphodiester internucleoside linkage, and wherein each remaining internucleoside linkage is a phosphorothioate internucleoside linkage.

26. The compound of claim 1, wherein the modified oligonucleotide comprises a nucleobase sequence comprising a portion of at least 16 contiguous nucleobases complementary to an equal length portion of nucleobases 3901 to 3920 of SEQ ID NO: 1.

27. The compound of claim 1, wherein the modified oligonucleotide comprises a nucleobase sequence comprising a portion of at least 18 contiguous nucleobases complementary to an equal length portion of nucleobases 3901 to 3920 of SEQ ID NO: 1.

28. The compound of claim 1, wherein the modified oligonucleotide comprises a nucleobase sequence comprising a portion of at least 20 contiguous nucleobases complementary to an equal length portion of nucleobases 3901 to 3920 of SEQ ID NO: 1.

29. A composition comprising the compound of claim 1 or salt thereof and at least one pharmaceutically acceptable carrier or diluent.

30. A method for treating, preventing, or slowing progression of a disease related to elevated Apo(a) and/or elevated Lp(a) comprising administering to the patient in need thereof a compound of claim 1 or a salt thereof.

31. The method of claim 30, wherein the disease is a cardiovascular, metabolic and/or inflammatory disease, disorder or condition.

32. The method of claim 30, wherein the disease is hyperlipidemia.

33. The method of claim 30, wherein the disease is aneurysm, angina, arrhythmia, atherosclerosis, cerebrovascular disease, coronary artery disease, coronary heart disease myocardial infarction, peripheral vascular disease, peripheral artery disease, peripheral artery occlusive disease, retinal vascular occlusion, or stroke.

* * * * *